US012365907B2

(12) United States Patent
Saski

(10) Patent No.: US 12,365,907 B2
(45) Date of Patent: Jul. 22, 2025

(54) VECTOR FOR GENE TRANSFER AND GENE COPY PROLIFERATION

(71) Applicant: Clemson University, Clemson, SC (US)

(72) Inventor: Christopher Saski, Clemson, SC (US)

(73) Assignee: Clemson University, Clemson, SC (US)

( * ) Notice: Subject to any disclaimer, the term of this patent is extended or adjusted under 35 U.S.C. 154(b) by 551 days.

(21) Appl. No.: 17/433,117

(22) PCT Filed: Mar. 6, 2020

(86) PCT No.: PCT/US2020/021318
§ 371 (c)(1),
(2) Date: Aug. 23, 2021

(87) PCT Pub. No.: WO2020/185536
PCT Pub. Date: Sep. 17, 2020

(65) Prior Publication Data
US 2022/0162622 A1    May 26, 2022

Related U.S. Application Data

(60) Provisional application No. 62/815,628, filed on Mar. 8, 2019.

(51) Int. Cl.
*C12N 15/82* (2006.01)

(52) U.S. Cl.
CPC ..... *C12N 15/8202* (2013.01); *C12N 15/8216* (2013.01)

(58) Field of Classification Search
None
See application file for complete search history.

(56) References Cited

U.S. PATENT DOCUMENTS

| | | | |
|---|---|---|---|
| 5,270,201 A | 12/1993 | Richards et al. | |
| 11,492,629 B2 * | 11/2022 | Jugulam | C12N 15/8261 |
| 2007/0092906 A1 | 4/2007 | Murphy et al. | |
| 2009/0053706 A1 | 2/2009 | Laird et al. | |
| 2013/0333061 A1 | 12/2013 | Wu et al. | |
| 2016/0177404 A1 | 6/2016 | McKernan | |

OTHER PUBLICATIONS

Feeney et al. Targeting mitotic chromosomes: a conserved mechanism to ensure viral genome persistence. Proc. Biol. Sci. May 7, 2009;276(1662):1535-44. Epub Jan. 20, 2009. (Year: 2009).*
Koo et al. Extrachromosomal circular DNA-based amplification and transmission of herbicide resistance in crop weed Amaranthus palmeri. Proc. Natl. Acad. Sci. USA. Mar. 27, 2018;115(13):3332-3337. Epub Mar. 12, 2018. (Year: 2018).*
Extended European Search Report corresponding to EP 20769382.1, mailed Nov. 18, 2022 (11 pages).
Amaranthus palmeri eccDNA replicon, complete sequence, Database Embl. XP002807893, retrieved from EBI accession No. EM_STD:MT025716, Database accession No. MT025716 (2020).
Beere, Helen M., et al., "Heat-shock protein 70 inhibits apoptosis by preventing recruitment of procaspase-9 to the Apaf-1 apoptosome", Nat Cell Biol 2, 2000, 469-475.
Bell, Stephen P., et al., "ATP-dependent recognition of eukaryotic origins of DNA replication by a multiprotein complex", Nature 357, 1992, 128-134.
Cohen, Sarit, et al., "Extrachromosomal Circular DNA of Tandemly Repeated Genomic Sequences in *Drosophila*", Genome Res 13, 2003, 1133-1145.
Duke, Stephen O., et al., "Glyphosate: a once-in-a-century herbicide", Pest Manag Sci 64, 2008, 319-325.
Eckdahl, Todd T., et al., "DNA structures associated with autonomously replicating sequences from plants", Plant Mol Biol 12, 1989, 507-516.
Feeney, Katherine M., et al., "Targeting mitotic chromosom s: a conserved mechanism to ensure viral genome persistence", Proc Biol Sci, 1662, 1535-1544.
Gaines, Todd A., et al., "Molecular mechanisms of adaptive evolution revealed by global selection for glyphosate resistance", New Phytologist. 223: 1770-1775 (2019).
Hegedus, Dwayne, et al., "Molecular characterization of *Brassica napus* NAC domain transcriptional activators induced in response to biotic and abiotic stress", Plant Mol Biol 53, 2003, 383-397.
Koo, Dal-Hoe, et al., "Distinct DNA methylation patterns associated with active and inactive centromeres of the maize B chromosome", Genome Res 21, 2011, 908-914.
Koo, Dal-Hoe, et al., "Gene duplication and aneuploidy trigger rapid evolution of herbicide resistance in common waterhemp", Plant Physiol, 2018, 1932-1938.
Lanciano, Sophie, et al., "Sequencing the extrachromosomal circular mobilome reveals retrotransposon activity in plants", PLoS Genet 13, 2017.
Lopez-Maury, Luis, et al., "Tuning gene expression to changing environments: from rapid responses to evolutionary adaptation", Nat Rev Genet 9, 2008, 583-593.
Lynch, Michael, et al., "The Evolutionary Fate and Consequences of Duplicate Genes", Science 290, 2000, 1151-1155.
Molin, William T., et al., "Autonomous replication sequences from the Amaranthus palmeri eccDNA replicon enable replication in yeast", BMC Res Notes, 2020.
Molin, William T., et al., "Homogeneity among glyphosate-resistant Amaranthus palmeri in geographically distant locations", PLoS One, 2020.
Molin, William T., et al., "The EccDNA Replicon: A Heritable, Extranuclear Vehicle That Enables Gene Amplification and Glyphosate Resistance in Amaranthus palmeri", The Plant Cell. 32: 2132-2140 ( 2020).

(Continued)

*Primary Examiner* — Cynthia E Collins
(74) *Attorney, Agent, or Firm* — Myers Bigel, P.A.

(57) ABSTRACT

The invention relates to a circular vector for plant transformation comprising: a first tethering nucleic acid and a second tethering nucleic acid; a nucleic acid encoding a polynucleotide of interest (POI); a nucleic acid comprising an origin of replication; and two or more nucleic acids encoding replicon proteins and methods for using the same. Also provided are plants produced by the methods of the invention and products produced from the plant.

22 Claims, 6 Drawing Sheets
Specification includes a Sequence Listing.

(56) References Cited

OTHER PUBLICATIONS

Molin, William T., et al., "The unique genomic landscape surrounding the EPSPS gene in glyphosate resistant Amaranthus palmeri: a repetitive path to resistance", BMC Genomics. 18:91 (2017).
Moller, Henrik D., et al., "Extrachromosomal circular DNA is common in yeast", P Natl Acad Sci USA 112, 2015, 3114-3122.
Saski, Christopher A., et al., "Sub genome anchored physical frameworks of the allotetraploid Upland cotton (*Gossypium hirsutum* L.) genome, and an approach toward reference-grade assemblies of polyploids". Sci Rep 7(1), 2017, 15274.
Sears, John, et al., "The Amino Terminus of Epstein-Barr Virus (EBV) Nuclear Antigen 1 Contains AT Hooks That Facilitate the Replication and Partitioning of Latent EBV Genomes by Tethering Them to Cellular Chromosomes", J Virol, 2004, 11487-11505.
Snyder, Michael, et al., "Bent DNA at a yeast autonomously replicating sequence", Nature 324, 1986, 87-89.
Stinchcomb, D.T., et al., "Isolation and characterisation of a yeast chromosomal replicator", Nature 282, 1979, 39-43.
Koo et al. "Extrachromosomal circular DNA-based amplification and transmission of herbicide resistance in crop weed Amaranthus palmeri" PNAS, 115(13):3332-3337 2018.
Written Opinion and International Search Report corresponding to PCT/US2020/021318 mailed Jul. 28, 2020 12 pages.

* cited by examiner

VECTOR FOR GENE TRANSFER AND GENE COPY PROLIFERATION

STATEMENT OF PRIORITY

This application claims the benefit, under 35 U.S.C. § 119 (e), of U.S. Provisional application No. 62/815,628 filed on Mar. 8, 2019, the entire contents of which is incorporated by reference herein.

STATEMENT REGARDING ELECTRONIC FILING OF A SEQUENCE LISTING

A Sequence Listing in ASCII text format, submitted under 37 C.F.R. § 1.821, entitled 9662-71WO_ST25.txt, 577,450 bytes in size, generated on Mar. 5, 2020 and filed via EFS-Web, is provided in lieu of a paper copy. This Sequence Listing is hereby incorporated herein by reference into the specification for its disclosures.

FIELD

The invention relates to a vector for plant transformation and methods for using the same.

BACKGROUND

Genomic plasticity and adaptation is common to all life forms. A detailed understanding of the complex link between the genome and the phenome that governs adapted traits is one of the grand challenges of biology, from weed science to cancer evolution. Knowledge of the biological mechanisms and regulatory factors of adaptation will be critical in the $21^{st}$ century in delivering stable and secure food, fuel, fiber, and health innovations to the growing population.

Gene duplications are perhaps among the oldest and most frequent sources of genetic diversity in all organismal species. Gene duplications are a signature of genomic adaptation and evolution, and can be triggered by selective pressures to endow or enhance phenotypes for organisms to survive and adapt to environmental perturbations (both subtle and extreme). Little is known about the molecular mechanisms by which certain genes amplify and proliferate in the genome.

Extrachromosomal DNAs (eccDNAs) are one form by which genes can become amplified. EccDNAs are an understudied fraction of the genome that are present across Kingdoms, and in limited reports, have been shown associate with biological functions in the cell, such as, maintenance of genome stability and cell aging, and proliferation of oncogenes that contribute to tumor evolution and genetic heterogeneity in cancers. The presence and conservation of eccDNAs across Kingdoms and aggressive disease states suggests a selective advantage and a fundamental biological role in the cell.

Previous reports of eccDNAs show they can range in size from a few kilobases in plants to nearly 40 kb in yeast, with only a small body of insight into how these elements form and exist in the cell. There is little to no evidence that describes how eccDNAs function, persist in the genome, and contribute to genome dynamics and the enhancement of existing traits or presentation of new traits.

Genome engineering through technologies such as Crispr-CAS9 hold the promise to deliver quantum leaps in genetically tailoring plants to ensure food, fuel, and fiber security. However, the current approaches are hindered by both off-target and genome integration difficulties. The present invention overcomes these shortcomings in the art by providing a novel plant based vector for plant genetic engineering.

SUMMARY

One aspect of the invention is a circular plant vector comprising: a first tethering nucleic acid and a second tethering nucleic acid; a nucleic acid encoding a polynucleotide of interest (POI); a nucleic acid comprising an origin of replication; and two or more nucleic acids encoding replicon proteins.

A second aspect of the invention is a method of expressing a polynucleotide of interest in a plant or part thereof, the method comprising introducing into the plant or part thereof the circular plant vector of the invention, and selecting a plant or part thereof expressing the polynucleotide of interest.

An third aspect is a method of modulating the expression a polynucleotide of interest in a plant cell, the method comprising introducing into a plant cell the circular plant vector of the invention to produce a transformed plant cell expressing the polynucleotide of interest.

A further aspect is a method of producing a plant cell expressing a polynucleotide of interest, the method comprising introducing into a plant cell the circular plant vector of the invention, thereby producing a plant cell comprising the polynucleotide of interest.

Also provided are plants, plant parts thereof including cells that comprise the vector of the invention as well as crops comprising the plants of the invention and products produced from the plants of the invention.

DETAILED DESCRIPTION

Figure 1:
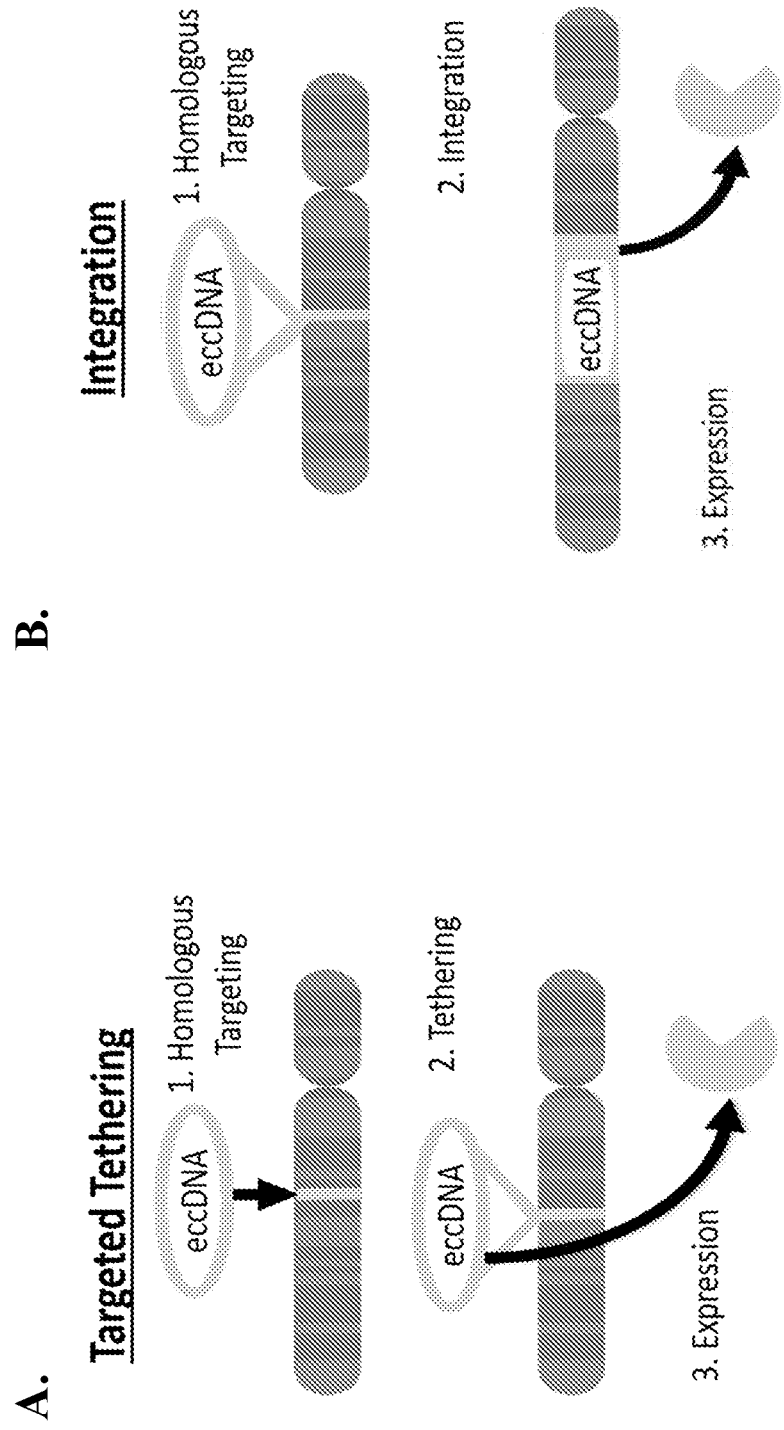
FIG. 1 provides a cartoon representation of unique tethering mechanism by which the eccDNA can tether to nuclear chromatin through a unique tethering mechanism (panel A) or tethering and nuclear integration into open chromatin (panel B) of a construct of the invention comprising eccDNA.

The present invention now will be described more fully hereinafter with reference to the accompanying drawings and examples, in which embodiments of the invention are shown. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention. All publications, patent applications, patents and other references cited herein are incorporated by reference in their entireties for the teachings relevant to the sentence and/or paragraph in which the reference is presented. In case of a conflict in terminology, the present specification is controlling.

Unless the context indicates otherwise, it is specifically intended that the various features of the invention described herein can be used in any combination. Moreover, the present invention also contemplates that in some embodiments of the invention, any feature or combination of features set forth herein can be excluded or omitted. To illustrate, if the specification states that a composition comprises components A, B and C, it is specifically intended that any of A, B or C, or a combination thereof, can be omitted and disclaimed singularly or in any combination.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present invention. The sequence of operations (or steps) is not limited to the order presented in the claims or figures unless specifically indicated otherwise.

As used in the description of the invention and the appended claims, the singular forms "a," "an" and "the" are intended to include the plural forms as well, unless the context clearly indicates otherwise.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount or concentration and the like, is meant to encompass variations of ±10%, ±5%, ±1%, ±0.5%, or even ±0.1% of the specified value as well as the specified value. For example, "about X" where X is the measurable value, is meant to include X as well as variations of ±10%, ±5%, ±1%, ±0.5%, or even ±0.1% of X. A range provided herein for a measureable value may include any other range and/or individual value therein.

As used herein, phrases such as "between X and Y" and "between about X and Y" should be interpreted to include X and Y. As used herein, phrases such as "between about X and Y" mean "between about X and about Y" and phrases such as "from about X to Y" mean "from about X to about Y."

The term "comprise," "comprises" and "comprising" as used herein, specify the presence of the stated features, integers, steps, operations, elements, and/or components, but do not preclude the presence or addition of one or more other features, integers, steps, operations, elements, components, and/or groups thereof.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

It will also be understood that, as used herein, the terms "example," "exemplary," and grammatical variations thereof are intended to refer to non-limiting examples and/or variant embodiments discussed herein, and are not intended to indicate preference for one or more embodiments discussed herein compared to one or more other embodiments.

As used herein, the terms "increase," "increasing," "increased," "enhance," "enhanced," "enhancing," and "enhancement" (and grammatical variations thereof) describe an elevation of at least about 25%, 50%, 75%, 100%, 150%, 200%, 300%, 400%, 500% or more as compared to a control.

As used herein, the terms "reduce," "reduced," "reducing," "reduction," "diminish," and "decrease" (and grammatical variations thereof), describe, for example, a decrease of at least about 5%, 10%, 15%, 20%, 25%, 35%, 50%, 75%, 80%, 85%, 90%, 95%, 97%, 98%, 99%, or 100% as compared to a control. In particular embodiments, the reduction can result in no or essentially no (i.e., an insignificant amount, e.g., less than about 10% or even 5%) detectable activity or amount.

A "heterologous" or a "recombinant" nucleic acid is a polynucleotide sequence not naturally associated with a host cell into which it is introduced, including non-naturally occurring multiple copies of a naturally occurring nucleotide sequence. As another example, the circular plant vector of the invention is a recombinant vector because it is non-naturally occurring and is therefore heterologous to any plant host into which it may be introduced.

A "native" or "wild type" nucleic acid, nucleotide sequence, polypeptide or amino acid sequence refers to a naturally occurring or endogenous nucleic acid, nucleotide sequence, polypeptide or amino acid sequence. Thus, for example, a "wild type mRNA" is an mRNA that is naturally occurring in or endogenous to the organism. A "endogenous" nucleic acid sequence is a nucleotide sequence naturally associated with a host cell into which it is introduced.

Also as used herein, the terms "nucleic acid," "nucleic acid molecule," "nucleotide sequence" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA, and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the term "nucleotide sequence" refers to a heteropolymer of nucleotides or the sequence of these nucleotides from the 5' to 3' end of a nucleic acid molecule and includes DNA or RNA molecules, including cDNA, a DNA fragment or portion, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Nucleic acid molecules and/or nucleotide sequences provided herein are presented herein in the 5' to 3' direction, from left to right and are represented using the standard code for representing the nucleotide characters as set forth in the U.S. sequence rules, 37 CFR §§ 1.821-1.825 and the World Intellectual Property Organization (WIPO) Standard ST.25, A "5' region" as used herein can mean the region of a polynucleotide that is nearest the 5' end. Thus, for example, an element in the 5' region of a polynucleotide can be located anywhere from the first nucleotide located at the 5' end of the polynucleotide to the nucleotide located halfway through the polynucleotide. A "3' region" as used herein can mean the region of a polynucleotide that is nearest the 3' end. Thus, for example, an element in the 3' region of a polynucleotide can be located anywhere from the first nucleotide located at the 3' end of the polynucleotide to the nucleotide located halfway through the polynucleotide.

As used herein, the term "gene" refers to a nucleic acid molecule capable of being used to produce mRNA, antisense RNA, miRNA, anti-microRNA antisense oligodeoxyribonucleotide (AMO) and the like. Genes may or may not be capable of being used to produce a functional protein or gene product. Genes can include both coding and non-coding regions (e.g., introns, regulatory elements, promoters, enhancers, termination sequences and/or 5' and 3' untranslated regions). A gene may be "isolated" by which is meant a nucleic acid that is substantially or essentially free from components normally found in association with the nucleic acid in its natural state. Such components include other cellular material, culture medium from recombinant production, and/or various chemicals used in chemically synthesizing the nucleic acid.

The terms "complementary" or "complementarity," as used herein, refer to the natural binding of polynucleotides under permissive salt and temperature conditions by base-pairing. For example, the sequence "A-G-T" binds to the complementary sequence "T-C-A." Complementarity between two single-stranded molecules may be "partial," in which only some of the nucleotides bind, or it may be complete when total complementarity exists between the single stranded molecules. The degree of complementarity between nucleic acid strands has significant effects on the efficiency and strength of hybridization between nucleic acid strands.

"Complement" as used herein can mean 100% complementarity or identity with the comparator nucleotide sequence or it can mean less than 100% complementarity (e.g., "substantial complementarity", e.g., about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like, complementarity).

A "portion" or "fragment" of a nucleotide sequence of the invention will be understood to mean a nucleotide sequence of reduced length relative (e.g., reduced by 1, 2, 3, 4, 5, 6, 7, 8, 9, 10, 11, 12, 13, 14, 15, 16, 17, 18, 19, 20 or more nucleotides) to a reference nucleic acid or nucleotide sequence and comprising, consisting essentially of and/or consisting of a nucleotide sequence of contiguous nucleotides identical or almost identical (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% identical) to the reference nucleic acid or nucleotide sequence. Such a nucleic acid fragment or portion according to the invention may be, where appropriate, included in a larger polynucleotide of which it is a constituent.

Different nucleic acids or proteins having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins. Thus, the compositions and methods of the invention further comprise homologues to the nucleotide sequences and polypeptide sequences of this invention. "Orthologous," as used herein, refers to homologous nucleotide sequences and/or amino acid sequences in different species that arose from a common ancestral gene during speciation. A homologue of a nucleotide sequence of this invention has a substantial sequence identity (e.g., at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100%) to said nucleotide sequence of the invention.

As used herein "sequence identity" refers to the extent to which two optimally aligned polynucleotide or peptide sequences are invariant throughout a window of alignment of components, e.g., nucleotides or amino acids. "Identity" can be readily calculated by known methods including, but not limited to, those described in: Computational Molecular Biology (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991).

As used herein, the term "percent sequence identity" or "percent identity" refers to the percentage of identical nucleotides in a linear polynucleotide sequence of a reference ("query") polynucleotide molecule (or its complementary strand) as compared to a test ("subject") polynucleotide molecule (or its complementary strand) when the two sequences are optimally aligned. In some embodiments, "percent identity" can refer to the percentage of identical amino acids in an amino acid sequence.

As used herein, the phrase "substantially identical," or "substantial identity" in the context of two nucleic acid molecules, nucleotide sequences or protein sequences, refers to two or more sequences or subsequences that have at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and/or 100% nucleotide or amino acid residue identity, when compared and aligned for maximum correspondence, as measured using one of the following sequence comparison algorithms or by visual inspection. In some embodiments, sequences may be substantially identical over the entire length of the coding regions. Furthermore, in some embodiments, substantially identical nucleotide or protein sequences perform substantially the same function (e.g., replicon proteins).

For sequence comparison, typically one sequence acts as a reference sequence to which test sequences are compared. When using a sequence comparison algorithm, test and reference sequences are entered into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and optionally by computerized implementations of these algorithms such as GAP, BESTFIT, FASTA, and TFASTA available as part of the GCG® Wisconsin Package® (Accelrys Inc., San Diego, CA). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction multiplied by 100. The comparison of one or more polynucleotide sequences may be to a full-length polynucleotide sequence or a portion thereof, or to a longer polynucleotide sequence. For purposes of this invention "percent identity" may also be determined using BLASTX version 2.0 for translated nucleotide sequences and BLASTN version 2.0 for polynucleotide sequences.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always $>0$) and N (penalty score for mismatching residues; always $<0$). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89: 10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleotide sequence to the reference nucleotide sequence is less than about 0.1 to less than about 0.001. Thus, in some embodiments of the invention, the smallest sum probability in a comparison of the test nucleotide sequence to the reference nucleotide sequence is less than about 0.001.

Two nucleotide sequences can also be considered to be substantially complementary when the two sequences hybridize to each other under stringent conditions. In some representative embodiments, two nucleotide sequences considered to be substantially complementary hybridize to each other under highly stringent conditions.

"Stringent hybridization conditions" and "stringent hybridization wash conditions" in the context of nucleic acid hybridization experiments such as Southern and Northern hybridizations are sequence dependent, and are different under different environmental parameters. An extensive guide to the hybridization of nucleic acids is found in *Tijssen Laboratory Techniques in Biochemistry and Molecular Biology-Hybridization with Nucleic Acid Probes* part I chapter 2 "Overview of principles of hybridization and the strategy of nucleic acid probe assays" Elsevier, New York (1993). Generally, highly stringent hybridization and wash conditions are selected to be about 5° C. lower than the thermal melting point ($T_m$) for the specific sequence at a defined ionic strength and pH.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleotide sequences which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example of a medium stringency wash for a duplex of, e.g., more than 100 nucleotides, is 1×SSC at 45° C. for 15 minutes. An example of a low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleotide sequences that do not hybridize to each other under stringent conditions are still substantially identical if the proteins that they encode are substantially identical. This can occur, for example, when a copy of a nucleotide sequence is created using the maximum codon degeneracy permitted by the genetic code.

The following are examples of sets of hybridization/wash conditions that may be used to clone homologous nucleotide sequences that are substantially identical to reference nucleotide sequences of the invention. In one embodiment, a reference nucleotide sequence hybridizes to the "test" nucleotide sequence in 7% sodium dodecyl sulfate (SDS), 0.5 M NaPO$_4$, 1 mM EDTA at 50° C. with washing in 2×SSC, 0.1% SDS at 50° C. In another embodiment, the reference nucleotide sequence hybridizes to the "test" nucleotide sequence in 7% sodium dodecyl sulfate (SDS), 0.5 M NaPO$_4$, 1 mM EDTA at 50° C. with washing in 1×SSC, 0.1% SDS at 50° C. or in 7% sodium dodecyl sulfate (SDS), 0.5 M NaPO$_4$, 1 mM EDTA at 50° C. with washing in 0.5×SSC, 0.1% SDS at 50° C. In still further embodiments, the reference nucleotide sequence hybridizes to the "test" nucleotide sequence in 7% sodium dodecyl sulfate (SDS), 0.5 M NaPO$_4$, 1 mM EDTA at 50° C. with washing in 0.1×SSC, 0.1% SDS at 50° C., or in 7% sodium dodecyl sulfate (SDS), 0.5 M NaPO$_4$, 1 mM EDTA at 50° C. with washing in 0.1X SSC, 0.1% SDS at 65° C.

In particular embodiments, a further indication that two nucleotide sequences or two polypeptide sequences are substantially identical can be that the protein encoded by the first nucleic acid is immunologically cross reactive with the protein encoded by the second nucleic acid.

Any nucleotide sequence and/or recombinant nucleic acid molecule of this invention can be codon optimized for expression in any organism of interest. Codon optimization is well known in the art and involves modification of a nucleotide sequence for codon usage bias using species specific codon usage tables. The codon usage tables are generated based on a sequence analysis of the most highly expressed genes for the organism/species of interest. When the nucleotide sequences are to be expressed in the nucleus, the codon usage tables are generated based on a sequence analysis of highly expressed nuclear genes for the species of interest. The modifications of the nucleotide sequences are determined by comparing the species specific codon usage table with the codons present in the native polynucleotide sequences. As is understood in the art, codon optimization of a nucleotide sequence results in a nucleotide sequence having less than 100% identity (e.g., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and the like) to the native nucleotide sequence but which still encodes a polypeptide having the same function as that encoded by the original, native nucleotide sequence. Thus, in representative embodiments of the invention, a nucleotide sequence such as SEQ ID NOs:3-8 or a polynucleotide of interest comprised in a vector of this invention may be codon optimized for expression in the particular plant species of interest.

In some embodiments, the nucleic acids, polynucleotides and polypeptides of the invention are "isolated." An "isolated" nucleic acid, an "isolated" polynucleotide or an "isolated" polypeptide is a nucleic acid, polynucleotide or polypeptide that, by the hand of man, exists apart from its native environment and is therefore not a product of nature. An isolated nucleic acid, polynucleotide or polypeptide may exist in a purified form that is at least partially separated from at least some of the other components of the naturally occurring organism or virus, for example, the cell or viral structural components or other polypeptides or nucleic acids commonly found associated with the nucleic acid, polynucleotide or polypeptide. In representative embodiments, the isolated nucleic acid, the isolated polynucleotide and/or the isolated polypeptide is at least about 1%, 5%, 10%, 20%, 30%, 40%, 50%, 60%, 70%, 80%, 90%, 95%, or more pure.

In other embodiments, an isolated nucleic acid, polynucleotide sequence or polypeptide may exist in a non-native environment such as, for example, a recombinant host cell. Thus, for example, with respect to nucleotide sequences, the term "isolated" means that it is separated from the chromosome and/or cell in which it naturally occurs. A polynucleotide is also isolated if it is separated from the chromosome and/or cell in which it naturally occurs in and is then inserted into a genetic context, a chromosome and/or a cell in which it does not naturally occur (e.g., a different host cell, different regulatory sequences, and/or different position in the genome than as found in nature). Accordingly, the nucleic acid, polynucleotides and their encoded polypeptides are "isolated" in that, by the hand of man, they exist apart from their native environment and therefore are not products of nature, however, in some embodiments, they can be introduced into and exist in a recombinant host cell.

By "operably linked" or "operably associated" as used herein, it is meant that the indicated elements are functionally related to each other, and are also generally physically related. Thus, the term "operably linked" or "operably associated" as used herein, refers to nucleotide sequences on a single nucleic acid molecule that are functionally associated. Thus, a first nucleic acid that is operably linked to a second nucleotide sequence, means a situation when the first nucleic acid is placed in a functional relationship with the second nucleic acid. For instance, a promoter is operably associated with a polynucleotide if the promoter effects the transcription or expression of said nucleotide sequence. Those skilled in the art will appreciate that the control sequences (e.g., promoter) need not be contiguous with the nucleotide sequence to which it is operably associated, as long as the control sequences function to direct the expression thereof. Thus, for example, intervening untranslated, yet transcribed, sequences can be present between a promoter and a polynucleotide, and the promoter can still be considered "operably linked" to the nucleotide sequence.

As used herein, "contact", contacting", "contacted," and grammatical variations thereof, refers to placing the components of a desired reaction together under conditions suitable for carrying out the desired reaction (e.g., transcriptional control, genome editing, nicking, cleavage, and/or amplifying nucleic acids).

Any plant (or groupings of plants, for example, into a genus or higher order classification) can be employed in practicing this invention including an angiosperm, a gymnosperm, a monocot, a dicot, a C3, C4, CAM plant, a microalgae, and/or a macroalgae. Thus, for example, types of plants useful with this invention may include woody, herbaceous, horticultural, agricultural, forestry, nursery, ornamental plant species and plant species useful in the production of biofuels, and combinations thereof.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell.

In some embodiments of this invention, a plant, plant part or plant cell can be from a genus including, but not limited to, the genus of *Camelina, Sorghum, Gossypium, Brassica, Allium, Armoracia, Poa, Agrostis, Lolium, Festuca, Calamogrostis, Deschampsia, Spinacia, Beta, Pisum, Chenopodium, Helianthus, Pastinaca, Daucus, Petroselium, Populus, Prunus, Castanea, Eucalyptus, Acer, Quercus, Salix, Juglans, Picea, Pinus, Abies, Lemna, Wolffia, Spirodela, Oryza* or *Gossypium*.

In additional embodiments, the plant, plant part or plant cell can be, but is not limited to, a plant of, or a plant part, or plant cell from wheat, barley, oats, turfgrass (bluegrass, bentgrass, ryegrass, fescue), feather reed grass, tufted hair grass, spinach, beets, chard, quinoa, sugar beets, lettuce, sunflower (*Helianthus annuus*), peas (*Pisum sativum*), parsnips (*Pastinaca sativa*), carrots (*Daucus carota*), parsley (*Petroselinum crispum*), duckweed, pine, spruce, fir, eucalyptus, oak, walnut, or willow. In some embodiments, a plant and/or part thereof useful with the invention may include, but is not limited to, *arabidopsis*, apple, tomato, pear, pepper (*Capsicum*), bean (e.g., green and dried), cucurbits (e.g., squash, cucumber, honeydew melon, watermelon, cantaloupe, and the like), papaya, mango, pineapple, avocado, stone fruits (e.g., plum, cherry, peach, apricot, nectarine, and the like), grape (wine and table), strawberry, raspberry, blueberry, mango, cranberry, gooseberry, banana, fig, citrus (e.g., clementine, kumquat, orange, grapefruit, tangerine, mandarin, lemon, lime, and the like), nuts (e.g., hazelnut, pistachio, walnut, macadamia, almond, pecan, and the like), lychee (*Litchi*), soybeans, corn, sugar cane, camelina, peanuts, cotton, canola, oilseed rape, sunflower, rapeseed, alfalfa, timothy, tobacco, tomato, sugarbeet, potato, pea, carrot, cereals (e.g., wheat, rice, barley, rye, millet, sorghum, oat, triticale, and the like), buckwheat, quinoa, turf, lettuce, roses, tulips, violets, basil, oil palm, elm, ash, oak, maple, fir, spruce, cedar, pine, birch, cypress, coffee, miscanthus, arundo, and/or switchgrass.

In nature, the eccDNA replicon confers the ability to a plant to sustain lethal amounts of the commonly used herbicide, glyphosate by way of massive gene amplification. The eccDNA replicon is a highly dynamic nucleic acid unit that evolved naturally in Palmer amaranth as an adaptive survival mechanism to rapidly increase gene copy number of the EPSPS gene in response to the herbicide glyphosate. Overexpression of the gene and its product of translation in Palmer amaranth confers resistance to glyphosate. While not wishing to be limited to any particular theory, the genesis of the replicon may be connected to repeated glyphosate applications. However, the replicon is stable and persists across generations without fitness penalty to the plant, and may be transferred to related plant species through hybridization. Copy numbers of the EPSPS replicon in resistant Palmer amaranth may be 100-fold higher than in sensitive plants.

The eccDNA replicon is a segment of DNA having a size of about 399 kb (SEQ ID NO:20), which is present in a circular form in the extra-nuclear space in resistant pigweed, and contains 59 predicted genes with functional signatures that may endow critical cellular processes necessary for stress avoidance, maintenance, stability, replication, and tethering of the eccDNA replicon. Encoded in the replicon are single copies of two prominent genes one for EPSPS and another for a reverse transcriptase. Expression of the reverse transcriptase is greater by about four times that of EPSPS. The amplicon contains many other gene fragments and repeat sequences. The EPSPS replicon sequence in resistant plants is not contiguous in the sensitive plants, indicating that the cassette is the product of fast adaptive evolution, derived from repeated transpositions over time. Natural hybridization between Palmer amaranth and spiny amaranth has resulted in transfer of the extra nuclear replicon into hybrid offspring with expression of glyphosate resistance traits, which indicates the unit is heritable and compatible between species.

The eccDNA element is a large, about 399 kb, plasmid-like structure that can exist outside of the chromosomes (termed herein as the eccDNA replicon). We have identified and sequenced this element to reveal very unique findings such as the putative ability to autonomously replicate and the discovery of an encoded copy of the EPSPS gene and other transcriptionally active genes that may be involved in extreme detoxification, transport, stress avoidance, and recombination. Interestingly, the presence and maintenance of the eccDNA replicon does not seem to endow a fitness penalty, suggesting a crucial evolved biological role. In fact, this unit may even endow a fitness boost, or even confer a global increase in abiotic stress resilience. Furthermore, we have found that the eccDNA replicon is stable across generations, and traits (glyphosate resistance) can be transferred to other plant species by hybridization (e.g., *Amaranthus palmeri* and *Amaranthus spinosa*), suggesting potential breakthrough uses as new ways to transfer and amplify DNA for trait enhancement. The repetitive content and the clustered palindromes that flank the EPSPS gene are also likely to yield additional structural and functional insights.

The present invention is directed to constructs utilizing elements of "eccDNA replicon" or "eccDNA element" in unique and non-natural configurations as a circular vector for use in genome modification in plants. Thus, in some embodiments, constructs or vectors of the invention may be provided as extranuclear plasmids engineered to amplify or introduce genes and biochemical pathways of choice into plants of interest, such as crop plants. Thus, in some embodiments, a plant vector of this invention may be tethered to the genome and not integrate into the genome, tethered or associated with the genome similar to the eccDNA element (FIG. 1, panel A). In some embodiments, a plant vector of this invention may be integrated into the chromosome (FIG. 1, panel B). In some embodiments, a plant vector of this invention is circular and self-replicating.

Polynucleotides suitable for use with this invention include those associated with association or tethering of extra-circularDNA (eccDNA) molecules to the nuclear chromosomes as a means to provide genomic persistence during cell division and to maintain the claimed circular vector in the plant germ line. Such polynucleotides may also include histone-binding and non-histone binding DNA association protein complexes and those that encode reporter polypeptides (e.g., an enzyme), including but not limited to, Green Fluorescent Protein, Red Fluorescent Protein, β-galactosidase, luciferase, alkaline phosphatase, and/or β-glucuronidase (GUS) as well as polynucleotides comprising origin of replication that can functions to facilitate target gene copy amplification.

Thus, in some embodiments, the present invention provides a circular plant vector comprising a first tethering nucleic acid and a second tethering nucleic acid; a nucleic acid encoding a polynucleotide of interest (POI); a nucleic acid comprising an origin of replication; and two or more nucleic acids encoding replicon proteins.

The term "replicon protein" as used herein, for the constructs of the invention means any protein that assists in the replication, tethering and maintenance (e.g., maintenance in the germ line of the plant, plant part or plant cell) of the vector and the POI (transgene).

In some embodiments, a first tethering nucleic acid may comprises a sequence having at least 90% sequence identity (e.g., 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% identity) to the nucleotide sequence of SEQ ID NO:1; the second tethering nucleic acid comprises a sequence having at least 90% sequence identity to the nucleotide sequence of SEQ ID NO:2; the nucleic acid comprising an origin of replication comprises a sequence having at least 90% sequence identity to the nucleotide sequence of SEQ ID NO:9; and the two or more nucleic acids encoding replicon proteins comprises sequences having at least 80% sequence identity (e.g., 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9% or 100% identity) to any one or more of the nucleotide sequences of SEQ ID NO:3-8, in any combination. In some embodiments, a circular plant vector of this invention may comprise, 5' to 3', the first tethering nucleic acid, a first nucleic acid encoding a replicon protein; the second tethering nucleic acid, a second nucleic acid encoding a replicon protein, and the nucleic acid comprising an origin of replication. In some embodiments, the circular plant vector may further comprise, 5' to 3', a third nucleic acid encoding a replicon protein, a fourth nucleic acid encoding a replicon protein, a fifth nucleic acid encoding a replicon protein, a sixth nucleic acid encoding a replicon protein, and a seventh nucleic acid encoding a replicon protein which are located between the second nucleic acid encoding a replicon protein and the nucleic acid comprising an origin of replication.

In some embodiments, a circular plant vector of the invention comprises, 5' to 3', a first tethering nucleic acid having the nucleotide sequence of SEQ ID NO:1; a nucleic acid encoding a polynucleotide of interest (POI); a first nucleic acid encoding a replicon protein having the nucleotide sequence of any one of SEQ ID NOs:3-8; a second tethering nucleic acid having the nucleotide sequence of SEQ ID NO:2; a third nucleic acid encoding a replicon protein having the nucleotide sequence of any one of SEQ ID NOs:3-8; a fourth nucleic acid encoding a replicon protein having the nucleotide sequence of any one of SEQ ID NOs:3-8; a fifth nucleic acid encoding a replicon protein having the nucleotide sequence of any one of SEQ ID NOs:3-8; a sixth nucleic acid encoding a replicon protein having the nucleotide sequence of any one of SEQ ID NOs:3-8; a seventh nucleic acid encoding a replicon protein having the nucleotide sequence of any one of SEQ ID NOs:3-8; and a nucleic acid comprising an origin of replication having the nucleotide sequence of SEQ ID NO: 9.

In some embodiments, a circular plant vector of the invention may comprise, 5' to 3', a first tethering nucleic acid having the nucleotide sequence of SEQ ID NO:1; a nucleic acid encoding a polynucleotide of interest (POI); a first nucleic acid encoding a replicon protein having the nucleotide sequence of SEQ ID NO:3 [AP_R.00g000200]; a second tethering nucleic acid having the nucleotide sequence of SEQ ID NO:2; a second nucleic acid encoding a replicon protein having the nucleotide sequence of SEQ ID NO:3 [AP_R.00g000250]; a third nucleic acid encoding a replicon protein having the nucleotide sequence of SEQ ID NO:4 [AP_R.00g000493]; a fourth nucleic acid encoding a replicon protein having the nucleotide sequence of SEQ ID NO:5 [AP_R.00g000494]; a fifth nucleic acid encoding a replicon protein having the nucleotide sequence of SEQ ID NO:6 [AP_R.00g000430]; a sixth nucleic acid encoding a replicon protein having the nucleotide sequence of SEQ ID NO:7 [AP_R.00g000496]; a seventh nucleic acid encoding a replicon protein having the nucleotide sequence of SEQ ID NO:8 [AP_R.00g000450]; and a nucleic acid comprising an origin of replication having the nucleotide sequence of SEQ ID NO: 9.

In some embodiments, the one or more nucleic acids of the vector of this invention, e.g., the first tethering nucleic acid, the second tethering nucleic acid, the nucleic acid encoding a polynucleotide of interest (POI), the nucleic acid comprising an origin of replication, and/or the two or more nucleic acids encoding replicon proteins, may be linked to one another directly or may be linked via one or more linkers (e.g, 1, 2, 3, 4, 5, or more), or any combination thereof. In some embodiments, two or more linker polynucleotides may be used in tandem to separate the nucleic acids comprised in the vector of the invention, e.g., the first tethering nucleic acid, the second tethering nucleic acid; the nucleic acid encoding a polynucleotide of interest (POI); the nucleic acid comprising an origin of replication; and/or the two or more nucleic acids encoding replicon proteins.

A linker for use in separating two or more of the nucleic acids of the vector of the invention may be composed of any set of consecutive nucleotides that allow the replication of the vector and expression of the POI. In some embodiments, a linker useful with this invention may have a length in a range from about 10 nucleotides to about 120 nucleotides or more (e.g., about 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 or more nucleotides in length, or more or any range or value therein; e.g., about 10 nucleotides to about 40 nucleotides, about 10 nucleotides to about 50 nucleotides, about 10 nucleotides to about 80 nucleotides, about 10 nucleotides to about 100 nucleotides, about 20 nucleotides to about 50 nucleotides, about 20 nucleotides to about 70 nucleotides, about 20 nucleotides to about 80 nucleotides, about 20 nucleotides to about 100 nucleotides, about 20 nucleotides to about 110 nucleotides, about 20 nucleotides to about 120 nucleotides, about 30 nucleotides to about 50 nucleotides, about 30 nucleotides to about 60 nucleotides, about 30 nucleotides to about 80 nucleotides, about 30 nucleotides to about 100 nucleotides, about 30 nucleotides to about 110 nucleotides, about 30 nucleotides to about 120 nucleotides, about 40 nucleotides to about 80 nucleotides, about 40 nucleotides to about 100 nucleotides, about 40 nucleotides to about 110 nucleotides, about 40 nucleotides to about 120 nucleotides, about 50 nucleotides to about 100 nucleotides, about 50 nucleotides to about 110 nucleotides, or about 50 nucleotides to about 120 nucleotides). In some embodiments, a linker useful with this invention may comprise, for example, a nucleotide sequence any one or more of SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, and/or SEQ ID NO:19.

When more than one linker (e.g., 2, 3, 4, 5, 6, 7, 8, 9, 10, or more linkers) is used to link the nucleic acids of a vector of the invention, the linkers may all be the same linker or the linkers may different from one another, or any combination thereof (e.g., some linkers may be the same as one another and others may be different).

In some embodiments, a circular plant vector of the invention may comprise a first tethering nucleic acid linked via a first linker to a nucleic acid encoding a polynucleotide of interest (POI); the nucleic acid encoding a polynucleotide of interest (POI) linked via a second linker to a first nucleic acid encoding a replicon protein; the first nucleic acid encoding a replicon protein linked via third linker to a second tethering nucleic acid; the second tethering nucleic acid linked via a fourth linker to a second nucleic acid encoding a replicon protein; the second nucleic acid encoding a replicon protein linked via a fifth linker to a third nucleic acid encoding a replicon protein; the third nucleic acid encoding a replicon protein linked directly to a fourth nucleic acid encoding a replicon protein; the fourth nucleic acid encoding a replicon protein linked via a sixth linker to a fifth nucleic acid encoding a replicon protein; the fifth nucleic acid encoding a replicon protein linked via a seventh linker to a sixth nucleic acid encoding a replicon protein; the sixth nucleic acid encoding a replicon protein linked via an eighth linker to a seventh nucleic acid encoding a replicon protein; the seventh nucleic acid encoding a replicon protein linked via a ninth linker to a nucleic acid comprising an origin of replication; and the nucleic acid comprising an origin of replication is linked via an tenth linker to the first tethering nucleic acid. In some embodiments, a linker that allows a vector of this invention to replicate and the polynucleotide of interest comprised there to be expressed may be any nucleotide sequence having a length of about 10 nucleotides to about 120 nucleotides. In some embodiments, each of the first linker, second linker, third linker, fourth linker, fifth linker, sixth linker, seventh linker, eighth linker, ninth linker, and tenth linker comprise a nucleotide sequence of any one of SEQ ID NOs:10-19, in any combination, or each of the linkers may comprise any two or more of the nucleotide sequences of any one of SEQ ID NOs:10-19, in any combination (e.g., two or more linker polynucleotides in tandem). In some embodiments, the first linker is SEQ ID NO:10, the second linker is SEQ ID NO:11, the third linker is SEQ ID NO:12 or SEQ ID NO:13, the fourth linker is SEQ ID NO:10 or SEQ ID NO:11, the fifth linker is SEQ ID NO:12 or SEQ ID NO:14, the sixth linker is SEQ ID NO:15, the seventh linker is SEQ ID NO:16, the eighth linker is SEQ ID NO:17 or SEQ ID NO:18, the ninth linker is SEQ ID NO:19 and the tenth linker is any one or more of the nucleotide sequences of SEQ ID NOs:10-19.

A circular plant vector of the invention may comprise one or more polynucleotides of interest (POIs) (e.g., 1, 2, 3, 4, 5, 6, 7, 8, 9, 10, or more POI). A polynucleotide of interest may be any polynucleotide that imparts a desirable agronomic trait to the plant into which it is introduced. A polynucleotide of interest may encode a polypeptide that imparts a desirable agronomic trait to the plant or may confer such traits as male sterility, or may improve fertility and/or nutritional quality. Other suitable polypeptides include enzymes that degrade organic pollutants or remove heavy metals. Such plants, and the enzymes that can be isolated therefrom, are useful in methods of environmental protection and remediation. Alternatively, the heterologous nucleotide sequence can encode a therapeutically or pharmaceutically useful polypeptide or an industrial polypeptide (e.g., an industrial enzyme). Therapeutic polypeptides include, but are not limited to antibodies and antibody fragments, cytokines, hormones, growth factors, receptors, enzymes and the like.

Additional non-limiting examples of polynucleotides of interest that are suitable for use with this invention (e.g., to be expressed in response to exposure to nitrate, drought, and/or rehydration) include polynucleotides associated with nutrient uptake including transport and assimilation of organic and inorganic nutrients. Thus, for example, polynucleotides encoding polypeptides involved in nitrogen transport and assimilation, including but not limited to, nitrite transporter (NiTR1 gene), high affinity nitrate transporter, nitrate and chloride transporter, nitrate reductase (nr2), NADH-dependent nitrate reductase, oligopeptide and nitrate transporter, ammonium transporter (Osamt1.1; 1.3; 2.2; 3.1; 5.1), nitrate transporter (Atntl 1), symbiotic ammonium transporter, ammonium transporter, NADH-dependent glutamate synthase, nitrate transporter, ammonium transporter (Osamt1.1; 5.2), high affinity nitrate transporter (nar2.1), gln4, gl5, nitrate transporter (nrt1.1), amino acid transport protein, NADH-dependent nitrate reductase (nr1), nitrate transporter (nrt1-5), ammonium transporter (Osamt2.1; 2.3; 3.3), high affinity nitrate transporter (nar2.1; nar2.2), nitrate transporter (Glycine max nrt1.2), ferredoxin-dependent glutamate synthase, and/or high affinity nitrate transporter (nrt2.1)

Other non-limiting examples of polynucleotides of interest include those involved in resistance to insects, nematodes and pathogenic diseases. Such may encode polypeptides that include, but are not limited to, glucosinolates (defense against herbivores), chitinases or glucanases and other enzymes which destroy the cell wall of parasites, ribosome-inactivating proteins (RIPs) and other proteins of the plant resistance and stress reaction as are induced when plants are wounded or attacked by microbes, or chemically, by, for example, salicylic acid, jasmonic acid or ethylene, or lysozymes from nonplant sources such as, for example, T4-lysozyme or lysozyme from a variety of mammals, insecticidal proteins such as *Bacillus thuringiensis* endotoxin, a-amylase inhibitor or protease inhibitors (cowpea trypsin inhibitor), lectins such as wheatgerm agglutinin, RNAses or ribozymes. Further non-limiting examples include nucleic acids which encode the *Trichoderma harzianum* chit42 endochitinase (GenBank Ace. No. S78423) or the N-hydroxylating, multi-functional cytochrome P-450 (CYP79) protein from *Sorghum bicolor* (GenBank Acc. No. U32624), or functional equivalents of these, chitinases, for example from beans (Brogue et al. (1991) Science 254: 1194-1197), "polygalacturonase-inhibiting protein" (PGIP), thaumatine, invertase and antimicrobial peptides such as lactoferrin (Lee T J et al. (2002) *J Amer Soc Horticult Sci* 127(2):158-164) (See, e.g., U.S. Pat. No. 8,071,749) as well as the plant defense genes, including but not limited to, PR1, BG2, PR5, and NPR1 (or NIM1).

Also useful with the present invention are polynucleotides encoding polypeptides involved in plant hormone production or signaling including, but not limited to, auxins, cytokinins, gibberellins, strigolactones, ethylene, jasmonic acid, and brassinosteroids, as well as other polynucleotide and polypeptide sequences that regulate or effect root and leaf growth and development. Non-limiting examples of such polynucleotide and/or polypeptide sequences include GA-Deficient-1 (GA1; CPS), Gibberellin 20-Oxidase (GA20ox, GA5 (in At)), Gibberellin 2-beta-dioxygenase (GA2ox), Gibberellin 3-Oxidase (GA3ox), GA-Insensitive (GAI), GA Regulated MYB(GAMYB), GCA2 Growth Controlled By ABA 2 (GCA2), G-Protein Coupled Receptor (GCR1), Glycosyl Hydrolase Family-45 (GH45), tryptophan synthase alpha chain (e.g.,GRMZM2G046163, GRMZM2G015892), Auxin Binding Protein 1 (ABP1), IAA-amino acid hydrolase ILR1 (e.g., GRMZM2G091540), phosphoribosylanthranilate transferase, Indole Acetic Acid 17/Auxin Resistant 3(IAA17, AXR3), Indole Acetic Acid 3/Short Hypocotyl (IAA3, SHY2), IAA-lysine synthetase (iaaL), tryptophan monooxygenase (iaaM), IAA-Aspartic Acid Hydrolase (IaaspH), IAA-Glucose Synthase (IAGLU), IndoleAcetamide Hydrolase (IAH), Indole-3-Acetaldehyde Oxidase (IAO), IAA-ModifiedProtein (IAP1), Auxin Response factors (ARFs), small auxin up RNA (SAUR), Induced By Cytokinin 6 (Same as ARR5)(IBC6), Induced By Cytokinin 7 (Same as ARR4) IBC7, Viviparous-14 (Vp14), PLA$_2$ (Zhu J-K. *Annual Review of Plant Biology* 2002, 53(1):247-273), ATPLC2 (Benschop et al. *Plant Physiology* 2007, 143(2):1013-1023), inositol polyphosphate 5-phosphatase (At5PTaseI), calcium-dependent protein kinases (CDPKs), calcineurin B-like (CBL) calcium sensor protein CBL4/S0S3, CIPK-like protein 1, ACC (1-aminocyclopropane-1-carboxylate) synthase, ACC oxidase, phosphatase 2C ABI1, TINY, maize lipoxygenase 7 (GRMZM2G070092), allene oxide synthase (AOS) (e.g., GRMZM2G033098 and GRMZM2G376661), short chain alcohol dehydrogenases (ADH), Tasselseed2 (Ts2), Tasselseed1 (Ts1), Supercentipede1 (Scn1/GDI1, e.g., AT2G44100), RDH2 (Carol et al. *Nature* 2005, 438(7070): 1013-1016.), G-signaling proteins, *Morphogenesis of Root Hair* (MRH), AtAGC2-1 (e.g., At3g25250), Cellulose Synthase-Like D3 (CSLD3), xylosyltransferase 2 (e.g., At4g02500, AtXX2), xyloglucan endotransglucosylase/hydrolase 26 (e.g., AtXTH26, At4g28850), xyloglucan endotransglycosylase, xyloglucan galact-osyltransferase (MUR3 (e.g., AT2G20370), ARP2/3 (WURM/DISTORTED 1) complex, and germin-like protein (e.g., AT5G39110).

Other polynucleotides and polypeptides suitable for use with the present invention include those that confer the "stay-green" phenotype (See, Hortensteiner, S. *Trends in Plant Science* 14: 155-162 (2009)). Non-limiting examples of such nucleotide sequences include MtSGR, MsSGR (Zhou et al. *Plant Physiol.* 157: 1483-1496 (2011)), STAY-GREEN (SGR or SGN) (Jiang et al., *Plant J* 52: 197-209 (2007)), Park et al., *Plant Cell* 19: 1649-1664 (2007)), NONYELLOWING (NYEJ) (Ren et al., *Plant Physiol* 144: 1429-1441 (2007)), and/or GREEN-FLESH (GF) or CHLOROPHYLL RETAINER (CL) (Barry et al., *Plant Physiol* 147: 179-187 (2008)).

Polynucleotides involved in grain filling are also useful with the present invention and include, but are not limited to GIF1 (GRAIN INCOMPLETE FILLING 1) from rice.

Other non-limiting examples of polynulcoetides of interest that are suitable for production in plants include those resulting in agronomically important traits such as herbicide resistance (also sometimes referred to as "herbicide tolerance"), virus resistance, bacterial pathogen resistance, insect resistance, nematode resistance, and/or fungal resistance. See, e.g., U.S. Pat. Nos. 5,569,823; 5,304,730; 5,495,071; 6,329,504; and 6,337,431. The polynucleotide also can be one that confers increased plant vigor or yield (including traits that allow a plant to grow at different temperatures, soil conditions and levels of sunlight and precipitation), or one that allows identification of a plant exhibiting a trait of interest (e.g., a selectable marker, seed coat color, eta). Various polynucleottides of interest, as well as methods for introducing these polypeptides into a plant, are described, for example, in U.S. Pat. Nos. 4,761,373; 4,769,061; 4,810, 648; 4,940,835; 4,975,374; 5,013,659; 5,162,602; 5,276, 268; 5,304,730; 5,495,071; 5,554,798; 5,561,236; 5,569, 823; 5,767,366; 5,879,903, 5,928,937; 6,084,155; 6,329,504 and 6,337,431; as well as US Patent Publication No. 2001/ 0016956. See also, on the World Wide Web at lifesci.sussex.ac.uk/home/Neil_Crickmore/Bt/.

Polynucleotides conferring resistance/tolerance to an herbicide that inhibits the growing point or meristem, such as an imidazalinone or a sulfonylurea can also be suitable in some embodiments of the invention. Exemplary nucleotide sequences in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

In some embodiments, a polynucleotide may increase tolerance of a plant, plant part and/or plant cell to heat stress and/or high temperature. The polynucleotide may encode a polypeptide or inhibitory polynucleotide (e.g., functional RNA) that results in increased tolerance to heat stress and/or high temperature. Suitable polynucleotides include without limitation polynucleotides encoding water stress polypeptides, ABA receptors, and dehydration proteins (e.g., dehydrins (ERDs)).

In some embodiments, polynucleotides that encode polypeptides that provide tolerance to water stress (e.g., drought) may be incorporated into a vector of this invention and transformed into a plant as described herein. Non-limiting examples of polypeptides that provide tolerance to water stress include: water channel proteins involved in the movement of water through membranes; enzymes required for the biosynthesis of various osmoprotectants (e.g., sugars, proline, and Glycine-betaine); proteins that protect macromolecules and membranes (e.g., LEA protein, osmotin, antifreeze protein, chaperone and mRNA binding proteins); proteases for protein turnover (thiol proteases, Clp protease and ubiquitin); and detoxification enzymes (e.g., glutathione S-transferase, soluble epoxide hydrolase, catalase, superoxide dismutase and ascorbate peroxidase). Non-limiting examples of proteins involved in the regulation of signal transduction and gene expression in response to water stress include protein kinases (MAPK, MAPKKK, S6K, CDPK, two-component His kinase, Bacterial-type sensory kinase and SNF1); transcription factors (e.g., MYC and bZIP); phospholipase C; and 14-3-3 proteins.

Polynucleotide sequences that encode receptors/binding proteins for abscisic acid (ABA) are also useful in the practice of the present invention. Non-limiting examples of ABA binding proteins/receptors include: the Mg-chelatase H subunit; RNA-binding protein FCA; G-protein coupled receptor GCR2; PYR1; PYLS; protein phosphatases 2C ABI1 and ABI2; and proteins of the RCAR (Regulatory Component of the ABA Receptor) family.

In some embodiments, a polynucleotide sequence may encode a dehydration protein, also known as a dehydrin (e.g., an ERD). Dehyration proteins are a group of proteins known to accumulate in plants in response to dehydration. Examples include WCOR410 from wheat; PCA60 from peach; DHN3 from sessile oak, COR47 from *Arabidopsis thaliana*; Hsp90, BN59, BN115 and Bnerd10 from *Brassica napus*; COR39 and WCS19 from *Triticum aestivum* (bread wheat); and COR25 from *Brassica rapa* subsp. *Pekinensis*. Other examples of dehydration proteins are ERD proteins, which include without limitation, ERD1, ERD2, ERD4, ERD5, ERD6, ERD8, ERD10, ERD11, ERD13, ERD15 and ERD16.

Polynucleotide sequences conferring resistance to glyphosate are also suitable for use with the present invention. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene. Heterologous polynucleotides suitable to confer tolerance to the herbicide glyphosate also include, but are not limited to the *Agrobacterium* strain CP4 glyphosate resistant EPSPS gene (aroA:CP4) as described in U.S. Pat. No. 5,633,435 or the glyphosate oxidoreductase gene (GOX) as described in U.S. Pat. No. 5,463,175. Other heterologous polynucleotides include genes conferring resistance to herbicides that act to inhibit the action of acetolactate synthase (ALS), in particular the sulfonylurea-type herbicides (e.g., mutant forms of the acetolactate synthase (ALS) gene that lead to such resistance, in particular the S4 and/or Hra mutations), genes coding for resistance to herbicides that act to inhibit the action of glutamine synthase, such as phosphinothricin or basta (e.g., the bar gene). The bar gene encodes resistance to the herbicide basta, the nptII gene encodes resistance to the antibiotics kanamycin and geneticin, and the ALS gene encodes resistance to the herbicide chlorsulfuron.

Polynucleotide sequences coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides of interest include those coding for resistance to herbicides that inhibit photosynthesis, such as a triazine and a benzonitrile (nitrilase). See, U.S. Pat. No. 4,810,648. Additional suitable nucleotide sequences coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotide sequences conferring resistance to a protox enzyme, or that provide enhanced resistance to plant diseases; enhanced tolerance of adverse environmental conditions (abiotic stresses) including but not limited to drought, heat stress, high temperature, cold, excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Insecticidal proteins useful in the invention may be produced in an amount sufficient to control insect pests, i.e., insect controlling amounts. It is recognized that the amount of production of insecticidal protein in a plant useful to control insects may vary depending upon the cultivar, type of insect, environmental factors and the like. Suitable heterologous polynucleotides that confer insect tolerance include those which provide resistance to pests such as rootworm, cutworm, European Corn Borer, and the like. Exemplary nucleotide sequences include, but are not limited to, those that encode toxins identified in *Bacillus* organisms (see, e.g., WO 99/31248; U.S. Pat. Nos. 5,689,052; 5,500,365; 5,880,275); *Bacillus thuringiensis* toxic protein genes (see, e.g., U.S. Pat. Nos. 5,366,892; 5,747,450; 5,737,514; 5,723,756; 5,593,881; 6,555,655; 6,541,448; 6,538,109; Geiser, et al. (1986) Gene 48:109); and lectins (Van Damme et al. (1994) Plant Mol. Biol. 24:825). Polynucleotide sequences encoding *Bacillus thuringiensis* (Bt) toxins from several subspecies have been cloned and recombinant clones have been found to be toxic to lepidopteran, dipteran and coleopteran insect larvae (for example, various delta-endotoxin genes such as Cry1Aa, Cry1Ab, Cry1Ac, Cry1B, Cry1C, Cry1D, Cry1Ea, Cry1 Fa, Cry3A, Cry9A, Cry9C and Cry9B; as well as genes encoding vegetative insecticidal proteins such as Vip1, Vip2 and Vip3). A full list of Bt toxins can be found on the worldwide web at *Bacillus thuringiensis*

Toxin Nomenclature Database maintained by the University of Sussex (see also, Crickmore et al. (1998) *Microbiol. Mol. Biol. Rev.* 62:807-813).

Polynucleotides encoding polypeptides that are suitable for production in plants further include those that improve or otherwise facilitate the conversion of harvested plants and/or plant parts into a commercially useful product, including, for example, increased or altered carbohydrate content and/or distribution, improved fermentation properties, increased oil content, increased protein content, improved digestibility, and increased nutraceutical content, e.g., increased phytosterol content, increased tocopherol content, increased stanol content and/or increased vitamin content. Polynucleotides of interest may also include, for example, those resulting in, or contributing to, a reduced content of an unwanted component in a harvested crop, e.g., phytic acid, or sugar degrading enzymes. By "resulting in" or "contributing to" is intended that the polynucleotide of interest can directly or indirectly contribute to the existence of a trait of interest (e.g., increasing cellulose degradation by the use of a heterologous cellulase enzyme).

In some embodiments, a polynucleotide of interest may contribute to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced by xylanases. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) *Foundation for Biotechnical and Industrial Fermentation Research* 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) *Appl. Microbiol. Biotechnol.* 49:718).

In some embodiments, a polynucleotide useful with the present invention can be a polysaccharide degrading enzyme. Plants producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme or other glucoamylases.

Polysaccharide-degrading enzymes include: starch degrading enzymes such as alpha-amylases (EC 3.2.1.1), glucuronidases (E.C. 3.2.1.131), exo-1,4-alpha-D glucanases such as amyloglucosidases and glucoamylase (EC 3.2.1.3), beta-amylases (EC 3.2.1.2), alpha-glucosidases (EC 3.2.1.20), and other exo-amylases, starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-beta-D-glucanase (EC 3.2.1.39), beta-glucosidase (EC 3.2.1.21); c) L-arabinases, such as endo-1,5-alpha-L-arabinase (EC 3.2.1.99), alpha-arabinosidases (EC 3.2.1.55) and the like; d) galactanases such as endo-1,4-beta-D-galactanase (EC 3.2.1.89), endo-1,3-beta-D-galactanase (EC 3.2.1.90), alpha-galactosidase (EC 3.2.1.22), beta-galactosidase (EC 3.2.1.23) and the like; e) mannanases, such as endo-1,4-beta-D-mannanase (EC 3.2.1.78), beta-mannosidase (EC 3.2.1.25), alpha-mannosidase (EC 3.2.1.24) and the like; f) xylanases, such as endo-1,4-beta-xylanase (EC 3.2.1.8), beta-D-xylosidase (EC 3.2.1.37), 1,3-beta-D-xylanase, and the like; and g) other enzymes such as alpha-L-fucosidase (EC 3.2.1.51), alpha-L-rhamnosidase (EC 3.2.1.40), levanase (EC 3.2.1.65), inulanase (EC 3.2.1.7), and the like.

Further polynucleotides that encode enzymes which may be used with the present invention include those that encode proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*.

Other useful enzymes include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); cellobiohydrolases; esterases such as ferulic acid esterase (EC 3.1.1.73) and acetyl xylan esterases (EC 3.1.1.72); and cutinases (e.g. E.C. 3.1.1.74).

A polynucleotide of interest may also encode a reporter polypeptide (e.g., an enzyme) or selectable marker, including but not limited to Green Fluorescent Protein, β-galactosidase, luciferase, alkaline phosphatase, the GUS gene encoding β-glucuronidase, and chloramphenicol acetyltransferase. Further examples of selectable markers include, but are not limited to, a nucleotide sequence encoding aadA (i.e., spectinomycin and streptomycin resistance), a nucleotide sequence encoding neo (i.e., kanamycin resistance), a nucleotide sequence encoding aphA6 (i.e., kanamycin resistance), a nucleotide sequence encoding nptII (i.e., kanamycin resistance), a nucleotide sequence encoding bar (i.e., phosphinothricin resistance), a nucleotide sequence encoding cat (i.e., chloramphenicol resistance), a nucleotide sequence encoding badh (i.e., betaine aldehyde resistance), a nucleotide sequence encoding egfp, (i.e., enhanced green fluorescence protein), a nucleotide sequence encoding gfp (i.e., green fluorescent protein), a nucleotide sequence encoding luc (i.e., luciferase), a nucleotide sequence encoding mCherry (i.e. a red fluorescent protein), a nucleotide sequence encoding ble (bleomycin resistance), a nucleotide sequence encoding ereA (erythromycin resistance), and any combination thereof.

Additional examples of selectable markers useful with the invention include, but are not limited to, a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin.

Additional selectable markers include, but are not limited to, a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding Bla that confers ampicillin resistance; or a nucleotide sequence encoding aequorin which may be employed in calcium-sensitive bioluminescence detection (Prasher et al. (1985) *Biochem. Biophys. Res. Comm.* 126:1259-1268), and/or any combination thereof. One of skill in the art is capable of choosing a suitable selectable marker for use with the vector of this invention.

In some embodiments, a vector of the invention may comprise CRISPR-Cas structure and machinery for genome integration (e.g., DNA palindromes, helicase domain, integrase domain, nuclease, reverse transcriptase).

Where appropriate, a polynucleotide of interest may be optimized for increased expression in a transformed plant, e.g., by using plant preferred codons. Methods for synthetic optimization of nucleic acid sequences are available in the art. The nucleotide sequence of interest can be optimized for expression in a particular host plant or alternatively can be modified for optimal expression in monocots. See, e.g., EP 0 359 472, EP 0 385 962, WO 91/16432; Perlak et al., *Proc. Natl. Acad. Sci. USA* 88, 3324 (1991), and Murray et al., *Nuc. Acids Res.* 17, 477 (1989), and the like. Plant preferred codons can be determined from the codons of highest frequency in the proteins expressed in that plant.

Methods

Further provided are methods of using the vectors of the invention. In some embodiments, the invention provides a method of expressing a polynucleotide of interest in a plant or part thereof, the method comprising: introducing into the plant or part thereof a circular plant vector of the invention, and selecting a plant or part thereof comprising the circular plant vector and expressing the polynucleotide of interest.

In some embodiments, a method of modulating the expression a polynucleotide of interest in a plant cell is provided, the method comprising introducing into a plant cell a circular plant vector of the invention to produce a transformed plant cell comprising the circular plant vector and expressing the polynucleotide of interest. In some embodiments, the plant cell is a population of plant cells and following introduction of the vector, cells are selected from the population that comprise the vector and express the polynucleotide of interest.

In some embodiments, a method of producing a plant cell expressing a polynucleotide of interest is provided, the method comprising introducing into a plant cell a circular plant vector of the invention, thereby producing a plant cell comprising the circular plant vector and expressing the polynucleotide of interest. In some embodiments, the plant cell is a population of plant cells and following introduction of the vector, cells are selected from the population that comprise the vector and express the polynucleotide of interest.

In some embodiments, the methods of the invention may further comprise regenerating a plant from the plant part comprising the circular plant vector and expressing the polynucleotide of interest. In some embodiments, the methods of the invention may additionally comprise regenerating a plant from the plant cell comprising the circular plant vector and expressing the polynucleotide of interest to produce a plant comprising the circular plant vector and expressing the polynucleotide of interest.

In some embodiments, the methods of the invention provide a plant, plant part or plant cell that is stably transformed. In some embodiments, the vector comprising the polynucleotide of interest present in a stably transformed plant or part thereof (e.g., a cell) is tethered to the chromosome of the plant. In some embodiments, the vector or part thereof may be integrated into the genome of the plant or part thereof. In some embodiments, the vector or part thereof is not integrated into the genome of the plant or part thereof.

The invention further provides stably transformed plants and/or stably transformed plant cells or other plant parts produced by the method the invention. Also provided are seeds produced from the plants of the invention, wherein the seeds comprise the vector of the invention and polynucleotide of interest. The invention also provides products harvested from the stably transformed plants of the invention, the product comprising the vector and polynucleotide of interest. Further provided are processed products produced from harvested products from the plants of the invention including seed, the processed products comprising the vector and polynucleotide of interest.

In some embodiments, a crop comprising a plurality of the stably transformed plant of the invention is also provided. The crop may be grown, for example, in a field (e.g., a cultivated field, an agricultural field), a growth chamber, a greenhouse, a recreational area, a lawn, and/or a roadside and the like.

"Introducing," in the context of a polynucleotide sequence of interest (e.g., a circular plant vector of this invention), means presenting the polynucleotide sequence of interest to the plant, plant part, and/or plant cell in such a manner that the polynucleotide sequence gains access to the interior of a cell. Thus, the term "transformation" as used herein refers to the introduction of a heterologous nucleic acid into a cell. Transformation of a cell may be stable or transient. Thus, in some embodiments, a plant cell of the invention is stably transformed with a vector of the invention. In other embodiments, a plant of the invention is transiently transformed with a vector of the invention.

"Transient transformation" in the context of a polynucleotide means that a polynucleotide is introduced into the cell and does not integrate into the genome of the cell.

By "stably introducing" or "stably introduced" in the context of a polynucleotide introduced into a cell it is intended that the introduced polynucleotide is stably incorporated into the genome of the cell, and thus the cell is stably transformed with the polynucleotide. "Stable transformation" or "stably transformed" as used herein means that a nucleic acid molecule is introduced into a cell and integrates into the genome of the cell or tethers itself to a chromosome in the cell. As such, the integrated/tethered nucleic acid molecule is capable of being inherited by the progeny thereof, more particularly, by the progeny of multiple successive generations. "Genome" as used herein also includes the nuclear and the plastid genome, and therefore includes integration/tethering of the nucleic acid into, for example, the chloroplast genome/to the chloroplast DNA. Stable transformation as used herein can also refer to a transgene that is maintained extrachromasomally, for example, as a minichromosome. The phrase "a stably transformed plant, plant part, and/or plant cell expressing said one or more polynucleotide sequences or a vector of this invention" and similar phrases used herein, means that the stably transformed plant, plant part, and/or plant cell comprises the one or more polynucleotide sequences/vector and that said one or more polynucleotide sequences/vector are functional in said stably transformed plant, plant part, and/or plant cell. In some embodiments, a vector of the invention may be stably transformed into a plant or part thereof, e.g., plant cell, wherein the vector and/or part thereof is stably intergrated into the genome. In some embodiments, the vector comprising the polynucleotide of interest is not incorporated into the genome of the stably transformed plant but is tethered to a chromosome and is maintained stably in the plant or part thereof (e.g., plant cell).

Transient transformation may be detected by, for example, an enzyme-linked immunosorbent assay (ELISA) or Western blot, which can detect the presence of a peptide or polypeptide encoded by one or more transgene introduced into an organism. Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods. Transformation can also be detected by direct sequencing and/or hybridization protocols that are well known in the art.

A circular plant vector of this invention may be introduced into a cell of a plant by any method known to those of skill in the art. In some embodiments of the invention, transformation of a cell comprises nuclear transformation. In some embodiments of the invention, transformation of a cell comprises plastid transformation.

Procedures for transforming plants are well known and routine in the art and are described throughout the literature. Non-limiting examples of transformation methods include transformation via bacterial-mediated nucleic acid delivery (e.g., via *Agrobacteria*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)). General guides to the transformation of yeast include Guthrie and Fink (1991) (Guide to yeast genetics and molecular biology. In *Methods in Enzymology*, (Academic Press, San Diego) 194:1-932) and guides to methods related to the transformation of bacteria include Aune and Aachmann (*Appl. Microbiol Biotechnol* 85:1301-1313 (2010)).

A polynucleotide therefore can be introduced into a plant, plant part, plant cell in any number of ways that are well known in the art. The methods of the invention do not depend on a particular method for introducing one or more nucleotide sequences into a plant, only that they gain access to the interior the cell. Where more than polynucleotide is to be introduced, they can be assembled as part of a single nucleic acid construct, or as separate nucleic acid constructs, and can be located on the same or different nucleic acid constructs. Accordingly, the polynucleotide can be introduced into the cell of interest in a single transformation event, or in separate transformation events, or, alternatively, a polynucleotide can be incorporated into a plant as part of a breeding protocol.

In some embodiments, when a plant part or plant cell is stably transformed, it can then be used to regenerate a stably transformed plant comprising a vector of this invention encoding a polynucleotide of interest in or tethered to its genome. Means for regeneration can vary from plant species to plant species, but generally a suspension of transformed protoplasts or a petri plate containing transformed explants is first provided. Callus tissue is formed and shoots may be induced from callus and subsequently root. Alternatively, somatic embryo formation can be induced in the callus tissue. These somatic embryos germinate as natural embryos to form plants. The culture media will generally contain various amino acids and plant hormones, such as auxin and cytokinins. Efficient regeneration will depend on the medium, on the genotype, and on the history of the culture. If these three variables are controlled, then regeneration is usually reproducible and repeatable.

The regenerated plants are transferred to standard soil conditions and cultivated in a conventional manner. The plants are grown and harvested using conventional procedures.

The particular conditions for transformation, selection and regeneration of a plant can be optimized by those of skill in the art. Factors that affect the efficiency of transformation include the species of plant, the target tissue or cell, composition of the culture media, selectable marker genes, kinds of vectors, and light/dark conditions. Therefore, these and other factors may be varied to determine an optimal transformation protocol for any particular plant species. It is recognized that not every species will react in the same manner to the transformation conditions and may require a slightly different modification of the protocols disclosed herein. However, by altering each of the variables, an optimum protocol can be derived for any plant species.

Further, the genetic properties engineered into the transgenic seeds and plants, plant parts, and/or plant cells of the present invention described herein can be passed on by sexual reproduction or vegetative growth and therefore can be maintained and propagated in progeny plants. Generally, maintenance and propagation make use of known agricultural methods developed to fit specific purposes such as harvesting, sowing or tilling.

In some embodiments, plant vector of this invention is circular and self-replicating. In some embodiments, the eccDNA comprises origin of replication sites. In some embodiments, the eccDNA of a construct of the invention may comprise CRISPR-like structure and machinery for genome integration (e.g., DNA palindromes, helicase domain, integrase domain, nuclease, reverse transcriptase).

In some embodiments, one or more nucleic acids molecules of interest (e.g., genes, non-transcribe regulatory elements etc.) may be comprised in a construct of the invention comprising an eccDNA replicon for use in expression in a plant. In some embodiments, the one or more nucleic acids molecules to be introduced or overexpressed in a plant may be heterologous or endogenous to the plant in which they are introduced, thereby providing the expression/overexpression of the nucleic acids in the target plant. In some embodiments, the one or more nucleic acid molecules comprised in the eccDNA construct may have host genome homology.

In some embodiments, a nucleic acid molecule conferring a desired trait may be inserted into the replicon adjacent to or in tandem with the EPSPS (or another selection marker), and this expression cassette may then be introduced into a plant for expression (heterologous gene) or for overexpression (endogenous gene).

Recombinant plants may be selected for glyphosate resistance or for any other selectable marker, while the gene of interest is expressed/amplified in copy number. This invention may solve the problem of transgene recalcitrance. Constructs comprising the eccDNA and one or more nucleic acid molecules of interest may be used to tailor species-specific replicons, for transgene stacking, and for exploiting precision trait enhancement with effects that may be analogous to heterosis.

The constructs of the invention may be useful for trait enhancement and molecular breeding tools to increase gene copy number and transform crops with new genes expressing desired traits through the eccDNA intermediate tethered to the genome; apart from the difficulties associated with off-target effects described with traditional genome engineering. This technology may drastically reduce the time required to enhance and/or alter crop traits.

Advantages of the constructs of the invention include that they comprise eccDNA, which as described herein provides a natural vehicle to transfer novel genes into the genome, that they provide a unique mechanism for increasing gene copy number and that nucleic acid molecules of interest (e.g., genes, etc) may be expressed outside of the genome removing site specific gene silencing issue. Additional advantages may further include reduced regulatory cost due to gene construct being plant derived, more flexibility with regard to the means of gene delivery (integrative or tethering) and targeted gene delivery Potential applications include gene therapy delivery, transient expression of genes in transcriptionally relevant regions of the genome, targetable vector of genetic plant transformations and one step dose dependent trait delivery system.

The invention will now be described with reference to the following examples. It should be appreciated that these examples are not intended to limit the scope of the claims to the invention, but are rather intended to be exemplary of certain embodiments. Any variations in the exemplified methods that occur to the skilled artisan are intended to fall within the scope of the invention.

EXAMPLES

Example 1

Selective pressures in nature potentiate genomic plasticity as a mechanism of adaptation to sustain life[1]. The predominant source of this functional diversity in eukaryotes and prokaryotes is gene copy number variation, which endows these adaptive processes[2-4]. These unbalanced structural variations impart a considerable spectrum of phenotypic diversity[5]. However, the underlying mechanisms that give rise to gene copy proliferation are poorly understood. Here, we show a unique result of genomic plasticity, the amplification of a massive extrachromosomal circular DNA (eccDNA), which is an extra-nuclear vehicle used by the *Amaranthus palmeri* genome to rapidly increase crucial gene copy numbers required for plant survival under extreme abiotic stress. This functional eccDNA confers resistance to the herbicide glyphosate. Upon exposure and continued selection with glyphosate, the *A. palmeri* genome has undergone extensive shuffling to form a plasmid-like structure, a massive eccDNA replicon, that harbors the EPSP synthase gene and other encoded machinery whose functions traverse detoxification, replication, recombination, and membrane transport. The eccDNA can exist in the extra-nuclear space and may replicate autonomously to function as a vehicle for gene amplification. Furthermore, the eccDNA replicon is comprised of a complex arrangement of repeat sequences and mobile genetic elements interspersed among arrays of clustered palindromes that may be crucial for stability, DNA duplication, and/or a means of nuclear integration of the adjacent and intervening sequences. While the discovery of the eccDNA replicon may provide new approaches in understanding genome dynamics and the link between functional eccDNA and evolutionary mechanisms, it also holds potential to ignite a revolution in biotechnology and plant breeding as a new vehicle for DNA amplification and genome engineering.

McClintock[6] stated "a sensing mechanism must be present in plants when experiencing unfavorable conditions to alert the cell to imminent danger and to set in motion the orderly sequence of events that will mitigate this danger." Plants, being sedentary, are subject to the prevailing conditions in which they grow. Under favorable conditions, growth ensues and gene expression supports physiological needs. However, as the quote implies, when conditions become adverse, plants may alter their physiology by activation of diverse stress-avoidance signaling cascades[7]. One such stress avoidance/response mechanism is the amplification of the gene encoding 5-enoylpyruvylshikimate-3-phosphate synthase (EPSPS), which confers resistance to the herbicide glyphosate in *A. palmeri*. The EPSPS gene may be amplified 40 to 100-fold in highly resistant populations[8]. We examined the genomic architecture surrounding the EPSPS gene to discover structure, content, and putative mechanisms of DNA amplification and regulatory elements.

In glyphosate-resistant *A. palmeri*, previous work shows EPSPS distribution among many chromosomes, suggesting a transposon-based mechanism of mobility; while EPSP synthase activity was also elevated[9]. Amplification of the EPSPS gene and its product, EPSP synthase, ameliorates the unbalanced or unregulated metabolic changes, such as shikimate accumulation and loss of aromatic amino acids associated with glyphosate activity in sensitive plants[10]. Interestingly, EPSPS amplification also correlates with significant genome expansion (e.g., 11% increase in genome size with ~100 extra copies), which includes co-amplification of many other genes, transcription factors and repetitive elements[8]. Without wishing to be limited by any particular theory, the mechanism of amplification may be governed by a diverse array of master transcriptional regulators being activated to create novel combinations of response genes enabling the plant to circumvent the chemical assault[11]. Here, we present a mechanism of rapid adaptive evolution by a unique vehicle for massive gene copy amplification: The extrachromosomal DNA (eccDNA) replicon.

Example 2

Plant Material and Fiber-FISH

The glyphosate-resistant (GR) *A. palmeri* plants were collected in 2013 from a soybean field in Riley county, Kansas that was exposed to extensive use of glyphosate during the decade prior by Dr. Mithila Jugulam. Young leaf tissues were collected from fast growing plants of GR *A. palmeri*. Nuclei isolation, DNA fiber preparation, and fiber-FISH were performed following published protocols[30,31]. In total, 6 overlapping BAC clones comprise the minimal tile path of the replicon, which were analyzed in pairs by FISH on DNA fibers prepared from leaf tissue. Fiber-FISH images were captured with a Zeiss Axioplan 2 microscope using a cooled CCD camera CoolSNAP HQ2 (Photometrics) and AxioVision 4.8 software (Zeiss). The final contrast of the images was processed using Adobe Photoshop CS5 software.

Example 3

BAC Isolation, Sequencing, and Analysis

BAC library construction, partial tile path isolation, sequencing and analysis were described previously.[8] Two additional BAC clones, 08H14 and 01G15 on the eccDNA replicon ends, were determined by chromosome walking by hybridization with overgo probes designed from unique distal sequence on the terminal ends of the EPSPS cassette (clones 03A06 and 13C09). These two BAC clones were harvested and sequenced using Pacific Biosciences RSII sequencing to a depth greater than 100X, as described in Molin et al.[8] Raw single molecule sequence was self-corrected using the CANU Celera assembler (Koren et al., 2017) with the corOutCoverage=1000 to increase the output of corrected sequences. BAC end sequences were determined using standard Sanger sequencing methods and aligned to the reference assemblies with Phrap and opened in Consed (Gordon et al., 1998) for editing. BAC overlaps were identified using CrossMatch (Gordon et al., 1998) and ends joined manually to form a circular structure. The consensus eccDNA replicon was annotated using a combination of the MakerP pipeline (Campbell et al., 2014) with RNAseq (below) used as evidence with final manual curation. Functional domain scans and homology based annotations were determined by BLAST, InterproScan, and HMM using the SwissProt, non-redundant, and PfamA databases, respectively. Repeat characterization and masking were conducted with the RepeatMasker software (http://www.repeatmasker.org). MITE and helitron sequences were predicted with the detectMITE (Ye et al., 2016) and HelitronScanner (Xiong et al., 2014) tools. Circular figures were prepared using the Circos plotting toolset (Krzywinski et al., 2009).

Example 4

RNAseq and Plant Material

Glyphosate-resistant (GR) *A. palmeri* plants were collected in 2013 by W. M from a soybean field in Washington County, Mississippi that was exposed to extensive application of glyphosate during the decade prior. Young leaf tissues (2 cm) were collected from fast growing plants of GR *A. palmeri* and used as a source for the glyphosate exposure experiment. Glyphosate treatment experiments were conducted in a greenhouse at the Jamie Whitten Delta States Research Center of USDA-ARS in Stoneville, Mississippi set to 25/20° C. ±3° C. day/night temperature and a 15-h photoperiod under natural sunlight conditions supplemented with high-pressure sodium lights providing 400 μmol m-2 s-1. Seeds were sown on the surface of potting mix surface (Metro-Mix 360, Sun Gro Horticulture, Bellevue, WA) and lightly covered with 2 mm of mix, subirrigated and grown to the two-true leaf stage at which time they were sprayed with glyphosate solution (0.42 kg.ai.ha-1) using an air-pressurized indoor spray chamber (DeVries Manufacturing Co., Hollandale, MN) equipped with a nozzle mounted with 8002E flat-fan tip (Spraying Systems Co., Wheaton, IL) delivering 190 L.ha-1 at 220 kPa. All of the seedlings survived confirming glyphosate resistance in this 2013 population. Seedlings from this population that had not been sprayed were allowed to grow until 2.5-cm tall and were transplanted into 8 cm×8 cm×7 cm pots containing the same potting mix. Thereafter, plants were watered as needed and fertilized once two weeks after transplanting with a water-soluble fertilizer (Miracle-Gro, Scotts Miracle-Gro Products, Inc., Marysville, OH). When seedlings reached the six-leaf stage they were sprayed with either water, or water plus surfactant plus glyphosate using the spray chamber. The surfactant was 0.5% v/v Tween 20 and glyphosate was applied at 0.42 kg.ai.ha-1 after neutralization with 0.1 KOH solution. Leaves from the third and fourth nodes were harvested for RNA extraction at 0, 4 and 24 hours after treatment. Plants were held for two weeks post leaf harvest to verify survival following glyphosate treatment.

Total RNA was harvested at 4 and 24 h in biological triplicates using the RNeasy plant mini kit (Qiagen). Purified RNA was verified for intactness on a Bioanalyzer 2100 (Agilent) and subject to stranded mRNA-seq using standard TruSeq procedures and sequenced to a target depth of at least 15M reads per sample. Raw sequence data was preprocessed for adapter and low-quality bases with the Trimmomatic tool (Krzywinski et al., 2009) and cleaned reads aligned to the eccDNA replicon consensus assembly with Bowtie2 v.2.3.4.1(Langmead and Salzberg, 2012) and the following arguments:-no-mixed -no-discordant -gbar 1000 -end-to-end -k 200 -q -X 800. TMM and FPKM transcript quantification was determined with RSEM v1.3.0 (Li and Dewey, 2011).

Example 5

Cloning, Plasmid Construction and Yeast Transformation

The eccDNA ARS sequences were amplified from 23A10 BAC using primers 167,312F_CEN-SLIC and 168, 187R_SLIC (Supplementary Table 4). The yeast vector, pRS315, was linearized via PCR using primers pRS_ΔCEN-F and pRS_ΔARS-R such that the CEN6 sequence remained, but the ARS was removed. Q5 polymerase was used for all PCRs. The eccDNA ARS was assembled into pRS305 using a SLIC reaction. Constructs were confirmed with a restriction digest and sequencing. *Saccharomyces cerevisiae* (ATCC 208288) were transformed as previously described[45]. Yeast cells were grown in a YPD (10 g/L yeast extract, 20 g/L peptone, 20 g/L glucose) preculture overnight at 28° C. and 250 rpm. In a 250-mL baffled flask, 50 mL of pre-warmed YPD was inoculated to a final titer of $5\times10^6$ cells/mL. The culture was grown to a final titer of $2\times10^7$ cells/mL at 28° C. and 250 rpm. Cells were harvested by centrifugation at 3,000×g for 5 minutes. The cell pellet was resuspended in 25 mL of sterile milliQ water and centrifuged again three times before cells were resuspended in 1.0 mL of sterile water. Cell pellet was then resuspended in 360 μL freshly made transformation mix (240 μL PEG 3350 (50% w/v), 36 μL 1.0 M LiAc, 50 μL single-stranded salmon sperm DNA (2 mg/mL), 36 μL plasmid DNA plus sterile water). Cells were heat shocked at 42° C. for 40 minutes and resuspended in 1 mL of YPD for 2 hours at 28° C., 250 rpm. Recovered cells were plated on YSC-Leu+2% glucose plates and grown at 28° C. for 2 days and colonies counted. pRS305 lacks an ARS and served as a negative control while pRS315 contains an ARS and served as a positive control.

Example 6

Identification and Structure of the eccDNA Plant Replicon

Figure 2:
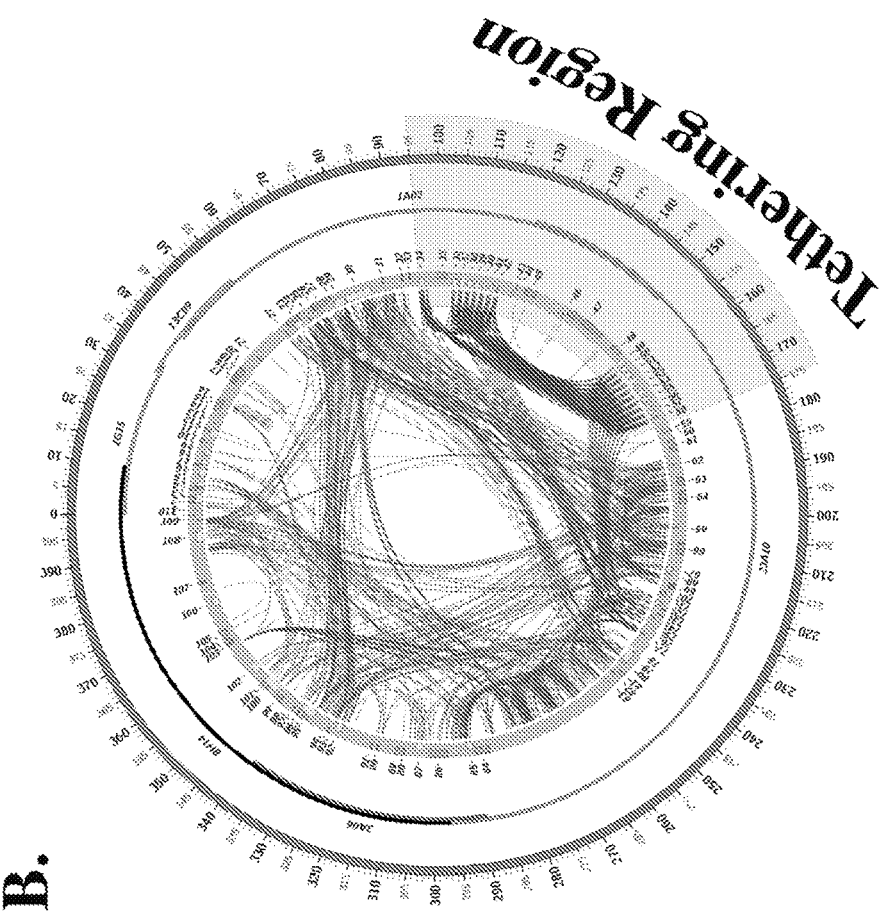
FIG. 2. The eccDNA Replicon. Panel A. The structure of the eccDNA replicon. The blue circular ideogram represents the replicon sequence (SEQ ID NO:20). The multicolored histograms represent the overlapping BAC tile path, the third inner track depicts the 110 putative protein coding gene sequences, those transcribed in the clockwise direction are depicted in green and counterclockwise in yellow. The internal links connect repetitive sequences to their respective internal matches; red (direct) and blue (inverted). Panel B. The eccDNA replicon with the predicted tethering region highlighted from ~95 kb to 175 kb. The red links are palindromic sequences (elevated A+T content) that may function in attachment to nuclear chromatin. Panel C. Fiber-FISH images of eccDNAs in GR *A. palmeri* with 80 EPSPS copies. (A) Circular form of eccDNA. (B) Linear form of eccDNA. (C) Dimerized circular form of eccDNA with head-to-tail tandem orientation. (D) Linear form of eccDNA with head-to-tail dimer. (E) Atypical fiber representing structural changes. Note: In the relatively long DNA fibers (D, E), two images were captured sequentially with an overlapping region and then they were combined into a single image using Adobe Photoshop. 1, BAC 01G15; 2, BAC 13C09; 3, BAC 22F22; 4, BAC 23A10; 5, BAC 03A06; 6, BAC 08H14, (Scale bars, 10 μm.). Panel D. Distribution of eccDNAs (red signals) on meiotic chromosomes in microsporocytes of GR *A. palmeri* during progression from the leptotene stage of meiosis I through anaphase of meiosis II (A-I) and pollen (J) detected by FISH (arrowheads point to the eccDNAs that are not associated with chromosomes). Brackets in G and I represent the lagging eccDNAs associated with chromatin bridges at anaphase to telophase stages.
Figure 2:
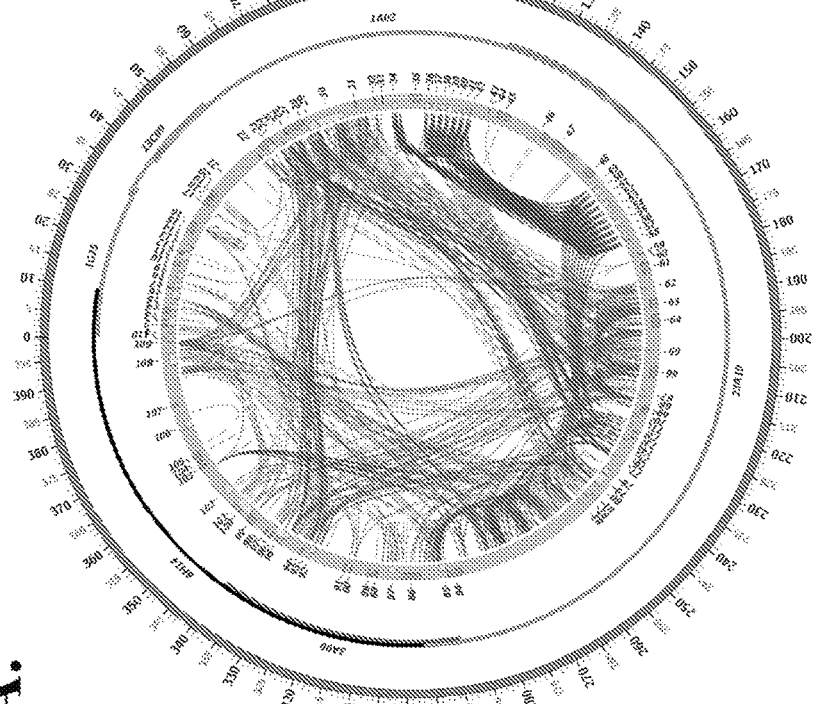
Figure 2:
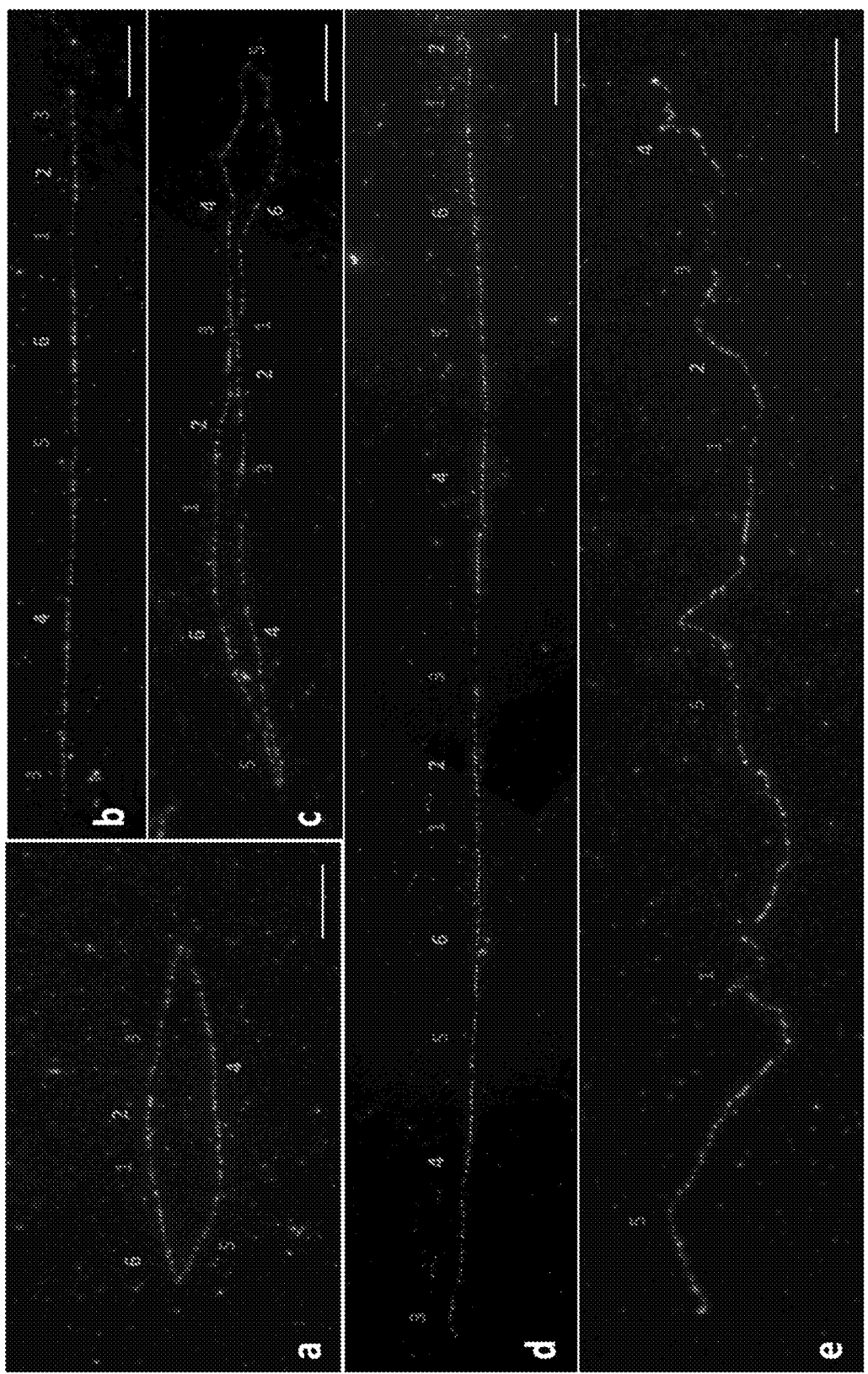
Figure 2D:
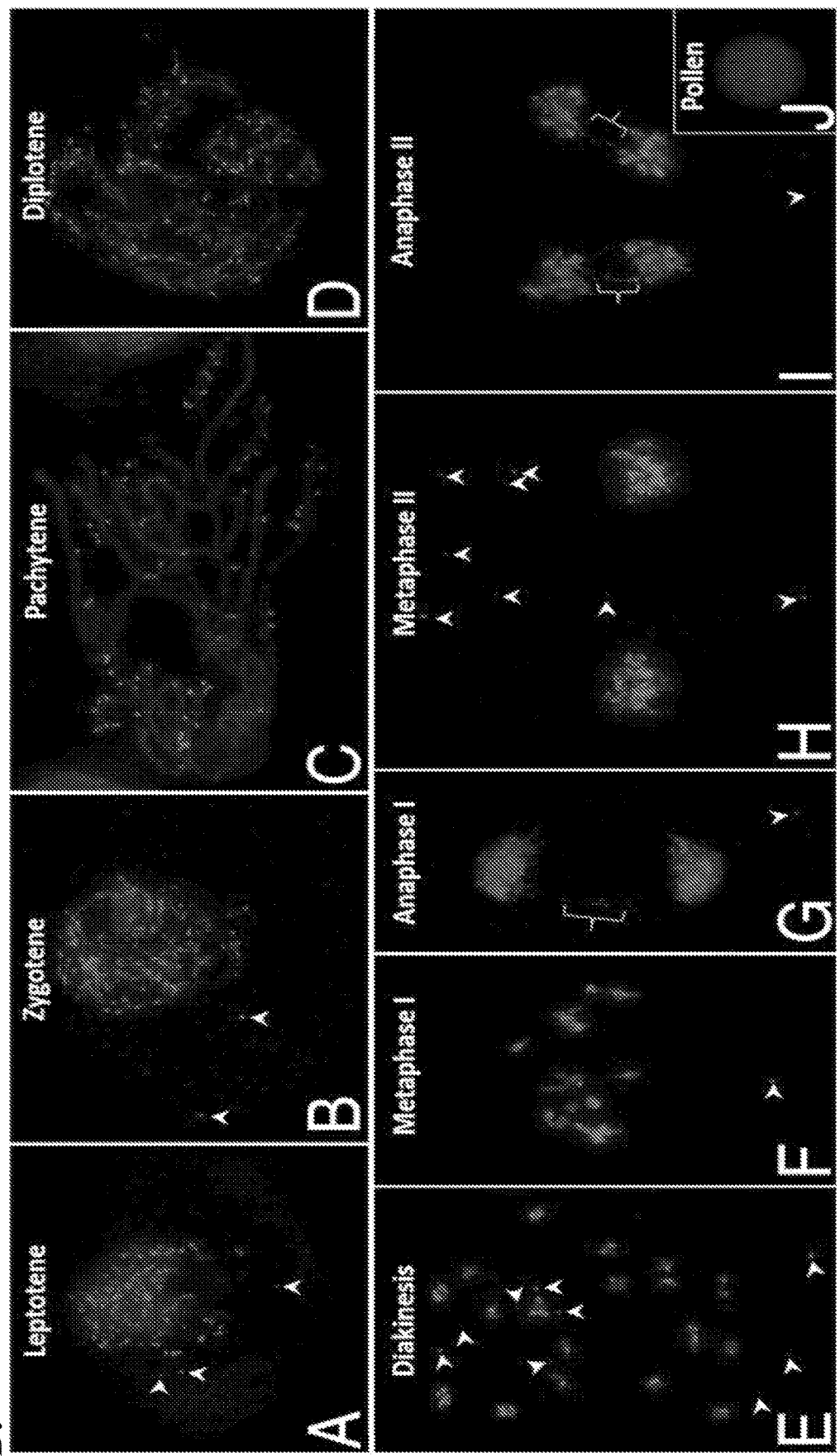

Advancing upon our recent work[8], FISH identified EPSPS signals that reside in the extra-nuclear space and in a seemingly random distribution on the mitotic metaphase chromosome in the glyphosate resistant *A. palmeri* nucleus (FIG. 2, panel A). Detailed resolution of the extra-nuclear signals revealed a circular, plasmid-like structure (FIG. 2, panel B). Fiber-FISH analysis of contiguous BAC clones (grouped into 2 pools for red/green labels) revealed relative BAC positions (FIG. 2, panel B) and further verified circular structure, (FIG. 2, panel B). Two-color FISH of contiguous BACs also reveal clear, consistent signals that illustrate each tiled BAC clone generates a linearized FISH signal (FIG. 5). Single-molecule sequencing of the BAC tile path further corroborates the circular structure as a massive extrachromosomal DNA element, much larger than anything reported to date.

The eccDNA replicon is comprised of 399,435 bp and contains 110 putative protein coding sequences, of which, 65 have expression profiles 24 hours after glyphosate exposure (FIG. 2, panel A and Table 1) in a glyphosate resistant biotype. The most transcriptionally active genes are the heat shock protein (Apr009) followed by the EPSPS gene (Apr035) and Apr073 (unknown function) (Table 1). Many of the eccDNA replicon encoded genes have functional signatures that may endow the critical cellular processes necessary for stress avoidance, maintenance, stability, and replication of the eccDNA replicon. These processes include DNA transport and mobility, molecule sequestration, hormonal control, DNA replication and repair, heat shock, transcription regulation, and nuclease activity, (Table 1).

For example, the replicon encodes 5 copies of aminotransferase-like genes (Apr 0003, 0005, 0030, 0069, 0099) that are ubiquitously expressed and crucial for proper cell division and differentiation[14]. A heat shock protein (Apr009) is a member of the Hsp70 family, which is upregulated by heat stress and toxic chemicals; and may also inhibit apoptosis[15]. There are 7 copies of protein suppressor of gene silencing genes that are required for post-transcriptional gene silencing, natural virus resistance, and the production of trans-acting siRNAs[16,17] (RNAi machinery). A gene with a NAC containing domain (Apr0084) was predicted, which represents a class of transcription factors that regulate plant defense[18] and abiotic stress responses[19]. Intriguingly, Apr101 harbors a SWIM domain which typically associates with RAD51 paralogs to promote homologous recombination[20,21]. Apr0102 contains a helicase domain, and Apr0105 harbors domains with endo/exo-nuclease and phosphatase activity. Apr107 contains a zinc binding reverse transcriptase domain and an integrase catalytic core, which are characteristic of a retroviral mechanism to integrate viral DNA into the host. This integrase is also found in various transposase proteins and is a member of the ribonuclease H-like superfamily involved in replication, homologous recombination, DNA repair, transposition, and RNA interference (Table 1).

EccDNAs are an understudied fraction of the genomes of plants, humans, and other eukaryotic organisms, and their contribution to genomic expansion, genetic diversity, and ultimately the phenome is not well understood. Furthermore, there is little evidence regarding the mechanisms by which eccDNAs may function, replicate, integrate into the host genome, or segregate during cell division. The presence of such a large eccDNA, compared to the 5.7 kb eccDNA in plants[21], ~20 kb in *Drosophilia*[22], and the ~38 kb elements in yeast[23,24], indicates a unique mechanism of genome plasticity and specialized purpose to increase gene copy abundance to survive a harsh abiotic stress.

Autonomous Replication

Figure 3:
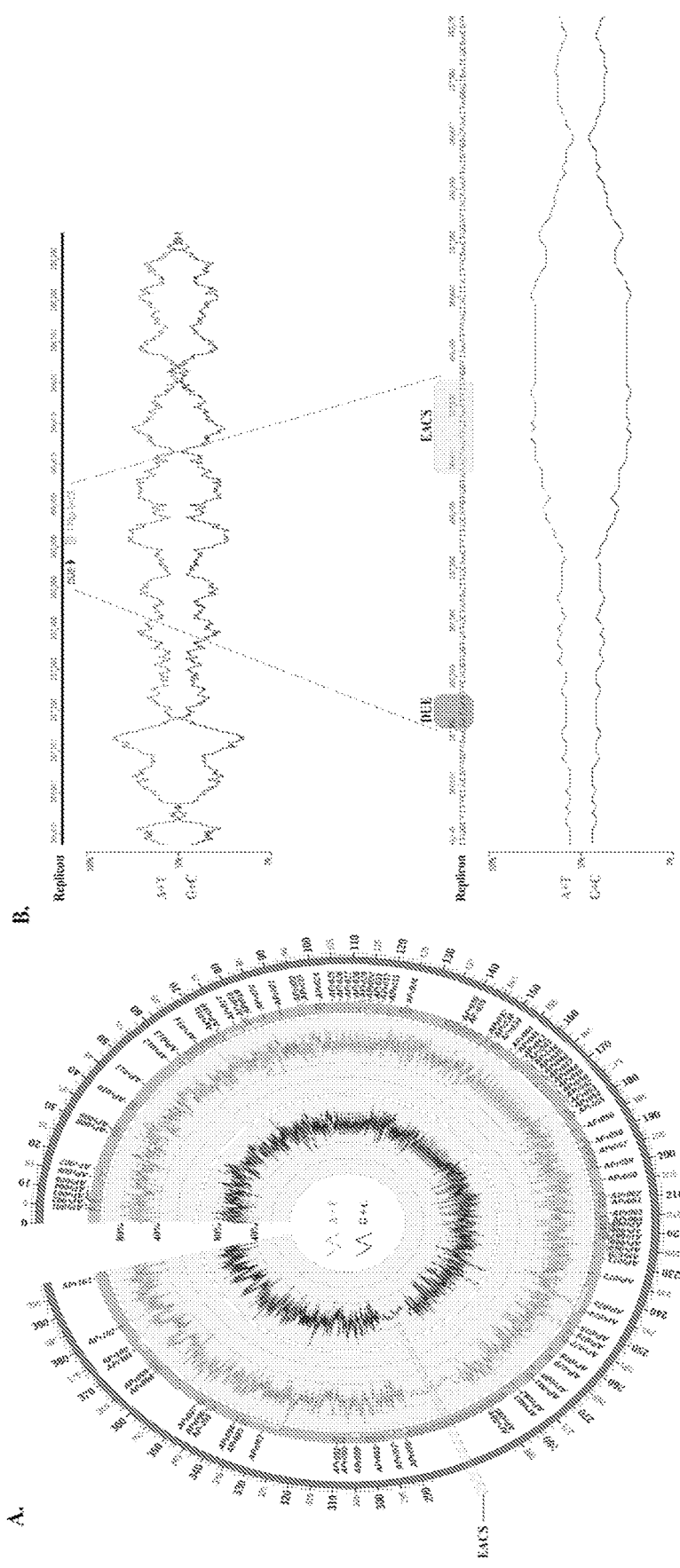
FIG. 3. GC/AT map of the eccDNA replicon, and origin of replication. Panel A. G+C/A+T map of the plant eccDNA replicon. The extended autonomous consensus sequence (EACS) region is highlighted in transparent yellow and serves as the origin of replication of the eccDNA replicon. Panel B. Top and bottom: A zoomed region of the DNA unwinding element and the extended autonomous consensus sequence regions that function as the origin of replication.

The eccDNA replicon is heavily punctuated with sharp changes in A+T and G+C content, which may imply biological function[26], including replication initiation sites[27] (FIG. 3, panel A). Autonomous replicating sequences (ARS) can function as origins of replication in eukaryotes[28], and plants have been shown to have conserved ARS structures and sequence features commonly found in yeast and higher animals[29]. A motif scan of the eccDNA replicon revealed a single exact match to the Extended Autonomous Consensus Sequence (EACS, 17 bp), previously described in yeast and other eukaryotes[28] (FIG. 3, panel B). Nearby, we identified a 9 bp DNA Unwinding Element (DUE)[30], which is adjacent to a region with elevated A+T content (approximately 73%) in a 40 bp window (20 bp +/−) that has a high propensity for bending (data not shown), which can implicate an origin of replication region[31]. By cloning +/−1 kb regions containing the putative origin of replication into a selectable ARS-less yeast vector, we observed dividing colonies, verifying that the eccDNA replicon ARS sequence is functional and can facilitate replication. Recombinant yeast growth was much slower with a lower abundance of colonies on plates with the eccDNA replicon, relative to the control ARS suggesting a possible role of cis-elements and trans-factors for efficiency in the plant[27]. For example, the eccDNA replicon encodes a DNA helicase (Apr_102), and replicon protein complexes (Apr_045), whose likely functions are required for genome stability, DNA recombination, repair, and replication. To our knowledge, no eccDNA reported as of this writing has been verified to contain a functional origin of replication, suggesting a selective advantage.

Repetitive Elements and Structural Organization

Figure 4:
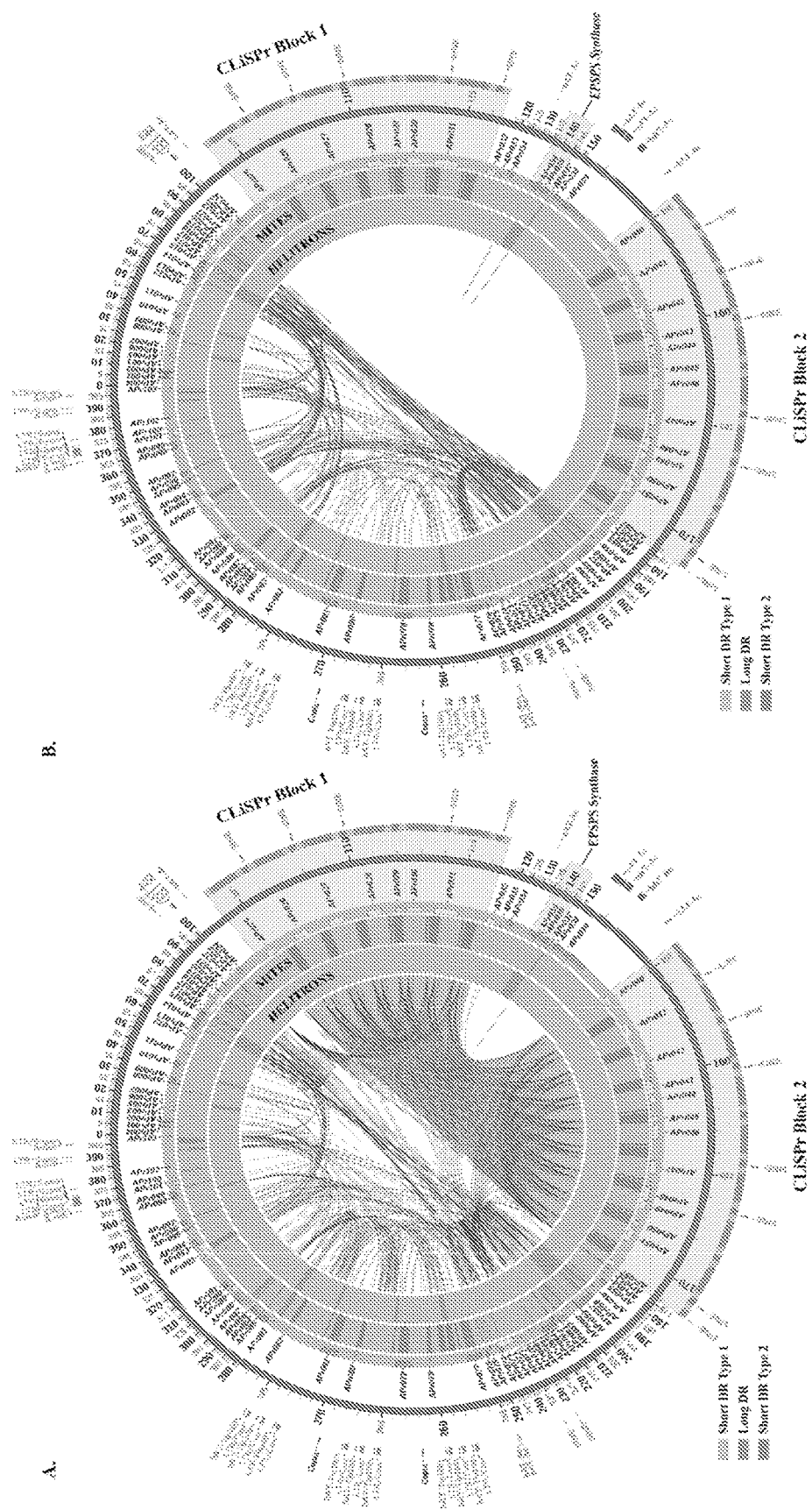
FIG. 4. Repeat structure of the eccDNA replicon. Panel A. circos plot of the *Amaranthus palmeri* eccDNA replicon and key repetitive structure. The outer colored histograms with labels are predicted repetitive elements with interesting arrangements. The highlighted repeat arrays are the clustered long and short interspersed palindromic repeat (CLiSPr) arrays that flank the EPSPS synthase gene. These repeat blocks are larger, asymmetric direct repeats. The inner tracks depict predicted MITE and helitron repetitive elements. The internal red links are direct repeats and their relationships within the replicon. Panel B. Everything in Panel A, except the direct repeats are hidden and inverted repeats are illustrated in blue.

The eccDNA replicon contains retroelements composed of SINEs, LINEs, and LTR elements, in addition to DNA transposons interspersed by predicted MITE and Helitron elements (FIG. 4, panel A, B). Flanking the EPSPS gene is an asymmetric set of direct repeats that are composed of arrays of clustered long and short interspersed palindromic repeat sequences (CLiSPrs), separated by identical MITES (FIG. 4, panel A). The complete palindromic array is bordered by LTR/ERVK, DNA/MULE MUDR and DNA/Td-Mar Stowaway elements (not shown). The CLiSPr block regions are also composed of elevated A+T segments (up to 80%) (FIG. 4, panel A), which may serve as a mechanism for stability or nuclear recognition sites for tethering, integration into open chromatin, or transcriptional hotspots. Downstream of the CLiSPr arrays are repetitive triplicate clusters of LTR-Cassandra and DNA hAT-Ac elements, each bordered by MITE elements. Still further downstream are clustered A-rich and LTR/Gypsy elements. These clustered arrangements may indicate functional relationships. The LTR/Cassandra and LTR/Gypsy elements divide the coding regions other than that contained within the direct repeats into 3 segments from 195 to 250 kb, from 287 to 355 kb and from 395 to 90 kb. The EACS and DUE sites are located at 287 kb just after the LTR/Cassanra repeats which is appropriately positioned to initiate transcription of transcribed genes.

The eccDNA replicon is a unique result of genomic plasticity and a massive eccDNA vehicle for gene amplification and expression of genes outside of the nuclear chromatin. The origin is unknown, but likely a result of mobile element activation and extensive *A. palmeri* genome shuffling invoked by heavy abiotic pressures. It has various functional modalities for integration, replication, stability and maintenance to ensure survival. Furthermore, because of the functional implications of the putative genes in the eccDNA replicon, the presence of this unit may also contribute a fitness boost and correlate with a general increase in abiotic stress resilience, or perhaps, an increased disposition to adapt. This vehicle may afford new directions in breeding and biotechnology through deeper understanding of genome interaction and integration, targeted gene amplification, and by transfer of novel pathways into new genomes through an engineered eccDNA intermediate.

Genome Tethering

The first cytological evidence of an eccDNA tethering to chromosomes in plants as a mechanism of genome persistence was recently reported (Koo et al., Plant Physiol 176, 1932-1938 (2018)). EccDNA maintenance has been extensively studied in DNA viruses that maintain their genomes as extrachromosomal circular DNAs, such as Epstein-Barr, Rhadinovirus, papillomavirus, and others (Feeney and Parish, Proc Biol Sci 276, 1535-1544 2009). A commonality among these viruses is genome tethering, which is facilitated by virus encoded DNA-binding proteins that associate with repeated sequences in the viral genome that also have an affinity with host cell proteins that associate with mitotic chromatin to ensure nuclear retention (Feeney and Parish, 2009). For example, the Epstein-barr virus has been reported to anchor to the host genome through interaction of encoded EBNA1 and the cellular protein EBP2 forming a protein-protein interaction or by directly associating to chromatin via an AT-hook motif that binds to A/T rich sequences on metaphase chromosomes (Sears et al., J Virol 78, 11487-11505, 2004), (Wu et al. Nature 575, 699-703, 2000). In Rhadinoviruses, a role has been suggested for the gene LANA, which is thought to interact with terminal repeat regions (TR) in the virus (comprised of long tandem repeats) (Russo et al. Proc Natl Acad Sci USA 93, 14862-14867, 1996), where the C-terminus of the protein attaches the TR and the N-terminus tethers the episome to the chromosome (Piolot et al. J Virol 75, 3948-3959, 2001). In Papillomaviruses, the E2 gene is a multifunctional DNA-binding protein that interacts with the E1 helicase for replication (Masterson et al. J Virol 72, 7407-7419, 1998) and facilitates genome association through interaction within the N-terminal trans-activation domain (Skiadopoulos and McBride J Virol 72, 2079-2088, 1998). Computational analysis of the eccDNA replicon revealed several genes which may function in the tethering mechanism. AP_R.00g000496 contains 2 core AT-hook motifs (GRP) and also encodes a zinc finger SWIM domain which is recognized to bind DNA, proteins, and/or lipid structures. The optimal binding sequences of the core AT-hook are AAAT and AATT, which when bound together forms a concave DNA conformation for tight binding (Reeves Environ Health Persp 108, 803-809, 2000). In the eccDNA replicion, there are 143 and 186 $(AAAT)_2$ or $(AATT)_2$ motifs, respectively. There are consistent clusters of tandemly repeated motifs in the CLiSPr repeats. These AT-hook gene products may interact with the A/T rich regions of the eccDNA replicon and other nuclear scaffold proteins. Furthermore, the helicase domain has recently been demonstrated to be an important regulator of the chromatin association, establishment, and maintenance of the Herpes virus. AP_R.00g000496 is predicted to encode a helicase motif which may also have a role in tethering of the eccDNA to nuclear chromatin.

The eccDNA replicon is a massive eccDNA vehicle for gene amplification, trait expression, maintenance and transfer of genomic information. This is the first report of an autonomously replicating functional plant eccDNA. The origin is unknown, but likely a result of mobile element activation and extensive genome shuffling invoked by heavy abiotic pressures. It has various functional modalities for integration, replication, stability and maintenance to ensure survival. Furthermore, because of the functional implications of the putative genes in the eccDNA replicon, the presence of this unit could cause a general increase in abiotic stress resilience, or perhaps, an increased disposition to adapt. This vehicle affords new directions in breeding and biotechnology through deeper understandings of its origin and function.

TABLE 1

Annotation of the eccDNA replicon.

| Gene | Start | Stop | Length | Orientation | pfam | Transmembrane | Gene3D | SwissProt_Best_Hit | Uniref | NR | Arabidopsis_ortho |
|---|---|---|---|---|---|---|---|---|---|---|---|
| Apr_00001 | 921 | 1421 | 501 | − | | | | | | | |
| Apr_00002 | 3042 | 3573 | 532 | + | | | | | | | |
| Apr_00003 | 3158 | 5405 | 2248 | − | Aminotransferase-like, plant mobile domain | | | | | | AT2G25010.1 |
| Apr_00004 | 4489 | 4862 | 374 | + | | | | | | | |
| Apr_00005 | 6479 | 7891 | 1413 | + | Aminotransferase-like, plant mobile domain | | | Serine/threonine-protein phosphatase 7 long form homolog (EC 3.1.3.16) (Protein MAIN-LIKE 3) | Protein MAIN-LIKE 1 | | AT2G25010.1 |
| Apr_00006 | 7091 | 7468 | 378 | − | Phospholipase-like | | | | | | |
| Apr_00007 | 7757 | 9018 | 1262 | − | Reverse transcriptase domain | | 0 | | | | |
| Apr_00008 | 10649 | 12631 | 1983 | − | | | | | | LINE-1 retrotransposable element ORF2 protein (ORF2p) (Long interspersed element-1) (L1) (Retrovirus-related Pol polyprotein LINE-1) [Includes: Reverse transcriptase (EC 2.7.7.49); Endonuclease (EC 3.1.21.—)] | AT5G11140.1 LINE-1 retrotransposable element ORF2 protein (ORF2p) (Long interspersed element-1) (L1) (Retrovirus-related Pol polyprotein LINE-1) [Includes: Reverse transcriptase (EC 2.7.7.49); Endonuclease (EC 3.1.21.—)] |
| Apr_00009 | 13208 | 13567 | 360 | + | F-box domain | | Leucine-rich repeat domain superfamily | F-box/LRR-repeat protein At3g60040 | F-box/LRR-repeat protein At3g60040 | | AT3G60040.1 |
| Apr_00010 | 13711 | 15042 | 1332 | − | | | | | | | |
| Apr_00011 | 16425 | 17870 | 1446 | − | Protein of unknown function DUF674 | | | | | | AT5G01150.1 |
| Apr_00012 | 19457 | 20446 | 990 | + | Transposase-associated domain | | | | | | |

TABLE 1-continued

Annotation of the eccDNA replicon.

| Gene | Start | Stop | Length | Orientation | pfam | Transmembrane | Gene3D | SwissProt_Best_Hit | Uniref | NR | Arabidopsis_ortho |
|---|---|---|---|---|---|---|---|---|---|---|---|
| Apr_00013 | 21711 | 23812 | 2102 | − | | Region of a membrane-bound protein predicted to be embedded in the membrane. | | | | | |
| Apr_00014 | 22679 | 23463 | 785 | + | | | | | | | |
| Apr_00015 | 25365 | 25610 | 246 | − | | | | | | | |
| Apr_00016 | 28768 | 31847 | 3080 | + | Heat shock protein 70 family | | Heat shock protein 70 kD, C-terminal domain superfamily | Probable mediator of RNA polymerase II transcription subunit 37e (Heat shock 70 kDa protein 1) (Heat shock cognate protein 70-1) (AtHsc70-1) (Heat shock protein 70-1) (AtHsp70-1) (Protein EARLY-RESPONSIVE TO DEHYDRATION 2) | Probable mediator of RNA polymerase II transcription subunit 37e (Heat shock 70 kDa protein 1) (Heat shock cognate protein 70 kDa protein 1) (Heat shock cognate protein 70-1) (AtHsc70-1) (Heat shock protein 70-1) (AtHsp70-1) (Protein EARLY-RESPONSIVE TO DEHYDRATION 2) | | AT5G02500.1 |
| Apr_00017 | 37190 | 37711 | 522 | + | Reverse transcriptase zinc-binding domain | | | | | | |
| Apr_00018 | 38096 | 38925 | 830 | + | | | | | | | |
| Apr_00019 | 39468 | 39692 | 225 | + | | | | | | | |
| Apr_00020 | 40235 | 41614 | 1380 | + | | | | | | | |
| Apr_00021 | 46539 | 46619 | 81 | − | | | | | | | |
| Apr_00022 | 56509 | 56703 | 195 | − | | Region of a membrane-bound protein predicted to be embedded in the membrane. | | | | | AT2G02520.1 |
| Apr_00023 | 58320 | 61752 | 3433 | + | | | | | | | |
| Apr_00024 | 59449 | 61445 | 1997 | − | | | | | | | |

TABLE 1-continued

Annotation of the eccDNA replicon.

| Gene | Start | Stop | Length | Orientation | pfam | Transmembrane | Gene3D | SwissProt_Best_Hit | Uniref | NR | Arabidopsis_ortho |
|---|---|---|---|---|---|---|---|---|---|---|---|
| Apr_00025 | 63843 | 64082 | 240 | − | | | | | | | |
| Apr_00026 | 65686 | 66162 | 477 | + | | Region of a membrane-bound protein predicted to be embedded in the membrane. | | | | | |
| Apr_00027 | 66201 | 70222 | 4022 | + | | | | | | | |
| Apr_00028 | 70996 | 71300 | 305 | + | | Region of a membrane-bound protein predicted to be embedded in the membrane. | | | | | |
| Apr_00029 | 71724 | 74293 | 2570 | − | | | | | | | |
| Apr_00030 | 74871 | 82009 | 7139 | − | Aminotransferase-like, plant mobile domain | Region of a membrane-bound protein predicted to be embedded in the membrane. | | | Protein MAIN-LIKE 2 | | AT2G04865.1 |
| Apr_00031 | 85431 | 85787 | 357 | + | | | | | | | |
| Apr_00032 | 90436 | 90867 | 432 | + | | | | | | | |
| Apr_00033 | 92585 | 92809 | 225 | + | | | | | | | |
| Apr_00034 | 95040 | 96323 | 1284 | − | | | | | | | |
| Apr_00035 | 99824 | 1E+05 | 2670 | + | Zinc finger, BED-type | | | Putative AC transposase (ORFA) | Putative AC transposase (ORFA) | | |
| Apr_00036 | 103778 | 1E+05 | 1180 | − | | | | | | | |
| Apr_00037 | 105687 | 1E+05 | 1282 | − | | | | | | | |
| Apr_00038 | 107705 | 1E+05 | 1282 | − | | | | | | | |
| Apr_00039 | 109723 | 1E+05 | 1282 | − | | | | | | | |
| Apr_00040 | 111929 | 1E+05 | 762 | − | | | | | | | |
| Apr_00041 | 113755 | 1E+05 | 950 | − | | | | | | | |
| Apr_00042 | 115769 | 1E+05 | 269 | − | | | | | | | |
| Apr_00043 | 119792 | 1E+05 | 643 | − | | | | | | | |
| Apr_00044 | 120533 | 1E+05 | 87 | + | | Region of a membrane-bound protein predicted to be embedded in the membrane. | | | | | |

TABLE 1-continued

Annotation of the eccDNA replicon.

| Gene | Start | Stop | Length | Orientation | pfam | Transmembrane | Gene3D | SwissProt_Best_Hit | Uniref | NR | Arabidopsis_ortho |
|---|---|---|---|---|---|---|---|---|---|---|---|
| Apr_00045 | 123017 | 1E+05 | 3052 | + | Domain of unknown function DUF223 | | 0 | | | | AT5G08020.1 |
| Apr_00046 | 134546 | 1E+05 | 309 | − | | | | Replication protein A 70 kDa DNA-binding subunit B (OsRPA70b) (Replication factor A protein 1B) (Replication protein A 1B) | Replication protein A 70 kDa DNA-binding subunit B (OsRPA70b) (Replication factor A protein 1B) (Replication protein A 1B) | | |
| Apr_00047 | 135665 | 1E+05 | 10489 | + | Enolpyruvate transferase domain | | Enolpyruvate transferase domain superfamily | 3-phosphoshikimate 1-carboxyvinyltransferase, chloroplastic (EC 2.5.1.19) (5-enolpyruvylshikimate-3-phosphate synthase) (EPSP synthase) | 3-phosphoshikimate 1-carboxyvinyltransferase, chloroplastic (EC 2.5.1.19) (5-enolpyruvylshikimate-3-phosphate synthase) (EPSP synthase) | | AT2G45300.1 |
| Apr_00048 | 150227 | 2E+05 | 2670 | + | Zinc finger, BED-type | | | | | | |
| Apr_00049 | 154182 | 2E+05 | 1180 | − | | | | | | | |
| Apr_00050 | 156092 | 2E+05 | 1281 | − | | | | | | | |
| Apr_00051 | 158108 | 2E+05 | 1281 | − | | | | | | | |
| Apr_00052 | 160123 | 2E+05 | 1282 | − | | | | | | | |
| Apr_00053 | 162329 | 2E+05 | 761 | − | | | | | | | |
| Apr_00054 | 164154 | 2E+05 | 950 | − | | | | | | | |
| Apr_00055 | 166169 | 2E+05 | 1283 | − | | | | | | | |
| Apr_00056 | 168376 | 2E+05 | 762 | − | | | | | | | |
| Apr_00057 | 170204 | 2E+05 | 951 | − | | | | | | | |
| Apr_00058 | 172221 | 2E+05 | 269 | − | | | | | | | |
| Apr_00059 | 176249 | 2E+05 | 643 | − | | | | | | | |
| Apr_00060 | 176990 | 2E+05 | 87 | + | | Region of a membrane-bound protein predicted to be embedded in the membrane. | | | | | |
| Apr_00061 | 179482 | 2E+05 | 3053 | + | Domain of unknown function DUF223 | | 0 | | | | AT5G08020.1 |
| Apr_00062 | 185934 | 2E+05 | 333 | − | | | | | | | |
| Apr_00063 | 189715 | 2E+05 | 2043 | + | | Region of a membrane-bound protein predicted to be | | | | | |

TABLE 1-continued

Annotation of the eccDNA replicon.

| Gene | Start | Stop | Length | Orientation | pfam | Transmembrane | Gene3D | SwissProt_Best_Hit | Uniref | NR | Arabidopsis_ortho |
|---|---|---|---|---|---|---|---|---|---|---|---|
| Apr_00064 | 193536 | 2E+05 | 3323 | + | Domain of unknown function DUF1985 | embedded in the membrane. | | | | | AT2G04865.1 |
| Apr_00065 | 203297 | 2E+05 | 333 | − | | | | | | | |
| Apr_00066 | 207352 | 2E+05 | 3045 | + | | Region of a membrane-bound protein predicted to be embedded in the membrane. | | | | | |
| Apr_00067 | 214319 | 2E+05 | 884 | − | | | | Protein SUPPRESSOR OF GENE SILENCING 3 (SlSGS3) | Protein SUPPRESSOR OF GENE SILENCING 3 (SlSGS3) | | AT5G23570.1 |
| Apr_00068 | 215871 | 2E+05 | 337 | − | | | | | | | |
| Apr_00069 | 218346 | 2E+05 | 534 | + | Aminotransferase-like, plant mobile domain | | | | | | AT2G04865.1 |
| Apr_00070 | 218956 | 2E+05 | 966 | + | | | | | | | |
| Apr_00071 | 220951 | 2E+05 | 397 | − | | | | | | | |
| Apr_00072 | 221672 | 2E+05 | 466 | − | | | | | | | |
| Apr_00073 | 223914 | 2E+05 | 825 | − | Zinc finger-XS domain | | | Protein SUPPRESSOR OF GENE SILENCING 3 (AtSGS3) | Protein SUPPRESSOR OF GENE SILENCING 3 (AtSGS3) | | AT5G23570.1 |
| Apr_00074 | 225483 | 2E+05 | 126 | + | | | | | | | |
| Apr_00075 | 227147 | 2E+05 | 93 | + | | | | | | | |
| Apr_00076 | 228415 | 2E+05 | 260 | − | | | | | | | |
| Apr_00077 | 233615 | 2E+05 | 218 | − | | | | | | | |
| Apr_00078 | 237893 | 2E+05 | 1329 | − | | Region of a membrane-bound protein predicted to be embedded in the membrane. | | | | | |
| Apr_00079 | 239442 | 2E+05 | 3053 | − | | Region of a membrane-bound protein | | | | | |
| Apr_00080 | 242931 | 2E+05 | 402 | − | | | | | | | |

TABLE 1-continued

Annotation of the eccDNA replicon.

| Gene | Start | Stop | Length | Orientation | pfam | Transmembrane | Gene3D | SwissProt_Best_Hit | Uniref | NR | Arabidopsis_ortho |
|---|---|---|---|---|---|---|---|---|---|---|---|
| Apr_00081 | 245168 | 2E+05 | 999 | + | | predicted to be embedded in the membrane. | | | | | |
| Apr_00082 | 246901 | 2E+05 | 162 | − | | | | | | | |
| Apr_00083 | 249161 | 2E+05 | 504 | − | | | | | | | AT1G74630.1 |
| Apr_00084 | 286115 | 3E+05 | 3802 | + | NAC domain | | | Pentatricopeptide repeat-containing protein At1g74630 | Pentatricopeptide repeat-containing protein At1g74630 SUPPRESSOR OF GAMMA RESPONSE 1 (NAC domain-containing protein 8) (ANAC008) (Protein SOG1) (SUPPRESSOR OF GAMMA RADIATION 1) | SUPPRESSOR OF GAMMA RESPONSE 1 (NAC domain-containing protein 8) (ANAC008) (Protein SOG1) (SUPPRESSOR OF GAMMA RADIATION 1) | AT1G25580.1 |
| Apr_00085 | 290238 | 3E+05 | 1604 | − | Phospholipase-like | | | | | | |
| Apr_00086 | 296929 | 3E+05 | 4894 | + | | Region of a membrane-bound protein predicted to be embedded in the membrane. | | | | | AT2G16900.3 |
| Apr_00087 | 303256 | 3E+05 | 1979 | − | | Region of a membrane-bound protein predicted to be embedded in the membrane. | | | | | |
| Apr_00088 | 308094 | 3E+05 | 720 | + | HAT, C-terminal dimerisation domain | | | | | | AT5G33406.1 |
| Apr_00089 | 309472 | 3E+05 | 1176 | + | Retrotransposon gag domain | | Aspartic peptidase domain superfamily | | | | AT3G30770.1 |
| Apr_00090 | 315064 | 3E+05 | 243 | + | | | | | | | |
| Apr_00091 | 316577 | 3E+05 | 390 | + | | Region of a membrane-bound protein predicted to be | | | | | |

TABLE 1-continued

Annotation of the eccDNA replicon.

| Gene | Start | Stop | Length | Orientation | pfam | Transmembrane | Gene3D | SwissProt_Best_Hit | Uniref | NR | Arabidopsis_ortho |
|---|---|---|---|---|---|---|---|---|---|---|---|
| Apr_00092 | 325546 | 3E+05 | 1564 | − | | embedded in the membrane. | | | | | |
| Apr_00093 | 327173 | 3E+05 | 453 | − | | Region of a membrane-bound protein predicted to be embedded in the membrane. | | | | | |
| Apr_00094 | 328686 | 3E+05 | 444 | + | | | | | | | |
| Apr_00095 | 333602 | 3E+05 | 4034 | − | | | | | | | |
| Apr_00096 | 334766 | 3E+05 | 1749 | + | | | | | | | |
| Apr_00097 | 337707 | 3E+05 | 357 | + | | | | | | | |
| Apr_00098 | 339252 | 3E+05 | 165 | + | | | | | | | |
| Apr_00099 | 343142 | 3E+05 | 2181 | + | Aminotransferase-like, plant mobile domain | | | | | | AT2G25010.1 |
| Apr_00100 | 345750 | 4E+05 | 4560 | − | | | | | | | AT1G64260.1 |
| Apr_00101 | 348059 | 4E+05 | 2326 | + | | | | | | | AT5G28780.1 |
| Apr_00102 | 353271 | 4E+05 | 2493 | − | DNA helicase | | 0 | ATP-dependent DNA helicase PIF1 (EC 3.6.4.12) (DNA repair and recombination helicase PIF1) | ATP-dependent DNA helicase PIF1 (EC 3.6.4.12) (DNA repair and recombination helicase PIF1) | | |
| Apr_00103 | 363148 | 4E+05 | 417 | + | | | | | | | AT2G01050.1 |
| Apr_00104 | 363601 | 4E+05 | 1251 | + | Domain of unknown function DUF4283 | | | | | | |
| Apr_00105 | 364878 | 4E+05 | 2631 | + | | | Endonuclease/exonuclease/phosphatase superfamily | | | | AT1G43760.1 |
| Apr_00106 | 374158 | 4E+05 | 2099 | − | | | | | | | AT4G04650.1 |
| Apr_00107 | 380760 | 4E+05 | 753 | + | Reverse transcriptase zinc-binding domain | | | | | | |
| Apr_00108 | 391831 | 4E+05 | 2907 | − | | | 0 | | | | AT5G46460.1 |
| Apr_00109 | 397776 | 4E+05 | 437 | − | | | | Pentatricopeptide repeat-containing protein At5g46460, mitochondrial | Pentatricopeptide repeat-containing protein At5g46460, mitochondrial | | |
| Apr_00110 | 399059 | 4E+05 | 162 | + | | | | | | | |

REFERENCES

1. Lynch, M. & Conery, J. S. The evolutionary fate and consequences of duplicate genes. *Science* 290, 1151-1155 (2000).
2. Beckmann, J. S., Estivill, X. & Antonarakis, S. E. Copy number variants and genetic traits: closer to the resolution of phenotypic to genotypic variability. *Nat Rev Genet* 8, 639-646, doi:10.1038/nrg2149 (2007).
3. Zmienko, A., Samelak, A., Kozlowski, P. & Figlerowicz, M. Copy number polymorphism in plant genomes. *Theor Appl Genet* 127, 1-18, doi:10.1007/s00122-013-2177-7 (2014).
4. Ponting, C. P. The functional repertoires of metazoan genomes. *Nat Rev Genet* 9, 689-698, doi:10.1038/nrg2413 (2008).
5. Iskow, R. C., Gokcumen, O. & Lee, C. Exploring the role of copy number variants in human adaptation. *Trends Genet* 28, 245-257, doi:10.1016/j.tig.2012.03.002 (2012).
6. McClintock, B. The significance of responses of the genome to challenge. *Science* 226, 792-801 (1984).
7. Lopez-Maury, L., Marguerat, S. & Bahler, J. Tuning gene expression to changing environments: from rapid responses to evolutionary adaptation. *Nat Rev Genet* 9, 583-593, doi:10.1038/nrg2398 (2008).
8. Molin, W. T., Wright, A. A., Lawton-Rauh, A. & Saski, C. A. The unique genomic landscape surrounding the EPSPS gene in glyphosate resistant *Amaranthus palmeri*: a repetitive path to resistance. *BMC Genomics* 18, 91, doi:10.1186/s12864-016-3336-4 (2017).
9. Gaines, T. A. et al. Gene amplification confers glyphosate resistance in *Amaranthus palmeri*. *Proc Natl Acad Sci USA* 107, 1029-1034, doi:10.1073/pnas.0906649107 (2010).
10. Duke, S. O. & Powles, S. B. Glyphosate: a once-in-a-century herbicide. *Pest Manag Sci* 64, 319-325, doi:10.1002/ps.1518 (2008).
11. Balderas-Hernandez, V. E., Alvarado-Rodriguez, M. & Fraire-Velazquez, S. Conserved versatile master regulators in signaling pathways in response to stress in plants. *Aob Plants* 5, doi:ARTN plt033 10.1093/aobpla/plt033 (2013).
12. Jackson, S. A., Wang, M. L., Goodman, H. M. & Jiang, J. Application of fiber-FISH in physical mapping of *Arabidopsis thaliana*. *Genome* 41, 566-572 (1998).
13. Koo, D. H., Han, F., Birchler, J. A. & Jiang, J. Distinct DNA methylation patterns associated with active and inactive centromeres of the maize B chromosome. *Genome Res* 21, 908-914, doi:10.1101/gr.116202.110 (2011).
14. Uhlken, C., Horvath, B., Stadler, R., Sauer, N. & Weingartner, M. MAIN-LIKE1 is a crucial factor for correct cell division and differentiation in *Arabidopsis thaliana*. *Plant J* 78, 107-120, doi:10.1111/tpj.12455 (2014).
15. Beere, H. M. et al. Heat-shock protein 70 inhibits apoptosis by preventing recruitment of procaspase-9 to the Apaf-1 apoptosome. *Nat Cell Biol* 2, 469-475, doi:10.1038/35019501 (2000).
16. Mourrain, P. et al. *Arabidopsis* SGS2 and SGS3 genes are required for posttranscriptional gene silencing and natural virus resistance. *Cell* 101, 533-542 (2000).
17. Peragine, A., Yoshikawa, M., Wu, G., Albrecht, H. L. & Poethig, R. S. SGS3 and SGS2/SDE1/RDR6 are required for juvenile development and the production of trans-acting iRNAs in *Arabidopsis*. *Genes Dev* 18, 2368-2379, doi:10.1101/gad.1231804 (2004).
18. Xie, Q., Sanz-Burgos, A. P., Guo, H. S., Garcia, J. A. & Gutierrez, C. GRAB proteins, novel members of the NAC domain family, isolated by their interaction with a geminivirus protein. *Plant Mol Biol* 39, 647-656, doi:Doi 10.1023/A:1006138221874 (1999).
19. Hegedus, D. et al. Molecular characterization of *Brassica napus* NAC domain transcriptional activators induced in response to biotic and abiotic stress. *Plant Mol Biol* 53, 383-397 (2003).
20. Durrant, W. E., Wang, S. & Dong, X. N. *Arabidopsis* SNI1 and RAD51D regulate both gene transcription and DNA recombination during the defense response (vol 104, pg 4223, 2007). *P Natl Acad Sci USA* 104, 7307-7307, doi:10.1073/pnas.0702347104 (2007).
21. Makarova, K. S., Aravind, L. & Koonin, E. V. SWIM, a novel Zn-chelating domain present in bacteria, archaea and eukaryotes. *Trends Biochem Sci* 27, 384-386 (2002).
22. Lanciano, S. et al. Sequencing the extrachromosomal circular mobilome reveals retrotransposon activity in plants. *PLoS Genet* 13, e1006630, doi:10.1371/journal.pgen.1006630 (2017).
23. Cohen, S., Yacobi, K. & Segal, D. Extrachromosomal circular DNA of tandemly repeated genomic sequences in *Drosophila*. *Genome Res* 13, 1133-1145, doi:10.1101/gr.907603 (2003).
24. Moller, H. D., Parsons, L., Jorgensen, T. S., Botstein, D. & Regenberg, B. Extrachromosomal circular DNA is common in yeast. *P Natl Acad Sci USA* 112, E3114-E3122, doi:10.1073/pnas.1508825112 (2015).
25. Windle, B., Draper, B. W., Yin, Y. X., O'Gorman, S. & Wahl, G. M. A central role for chromosome breakage in gene amplification, deletion formation, and amplicon integration. *Genes Dev* 5, 160-174 (1991).
26. Zhang, L. G., Kasif, S., Cantor, C. R. & Broude, N. E. GC/AT-content spikes as genomic punctuation marks. *P Natl Acad Sci USA* 101, 16855-16860, doi:DOI 10.1073/pnas.0407821101 (2004).
27. Bell, S. P. & Stillman, B. ATP-dependent recognition of eukaryotic origins of DNA replication by a multiprotein complex. *Nature* 357, 128-134, doi:10.1038/357128a0 (1992).
28. Stinchcomb, D. T., Struhl, K. & Davis, R. W. Isolation and characterisation of a yeast chromosomal replicator. *Nature* 282, 39-43 (1979).
29. Eckdahl, T. T., Bennetzen, J. L. & Anderson, J. N. DNA structures associated with autonomously replicating sequences from plants. *Plant Mol Biol* 12, 507-516, doi:10.1007/BF00036965 (1989).
30. Kowalski, D. & Eddy, M. J. The DNA unwinding element: a novel, cis-acting component that facilitates opening of the *Escherichia coli* replication origin. *EMBO J* 8, 4335-4344 (1989).
31. Snyder, M., Buchman, A. R. & Davis, R. W. Bent DNA at a Yeast Autonomously Replicating Sequence. *Nature* 324, 87-89, doi:DOI 10.1038/324087a0 (1986).

The foregoing is illustrative of the present invention, and is not to be construed as limiting thereof. The invention is defined by the following claims, with equivalents of the claims to be included therein.

That which is claimed is:

1. A circular and self-replicating plant vector comprising:
   a first tethering nucleic acid and a second tethering nucleic acid;
   a transgenic nucleic acid encoding a polynucleotide of interest (POI);
   a nucleic acid comprising an origin of replication; and
   two or more nucleic acids encoding replicon proteins; wherein
   the first tethering nucleic acid comprises a sequence having at least 99% sequence identity to the nucleotide sequence of SEQ ID NO:1;
   the second tethering nucleic acid comprises a sequence having at least 99% sequence identity to the nucleotide sequence of SEQ ID NO:2;
   the nucleic acid comprising an origin of replication comprises a sequence having at least 99% sequence identity to the nucleotide sequence of SEQ ID NO:9; and
   the two or more nucleic acids encoding replicon proteins comprise sequences having at least 99% sequence identity to any one or more of the nucleotide sequences of SEQ ID NO:3-8, in any combination.

2. The circular and self-replicating plant vector comprising of claim 1, wherein the vector comprises 5' to 3', the first tethering nucleic acid, a first nucleic acid encoding a replicon protein; the second tethering nucleic acid, a second nucleic acid encoding a replicon protein, and the nucleic acid comprising an origin of replication.

3. The circular and self-replicating plant vector comprising of claim 2, wherein the vector further comprises between the second nucleic acid encoding a replicon protein and the nucleic acid comprising an origin of replication, 5' to 3', a third nucleic acid encoding a replicon protein, a fourth nucleic acid encoding a replicon protein, a fifth nucleic acid encoding a replicon protein, a sixth nucleic acid encoding a replicon protein, and a seventh nucleic acid encoding a replicon protein.

4. The circular and self-replicating plant vector of claim 3, comprising 5' to 3',
   the first tethering nucleic acid having the nucleotide sequence of SEQ ID NO:1;
   the transgenic nucleic acid encoding a POI;
   the first nucleic acid encoding a replicon protein having the nucleotide sequence of any one of SEQ ID NOs: 3-8;
   the second tethering nucleic acid having the nucleotide sequence of SEQ ID NO:2;
   the third nucleic acid encoding a replicon protein having the nucleotide sequence of any one of SEQ ID NOs: 3-8;
   the fourth nucleic acid encoding a replicon protein having the nucleotide sequence of any one of SEQ ID NOs: 3-8;
   the fifth nucleic acid encoding a replicon protein having the nucleotide sequence of any one of SEQ ID NOs: 3-8;
   the sixth nucleic acid encoding a replicon protein having the nucleotide sequence of any one of SEQ ID NOs: 3-8;
   the seventh nucleic acid encoding a replicon protein having the nucleotide sequence of any one of SEQ ID NOs: 3-8; and
   the nucleic acid comprising an origin of replication having the nucleotide sequence of SEQ ID NO: 9.

5. The circular and self-replicating plant vector of claim 3, comprising 5' to 3',
   the first tethering nucleic acid having the nucleotide sequence of SEQ ID NO:1;
   the transgenic nucleic acid encoding a POI;
   the first nucleic acid encoding a replicon protein having the nucleotide sequence of SEQ ID NO: 3;
   the second tethering nucleic acid having the nucleotide sequence of SEQ ID NO:2;
   the second nucleic acid encoding a replicon protein having the nucleotide sequence of SEQ ID NO:3;
   the third nucleic acid encoding a replicon protein having the nucleotide sequence of SEQ ID NO:4;
   the fourth nucleic acid encoding a replicon protein having the nucleotide sequence of SEQ ID NO:5;
   the fifth nucleic acid encoding a replicon protein having the nucleotide sequence of SEQ ID NO:6;
   the sixth nucleic acid encoding a replicon protein having the nucleotide sequence of SEQ ID NO:7;
   the seventh nucleic acid encoding a replicon protein having the nucleotide sequence of SEQ ID NO:8; and
   the nucleic acid comprising an origin of replication having the nucleotide sequence of SEQ ID NO: 9.

6. The circular and self-replicating plant vector of claim 4, wherein the vector further comprises one or more linkers for linking at least two of SEQ ID NOs: 1-9.

7. The circular and self-replicating plant vector of claim 6, wherein
   the first tethering nucleic acid is linked via a first linker to the transgenic nucleic acid encoding a POI;
   the transgenic nucleic acid encoding a POI is linked via a second linker to the first nucleic acid encoding a replicon protein;
   the first nucleic acid encoding a replicon protein is linked via third linker to the second tethering nucleic acid;
   the second tethering nucleic acid is linked via a fourth linker to the second nucleic acid encoding a replicon protein;
   the second nucleic acid encoding a replicon protein is linked via a fifth linker to the third nucleic acid encoding a replicon protein;
   the third nucleic acid encoding a replicon protein is linked directly to the fourth nucleic acid encoding a replicon protein;
   the fourth nucleic acid encoding a replicon protein is linked via a sixth linker to the fifth nucleic acid encoding a replicon protein;
   the fifth nucleic acid encoding a replicon protein is linked via a seventh linker to the sixth nucleic acid encoding a replicon protein;
   the sixth nucleic acid encoding a replicon protein is linked via an eighth linker to the seventh nucleic acid encoding a replicon protein;
   the seventh nucleic acid encoding a replicon protein is linked via a ninth linker to the nucleic acid comprising an origin of replication; and
   the nucleic acid comprising an origin of replication is linked via a tenth linker to the first tethering nucleic acid.

8. The circular and self-replicating plant vector of claim 7, wherein first linker is SEQ ID NO:10, the second linker is SEQ ID NO:11, the third linker is SEQ ID NO:12 or SEQ ID NO:13, the fourth linker is SEQ ID NO:10 or SEQ ID NO:11, the fifth linker is SEQ ID NO:12 or SEQ ID NO:14, the sixth linker is SEQ ID NO: 15, the seventh linker is SEQ ID NO:16, the eighth linker is SEQ ID NO:17 or SEQ ID NO:18, the ninth linker is SEQ ID NO: 19 and the tenth linker is any one of SEQ ID NOs: 10-19.

9. The circular and self-replicating plant vector of claim 1, wherein the circular and self-replicating plant vector comprises two or more polynucleotides of interest.

10. A method of expressing a polynucleotide of interest in a plant or part thereof, the method comprising:
    introducing into the plant or part thereof the circular and self-replicating plant vector of claim 1, and
    selecting a plant or part thereof expressing the polynucleotide of interest.

11. A method of producing a plant cell expressing a polynucleotide of interest, the method comprising:
    introducing into a plant cell the circular and self-replicating plant vector of claim 1, thereby producing a plant cell comprising the polynucleotide of interest.

12. The method of claim 11, further comprising regenerating a plant from the plant cell to produce a plant expressing the polynucleotide of interest.

13. The method of claim 12, wherein the plant that is regenerated is stably transformed with the polynucleotide of interest.

14. The method of claim 10, wherein the vector comprising the polynucleotide of interest is tethered to the chromosome of the plant.

15. A stably transformed plant produced by the method of claim 13.

16. A stably transformed plant cell produced by the method of claim 11.

17. A seed of the plant of claim 15, wherein the seed comprises the vector comprising the polynucleotide of interest.

18. A product harvested from the stably transformed plant of claim 15, the product comprising the vector comprising the polynucleotide of interest.

19. A crop comprising a plurality of the stably transformed plant of claim 15.

20. The circular and self-replicating plant vector of claim 6, wherein the one or more linkers have a length in a range of about 10 nucleotides to about 100 nucleotides and/or the one or more linkers are the same or are different from one another, or any combination thereof.

21. The circular and self-replicating plant vector of claim 7, wherein each of the first linker, second linker, third linker, fourth linker, fifth linker, sixth linker, seventh linker, eighth linker, ninth linker, and tenth linker are selected from the group of nucleotide sequences of SEQ ID NOs: 10-19, in any combination.

22. The method of claim 10, wherein the method further comprises regenerating a plant from the part thereof expressing the polynucleotide of interest.

* * * * *

UNITED STATES PATENT AND TRADEMARK OFFICE
CERTIFICATE OF CORRECTION

PATENT NO. : 12,365,907 B2  
APPLICATION NO. : 17/433117  
DATED : July 22, 2025  
INVENTOR(S) : Christopher Saski Page 1 of 2

It is certified that error appears in the above-identified patent and that said Letters Patent is hereby corrected as shown below:

In the Specification

Column 18, Line 7: Please correct "CBL4/S0S3" to read --CBL4/SOS3--

Column 18, Line 31: Please correct "(NYEJ)" to read --(NYE1)--

Column 19, Line 45: Please correct "PYLS" to read --PYL5--

Column 30, Line 24: Please correct "kg.ai.ha-1" to read --kg·ai·ha-1--

Column 30, Line 28: Please correct "L.ha-1" to read --L·ha-1--

Column 30, Line 40: Please correct "kg.ai.ha-1" to read --kg·ai·ha-1--

Signed and Sealed this  
Eleventh Day of November, 2025

John A. Squires  
*Director of the United States Patent and Trademark Office*

CERTIFICATE OF CORRECTION (continued)
U.S. Pat. No. 12,365,907 B2

Column 35, Table 1, Row corresponding to Gene Apr_00008: Please delete the row corresponding to Gene Apr_00008 and replace with the following:

Table 1. Annotation of the eccDNA replicon.

| Gene | Start | Stop | Length | Orient-ation | pfam | Transmem-brane | Gene3D | SwissProt_Best_Hit | Uniref | NR | Arabidopsis_ortho |
|---|---|---|---|---|---|---|---|---|---|---|---|
| Apr_00008 | 10649 | 12631 | 1983 | - | Reverse transcriptase domain | | 0 | LINE-1 retrotransposable element ORF2 protein (ORF2p) (Long interspersed element-1) (L1) (Retrovirus-related Pol polyprotein LINE-1) [Includes: Reverse transcriptase (EC 2.7.7.49); Endonuclease (EC 3.1.21.-)] | LINE-1 retrotransposable element ORF2 protein (ORF2p) (Long interspersed element-1) (L1) (Retrovirus-related Pol polyprotein LINE-1) [Includes: Reverse transcriptase (EC 2.7.7.49); Endonuclease (EC 3.1.21.-)] | | |

Column 45, Table 1, Row corresponding to Gene Apr_00084: Please delete the row corresponding to Gene Apr_00084 and replace with the following:

Table 1. Annotation of the eccDNA replicon.

| Gene | Start | Stop | Length | Orient-ation | pfam | Transmem-brane | Gene3D | SwissProt_Best_Hit | Uniref | NR | Arabidopsis_ortho |
|---|---|---|---|---|---|---|---|---|---|---|---|
| Apr_00084 | 28611 | 3E+05 | 3802 | + | NAC domain | | | SUPPRESSOR OF GAMMA RESPONSE 1 (NAC domain-containing protein 8) (ANAC008) (Protein SOG1) (SUPPRESSOR OF GAMMA RADIATION 1) | SUPPRESSOR OF GAMMA RESPONSE 1 (NAC domain-containing protein 8) (ANAC008) (Protein SOG1) (SUPPRESSOR OF GAMMA RADIATION 1) | | AT1G25580.1 |

SEQUENCE LISTING

<160> NUMBER OF SEQ ID NOS: 20

<210> SEQ ID NO 1
<211> LENGTH: 12375
<212> TYPE: DNA
<213> ORGANISM: Amaranthus palmeri

<400> SEQUENCE: 1

| | | | | | |
|---|---|---|---|---|---|
| taatagacag | gtacaattaa | tttattagta | aattcaataa | ttagccaaat | tgtaggaatg | 60 |
| tcaagagtct | tgacaattga | ttcgtcatag | gagtatattt | ttacagacac | acaaaaccaa | 120 |
| aagccaaatt | gtagtaatgt | caagagtctt | gacgattggt | tcgtcaatcg | tcttatatta | 180 |
| tacactcatc | aaagcaaaag | cccgtctctt | tactcgaaaa | aataggaaag | taattgaaga | 240 |
| gaaatggatc | ggggttcgag | aacatgttcg | gtttcaatag | agacgttctc | tgcaccaaga | 300 |
| ttacactaat | tagcctaaat | ccaacatgag | tacaaattat | acccaaaaaa | ggttttcac | 360 |
| agacataaac | ataatggcaa | tggggttatg | gaatgttgtt | gtagacataa | gctatcattc | 420 |
| atccttctag | atcaacagaa | atatcaaaca | tcaaacttat | cattggcatt | gagctccagc | 480 |
| cgactttcag | agttacttga | cgtctcatgg | atactatggg | tgtcaacatg | agaaacctca | 540 |
| gcaatatcac | aaggcaggtc | acctgattcg | tcgtctgcga | ctgcatccat | tttccgctct | 600 |
| ccagcaacat | tttccagtcc | tgtactattt | ccagaatcca | tttcaatgtc | aatttgctct | 660 |
| tgtgggcat | attctagaga | cgcttcaaat | actcttgcac | cattttcaat | ttaacttaaa | 720 |
| ggatgggatt | ccaccagaac | agctgaatgg | atgtagttca | ttggctctgt | gtcctttgaa | 780 |
| ctggtatact | cgacaagatt | tttcttatca | acactatcag | ttgtatcatg | catctcatta | 840 |
| accaaatctt | ttgatgttgt | tccctctacc | tcaacctcct | gacttggagt | tgtgcaatga | 900 |
| tttatacatg | tactagacat | tcgtgttgct | atcttggttt | gtctttggaa | gagaataaag | 960 |
| gtgtgtaatt | atgttcaaca | agaatttttt | tacatacttt | ttcttgcatt | ttttttttgac | 1020 |
| ttttagttttt | tgttttgatg | gatgttggct | tcacttgaga | attttttgtgc | caattttttcc | 1080 |
| atgttttact | tgcttttagg | cagtcaatat | ggtcggtatg | tgaaaggact | cgactcattt | 1140 |
| agttttcttg | ctcatgtggt | gttatgttct | gcacaggaac | aagatgccgc | aagcttccaa | 1200 |
| gtaagccacc | tcataatcgt | atggtatgtt | gtgtaatttg | caaatgtggc | ccttcttttg | 1260 |
| accataaacc | acgtgcccct | ctttattcat | tgaggggtca | cattctgctt | cttttgtccc | 1320 |
| atcatcatag | catacatctt | ccccataaat | taaagtagta | ggggtaataa | catgtttaga | 1380 |
| attagttggt | tttaaaattt | caatatcatc | ttcaataaat | tgtacctagg | gtaaatacaa | 1440 |
| aataaaagac | aggtacaatt | aatttattag | taaattcaat | aattagccaa | attgtaggaa | 1500 |
| tgtcaagagt | cttgacaatt | gattcgtcat | aggagtatat | ttttacagac | acacaaaacc | 1560 |
| aaaagccaaa | ttgtagtaat | gtcaagagtc | ttgacgattg | gttcgtcaat | cgtcttatat | 1620 |
| tacactcatc | aaagcaaaag | cccgtctctt | tacttgaaga | aataggaaag | taattgaaga | 1680 |
| gaaatggatc | ggggttcgag | aacatgttgg | gtttctgtct | caaaagagac | gtttgagtga | 1740 |
| gataactcac | tctcctcttc | atcttccatt | ttaattaaat | tagggatctg | acctgggttg | 1800 |
| tcttcattct | caccatggtt | gccggtggtg | ttttgggtta | cagaaaaacc | gatggctgct | 1860 |
| cttccttctt | tactttgatc | tgacctgggt | tgtcttcact | ctcctcttca | tcttccatt | 1920 |
| ttttttattt | tttttttctga | atttttttttt | caaactgggg | gtacaactgt | acccccttgt | 1980 |
| cacttaattg | ggtccgccca | tgtaatagac | aggtacaatt | aatttattag | taaattcaat | 2040 |
| aattagccaa | attgtaggaa | tgtcaagagt | cttgacaatt | gattcgttat | aggagtatat | 2100 |

| | | | | |
|---|---|---|---|---|
| ttttacagac | acacaaaacc | aaaagccaaa | ttgtagtaat | gtcaagagtc ttgacgattg | 2160 |
| gttcgtcaat | cgtcttatat | tatacactca | tcaaagcaaa | agcccgtctc tttactcgaa | 2220 |
| aaaataggaa | agtaattgaa | gagaaatgga | tcggggttcg | agaacatgtt gggtttctgt | 2280 |
| ctcaaaagag | acgttctctg | caccaagatt | acactaatta | gcctaaatcc aacatgagta | 2340 |
| caaattatac | ccaaaaaagg | ttttttcacag | acataaacat | aatggcaatg gggttatgga | 2400 |
| atgttgttgt | agacataagc | tatcattcat | ccttctagat | caacagaaat atcaaacatc | 2460 |
| aaacttacca | tcattggcat | tgagctccag | ccgactttca | gagttacttg acgtctcatg | 2520 |
| gatactatgg | gtgtcaacat | gagaaacctc | agcaatatca | caaggcaggt cacctgattc | 2580 |
| gtcgtctgcg | actgcatcca | ttttccgctc | tccagcaaca | ttttccagtc ctgtactatt | 2640 |
| tccagaatcc | atttcaatgt | caatttgctc | ttgtggggca | tattctagag acgcttcaaa | 2700 |
| tactcttgca | ccattttcaa | tttcacttaa | aggatgggat | tccaccagaa cagctgaatg | 2760 |
| gatgtagttc | attggctctg | tgtcctttga | actggtatac | tcgacaagat ttttcttatc | 2820 |
| aacactatca | gttgtatcat | gcatctcatt | aaccaaatct | tttgatgttg ttccctctac | 2880 |
| ctcaacctcc | tgacttggag | ttgtgcaatg | atttatacat | gtactagaca ttcgtgttgc | 2940 |
| tatcttggtt | tgtctttgga | agagaataaa | ggtgtgtaat | tatgttcaac aagaatttttt | 3000 |
| ttacatactt | ttttcttgca | tttttttttttt | tgacttttag | tttttgtttt gatggatgtt | 3060 |
| ggcttcactt | gagaattttt | gtgccaattt | ttccatgttt | tacttgcttt taggcagtca | 3120 |
| atatggtcgg | tatgtgaaag | gactcgactc | atttagtttt | cttgctcatg tggtgttatg | 3180 |
| ttctgcacag | gaacaagatg | ccgcaagctt | ccaagtaagc | cacctcatat tcgtatggta | 3240 |
| tgttgtgtaa | tttgcaaatg | tgatgtggcc | cttcttttga | cataagccaa cgtgcccctc | 3300 |
| tttattcatt | gaggggtcac | attctgcttc | ttttgtccca | tcatcatagc atacatcttc | 3360 |
| cccataaatt | aaagtagtag | gggtaataac | atgtttagaa | ttagttggtt ttaaaatttc | 3420 |
| aatatcatct | tcaataaatt | gtacctaggg | taaataaaca | ataaaagaca ggtacaatta | 3480 |
| atttattagt | aaattcaata | attagccaaa | ttgtaggaat | gtcaagagtc ttgacaattg | 3540 |
| attcgtcata | ggaatatatt | tttacagaca | cacaaaacca | aagccaaatt gtagtaatgt | 3600 |
| caagagtctt | gacgattggt | tcgtcaatcg | tcttatatta | cactcatcaa agcaaaagcc | 3660 |
| cgtctcttta | cttgaagaaa | taggaaagta | attgaaatga | aatggatcgg ggttcgagaa | 3720 |
| catgttgggt | ttctgtctca | aaagagacgt | ttgagtgaga | taactcactc tcctcttcat | 3780 |
| cttccattttt | aattaaatta | gggatctgac | ctgggttgtc | ttcattctca ccatggttgc | 3840 |
| cggtggtgtt | ttgggttaca | gaaaaaccga | tggttgctct | tccttcttta ctttgatctg | 3900 |
| acatggggttg | tcttcactct | cctcttcatc | ttccatttttt | tttttatttt tttttctgaa | 3960 |
| tttttttttca | aactgggggt | acaactgtac | cccttgtca | cttaattggg tccgcccatg | 4020 |
| taatagacag | gtacaattaa | tttattagta | aattcaataa | ttagccaaat tgtaggaatg | 4080 |
| tcaagagtct | tgacaattga | ttcgtcatag | gagtatattt | ttacagacac acaaaaccaa | 4140 |
| aagccaaatt | gtagtaatgt | caagagtctt | gacgattggt | tcgtcaatcg tcttatatta | 4200 |
| tacactcatc | aaagcaaaag | cccgtctctt | tactcgaaaa | aataggaaag taattgaaga | 4260 |
| gaaatggatc | ggggttcgag | aacatgttgg | gtttctgtct | caaagagac gttctctgca | 4320 |
| ccaagattac | actaattagc | ctaaatccaa | catgagtaca | aattataccc aaaaaaggtt | 4380 |
| tttcacagac | ataaacataa | tggcaatggg | gttatggaat | gttgttgtag acataagcta | 4440 |

-continued

```
tcattcatcc ttctagatca acagaaatat caaacatcaa acttaccatc attggcattg    4500
agctccagcc gactttcaga gttacttgac gtctcatgga tactatgggt gtcaacatga    4560
gaaacctcag caatatcaca aggcaggtca cctgattcgt cgtctgcgac tgcatccatt    4620
ttccgctctc cagcaacatt ttccagtcct gtactatttc cagaatccat ttcactgtca    4680
atttgctctt gtggggcata ttctagagac gcttcaaata ctcttgcacc attttcaatt    4740
tcacttaaag gatgggattc caccagaaca gctgaatgga tgtagttcat tggctctgtg    4800
tcctttgaac tggtatactc gacaagattt ttcttatcaa cactatcagt tgtatcatgc    4860
atctcattaa ccaaatcttt taatgttgtt ccctctacct caacctcctg acttggagtt    4920
gtgcaatgat ttatacatgt actagacatt cgtgttgcta tcttggtttg tctttggaag    4980
agaataaagg tgtgtaatta tgttcaacaa gaattttttt acatactttt ttcttgcatt    5040
ttttttttga cttttagttt ttgttttgat ggatgttggc ttcacttgag aattttttgtg   5100
ccaattttc catgttttac ttgcttttag gcagtcaata tggtcggtat gtgaaaggac     5160
tcgactcatt tagttttctt gctcatgtgg tgttatgttc tgcacaggaa caagatgccg    5220
caagcttcca gtaagccac ctcataatcg tatggtaagt tgtgtaattt gcaaatgtga     5280
tgtggcccctt cttttgacca taagccacgt gcccctcttt attcattgag gggtcacatt   5340
ctgcttcttt tgtcccatca tcatagcata catcttcccc ataaattaaa gtagtagggg    5400
taataacatg tttagaatta gttggtttta aaatttcaat atcatcttca ataaattgta    5460
cctagggtaa ataaacaata aaagacaggt acaattaatt tattagtaaa tgcaataatt    5520
agccaaattg taggaatgtc aagagtcttg acaattgatt cgtcatagga gtatatttt    5580
acagacacac aaaaccaaaa gccaaattgt agtaatgtca agagtcttga cgattggttc    5640
gtcaatcgtc ttatattaca ctcatcaaag caaaagcccg tctctttact tgaagaaata    5700
ggaaagtaat tgaagagaaa tggatcgggg ttcgagaaca tgttgggttt ctgtctcaaa    5760
agagacgttt gagtgagata actcactctc ctcttcatct tccatttaa ttaaattagg     5820
gatctgacct gggttgtctt cattctcacc atggttgccg gtggtgtttt gggttacaga    5880
aaaaccgatg gttgctcttc cttctttact ttgatctgac ctgggttgtc ttcactctcc    5940
tcttcatctt ccattttttt ttatttttt tttctgaatt tttttttcaaa ctgggggtac    6000
aactgtaccc ccttgtcact taattgggtc cgcccatgta atagacaggt acaattaatt    6060
tattagtaaa ttcaataatt agccaaattg taggaatgtc aagagtcttg acaattgatt    6120
cgtcatagga gtatatttt acagacacac aaaaccaaaa gccaaattgt agtaatgtca    6180
agagtcttga cgattggttc gtcaatcgtc ttatattata cactcatcaa agcaaaagcc    6240
cgtctcttta ctcgaaaaaa taggaaagta attgaagaga aatggatcgg ggttcgagaa    6300
catgttgggt ttctgtctca aaagagacgt tctctgcacc aagattacac taattagcct    6360
aaatccaaca tgagtacaaa ttatacccaa aaaggttttt tcacagacat aaacataatg    6420
gcaatggggt tatggaatgt tgttgtagac ataagctatc attcatcctt ctagatcaac    6480
agaaatatca acatcaaac ttaccatcat tggcattgag ctccagccga ctttcagagt     6540
tacttgacgc tcatagata ctatgggtgt caacatgaga aacctcagca atatcacaag     6600
gcaggtcacc tgattcgtcg tctgcgactg catccatttt ccgctctccg caacattttt   6660
ccagtcctgt actatttcca gaatccattt cactgtcaat ttgctcttgt ggggcatatt    6720
ctagagacgc ttcaaatact cttgcaccat tttcaatttc acttaaagga tgggattcca    6780
ccagaacagc tgaatggatg tagttcattg ctctgtgtc ctttgaactg gtatactcga     6840
```

```
caagattttt cttatcaaca ctatcagttg tatcatgcat ctcattaacc aaatcttttg   6900
atgttgttcc ctctacctca acctcctgac ttggagttgt gcaatgattt atacatgtac   6960
tagacattcg tgttgctatc ttggtttgtc tttggaagag aataaaggtg tgtaattatg   7020
ttcaacaaga attttttttac atactttttt cttgcatttt tttttttgact tttagttttt   7080 gttttgatgg atgttggctt cacttgagaa ttttttgtgcc aattttttcca tgttttactt   7140 gcttttaggc agtcaatatg gtcggtatgt gaaaggactc gactcattta gttttcttgc   7200
tcatgtggtg ttatgttctg cacaggaaca agatgccgca agcttccaag taagccacct   7260
cataatcgta tggtatgttg tgtaatttgc aaatgtgatg tggcccttct tttgaccata   7320
agccacgtgc ccctctatat tcattgaggg gtcacattct gcttcttttg tcccatcatc   7380
atagcataca tcttccccat aaattaaagt agtaggggta ataacatgtt tagaattagt   7440
tggttttaaa atttcaatat catcttcaat aaattgtacc tagggtaaat aaacaataaa   7500
agacaggtac aattaattta ttagtaaatt caataactag ccaaattgta ggaatgtcaa   7560
gagtcttgac aattgattcg tcataggagt atattttttac agacacacaa aaccaaaagc   7620
caaattgtag taatgtcaag agtcttgacg attggttcgt caatcgtctt atattacact   7680
catcaaagca aaagcccgtc tctttacttg aagaaatagg aaagtaattg aagagaaatg   7740
gatcggggtt cgagaacatg ttgggtttct gtctcaaaag agacgtttga gtgagataac   7800
tcactctcct cttcatcttc cattttaatt aaattaggga tctgacctgg ttgtcttca   7860 ttctcaccat ggttgccggt ggtgttttgg gttacagaaa aaccgatggc tgctcttcct   7920
tctttacttt gatctgacct gggttgtctt cactctcctc ttcatcttcc atttttttat   7980
tttttttttc tgaattttttt tttcaaactg ggggtacaac tgtaccccct tgtcacttaa   8040
ttgggtccgc catgtaatag acaggtacaa ttaatttatt agtaaattca ataattagcc   8100
aaattgtagt aatgtcaaga gtcttgacaa ttgattcgtt ataggagtat attttttacag   8160 acacacaaaa ccaaaagcca aattgtagta atgtcaagag tcttgacgat tggttcgtca   8220
atcgtcttat attatacact catcaaagca aaagcccgtc tctttactcg aaaaaatagg   8280
aaagtaattg aagagaaatg gatcggggtt cgagaacatg ttgggtttct gtctcaaaag   8340
agacgttctc tgcaccaaga ttacactaat tagcctaaat ccaacatgag tacaaattat   8400
acccaaaaaa ggttttttcac agacataaac ataatggcaa tggggttatg gaatgttgtt   8460
gtagacataa gctatcattc atccttctag atcaacagaa atatcaaaca tcaaacttac   8520
catcattggc attgagctcc agccgacttt cagagttact tgacgtctca tggatactat   8580
gggtgtcaac atgagaaacc tcagcaatat cacaaggcag gtcacctgat tcgtcgtctg   8640
cgactgcatc cattttccgc tctccagcaa cattttccag tcctgtacta tttccagaat   8700
ccatttcaat gtcaatttgc tcttgtgggg catattctag agacgcttca aatactcttg   8760
caccattttc aatttcactt aaaggatgag attccaccag aacagctgaa tggatgtagt   8820
tcattggctc tgtgtccttt gaactggtat actcgacaag attttttctta tcaacactat   8880 cagttgtatc atgcatctca ttaaccaaat cttttgatgt tgttccctct acctcaacct   8940
cctgacttgg agttgtgcaa tgattataac atgtactaga cattcgtgtt gctatcttgg   9000
tttgtctttg gaagagaata aaggtgtgta attatgttca acaagaattt ttttacatac   9060 ttttttcttgc attttttttt gacttttagt ttttgttttg atggatgttg gcttcacttg   9120 agaattttttg tgccaatttt tccatgtttt acttgctttt aggcagtcaa tatggtcggt   9180
```

-continued

```
atgtgaaagg actcgactca tttagttttc ttgctcatgt ggtgttatgt tctgcacagg    9240
aacaagatgc cgcaagcttc caagtaagcc acctcataat cgtatggtat gttgtgtaat    9300
ttgcaaatgt gatgtggccc ttcttttgac cataagccac gtgcccctct atattcattg    9360
aggggtcaca ttctgcttct tttgtcccat catcatagca tacatcttcc ccataaatta    9420
aagtagtagg ggtaataaca tgtttagaat tagttggttt taaaatttca atgtcatctt    9480
caataaattg tacctagggt aaataaacaa taaaagacag gtacaattaa tttattagta    9540
aattcaataa ctagccaaat tgtaggaatg tcaagagtct tgacaattga ttcgtcatag    9600
gagtatattt ttacagacac acaaaaccaa aagccaaatt gtagtaatgt caagagtctt    9660
gacgattggt tcgtcaatcg tcttatatta cactcatcaa agcaaaagcc cgtctcttta    9720
cttgaagaaa taggaaagta attgaagaga atggatcgg ggttcgagaa catgttgggt    9780
ttctgtctca aaagagacgt ttgagtgaga taactcactc tcctcttcat cttccatttt    9840
aattaaatta gggatctgac ctgggttgtc ttcattctca ccatggttgc cggtggtgtt    9900
ttgggttaca gaaaaaccga tggctgctct tccttcttta ctttgatctg acctgggttg    9960
tcttcactct cctcttcatc ttccattttt tttatttttt tttctgaatt tttttttcaaa   10020 ctgggggtac aactgtaccc ccttgtcact taattgggtc cgcccatgta atagacaggt   10080
acaattaatt tattagtaaa ttcaataatt agccaaattg tagtaatgtc aagagtcttg   10140
acaattgatt cgttatagga gtatttttt acagacacac aaaaccaaaa gccaaattgt   10200
agtaatgtca agagtcttga cgattggttc gtcaatcgtc ttatattata cactcatcaa   10260
agcaaaagcc cgtctcttta ctcgaaaaaa taggaaagta attgaagaga atggatcgg   10320 ggttcgagaa catgttgggt ttctgtctca aaagagacgt tctctgcacc aagattacac   10380
taattagcct aaatccaaca tgagtacaaa ttatacccaa aaaaggtttt tcacagacat   10440
aaacataatg gcaatggggt tatggaatgt tgttgtagac ataagctatc attcatcctt   10500
ctagatcaac agaaatatca aacatcaaac ttaccatcat tggcattgag ctccagccga   10560 cttcagagt tacttgacgt ctcatggata ctatgggtgt caacatgaga acctcagca   10620 atatcacaag gcaggtcacc tgattcgtcg tctgcgactg catccatttt ccgctctcca   10680
gcaacatttt ccagtcctgt actatttcca gaatccattt caatgtcaat ttgctcttgt   10740
ggggcatatt ctagagacgc ttcaaatact cttgcaccat tttcaatttc acttaaagga   10800
tgagattcca ccagaacagc tgaatggatg tagttcattg gctctgtgtc ctttgaactg   10860
gtatactcga caagatttt cttatcaaca ctatcagttg tatcatgcat ctcattaacc   10920
aaatcttttg atgttgttcc ctctacctca acctcctgac ttggagttgt gcaatgattt   10980
atacatgtac tagacattcg tgttgctatc ttggtttgtc tttggaagag aataaaggtg   11040
tgtaattatg ttcaacaaga atttttaca tactttttc ttgcattttt ttttgacttt   11100 tagttttgt tttgatggat gttggcttca cttgagaatt tttgtgccaa ttttccatg   11160 ttttacttgc ttttaggcag tcaatatggt cggtatgtga aaggactcga ctcatttagt   11220
tttcttgctc atgtggtgtt atgttctgca caggaacaag atgccgcaag cttccaagta   11280
agccacctca taatcgtatg gtatgttgtg taatttgcaa atgtgatgtg gcccttcttt   11340
tgaccataag ccacgtgccc ctctttattc attgaggggt cacattctgc ttcttttgtc   11400
ccatcatcat agcatacatc ttccccataa attaaagtag tagggtaat aacatgttta   11460 gaattagttg gttttaaaat ttcaatgtca tcttcaataa attgtaccta gggtaaataa   11520
acaataaaag acaggtacaa ttaatttatt agtaaattca ataattagcc aaattgtagg   11580
```

```
aatgtcaaga gtcttgacaa ttgattcgtc ataggagtat attttttacag acacacaaaa   11640 ccaaaagcca aattgtagta atgtcaagag tcttgacgat tggttcgtca atcgtcatat   11700
attacactca tcaaagcaaa agcccgtctc tttacttgaa gaaataggaa agtaattgaa   11760
gagaaatgga tcggggttcg agaacatgtt gggtttctgt ctcaaaagag acgtttgagt   11820
gagataactc actctcctct tcatcttcca ttttaattaa attagggatc tgacctgggt   11880
tgtcttcatt ctcaccatgg ttgccggtgg tgttttgggt tacagaaaaa ccgatggctg   11940
ctcttccttc tttactttga tctgacctgg gttgtcttca ctctcctctt catcttccat   12000 ttttttttatt tttttttctg aattttttttt caaactgggg gtacaactgt acccccttgt   12060
cacttaattg ggtccgccca tgtaatagac aggtacaatt aatttattag taaattcaat   12120
aattagccaa attgtaggaa tgtcaagagt cttgacaatt gattcgtcat aggagtatat   12180
ttttacagac acacaaaacc aaaagccaaa ttgtagtaat gtcaagagtc ttgacgattg   12240
gttcgtcaat cgtcttatat tatacactca tcaaagcaaa agcccgtctt tttactcgaa   12300
aaaataggaa agtaattgaa gagaaatgga tcggggttcg agaacatgtt gggtttctgt   12360
ctcaaaagag acgtt                                                    12375

<210> SEQ ID NO 2
<211> LENGTH: 18151
<212> TYPE: DNA
<213> ORGANISM: Amaranthus palmeri

<400> SEQUENCE: 2
aatagagacg ttctctgcac caagattaca ctaattagcc taaatccaac atgagtacaa     60 attatacccca aaaaggtttt ttcacagaca taaacataat ggcaatgggg ttatggaatg    120
ttgttgtaga cataagctat cattcatcct tctagatcaa cagaaatatc aaacatcaaa    180
cttatcattg gcattgagct ccagccgact ttcagagtta cttgacgtct catggatact    240
atgggtgtca acatgagaaa cctcagcaat atcacaaggc aggtcacctg attcgtcgtc    300
tgcgactgca tccatttttcc gctctccagc aacattttcc agtcctgtac tatttccaga    360
atccatttca atgtcaattt gctcttgtgg ggcatattcc agagacgctt caaatactct    420
tgcaccattt tcaatttaac ttaaaggatg ggattccacc agaacagctg aatggatgta    480
gttcattggc tctgtgtcct ttgaactggt atactcgaca agatttttct tatcaacact    540
atcagttgta tcatgcatct cattaaccaa atcttttgat gttgttccct ctacctcaac    600
ctcctgactt ggagttgtgc aatgatttat acatgtacta gacattcgtg ttgctatctt    660
ggtttgtctt tggaagagaa taaaggtgtg taattatgtt caacaagaat ttttttacat    720
acttttttct tgcatttttt tttgactttt agttttttgtt ttgatggatg ttggcttcac    780
ttgagaattt ttgtgccaat ttttccatgt tttacttgct tttaggcagt caatatggtc    840
ggtatgtgaa aggactcgac tcatttagtt ttccttgctca tgtggtgtta tgttctgcac    900
aggaacaaga tgccgcaagc ttccaagtaa gccacctcat aatcgtatgg tatgttgtgt    960
aatttgcaaa tgtggccctt cttttgacca taaaccacgt gcccctcttt attcattgag   1020
gggtcacatt ctgcttcttt tgtcccatca tcatagcata catcttcccc ataaattaaa   1080
gtagtagggg taataacatg tttagaatta gttggtttta aatttcaat atcatcttca   1140 ataaattgta cctagggtaa ataaacaata aaagacaggt acaattaatt tattagtaaa   1200
ttcaataatt agccaaattg taggaatgtc aagagtcttg acaattgatt cgtcatagga   1260
```

```
gtatattttt acagacacac aaaaccaaaa gccaaattgt agtaatgtca agagtcttga   1320
cgattggttc gtcaatcgtc ttatattaca ctcatcaaag caaaagcccg tctctttact   1380
tgaagaaata ggaaagtaat tgaagagaaa tggatcgggg ttcgagaaca tgttgggttt   1440
ctgtctcaaa agagacgttt gagtgagata actcactctc ctcttcatct tccatttta    1500
ttaaattagg gatctgacct gggttgtctt cattctcacc atggttgccg gtggtgtttt   1560
gggttacaga aaaaccgatg ctgctcttc cttctttact ttgatctgac ctgggttgtc    1620
ttcactctcc tcttcatctt ccatttttt ttatttttt ttctgaattt ttttcaaac      1680
tgggggtaca actgtacccc cttgtcactt aattgggtcc gcccatgtaa tagacaggta   1740
caattaattt attagtaaat tcaataatta gccaaattgt aggaatgtca agagtcttga   1800
caattgattc gttataggag tatattttta cagacacaca aaaccaaaag ccaaattgta   1860
gtaatgtcaa gagtcttgac gattggttcg tcaatcgtct tatattatac actcatcaaa   1920
gcaaaagccc gtctctttac tcgaaaaaat aggaaagtaa ttgaagagaa atggatcggg   1980
gttcgagaac atgttgggtt tctgtctcaa agagacgtt ctctgcacca agattacact    2040
aattagccta aatccaacat gagtacaaat tatacccaaa aaaggttttt cacagacata   2100
aacataatgg caatggggtt atggaatgtt gttgtagaca taagctatca ttcatccttc   2160
tagatcaaca gaaatatcaa acatcaaact taccatcatt ggcattgagc tccagccgac   2220
tttcagagtt acttgacgtc tcatggatac tatgggtgtc aacatgagaa acctcagcaa   2280
tatcacaagg caggtcacct gattcgtcgt ctgcgactgc atccattttc cgctctccag   2340
caacatttc cagtcctgta ctatttccag aatccatttc aatgtcaatt tgctcttgtg    2400
gggcatattc tagagacgct tcaaatactc ttgcaccatt tcaatttca cttaaaggat    2460
gggattccac cagaacagct gaatggatgt agttcattgg ctctgtgtcc tttgaactgg   2520
tatactcgac aagatttttc ttatcaacac tatcagttgt atcatgcatc tcattaacca   2580
aatcttttga tgttgttccc tctacctcaa cctcctgact tggagttgtg caatgattta   2640
tacatgtact agacattcgt gttgctatct tggtttgtct ttggaagaga ataaaggtgt   2700
gtaattatgt tcaacaagaa tttttttacat acttttttct tgcattttt ttttgactt    2760
ttagttttg ttttgatgga tgttggcttc acttgagaat ttttgtgcca attttccat    2820
gtttacttg cttttaggca gtcaatatgg tcggtatgtg aaaggactcg actcatttag    2880
ttttcttgct catgtggtgt tatgttctgc acaggaacaa gatgccgcaa gcttccaagt   2940
aagccacctc atattcgtat ggtatgttgt gtaatttgca aatgtgatgt ggcccttctt   3000
ttgaccataa gccacgtgcc cctctttatt cattgagggg tcacattctg cttctttgt    3060
cccatcatca tagcatacat cttccccata aattaaagta gtagggtaa taacatgttt    3120
agaattagtt ggttttaaaa tttcaatatc atcttcaata aattgtacct agggtaaata   3180
aacaataaaa gacaggtaca attaatttat tagtaaattc aataattagc caaattgtag   3240
gaatgtcaag agtcttgaca attgattcgt cataggaata tattttaca gacacacaaa    3300
accaaagcca aattgtagta atgtcaagag tcttgacgat tggttcgtca atcgtcttat   3360
attacactca tcaaagcaaa agcccgtctc tttacttgaa gaataggaa agtaattgaa    3420
atgaaatgga tcggggttcg agaacatgtt gggtttctgt ctcaaaagag acgtttgagt   3480
gagataactc actctcctct tcatcttcca ttttaattaa attagggatc tgacctgggt   3540
tgtcttcatt ctcaccatgg ttgccggtgg tgttttgggt tacagaaaaa ccgatggttg   3600
ctcttccttc tttactttga tctgacatgg gttgtcttca ctctcctctt catcttccat   3660
```

```
tttttttttat ttttttttct gaattttttt tcaaactggg ggtacaactg taccccttg    3720
tcacttaatt gggtccgccc atgtaataga caggtacaat taatttatta gtaaattcaa    3780
taattagcca aattgtagga atgtcaagag tcttgacaat tgattcgtca taggagtata    3840
tttttacaga cacacaaaac caaaagccaa attgtagtaa tgtcaagagt cttgacgatt    3900
ggttcgtcaa tcgtcttata ttatacactc atcaaagcaa aagcccgtct ctttactcga    3960
aaaaatagga aagtaattga agagaaatgg atcggggttc gagaacatgt tgggtttctg    4020
tctcaaaaga gacgttctct gcaccaagat tacactaatt agcctaaatc caacatgagt    4080
acaaattata cccaaaaaag ttttttcaca gacataaaca taatggcaat ggggttatgg    4140
aatgttgttg tagacataag ctatcattca tccttctaga tcaacagaaa tatcaaacat    4200
caaacttacc atcattggca ttgagctcca gccgactttc agagttactt gacgtctcat    4260
ggatactatg ggtgtcaaca tgagaaacct cagcaatatc acaaggcagg tcacctgatt    4320
cgtcgtctgc gactgcatcc attttccgct ctccagcaac attttccagt cctgtactat    4380
ttccagaatc catttcactg tcaatttgct cttgtggggc atattctaga gacgcttcaa    4440
atactcttgc accattttca atttcactta aaggatggga ttccaccaga acagctgaat    4500
ggatgtagtt cattggctct gtgtcctttg aactggtata ctcgacaaga ttttcttat    4560
caacactatc agttgtatca tgcatctcat taaccaaatc ttttaatgtt gttccctcta    4620
cctcaacctc ctgacttgga gttgtgcaat gatttataca tgtactagac attcgtgttg    4680
ctatcttggt ttgtctttgg aagagaataa aggtgtgtaa ttatgttcaa caagaatttt    4740
ttacatactt ttttcttgca ttttttttg acttttagtt tttgttttga tggatgttgg    4800
cttcacttga gaattttgt gccaattttt ccatgtttta cttgctttta ggcagtcaat    4860
atggtcggta tgtgaaagga ctcgactcat ttagttttct tgctcatgtg gtgttatgtt    4920
ctgcacagga acaagatgcc gcaagcttcc aagtaagcca cctcataatc gtatggtaag    4980
ttgtgtaatt tgcaaatgtg atgtggccct tcttttgacc ataagccacg tgcccctctt    5040
tattcattga ggggtcacat tctgcttctt ttgtcccatc atcatagcat acatcttccc    5100
cataaattaa agtagtaggg gtaataacat gtttagaatt agttggtttt aaaatttcaa    5160
tatcatcttc aataaattgt acctagggta aataaacaat aaaagacagg tacaattaat    5220
ttattagtaa atgcaataat tagccaaatt gtaggaatgt caagagtctt gacaattgat    5280
tcgtcatagg agtatatttt tacagacaca caaaaccaaa agccaaattg tagtaatgtc    5340
aagagtcttg acgattggtt cgtcaatcgt cttatattac actcatcaaa gcaaaagccc    5400
gtctctttac ttgaagaaat aggaaagtaa ttgaagagaa atggatcggg gttcgagaac    5460
atgttgggtt tctgtctcaa aagagacgtt tgagtgagat aactcactct cctcttcatc    5520
ttccatttta attaaattag ggatctgacc tgggttgtct tcattctcac catggttgcc    5580
ggtggtgttt tgggttacag aaaaaccgat ggttgctctt ccttctttac tttgatctga    5640
cctgggttgt cttcactctc ctcttcatct tccatttttt tttattttt ttttctgaat    5700
tttttttcaa actgggggta caactgtacc cccttgtcac ttaattgggt ccgcccatgt    5760
aatagacagg tacaattaat ttattagtaa attcaataat tagccaaatt gtaggaatgt    5820
caagagtctt gacaattgat tcgtcatagg agtatatttt tacagacaca caaaaccaaa    5880
agccaaattg tagtaatgtc aagagtcttg acgattggtt cgtcaatcgt cttatattat    5940
acactcatca aagcaaaagc ccgtctcttt actcgaaaaa ataggaaagt aattgaagag    6000
```

```
aaatggatcg gggttcgaga acatgttggg tttctgtctc aaaagagacg ttctctgcac   6060
caagattaca ctaattagcc taaatccaac atgagtacaa attatacccca aaaaaggttt   6120 ttcacagaca taaacataat ggcaatgggg ttatggaatg ttgttgtaga cataagctat   6180
cattcatcct tctagatcaa cagaaatatc aaacatcaaa cttaccatca ttggcattga   6240
gctccagccg actttcagag ttacttgacg tctcatagat actatgggtg tcaacatgag   6300
aaacctcagc aatatcacaa ggcaggtcac ctgattcgtc gtctgcgact gcatccattt   6360
tccgctctcc ggcaacattt tccagtcctg tactatttcc agaatccatt tcactgtcaa   6420
tttgctcttg tggggcatat tctagagacg cttcaaatac tcttgcacca tttttcaattt   6480 cacttaaagg atgggattcc accagaacag ctgaatggat gtagttcatt ggctctgtgt   6540
cctttgaact ggtatactcg acaagatttt tcttatcaac actatcagtt gtatcatgca   6600
tctcattaac caaatctttt gatgttgttc cctctacctc aacctcctga cttggagttg   6660
tgcaatgatt tatacatgta ctagacattc gtgttgctat cttggtttgt ctttggaaga   6720
gaataaaggt gtgtaattat gttcaacaag aatttttttta catacttttt tcttgcattt   6780 ttttttttgac ttttagtttt tgttttgatg gatgttggct tcacttgaga attttttgtgc   6840 caatttttcc atgttttact tgcttttagg cagtcaaat ggtcggtatg tgaaaggact   6900
cgactcattt agttttcttg ctcatgtggt gttatgttct gcacaggaac aagatgccgc   6960
aagcttccaa gtaagccacc tcataatcgt atggtatgtt gtgtaatttg caaatgtgat   7020
gtggcccttc ttttgaccat aagccacgtg cccctctata ttcattgagg ggtcacattc   7080
tgcttctttt gtcccatcat catagcatac atcttcccca taaattaaag tagtaggggt   7140
aataacatgt ttagaattag ttggttttaa aatttcaata tcatcttcaa taaattgtac   7200
ctagggtaaa taaacaataa aagacaggta caattaattt attagtaaat tcaataacta   7260
gccaaattgt aggaatgtca agagtcttga caattgattc gtcataggag tatatttta   7320 cagacacaca aaaccaaaag ccaaattgta gtaatgtcaa gagtcttgac gattggttcg   7380
tcaatcgtct tatattacac tcatcaaagc aaaagcccgt ctctttactt gaagaaatag   7440
gaaagtaatt gaagagaaat ggatcggggt tcgagaacat gttgggtttc tgtctcaaaa   7500
gagacgtttg agtgagataa ctcactctcc tcttcatctt ccatttttaat taaattaggg   7560 atctgacctg ggttgtcttc attctcacca tggttgccgg tggtgttttg ggttacagaa   7620
aaaccgatgg ctgctcttcc ttctttactt tgatctgacc tgggttgtct tcactctcct   7680
cttcatcttc catttttta tttttttttt ctgaattttt tttcaaactg ggggtacaac   7740
tgtaccccct tgtcacttaa ttgggtccgc catgtaatag acaggtacaa ttaatttatt   7800
agtaaattca ataattagcc aaattgtagt aatgtcaaga gtcttgacaa ttgattcgtt   7860
ataggagtat attttacag acacacaaaa ccaaaagcca aattgtagta atgtcaagag   7920
tcttgacgat tggttcgtca atcgtcttat attatacact catcaaagca aaagcccgtc   7980
tctttactcg aaaaaatagg aaagtaattg aagagaaatg gatcggggtt cgagaacatg   8040
ttgggtttct gtctcaaaag agacgttctc tgcaccaaga ttacactaat tagcctaaat   8100
ccaacatgag tacaaattat acccaaaaaa ggttttttcac agacataaac ataatggcaa   8160
tggggttatg gaatgttgtt gtagacataa gctatcattc atccttctag atcaacagaa   8220
atatcaaaca tcaaacttac catcattggc attgagctcc agccgacttt cagagttact   8280
tgacgtctca tggatactat gggtgtcaac atgagaaacc tcagcaatat cacaaggcag   8340
gtcacctgat tcgtcgtctg cgactgcatc cattttccgc tctccagcaa cattttccag   8400
```

```
tcctgtacta tttccagaat ccatttcaat gtcaatttgc tcttgtgggg catattctag    8460
agacgcttca aatactcttg caccattttc aatttcactt aaaggatgag attccaccag    8520
aacagctgaa tggatgtagt tcattggctc tgtgtccttt gaactggtat actcgacaag    8580 attttctta tcaacactat cagttgtatc atgcatctca ttaaccaaat cttttgatgt     8640
tgttccctct acctcaacct cctgacttgg agttgtgcaa tgatttatac atgtactaga    8700
cattcgtgtt gctatcttgg tttgtctttg gaagagaata aggtgtgta attatgttca     8760 acaagaattt tttacatact ttttctttgc attttttttt gacttttagt ttttgttttg    8820
atggatgttg gcttcacttg agaattttg tgccaatttt tccatgtttt acttgctttt     8880
aggcagtcaa tatggtcggt atgtgaaagg actcgactca tttagttttc ttgctcatgt    8940
ggtgttatgt tctgcacagg aacaagatgc cgcaagcttc caagtaagcc acctcataat    9000
cgtatggtat gttgtgtaat ttgcaaatgt gatgtggccc ttcttttgac cataagccac    9060
gtgcccctct atattcattg aggggtcaca ttctgcttct tttgtcccat catcatagca    9120
tacatcttcc ccataaatta aagtagtagg ggtaataaca tgtttagaat tagttggttt    9180
taaaatttca atgtcatctt caataaattg tacctaggga aaataaacaa taaaagacag    9240
gtacaattaa tttattagta aattcaataa ctagccaaat tgtaggaatg tcaagagtct    9300
tgacaattga ttcgtcatag gagtatattt ttacagacac acaaaaccaa aagccaaatt    9360
gtagtaatgt caagagtctt gacgattggt tcgtcaatcg tcttatatta cactcatcaa    9420
agcaaaagcc cgtctcttta cttgaagaaa taggaaagta attgaagaga aatggatcgg    9480
ggttcgagaa catgttgggt ttctgtctca aaagagacgt ttgagtgaga taactcactc    9540
tcctcttcat cttccatttt aattaaatta gggatctgac ctgggttgtc ttcattctca    9600
ccatggttgc cggtggtgtt ttgggttaca gaaaaaccga tggctgctct tccttcttta    9660
ctttgatctg acctgggttg tcttcactct cctcttcatc ttccatttt tttattttt     9720 tttctgaatt tttttcaaa ctgggggtac aactgtaccc ccttgtcact taattgggtc    9780
cgcccatgta atagacaggt acaattaatt tattagtaaa ttcaataatt agccaaattg    9840
tagtaatgtc aagagtcttg acaattgatt cgttatagga gtatatttt acagacacac    9900 aaaaccaaaa gccaaattgt agtaatgtca agagtcttga cgattggttc gtcaatcgtc    9960
ttatattata cactcatcaa agcaaaagcc cgtctcttta ctcgaaaaaa taggaaagta    10020
attgaagaga aatggatcgg ggttcgagaa catgttgggt ttctgtctca aaagagacgt    10080
tctctgcacc aagattacac taattagcct aaatccaaca tgagtacaaa ttatacccaa    10140
aaaaggtttt tcacagacat aaacataatg gcaatggggt tatggaatgt tgttgtagac    10200
ataagctatc attcatcctt ctagatcaac agaaatatca aacatcaaac ttaccatcat    10260
tggcattgag ctccagccga ctttcagagt tacttgacgt tcatggata ctatgggtgt     10320 caacatgaga aacctcagca atatcacaag gcaggtcacc tgattcgtcg tctgcgactg    10380
catccatttt ccgctctcca gcaacatttt ccagtcctgt actatttcca gaatccattt    10440
caatgtcaat ttgctcttgt ggggcatatt ctagagacgc ttcaaatact cttgcaccat    10500
tttcaatttc acttaaagga tgagattcca ccagaacagc tgaatggatg tagttcattg    10560
gctctgtgtc ctttgaactg gtatactcga caagattttt cttatcaaca ctatcagttg    10620
tatcatgcat ctcattaacc aaatcttttg atgttgttcc ctctacctca acctcctgac    10680
ttggagttgt gcaatgattt atacatgtac tagacattcg tgttgctatc ttggtttgtc    10740
```

```
tttggaagag aataaaggtg tgtaattatg ttcaacaaga attttttac atactttttt    10800
cttgcatttt tttttgactt ttagttttg ttttgatgga tgttggcttc acttgagaat    10860
ttttgtgcca attttccat gttttacttg cttttaggca gtcaatatgg tcggtatgtg    10920
aaaggactcg actcatttag ttttcttgct catgtggtgt tatgttctgc acaggaacaa    10980
gatgccgcaa gcttccaagt aagccacctc ataatcgtat ggtatgttgt gtaatttgca    11040
aatgtgatgt ggcccttctt ttgaccataa gccacgtgcc cctctttatt cattgagggg    11100
tcacattctg cttcttttgt cccatcatca tagcatacat cttccccata aattaaagta    11160
gtaggggtaa taacatgttt agaattagtt ggttttaaaa tttcaatgtc atcttcaata    11220
aattgtacct agggtaaata aacaataaaa gacaggtaca attaatttat tagtaaattc    11280
aataattagc caaattgtag gaatgtcaag agtcttgaca attgattcgt cataggagta    11340
tattttaca gacacacaaa accaaaagcc aaattgtagt aatgtcaaga gtcttgacga    11400
ttggttcgtc aatcgtcata tattacactc atcaaagcaa aagcccgtct ctttacttga    11460
agaaatagga aagtaattga agagaaatgg atcggggttc gagaacatgt tgggtttctg    11520
tctcaaaaga gacgtttgag tgagataact cactctcctc ttcatcttcc atttttaatta    11580
aattagggat ctgacctggg ttgtcttcat tctcaccatg gttgccggtg gtgttttggg    11640
ttacagaaaa accgatggct gctcttcctt ctttactttg atctgacctg ggttgtcttc    11700
actctcctct tcatcttcca tttttttta ttttttttt ctgaattttt ttttcaaact    11760
gggggtacaa ctgtaccccc ttgtcactta attgggtccg cccatgtaat agacaggtac    11820
aattaattta ttagtaaatt caataattag ccaaattgta ggaatgtcaa gagtcttgac    11880
aattgattcg tcataggagt atattttac agacacacaa aaccaaaagc caaattgtag    11940
taatgtcaag agtcttgacg attggttcgt caatcgtctt atattataca ctcatcaaag    12000
caaaagcccg tctctttact cgaaaaaata ggaaagtaat tgaagagaaa tggatcgggg    12060
ttcgagaaca tgttgggttt ctgtctcaaa agagacgttc tctgcaccaa gattacacta    12120
attagcctaa atccaacatg agtacaaatt atacccaaaa aaggttttc acagacataa    12180
acataatggc aatgggtta tggaatgttg ttgtagacat aagctatcat tcatccttct    12240
agatcaacag aaatatcaaa catcaaactt accatcattg gcattgagct ccagccgact    12300
ttcagagtta cttgacgtct catagatact atgggtgtca acatgagaaa cctcagcaat    12360
atcacaaggc aggtcacctg attcgtcgtc tgcgactgca tccattttcc gctctccggc    12420
aacatttcc agtcctgtac tatttccaga atccatttca ctgtcaattt gctcttgtgg    12480
ggcatattct agagacgctt caaatactct tgcaccattt tcaatttcac ttaaaggatg    12540
ggattccacc agaacagctg aatggatgta gttcattggc tctgtgtcct ttgaactggt    12600
atactcgaca agatttttct tatcaacact atcagttgta tcatgcatct cattaaccaa    12660
atcttttgat gttgttccct ctacctcaac ctcctgactt ggagttgtgc aatgatttat    12720
acatgtacta gacattcgtg ttgctatctt ggtttgtctt tggaagagaa taaaggtgtg    12780
taattatgtt caacaagaat tttttacat actttttct tgcattttt ttttgacttt    12840
tagttttgt tttgatggat gttggcttca cttgagaatt tttgtgccaa tttttccatg    12900
ttttacttgc ttttaggcag tcaatatggt cggtatgtga aaggactcga ctcatttagt    12960
ttcttgctc atgtggtgtt atgttctgca caggaacaag atgccgcaag cttccaagta    13020
agccacctca taatcgtatg gtatgttgtg taatttgcaa atgtgatgtg gcccttcttt    13080
tgaccataag ccacgtgccc ctctatattc attgagggt cacattctgc ttcttttgtc    13140
```

```
ccatcatcat agcatacatc ttccccataa attaaagtag tagggtaat  aacatgttta  13200
gaattagttg gttttaaaat ttcaatatca tcttcaataa attgtaccta gggtaaataa  13260
acaataaaag acaggtacaa ttaatttatt agtaaattca ataactagcc aaattgtagg  13320
aatgtcaaga gtcttgacaa ttgattcgtc ataggagtat attttacag  acacacaaaa  13380
ccaaaagcca aattgtagta atgtcaagag tcttgacgat tggttcgtca atcgtcttat  13440
attacactca tcaaagcaaa agcccgtctc tttacttgaa gaaataggaa agtaattgaa  13500
gagaaatgga tcggggttcg agaacatgtt gggtttctgt ctcaaaagag acgtttgagt  13560
gagataactc actctcctct tcatcttcca ttttaattaa attagggatc tgacctgggt  13620
tgtcttcatt ctcaccatgg ttgccggtgg tgttttgggt tacagaaaaa ccgatggctg  13680
ctcttccttc tttactttga tctgacctgg gttgtcttca ctctcctctt catcttccat  13740
ttttttatt  ttttttttctg aatttttttt  tcaaactggg ggtacaactg taccccttg   13800
tcacttaatt gggtccgcca tgtaatagac aggtacaatt aatttattag taaattcaat  13860
aattagccaa attgtagtaa tgtcaagagt cttgacaatt gattcgttat aggagtatat  13920
ttttacagac acacaaaacc aaaagccaaa ttgtagtaat gtcaagagtc ttgacgattg  13980
gttcgtcaat cgtcttatat tatacactca tcaaagcaaa agcccgtctc tttactcgaa  14040
aaaataggaa agtaattgaa gagaaatgga tcggggttcg agaacatgtt gggtttctgt  14100
ctcaaaagag acgttctctg caccaagatt acactaatta gcctaaatcc aacatgagta  14160
caaattatac ccaaaaaagg ttttcacag  acataaacat aatggcaatg gggttatgga  14220
atgttgttgt agacataagc tatcattcat ccttctagat caacagaaat atcaaacatc  14280
aaacttacca tcattggcat tgagctccag ccgactttca gagttacttg acgtctcatg  14340
gatactatgg gtgtcaacat gagaaacctc agcaatatca caaggcaggt cacctgattc  14400
gtcgtctgcg actgcatcca ttttccgctc tccagcaaca ttttccagtc ctgtactatt  14460
tccagaatcc atttcaatgt caatttgctc ttgtggggca tattctagag acgcttcaaa  14520
tactcttgca ccattttcaa tttcacttaa aggatgagat tccaccagaa cagctgaatg  14580
gatgtagttc attggctctg tgtcctttga actggtatac tcgacaagat ttttcttatc  14640
aacactatca gttgtatcat gcatctcatt aaccaaatct tttgatgttg ttccctctac  14700
ctcaacctcc tgacttggag ttgtgcaatg atttatacat gtactagaca ttcgtgttgc  14760
tatcttggtt tgtctttgga agagaataaa ggtgtgtaat tatgttcaac aagaattttt  14820
ttacatactt ttttcttgca ttttttttt   gacttttagt ttttgttttg atggatgttg  14880
gcttcacttg agaattttg  tgccaatttt tccatgtttt acttgctttt aggcagtcaa  14940
tatggtcggt atgtgaaagg actcgactca tttagtttc  ttgctcatgt ggtgttatgt  15000
tctgcacagg aacaagatgc cgcaagcttc caagtaagcc acctcataat cgtatggtat  15060
gttgtgtaat ttgcaaatgt gatgtggccc ttcttttgac cataagccac gtgcccctct  15120
atattcattg aggggtcaca ttctgcttct tttgtcccat catcatagca tacatcttcc  15180
ccataaatta aagtagtagg ggtaataaca tgtttagaat tagttggttt taaaatttca  15240
atgtcatctt caataaattg tacctagggt aaataaacaa taaagacag  gtacaattaa  15300
tttattagta aattcaataa ctagccaaat tgtaggaatg tcaagagtct tgacaattga  15360
ttcgtcatag gagtatattt ttacagacac acaaaccaa  aagccaaatt gtagtaatgt  15420
caagagtctt gacgattggt tcgtcaatcg tcttatatta cactcatcaa agcaaaagcc  15480
```

```
cgtctctttta cttgaagaaa taggaaagta attgaagaga aatggatcgg ggttcgagaa    15540
catgttgggt ttctgtctca aaagagacgt ttgagtgaga taactcactc tcctcttcat    15600
cttccatttt aattaaatta gggatctgac ctggttgtc ttcattctca ccatggttgc     15660
cggtggtgtt ttgggttaca gaaaaaccga tggctgctct tccttcttta ctttgatctg    15720 acctggggttg tcttcactct cctcttcatc ttccattttt ttattttttt tttctgaatt   15780
tttttttcaa actgggggta caactgtacc cccttgtcac ttaattgggt ccgcccatgt    15840
aatagacagg tacaattaat ttattagtaa attcaataat tagccaaatt gtagtaatgt    15900
caagagtctt gacaattgat tcgttatagg agtatatttt tacagacaca caaaaccaaa   15960
agccaaattg tagtaatgtc aagagtcttg acgattggtt cgtcaatcgt cttatattat    16020
acactcatca aagcaaaagc ccgtctcttt actcgaaaaa ataggaaagt aattgaagag    16080
aaatggatcg gggttcgaga acatgttggg tttctgtctc aaaagagacg ttctctgcac    16140
caagattaca ctaattagcc taaatccaac atgagtacaa attataccca aaaaaggttt    16200
ttcacagaca taaacataat ggcaatgggg ttatggaatg ttgttgtaga cataagctat    16260
cattcatcct tctagatcaa cagaaatatc aaacatcaaa cttaccatca ttggcattga    16320
gctccagccg actttcagag ttacttgacg tctcatggat actatgggtg tcaacatgag    16380
aaacctcagc aatatcacaa ggcaggtcac ctgattcgtc gtctgcgact gcatccattt    16440
tccgctctcc agcaacattt tccagtcctg tactatttcc agaatccatt tcaatgtcaa    16500
tttgctcttg tggggcatat tctagagacg cttcaaatac tcttgcacca ttttcaattt   16560
cacttaaagg atgagattcc accagaacag ctgaatggat gtagttcatt ggctctgtgt    16620
cctttgaact ggtatactcg acaagatttt tcttatcaac actatcagtt gtatcatgca   16680
tctcattaac caaatctttt gatgttgttc cctctacctc aacctcctga cttggagttg    16740
tgcaatgatt tatacatgta ctagacattc gtgttgctat cttggtttgt ctttggaaga    16800
gaataaaggt gtgtaattat gttcaacaag aattttttta catactttt tcttgcattt     16860 ttttttgac ttttagtttt tgttttgatg gatgttggct tcacttgaga atttttgtgc    16920 caattttcc atgttttact tgcttttagg cagtcaatat ggtcggtatg tgaaaggact    16980
cgactcattt agttttcttg ctcatgtggt gttatgttct gcacaggaac aagatgccgc    17040
aagcttccaa gtaagccacc tcataatcgt atggtatgtt gtgtaatttg caatgtgat    17100 gtggcccttc ttttgaccat aagccacgtg cccctcttta ttcattgagg ggtcacattc    17160
tgcttctttt gtcccatcat catagcatac atcttcccca taaattaaag tagtaggggt   17220
aataacatgt ttagaattag ttggttttaa aatttcaatg tcatcttcaa taaattgtac    17280
ctagggtaaa taaacaataa aagacaggta caattaattt attagtaaat tcaataatta    17340
gccaaattgt aggaatgtca agagtcttga caattgattc gtcataggag tatatttta    17400 cagacacaca aaaccaaaag ccaaattgta gtaatgtcaa gagtcttgac gattggttcg    17460
tcaatcgtca tatattacac tcatcaaagc aaaagcccgt ctctttactt gaagaaatag    17520
gaaagtaatt gaagagaaat ggatcggggt tcgagaacat gttgggtttc tgtctcaaaa    17580
gagacgtttg agtgagataa ctcactctcc tcttcatctt ccattttaat taaattaggg    17640
atctgacctg ggttgtcttc attctcacca tggttgccgg tggtgttttg ggttacagaa    17700
aaaccgatgg ctgctcttcc ttctttactt tgatctgacc tgggttgtct tcactctcct    17760
cttcatcttc cattttttt tattttttt ttctgaattt ttttttcaaa ctgggggtac    17820
aactgtaccc ccttgtcact taattgggtc cgcccatgta atagacaggt acaattaatt    17880
```

| | | | | |
|---|---|---|---|---|
| tattagtaaa | ttcaataatt | agccaaattg | taggaatgtc | aagagtcttg acaattgatt | 17940 |
| cgtcatagga | gtatattttt | acagacacac | aaaaccaaaa | gccaaattgt agtaatgtca | 18000 |
| agagtcttga | cgattggttc | gtcaatcgtc | ttatattata | cactcatcaa agcaaaagcc | 18060 |
| cgtcttttta | ctcgaaaaaa | taggaaagta | attgaagaga | aatggatcgg ggttcgagaa | 18120 |
| catgttgggt | ttctgtctca | aaagagacgt t | | | 18151 |

<210> SEQ ID NO 3
<211> LENGTH: 1059
<212> TYPE: DNA
<213> ORGANISM: Amaranthus palmeri

<400> SEQUENCE: 3

| | | | | |
|---|---|---|---|---|
| atgaaggcca | ccctctttga | agatgatatt | gatgcatatg | cagatttaat acaacagaac | 60 |
| catgaatact | ttatttctaa | tccaactatt | cgaagcgtgg | aagagcaata ccgttcaaaa | 120 |
| tctggtgaat | accagatgac | ctttaacagt | cgcacaacta | ttcaacccac tggttctgca | 180 |
| acccagctat | ctgaaccaag | ctattatact | atttctacaa | ttcctcgaat ctctggtttt | 240 |
| tatgatagat | ttggtacgta | aatgaagttt | tgattatttc | tttagtattt agtctaatat | 300 |
| ttatattata | catcaacctt | tgttaaacg | ttatgttttc | cacactactt taagtcaaaa | 360 |
| tttgttttac | tttagatat | actcggtatt | atcctcttta | ttggagatac tcgtactgtc | 420 |
| aatggagcat | ttgatcaaaa | gaatagcgtt | tctgaaataa | tgattactga tcataggtat | 480 |
| tttcttaaac | tcttatcgta | tacactttt | gaagcacatc | tatttaatta gttttgtta | 540 |
| tattgatcaa | tgattttttt | cttacaatta | attatacaat | gatgtagctc acatcaacct | 600 |
| ttaacaattt | ctgcttggaa | tgatctttcc | gactatttta | aggagaagcc tattgcatat | 660 |
| tccatttcg | ggtttacttc | tcttcgagta | acttcacata | aaggttagac ttaaatcaaa | 720 |
| tgaggcattt | aaataggatt | cgaggaagta | tatgttatcc | tcgccatgtg aaaatcagtt | 780 |
| gtgttttatt | atttgtgatt | aacactcact | tttgcaaaaa | ttaggattcg ggttatcaac | 840 |
| cacaatgtcc | tcatcaatta | taactgcacc | aacaggtgaa | aaggcagaat tgctaagaaa | 900 |
| atggtaacgt | atcccgcata | gaattttac | gtaagatcaa | ctattataca aataactcat | 960 |
| ggttccattt | atacagggct | tcttcccatg | cagacttgct | tcatgaacgc aaacaacaaa | 1020 |
| ttttacaaag | tcgcatttca | tcaacaaagc | gacaattga | | 1059 |

<210> SEQ ID NO 4
<211> LENGTH: 3801
<212> TYPE: DNA
<213> ORGANISM: Amaranthus palmeri

<400> SEQUENCE: 4

| | | | | |
|---|---|---|---|---|
| tgatgatgaa | cgttatgtta | gggctaggcg | agacaattcc | tcttggagac gcctcagatc | 60 |
| accttgtagc | atctgtggag | agcgcctcac | aaccttctat | aagcacttga aaagccattg | 120 |
| tgatgcgagc | acctgccatg | taaatctgta | ttggcataag | gttcgaggtg taggtagata | 180 |
| tgatgatgga | cgttaagaga | caattctaaa | ggctgcaaat | cagaaagcaa tgctatttat | 240 |
| tgatctcaac | aaatttgaag | ctctgaaatt | gtttgaatac | ttgaactatt tatgtctgta | 300 |
| aatctgtatt | ggcgttcatt | atttgttatt | cttttgcttt | tagattgtag tgatgtaatg | 360 |
| aatggctcat | taaattgcct | gtgcatgcat | tcatccatga | cttttcctga cttttccatct | 420 |
| tgcttccgtt | gtccctaaga | gtttgcaaca | acacatacag | cccaatgaga aagagcgaag | 480 |

```
atgtgtggaa aagaataaga aagtggtgag gacattatct aaaagcgatg gaccataata    540
gatgggacaa agatgtgtgg aaaataatgt ttttcgcatt tcaatgagtt catactttaa    600
attagcatct taactaaaat tttctagttg gtgtcattga agaccatgct agtaagaaaa    660
actttgtaaa aaaatagcaa caaaaacacc actacgttct atttgaagaa tttgtcatag    720 tgcttttaa gtgagcggat gactacagtg caatcttatg gtcgatgggg tggcttatta     780
atatttcatt atcttaatgc cattaagtgg ttcccaactg aatgtggttt ggaagggccg    840
gatgtacgct accttacccct tgttagtgat accaaagagg ttatttccga taaacccttg   900
ctaaacatca tctataattt cacattagta taaagtgcgc atgatttaat gagccttgtt    960
aatctttggt ctcattgaaa tagggagacat agtaagtatc taaaatataa attttaaaat  1020
tgcatactta gaacatattt ttcttcctct ttctcaggtt gttcaggagt ggcctggatt    1080
accaagaggt gtaaaatttg atccaactga ccaggagata atccaacatt tacttgcaaa    1140
atctggcatt ggaaatgaga caccgcatcc cttcattaat gagtttatcc ctactgttga    1200
ggaagaggat gggatttgtt acactcatcc tcagaattta ccaggtcggt tgcaatttat    1260
tgttcatgct agcttcttaa ttatattgag aatcgtgtct tgtctcagtt agagtaagta    1320
ccacttttcc taggtaagat ccttgattcg attctcattt agccatcccc ttttctcaac    1380
tataataaaa aatagggaaa tttcatgtgg tgaccctgag ttcttggctt ttccacgtag    1440
tagacaataa attcacgtgg tgatcctaag cttccaactt ttccatgtgg taaacaaaat    1500
gtaaattttt ggttaaatta agtactcatt tcgactggat tacaaaatat gtggcaaatt    1560
agggtgatcg cgacgtcgat tttttgaata agaagtcatt atgttcggga aaaatagcgt    1620
aaagttaaca aaaattctac tctttctagt ttctaccatg aaagttgaaa caccacgtgg    1680
attaaaaaaa tgcttgcctt ccacgtagaa aagccgataa ttcagggtta ccacgtggaa    1740
tttccctaaa aaataactat agcaatgtat tcacccttt gaatttgact ttgattaata     1800
aggtgtcaag caagatggaa ctgcatctca ttttctttcat agagctatca aagcgtataa   1860
cactggtaca cgcaagcgtc gaaaaatcca tggggttgat ttgggtgatg ttcgttggca    1920
caagaccgga cggactaagc caatttctct taatggtgta caaaaaggat gcaagaaaat    1980
tatggttctt tatgtcagtt ctgctaaagg tggtaagccg gagaaaacaa attgggttat    2040
gcatcaatat caattgggta cagaggaaga tgagaaagat ggagaatatg ttatttcaaa    2100
agtgttatat cagcaacaac cagggaaaca aattgacaag actaccgggt atgttttga    2160 tgcaatagat gacattagtg taaaactaga tcctgtgact cctgagcctt ctcgacatat    2220
gactcctgag cctcctcgaa aggaaatcca gcttgaccctt gcagaaatga cctcatacag   2280
ttgcattgac ttttcaccc aggtactgtg ttggaacttc cttttctagcg tgcgatgcat    2340 cttttgacgg tgatttacat gtgacaataa ttcttgtgca atatggatgc ttttctgaca    2400 gcatttatc agtaaacatt ttcttttagaa ttaaacagta tcctgagaaa atttatttta    2460
tcatttaaga agtatatatg acaaatagaa aagggcttat tttttcaaac aaacattaac    2520
gaccagaatc gaccctctat agaaagggcc tatttctttc agtttgtcta gtgcccacaa    2580
aatgtcaaga acggcaccgc gcaaaactta tgcagtacaa aatttaatgt gattctgttg    2640
cactatcgtg taggtatttt tcactatttt acccggatag aagaaagtgt gtttgcttgg    2700
taatacggtg cttattagtg ttacacttac atagctctct tgaaagtttt ctgttttcat    2760
atcatgattg ttggtcagtt tattgggttt tttgtcatca catacaactc tgaatttaca    2820
ggatcaacac atagatttcg aaaagcatca tgacatgttt cctgacgaag tgcaacaacc    2880
```

```
taaaacacaa caaactgaga ttaccaaatc aagttatact gatgctgctg cttcaacact   2940
tgtagatgat caagctctag aacacgatga caaccaggtt tgtggggaaa atttgtggtt   3000
tagtgagtca caatttacga taaattctca acaattagcg aaaggcctct ctttatgtga   3060
tgatttgctt cgaagtcagt ctcaagacag aggcgaaact gccaacaatg tgccaaacaa   3120
gaaatctgtt ctttcggagt atgctaagtt gggtccggaa catctaaaga aggatttgga   3180
agagtgccag aatttggtcc ttgatcctgc aaacatagat ttaggtacac cacctgattt   3240
cagactaagt cagctggtaa gcccgatgac attttcccac tctttttttt gttttgatct   3300
tatatatgat gatgtatcgt tgcacccgac attatctctc atttgtctat ctaggaattt   3360
ggatcacaag aaagctttgg caactgtggt ttaggcaaga tctgctacta accgtggtac   3420
cattacaatt ttcccgtttc gactccataa agtcaagggc atcacaacac tgtaggtaac   3480
gttttgatgc agatttccac caatattttt gttgtaaaac ttcggtgtag atcaaatgta   3540
tagtgttctc tccgtcattt tctttgcttt tctcagttat tcttagtttt tagtaatcaa   3600
tgtgattagt catcatctgt catacagtcg gtttccttac cttgtaacag atcaatggta   3660
ccttcatgta tgcatgcgat ctaaattttg ttaatgtgaa acttggcaag ggcgtctat   3720 aatgctgaca ctgacttacc gtgtacttt gctcgtaaag gaatcttatt atctatgtgt   3780
attgcagcgg atgaaatcta a                                            3801

<210> SEQ ID NO 5
<211> LENGTH: 1603
<212> TYPE: DNA
<213> ORGANISM: Amaranthus palmeri

<400> SEQUENCE: 5
caagtaaatc ctgctcctaa tggtttttca atacccactt catcagtaaa aggaagcatc     60
ttagacaaat tagccatacc ttcatcatat tccttctcta aatcatctag tttggctact    120
tccttaagga gtctcgactt cttaacggag gcttgaatct tcaacagtcc gaggttgtgc    180
aaagactcca ccggtggctt gctttggtgc aattccaagg ccttctcgac atacggagta    240
agccaactta catcaaagca aatgactctc agatcagtta atgtagactt caaattatga    300
gattgattgt cgctcatgtc taaggccgag ttttcctcaa gggtcaggac tacattcgct    360
accaactcta atgctcttga tttcaagtca ccattagata aaatgcaatt ttctatgatg    420
tttccgtgtt ttgaccagat cttctgcaat gtcgggatca aattagactt tatatcgagt    480
ccctcaaact ttgtcgttgg tgttttgctc gtgttactct gcaagtgaaa gcaaaaggat    540
aagctaacat taatcgatac tagagtagag ctccgacaaa agttcaaccc ttgcaatttg    600
ttagtctact agagtatata acatatccta gagcctcaac cattagctca agcttttggt    660
tgagttggtt ccttgccatg ttattagagc cagtgtgaca agaggtcata ggttcaaatc    720
tcaaccccct aattgaagtc gtatatttag cgctaggtat gagaagggca tgtgctacat    780
ccacacttct agcgtaaagg gctctcgtgt gaggaggcgt gttagggtat ataacatatt    840
ttggggcctt atgtgatacc ccagatttag cttgaaaaga gattgataga ctactcatat    900
caacaaggtg catcttcttt tctagggagc ccatttacta agaactccac agttaagcgt    960
gcttggtggg gagcaatctt aggatgggtg acctcttggg aagttttccg ggtgcgcacg   1020
agtgggccca agtgcgctg gaaagacttg tgttggtctg tggggctagt ctacagtctc   1080
catgagtagt caccggtggt ccgttgggcc agggtgttac aaatggtatc agagcaaccc   1140
```

```
tgcgaccgtg gctgattgtg tgttcagcgc acctagcggg ggaaaagatc ccgaagtgac    1200
ggtccaacga ggacgttgta ttcttaagtg ggggtgaatg tgataccca gatttagctt     1260 gaaaagagat tgatagacta ctcatatcaa caaggtgcat cttctttct agggagccca     1320 tttgctaaga actccacagt taagcgtgct tggtggggag caatcttagg atgggtgacc    1380
tcctgggaag ttttccgggt gcgcacgagt ggggccaaag tgcgctggaa agacttgtgt    1440
tggtctgtgg ggctagtcta cagtctccat gagtagtcac cggtggtccg ttgggccggg    1500
gtgttacacc ttaaccatca gcttaagcgt ttggttggca gtttgctcac ttaaaaaaca    1560
acgttcatat agagtaattt aatacctgat ttgtagaagt cat                      1603
```

<210> SEQ ID NO 6  
<211> LENGTH: 744  
<212> TYPE: DNA  
<213> ORGANISM: Amaranthus palmeri

<400> SEQUENCE: 6

```
atggaatgga ttaggagata tgtgacgcaa agaagtgcgg caaaaaggga aggattgagt     60
aactttgagg gtgttttaat gccatccgtt aggaaattaa ttgaaaaaaa tgcaagggac    120
atatacggtt tgagggtaat cccagtggat gtatttgagt ttgaggtgga tgatggtgaa    180
gagtcgtacg ttgtcaacct aacgaacaag acttgccatt gtggaagttg acactaatt    240 gggatacctt gcaaacatgc aatggcttgt attgttctta ggaaattaga cgccaacgaa    300
tttgttcacg aggcctatca tatagaaagg tatgcgaaga cctatggtcc taagtttcat    360
ggtatgccag gcataaaat gtggcccaca accactttcg ccaaaccact tccgcctcca    420
ttccgcaaaa tgcctggaag acctgacaag aggaaaagaa agaaggaggc tgacgaagga    480
aagggaggga ataaagctgc tactgttgtt agagaataca agccacgaaa atgtagcaac    540
tgtggtgatc ttggtcacta caaaaagaaa tgtaagaatc cacccaaacc gccaacgacg    600
aaggagaaat caagggtgg taggcctaaa aaggggtctt cttcaactca gcaattaaca    660
acaaatgata tgccatgcac cagcagtcaa ccacaaacac aatccgcttc atgtgtaatc    720
gatcaaatta gtcaaatcaa gtag                                           744
```

<210> SEQ ID NO 7  
<211> LENGTH: 2492  
<212> TYPE: DNA  
<213> ORGANISM: Amaranthus palmeri

<400> SEQUENCE: 7

```
caaatgttga agacaagctg ttgttcttct tcttcaagct tcttcttcaa tggcttcaat     60
ggcttcttct gggttgaatt aaggtttgtt ttattaacat accagaatat gatcagactg    120
ttcttctcct tcaagcttct tcttcaatgg cttcaaatct ctaaaaatta atacaaattc    180
cagatttttt aaaatttcag atttgttttc aatttgggtt gattttagtg ggatggttgc    240
tggatcttat aaaaaacaaa tttgagcaat taccccatttt aaatctctaa aaatttgttg    300
atttgttctt catttgggtt gaattagggt tgaagataaa gaatggaatg gcttgttctt    360
caatttgttg atttgttctt catttgggtt gaattagggt tcaatttgtt tttgggtttg    420
aattaatcaa aggattttca gcaatttagc aatttagttt ttgagttttc attgttttg     480 ggttttcatt ttttagtgag aattgaaaaa agaaaaaaat tggtgagaaa taaatgtaaa    540
aaagaaaaaa gaaaccccat ttttgatata tatgaaaggt tgatagactt acaggaaaag    600
gctgatagtc atgatcttga agcatagcaa gtctttgagc aaccaaggaa agcttcaatt    660
```

```
ctttctttga cattgctgat ttttcctttt tctgctgaaa aaacaaaaca gacaaaaagt      720
gagtaaaaat agaaggaacc agtttgattg aagaaattta gagtaaaaca cagaaatgaa      780
tagatgaaaa accatggggg aaattgattt tgatgaagaa tgatctaagt tagccatgtt      840
tttggggttt ccttcacgag agaatagact atggccttgt tttatgggaa attgattttg      900
atgaagaatg atctaagtta gccagaaatg atctaaaaag aacccagaaa attttcccca      960 caaaactct gattctgaat caataaatac tgaatctaag ttagccagaa atgggaaatt      1020
gattttgatg aagaaacgtt tgtaactgaa aatagaacca gatttttttt tttttttttt     1080
tttttttttt tttgggttga taatggtgaa gatgaagatg gtgaagatgg tgaagatgaa     1140
gatggtgaag atggtgaaga tgaaatggtg aagatgaaga tggtgaagat aagaagatga     1200
agatggtgaa gaagtaaccg gttcatccgg ttataagtca tccatatctt tttgggaata     1260 tacccccaa agttcgtatg tttaaataat aaacgaaagt ttgtatgttt aaaagaaaat      1320
gggtcaaagt ttgtatgttt aaaagtaaat tttccttatt ttaattatat agtagtgaga     1380
aataataatt gtatggtatt atgagagaaa ataataaaa tagtagtatg aagtaatgat      1440
tgtattgaac gtatgagaga gaaaataatt gaatagtagt gtgaagttag aaaagtgggg     1500
ttttaagggc ctcttctctt cgtctgatct gattggataa agtctgaatt tactaaggtc     1560
tgatctgatc tgatctgatc tggtctgatc tggtctgatt cagtctgatc tgatctgaat     1620
ctttctgatc tagtctggtc tgatctggtc tgatctgatc tggtctagtc tgatctgatc     1680
tgatctgatt tgatttcata agttattat tattattttt attattatta ttattattat      1740
tattattatt attattatta ttattattac tattattatt attattatta ttattattat     1800
tattattatt aattactagt atagaaaccc gtgcaatgca cggattttc ttaatagaag      1860 ttaacataaa aatattaatt ataattaatg atttaattat atattatctt aatcatattt     1920
atgagtctcc cttcaaatat aaataacatt tataataata taataataaa tacgtaacaa     1980
agcattagat atgaatattt atgtgaatca tacatactta atttctgaaa aaactataag     2040
atatcaaaag taatattgta taacatctaa aggttttgaa agacctcttt gtatacaaca     2100
ttatcagtgc tagaagttat ctcatcattc ttatcacata tgagaatttt tagaccttt      2160 ctgctagtaa ctctagaaca tgcgacatat aattgtccat gactaaaaac aggcttagga     2220
aggaacaaac taacgtgcga taacgattgt ccttggctct tattgatcgt catggcgaaa     2280
cacaatgaca ccggaaattg ccttctttga agagcaattg ggattttaga gctatcagaa     2340
ggtgtgagag tgatccttgg aatgaaaatc ttatcaccaa tgttagatcc ggatataaca     2400
gttgctttta taactcgttc acctaaatga tcaactaata accgtgtacc attgcataag     2460
ccagctgaat gattcatgtt ccttagcatc at                                   2492
```

<210> SEQ ID NO 8
<211> LENGTH: 1251
<212> TYPE: DNA
<213> ORGANISM: Amaranthus palmeri

<400> SEQUENCE: 8

```
atgcaattga aatatgtacc ccctgtagtt gagaatggtt gtcaagttgt tcatattgat       60
gctcatgatg ctagtgactt agtaaaattg tgggaacgag ctgttgttgt ctatattgtt      120
gggagtcaag tttccataga aattcttaaa ggcttcattc gtaaacattg gcacaatgtt      180
agcatgcccg ctatccaccg tcatgaagaa ggatatttta ttttgagatt taattcggac      240
```

-continued

| | |
|---|---|
| aatgaatgtg aggaaataat aaaaggagga ccctattttc ttaatcgtgc acctatggtt | 300 |
| gtgaaaaagt ggaataggag ctttgatttt agagaagaaa ttatgagagt aatcccggtg | 360 |
| tgggtaagac ttcctaacct cccgctccat tgttggggag tggatacttt gagtagaata | 420 |
| gtaagtgcta taggggttcc aattcttgca gacgaatgca cggcgaaaca actaaaagtg | 480 |
| tcttatgcta gagttttagt tgaagttgat gtaacacaag agtttattaa ggagataaaa | 540 |
| gttcgagaaa attcgggaag agaatttgtt caattagcga ttccggaatg gaaaccgttc | 600 |
| tattgtagca aatgtgataa gttggggcat aattgtcatg ggaatgcaaa tgaaatacaa | 660 |
| ggcattccta aaagaatctc tagggaggag aatggtacta tggagaacaa gaaggtttgg | 720 |
| ataccttcaa ccattgtgag tatgttacaa ggagtccata cagtgagcca gcttagacat | 780 |
| aaattaaaag agggctgttt gggagagaat gaagatcagt ctgttgaggg agttactacg | 840 |
| atacaagatc agaacattgg ttccatgatg caaggtcaga acacgagtaa aactgatgtg | 900 |
| caggctgctg tttcctcgtg tgtagatcag tctgctgagg gagctgctgt tgtgacgtgc | 960 |
| tcaggtcaga caattgaggg tgctactgat cctagtacag gagctgttct cacccaacaa | 1020 |
| tttgatacga ttgggcagtg ttcagatcag aaaagcgctg acgaagaggg ctggacacct | 1080 |
| gtttcgtatg gtaaatcatc caaaaaggtc cagattacag tatcacacag gggtactcaa | 1140 |
| aatgctagaa cagaaactga tccaaggctt atagtgaaag agaaacttga tgttgctgca | 1200 |
| gctcaaaata atccaaggga cgggaaccct ataattccct cccgaaaatg a | 1251 |

<210> SEQ ID NO 9
<211> LENGTH: 1017
<212> TYPE: DNA
<213> ORGANISM: Amaranthus palmeri

<400> SEQUENCE: 9

| | |
|---|---|
| taagtatcta aaatataaat tttaaaattg catacttaga acatatttt cttcctctttt | 60 |
| ctcaggttgt tcaggagtgg cctggattac caagaggtgt aaaatttgat ccaactgacc | 120 |
| aggagataat ccaacattta cttgcaaaat ctggcattgg aaatgagaca ccgcatccct | 180 |
| tcattaatga gttatcccct actgttgagg aagaggatgg gatttgttac actcatcctc | 240 |
| agaatttacc aggtcggttg caatttattg ttcatgctag cttcttaatt atattgagaa | 300 |
| tcgtgtcttg tctcagttag agtaagtacc acttttccta ggtaagatcc ttgattcgat | 360 |
| tctcatttag ccatcccctt ttctcaacta taataaaaaa tagggaaatt tcatgtggtg | 420 |
| accctgagtt cttggctttt ccacgtagta gacaataaat tcacgtggtg atcctaagct | 480 |
| tccaactttt ccatgtggta aacaaaatgt aaatttttgg ttaaattaag tactcatttc | 540 |
| gactggatta caaatatgt ggcaaattag ggtgatcgcg acgtcgattt tttgaataag | 600 |
| aagtcattat gttcgggaaa aatagcgtaa agttaacaaa aattctactc tttctagttt | 660 |
| ctaccatgaa agttgaaaca ccacgtggat taaaaaaatg cttgccttcc acgtagaaaa | 720 |
| gccgataatt cagggttacc acgtggaatt tccctaaaaa ataactatag caatgtattc | 780 |
| acccttttga atttgacttt gattaataag gtgtcaagca agatggaact gcatctcatt | 840 |
| tctttcatag agctatcaaa gcgtataaca ctggtacacg caagcgtcga aaaatccatg | 900 |
| gggttgattt gggtgatgtt cgttggcaca agaccggacg gactaagcca atttctctta | 960 |
| atggtgtaca aaaaggatgc aagaaaatta tggttctttta tgtcagttct gctaaag | 1017 |

<210> SEQ ID NO 10
<211> LENGTH: 50

```
<212> TYPE: DNA
<213> ORGANISM: Amaranthus palmeri

<400> SEQUENCE: 10
ctctgcacca agattacact aattagccta aatccaacat gagtacaaat        50

<210> SEQ ID NO 11
<211> LENGTH: 50
<212> TYPE: DNA
<213> ORGANISM: Amaranthus palmeri

<400> SEQUENCE: 11
aacaaccatt aaataattct ttttatttca cttgctgtta gggtgatttg        50

<210> SEQ ID NO 12
<211> LENGTH: 50
<212> TYPE: DNA
<213> ORGANISM: Amaranthus palmeri

<400> SEQUENCE: 12
caacaatagc tttcgtcaag aaaaaaacag tatatcttac aattcacatg        50

<210> SEQ ID NO 13
<211> LENGTH: 50
<212> TYPE: DNA
<213> ORGANISM: Amaranthus palmeri

<400> SEQUENCE: 13
gaaagtaatt gaagagaaat ggatcggggt tcgagaacat gttcggtttc        50

<210> SEQ ID NO 14
<211> LENGTH: 50
<212> TYPE: DNA
<213> ORGANISM: Amaranthus palmeri

<400> SEQUENCE: 14
ttagatgcgc ggtgcgagta agccaataag gtttgaggcg taggtagata        50

<210> SEQ ID NO 15
<211> LENGTH: 50
<212> TYPE: DNA
<213> ORGANISM: Amaranthus palmeri

<400> SEQUENCE: 15
atatggtcta cagaggctac cctttcttgg agtctttgga tcaggtgctg        50

<210> SEQ ID NO 16
<211> LENGTH: 50
<212> TYPE: DNA
<213> ORGANISM: Amaranthus palmeri

<400> SEQUENCE: 16
atagccggtt ttttgaagct tttttaacct tttttaaccg gttaccctct        50

<210> SEQ ID NO 17
<211> LENGTH: 50
<212> TYPE: DNA
<213> ORGANISM: Amaranthus palmeri

<400> SEQUENCE: 17
tattggagca ccaactttta acaatagctt atggttagga actccagatg        50

<210> SEQ ID NO 18
```

```
<211> LENGTH: 50
<212> TYPE: DNA
<213> ORGANISM: Amaranthus palmeri

<400> SEQUENCE: 18
aattgatgaa ttagagagac aaggtaacta gtcctactcc acctattggt          50

<210> SEQ ID NO 19
<211> LENGTH: 50
<212> TYPE: DNA
<213> ORGANISM: Amaranthus palmeri

<400> SEQUENCE: 19
ttatttcttc ttggaacgtg cggggcatga atagccccat taaaatcagg          50

<210> SEQ ID NO 20
<211> LENGTH: 399435
<212> TYPE: DNA
<213> ORGANISM: Amaranthus palmeri

<400> SEQUENCE: 20
aagcttgtgt ttccattcaa caatggaaga cacccacaaa ctaatacaag aagaagactc    60
tcttggttac tctaaaccct agcctctctt agtgtattag actctcttac atgccctaag   120
actcccctaa tactccttttt atagtgtaga gatgtattag gaaacttggg gccaaaggct   180
ttaaaggccc acaaaccgta acaataaaac agtgaaaagg acgctgctgc cactgtgctc   240
cgctcgaccc gagctcccag gctcgacctg gtcgagcact ccactccaaa gctactgcct   300
catttctggt ttgttgctcg acctataccg ctcgacccag gctcattgct cgacctggtc   360
gagccccccct caaatcagct actggaagcc tgctgcacta aggctcgacc ttgggctgtc   420
ttcactcgac ccattgctcg atggtttcca gctgctcgac tgatttggca cctcaatttg   480
gtgcttgtgg ctacttcacc atcgcaacac caaccttcgt tcttcgtcgt accatcatca   540
cggcacccca aagactcgtc acatgagtga gatttgagtc ttgctttaac atgtatgatt   600
gagtatatgc tactggtaca gcagcttgct gatttctgta attcctgtgt tcattgtgca   660
tgattaagta tatgcttttg gtacagcagc ttgctgattt ctgtaatgct tatacacatt   720
acattgcaca aactgattac acaaactgat ttctgtaata ctcactggtt ttgtaatgct   780
tatgaaccaa cccattaata ttcttgcatc aaaatgctgc tgatatcttg catcaaaatc   840
attacagact gattgagtcc ggtggtcctt ttgtcccctt tttcttcgaa tccggccacc   900
actctgggta tccaacgagt ttaaagcact cgttctttgt gtgtctcaag tgtgtctttt   960
ccttgctgaa ttttattagt tttaaccgtt aggtagaata tttgcaggcc atcccttccg  1020
ctactgtaga ccgttttcaat ccctcgccat agatttttgg cagttgggta atcaaggtac  1080
tgactcacca agtccggatc tatattctcc aggatccatg agataacaat cgagtcgttt  1140
ctggaccatt ggttgtacgt tgggtcatcg gtgggtggac gatcgtcgat gatgtgtttg  1200
agtcgatccc gtccactaat gcccaaatgc atcagcctgg cccatatgga ataattgtgg  1260
ttgtttaatt tctctgagac tgtgagagta tggttactgg aatgatttgt gggttctatg  1320
ggtgtcggtt tgctgggtt taactggcct agcagttgca gcagctggcc cattgtaacc  1380
ggctgatctg gtgtaatgac tgtctttgat tcgtcttcca ttgttatttt ttaagaggta  1440
ggttaacggt atatgatgaa gctgcaaaaa cgattcagaa tcgttgccgc tctgatacca  1500
tgattaaagg taagaacaca aggttttggg ttttctgtta ctgtgttatt catctcccaca  1560
gctgagccaa ggtataaata tacaagctat tctctaaact ccctaaaata ataatattac  1620
```

```
agtatgtaca tttgcctaat ataattcgga caatattgca ctaattattc catgaatata   1680
atcaagccgt gaatattgct catatattct aacagagtat atgctactgg tacaacagct   1740
tgctgatttc tgtaattcct gtgttcattg tgcatgattg agtatatgct tttggtacag   1800
cagcttcctg atttctgtaa tgcttataca cattacattg cacaaactga ttacacaaac   1860
tgatttctgt aatactcact ggttttgtaa tgcttatgaa ccaacccatt aatattcttg   1920
catcaaaatg ttgctgatat cttgcatcaa aatcattaca gactgattga gtatatgctt   1980
ttgtaatgct tatacattac tgattataca caagcagcat acattacatt gcacaaactg   2040
attacacaaa atcagcatac actaataaac atcatttgat gaacaaaatc agaattatgg   2100
tataggcttg cttgctgata tgaacaacat catttgcttg cttgctgata tgaacaacaa   2160
aatcagaatt ggtaaatgaa cattcccttt gcacactaac acagcataca gttggtatat   2220
gaacagcata tcagtacaca aattgcacaa tgcacactgc acacagcaca cagcacatcc   2280
ctatacagaa gtgagaattt atttgaggac cttttgcaac tctcgccggt gatttctctt   2340
acaaaccaaa cggccgtttg gtttcttgaa tatcaactcc aaactattgc gtctgggttt   2400
ctgtcctgct gcttttagt ctcctgtcgc ctgctccctc gcgagtcgct atcacgttgg   2460
gtttctgtcc tgcggctgcc ggcttgccta cttcccaccg actagtccac caccatacca   2520
attactaacc caccgtcaaa caatcaaacc aatttcagat tttcaggtat tattattaat   2580
taaatgtttt attttcaaat ccccaattct caaaaattag ggtttttttt attgttattt   2640
taaactcaag ttagtttctt gaattattaa tgttattgtt tgttacattt tttgttattt   2700
catatgttat aattctatat atatgttaat gttaatgtga tttgtgaaga agtgaatgtg   2760
tttggactttt gaaatttgaa tgtgtttgca cttttgtaatt tggtattatt gatttattgt   2820
taattgttat tgttatttca ggttgtattt cttttctaac gttgtttgta atcaacctct   2880
tttttcaaaa aactacctga tataaaattt ttttcaaaaa actaccttgt ataatattaa   2940
agtttgcaaa agactacctt gttatgaatt ttcgtcattg actgttagtt ttcacattga   3000
ttgacacact ctttacacgt gcaacctcta aaccctcct tctgatatga acaacatcat   3060
ttgcttgctt gctgatatga acaacaaaat caaaattggt aaatgaacat tccctttgca   3120
cactaacaca gcatacaatt ggtatatgaa cagcatatca gtacacaaat tgcacaatgc   3180
acacagcaca cagcacatcc ctatacagaa catcatttgc acacattccc tatacataca   3240
caacatacac attctataca gcacatcaga ttatacagca catgaacaat tggtgtttgc   3300
tgtttggtat gcaaaacata tacacattat gcttgcactg atcttgggtt tgttgtttgc   3360
ttgcacactt atcagaacac tgatgtttgc ttgcacactg attagaacat tatgcaattc   3420
agaacagctc tacttgcaaa atacacacag cacagctcta cttgcacatt gatgtttgct   3480
tgcacagctc tacttgcaca cagcacacag cacacagcac acagcacagc tctaccaaca   3540
tcagaacagc agaccaaata cacaaatact gcacacagc acacctatac acatatgctt   3600
gcacacaaac tcaaatcaga acatcatacc aacatcatat atattagtag aaaatacaca   3660
agttcttgcc aaatacatta gttgaaaatt acaatccaaa ctactacaca agttcttgca   3720
aaatacaata gcaccaaaat atacttgttc ttgccaaata cattagttga aaattacaaa   3780
ccaaactact acactaagta cattacttga aaatacatga gttcttgcaa aaaaatccat   3840
tacaatccaa actacttgat ttgactaatt tgatcgatta cacatgaagc ggattgtgtt   3900
tgtggttgac tgctggtgca tggcatatca tttgttgtta attgctgagt tgaagaagac   3960
```

-continued

```
cccttttag   gtctaccata   attctgatga   gttgaagaag   accccttga    tgataatatt   4020
aaatattta   agtcctttaa   aataaatata   tacataataa   ttgtaaatat   tactcctctt   4080
ccaaatgatt  tttatgccat   ccggtctcat   ccggtccaac   ccggaatttt   cccggtctag   4140
accggaccgg  accggaaacc   cggaattgga   aaatattaag   acccgagac    cggaccggat   4200
gcacccggtc  cgatccggtt   ccggtccggt   cttagccggt   tccggtccgg   accgccggtc   4260
cggtcttatt  ttgcacaccc   ccaagggtct   ttgtgcttaa   tgaaaggag    cttaccatca   4320
cttctgttga  ggctgcccta   atcttagggt   tgcgtgctgc   aggtaaaccc   gtgattctgc   4380
atgaagatga  ccagttatcc   aagttggaag   aagagtatgg   agccacacaa   agtaagctcc   4440
tctttgactt  gcaggctaat   cgagtataga   tattaacctt   tggcgtaatg   gatgatgttg   4500
tggtatttgt  tctcattgaa   tgtttcactt   ttccttccag   ctcttcgacc   aatagctctt   4560
gtatgatatc  aatattcaac   tccgctgctg   ttggctgcag   cttccaggtt   acctaaatgt   4620
accatgtaaa  ataaaaaaca   gcagcataac   acattaaata   tcaagttgtt   ctgtgtatgt   4680
tgagtggtgg  cttcagttca   tagaacaaaa   tattgttagt   aggataaatt   tacaactaac   4740
aagcacaata  ttgaaaaaac   aacactcatt   tgattctctt   caagctcatt   aaacttagtt   4800
gtgaaccagt  gcctttgact   attacaccta   gcactttccc   aacggcaagc   tcgcggaaag   4860
tttgaagaat  aactaaggga   aattggtcgc   ccaatgtcta   tatgctcgta   ggaccatatc   4920
tgatatcaaa  atattcaaca   tctccaatca   ttagagccaa   catttctatg   ttgatatttg   4980
atgtaaaact  gaaacataac   tacttgataa   cttacttgga   gaagaatcag   acaaccttca   5040
atgcttttgg  tctgctcttc   ttttcttta   gatagccaat   tgaaaacgtc   ctccactact   5100
gcaactcccc  aagcatactc   gcatactcta   tcaagatctt   tcagaaggga   aagatagcgt   5160
gaatctacct  ttgcactaga   actcgggaaa   aggagcgtcc   caaagatgaa   caacaagaaa   5220
gtcctcacga  aatcctcatt   atgaagttca   ccaagagact   gcaatcttct   ctcagcgaaa   5280
gtggttgtgg  gccacatttt   atgccctggc   ataccatgaa   acttaggacc   ataggtcttc   5340
gcatacctt   ctatatgata   ggcctcgtga   acaaattcgt   tggcgtctaa   tttcctaaga   5400
cacatctta   tcgaccttct   ctaaagtgca   agacaaagca   tgtttgttta   tatgtttaaa   5460
gttatcgtca  tagtcatgaa   tattgttact   tgctttaaca   agttaagtcc   taaatttatt   5520
tgatggatgc  atgcaaattg   atgattacat   gcttgaaact   tgatggatta   aagtctgttc   5580
tgtaaacctg  ttgaaatcac   ttttcatttc   ccacttggca   ggctggaaac   ttcactcagg   5640
gtcggccctg  agataatagg   ggcccggggc   gaaaaataat   ttatgggccc   taactatatc   5700
aattattttt  atcaaaatac   tataacttca   aattaccacg   taaaagtcca   tataacaaat   5760
tcacaattcc  atctatcatc   aaatagcaaa   tagaaaatat   taaacattca   caaatatagg   5820
ttaaatcaat  aaatataaaa   ttattcgaat   aaacacaaaa   aaatggatta   taataaaaga   5880
aaataaatag  aaaaaaatca   taaattttga   atatatagtc   acacaacaag   ttaaccacaa   5940
gaaaattaaa  atattataat   tataataata   ttaaaaaata   ctccctccgt   cccattagtt   6000
ttgtccactt  tacctttttgc  acacatgccg   aggcaacatt   ttaatcttta   atatctttaa   6060
ttgtgtataa  ttaaaaatta   taaaaatttg   atatcaataa   tctttgcatt   gagacgaaca   6120
aaataagatc  ccacatgact   atattttaac   ttatagatta   agaacaaaat   acaaattaag   6180
agtgattagt  gaatagtaac   caaaaactaa   agtggacaca   ataaaaggga   tggagggagt   6240
attataattg  ttaaataata   ttaaaaaaaa   ttttagtatt   ataattgtta   aataggaata   6300
atattaagtg  tacgtgcgtt   ctttctttt   ttctacaaca   actctactta   cttatactaa   6360
```

```
acaatgaaat gtaatatcag tacttgatgc tgcagcttaa tggcaaaaca tggtgctcac   6420
ttagcacgca tcatgagttc gattcctggc aaaagcaaca aattaagcaa ttttttttat   6480
gggccctggg cgtaggccca gctcgcccct gcccagggcc ggcactgact tcactaccaa   6540
gttttcgatg tcgtcatttg ttaagaaagt ggaagagtta actcatgatc agagaacaac   6600
tttagaaaaa gtaggatttg gatatttgat tcgtattcat caccataccc tccggaaaaa   6660
ccttttggtt gaatttgaat ggatggagag aagattgcag tctcttggtg aacttcataa   6720
tgaggatttt gtgaggactt tcttgttcat ctttgggacg ctcttttttcc cgagttctag   6780 tgcaaaggta gactcacgct atctttccct tctgaaagat cttgatagag tatgcgagta   6840
tgcttgggga gttgcagtag tggaggacct tttcaattgg ttatctaaaa gaaaagaaga   6900
gcagaccaaa agcattgaag gttgtctgat tcttctccaa gtaagttatc aagtagttat   6960
gtttcagttt tacatcaaat atcaacatag aaatgttggc tctaatgatt ggagatgttg   7020 aatatttga tatcagatat ggtcctacga gcatatagac attgggcgac caatttccct   7080
tagttattct tcaaactttc cgcgagcttg ccgttgggaa agtggtaggt gtaatagtca   7140
aaggcactgg ttcacaacta agtttaatga gcttgaagag aatcaaatga gtgttgtttt   7200
ttcaatattg tgcttgttag ttgtaaattt atcctactaa caatattctg ttctatgaac   7260
tgaagccacc actcaacata cacagaacaa cttgatattt aatgtgttat gctgctgttt   7320
ttgattttac atggtacatt taggtaacct ggaagctgca gccaacaaca gcggagttga   7380
atattgatat catacgagag ctattggtcg aagagctgga aggaaaagtg aaacattcaa   7440
tgagaacaaa taccacaaca tcatccatta cgccaaaggt taatatctat actcgattag   7500
cctgcaagtc aaagaggagc ttatttgctt gcaaaacccc acatttgtta agaaaagaaa   7560
tccaacgatg agtgatgatg ataaacttg agaaataaac ggaaaaaata tacttttcta   7620
taattgttaa ttgagtcatt tataattaaa attcaaatta attgttttg ctttggggtt   7680 atacgtgatc tttgtatcct ctgatcagga ttttaaagat ggtatattgt atgaggaaat   7740
aaatggaggt gtgggcttat gtaagcttaa tccgcagtcc gaggttgtgc aaagactcca   7800
ccagtggctt gctttggtgc aattccaagg ccttctcgac atacggagta agccaactta   7860
catcaaagca aatgactctc agatcagtta atgtagactt caaattatca gattgatcgt   7920
cgctcatgtc taaggccgag ttttcctcaa gggtcaggac tacattcgct accaactcta   7980
atgctcttga tttcaagtca ccattagata aaatgcaatt ttctatgatg tttccgtgtt   8040
ttgaccagat cttctgcaat gtcgggatca aattagactt tatatcgagt tcctcaaact   8100
ttgtcgttgg tgttttgctc gtgttactct gcaagtgaaa gcaaaggat aagctaacat   8160 taatcgatac tagagtagag ctaacattaa tcgatactag agtaaagctc cgacaaaagt   8220
tcaacccttg caatttgtta gtctactaga gtatataaca tatcctagag cctcaaccat   8280
tagctcaagc ttttggttga gttggttcct tgccatgtta ttagagccag tgtgacaaga   8340
ggtcataggt tcaaatctca acccctaat taaagtcgaa tatttagcgc taggtatgag   8400
aagggcatgt gctacatcca cacttctagc gtaaagggct ctcatgtgag caggcgtgtt   8460
agggtatata acatatttg gggccttaac catcagctta agcgtttggt tggcagtttg   8520
ctcacttaaa aaacaacgtt catatagagt aatttaatac ctgatttgta gaagtcatat   8580
atggtctaca gaggctaccc ttccttggag tctttggatc aggtgctgaa actaaaaaca   8640
gaaccaatct taaacttcga aaagggcatg atacaatact atttcataca ggtagttaga   8700
```

-continued

```
ttagctacct tcctcaacaa cacgctcccc ttcatttatg gtagagggtg gtctgctttg   8760
tcgagtagca gtagtagtat ttgaatcaga ctgcattact tcttctacct caggctcgct   8820
tcacaaacaa acattactta agtcggaatt tgagcattgc ttcagatctt cggattctta   8880
ggcatgcggt atagtacaca acaaattctt aaaagttgga gatacaataa aacagaacat   8940
ccaaagaaaa aatacctgat cgatcctatc atcatacct atagattcca ctcacctaaa   9000
aatttattgt aacattatcc tataacacgg gtggaggact tattttctag cttgtaaatg   9060
ttaacacaaa gaattttttt gttcattaac ctaatgtcat taaatgactc ctacttgtgt   9120
aaggttggga ctcagatata cacaacatta tccaacaaaa cgattatttc tgattgacct   9180
ttggtggaaa acatctttcg cagtccgcaa aatcaaataa ataagagttg cacaatgtta   9240
atgagaaagt agattgcaat cctctttta gaaatcaaaa tgattaccaa gatgctaatt   9300
gtacttaatt tattctacta acaccacaca agaaatcatt cttcaatcaa tgctaaacct   9360
tacctctcat ttttccttac agctgagctt ctcatattat tctttatgct aatgatcaaa   9420
acactcaggt tgatacatta ccaatcctct caaagactca aagatcatca aataaatctt   9480
aactagctag tcaactacca ccagtggaag caacatgtta tgctccaagc ctccactcaa   9540
gttcttggac atatatatct taaggcttta accataaact taagcttttg tttgcggttg   9600
agttggttct ttgacatagt ataagtatca accgccaatg tgacaactct gacaagaggt   9660
catgagttcg agtctcaatc accaagccaa tggacgagac cccagtatat attatatact   9720
cttacacatt cgcctcactc tacctgtaac accccagccc aaaggaccac cggtgactac   9780
tcatggagac tgtagactcg cccccacagac caacacaagt ctttccagcg cactttggcc   9840
tcactcgtgc gcacttagga aaacttccca ggaggtcacc caacctaaga ttgctcccca   9900
ccaagcacgc ttaactgtgg agttcttagc aaatgggctc cctagaaaag aagatgcacc   9960
ttgttgatat gagtagtcta tcaatctctt attaagctaa atctggggta tcacactacc  10020
tcccagcatc ataaaaccta aagacaaaga gttggggggt acaagaaaca accaagtacc  10080
taaaaacacc ttaaaaacta gtctttaagg catccaaagt gttgaattaa gtattgaatt  10140
aagcttgtag ctccacttac cactttctat ccctaacaga agtatacaaa aattagatta  10200
tgtgagcgct caaacaaaga catctaaaac tgaagggcaa aacatgtaat ataagcacta  10260
aacgaacaca taaccacaa tcaatatgga cataacaaaa gatttgtcac ctagattgag  10320
attgagattg ggattcagat tcagattgcg attgggattg agattgagat tcagattgct  10380
gatgaagaca cataatctgt gaaaaccaat caggggagag caatgaacat aagctctgaa  10440
ggaagcttga aaaactcctt caacagttgg ctataaccat tattgaatta gattattatt  10500
ttgtgactaa tttttgtcct tagtttgcta tcagcataac tatctatact taatactaaa  10560
ataaacacca cctactgcca cgtgtcgtgc tttcagagaa ttttttcctg cctaaaatct  10620
tattctatgt acatctacat ttgaaaactt aaagattacc aaaattgtta ttattaatct  10680
tattctttgt acgactgatg cgcaagcctt taccttctaa agaagccctc cactcatcca  10740
gtttattatt aacctcctct ttagactccg ctaccagcac aatatcatcc gcaaaaagca  10800
tgcaccacag aaccgtctcc caaatagatt tggagatctc atccataatg atcgcaaaaa  10860
taaaagggct tagcgcagat ccctggtgta gtccaacttt taccggaaaa gcttctgtta  10920
accccaccgg tgtctgaatg ttggtcgaaa cattgtcata catatctcgt ataatctcaa  10980
tatagataga agagataccc ttagccttga ggctatccca aataacttgt cgtggtatgc  11040
tatcgtacgc cttctccaag tctatgaata tcatatgcag gtccttcttc cggtctctat  11100
```

```
attttttccat cagccttctc aatacatgga ttgcctccat ggtagaccta ccaggcataa  11160
agccaaattg gttctctcta atcacagctt cttgtcttat cttcctctct atcaccctct  11220
cccacaattt catggtgtgg cttaaaagtt tgatacccct atagttccca cattcttgcg  11280
catcgccttt gttttttaaac aggggtatta tagtactgct tctccattct tctggcatct  11340
tgtgtgtcct tagtataaca ttaaagaggt tagtcagcca acgaatgccc tcatcccta   11400
aaccctttcca tacctcaatc ggtatgttat ttggcccgac tgcctttgat cgcccatct   11460
tcttgagggc ttcttttact tcctcggggg tgatagcgca cgctaaccca aaaatactgg  11520
gtctatgggc atcgaaagtt cgactatcat ccccccttgg ccctctatac tcattgagca  11580
ggtccgagaa atacttacgc catctggttt taatctcttc ctgtctcaaa aggactcgcc  11640
ccccttcatc tttgatgtat ttcaccgcct ctaagtcccg atgttgcatg gccctggccc  11700
tagccaactt aaaaatatcc ttctcccctt ctttggaatc tagcttctgg taaaactcct  11760
catacgcccg ttttttacc tctataaccg ctttttttgc cgccttcttc gcttctttgt   11820
agcttctcct cttttccgcc ctagcctcct cctcagtgca agccataaga tccctaaaac  11880
tcttgttttt gtccttaatt atcttctcca cttcctcatt ccaccaccac gcctctctgt  11940
acacctttgg ttttcccgat gctaccccca aagtctcttt tgccactcct cgaatggtat  12000
ttgccatatt cacccacata tcatacgcgt cctcagattg acttgggaat cctaaatcac  12060
taatcctatt ggccaaggta gtggccacat ccccttgag  tctccccac atgatctttc  12120
ccctaagctc ggctttttc  tctgcaatct tcttcctcat cctaaaaacc ataactaaaa  12180
gcctgtgttg tgtaggcatc tctgtaccca acactacttt acagtccaag caagaggatc  12240
gatcaacttt gcgcactaag aagtagtcaa cttgtgttgc gtgacctccg ctcttgtatg  12300
taatcaaatg ctcatctttc ttcctaaaga gcgagtttgc aaccaccaaa tctctggcta  12360
acgcgaactc tagtagaaac tccccgcttt catttctcgc tcccagacca aacccgccat  12420
ggaccgaatt ataggtaccc gcatctctcc ctatatgtcc gttaaagtct ccacctaaga  12480
aaatcttctc atcttccggg atcgaactca aaagggctcc taggttatcc aaaaactcgc  12540
gtttaacctg atcgtccaac ccaacttgtg gcccataagc acttacaaac gacactactt  12600
cttctcccac tacgatccta actaacatca tcctgtcgtt acacctcctt acttctacta  12660
cctgctctag gataacgtta gatactagga tgcccacccc gctacgtttg ccgtccaaac  12720
ctgcatacca caacttgtat ccctttatac ttttagcttt ccgacccttc cacctagtct  12780
cctgaacaca agctacatga atcctgtact tagaaagctc attggccagc tctaaagact  12840
tggcttctaa ggtacctatg ttccaagtac ccactcttag ttccaggtcc agtttacgtt  12900
gccccctcg cccccccccc ccctccttgg acctgacctt aggttaccat gattgctttc   12960
taactctata ttcagaaaac aaagggccta gcagataaaa acagtacaca ggcaagagca  13020
aaggcaacag cacaaagaca ctccaacaga ttgaaaaaca cctcaagact taaaacaaga  13080
ccaaaaacaa aacacttcaa ccaaccaaaa caccaaaaaa cacctcagaa cttaaaacaa  13140
ataaaaagct ggtaaaaatc aaatccaaaa agattatcca acaaaaaaat atccagacaa  13200
tacaccgatg aagaggctat tcctaagctt aaacaaaaac cacccaacct ataccaaaag  13260
accaaaggcc aaatcaaaga agaggaaac acccaaaaca ccaaaaacca aaccaaaac    13320
aaaaccaaaa acaaacccaa agaaagttaa tcaagaaaca ccaaaaaaca aaaccaaaaa  13380
caaaaccaaa aacaagagca aaaaaacact aactaaggca gaatcaaaaa aagaaaaaat  13440
```

-continued

```
aaaaataaaa acgaaatgca caccaaagca aagcaaaacc aaagaaaaag ggtacagaga   13500
aaccaaggaa aagggaaaca ataaatgtat aaatcacaat caagaagag accaagaagt    13560 tccctaaaca ccaaatcaaa ccgaaaacaa aaactacaag aagagacaca gaaacggctg   13620
atcacgagag aaaactaaaa acaacaaacc ggacggtgac ggtggcgggg aggagtataa   13680
tccgccgcga aattctgcac ccaactggca gtgaacgagg gcggtgacgg tgacgggatg   13740
gaggagtgac ggtgacgagt gaacaaggac ggtggtctgc tgcttgctga tcttgttcgt   13800
gtacccaagc atggggagat atttgtttcc agaaacataa aagtaaatat ttgaatagtt   13860
agggaaataa atacacatca aataaatttc aataaatgtg atgcaaacct ctcgaaaaat   13920
aatagtttca agtcttggtg aattatcaag aaggtaccag atgtgtaccc aagcattaaa   13980
atcaaacgga ccaagttcca accatgctac attaggaaag ttaggaagcc cataatatct   14040
cccctttgac aaagaagaca cacctttatt aatatttaat aaagtatgca ctaatcccac   14100
aaagttaagg aaggaagaga agaatcatac cattaaagtt tccccaagaa gagaaaaatg   14160
tgtaacacta tgtatgtgag tcacaagtgc agaagccagc ttattgatac tcgaaagccc   14220
ataatcacca ggggtaatga ttgtcagata tgccaaacta gaggcatgaa tatcaatcca   14280
gtcttcgtga gccatattaa taatcgttaa cttcttaagt gtggtggaat gcatggagtc   14340
ccttgccctt atccgacaat tctcaagagt aagttcttct agggaaaaac atccagaaaa   14400 gaaccttta catgattttg aatcacaaaa tgttatgcat ttgagatgaa ggttcttgag    14460
atttggtaag cttatcgatg ttagaacttc aaggagaaga aaaaattctt cttgacgagt   14520 taaaagcca atttgaagta ccacaagtgt ttttgaattg aagaggtcac atggaaaact    14580
acataagttg taccatggtg agttttctaa atcctcatct gcttcaaagc gaagataaag   14640
ctcttgaact tgtttatgta tggcagcatt aatccaatta tagggatgta atctatatgg   14700
gtttaaatga gttttttaaac tgaagagttt gatggcagaa acttggtgtg atcccaaaac   14760
atcatacaca aatttcttaa atcttatctt tcgaaaaaaa ttttgtgcgg ttgatgtacc   14820
tcccactact acttccaaat ctaatctctc atcatcaaaa cgaagattag tcgttaactg   14880
gaaaagatat ctccatctag ttgataaaat acttgtagaa actgcacaat ctgttggtag   14940
ataatcaaga attggaacaa gtatttcatc aggcaaacga ctaattctat ccattttttt   15000
cccatatatg ttatcacctt caagtctact acaaatatcc atggttcgat caactcttga   15060
tttgtgcaca cttgattggt aatactagca atctgcacta acaaaattaa agagtttatc   15120
cctatgccat aaggtttctt tatacatgaa tgaagaggaa tatgggtaaa cacttcaaat   15180
tgtattcatg tataaagctg accaaaaaag aacaacaagt tgtgaatgtt tgtttgaaga   15240 tgagggctt atatagcttg tatatgtgcg tataaggtgt caatgaaaat cttaggatgt    15300
ttacaatatt atggtataaa aataggaggc atgtattaag acaatttggg ataaaaagaa   15360
tgatttgttg aaggcatata agctgccaga atcaaagaga attgtggaac ttctttgtct   15420
aacgtctccc tctaacgtct ccctgcccct ttcatctttc atcttccttg tcaagcacga   15480
caccgtagcc acgcaggtga acacgaacaa gatcagcaag cagcagacca ccgtccttgt   15540
tcactcgtca ccgtcactcc tccatcccgt caccgtcacc gccctcgttc actgccagtt   15600
gggtgcagaa tttgttgtgt taattaactg ttggctgaag atgtccaagc tacttgttac   15660
ttcaataaat ctcaaatcat tcataaatcg ctacaacaaa acatggagct tttagacagt   15720
tttttttaga cacaataaaa agcgtctaaa aaatttttaaa gctgttagac gctattgttt  15780
agacgcataa aacagttgct aaaataatct taaaaagcgt taaaaaaccc atttcaaatt   15840
```

```
tgttaagagg aaaaggctga aaaagcgggt agatttaatt tctaaaataa taaaaaaaat   15900
aaaaccgcca ttcacacgca taactggcct ctctcattac gagcttcatc ccttcactgc   15960
catttcttgc cttcagtcaa aaaaccgcct ttcatcccgt actttgttgg aatcgtttct   16020
caatctattt tcagccatta atctgactgt tcatcccttc tcttcaacca tcaatttctc   16080
aatctattca aaccattaat caatctaaga aatcgtcaag cacgattttt caacactggg   16140
taccaatcat tcggaattgt tcaacacgat tgttgaaata gtcaagcagc acgattcttg   16200
aaatccaaat attgaaatcg attttgcctt ttctgtcagc acgattgttg aaatccatat   16260
attaaagcgg gtaattctct taaactgatc tacaaaatca gtgtatttgt tttctttcat   16320
catcccaaat gatacttaga acactaactt aaattttaac tgcgatgatt caaaactgat   16380
ctacgattgt tcaactttta taaaatgctc ttttaaatgt taacctcatg ttctcgtccc   16440
aaatctgcag aaaacatcat ctccctcaaa ttgtcctatt caaatcacat actcaggtat   16500
ggtttcttga attaagttaa acgaatggtt aatttaggtt aattcaaggc ttaaacaact   16560
gaaattttgt catagttttt taattctatt tttacggatg aattgttgtg taggttaatt   16620
accattgatg ttttacaatt tcaagaaggt ggtttcacat aatcaatatg ttttttgtgt   16680
ttttgttgt tttctgttgg ataataattt agttagttgt tgattctaag tgatcgtttt   16740
cttagcttat atttatcaat agataatgtg tctatcactc gatggctttt ataattggtg   16800
attctgagta gtttgttgta tctgtctttt agtgtcaatt tgcttgtgtg cttttgaggg   16860
gatatgttga tcctgtgccc ctgttggttt tgagggtatg atgttatact tgagtttcta   16920
ctctccttgt taatgtatga gatgctgcta gtagctgtat agttgctgct gttgagttgc   16980
tattgaagct attaattgtc ttagtgctgt tataaatgct gcatcagttt gctgttgttg   17040
attgctacat atcctgttga gatagtgtct gttttaatgt tgttgttgtt gctttgaagc   17100
tgttgggaag gtgcttaagt gtgctgattt atttcttgac ttatgttgct ggagcatgct   17160
catgtgcaag tgttttttgt tgctgatctc tggtccaagt gttgctgtga tgctgtatta   17220
gtgctgctta atacattcta tgcttatgtc actataccgc tattacaaaa ttaagaagga   17280
aaaaaaataa aagaattgtg cacgattatt acctccttac gtccaaattt aacctctttt   17340
tgttccacgg aagtcaggtc cttggtaagg aacataataa gagacattga tagaagttta   17400
gtttctaaat tatccatcac cacataactc gttgtcccctt tcacatatgt tggattcatt   17460
gttgacactg acccagaaac actatcagag atcattagac caggtttgtg attcaaacaa   17520
taattatcca cattcctata aatacaggag ctagtggagc aataacggta agtcggcctg   17580
ttaccgagac tagcagatgg cgccagcaat gggccaatct tagaagtaga gggattcagc   17640
actgaatttt tgtcgaaacc agtctcgaga caagcattgt caaaagactg gatgcatttg   17700
tagagatcat caaggctcca actcatctca tgtttatttt cttgaatgaa tttaacaaca   17760
gtagcaagca gtaacgacag tatgtggaag atgaaatcaa caactccctt gcttgcttct   17820
gcaaacacaa ccttcttagt cttttttgtct accattagct tcaaactcat ttttgcttat   17880
tttgtttagg gtatatatgt ttaatgttga gaattgaaat ggttattgtt tcttacaata   17940
ggagtactat ttatagaaag cactactgac caaactggaa tctgtaagat caatatagta   18000
agttattact aagttgtagg tatttattta gaattgaagc ataaattga caataaggct   18060
aatagcctag tatggattaa ttaccactct tcaacttccc ttttcagaag cctacattct   18120
ttgttctcca tctcactaac ccaaacttga acccaaattc tttaataaga cggttttatg   18180
```

```
gtgttatcat ttggtacaac taatccgtac acatcttaac atattggtgt tgtaaattag    18240
ttgctgtcac aatcttgagt aacttgattt ctgaatttta tgcaataaat taaattggat    18300
tttagaaatt tgtagtgcaa acttgcaaat tgttgtttct tgttttatgc acacacacac    18360
attcgagtgc tgtttaaaat catcattgat tcctgatatt tttgtttgat tcacttgatt    18420
ctttgtagtg caaatttgca aattgctgtt tcttgtttta tgcacacaca cacacattcg    18480
agtgctgtta aaaatcatca ttgattcctg atatctatgc gcttggttct attgtggagt    18540
acaggattgt gagaaatttg ttgtgttaat taactgttgc agtgtagtat tacaggtttg    18600
agctattgta atcctaagtc cactaattaa cgcaaaaacc aagttatttt tgacgaggct    18660
acaaccatgg ctttgtattt agcctttgag cgtcatctag atacagtccc ttgccttttg    18720
aattttcgac taataaagaa ccaaggagaa taatatatct aataataaag cgccttgagt    18780
caatgttttt tccctagtca tagcattttt gttagtggct ttaagtaagt taatgggtga    18840
ttaataaaag taatcttcga cctgatttct cttacaaata aatggacaga gcatgtgcct    18900
attatatata aaactgtata taattgttta attccttctg caggatattg tccaaaaacc    18960
tcaactttgg aatactttag tgttgataaa atttgatgcg gatcacaaag tgaggtgtgt    19020
atgtcgttta tctccttata ttattttatt gcgatgatta ttattatttg gcctgtacat    19080
atcaatttga gtactaaatt ttaatgagtt cattttacaa acatattatc ccgaaacttt    19140
tacaatgtta tgtttattta cttcaataca atgatgctac ccatgatttt gaatcctgga    19200
tttacaattg tctaccacat tttgaatgaa tttgacttac tattttgaat gagtttgtga    19260
atattgtgag atgtttaatt tcattaataa aaatagggtt taatgtttgt tttgtgcatt    19320
tcaattttgt ttgttctttc ctttgtggga aaaaatttga ttatcgcctt gttttttttg    19380
gtaaatgtac tgcatgcctc atatgtgtag tagaattttt tttgcataat attaactgta    19440
tatggttgtt attaggatgt ctcaacatat agataagagt tggatagata aaccaagaaa    19500
cactgaagct tatattaaag gaatttatga gtttatagaa tttgcaaaga aaggattaca    19560
aaatggaaag attatatgcc catgtaacaa gtgtcaagtt gatagaaaga aacttcttcc    19620
attagatgac gttgaaagac acattttgtt taaaggcttt tataaggaat acaaggagtg    19680 gattttcat ggacctctaa gtgtcgctga aaatgtttgc aatcaaatag ggattccgtt    19740
tgaagtttct aatgattcag aagttatagg tcaggatgat atatcagggt tacttcgaga    19800
tgctttaggg gtaaatatcc ctagtgttcc cgagtttgtt agcgaacatg acgatgatag    19860
tagagccaat gaagcaaatg atgagtctaa tgatcaattt gattttgatg aacatttttc    19920
ccaagagccc aatgttgact cttcctttga agaggttaaa tataataggc tacgagaatc    19980
ttcaacagaa cctctcttatg aaggttgcac ttccttttca aagttatcat tcatattgca    20040 tcttttcat cttaagtgca tgtttaagtg gcccgataaa tccttctcaa tgttgatcaa    20100
tcttttactc gatgcatttc ctcaaataaa aatttttcct tcctcgtatt atcaagcaaa    20160
gaagttgatc atggatttgg gtttaggata tgaaaagatc catgcttgtc ccaacaattg    20220
cacattatat tgggggtgaaa tggcggagaa agattgttgc cctaaatgtt ccacttcaag    20280
atggaagagt gaaaatgaca agggtaaagt tccggtaaag gtgatgagat attttccgtt    20340
aattcctaga ttaaaaagga tgtatatgtc atctaagatt tcgaaagaca tgaggtggca    20400
cgattgtaaa aagccatcaa tttgtgttct gactcgtgct gtgtgatggt tatgattcag    20460
cacagtagat caatttactg gagaagcgaa gcctgtcaca cttccgctgg atgaaaatca    20520
ggtaaatagc tggtgtatac gacattctat gaaaacagga tatgattttc tgaaatgtct    20580
```

```
ccactctatt cgtttttatt gacaattgtt tgctacatta gatatcttgt tgagtgacaa   20640
gcatagtgct aaatattgtc ccatcaccat atcacgacca tattgtaaag gtttttgagg   20700
ttattgcaac taaaatatat gtcgagacaa ccgagaatcc atctacatta tatttatttc   20760
acaacttcta acattaccat gaccctgacc gtaaccataa ccatagccgt aagtataaac   20820
tatggtaacc agcagtctcg aactctcaat acgctttcaa tagacgaaag tcccaaaagc   20880
ttctagaatc tagtagcttt tcaggtgatg gtgatttgtg aaatgtggtg ctaatagctg   20940
atcttggata gcttcaaaat ctgtttggcc ttacttctaa ttttggatt ttgcagtgta    21000
ttatttcctt gtttcccta tatatcccctt ggcgtaatag tgcaattaat cgatttattg   21060
tatggttata cagatcatca aaggcctgaa ggatgtattg gttggtatga agttggagg    21120
tagattccga acctttattg tgtttgcgta tttatataag tatttttaa attagtgtcc    21180
gagcatatta ttgaatacat tgtattagat tagttattgt tatgcgaacc ccttctgaaa   21240
gccaaggaaa atcacctgag ttagttggat atttggatgt ttcttttgt gcatctgtgc    21300
atattttcag tgtctagagg gcactgcttt taacaaccta gcgatcagac cgcattcact   21360
acccatgaag gctgtagact gccccacgga ccaacacaag tccttcaac acacattagc    21420
ttcactcgtg tgtaccattt cccaaaatgt cactcatcct aagatgacta tggtctctcg   21480
aaaacaggaa taatatgttt tcatttgctg gcgcgtctct ttatcgatcg actgattgat   21540
tttgcttcat cgtatacttt cagggaaaag aagagcctta attccaccgt ccataggata   21600
tgtaaacgaa aacttgaaac ccatcccaga agaggtttat attctctcgt aaatgctgca   21660
tttgcgttgt atgagatcgt tttcctagct tctaatcatt ttcgtgcatg ttactctaat   21720
gcagtttggc cctcgacgta gccttctgtc tcacgcgaat gagcccctgg tatttgaggt   21780
gcagcttttg aaaatactgt gatgctttgg ccttcgggtt taaaacgttg ctcagtttgc   21840
acaacaaatg aactcatacc taagctcgt tttcgaattt cattttgttt gtaaattctg    21900
tacaactaaa ctgattatag ggtttctaaa attgaaaatt gccaccttt tttccaagca    21960
aaagtaccaa atctagtaat taacaatcca ccttgaaaga ttatatttta cctttctacc   22020
tgtagatttt gacttgtgtc gttgtgcggg atactgaatc gataaatatg attataactt   22080
tctttgttcc catgatattg acgcatgtca tggactagat atgccatgag atgtaattgc   22140
taaagatcaa acaaaaatgt aaagagaata taacaatttg aatgtaaaat ggaaatgtat   22200
atagaagatt gaatgtaata aacgaacaat tacaaaagat agaattacaa gcttcgaga    22260
ggcttgttct ctcccaatga gtataatact ccacttaaat ctaatacttg gatgatttcc   22320
taattcccct cccttcccct ctatttatac taattatgcc cacataatat tctcccactt   22380
aactaattac tcaatattat ttattattta attcctataa tacccccttct cagccatcca  22440
tgacataccg acccctaaaa aatccacctt gtcctcaagg tgggtaaaaa ttgaattggt   22500
tgtcaatttt aaataagaat ggtagcttga tctgatatgt cagggtagaa tatgtggtca   22560
tagaaaaaat taaagaaga tgtgaagctt tgcatgtgtc agtaaaaagc atgagtgagt    22620
gggtcacttt tttcaacctc ccacaatgta ctctattgcc ctctttaccc ttaccttctt   22680
tattaaaagt tactgccatt actgttgtct tactactcat tccctcaaca ctcttcctag   22740
tttctactcc ataaccacga aactgctcat caccataccg ccacttccaa cacctcattt   22800
cccgtcgcct tctccggtcg ccgccactgt ctccaacttt gccgtcacaa tttcttacac   22860
cgactactct aagatcccta ttttcataaa acacagtttg aaaccctaac ccttcaccat   22920
```

```
acatggacgc ccagtcctct tcccaacggt gtcgacgttt cctcctctgt cgccacaaca   22980
gattctccgg ccaccccgca ccaccgcacc taccgctagt tgcttgtgcc acctgaaaat   23040
catgaagtac tgttttgttc tgccgtcgca ctccttccct ccttttgtgt ttcgtcatcc   23100
aaaattgtaa ggagacaatt gctggaactt ttatggtcaa cattcgagct ctactcatga   23160
ggtcttcacg accattagca cgcttgaccg gtatgagatc tcctgctgta actgttatag   23220
atttgtcgac agcagctgca acctctgtgt cacacgaatt ctcaagctct tcttcattct   23280
ccaggacctc atcacattct tctaaatctt cttcactgta ttttcagta agtttggtct   23340 tctggatctc ctgcattgta gtgttctttt ctacttcatc ctccccaatg acctcatcac   23400
ggtcttctga atctacacct tccttctcat gatgaactct cttttaagct tcttggaga   23460 ttctttggag tatagcgtca aaacgagcat ctgatttttt cttactctct aaatattttt   23520
gttgaagctg ctcacgatgc tggtccagat ttgcttgaga ctgtttggcc atctgctctt   23580
ggtgtgcgat gttgttattg attcagtga ttaatccctc catcagagat attactctgt   23640
taaagtcatt ttggaggtct tgacgtgttt cagcactata cggacctcga atgctgttgg   23700
ttttggactc aagaacacca tcagagtaca aattctggat atcacgatcg tatcttcgac   23760
caccacggac cgaacggctc tgataccaat tgtcatggac tagatatgcc atgagatgta   23820
attgctaaag atcaaacaaa aatgtaaaga gaatataaca atttgaatgt aaaatggaaa   23880
tgtatataga agattgaatg taataaacga acaattacaa aagatagaat tacaagcttt   23940
cgagaggctt gttctctccc aatgagtata atactccact taaatctaat acttggatga   24000
tttcctaatt cccctccctt ccctctatt tatactaatt atgcccacat aatattctcc   24060
cacttaacta attactcaat attatttatt atttaattcc tataatacccc cttctcagcc   24120 atccatgaca acgcagtagt tgtatgttta gtgtagatct gtgccattct tgttatatca   24180
aatgacgagt tatactttgc tattagtttt catccaacga gttttaccct atcggctatg   24240
tctaattgtt agtctatata aaagtggca aagttgatt caacctacta attcgacttg   24300
aatttaatct aagtttagtt aattaaatgg atcgatttga cctaattaat ttattaaatg   24360 actaaaattat taaaaattat atttcaacag atttactctt ttacctaatt tatttataaa   24420
ctaaatatat gaaccatatg tataaaaaaa ggaaaaatta cctagaataa tccaaacttt   24480 tcataattttt cttacaataa tctcaactat tgattaacca tgaataatcc atactttatg   24540
aggtatatat ctagagtaaa cttaaatatc cgaatgactt gctatagtag gtaattttc   24600 aaaaaaaata aactgaaaat taatataaac ttacagaaat agtttaaaaa ttagtataac   24660
aagttctaaa agaattttaa cattttttg acattattt atctttaaaa aataaaaca   24720 tgctatagca gatcatccga ttacttgagt ttgttctagg ctaataccc ttctaggtaa   24780 tttttcctaa ttataattaa ttataataat cataattagg aaaaattacc gtgaataata   24840
caacaattgg ttaattttac tacaataata ttaataccaa cttaggggat attttcctaa   24900
aataatacca actttagttt attaactaat ttaccaactt tttttgtctt acaattacct   24960
atagtttgat ttttaacata tcggaaaaaa tttatatga aacacccct ttaaattagt   25020 attattcata ataattcaat aattggtatt aatgtattat tgtagagaac ataacaaaat   25080
gtcgtgttat tgacgatgat ttttccttat aattatcata atcataaatt ctactaaaac   25140
aataggagaa tgtgataagt gtcacaaatt taagagttat ttttgcgcct aattctattt   25200
aaattatttt aggtagtttt ttaaatttaa ttttattcca tggatttgct taattaattt   25260
aatccatatt tgattttgcc tcatatgttt tttcattgat gattcttttc actcctataa   25320
```

```
tagcctttaa taaccaattt tttgtcatat attttgggga aatttcacgt ggtaaccctg   25380
agattttggg ttttccacgt ggtaaccaaa acttttaaaa aatccacgcg gtaaccctga   25440
gttttacgta aatgttccat catgaccttt ttgcacataa aaattttagc aaacgttaat   25500
tttgaagctt tatggctgtt gtatgcatat ttatgcgact caacattcga aatgccatca   25560
atttgaacca ttttgcccaa aatataaccc tcaaatctac cattttttcat ccaaatctta   25620 ttttttttccc ccaaatccaa agatggtaga gtttaggttt atattttggg gaaaatagtt   25680
gagactgatg acatttaaaa tggtgagtca catatatagg cgtacaacaa ccttaaagct   25740
ttgaaattaa tgtttcttaa cgttttctaa cattttatgt gcaaaaggtc atggtgaaac   25800
aattaggtaa acctcaggat taccatgtga attttttaaa agtttggtt accacgtgga   25860 aaacccaaaa cttcagagtt accacatgga atttccctat atttttttcaa aaattcttat   25920 gattccgtac ttagcactac ctatcacact tcccccacaa gccacaatat tcactatact   25980
ttagtcttct ctttttcaaa aaaaaaata aaaagtttt gaaatgactt atatataaag   26040
cttgtttgtc ttggaagttc catgcatttc cttatatagc aagttttga tgccctaaac   26100 tgaagagtga acagcgagtg gtgaaaatga agcgacaaag agaagaatcg ccggcaattg   26160
gaatcgatct cggaacaacc tactcatgtg tgggtgtttg gcagcatgac cgtgtggaaa   26220
tcatcatcaa tgatcagggc aaccgaacta ctccttcttg tgttgctttc gaccataatc   26280
atcgtcttct tggtgaagct gctaaaaacc aggctactac taatcctgct aacactatct   26340
ttggttcaat ttctcatctc tttctttttt ttctttttcta ctttttgttc atggatttgc   26400 cctttttgatt tagcattttt taaggaaaat gtgaatattt gttaataatc gaaagaaat   26460 attgaagtgt gtggattatt ccaaaaatgg aaatgatccg aaatgagaga gtaagaatag   26520
ttaaaaataa ttcttttggt tattttttgtt ttgctataaa tttagactct ttgataattt   26580
catggtacgt tatagataat taaagggtg agaggcttat agttagaact agaaggccct   26640
gaatatgttg tattccctg tcccaaaaga attgctataa gtagaaagtg agtgatttat   26700
gaagggttca agggaaaagg tgtttttatg ggtttatgag aaatgtgtag attgaattag   26760
gaaacgtatg gatgaaaatc aaagaatgac cgaataagtt ctatcatgcc ctcctatctg   26820
agaatattta ggactacaag tgttgatgct gctcattgta cattcacta aacaaatgag   26880 gggtttgaat ctataatttt cggtcacatt tgatacccac gtaaaccgt atgtaatgta   26940 taaaatttga tgttttttca tctactgctt aaacaagcaa taaagtagtt tccaagtcaa   27000
gggtttagct tgttggcatt agtcattaca ttagtgatca tgctttgctg gtaatttttg   27060
taccaagatc aaatctaacc atgttctgta atttgatagg gatgcttcgt agtatagaca   27120
tttatattag agtctagtaa aacttgagtg atgtcaggta accaattttc aagtaaggcc   27180
caatatacta accagtatgt gggcaacaca acataaagag tgataaagaa ctttgctatg   27240
ataaagtagt attgcacaca aagtttgttt gcctcaccta aactcccatt caagtccgac   27300
cctataaagg ggctggaggg gcttgtgcct caagtccatc cataaatatt agataaacaa   27360
tgctttgata gttaataatt aggggcctat aataattaat gttttgcctt gggcttctca   27420
aatctcagag tcgacactgc tcacactgga ctagttttga gaagcactta gccttctttg   27480
gattttggtg ttctgcacac atgccttatg aatgcacaag caacctattt atatcaccag   27540
ttcctactat agcaagccga actttgcttt ccttttcatg cttctgtcgt aatttgttaa   27600
tgttttggag ctagcaacag agggtgacaa tagggcttga aaagtttact atcattcatc   27660
```

```
attggtgccc atgttttaca taaatttcga gttgcattta attttattga gccagtgcga  27720
atatattagt gaagcaaaga ttaagtgaat ataatgtcat atttcaagag ttgttaatta  27780
ccattcatta gccccaagtt ttctcctttg gagagttacc ttcattgggg cactttgtct  27840
caacaaatac aatatctact gcatatgatg gttgctttgt taatgaatga agttattgca  27900
ggcttagaac atgggtttct acctactaga aatatttcca tgcaggtaga gcccaaagta  27960
cccaacatta aaatgtcgtt gatcagtctt ttttcttttt gtgctcttat atccattata  28020
tctaggtgat tttggatctt ataaacacct acacatgaat aacatttcat tacaaatctt  28080
attaagtggg gtaggatgta cgcaaccttt tccttgttag tattaacaaa ggggttttta  28140
gttgacccct agtagttgga ctatgatgtt gaaatactga agagtagaag cttgtttggg  28200
ttgcttcaat aattttacga attgatacat atattccatt atgttaccta aatttttttt  28260
tatagatcgt acacaaagta tagtataaca ttatgcgaag gtccactttc accctgaaat  28320
agacacagaa tatccaaaat gagtcccatc aaacagaccc accagatatg tttggcacat  28380
aatatatgta actgctacaa tttttttgag gttttcatgg tatttgaaaa ataatcaaat  28440
tctgatgttt tggtgggaat ttctttttat tagtgattgt caaattgatt taattgatgt  28500
atcttgattg cattgtggca aatacttgtt gatttgattt aatttcttat ctactcgact  28560 ccattttgc  aattaaccaa cacagatgcg aagaggctta ttgggagacg gtttactgat  28620
gaaacagtgt agaatgacat aaaactctgg ccttttaagg ttattgcgga ctctactgaa  28680
aatactaaac ccataattgt ggtcacctac aaaggagaag agaagaaatt tgttgccgag  28740
gagatatctt caatggtcct gatgaagatg aaggagacag cagagaccta ccttggcatg  28800
aatgtgaaaa atgctgtagt cactgtgcca gcctatttta atgattcgca gcggcaagca  28860
actaaagatg ctggtaccat tgcaggactt aatgtcatgc gcattatcaa tgaaccaact  28920
gcggctgcaa ttgcctatgg gcttggtaag atgagtgccg taagaaaaga ggtgaagaat  28980
gtgttggtgt ttgatcttgg tggagggact tttgacgtgt ctttggttca aattggagag  29040
catgcttttg aagtgaaagc agttagcggg gatacccacc ttggtggaga ggattttgac  29100
agtagaatgg ttagccattt tgtggcagaa ttcaagagga acatagcaa  ggacatcagt  29160 aaaaacagta aggctcttgg aaggctaaga gccgcttgtg aaaaggcaaa gagaatgctt  29220
tcatcagtca ctgaaactac tatcgatata gattgtctat ttgagggtat tgattttaac  29280
tcaactatct cacgtgctaa attcgaaagg ctgaacatgg atttgttcac caattgtctg  29340
gttcttgttg aggtttgttt gaaggatgcg aagatggaaa agggtaatat tcatgatgta  29400
gttctcgttg gtggatcgac taggattccc aaagttcaag atttactaaa agaattcttc  29460
aatgggaaag aactctgcaa aagccttaat cctgatgaag cggttgcata tggtgcggca  29520
attcaagctg caatcttgag tggtgtacgt aacaaaacag actttacgct tgtagatgtc  29580
actcctttat ccctcggtct tcatcttcaa aatcataaaa tgaaaatttt tattccaaaa  29640
aacattccag ttccaacaaa aaagtatgac attttaagaa cagtagctga caaccaaaca  29700
agtgtgcatt ttcctgtata tgaaggtgag agacctattg ctacagaaaa caactttttg  29760
ggcaaatttg tgtttgatat tcctccagct ccaaaaggtc aggaaaagtt taacgtttgt  29820
tacgaactcg atgttgatgg catcctgacc gtgtcagctc aacacatagg cactaataac  29880
aagaaacaaa taactatcac aaatcacagc ggtaggttat ccaaagacga gattgatcga  29940
atggttgaag aggctaaaaa atacaaggca gaggatgaga cctacaaaga agttatgaaa  30000
accaaacttg cattgcagaa ctatgttgat tctatgtggg atatgttgac agtttgcagg  30060
```

```
aagaagtttc tagaagaaga cgtcacaaag gcggagaatg ccatcgagca aacaatccag  30120
tggctggaat ggaatttcga tcttactgat gctcgtaaat ttgaggagaa gatgcaggag  30180
ctaaagagca ttattgaacc cataattgct gggttgcctt gaaaaagcgc ccagtctaat  30240
gtctatgtga tgattatgta tgataccaaa gtgtatgttt ttgctgtcct aaattgttgt  30300
acgaggtcgt ttcacaatca gacgtatcct cacaaaattc tctcttttgc cgttgaaaat  30360
atgttattgc tatatacttc ctccgttccg aaatactcgc tacatttcat ttttgagcac  30420
tattcatcgt tcaagcttat tttacatatt acgagtaatg tgtaagtaaa aatatagtca  30480
agtaggatct tgtttgaatt gtctaatcgc atactctcat aatattaaat tttataatt   30540 tttagataag tgtagtttaa gatattaatg atcaaaattg tacattggat tgcgtaaaaa  30600
agtgaaatgt agcaagtatt atggaacgga ggaaatatat atatatatat atatatatat  30660
atatatatat atatatatat atatatatat atatatatat atatatatat atagaaatgg  30720
gatcatatga gaccacccc tttatgtgag accatttctt atatgagacc atctcattta   30780
tcaaatgagc aaaaaatttt gttgctcatt tgataaatga gcaaaaaatt ttgttgctca  30840
tttgagaaat gagcaaaaca ttttttgctc atttcataaa tgagcaaaaa ataattgctc  30900
atttgataaa tgagcaaaga attgtttgct catttgataa aatagccaga acttgtttgc  30960
tcatttgata aatgagcaaa gaattgtagc tcatgtatca gctcatgtga taattaaaca  31020
taaaatcgtt tctcatcaca tattatcaaa acaagcagca aagtaccagt gcgttttgga  31080
caagaatata ttaccaaaaa aaactttcac attgatttca aattgatgat gttgattatg  31140
aaaatgatga tgatgatgat gatgatgatg atgatgatgt tgatgatgat gatgatgatg  31200
aagttgatga tgatgatgac gatgatgatg atgatgatga tgatgatgat gaagatgatg  31260
atgatgaaga tgatgacgac gacgacgacg atgatgatga ttttccccat tttccacccc  31320
aagttttaca ttttaatatt ttacacttaa accaaacaat ataaaatggg aaaacacttt  31380
tcagtgaaaa tgttttacgc cctaccaaac ggagccttag taataaactt aagttagggg  31440
tcctaagaag gaaaaacaat atctattcat cctgattttg atgcaagaac caatacaaga  31500
gtataaactt aagttagggg tcctatgaag attatgatga tgactatgat gatgatgaag  31560
ataatgaaga tgattttgat gatgatgatg atgatgaaga tgaagatgaa gatgaagatg  31620
atgatgaaga tgatgatgat gatgatgatg atgatgatga tgatgatgat gatgatgatg  31680
atgatgatga tgatgaagat aatggagatg attttgatga tgatgatgat gatgatgatg  31740
aagatgaaga tgaagatgaa gaggatgatg atgatgatga tgatgaagat gatgatgatg  31800
atgatgaaga tgatgatgat aatgatgatg atgatgttga taaatgaact aagaatagtt  31860
gctcatttga taaatgagca ggtctcacat ggtctcacat aagagggtgg tctcactgga  31920 tcctgacct atatatatat atatatatat atatatatat atatatatat atatatggag  31980
tattatttag tgcagaaaat cttaactatt ttgttgactt ttttctgtga ttgttgtctt  32040
ttatagttga gattgtcaaa ggaattatca aatggtctat ttttgtctta ttattgtact  32100
tcataagttt attatgctat aatattgaag taatactcca tccgaatcag tttagatatt  32160
ctatttggga tttcacggat ttttagggtt gagtggagtc cataaaaagt aggtcaaaaa  32220
tcaatagccg acaaatagct tttgggtgtt tgacccaaaa aaattttaaa caaaagtca   32280 tttgtaaaat ttttttact gtttgaccaa tcataaaatc aaaagttaaa agccagaagc   32340
taaaaattaa cccaaaaatc aattaaaaag tttattgtaa aatatatcca taatttctat  32400
```

```
gattttaatt ttatagataa cttcaaaaag actaaaaata taatacttaa taaaaaaaga   32460
gtattcacat tttatccaat gaaattttac ctatttgtga cttacgaaac atgttaaatg   32520
ctactcttat ttgttattcg gataaaggtc aaagttattc ggataaaaac tgatccatct   32580
tagtttctcc tattttgcta catatataat tatgtatgat attaatttgt taattacgat   32640
ataatatgat gttccaccta gacaatctca ctaaaattca caatttattt atctcttcta   32700
aattaaatcc tatatataat aatttataaa aaatcactt  tacctacaaa acttccatct   32760
gatcgtcgtc atcattaaga atttaatatt tcgcttaaaa atagggtcgt tgtgaggaaa   32820
tatatcatga ctattttata cctgtgccct tgaaggggag tgtcaccgaa atgctatcaa   32880
ttttacaaca ctcccgtctc tcccctcctc acattattag agagacgtat ctcaaaccaa   32940
atccattaaa aattaatatc tattttaccg tattgttaat acctatttaa attattctta   33000
atgctaactt atgattttga tgatgatgat gatgatgatg aagatgaaga tgaagatgaa   33060
gaggatgatg atgatgatga tgatgaagat gatgatgatg atgatgaaga tgatgatgat   33120
aatgatgatg atgatgttga taaatgaact aagaatagtt gctcatttga taaatgagca   33180
ggtctcacat ggtctcacat aagagggtgg tctcactgga tcctgaccct atatatatat   33240
atatatatat atatatatat atatgagta ttatttagtg ctgaaaatct caactatttt    33300 gttgacttt  ttctgtgatt gttgtctttt atagttgaga ttgtcaaagg aattatcaaa   33360
tggtctattt ttgtcttatt attgtacttc ataagtttat tatgctataa tattgaagta   33420
atactccatc cgaatcagtt tagatattcc atttgggatt tcacggattt ttagggttga   33480
gtggagtcca taaaaagtag gtcaaaaatc aatagccgac aaatagcttt tgggtgtttg   33540
acccaaaaaa atttaaaca  aaaagtcatt tgtaaaattt tttttactgt ttgaccaatc   33600
ataaaatcaa aagttaaaag ccagaagcta aaaattaacc caaaaataaa ttaaaaagtt   33660
tattgtaaaa tatatccata atttctatga ttttaatttt atagataact tcaaaaagac   33720
taaaaatata atacttaata aaaaaagagt attcacattt tatccaatga aattttacct   33780
atttgtgact tacgaaacat gttaaatgct aatcttattt gttattcgga taaaggtcaa   33840
agttattcgg ataaaaactg atccatctta gtttctccta ttttgctaca tatataatta   33900
tgtatgatat taatttgtta attacgatat aatatgatgt tccacctaga caatctcact   33960
aaaattcaca atttatttat ctcttctaaa ttaaatccta tataataa   ttataaaaa    34020 aatcactta  cctacaaaac ttccatctga tcgtcgtcat cattaagaat ttaatatttc   34080
gcttaaaaat agggtcgttg tgaggaaata tatcatgact attttatacc tgtgcccttg   34140
aaggggagtg tcaccgaaat gctatcaatt ttacaacact cccgtctctc ccctcctcac   34200
attattagag agacgtatct caaaccaaat ccattaaaaa ttaatatcta ttttaccgta   34260
ttcttaatac ctatttaaat tattcttaat gctaacttat cgaattctta atgactactt   34320
tcaatatctt aaaagtctac ttatattatt cttaatggct actcaaaata ttttaaaaat   34380
aagtagttac attggatcca ttctttctat gactctcttt ataaatagcg ttgaagtcac   34440
ccatgaacaa acacggagca ttgtagttca gatttcccat atccttccac atatcccgac   34500
ggtctctaac actatggagg ccttcttttt tgttcttccc atttactttt tgcacagttt   34560
tcaaagcaac tttcgagcct aaatatctct aaatatgcct tataaaaaat tataaaaaat   34620
atatgataaa aaagtataca ttaagacgaa tctaaggaga tctcatatgg atatattaaa   34680
aaagaacgga gagagtacat tattacaatc aaagtaatta gattacttta attgtaatct   34740
aattacaata ttttccttta atacaatatg ttgtaccgtc aaaataatta acttccggta   34800
```

| | | | | | |
|---|---|---|---|---|---|
| atattagaaa | atattttttgt | aatgacaata | tattatttca | tccaaaatgg | attgagtttt | 34860
| tatgttgtta | tattaattca | attatatatc | attattatat | ttttaatta | ttattatttc | 34920
| ataataataa | tatgcaaatt | ttttgattac | tgtattactc | ttttatttaa | ttagttagtc | 34980
| agtgagccaa | tatattttta | taaacaatta | ctcaaaataa | atactttttca | ataatatcag | 35040
| aaaatgtttt | aagtaaatga | cattatattt | ttttttttaaa | ttaatgacat | tatattaata | 35100
| ttactttttta | aactattata | atttcataat | aatgatatgc | aaattttttt | taattttttct | 35160
| tttatttaat | tatttattga | gccattataa | ttttataaac | catttgaatg | tattcttaaa | 35220
| tattattgaa | aatatgtcttt | acatttggta | aaattaagct | gaattgtcta | tgattgtaat | 35280
| aatgtactct | ctccgttttc | tgatattcta | cccatcatat | catacaatat | tataattttg | 35340
| atgttaaatg | acaaatggca | atctaatagc | catttgccaa | ttaatgcatc | aaaattaatg | 35400
| gtgatttaat | tataaaatat | atagaatctc | aatatattaa | atggtttttac | aatttgaaat | 35460
| tattaaaatt | attgcaataa | tagtatccta | ttcttttgaa | aatatgtcttt | acatttggta | 35520
| aaattacgta | tagtttaaaa | aaactttttct | ttgtctacca | tgtagaaaaa | ttaaaaggtc | 35580
| aatatcacta | cgtagaaaaa | gctaaaaata | catagttacc | acgtgtaatt | tctcaaacta | 35640
| taaatatatt | taatttaaaa | aaaactatta | atatatttaa | taaaaaataa | aaaacataca | 35700
| ataaaatttt | agacgttaag | atcaatttaa | tatgatctta | catgtttata | tttaatttgt | 35760
| aaaattcaat | aaagaatcat | ttatttatttt | cttttatactt | aattaaaata | ttccttacct | 35820
| taaaaaaaat | aaataaataa | ataaaatatt | ccttattatg | agaatatgaa | tgacaacgaa | 35880
| tgtgtttttt | tttttttgaat | agggacaacg | aatgtagttt | gttgtcttta | aaacaataag | 35940
| aatcttacac | taaaatgtcc | ttacaaatta | actcaacttc | tcaaatactc | cacaacatat | 36000
| gtacttcttc | cgttccattt | tacttgcaac | acttaccatt | ttgaaagtttt | catattactt | 36060
| gcaacattac | tattttttggc | aaaaataatc | tacttacttt | attctcactt | tattcctacc | 36120
| acatatcacc | atcaatcata | catcatctca | ttaattattt | aatataccca | caagtcacaa | 36180
| ccactatcta | tttataacaa | ttttttttttat | ttctaccccta | tatatcacca | tcaatcatac | 36240
| agcatccatg | caatgcatgg | atctttaaat | ctttaaatat | aaagtataaa | tttaagatta | 36300
| tcaatttaaa | attatcatta | ttgtatattt | tttaattaat | atacaatatg | caatataatt | 36360
| atgctatata | aattacataa | gttcgctatc | ttataaaatag | cgtaaaatag | gttattagtt | 36420
| tttataatttt | taaagaaaaa | tcttgttcag | taagacaatt | gttttttgttc | acaatgataa | 36480
| atagtttaaa | tgtatcaaat | atttcatcct | tattataggg | gtcaatgagg | gtatttttttt | 36540
| catttgatta | tatatagaaa | atattgtcta | ttttttttttaa | gagtgtaata | ttataaatta | 36600
| ttgtctttga | tattaatcag | atatgtgatt | atatttttga | agatattatt | tttcaattaa | 36660
| ttaataaaga | gttggttgta | agttgtaact | tgtaagaagg | gtattatttta | aatactgact | 36720
| tgctattttaa | aaattgaatt | catgtaatta | atttactgcc | ttttataaac | ctttgacatt | 36780
| tgatatatcc | cttgagaaga | tgacacgtgg | attttcacag | ttcttttgat | aagatttatg | 36840
| attattgcct | ttgatattaa | tcagatatgt | gattatattt | ttgaagatat | tattttttcaa | 36900
| ttaattaata | aagagttggt | tgtaagttgt | aacttgtaag | aagggtatta | tttaaatact | 36960
| gattactat | tttaaaattg | aattcatgta | gttaattac | tgccttttat | aaacatttga | 37020
| aatttgacat | atctcttgaa | aaaatgacac | gtggattttc | atagtttttt | taataagatt | 37080
| tatgattcta | aaattgtttta | ttaaagtata | caaaaaacta | taattttata | ctaatgatat | 37140

```
gtaattgcat ctgtggattt ttaagaagat catcaagcag agaagcacgg tagaagaact    37200
gggtggctgg agggctatta aggcagggca taccttcact attggtaaag tgtatgagct    37260
tctcattgcg gacatcccaa gggtcacgtg ggggaatatc atggagaaga atatagctaa    37320
cccaagcgca agattcatca catggctagc cattcagaac aggttgtcaa ccaaagacag    37380
aataggcaaa tgggctgagc taacaaatga aaattgttcc ctttgcaatg gaaacactga    37440
aacagtgcag cacctcttct tcgactgccc gaatgctcaa gagattagaa gccgggtctt    37500
caagttcctt cctcgaagac ttgagggggc aaacctccag gaggatatcg cgagcataag    37560
taaactgagc aagaaaaaga cagatcgagc aaggattatc gtgggcctat ggacggaaat    37620
gatctacaat atctggaagc aacgcaacag aaagattttt gtcaaccacg tccttagtat    37680
aaaaggaggt tgtagattgt atagtgttta gaaccgcagg gagagcaaat agtaggatgt    37740
tagatatgat tgttagtagg tagcttttgg cttttttggc tttcgctctg ttgtttttgt    37800
tgagcgtcag cgttttttggg gccgcgagcg ggagttaatt tccctctcgt ctgttttgt     37860 atcttttgtc tctcttggta tataatacaa agaaattggc aaaaaaaaaa atatgtaatt    37920
gcatctctat ttagagatca ttttataaac acaaattgag caatttttt tttttaatga     37980 aattgtaatt aaacattggg ccttacaagt tacaaaagag atagatctaa ggttcaaagc    38040 ttttttctt atcctctaac aataaaaatgt ttcgatgagt gtaacactgt tcattatgaa    38100
cagtgaattc actgtttact ccgcttcttt cgttcagctt tcctttcttc cttctttccc    38160
atttccattt cctgctttt catttcctct tcctgcttct ttcacttact tcagaattcg     38220
aattgccatg gatgatccat tgatttgctt ctcttctact ttcccttcg gagaggtatc     38280 attaattact ttttctttc catctttga ttcttatttt tgcttgattt tttctgattt       38340 ggttttcta gggttttgat ttgtttttc taattctggt tttgtaagag actaacaagt      38400
tgagacatac acgccaaggc ccataaaggt ggcactggca agacttcagc gatgtcggcg    38460
gtgaggatta tataggaatg gccggcagga aacttcaatg gcaacaacag taacaacagt    38520
aacaagagta cttggtctga atcaatctac tacaggtatc gattgttttt attttggatt    38580
tcgaaagtaa ataactaaat caataaaaaa taaaaaatc aaagacatgt taatttcagg     38640
tggggagtta gttttccacc ggaaagtggc gttttggagg cgctgaagct gcaattccca    38700
atgttggtga tgaataaaat ttcattcgag aggattgatg aagtgaagaa agaggatact    38760
gagaggaggg ctggtgaagc aaaagctggt gatttggagc ttttgaaggg gatgtgtagt    38820
tggatgagta gagaaatgga ggatttacag aaggagaata gggaaatgaa agaggcattg    38880
gaatgtatga agaagaaagt tccgatttcg aggggtcgag gttaggaaag agggagggat    38940
tgatggggaa agggatgaat caattgagag gtggaggagc aagaaaaatg gtggaaatgg    39000
tgttgttgat gagggtggac aaaaggaatc aaagaagtca agtagtagaa tgagtgaaat    39060
ggagaacgaa ttgcaaaagt ttagtattgc tatgagatct tatatgcaac taatgcaagt    39120
ttagtatttt gatgtagtaa taaaataaaa tatgagttttt ttagaatgta aagctttga     39180 aatagtatgg gaacgatatc ttgtgttatc actcatttga tctatttatg tgaatattgt    39240
tggaatattt gcttgaataa atgacctttg agaattccca ttttaaagca ttctagagtg    39300
caaggaagag gggagcatta taggcatagt ttattacaag agttttttaat tcttagtgga   39360 taaccaatgt tacatggaat gaaatcagat ttgaagcaag aaacacaacg tgaaactact    39420
gactttcata agtggcgtt tcggaggcgg tgaagccgca attcccaatg ttggtgatga     39480
ataaaatttc attcgagagg attgatgaag tgaagaaaga ggatactgag aggagggctg    39540
```

```
gtgaagcaaa agctggtgat ttggagcttt tgaagggat gtgtagttgg atgagtagag   39600
aaatggagga tttacagaag gagaatagg aaatgaaaga ggcattggaa tgtatgaaga   39660
agaaagttcc gatttcgagg ggtcgaggtt aggaagagg gagggattga tggggaaagg   39720
gatgaatcaa ttgagaggtg gaggagcaag aaaaatggtg gaaatggtgt tgttgatgag   39780
ggtggacaaa aggaatcaaa gaagtcaagt agtagaatga gtgaaatgga gaacgaattg   39840
caaaagttta gtattgctat gagatcttta atgcaactaa tgcaagttta gtattttgat   39900
gtagtaataa aataaaatat gagttttta gaatgtaaag cttttgaaat agtatgggaa   39960
cgatatcttg tgttatcact catttgatct atttatgtga atattgttgg aatatttgct   40020
tgaataaatg accttgaga attcccattt taaagcattc tagagtgcaa ggaagagggg   40080
agcattatag gcatagttta ttacaagagt ttttaattct tagtggataa ccaatgttac   40140
atggaatgaa atcagatttg aagcaagaaa cacaacgtga aactactgac tttcataaag   40200
tggcgtttcg gaggcggtga agccgcaatt cccaatgttg gtgatgaata aaatttcatt   40260
cgagaggatt gatgaagtga agaaagagga tactgagagg agggctggtg aagcaaaagc   40320
tggtgatttg gagcttttga aggggatgtg tagttggatg agtagagaaa tggaggattt   40380
acagaaggag aatagggaaa tgaaagaggc attggaatgt atgaagaaga aagttccgat   40440 ttcgagggt cgaggttagg aaagaggag ggattgatgg ggaaggat gaatcaattg   40500 agaggtggag gagcaagaaa aatggtggaa atggtgttgt tgatgagggt ggacaaaagg   40560
aatcaaagaa gtcaagtagt agaatgagtg aaatggagaa cgaattgcaa aagtttagta   40620
ttgctatgag atcttatatg caactaatgc aagtttagta ttttgatgta gtaataaata   40680
aatatgagtt ttttagaatg taagcttttg aatattatgg gaacgatatc ttgtgttatc   40740
atcatttgat ctatttatgt gaatattgtt ggaatatttg cttgaataaa tgaccttga   40800 gaattcccat tttaaagcat tctagagtgc aaggaagagg ggagcattat aggcatagtt   40860
tattacaaga gttttttaatt cttagtggat aaccaatgtt acatggaatg aaatcagatt   40920
tgaagcaaga aacacaacgt gaaactactg acttcataa ttttttaatt cttagagtga   40980
gttttttgtt aaggacaatt tttaatagga tcatttgttg agttttgg ttcattta   41040 acaaaaagga agtttgtgtt gaagaattaa tttaatgcca tgtttgagaa caaatatttc   41100
atttgaaaat ttgaaattga attaaaatta ttgtctggca aatcaaaaaaa atttaaatct   41160 ggattggat caaatttcaa attgttttta aagtagttaa agttgaaaat ttgagaatga   41220
ctgcccaaac cttgttattc tcaaatcctt tattcatgat ttcataattg aaattcataa   41280
ttataaatga aatacttgtt cacaaatact acataattga attctatgg tatgattttt   41340 tactttgatt attgtaaaac taatgtaat tgacaatatt tctcagcttg aaccgggtaa   41400 cattgttta aagattattg tatctacacc ttctatcact gttaacaatg tcaccaaaag   41460
catcacgaat aagatacatt ttattaggtg aatgatggat ctatattttt ttaattagta   41520
tagatagatc ggaacagatt ctaaggaagt gtatcttatt tctattgcct ttgataatcc   41580
aagcatggtt ttttgcttaca aaatgaaaca atgattgatg caatttaat tactatggaa   41640 atgttaacat tattggtatg atcattccag cttttaaatt gattgcttgt gcatcataat   41700
cttctttttg atgtgtaagt aggagcttct aaagcacaaa ttgcaaagct tttgtaagcg   41760
atcaaaattt ccaactatag tgttgtttga tcccgtccca ctcacttgt ttctgtgtac   41820 ttaatattcg ttttgatgtg catcataat taattactta tgcattggtg ttttgttaag   41880
```

```
caacttcttg tgtttgatct cgttgaactc tctatgtttc actggctaag atattgcata    41940
ggtaggaaga tgaaattata agcaaaggtt ttcttacagt ttattttttg atcaaatgaa    42000
tagtaagttt tcgttttact aaggtgctac gtgtgttggt gaatggacca gattcgttct    42060
tacttttatc atcttttgaa tcatcccttg cctttcattg aaggaaaaca tatagtactc    42120
tattaatttg aatgaccacg accttcaaaa aatcaattta tatcaataaa gcaacgaagc    42180
tgctgactta attaggtatg tatatctata acttgtagta tgtccttcag ttggatctct    42240
ttcaaaaaga aaaattaata gtgctccata taattgaaat cctttaattg atatcaagaa    42300
cttgatgttc tttatcaaat tcaagggaga aatgttttat gtctgaaatg ggtagcataa    42360
gttttcaaaa ttctaaacct taacaaagac aactttccat aataagctaa tgtagtcgat    42420
ttgttttttt tttctctttt gaatatggag gataggcact tgttcttaaa tagtttgctt    42480
cacttatttc ttttgaatat tgaggatata aacttgtgct aaagtagtca attagttact    42540
caatttcttg gtggaaagtt atatcttcaa cctggctgtt ctaattgttc agcttggttg    42600
ttttcatgtt gtcatgcaca atagttttgt tcagcatggt tgtttgcatt gttgtcatga    42660
ataataattc attgttgtta aatctataac gttggaactt attagggaat ttgccttgga    42720
atctgaagat agagagtctg gtttagataa tcaacctttg tctttgctca tgaaaaggta    42780
attactactg cattgtgctg ttcatattat tatatttact gatgtttaat aaaggatcaa    42840
atttgggttt agtatatgtc actgcttatg gtggtgatga atcatctttc tggcattttc    42900
acgatttgcc tgagcttctc tgaaagtcaa aacatttcag gtaatttatt ttgtgttgtc    42960
catggctgtt tcttcatagg gtttaatttt gttaaattta gggttttaac gattttgaat    43020
ttgagttctg ttgtttcaat tttttgcaga tgatttcgat taaattgagc gatatttcct    43080
agaccttagc tcccaaacta atctacgcct aacttttccc tgtctgatcc tctttcctct    43140
tccattgttt ttcgtttttc aacttaatgt tcatactatt tcctagaagt atttctcttc    43200
tctatttcca tcatcttctt gacttcttct tcaatctcct catttatgca tataagtcag    43260
gagaaattca aatagatatt ggttgtcggc gcctgactta tcttcaatat tgctctttgc    43320
agtttcatcg tcgaggttag tggttatttc tttatcatct aaacaattac tggaaacatg    43380
attttgagta tttaggtttt gttttacat gcttgcttag gtatgtgttc aattttttgca    43440
aatgttagaa attattacat gcttgcttag attagtttag gctatgaagt taggcgtagg    43500
atattagatt tgttttttt ttttgttgtt ggatttgttt tgattgttca ttgactaatt    43560
attgtttcgg tttagggttt gtgctttgat ttgctgaaga aataagctgt tttgctttga    43620
tttgttgaag aaatcagctg ttttttgccca ctttgttttg actttaattg atttcttgct    43680
attttattgc ttctacatta ttttattcaa cctaaatcaa ctttggattt gtcatttgtt    43740
gacgcctggt accacataaa ttttattttc acatattgaa actggtttgt attctctgag    43800
ttgaaggaac accaaaaatg gagtctttgt catctcatta tactggcaga tccattataa    43860
atgatatctt gttttctcac tccttttttct tcaccttctt ttttcatgtc ttctactaaa    43920
acctttctt agttattaac tctatttctt ataccctaa tcccttcaat ccatttttct    43980
ctctcgcaac atggacacct ctaattctaa ggtgcattta ttttctccct tttgtcatct    44040
ttaatcatgg atttgctgat ttttatgatg atttctttag caacattgaa ttcaacactt    44100
cattgtatat atagattgta gtagaattga agtaggaac tattatagtt tcaaattatg    44160
aaaaggaatt tagtgggttt atgtagaatt aaaatttaac acacttcaat ttctttacta    44220
tatgtgctgt aaaatcaatc attttgtatt gttcaatttt cttgtataat tagttttatt    44280
```

```
gattgatttt agcttctggg tattagtcct ttttttttctg tatttgtttt gcatatttttt    44340 tgatttccca ttttgccaat tttggtctgg aatgtttgtt aaagtatcta aaattagata    44400
ttggagagta acactgtaat agctgttatg attttgttga attactaatt atagtatctg    44460
tctattgtaa taaggaaaga atattttttaa ggaaaaagaa cattttttact ttgatttgtt    44520 aaattggatt tattatgtat tattattgga tcccaatgct tgaattgagc tgagatctaa    44580
tgaaaagtga cactcatgtt gatgtgttct aaaatcctgt tatagaagcc tatgatgcac    44640
ttgatccaaa tggaaacatt accttcaaat gggatgttat caactggact cctaatggat    44700
atgttgtaag tatttttttc acccatcttc tcttgttcac ttcattttat tttcaactaa    44760
taaggaatcg agatgatttt agttatcaat agcaactttt atttttatgct gctacctgtt    44820 ggaaaaataa cccatatgtg attccacatc gaacaattaa agagagtttg actaacatat    44880
aagcttgatg ggctactcat cctattaaaa ctttgtttta ggatggaacc tcatcggatt    44940
tatgtgcaac caactctatt cttatggggt gttgttgtgt acaagtctgt taacgaatttt    45000 atcactacct cctaagatgt tggaatgttc ttcatcactt tcaatgcaaa cctcctaagt    45060
tgcctatcat taatgtgggt atcaattatg agaatcatgg attagcctat tatttgaggg    45120
tcttcccttt caccccttgag acaaggttcg atcctcacca tgtacaagaa agactaattc    45180
cctttccctt cattgcatgt aaggatttcc aaatgtgggc atcatttatc tattatttga    45240
atgaatcatc attagttatt gtgaagattt ccaaatcagt tgcataatct attgatcaat    45300
tttccaaatt tttacatgag atggttatgg tgggtgggga aaccaagaaa tttggtaagt    45360
ttatttgctt acaatttctt tgcattttat caaataatgg gcacactata ggactgaagc    45420
aatttgtgac attttgatct ataattcaat tatgaaactt tttttccttt gatgataatt    45480
gagacacgta agcaataata aatagtgatg atgtcagcgt gttttgtttt agtaatagtt    45540
tgatggttga ccataatgcg gtggtttctt gttcagcact tcaatgaata tggatctcat    45600
tgttcagtga agtgtctaaa ttaatctaat ttcatgtttt taggttgcaa gtttgtttga    45660
cttgagattg aatatggtag aaagtacaaa atgctttgat tcattttgat gtgactagaa    45720
agtccttatt gttttctttg aagtgtctgg tacaattgag gtacatttta tctcttttta    45780
ttataacaaa tgttcaatag tgtgtgaatt ccgaaagtcg attaggtcac gtattttctg    45840
cttaaagttg catttaaata attagtcact tcgtgccatt gagtgtgcta aattttccaa    45900
tcgatccatc ccattgatta tgctacatct cctttaatga agtgttcct actgttttca    45960 ttagttttat caacacatgt cttctctctt ctaatatcat caaaaaacca acattgatta    46020
aatttagggg cagagtattt tgtattgaat ttcggggcac aaatgagcac ttgttgctta    46080
tgcgacctat atgttagttt aatagttttt ttttataaat attttttattt ttttttatca    46140 tttgagcata taggttggtg gtcaccaaca attatctgaa taaatgatcg caaaacaatt    46200
tatatcccaa accacaagtt cacagttagt gttgtgagaa atctaaccca aaagatgcat    46260
tggtgcattt aattgaagtt ctccttttttt cagaatattg ttcttgagaa aatgttatttt    46320 acctttttcca ttagtttgaa caggtttcat tctttttttca gaatagtgag tatatcattt    46380
tctcattaat attgattttg tctcttctgt aattttgaat ttcttgttta tttcctcttg    46440
gtttcattct tttgctgtaa gttttttttc ttttgcagcc aatcggtttt taaacgcgag    46500
ttccagatgt cagacgacca agagacttac atgaacactt aaatatggaa aatcaagaag    46560
ctgatcaaag tattggaaat tgcctgggga aatggaacaa gcatgttctc tctcatcatg    46620
```

-continued

```
ccaccaaaat atcaagtcgt tgggattacc aaaatgttga aagatgaata cggtactgtt    46680
tcgaacatca agagtatggt gaatcgtcag tctctgctag cagctattaa atctgcccag    46740
taacgattga aattgtgtag taaggtacct cttaattatt tggttcttaa cactggaaca    46800
attgtgactg agaatggtaa ggaattgaga gcaactattg attttgagcc tttcagatgt    46860
cgaagttgtg ctgtcgatct gctgttggtg catagctgtt ggagctgctg cttgcttatc    46920
aatcagcttg cagcttctgt ccatgagctg ttatcgatat taacactact gttgtgacta    46980
aacgctgtgt caagagaggc tgtgagggtt gttacgacaa tgtagaagtg cagttgtcga    47040
ggtgctgttt atgagtaatt gaagctattg cttgcttgtt gatcacttgc tgtctcaatt    47100
ggcactactg tggatacaag atatttcgag ggaggctgcg agggttgtta tagcgatttc    47160
aatgtggtgt tgttgagttt tgattcgtgc gtagctggcg aagctggtgc ttgcttgttg    47220
tcagtttgtt aactaaatta gtagaatgat ttgtgtcttg tgagcctcac aattttgtct    47280
atttctcccc taattttcaa cctattccat cagttattgt ttgattttgt attgcctcat    47340
ggtcaaatcc taccgtttta caaattgacc aagttacagc atatacccaa atacttgtga    47400
attttctgat ttgtttgctt gatcttaggt tcttgcttta actgttgtca attttacct     47460 tgtgttattt cacttgtaac ataaaccgta atttatcaga ctaccgaaag tacatagcag    47520
taaaagaagt aaaatgaaca attagccacc tcacactctt tggtggagag aacctcaggc    47580
attaagacaa ctcttggaag ttggaataaa tcaacataat tagattcata aatgtcgaat    47640
gacaaccgta acaaaaacct gtatgatact tgatgttgat acgagaaaag cttttttgcag   47700 aatattatat tattataccct ccaaaaacaa ttagtagcca atcatgacaa aactagcaac   47760
atgatttatg taaataatta gtcattccaa tgaaatcagt agtatactca caatatacga    47820
aaaataatca ctattcacat atgtccctta atttgtgact tatagtaatc tataaattaa    47880
aatatagtca agtgagattt tgtttgattc atctcgatgt aaagattatt aatatcaaat    47940 tttaaaatt ttatattcta cataattata gattttaaga attgaattag tgcattggac     48000
tgcatgaaaa agagaaatgt tgcaagtatt ttggaacgaa tgtagtatta gattgaatca    48060 ttttctaag ttacaagcaa taaaatgtat tgattttaat ggattaaaag aagtatcaaa     48120
tcagatgttt ggggacttta cggaaaattt gattttaaag gtttgaactt tgcctcattt    48180
gcttctgaag gtttgaactt tcgttttatcc tagaaaggtt cgaactttat agtgcatctt    48240
catctaaagg ttccccggt tttggtaacc tttaatatgt tggaatttag agtatatagt     48300
ggacatcgga aaagatttaa ttaattaaat taaataaata atttgattaa attaattaag    48360
tatatcccaa ggttacaagc aacaagtgat tttagagaaa ttaaaagtca ctagtcgcga    48420
acaaattcgc ggatcgcgaa atgcaggcag aatgttctg ttttgtgaaa attgaaattc      48480
gcgaccagtg actattttcg cgacccgcga aaatctgaaa tttctggatt ttttccttgc    48540
gacgttttgc tttgtttga tggttatata ataacttact acagttatta tgattacttt     48600
tagccatgtt atttgggatg taagggttga gtgaaaggcg acatgagttc gtgaatcgat    48660
ctcttgtttc acggatcaac ctagtgtttc atgaagtaat atgttgcttc atgaaccggt    48720
gtgagctatt ctataaatat agaatgcttg tgtgttgttt tagtgatcta aacatccat     48780 ttttctgatt ttcttctctt atgcatttca atcaagaaca tgtaatcctt gattgtgtat    48840
ttccatattt cttaccattt aagttacttt tatgtcattc caatatccct tgtgctaggaa   48900 attggtgtaa ttctttgtat ctcaaaacat atttccggtt gattcccaag caccgtagta    48960
gggaggaaat gatgttttag gaaagagcat ctcgcctaga atttatatca agatccaaca    49020
```

```
aaatcttctt gttactttgt tcgatatatg gtgattccca atgatgtaat ctacatttgg   49080
tgtatgttaa gcaaaggttt gaacttgtca tatgtaattt ggttttctac tacaaacttg   49140
taactttatt ttatatgttt tttataaaat taaagtcaca tttctaacaa tctaaaacat   49200
catcttctaa agtaagtatg acaagtttca atgtttacca caaactttgt catatttgac   49260
aaatttgttg ggaaagtttt ttaagtttgc ttatatgaaa attacaccat gatcgggtga   49320
cgagattatc gtagagattt ttgaaatggt gcattggttc ggtaaaagaa tgtgttggtt   49380
tgttaaagag acacgttggt tcatcaaaga atatgtttgt tcaataaaga gacacgttgg   49440
ttcatgaaag gatgcgttgt ttcatgaaga gttgcgttgt ttctatcttg atcaagttat   49500
gtaagagaga tggacattat tacatggtag agatgataaa tctcaagtat gtaagttttc   49560
tatgttaatt tcatatgtct attattttat gatgatgatg gagatgtaca atatgttaca   49620
tttttaaaca agttttata tccatgatga aatttggtaa agtatgtgat catggttatt   49680
tgatcatggt tatcatttgg tgtaaatgat gatactccat tttatttatc aaagaaaatt   49740
gatagttgga agtataagta acttaccatg attttttatga tgattaatat tatcatcaaa   49800
gatggataat gtttgctatc ttttgtgttt acaagttttg ttttatgcat gataagatga   49860
taattttcat gatcatgtct tgacatattt tttgacatgt atatcttatt ttatatatat   49920
catgtcttgt tctatgatga taagtgttat tatcaagttg gataaaattg ctttttatagt  49980 tcttttatag taatatgtta agttttggat ctttgcatgt tttgtatgac aagataattt   50040
tgtcatataa gttgaacatt atgtgtttgt tatgtgtggt tatcttttga ccaagttcaa   50100 taatgtctttt gttattgatg tatgtttcac ttttgagtga attgttttttt aaaaggttgc  50160 atgatccatg tttgattaac aatgaagtta attaaagtat atagtatata tttttgctat   50220
gttgttctta acaaaagttc atgttgcatt gttgttcatg catgtgtaga attatttcta   50280
tgtagtgttt gtgcatgatt caagttagtc tttatgatat attctttgat tggtgcatga   50340
ttaccaatgt tgtttaaatt tggacatata attttttatat gagattgtca tatgtatact   50400
tttacccaag gttatattaa tttattaata tttgaaatgg gtacaaagtt tatgacatga   50460
ataaatttaa aggtttatca tcaaagattc attaaaagta attttaatgt aaaagagatg   50520
attaaacaag aatttgaaaa tctaataatg ttattaaata aaggttgaaa gttgtcaaca   50580
ttattttaaa ctcggaattt tatttattaa agttgtttgt tatggaggtt aataaattcc   50640
ataatgttaa ataaataaag gagtttaatg gttatataag tgattttata tattaaataa   50700
atgataaaga caagtttgtc tcgttcattt agatatatat gatggattaa tcttatatgg   50760
aataaatgtt gatttgctaa gtaaagcaag atatgaattt atttattatt acattgatta   50820
atgtattaat tgaaattcat atgttactct taatctagag tatgtgtcaa cgctttaagt   50880
tttattatgg taattaaaat tacataatat gttattattt tgattttcaa gatatgcatt   50940
atttgcatga gtatatgtaa agttttatat actaatattt attttggaga aaagtactaa   51000
ataagtttta ttccggttaa tgggtatgtt atcttatgtt gtcggataac gccaaatata   51060
tttggtgtga caatacagaa agttttaact attttaagtta agttgatat taaatgtttt   51120 ctttggttta aaatatttga ttttatagaa aaatcttaat cattttggta caaggatat   51180 ttattttgaa ttacctcaaa ggttcaaaat aaggatgcat ttatatagat tatgttattt   51240
ataacatcta ctatgagttc tatttattag aacaagagat attatatatc aatgatgttt   51300
gattataata caaagtgatg caatatttat ttggaaattt aattttcaat gatagatagg   51360
```

```
tctaaatacc tacaagtttta atttgtacaa ataagtgatt atgatatttt gatctttaat    51420
agattgactt gttaatcttt tgataaaact tgtatttcta aaagagaaaa atataagttt    51480
gttttactaa ggaaagtttt taacgaagtt tggttttgtt aaagttttca agtaaaaag     51540
ttttaatatc ttgtattcat atttctaata tgaaggttta cccatgatta tgttttgata    51600
cttaagtatc atataagttt ttagctttct taaagaaagt aagtaatgat gtgttcatca    51660
tgggaataat gtttgaagtt tagtaactta atctccatgc aagtataaca atatgttata    51720
gatagatttt catattatat atgaagattg atgagcatga attattgttc aagatttatt    51780
aagtggtatt atacttaata tgataattta ttattgaatt tatttcaata agtttaccga    51840
aaatacaatg gttaaataat tgtttgtatt ttcatatggt atgttatatc ataaattttt    51900
ataaattatg atttatttgt tttggaatat aattgtataa gttaagatga caaagtaata    51960
tgtcatattc cttctatgaa ggaaatgggg gaggtaaaat gttaaattaa ttttaacata    52020
aagtttaagg actaagaaat ataagtattt tattatactt atggtaaagt ccaagtttac    52080
catcatgtct tccaattgta attatttcct agatatttgg aatgattata aaattggatg    52140
taattttaac ttatacaaga ttcaaattgt ttatagttgt caagtaaagt tttacttaca    52200
acttaaagtt cctttaatag gaaattattt gaatagtcca aaatgtttat gttgtaccat    52260
ggatttaatt aatcttatag tagaagttct tcaagtttga agaggtactc aagtatgagt    52320
ttgatcttta gtgaattggc cattctctat gttgatcaaa gtatatgtgt ttgtggggga    52380
ggtataccaa gttttgatca cccaagaaca aacaaagttt taacttattc tactatgata    52440
ttaatgttat ttgtaaactg tatagtttaa aatactcatc tttgtgatgt cttaagtcaa    52500
ggttgtgcac aaaaacaatc tagtttgatt gacaagtggc ttgtataaag tattgatagt    52560
cgagtgtaac tttgataatg ccatgacgtc taatttaggc gaagccgcaa attagggctt    52620
atcaaagaag ggatcacatt tcttgactat gtgaacaaag ttcaaagcta gataaagtat    52680
tctgacaaaa tctaggaatt tcattgttta atgaaattgg tacatgccca ttcttcaaca    52740
ccatgagtga aacccaattc gacgctagaa gaaacatcta gtcttgaatt caatgtggat    52800
tgatcgctca tcagatgttg ggaagcaaca cttaagtgat cctaagttgc tttattcgtg    52860
atgttgacaa acgcggtagt agagtcgttc ctcgaagtct ccatttctag agttatgaag    52920
atctctagat tgagtgcttt attcacgaaa gcatggtata ttagggagaa gctacctata    52980
taagttcaag atttggccgt cttaaagaaa tcaaggggca tacttatgat ttcaatgaac    53040
ttatgaatag atatggacac agggcctttta acgtgtcaag gacatgaaag taatgaatta    53100
tttcgtgtgt actactcctt caattggttg gatatatctg cttaattcaa tccgtacgga    53160
cattagggga tatgatcaat tgtaaagatg cgtggtacta ggtgtcaatt caattcgtac    53220
gaacattggc attgatgcat gaaatgggtt ggtattatgg tttgcttaag aagaaaagga    53280
ttatacactc taaatggggg aggattgttg gaatttagag tatatagtgg acatcggaaa    53340
agatttaatt aattaaatta ataaataat  ttgattaaat taattaagta tatcccaagg    53400
ttacaagcaa caagtgattt tagagaaatt aaaagtcact agtcgcgaac aaattcgcgg    53460
atcgcgaaat gcaggcagaa tgtttctgtt ttgtgaaaat tgaaattcgc gaccagtgac    53520
tattttcgcg acccgcgaaa atctgaaatt tctggatttt ttccttgcga cgttttgctt    53580
tgttttgatg gttatataat aacttactac agttattatg attacttttta gccatgttat    53640
ttgggatgta agggttgagt gaaaggcgac atgagttcgt gaatcgatct cttgtttcac    53700
ggatcaacct agtgtttcat gaagtaatat gttgcttcat gaaccggtgt gagctattct    53760
```

```
ataaatatag aatgcttgtg tgttgtttta gtgatctaga acatccattt ttctgatttt    53820
cttctcttat gcatttcaat caagaacatg taatccttga ttgtgtattt ccatatttct    53880
taccatttaa gttacttta tgtcattcca atatccttgt gctaggaaat tggtgtaatt     53940
ctttgtatct caaaacatat ttccggttga ttcccaagca ccgtagtagg gaggaaatga    54000
tgttttagga aagagcatct cgcctagaat ttatatcaag atccaacaaa atcttcttgt    54060
tactttgttc gatatatggt gattcccaat gatgtaatct acatttggtg tatgttaagc    54120
aaaggtttga acttgtcata tgtaatttgg ttttctacta caaacttgta actttatttt    54180
atatgttttt tataaaatta aagtcacatt tctaacataa tagcaggtta ccatcttcaa    54240
ccttcttctt caagctctcc atcaatggct tcttcaacat cttcttcctt aacctcccta    54300
atggcttctt ccttaaacct cttcatcaat ggcacataac aaagcctttc aaaccccaat    54360
attactattt ttctcattgt ttcataaaat atccaaaata ctttgaaatc gatttagagg    54420
aacaacccac aattgaattg ggcatacaag ttcgaatttg gagtacaatt gaataattct    54480
ttgaataatt tggagtacac aattgaataa tttggagaaa ttttctgaaa ttttttttaat   54540
tttgggtatt atttgaataa ttctttgaat aatttggagt acacaattga ataattcttt    54600
gattttttggt aaaagttcga attttgggtt gaattcaaca ttacaaaaca ataaaatacc   54660
cccaaaacaa tcaagatagc atttacccc  aatttgatat gtaacattat aaacaaacta    54720
attgaaggct aaagcttaat caaaaatcct aaatattgag attgcaaacc aaaaaacagt    54780
caaaacaata aagtaggcat acaaaacaat aaagtagcat ttaccccccaa gttgatttta   54840
ttacggttac aaaaatggag gatatggagg atatggaggt ttaaggcttt gagattgttg    54900
gaaatggttg aagatgaaga ggtttgagat tgtatggaat ggtttaagat gaagaggttt    54960
gagattgtat ggaaatagag gtttgaggct tgaagaggtt gaacaaaaat ggaggttgaa    55020
gaagaagagg ttgaagatga aaagaggtgg aagatgaagc tgataaagaa tcacttattt    55080
agccgataat aggtcatccg catctttaga tgcagatgac ccccaaagtt cgaacctttc    55140
taggataaac gttagttcga acctttagaa gcaaatgagg caaagttcga acctttacaa    55200
tcaaatttc cggga ctttta ccttactaag cattcttaaa tatcagttgt tataagaaat    55260
gggttataaa tttgtaatag tgcattgagt ggtcagattt atacaatttt gtccttataa    55320
ttggtgataa caaatgaggt tatttttcaat taactcttat agtaaacagt atttgctact    55380
tcaaataaat aggaagtgga ttacaaacaa tacgattggc ttgaattatc atagtccaaa    55440
ctaacgttac aagcctttgc tatttatata tacttttctc caaactaaag atactacata    55500
tagcaacata acctggttgc tttctatcaa cagaataaat taagtattgc attatagcct    55560
cctagacttg ttggtagact tttctccatt tatttgttga tctttgcgga ctccattgcc    55620
tattactatt tatatatctt caactcttgt attatttcca cttttataac aatttgacat    55680
tcaaatattt ttatttgtat tattgtaaat aggagtacat aaaataacat tattaaattc    55740
gatagtgtaa cttgggggac cgcgtgcgta gcacgcggcc ccacaactag ttaaattaaa    55800
taaataaatc ttcataagca acctcaataa atttagcggc aaaacaacga atcttacat    55860
gacgtggcaa gctctgattg gataatccat gtatgtatgt atgtatgatg tcgaaaaaac    55920
catgatgatg gagaggatac atatacatga tacatcataa ttccgggtcg ggtacccgac    55980
ctgccttaac cgggtcgggt catgggccga taaattattg acttgggtac ccgtttgacc    56040
cggatagctt tttttgattt attttttattt tcaaggtatt acatttttatt gattcatctt   56100
```

```
caatatgtaa gaatcacact caagaagacc ccgaaataat cacatgacta tgttcaaaaa    56160
tacctggtcg agaccaaggt gcacctcttt ctcttccagg gcagaaacat ccttaacatg    56220
aaacttatta atgagtgtaa ttccactaat ggtagacatt ggcttaactt caagattatc    56280
cataaccata taagttagat ataagtacta tgttattcat tttgagccac ctactctaat    56340
gtaagatata agtagtatgt attgttatgg aacaattatg gtatgaaagc aagtaatcca    56400
aaaaaggatt ttctataatt agcttcaaca ttcaagtttg caaaagcgtt acaacaacat    56460
ttccatatct tcctacataa caaatattct tacagtataa tctaaaggtt acataacctt    56520
tattagtaca accaacaaca agaaaaaacc aaataaaaac cctaaaataa aacatgatat    56580 ctctttttcca agctttctct ccttcatcaa tttcttctta agccttttgt attctgaaat    56640
tgcttgttct ttctgatgtt ccaagcaaca aagccttgat gtcaatatct tgaaatcaac    56700
catttcaagt tcatcgatcc actaaaactt cttgcatccc ctccaattag tgttaggatc    56760
gaaaaattgg catgcattga aacgtctacc tggattttct ttagtccacg aaattcgctg    56820
tgcaaaaagg aaattcgcaa ccacatctgt caagcttcga ttgttggag tgagaggaat    56880 ccatgaattg atttgggctt gaaagaaaaa gaggcggatt agggttcata cgaaattggg    56940
gaaatgtgaa aggtttgaac gaaattgggg aaagggaaaa ggtttgaact aaaaacgtgc    57000
tttaaaacct aagaaatcaa agaaacaatt aaagggaaag gtttaaaaga aggtcacgtg    57060
caagtcacgt gaaaagtcaa actaactttt gacggtcaac taactgaaac cgtcaagagg    57120
ttgtgtttaa caaacgttaa tatcatataa ggtagttttt tgcaaaaaaa atagaatagg    57180
tagttttttg caagttaccc attagaatag gtagtttttt gtaattttc ctttatttaa    57240 ataaagagat aaatgattcc ttgttagatg aactaaataa atagttgaat tgaagtggaa    57300
agagggagta gtccacatta tatgatcaat ttatttattg tgaacaacca agaagtgtca    57360
agcaagctgg tgaaggagaa tgaagcaaag tgaacagcca atgttccaac aaacagaagc    57420 acaaagaac atacagtggc ggatctaggg ttcacactcc ctagaggcac caacatagag    57480
atgaaaaata tgcacctggt gcacaaccca ctttcggcac atcagttact tgggaaaacc    57540
gttatgaggt ggaactaaag taagcatttg aataattcaa aaaaagtaa gcatttgatt    57600 ttatatttga cacctaagag aattgtctaa ttcaaaaacc taacaaattc ttcgattcgc    57660
aatttcgaat atcacaaagt ggaattaaga gaattctctg aaaatatatt tgacaaacaa    57720
gtcatagttc catttgattt taaaacttcc gttttaaact gtaaatcgaa attttacaac    57780
catcaaagaa ggaattttaa gcgaaaaggg aaaaatatc aaatgatgta aacctaatcc    57840
taacttacca aaacttaatt caaacccaaa cggtctcttt cctttcccta ctaagaagta    57900
agaatgtaga acaacaccca taaaataaaa caactctatt ttctctcaga attactgaac    57960
aatcttcatc aacatcaatg gttttttttt tttttttttt tttttttttt ttttttttat    58020
tttaaatttc tgggtctttc tcttaaattt ctgggtcatt tacaaaaatt aaaaaaacgt    58080
ttgctcttca ctttgcgttc tttcagtttc tcttcatcag cttgctttct tcctccctgt    58140
gcgactggtt ctaccttaag aaaaagcttt tcttcaccca ctcacttcat attcataatt    58200
cctctcactt aagtaaatca atcaactaca ttctaccaaa cacgcttctc aaagtgaaca    58260
aaccctaatt ctccttggag aatcgcttga cgccatcaaa gaaggaattc tcaagcgaaa    58320
tgggaaaaaa atctgcaaaa ccatcaaaga aggaaatcga aagttcaag taagcattgt    58380 tgtaattttt ataactgtaa atatccgatt ttcatagaat ttttttgtaaa tatccgacat    58440 tcttacgatg caggagaaga atcgagaatg acgcagaaaa atcgacagca cctatcatac    58500
```

```
caaaacaacc aagaatgtat tataattcaa acctttagta actgccattt ttttggttta   58560
gaattgctga tttttctgtg aaattagata cttgttacat acaaatttaa gtacttgtga   58620
attgctgtta caaccggtg aatttctgtt acaaataat gttgttgtta caaacttcaa    58680
tattgttgtt ataaacttgt gaattgctgt ataaactgg tgaattgctg ctataacttt   58740
ctgaattgct gctataaatt tctgagatat tgttacaaac tttggaattg tgttaaactg  58800
gtgaactgct gttataaatt ggtgaattgt tgtaaatatt tgaattgcta ttataaacta  58860
gtgaattgtt gttataaact ttaatattgt tttcatatct ccttaaccac aacaccaatt  58920
ccaatgattc caaagccaaa tgtttctcaa ctcaatgaag aatcccgtgt aaatttagtt  58980
ttgaaaagaa atcacaatac tatccccgaa acgccactgt tttcgacccc aaatgcagtc  59040
agtttctgac agcttctgtt cttcttgttt ttgtcgactt tggctgcttc tttccaacaa  59100
aaccaattga gttatgcacc ccacaaggga ttcaaggctt tgataccatt tgcaccatat  59160
ttggacccaa aggtgagaac aaattgggtt gtttgtggaa ttaaattgga ccctctaaaa  59220
actactgaaa ttgaaaaaga tatgatcaga tttctctgat tttggacgtt tcaaggcttc  59280
actcaccttt tcaacccttg cccttcaact tcaatcaaag cttcactcac cttgatcttg  59340
gttgaatctt gctatgttct cccgttgctt cactcacaaa gaaagaaga tagaaaagga   59400
aatgccaagc attctccaaa gaaactttat taatcatcaa aactgagttt acaatgcatc  59460
atggctaaga gacactctaa aattagttaa ggctttaaac aactcagccc atctaaaatt  59520
aacggttagg aggcacgtga catacttgtg catataatgc tgctggctga cataacgcat  59580
aaccacccaa actgaattgc atatattgaa ccaataccta cgctgctgct gtactagttt  59640
aattttcacg atgtcttgct gttctgaata cacaacccaa actgcacaag tgatcttcct  59700
attgatcata gctaaaccaa gcatcttgct gcacatataa aagttcctga accttctgtg  59760
ctgcacatgt tttatgtgct gaacaaacaa cttgctgctg tacttactgc actaataatt  59820
ttccttcagt gctgcaccttt taacgaacca accagtttca agcatgatca gaaaaccttc  59880
tcaacgacac acaatattca gatttttgacc caatactgca catctgaaca gaacattgat  59940
ttgctcttgc atttactgat tttctacatc agctaccaaa ataacgaacc acatgctgac  60000
cttgctactt gttttattac gaatctgttc cacaactaca ctaccattct tttgacttaa  60060
cttagaaacc atgtttccca aaatcatcaa gcatgtaagg atgaatgccc tcacttgctt  60120
gatgaaccaa acccatatat taaacaaact aaccaagttg attagcttgc ttgtgttgcc  60180
acaactccaa ctaacttgtt gcattttacc cttcttagca aaaactctac ctcgaatctt  60240
tgtaggatta aattcaacaa atctactcac atgaacatac tccaatacca agttgattag  60300
cttgcttgtg ttgccacaac tccaactaac ttgttgcatt ttacccttct tagcaaaaac  60360
tctacctcga atctttgtag gattaaattc aacaaatcta ctcacatgaa catactccaa  60420
taaggcgat ttttcaagca caaaatccac cttgaaaaac ccatacttac tagcttgctc   60480
aattttgtaaa agaaccgcca atcttggatg agaatcaatt atttctacgc attcttttgt  60540
agaacccata tcctccatgt aagttgtctc aacaacctct tcaagctctt taataccctc  60600
aacacaaggt atttcaacca cttcttcaag aatcccgtgt aaaaacagtt ttgaaaagac  60660
atcacaatac gatccccaaa aattaaaaaa acatgaaaat acagcaaatg aacactgacg  60720
gagcagcagc tgaacagggg accttgacat gggtccagat gattctctaa ggactcatag  60780
aattccttg gtccttgact tcaagttcca tgtaccaaga tgccattcct tgtgttttct   60840
```

```
tggtcattga tgtccagacc tgttctccac atgttgcaca aggtcagctg gtcgcgagtt   60900
ttcacgtgtg cactggtttg ttctgacagc ttcttcgatt gaccagggga acttgagtct   60960
tgtttctggt ggctccaatg atggttagaa gtgttcttgg accataacag caacgcccat   61020
gtgtaaagat tccaaaacta ctcttggagt cttcaaagac gcacatattt tttctagaag   61080
ttgcttccaa ggtctgctgt tcgccataat tgtgctgctg gttctgtggg ttgttattag   61140
tgattttctg gttgttttc acggtcttgt tcacttcttg ataatccttt acattcgttg    61200
agtctgcgta tgaaccaagt gtgccaagga tacttggttc accttaagac ctgcaccata   61260
tcaaacatgg tgcagttata aactgtaata ttgttatatt ggaggtgtaa atgtctgtta   61320
tgcattttat tgttcataat gtcttggctc aattaaatta tcttgcatac ataatctctt   61380
atcaggagtg ttgaagcaac atacagagat gccttactac aaagaatacc tccaaaagca   61440
ttcatcaata tgcttaaaaa gggtatgtct gagaatcaca aggaagccat aagaaatatt   61500
ggtttcggag ggttcttaga cctggatatt ggctggacat ccaggggatt tttctgtgct   61560
gaattggtaa atagctttga cgttgctaga agatcattag tatttccttc caaggagcgg   61620
ataaagatta agcctaagga tgtacatctg gtctatggag ttcccgccag aggagctaag   61680
attgatgtct ccaaaaatac agatgcagaa atcaaccttt cttacaggt attgaggact     61740 gaatactact aatgttataa ctttattttt atcgttataa actataattc gttgttatac   61800
actttaagtt ttggttgagt gcttgacatt cgtaaatcga tttgtttaat tttggttgag   61860
tgcttgacat tcgtaaatcg atgatatttt ttccatcgtg ttgctattat aacttttatt   61920
ttattgttat aaactataat tcgttgttat acactttaag ttttggttga gtgcttgaca   61980
ttcgtaaatc gatttgtttta attttggttc agtgcttgac attcgtatat caattatatt   62040
ttttccagcg tgatgctata attcgaagtg ttttgctta attgcggtgt ttaattgggc    62100
tcctgtaaaa tatgtacctc ttgtacaacc cacttccggt acatcggtta catggaaaac   62160
tcgtggttcc aaaagaaaga attatgatgt ggatgagggt agttgagtgc ttgacattcg   62220
taaatcgatg atattttttc catcgtgttg ctattataac ttttatttta ttgttataaa   62280
ctataattcg ttgttataca ctttaagttt tggttgagtg cttgacattc gtaaatcgat   62340
ttgtttaatt ttggttcagt gcttgacatt cgtatatcaa ttatattttt tccagcgtga   62400
tgctataatt cgaagtgttt ttgcttaatt gcggtgttta attgggctcc tgtaaaatat   62460
gtacctcttg tacaacccac ttccggtaca tcggttacat ggaaaactcg tggttccaaa   62520
agaaagaatt atgatgtgga tgagggtagt tccaaaagaa tgagttatga tgtggaacag   62580
aatagaactg aagagccgag tggacttgaa caatatttac tcttatatta tattaccttg   62640
tatatcatgg ttcttattgt taaagtcata gaaagatccg atgtctttct ttctatactt   62700
tggcatgtca aacttacaag taatgtatag aaagattgag ataatattga cactttatcg   62760
atcccacacc attttctcaa aagagcccat tgtaagtttt gtattgtaag ttttttgctt   62820
tcagctacga aactattaat gtcacgaaca gaagctacat cctcaagttt acctctaaag   62880
taattaagtg actcctaact ggaatgtctc aaccaaattg aagtgaaatt tgaggatgta   62940
gcttataatg ggctctttg agaatatact cttgtattgg ttcttgcatc aaaatcagga    63000
caaatagata ttgtttttc taagatgtac cttataatgg gatcttttga gaatatatac    63060
tcttgtattg gttcttgcat caaaatcagg atgaatagat attgttttc cttcttagga    63120 cccctaactt aagtttatta ctaaggctcc gtttggtagg gcgtaaaaca ttttcactga   63180
aaagtgtttt cccattttat attgtttggt ttagtgtaaa atattaaaat gtaaaacttg   63240
```

```
gggtggaaaa tggggaaaat cattttttcac cttattgaaa acattttccc ctcaatttag   63300
aaggaaaata ttttccatca caagtggagg gaaaacattt tccatcacaa gtggagggaa   63360
aacaattgaa aatctgtgta taatgttatg aatcagagtt ttgatcgaat ataatcacaa   63420
attcaagaaa agtaataact tgttacaaac ttacttattg ttaaaaccgc aactcaacta   63480
ttttgaggat cccattatca atggcagaca aacgtagttg attttttaagg attcgaacct   63540 tatcctttag cttttttgagg attcaaacct tatccttacg tttgtccgcc attgataatc   63600
tgatcctcaa aaagacaaac gtaaggataa ggttccaatc ctcataaagc caaaggataa   63660
ggttcgaatc ctcaaaaatc aactacgttt gtccgccatt gataatacga tcctcaaaat   63720
agttagagga gcccacacac tcggaaaaca cgggattttg caggtgaact ggatatgcaa   63780
ccgccagcca taaataattg agggtcgtgt aaacttatat atcaatttga aggttgtaat   63840
gatcaactta cctgagaggg ttctacacag ttgcaccatt tcaagacttt tcccattcca   63900
atcaattctg ctttagtgcg cttaacaata tttaagcctt tactgttaat ttccttgttg   63960
taattgtgac taaaaattcg ccataaatcc aagtcatgcc aggaatactt ttcagaaata   64020
atttgtggga agacatattt atttatcgca tataaataat gttccttctc tgcttcaatc   64080
atctgtcaat aaaaatccaa gagaacaagc ttaccacaac gctcaaagaa cttatcctca   64140
acatataaac attactaaat cttaaaaaaa aaaaaaattc tctcaacata ttacagtaat   64200
agcactggat gagacactcg caacaacaat agtacaacga caacaactgc acaaaacgac   64260
caccaacaac agtagcagca gcagacgcaa ccaagagaac aagtttataa caatacagga   64320
gtttataaca atgtgacata agtttgtaac aataaagcag aagtttgttt tgggatgaaa   64380
ttgactctat ttcagaaatg tgaatgaaat ttgcaatatg ttttaagtta aatgtgaaga   64440
tttaagaatc atatttgact taaatgtgaa gatttaagaa ttatatttga cttttgatgg   64500
aaatgtggtt gttttgtgtg aattgttgtg gttgtttgtg tgaagtgtag tagttgtttg   64560
ttgttaggga cgatttggag gcgctgctac ctcggctctg ttggtgctgc agtagtgcta   64620
ctgctgttgt tggttgcgtc tgctgctgct acttttagtg gtcgttttgg gcagttgttg   64680
tcgttgtact attgttgtta caaacttgtg aatttctgtt ggttgagtgc ttgacattcg   64740
taaatcgatt tgtttaattt ttgttgatga tatttttttcc atcgtgttgc tataatttga   64800
agtgtttttg cttaattgcg gtgcttaatt ggacttttga ttgttgattc tgatgatatt   64860 tgttcatttta ttgatgatat ttgttcattt taagacacaa tacagaagta tataacaatt   64920
agacagaagt ttataacaat aaagcagaag tttgtttcgg gatgaaattg actctatttc   64980
agaaatgtga atgaaatttg caatattttt tgagttaaat gtgaagaatt aagaatcatt   65040
tttgacttaa atgtgaagat ttatgaatca tatttgactt tgatggaaa tgtggttgtt   65100 ttgtgtgaat tgttgtggtt gtttgtgtga agtgtagtag ttgtttgttg ttagggacga   65160
tttggaggcg ctgctacctc ggctctgttg ttgctgcagt agtgctactg ctgttgttgg   65220
ttgcgtctgc tgctgctact gttagtggtc gttttgggca tttgttgtcg ttgtactatt   65280
gttgttagaa acttgtgaat tgctgttggt tgaatgcttg acattcgtaa atcgatttgt   65340
taattttggt tcagtgcttg acattcgtaa atcgattata ttttttccag cgtgctgcta   65400
taattcgaag tgttttttgct taattgcggt gtttaattgg acttttgatt gttgattttg   65460
atgatatttg ttcattttatt gatgatattt gttcatttta agacacaata cagaagttta   65520
taacaataaa gcagaagttt gttttgggat gaaattgact ctatttcaga aatgttgtta   65580
```

-continued

| | |
|---|---|
| gtggtcgttt tgggtagttg ttgtcgttgt actattgttg ttacaaactt gtgaattgct | 65640 |
| gttggttgat tgcttgacat tcgtaaatcg atttgtttaa ttttggttgt gtgcttgaca | 65700 |
| ttcgtaaact tttattttat tgttataaac tgtaatttgt tgttatacac tttaagtttt | 65760 |
| gtgctgtgtt atactgtgtg tattcagaaa tggagagccc aattcggatt aacgtatgga | 65820 |
| agtccttcaa atgccagtct agtgaaaaga atagaagaac aaacaagaga ggctgttgtt | 65880 |
| tccgaggagt ttttattaaa ttttgtcgta gctgctgtaa attgctgtat taggtcaaca | 65940 |
| aacaatcagt cagtttactt taaattttta cattgttgta aagatatttc aaaaataaac | 66000 |
| tcttatgact ggtcttcttt tactcaccaa caactgttag actcagttac agagtggaag | 66060 |
| gatggatcat cattcttcac aggtccactg ccctttctca tggtaagaat aactaactgt | 66120 |
| tacaaatttc tttatgatgt acaaaagttt aataaacttt aattttatg cttttatacc | 66180 |
| agattaacta ttttgataga atgaaaagag gaaatttac atccccaaga caattccctc | 66240 |
| ttatatcagt atggaacaag gatatggtta aatcaaggat aaatattgag cagaaaaagg | 66300 |
| ggtatggaaa tggtgttgtc atgcgccgat tgaagcctcc ccaagaggct gaaaagcctg | 66360 |
| cccctaagat gaaggagttc tataaaaaat ttgcttcaaa ttgcactgag atttataaag | 66420 |
| tttgggcagc tgcccaagag gctgaagggc ctgcccctgc catggaggtg ttctttgaag | 66480 |
| aatgtgcttt aaacatcact gaaatttatg aagtttgggc acaaacacaa gaacctggac | 66540 |
| aatcttcttc tgttgtatct gctggtgaac tgctgttata aatttctaaa ttgctactat | 66600 |
| aaatttctga gctgttacaa actctaatgg aaatgtggtt gttttgtgtg aaatccaagt | 66660 |
| tatttaccac cgctggattt ttatcttgca ggacaatctc atgatttccc actgaaaaat | 66720 |
| tctagtctag ctgctcatga ttccccttct cctgttgtat ccgtcgaacc taccgctgct | 66780 |
| catgatgctc ctgaacctgg acaatcttct cctgttgtat ctgctggtga attgctgtta | 66840 |
| taaatttcta aattgctgtt ataaatttct gagctgttac aaactctaat ggaaatgtgg | 66900 |
| ttgttttgtg tgaaagccaa gttatttacc accgctggat ttttatcttg caggacaatc | 66960 |
| tcatgatttc ccgctgaaaa attctagtct agctgctcat gattcccctt ctcatgttgt | 67020 |
| atccgtcgaa cctaccgctg ctcatgatgc tcctgaacct ggacaatctt ctcctgttgt | 67080 |
| atctgctggt gaattgctgt tataaatttc taaattgctg ttataaattt ctgagctgtt | 67140 |
| acaaactcta atggaaatgt ggttgttttg tgtgaaagcc aagttattta ccaccgctgg | 67200 |
| attttttatct tgcaggacaa tctcatgatt tcccactgaa aaattctagt ctagctgctc | 67260 |
| atgattcccc ttctcatgtt gtatccgtcg aacctaccgc tgctcatgat gctcctagtg | 67320 |
| aacaaccgaa agttaaacgt aagagatcaa aaacagtagg tcaatgtaag agaatgtgat | 67380 |
| cactaactaa tacaaaatgt tgaacaaccg aaagttaaac agcaggacat tgttctgcat | 67440 |
| ttcatattgg ttagtgatca cattctatgt aagtactagc gacattgttc tacatttcgt | 67500 |
| attagctagt aatcacattc tatgtaagta ctagcgacat tgttcaacat tttgtattag | 67560 |
| atagtactag caacattctt cacctgttgt atctgctggt gaattgctgt tataaatttc | 67620 |
| tgagctgtta caaactctga tggaaatgtg gttgttttgt gtgaaagcca agttatttac | 67680 |
| caccgctgga tttttatctt gcaggacaat ctcatgattt cccgctgaaa aactctagtc | 67740 |
| tagctgctca tgattcccct tctcctgttg tatccgtcga acctaccgct gctcatgatg | 67800 |
| ctcctgaacc tggacaatct tctcctgttg tatctgctgg tgaattgctg ttataaattt | 67860 |
| ctaaattgct gttataaatt tctgagctgt tacaaactct aatggaaatg tggttgtttt | 67920 |
| gtgtgaaagc caagttattt accaccgctg gatttttatc ttgcaggaca atctcatgat | 67980 |

```
tttccactga aaaattctag tctagctgct catgattccc cttctcatgt tgtatccgtc    68040
gaacctaccg ctgctcatga tgctcctagt gaacaaccga cagttaaacg taagagatca    68100
aaaacagtag gtcaatgtaa gagaatgtga tcactaacta atacaaaatg ttgaacaacc    68160
gaaagttaaa cagcaggata ttgttctgca tttcatattg gttagtgatc acattctatg    68220
taagtactag cgacattgtt ctacatttcg tattagctag tgatcacatt ctatgtaagt    68280
actagcgaca ttgttcaaca ttttgtatta gctagtacta gcgacattct tcacctgttg    68340
tatctgctgg tgaattgctg ttataaattt ctgagctgtt acaaactctg atggaaatgt    68400
ggttgtttta tgtgaaagcc aagttattta ccaccgctgg attttttatct tgcaggacaa    68460 tctcatgatt ccccactgaa aaattctagt ccagctgctc atgattctcc ttctcctgtt    68520
gtatccgtcg aacctaccgc tgctcatgat gctcctagtg aacaaccgaa agttaaacgt    68580
aagagatcaa aaacagtagg tcaatgtaag agaacgagaa gaatagtcca aaaccttcca    68640
ctgaaccaaa gatctccatt tatagttcag aaagaaaaag cattatcaga agttaattaa    68700
aagagagttg ttgattatgc tttgttgctt gaagacgaaa cgtaagtgtt ccaaacttta    68760
caattaaact tcaattctag ccttatattt gtgtacaaca tactaatgtt accttacgtt    68820
gatgaatatg aagggaattg ttattttgtg atggcttgaa caatatcacc agattcgaat    68880
tttcatcatt gaaggagggc actcatattg taaatgaaat gattgatact tgggcacaca    68940
ttctcaatga agcaaacaga aaaaaaaccc tcattcaaag gaaaagaaag agagattttt    69000
cttcaccaca ttgcccatgg taaacattgt tccaaactta ttctctttgt attatagttc    69060
aatatagttc ttattaacta ttagcatgtt gtgattaact aaatacatat tgctataata    69120
tatatatata tatatatata taaatatat atatatatat atatatatta tatatatata    69180
tatatatatt gttacaaact agtaatgaac tgttataaac taataataga ttgctataaa    69240
cttttggttg aattgtggtt aattcattgt tatattttg cacattatag caccttatca    69300
cttgcaacta tcttggtaca tgggattcca tgtacaataa gtttaaagaa aggatggaag    69360
tagaaatgga cctctacaag gtgacaaact ttagtaaatt tgatctggta agctaatctc    69420
ataaagtact tgttataaat cttgttataa atttaatac ttttttaatct gaaaaataac    69480 aaaaaaaaaa aattgttgca gatattcttt ccagtaatag cttctgagca ctactacatt    69540
ttttgtttca actttctgtc caatagactt gagattattg acaacagatt tttagaaagc    69600
ggagtgtcac gggaatccaa ataccaaaat tatccagaaa aaatggtatg aacctatgaa    69660
ttcaaattta atattgttgt tatatactgt attgttgtta caaacttgtg aattgctgtt    69720
gtaaacttgt gaaattcaaa taccacgttt gttttattgt tctaaactga tatactaatg    69780
cattaacctc ttttttgtata aagatagacg catttttcaaa tttccttgat gaaaaaagtc    69840
taggaaaaga tggtgaccctt gttgctcagt tcgatattgt cataaacaaa atgaaatgga    69900
gaaaaaatga caatttcatc gattgtggat tatttaccat gaagcatatg gaagaatacc    69960
agggacaagg tgaaaattgg gacatccaaa ttaacataaa tgacgtgagt tgttataaac    70020
tattgtttat atgttataaa ttatgatatt gatgttataa atatatgtat tattgttata    70080
aactaatgtt cttactgttc aggctgaaat caggaagaac ctcagaattg attactgtgg    70140
aagaattata acttcaacat taaaccaaaa acgaaaggaa gtgatttcaa attcaaagaa    70200
gtataacttc aacattttgt aattaagaac attattgtta gtattgtggt agttttaatt    70260
ctgatttgtt ataaactatt gtacatttgt tataaactca tgtaatattg ttattgttat    70320
```

```
ggatatcaaa acctaacact agtgaatata gttattatta tgtgcttctg tcatactccc    70380
tccaattcag ttcagttgtc ccatttggga ttggcacgga tattaagagt gagtggtagt    70440
tgggtatttt aattgattaa ataattgtaa agatggtagt tgggtatttt aattgattaa    70500
attaattgta aaggtggtag ttgggtattg ggaattgtaa aagtggggtt ttaatttgat    70560
taaattaatt gtaaaggtag tagtgggta ttgggaattg gaaaagtgag ggtatttagg     70620
taaaaaaaga tgtatcaaaa tagaaatggg acaattgatg tgagttgtcc caataaggaa    70680
atgggacaac tgaactaaat tggagggagt atcatttagc agaggaattt ataacagcaa    70740
ttcacaagtt cataacagca attcagaaat ttacaacaat tcaccagttt ataacagcaa    70800
ttcacaagtt tataattcta aactgatata ctaatgcatt aacctctttt ttgtataaag    70860
atagacgcat tttcaaaatt ccttgatgaa aaaagtctag gaaaaaatgg tgaccttgtt    70920
gctaagttcg atattgtcat aaacgaaatg aaatggagaa aaaatgacaa tttcatcgat    70980
tgtggattat ttaccatgaa gcatatggaa gaataccagg gacaaggtga aaattgggac    71040
atccaaatta acataaatga tgtgagttgt tataaactat tgtttatatg ttataaatta    71100
tgatattgat gttataaatt atgatattga tgttataaat atatgtatta ttgttataaa    71160
ctaatgttct tactgttcag gctgaaatct tgaagaagct cagaattgat tactgtggaa    71220
gaattataac ttcaacatta aaccaaaaac gaaggaagt gatttcaaat tcaaagaagt     71280
ataacttcaa cattttgtaa ttaagaacat tattgttact attgtggtag ttttaattct    71340
gatttgttat aaactattgt acatttgtta caaaatcatg taatattgtt attgttatgg    71400
atatcagaac ctaacactag tgaatatagt tattattatg tgcttcagtt atatcattta    71460
gcagaggaat ttataacagc aattcaatgg tttataacag caattcagaa atttacaaca    71520
attcaccagt ttataacagc aattcacaag tttataacag caattcagaa atttacaaca    71580
attcaccagt ttataacagc aattcacaag tttataacaa caatactgtt tataacttgc    71640
tcggtctagg gccaagatgg agttcgaagt tcggtccctg tatacggagg cctagaatct    71700
tctgaataaa tcatcagcta ttgttataaa ctcaatgttc ttgaattaaa atcaggacat    71760
gccacaaacc tccttccggg gttttcaact gtccatctcc ttagcgtaga taagtcatgt    71820
ccacaatagc attttactcg gttttcataa caatttgaag agcttgacat ctgaaattca    71880
ataagtagtt gttcagtagt taccccctagt taagattttg aataacccct caccaaatct   71940
agttgtagct accccaactt tagttttttta gtgacccttta atcaaattga ttgaaacaaa   72000
ttcaataaat taataattca tacatcaaat catctggtaa cttctttaat aacaacaaac    72060
aactactaca cttaacacac acaaccatga agcatatgga agaataccag ggacaaggtg    72120
aaaattggga catccaaatt aacataaatg atgtgagttg ttataaacta ttgtttatat    72180
gttataaatt atcatattga tgttataaat atatgtatta ttgttataaa ctaatgttct    72240
tactgttcag gctgaaatct tgaagaagct cagaattgat tactgtggaa gaattataac    72300
ttcaacatta aaccaaaaac gaaggaagt gatttcaaat tcaaagaagt ataacttcaa     72360
cattttgtaa ttaagaacat tattgttact attgtggtag ttttaattct gatttgttat    72420
aaactattgt acatttgtta caaaatcatg taatattgtt attgttatgg atatcagaac    72480
ctaacactag tgaatatagt tattattatg tgcttcagtt atatcattta gcagaggaat    72540
ttataacagc aattcaatgg tttataacag caattcagaa atttacaaca attcaccagt    72600
ttataacagc aattcacaag tttatagcag caattcagaa atttacaaca attcaccagt    72660
ttataacagc aattcacaag tttataacaa caatactgtt tataacttgc tcggtctagg    72720
```

```
gccaagatgg agttcgaagt tcggtccctg tatacggagg cctagaatct tctgaataaa   72780
tcatcagcta ttgttataaa ctcaatgttc ttgaattaaa atcaggacat gccacaaacc   72840
tccttccggg gttttcaact gtccatctcc ttagcgtaga taagtcatgt ccacaatagc   72900
attttactcg gttttcataa caatttgaag agcttgacat ctgaaattca ataagtagtt   72960
gttcagtagt taccctagt taagattttg ataacccct caccaaatct agttgtagct   73020
accccaactt tagttttta gtgaccctta atcaaattga ttgaaacaaa ttcaataaat   73080
taataattca tacatcaaat catctggaaa cttctttaat aacaacaaac aactactaca   73140
cttaacacac acaaccacaa caattcacac aaaacaacca catttccatc aaaagtcaaa   73200
tatgattttt aaatcatcac atttaagtca aaaatgattc ttaattcttc acatttaact   73260
caaaacatat tgcaaatttc attcacattt ctgaaataga gtcaatttca tcccgaaaca   73320
aacttctgct gtctcattgt tataaactta tgtattgtgt cttaaaatga acaaatatca   73380
tcaataaatg aacaaatatc gtcagaatca acaatcaaaa gtccaattaa gcaccgcaat   73440
taagcaaaaa cacttcgaat tatagcaaca cgatggaaaa atatcatcaa caaaaattaa   73500
acaaatcgat ttacgattgt caagcactca accaacagca attcacaagt ttgtagcaac   73560
aatagtacaa cgacaacaac tgcccaaaac gaccactaac aacagtagca gcagcagacg   73620
caacccacaa cagcaatagc actactgcag caccaacaga gccgaggtag cagcgcctcc   73680
aaatcgtccc taacaacaaa caactactac acttcacaca aacaaccaca acaattcacc   73740
caaaacaacc acatttccat cataagtcaa atttgattct taaatcttca catttaagtc   73800
aaatatgatt cttaaatctt cacatttaaa tcaaaacata ttgcaaattt cattcacatt   73860
tctcaaatag agtcaatttc atcccaaaac aaaattctgc tttattgtta taaacttatg   73920
tctcattgtt ataaaggtct gtattgtgtc ttaaatgaac atatatcatc aataaatgaa   73980
caaatatcat cagaatcaac aatcaaaagt ccaattaagc accgcaatta tgcaaaaaca   74040
cttcgaatta tagcaacacg atggaaaaaa tatcatcgat ttacgaatgt caagcactca   74100
accaaaatta aacaaatcga tttacgaatg tcaagcactc aacgaacagc aattcacaag   74160
tttgtaacaa ccatagtaca acgacaacaa ctgaaaacga ccactaacaa cagtagcagc   74220
agtagacaca accaacaaca gcagtagcac tactgcagca ccactccaac accacaaaca   74280
aaggcaacaa catgccaaat cagaaacgca ccaacagcag ctctggaatg ctagaacagc   74340
actccaacaa gtagcagaac agcagaccac taatcaaaca ccaacagccc caaccaaact   74400
cagaagctag taggaaacaa agtgagtaac ctaccagcaa gaagcccaaa taaaccaaca   74460
agggctacag cccccttaacc ctaatactaa attaaaaaat taaaaaggat gaaacaaaag   74520
aaacttaccc acaaccttga atggttcagc ctcctgctgt tcaggaaaaa catgaatcaa   74580
cgcgagagct gagttcaaac acaaggattt cgcaatgacc gttcaaacgc aaaattccta   74640
ttattcaagg atcatccacc ccaaacttta gaggaaatga agggagaaaa tatcttcatt   74700
tatatattag attacaaggg aagggaattg aaggggagaa aaatgaacag atagatcatt   74760
tcaatgactg tcagaaataa atctcctcaa aaatagacaa atttgttcct ccctccatta   74820
ccttccctta cttcccttcg gtgttatagt acagacattg tcgaaaattt tttacctaaa   74880
gccttaacat tttcctgtcc gaaagcttca tcatgtgcac cgcagcatca acaatcacca   74940
gtctattatt tgtttgtagt ctctgcaaat gtacataaaa cacattaact caaatatgtt   75000
gaattcttga caactatcac caaataaacc caaataaact actggattct gggcaactat   75060
```

```
caccaaataa acccaaataa aaaaacgagt gaagaaaaac aagatcacta accaaaaatt    75120
ggaaaagaag attgagaaac tgaaatctgt caaacaaatc aggttgggtc aggttcgggt    75180
tcgggttata taaacaggtt agaaacccct tgacccaaac acaacccgtt taacaaagag    75240
ttggttttat aatattatat agttactcct aaacaaacta caacttgatt atagtttaag    75300
tttcatacac tcttacttac aatgattctt cttcttcacc cttgacagca tatggatagc    75360
ctacttcaag gaccgtttct gaaatgaaaa aaaaaatgtt agcatgacaa ttctatgact    75420
cccaagcaaa aaaaaaaaa aaaaagata agaaaaagaa catactttc ttttgttcat        75480 atgtttcaat tgatcttctg gaaaggtgaa tcgttttggc gatttcccct ttgtttctct    75540
tttacttgga gatcttattt taaaaatccg aacttcctga gtgggggag aaacttgaac      75600 ttcatcgtta ggtgaagaaa ccaagacatc atgatcgggg ggagaatggg tatgagaaat    75660
aaggggagta gagggaaatg gaatggtgct aggactagga gaatgggtat gagaaataag    75720
gggagtagag ggaaatggaa tgaagctagg actaggagaa tgggtatgag aaataagggg    75780
agtagaggaa atggtgctag gactaggact acagtgtgaa gaattcatgc tctcctcatc    75840
agcagtcaca gattcccaga cctcaatata tttttgtaa agtagtttga aattttgttc    75900
aaccccccct ttagtagact tggagttgat cttcaataaa ttggatccaa aactggaaag    75960
gtccacatca tcgaaaatct tgaattgttt tgctacaaca tgtggaagat gattttccac    76020
atgattgaaa caaacattg gtgtgatgat ggagcaaaac tgaatatgtc ttcgcaaatg      76080
atcaggcaac acaattgact gatatgggtg ccaattaata cactgtttca tacaacatca    76140
aaaaaaagtc acctcatcaa tcaaagataa agaaatataa tacaattaaa atgaaaattg    76200
aaatcacgca caagtgcttt tacctctgtt gcgttagcca aaagattttt tgcctgttgc    76260
agcttctcgg agagtgttgt gaccttcaga tttgatacat aacctttgcc tttcaagttg    76320
atcgtgtgta gcaaaggagc agtgttattg ttctcttgat tcatggccac accaaaaatc    76380
tccgctagac ctttaatacg gtagaagaag aaaccctgta aaaaaatgt tagatgatga    76440 aaatgacaag ataagagaaa ataagttaaa taagtgttct taccaccaca agccatgtaa    76500
atccattgat tagcttcttt ttcccatggc ccttcaattc tctataaaga tacgccaata    76560
atgccgcacc ccaagcatat gagttcactt ggtccaaatg ttcaacgaac tggaccaaag    76620
tggctcgaca ttcatgtcca cttgtagaag gagctatgat acagcatatc aaaatcaaca    76680
gaattgcctt tatcctctta tcatctgatc tcgtgtgatc tttggcaatt ctatccaatg    76740
ttgtcaaact tataatatta gttccttgct cttcaaaaac tctcatgaaa gcctcattat    76800
caactgtttt gtcgaagatg actggctttc ccacaatggg taaaccagtc aagtacaaaa    76860
cgtcctccaa agtgggtttt aacctctcgc catctatgca gaaacacata gaactctttg    76920
gcgttagatt atagtggttg acctttttgat atttattgaa gaacaattct aataattgaa    76980
ccggaagttc aaagctttct gttttcaaat gaagtagtcg tagcaaagaa cttccaggac    77040
cattagaatc aattcttgct ttgatacgag ccttcaaatc gtcatcaagc tctgaatata    77100
gtgtatgtac agtcttaagc ttcgaactcc ctttggagga atgtcctcca tcctgtaaaa    77160
taaaaagata aattgcatca ttaaataatt cacaaattcg aatgtactga agaactgaag    77220
taagtttact tactgttctg attgtctttg cggttgattt gttatgtctc attgctgaaa    77280
aacaagcgtt tgtgacattg tttaagttag gaatatgaag aacaaaccgt atatcacaag    77340
aaccaaattt cagtgggctt tcgagttcat gtcatataga acactaggct tgtgtgtgca    77400
atttataaca gcctacccta acagcaattt agaaatttcc ttacagcaat tcagaaagtt    77460
```

```
atagcagcaa ttcaccagtt tataacaaca attcaaaagt ttataacaac aataataagt    77520
ttgtaacaac aacattattt tgtaacatca attcacaagt ttgtaacagc aattcacaag    77580
tacttaattt tgtatgtaac aagtatctaa tttcacagaa aaatcagcaa tgtgaatttg    77640
tgaagtaaac aatgtcaaac cacacataga tacttaaagt taggaatatg aagaacaaac    77700
cgtatatcac aagaaccaaa tttcagtggg cttccgagtc ttatggtata aaccatataa    77760
gtcaagatta ctaagcaaat ggtagcaata gagtatagaa aatagacaaa gcaagacggt    77820
agaccattac agaaagcaaa atacagagtg ccaacttgtt ctttcatttt gttaaataaa    77880
ctagattcca tatatacaat aattcatagt tgtcttctag atttcaatta cattgattcc    77940
atatatacaa tggttccaac aaaaacatca gactaacatg atgaccctat acaagctttg    78000
aaatgatcca aaatactatg aaagtaagaa cacatttgac acagatgaga ctccatccac    78060
aacttctttt tgaaatcttc ctaatctttt gatttgacaa ttcagatttt cttttaagaa    78120
taccaacttc ttttttaaga ctgtctcttt cagccattag ctttaaaatg acatcttttt    78180
gccaatcggt cattggtgtg tccacccacc taaagaagga gcatcctctg attttggttc    78240
ttgaattaaa atcaggacat gccacaaacc tccttccggg gttttcaact gtccatgccc    78300
ttagcgtaga taagtcatgt ccacaatagc attttactcg gttttcataa caatttgaag    78360
agcttgacat ctgaaattca ataattagtt gttcagtagt taccectagt taagattttg    78420 aataacccct caccaaatct agttgtagct accccaactt tagtttttta gtgacccta    78480 atcaaattga ttgaaacaaa ttcaataaat taataattca tacatcaaat catctggtaa    78540
cttctttaat aacaacaaac aactactaca cttaacacac acaaccacaa caattcacac    78600
aaaacaacca catttccatc aaaagtcaaa tatgattttt aaatcatcac atttaagtca    78660
aaaatgattc ttaattcttc acatttaact caaaacatat tgcaaatttc attaacatt    78720 ctgaaataga gtcaatttca tcccgaaaca aacttctgct ttattgttat aaacttctgt    78780
ctcatagtta taaacttatg tattgtgtct taaaatgaac aaatatcatc aataaatgaa    78840
caaatatcat cagaatcaac aatcaaaagt ccaattagca ccgcaattaa gcaaaaacac    78900
ttcgaattat agcaacacga tggaaaaaat atcatcaaca aaaattaaac aaatcgattt    78960
acgaatgtca agcactcaac caacagcaat tcacaagttt gtagcaacaa tagtacaacg    79020
acaacaactg cccaaaacga ccactaacaa cagtagcagc agcagacgca acccacaaca    79080
gcagtagcac tactgcagca ccaacagagc cgaggtagca gcgcctccaa atcgtcccta    79140
acaacaaaca actactacac tacacacaaa caagtgaaac aactaggggt gttcataacc    79200
gggtacccgg ctaaacgggt acccggaaag ccgggtaccc agttagccag ttacctatt    79260 ttgcggcccg tgtcccattt aatgcgggta cccggttagc gggtgccgg ataaaacggg    79320 tcgggacacc gggtacccga ttattatttt tggtgatttt tcaaatttaa ttattatttt    79380
aaagatcgaa ttccgagtag atattaggca gtcgaaggta gacaaacacg agtttatatg    79440
ttttaagaat ttttacagta ggaccagaca gcagcgcgtg gcgcgtgaat ttttgagca    79500 agtaagcaaa caaagatttt gtggatttca tctgccatta ggaacagtgg ggatgatggt    79560
gggtatgtaa aaggggttgt aacatatatg gttattattt ggtttttctt gttgttggtt    79620
gtattaataa aggttatgta acctttagat tatactgtaa gaatatttgt tatgtaggaa    79680
gatatggaaa tgttgttgta acacttctgc aaacttgaat gttgaagcta attatagaac    79740 atccttttt tgattacttg cttccatacc ataattgttc cataacaata catactactt    79800
```

```
atatcttaca ttagagtagg tggttcaaaa tgaataacat agtacttata tctaacatat    79860
atggttatgg ataatcttga agttaagcca atgtctacca ttagtggaat tacactcatt    79920
aataagtttc atgttaagga tgtttctacc ctggaacttt gaattttttt tagttttcga    79980
cccgccattt atgaggcggg tcagcgggtc ggcgggtcgg gtcggcggg tcgggtagtt     80040 ttgaacaccc ctacaaacaa ccacaacaat tcacacaaac acaaccacat ttccatcaaa    80100
agtcaaatat gattcttaaa tcttcacatt taagtcaaat atgattctta aatcttcaca    80160
tttaagtcaa atatgattct taaatcttca catttaactc aaaacatatt gcaaatttca    80220
ttcacatttc tgaaatagag tcaatttcat cccaaaacaa aattaagctt tattgttata    80280
aacttctgtc tcattgttat aaacttctgt attgtgtctt tactcttaac atgaaatatg    80340
attattgtcg tttttcttc taatctacct tctcttttc gtttgaaagc tcaacaccat      80400
tggtgacaac aacaactgca agctctgttg cccctaccaa caatgctgcc agtcattcac    80460
atttctgaaa tagagtcaat ttcatcccaa aacaaaatta gctttattg ttataaactt     80520 ctgtctcatt gttataaact tctgtattgt gtctttactc ttaacatgaa atatgattat    80580
tgtcgttttt tcttctaat ctaccttctc ttttcgttt gaaagctcaa caccattggt      80640
gacaacaaca actgcaagct ctattgcccc taccaacaat gctgcagca caaaaaggtt     80700 agaaagaaat catgggcata tggttacaaa agagaggag caaaaggttc agtgccaatg     80760
gtgatttcaa cccaaggttc ttcaagctct cagcaacaaa agaagtgta tttgtaatgt     80820 ctgttatgtt tgctaggtta tgttggaact tttatgtttt gttgtctttg taagatataa    80880 gtagggtgt tcaaaacaac ccgacccgcc cgacccgacc cgccgacccg ccgacccgcc     80940
tcataaatgg caggtcgaaa actaaaaaaa ttcaaagttc cgggtcgggt acccgacccg    81000
ccttaaccgg gtcgggtcat gggccgataa tttattgact caggtactcg tttgacccgg    81060
atagcttttt ttgatttttt tttattttca aggtatttca ttttattgat tcatcttcaa    81120
tgtgtaagaa tcacactcaa gaagaccccg aaataatcac atgactatgt tcaaaaatac    81180
ctggtcgaga ccaaggtgca cctctttctc ttccagggaa atggaatggt gctaggacta    81240
ggagaatggg tatgagaaat aagggggagta gaggaaatgg tgctaggact aggactacag    81300
tgtgaagaat tcatgctctc ctcatcagca gtcacagatt cccagacctc aatatatttt    81360
ttgtaaagta gtttgaaatt tgttcaacc ccccctttag tagacttgga gttgatcttc     81420
aataaattgg attcaaaacg gaaaggtcca catcatcgaa atcttgaat tgttattcat      81480 tttgaaccac ctactctaat gtaagatata agtagtatgt attgttatgg aacaattatg    81540
gtatggaagc aagtaatcaa aaaaaggatg ttctataatt agcttcaaca ttcaagtttg    81600
caaaagcgtt acaacaacat ttccatattt tcctacataa caaatattct tacagtatga    81660
tctaaaggtt acataacctt tattagtaca accaacaaca agaaaaacca aataaaaacc    81720
ctaaaataaa acatgatatc tcttttccaa gctttctctc cttcattaat ttcttcttaa    81780
gccttttgta ttctgaaatt gcttgttctt tctcatgttc caagcaacaa agccttgatg    81840
tcaatatctt gaaatcaacc atttcaagtt catcgatcca cttaaacttc ttacatcccc    81900
tccaattagt gtcaggatcg aaaattggca agcattgaaa tttgaaacgt ctacctggat    81960
tttctttagt ccacgaaatt cgctgtgcaa aaggaaatcg caaccacatc tgtcaagctt    82020
cgattgtttg gagtgagagg aatccatgaa ttgatttggg cttgaaagaa aaagaggcgg    82080
attagggttc atacgaactt ggggaaaggg gaaaggtttg aactaaaaac gtgctttaaa    82140
acctaagaaa tcaaagaaac aattaaaggg aaaggtttaa aagaaggtca cgtgcaagtc    82200
```

```
acatgaaaag tcaaactaac ttttgacggt caactaacta aaaccgtcaa gaggttgtgt    82260
ttaacaaacg ttaatatcat ataaggtagt tttttgcaaa aaaaattaga ataggtagtt    82320
ttttgcaagt tacccattag aataggtagt tttttgtaat ttttcctttg tttaaataaa    82380
gagatatatg attccttgtt agatcaactc aagaaatagt tgaattgaag tggaagagg     82440 gagtagtcca cattatatga tcaatttatt tattgtgaag aaccaagaag tgtcaagcaa    82500
gctggtgaag gagagtgaag caaagtgaac agccaatgtt ccaacaaaca gaagcacaaa    82560
agaacataca gtggcggatc tagggtttac actccctaga ggcaccaaca tagagatgaa    82620
aaatatgcac ctggtgcaca acccacttct ggcacatcag ttacttggga aaaccgttat    82680
gaggtggaac taaataccat tgtaaagccg agtgaactca tgaagagcgt tgcaaacgaa    82740
ctacttttaa tggtgcaagg tgaagaatgt tctagtttag atgtcattaa atgtctaaac    82800
gaactcatga agagccgagt gaactcatga agagcgttgc acatcagtta cctgttgtac    82860
aacccacttc cgacatctca tgaagagcca ggtgaagaac gtttattcat tcgttaactt    82920
tcttacacgt ttattgcata gaactttata cttgatcttc tgaagatgtc attaaatgtc    82980
taatttctta acaaaaaata atactttttt caatgatcaa cctatacatc acttatttcg    83040
gactctttgt caagaaagat cctttatttt cacttttata gatcaatttg atagcaaact    83100
aacccaaatt atccggtcaa actaaacact tcatcatcct aagaattaat gtcctttatt    83160
catgaactag tcttactcct gacaacatgt aaatcatgaa atacaactaa gaatcaagcc    83220
ctaaaagcag tcgttttgac cacttgtata caagaaatca taaaatttct tgtggcattt    83280
cattgtagaa atcataaagt attacaacac ttattaaagg ggtcaattca aatacaaaac    83340
aaagtagtaa attttcattg taacatttca tcaagcactt catatttata caaaagaaat    83400
cataaaattt aactacaaat gtgtaaaatg taaccttaaa ccataaaatc aagacaatgt    83460
tacaaacaat caatctatta taagtcaaat gacaacaatc atgaacaaag aatcaatttg    83520
caaattgaaa aaaattaggg ttcataccttt aaatgaggat gtgaacagtg gcggatctag    83580
aattcacact ccctagggcc accaacatat agatgaaagt ttgtgaaaat tttagcaaag    83640
tttgcgaaaa tcatgaaata caactaaaca attcatctta aatcctagca gaacgttata    83700
gtccacatca taaattatga taaatttatc aataatccac aaccctaatt aaacctaatt    83760
taaaacttaa aaaccctat tacaaccaaa tttatcaata atcaacatca accaactcat    83820
tcatataacc ataaacaacc ctaattaaac ctaatttaca tagtataaat ataaatacaa    83880
ctacatacac attcatcaat tttgatcaat ttaaacctaa tttacaaaat cgaaaatgaa    83940 aaaataccttt gaatttttcg tgggtttgag aacttgaaga agacaataat ggtgggttgt    84000
gtataaccta tacaatgaaa caaaattaaa attagtataa aaaaactaag ccctaaaagc    84060
aaactaatga agcttgacca acaatgggta taccttgaag aagagcaaga atcaagccct    84120
aaaagcagtc gttttgaccg cttgtataca agaaatcata aaatttattg tggcatttca    84180
ttgtagaaat caaaagtat tacaacactt attaagggg tcaattcaaa tacaaaaaaa    84240
agtagtaaat tttcattgta acatttcatc aagcacttta tatgcataca aagaaatca    84300 taaaatttaa ctacaaatgt gtaaaatgta accttaaacc ataaaatcaa gacaatgtta    84360
caaacaatca tactccagca caaaatcaac atcacaccta gtcgctaaat aactaatttg    84420
tataagatga aaggcattat tctgaattga tacagtggcc accctaaagt catcttcctt    84480
acctagcata catacatcat cattcatccc cataaaaaca aatactcaag atgaaggcaa    84540
```

-continued

```
gaataataac aaagcacaat aacattgaca taatgacata taatatctaa ttcaatcaag    84600
aaactatctt gaattttgaa ataagaaaaa aaaaaaactg attttgggga attaaggatt    84660
tataaaatat aacatttaat taataataat acctcaaatt ggtggccgta tggactggac    84720
gtatgattgt cagtggtggc ctcctgtccg gtggcggtgg gctgtgggca gtaggaaagc    84780
cggcggcagt acacactcag cagggtgttc tgtttggtga atgaagcgaa tcagtggggt    84840
gcataattca attggttttg ttggaaagaa gcagccaaag tcgacaaaaa caagaacaga    84900
agctgtcaga aactgactgc atttggggtc gaaaacagtg gcgtttcggg gatagtattg    84960 tgatttctt tcaaaactaa atttacacgg gattcttcat tgagttgaga acatttggc     85020 tttggaatca ttggaattgg tgttgtggtt aaggagatat gaaaacaata ttaaagttta    85080
taacaacaat tcactagttt ataatagcaa ttcaaatatt tacaacaatt caccaattta    85140
taacagcagt tcaccagttt aacagcaatt ccaagtttg taacaatatc tcagaaattt     85200
atagcagcaa ttcagaaagt tatagcagca attcaccagt ttataacagc aattcacaag    85260
tttataacaa caatattgaa gttgtaacaa caacattatt ttgtaacaga aattcaccag    85320
tttgtaacag caattcacaa gtacttaaat ttgtatgtaa caagtatcgc ttgagaattc    85380
cttctttgat ggcgtcaagc gattctccaa ggagaattag ggtttggtga atgaagcgaa    85440
tcagtcagcg tcagcgaggc tgcgacctgc gagggaacca aggagcagca gccagcaggc    85500
caaacgtccg gtggaaagaa gcaactcagg tgaagcgatt ctccgtcagg cgtcaagcga    85560
ttctccaagg agaattaggg tttgttcact ttgagaaggg tgtttggtag aatgtagttg    85620
attgatttac ttaagtgaga ggaattatga atatgaagtg agtgggtgaa gaaaagcttt    85680
ttcttaaggt agaaccagtc gcacagggag gaagaaagca agctgatgaa gagaaactga    85740
aagaacgcaa agtgaagagc aaacgttttt ttaattttg taaatgaccc agaaatttaa     85800
gagaaagacc cagaaattta agttgggatt aggtttagat catttaatat aatcatcata    85860
caatcttata aaaagagtgt aaaattccac atggcactct ctcaatgatt tgccatattg    85920
aatgtcttac caaagttagc attaactcat tcatttaata tatgagtagt atatcacaat    85980
tagatatatt ttataatttt cttggaattt aacattttct tgaatgtaaa agacacataa    86040
gattttcaat taaagtttct taggatgcat atttgttttt ttatattgaa gtatttgtta    86100
attaataaaa aatataatta aaattttaat ttctaaatat gtatacatga taatcaaaaa    86160 ttatttgag aatgagaaaa aatcatctta taaacattgt tgattacaca tatttgcctt     86220
aaaaatttta atttcaaaat atatatacat gataatcaaa aattatttg agaatgagga     86280 aaaatcatcc tataaacatt gttgattaca catatttgcc ttaaaaagta tgacaatttt    86340
aattgataca tctattaaca atcgaatttt tattcattga aatcagtaca tattctaaaa    86400
ttgtttatta agtatacaa aaattacaat tttatactaa tagcatgtaa ttgcatctct     86460
atatagaata taataattat ataaaatttt atactaataa tttcgtgcat tgcacgagtt    86520
tctatactag tatgtattat ttggcactag tttgatataa atttatactt aataaagatg    86580
gggctgaagc ttggctctgt ttgggtgact ttaattgttc atctttatct tattcaaaga    86640
ttttcattca aatgtagtta tcagtatatt aataatatta caattatcaa ctgaattaat    86700
tatttgcgaa aaaataaact gagtaataag agagattagt aaatttagaa aacaaatatg    86760
cattttaggt tagtaaatgg cggatatatt atatgtagtg tgggtcgacc tagttatgta    86820
tataataata tcatttaaaa aaataaaaaa gtggtaaatt ttattttcgc aattaatact    86880
tataattatc cgacacggcc cggcccgacc ctttacacca aagcctgtta atgacccgcc    86940
```

```
ccattattaa cccgacccgc taatgaccca ttaaaatatt acccgacccct tgacccgttg    87000 ggtcgaccta gttatgtata taatgatatc tcttttccaa gctttctctc cttcatcaat    87060
ttcttcttaa gccttttgta ttctgaaata agccttttgt attctgaaat tgcttgttcc    87120
ttctgatgtt ccaagcaaca aagccttgat gtcaatatct tgaaatcaac catttcaagt    87180
tcatcgatcc actaaattac gcaaaaaagc gttaactgct attgttgttc ttgtagttcc    87240
atgtaaaaac gcgcggtttt attatggtaa actaaacgag caggttttga aagttgattg    87300
ttcttgtatt actttgtaaa accgcgcggt tttacatagt tgcactattg ggtttgacgc    87360 atttttaaa ggccgtcaaa tcagtatgat aaaaataggg atgatttatg attgatggta    87420
atatgtgggg taaaaataaa aaaagttat tacttcatcc gctccatttt acataggtgc     87480
aagaagcgat gtacaaccag gcccgaccca agggtaggcc aaaggcccaa cttaaatgtt    87540
tagagattta gaaagtcat aaatttgtaa gacatttcat cccaaagata aattagagtt     87600
tataacggac attcacaagt ttataacaac aatacaattt ataacttgct cggtctaggg    87660
ccaatatgga gtttgaagtt cggtccctgt ataaggaggc ctagaatcct tctgaattac    87720
acgcaatata gttttacttg caaattagga gttcgaaaga aatgatgtgg aagagaataa    87780
aactgaagag tcgagtggac tcatgaagaa agttgcagac taactacttt aaatagttcc    87840
aagtgaagaa tgttctgatt tggatatttt gagggtttta atgtttctac aagccaccgc    87900
taaggataag gctcgcatcc tccaaaatca actacgtttg tctggccata tataatgttt    87960
caacaagcaa ttttagggtg gcctaaccct tgggtcgggc ctggttgtac atcgcttctt    88020
gcacctatgt aaaatgaagc ggatgaagta ataactttt ttatttttac cccacatatc     88080
accatcaatc ataaatcatc cctatttta tcatactgat ttgacggcct tcaaaaaatg     88140
cgtcaaaccc aatagtgcac ctatgtaaaa ccgcgcggtt ttacaaacct gctcgtttag    88200
tttacctttg taaaaccgca cggttttatt gcataactgc aaataattag ttgtggtctc    88260
gatcctccca acttttttag tattttttct ctaaaaaaaa ggccgctatt aatgtgtttt    88320
tctctatcta accgcacggt tttacgggca attacacgga tctacaagaa caatatacaa    88380
agtatatcaa ctttcaaaac ctgctcttgt taagagtatt aaaataaaac cgcgtgcttt    88440
tattaggtac cacaagaata taagcgctta aacctgctct tgttttgagt atcattttaa    88500
aaccgcgcgt tttatatgg aaccacaaga accatatcag cgcttaaacg tttttcttat     88560
aaaaccgtac ggttttatat gagaactgca aataattgtg aactcgattc tattttaaa    88620 attctctaaa aaaaggccac tgttaatgtg tatttctcta tccaaccgca cggtattacg    88680
ggcaattaca aggcttttaa gtattaaatt tcgattatcc tttatgatta gtaatcattt    88740
cataaaaata taccaaaatc tgcccttggt tagcgtatct gtgtaacacc gcatggtttt    88800
acggacaatt acaacgcttt tatgtattaa atttcgatta tccattatga ttagtaatca    88860
tttcataaaa atatacaaaa acctgcccct tggttagcgga tctgtttaaa accgcgcggt    88920
atttatatgg tactacaaga acaatataag cggttaaacg ctttattgcg taaaaccgca    88980
cagttttatt tgataactgc aaattattgt gttctctatc aaaccatgcg gttttacggg    89040
caattacaag gctttattaa attttcatta tccattatga ttagtaatca tttcctaaaa    89100
atataccaat ataagcgctt aaacgcttta gtaatcattt cctaaaaata taccaaaacc    89160
tactcttggt tagaaaatct ctataaaacc gcgcggtttt actcggtact ataagaacaa    89220
tatacaaagt atcacccttg caaaacctgc tcttgtttag agtatctgaa taaaaccgcg    89280
```

```
cgttttttct tgtactacta aagcaatata tatgcttaaa cgcttttatg cgtaaaaccg   89340
caagctttta ttctaagtgc aaataattag ttgcttaaac gcttgtgtgc gtaaaaccgc   89400
gcggttttgt atggtgctac atgacgaagt ttatacagca attcactagc ttaggacaac   89460
attgaaattt gtaacaacaa tattattttg taacagagat tcactagttt ataacaacaa   89520
ttcacaagta cttattgctg tgtaaacata ctagtattta acaccaacta ttcaaaacct   89580
gatttatcaa aataaaaccg cgcggttgtt tatggtacta aaagaatatt ttcagtgctt   89640
aaatattctg ttgtgtaact gcgaacagcc ttggcttttt ttttttttt tttgaaaatt   89700 tccctcctgt tcgcacttag taagtgcata cagctccaaa cctttgtcca gaccaagtag   89760
acgcttagtt ttgggataac tttgatttgg gtcttatttc atttttttg ttttataatc   89820 ttatcctttt caaattttca gaagcgatgt acaaccaggc ccgacccaag cgtaggccaa   89880
aggcccaact taaatgttta aagatttagg tccaacaaaa aagtcattaa ttttgcaaga   89940
cagattgcat ttaacttcca gttcaattat tagaattatt cttaaatgaa tatcaacggg   90000
tcatataatc taacgccaaa gagttatatg tgtttctgca taaatggcga gagattgcct   90060
gatgttgtat gaaacagtgt attaattggc acccatatca gtcaattgtg ttgtctgatc   90120
atttgcgaag acatattgag ttttgctcaa tttacaagtg gacatgaatg tcgagccgct   90180
ttggtccagt tcgttgaaca tttggaccaa gtgaactcat atgcttaggg tgcggcatta   90240
ttggcgtatc tttatagcga attgaagagg cataggaaaa agaagctaat caatggattt   90300
acatggcttg tggtggtaag aacacttatt caacttcttt tctcttatct tgtcattttc   90360
atcatttaac attttttttc acaggatttc ttcttcttcc gtattaaagg tctagcggag   90420 attttttggtg tggacatgaa tcaagagaac aataacactg ctccctttgct acacacgatc   90480 aacttgaaag gcaaaggtta tgtatcaaat ctgaaggtca caacactctc cgagaagctg   90540
caacaggcaa aaatcttttg gctaacgcaa cagaggaaag cactcgtgcg tgttttcaat   90600
tttcatttta attgtattat atttctttat ctttgattga tgaggtgact ttttcttgat   90660
gttctatgaa acagtgtatt aattggcatc catatcagtc aattgtgttg cctgatcatt   90720
tgcgaagaca tagaaagatc tgttatgtct ttctttctat actttggcat gtcaaactta   90780
caagcaatgt atagaaagat tgagataata ttgacacttt atcgatctca cacttcttcc   90840
tatatatatc caaccgttaa tgtgtgaact cgattctatt tttaaaattc tctaaaaaaa   90900
ggccactgtt aatgtgtatt tctctatcca accgcacggt attacgggca attacaaggc   90960
ttttaagtat taaatttcga ttatcctta tgattagtaa tcatttcata aaaatatacc   91020
aaaatctgcc cttggttagc gtatctgtgt aacaccgcat ggttttacgg acaattacaa   91080
cgcttttatg tattaaattt cgattatcca ttatgattag taatcatttc ataaaaatat   91140
accaaaacct gcccttggtt agcggatctg tttaaaaccg cgcggtattt atatggtact   91200
acaagaacaa tataagcggt taaacgcttt attgcgtaaa accgcacagt ttatttgat   91260 aactgcaaat tattgtgttc tctatcaaac catgcggttt tacgggcaat tacaaggctt   91320
tattaaattt tcattatcca ttatgattag taatcatttc ctaaaaatat accaatataa   91380
gcgcttaaac gctttagtaa tcatttccta aaatatacca aaacctactc ttggttagaa   91440
aatctctata aaaccgcgcg gttttactcg gtactataag aacaatatac aaagtatcac   91500
ccttacaaaa cctgctcttg tttagagtat ctgaataaaa ccgcgcgttt ttcttgtac   91560 tactaaagca atatatatgc ttaaacgctt ttatgcgtaa aaccgcaagc ttttattcta   91620
agtgcaaata attagttgct taaacgcttg tgtgcgtaaa accgcgcggt tttgtatggt   91680
```

```
gctacatgac gaagtttata cagcaattca ctagcttagg acaacattga aatttgtaac   91740
aacaatatta ttttgtaaca gagattcact agtttataac aacaattcac aagtacttat   91800
tgctgtgtaa acatactagt atttaacacc aactattcaa aacctgattt atcaaaataa   91860
aaccgcgcgg ttgtttatgg tactaaaaga atattttcag tgcttaaata ttctgttgtg   91920
taactgcgaa cagccttggc tttttttttgt tttttttgaa aatttccctc ctgttcgcac   91980
ttagtaagtg catacagctc caaacctttg tccagaccaa gtagacgctt agttttggga   92040
taactttgat ttgggtctta tttcattttt ttttgtttta taatcttatc cttttcaaat   92100
tttcagaagc gatgtacaac caggcccgac ccaagcgtag gccaaaggcc caacttaaat   92160
gtttaaagat ttaggtccaa caaaaagtc attaattttg caagacagat tgcatttaac   92220
ttccagttca attattagaa ttattcttaa atgaatatca acgggtcata tatatataaa   92280
ctccgaacgt tagcgagggc tcttcgaatg tctctaaatt tgcttcgaac tttaatgtgg   92340
cttccgcaaa tgtctcgaaa tgctcaccga gcttttacga tgactttgcg aatgtctcga   92400
agcacgtgtg tcttcttcga ttatgatgcc taagcctcga actcgatctg tttcacctcg   92460
aaatctccaa aaatacctga ataatctca aacaccgcg aagacaagaa caaggtaaaa   92520
tcgagtgtaa aatgtgtaaa accaatgaga aatgacgaga ctcgacacca taatgggggt   92580
ataaatgtgc aatgacgctc atgtgtttga ttatggtttg tgtttcgctc ataatcttcc   92640
gactaaagat gagtcgggaa tcaaacacct aatagggca aatcatgggg attgtgtcat   92700
atctaactcc agcacagaac aaactaaacg gaccaagtcg aacaggttag caaagggttg   92760
taatgttggc ttagggttaa agtggatata tttgggaatg tggagctaag tagaggatag   92820
caagtgaccc taaacgaaac aaccacaaac atatcatcat aaaccaataa acatcatatc   92880
cacaaccata ataacccaat aatctcatga aagcacaaat gatctctatc ataaaacatt   92940
atcaaaaatc tgaaaactca ataaaatctc ataagcacat gtatctccaa gctcatctcc   93000
caaataaaat atcgatctcc tcactcatat aaatgtaagt gtataaaact caatgaagaa   93060
taagagagag gtctcctcaa gcataaaaca tgtatgaata atctcaataa taagcatggg   93120
aggaaatagg agaaaaataa tatgagctgg ataagaatga atagagtcat gaaaaccaac   93180
aaccaaaaac ataaccaata acccactaaa tcgctgtagc acacaacaaa ccccaccatc   93240
actaagctat cctctaggta agaaaaggga caatttggct catgtggagg ctaaacaatg   93300
tggctacaaa agaataggaa aaggcaaaaa cttggcttaa cctaaagtca aatttcatct   93360
agggtaggct atttggctat gtagctcaat tctagcgaac gtgttatcat ccctggctc   93420 aagaaaagcc gactacgctg gagaagaacc gacacaatac ttagatcccc taactagcac   93480
acagaatgaa tggaactcgc aaggagtcca agaaggctca atcctcacag gctagtcgaa   93540
atgcgcctct aaaggtagtc atccaagcca ccaaccaagc aaacccagtt cccccaagct   93600
atgtggaaaa atagtcagac tctaggtccc aaaacaggca caaggctaag gaaatacgag   93660
tttgcataag atcagaccac agaagaacac accagaagct cgcatgctag tttcacaact   93720
caaccatctt atagaaaact aaacatgaat atgaaatata tacactatat catgaatgca   93780
agatgagtat gcaaaatata tacaaaaaat atatatgcaa tgaactaaac tataactaca   93840
tgaaactaaa tgcacaaaca agcgggtgga agtgacaatg gagttgacca tccctccccc   93900
aagctaaagc tttgctagtc tctaacaaag aaaaagagaa gagaaagata aaacattaag   93960
aaacatggtc aacaagattg tcgcgacgcc caacacaaac acaagctagc caaaagaga   94020
```

```
gaaaaaggtc atacctaggc agtggcggac ccaggaattt caaactgggg gtacaaaaca   94080
cgaacgtcat acagtggcgg acccaggaat tccaaacgag gtcttgccat cgaatctcac   94140
ctagccctcc cctcccatca acctacccca tattaaaaat aaataaaaat aaaaataaaa   94200
atacttgcgc tgggcagtca tgtgacactt gaaggaatga accctaatca actcaaagtc   94260
tctagcatca caaacgatgg gcgaaaattt tttcaaatat tctgaccaac tcatgcaagt   94320
caattgtgaa aaattcaaag ataatgttgt catctaaaga ttttttaaat aaaaatagaa   94380
aaattcaaga aaaattttat gtgagagatc gggaacatat aaacaattat ttaaactcaa   94440
gttttccgac aaggaaattt ttcccgctcc tctaacttta atttcttccc cgttagcggt   94500
tttaatcaaa attttagtcg gtttctcata cgtgacgaaa tcatcgggat catatgacat   94560
ggtatccgtc gctccgcaat cgaaaatcca actaaaatta ctcatatggc gtgtgacatt   94620
ggaattaaag ttagagtggc ccttcttttg accataagcc acgtgcccct ctttattcat   94680
tgaggggtca cattctgctt cttttgtccc atcatcatag catacatctt ccccataaat   94740
taaagtagta ggggtaataa catgtttaga attagttggt tttaaaattt caatatcatc   94800
ttcaataaat tgtacctaga gtaaataaac aataaaagac aggtacaatt aatttattag   94860
taaattcaat aattagccaa attgtaggaa tgtcaagagt cttgacaatt gattcgtcat   94920
aggagtatat ttttacagac acacaaaacc aaaagccaaa ttgtagtaat gtcaagagtc   94980
ttgacgattg gttcgtcaat cgtcttatat tacactcatc aaagcaaaag cccgtctctt   95040
tacttgaaga aataggaaag taattgaaga gaaatggatc ggggttcgag aacatgttgg   95100
gtttctgtct caaagagac gtttgagtga gataactcac tctcctcttc atcttccatt   95160
ttaattaaat tagggatctg acctgggttg tcttcattct caccatggtt gccggtggtg   95220
ttttgggtta cagaaaaacc gatggctgct cttccttctt tactttgatc tgacctgggt   95280
tgtcttcact ctcctcttca tcttccattt tttttttatt ttttttttct gaattttttt   95340
ttcaaactgg gggtacaact gtaccccctt gtcacttaat tgggtccgcc catgtaatag   95400
acaggtacaa ttaatttatt agtaaattca ataattagcc aaattgtagg aatgtcaaga   95460
gtcttgacaa ttgattcgtc ataggagtat attttttacag acacacaaaa ccaaaagcca   95520
aattgtagta atgtcaagag tcttgacgat tggttcgtca atcgtcttat attatacact   95580
catcaaagca aaagctcgtc tctttactcg aaaaaatagg aaagtaattg aagagaaatg   95640
gatcggggtt cgagaacatg ttgggttct gtctcaaaag agacgttctc tgcaccaaga   95700
ttacactaat tagcctaaat ccaacatgag tacaaattat acccaaaaaa ggtttttcac   95760
agacataaac ataatggcaa tggggttatg gaatgttgtt gtagacataa gctatcattc   95820
atccttctag atcaacagaa atatcaaaca tcaaacttac catcattggc attgagctcc   95880
agccgacttt cagagttact tgacgtctca tggatactat gggtgtcaac atgagaaacc   95940
tcagcaatat cacaaggcag gtcacctgat tcgtcgtctg cgactgcatc cattttccgc   96000
tctccagcaa catttttccag tcctgtacta tttccagaat ctatttcaat gtcaatttgc   96060
tcttgtgggg catattctag agacgcttca atactcttg caccatttttс aatttcactt   96120 aaaggatggg attccaccag aacagctgaa tggatgtagt tcattggctc tgtgtccttt   96180
gaactggtat actcgacaag attttttctta tcaacactat cagttgtatc atgcatctca   96240
ttaaccaaat cttttgatgt tgttccctct acctcaacct cctgacttgg agttgtgcaa   96300
tgatttatac atgtactaga cattcgtgtt gctatcttgg tttgtctttg aagagaata   96360 aaggtgtgta attatgttca acaagaattt ttttacatac ttttttcttg catttttttt   96420
```

```
tgactttag ttttgtttt gatggatgtt ggcttcactt gagaattttt gtgccaattt    96480
ttccatgttt tacttgcttt taggcagtca atatggtcgg tatgtgaaag gactccactc    96540
atttagtttt cttgctcatg tggtgttatg ttctgcacag gaacaagatg ccgcaagctt    96600
ccaagtaagc cacctcataa tcgtatggta tgttgtgtaa tttgcaaatg tgatgtggcc    96660
cttcttttga ccataagcca cgtgcccctc tttattcatt gagggtcac attctgcttc    96720 ttttgtccca tcatcatagc atacatcttc cccataaatt aaagtagtag gggtaataac    96780
atgtttagaa ttagttggtt ttaaaatttc aatatcatct tcaataaatt gtacctaggg    96840
taaataaaca ataaaagaca ggtacaatta atttattagt aaattcaata attagccaaa    96900
ttgtaggaat gtcaagagtc ttgacaattg attcgtcata ggagtatatt tttacagaca    96960
cacaaaacca aaagccaaat tgtagtaatg tcaagagtct tgacgattgg ttcgtcaatc    97020
gtcttatatt acactcatca aagcaaaagc ccgtctcttt acttgaagaa ataggaaagt    97080
aattgaagag aaatggatcg gggttcgaga acatgttggg tttctgtctc aaaagagacg    97140
tttgagtgag ataactcact cttagaggtg ttcattcggg tcatcgggtc agtttcagac    97200
gggtgtaatt cgaatcagta aattttcggt tgtatgcagc aacgggtcat actcgggtca    97260
gatcggttag ttacgggtcg gtttaacaat ggttgttcac gttatcgggt tcacgccggt    97320
ttgttatcgg ttgaaattcg agtcgcgtgc caatcgagct cgggttgtca tcggtctaaa    97380
attagttcgg ttttatcggg cacaaatcgg gttcgagctt tatttttcgg gtagttatcg    97440
gttacggaca actatggatc gggtcaatat cgaaataagt taatagttgg atttttaatt    97500
gatgtatatt attcatttac ttacaaaaac tattatttaa gtatttaagt atttaacaat    97560
gcatcatgtt gctacttttg acaatcgatt taatattaaa gctcgataat cgaaattcaa    97620
tctgtttgga taaattaaaa gactataaga ctaagactaa tcgaaactat cttatagaat    97680
atagactatt accatattac atacttaatc ttacaagtgt tattaactta ttgagtactc    97740
taacctaata ctctctccaa ttcagagtaa ttgtctcgat ttattattag gctagtaatt    97800
aaaatatatt aaatagaggg atatttatga aaattccaaa tgagacattt gttcttaatt    97860
aaagggagca taagctattc gaatatacat tactctatta ccctaattag cgatcgtatt    97920
tcaaagttta agaattgaaa cttattctaa taaagtgaat tagattaatc aagaaatatt    97980
cataactacc taatatgata ttatgtattt atacttatta gtgaccttga atactttaaa    98040
ctaataaatc tattacatta ataataatcg tatgtaattt aaagcttaat aatgctcgaa    98100
actagatcta attggagtta atgaaactaa tacaatctat cttatagaag tagttataga    98160
ctatcattga cagttaattc aacgttaata gtgatcttga atacttatac tctaaagtaa    98220
ttatgttgat caaattcata ataaaaatat ttaaatttg ataatacaat attactcaaa    98280
taaattactt tagataacta attgtccaat ttgataatac attactcaat tgatacatca    98340
attattctaa gtcgttggat ctttgtatat agacgtgtga gatcttacca tatcagcaat    98400
ccatgagttg tacttgcaca aaaggttatt ggttattaag aatagcacac ggatcaatat    98460
tctaaggcgt tggatttta atgcagaatg gccaagaaca ctcactcact cactcacagt    98520
ctcacacagc tatcacaaca caaaccctaa aaaatttatg tttgtttctt tcacttcttc    98580
tcccataatt gctgctggac gcctggagtc catcttctct gcgcctttt tacattctaa    98640 gccctcttta ttctgtgtgc ggcatattgt ccggtgtccc cttctccgca ctgaattttc    98700
tctccttttc aaagtcttta gcattaggta aatcctaaaa ccctaaattc atagtaattt    98760
```

```
ttaatgctta gttttttagt ttcatgttta ttaagttaca atctttatgt atgtttatac   98820
tttggatttg tatgtacatc agatttcgta tatcttgaag gaccatctat gtttttacat   98880
gaatttttta tggttttgaa ggaccatttt ttgtttaaac aaaaatgaaa agagatgaat   98940
gattgatcca taattcaaga ggttggtgga tttgaatcac gccattttt tttgattcta    99000 aaatgtataa ttgtgtttag ttgtgtcaat gttttgaca tgagaaatta ctatttaatg    99060
gtagttgcta ttttgttca tgatgaattg atgactacaa tgctaatatg gaaatcctta    99120
attagcttgc tcttggggtt tagttgtgtc aatgttttg acatgagaaa attggttcag    99180
gaggttgtta atagttatgt actctatccc attttagtt taagatacat ttcgtcctac    99240
tttctttaat ttacttattt caagatgtta agttaggtga taaatgtttt agatgtttga   99300
atcatacaga tttaatcttc cgtgacataa ttgcagtttc gaatatttta gaggcctgat   99360
tcatcaagtt gctaacgtct aagcttaaga taagtttagt agtttctata ctgatagtcg   99420
gtattacata gtaatgatta atgttgtttt tgaattact gtaacaagaa aaagagagtt    99480
gtatcctgtt aattgtctct gaacttcctt ttaatctaaa atgtaattag actttggggt   99540
aacttggcac ttttaaactg atttctttt gtgcctatta attgattgtt gaatacccat    99600
aagaagaaaa ttgtttttgt gattgagttg ttttcatgga ttaagtagtc atataatgag   99660
aattggataa aaataataga ctatatagtt ctatggatta agtagtcata tgatgatgat   99720
gatgactttg tttgttgtaa atgggttttg aaataattca ttgggttaat ttttaatact   99780
ttattggttt tgaaaatttg ctacaataaa ttaaggagct ttttggatga ggggttgata   99840
tgttgtcatt cttaattgga ggaagatgaa tgctaatgag gcaaatgaag ctaatggttt   99900
tgaatttgac aatatttcta acacaggtat tttgttaatc taatggttca agtaccttat   99960
aagttatatc aatatgtttt gtgtacttta tcattgtttg cgattgtgac aatattgaga  100020
tagattacta acatgtgtat tatatttatt gaaattaaca gcgtttgaag agttacaaat  100080
gattgaacaa caacgacaag atgagttact aagatcccaa caaactagtg catccactcc  100140
aaggaatgtg aacccgaacc ctagacaagt tgtccaacgt ccaattcgtc caccaaagcg  100200
tgcaaaaact agtagtggaa gaggtggagt ttctttagct ggaggtcgaa ggcgaactag  100260
aactgagttt caagaggata ttgtagggct tggaaagcgt acctcaccag tttgggatca  100320
ttttaccata gtgcctgaga aggatgataa cgatgttgtt atttcattac acgctgtttg  100380
tcgccattgt aagaatactg actatagagc tgaaggtcat tatggaacct ccaattgtag  100440
aaatcacctt aagagttgtg aaccttacca agaatggctt gctaaaaatg gtgatctcat  100500
tggtgatttt aaccagagaa aatattgttc tctgtttgca gaggccatta tgtaccatgg  100560
atatccctta agcatggttg agcacaaatt tacaaggaag ttgcatcgtt acttaaatcc  100620
aaaggtgaag aacatatcta gatccacaat tactcgatgg tgcatgagga aaaactctaa  100680
gttgaggaag atgttattcg aaactttaaa ggatttagat agcaaggtgt ctttgacatg  100740
tgacatttgg acagcttgca catctcgtgg atacttgact ttaacggctc attatattga  100800
caaagattgg tgtttgaagt cgaaagttct caattttgt catttccctc cccctccac   100860 tggtcatgcg atttatgagc ttgtttatgc aatgatcaag gattggggtc ttgaatcaaa  100920
ggttatgtgc atgactgttg acaatgcaac caataatgat tccatgatcc ccttgttaca  100980
agaatgttta aatggtcatt cgtctttcc atgtgatggt gcacattttc atattcgttg   101040
tgcggcgcat attttgaatt tgattgttaa agatggatta aaagcaattg atcccgctgt  101100
cacacttgtg cgtgataatg tcaagtacat tgattcatcc gaggcaagga tgaataggtt  101160
```

```
tagagatttt gtatctcaga tagaaaaacc ttcttcgcta aaattatggt tggatattgt   101220
aacgagatgg aactctacgt atctaatgtt gaagcgagct cttcactata gagttgcgat   101280
gaatcgcttt ggtagtatac tgagcctgac tacaccttca agctcactga tcgcgagtgg   101340
gaatcagttg aaaacatggc ttctattctt gaacctttct atgaaatgac taatcttttc   101400
tctgggtcag attatcccac tgcaaatcta tattttgaac aagtttgtaa ggcaaaatac   101460
catctgcgac gtgcttgtga aagtgaggat gcttgcatta gagagatggg aaattagatg   101520
tttgagaagt tggagaaata ttgggggag tcctctttaa ttttgtcgat tgctgcggtg    101580
tttgacccta ggcataaaat tccatatcta aacatcatt ttagaaaggt ttatcaatct    101640
gaggatgagg tttatcaaca aattgagaga gttcgcactg gacttgtcaa tcttttaat    101700 gattacaagt ctaaacttac tttatcgact aaagctcatc aagcttctgc atctgaagat   101760
cgggcatcag ttggtacatg ctctcgtgat tttgatggct atgaggtatg tattacttaa   101820
tttattatta ttaatattta tttcaatatg tttgtctttc cattataata tttataccat   101880
taacaagttt catatgtttt atcgtttttt tacagagttt tgaaagttct caagaagcac   101940 gttttcttc aaatattata tcagaagtgg aaaaatatct tgaatcacct ttgcacatgc     102000
atggtgattc caaatttgat attttgttgt attggaaaga ccaacaagct acttatccaa   102060
ttatgtctaa aatagctaaa gacatattgg ctatcccaat aaccacagtt gcatccgaat   102120 caacttttc tatgggagga agaatcttga atagatggag agcatcccctt ttatcaagac   102180 atgttgaagc cttgatttta actcgtaatt ggttgtttgg atatgaagaa gaacctgatg   102240
aagtaggatt aaatgttggc aatgacttag tccccgatgc agaatctcat gctaagggag   102300
atcagggtcc aagtggatcc tcatctttag aatctggtac gtattttatt tttaaaatta   102360
aggttagttg attatcaaat tttattataa ctcgtgtttt gtgtactta tgtactcagt    102420 tatgattgt tcacttgatt gttgccatcc aagtgatgtt ggttcttacg gatctgaatg    102480
tgagtcaaat tgaaacacgg aatctagaca caagtaattt aaccttacaa gccacgtgga   102540
aacttgatag ccatttgggt tgggtgaatg ttatccatga gtcttagtct tataggcaac   102600
tttctaatag ccttatttac ttgggactag gcaattagag atgtttcctt tgctatgatt   102660
catgttggta gctttgcctg agtctttcat aacgtttcct tgctgaaaat gcgacgattg   102720
ttgaccttga gaggcattac aatgatctca ctggagttgg aacttgatat tccggtagca   102780
aagttttagg cgtttatttt tttatctttc ttataagatt taattatttt cttttaatac   102840
ttttttgttt gtttttgttc aagattgaaa tgttgtacca caagctaagc agcagtacgt   102900
gagagatttt ggtgctggtt gtcgactttt atgtttcatt ttggagaaag tgttttgtgg   102960
tggacatact cacgtacatc tggtggatga cacttttgtg gtggatatat agctatttat   103020
agttgttgat tgaatgctaa ttttttgggt taagacttga tatttgtata tttaaatttg   103080
atggatgtat aagggatgta aattttgg gttaaaactt aatatttgta tatttgaatt     103140
aggtggatgt ataagtgatg gatgtaaatt tttggggttt aatgcttgaa caattggtgg   103200
attactaaca tgaaatatgt aattagcaat agaaaccaag aaaagtctag gtggaagtgt   103260
tgaagaaact atcaagtttt tgtattgttc cacttcaata tgtttctaag gttttttgtaa  103320 tgtgcttatt ggtttatagt ggatatcaat atcaagggaa atcttattta tttatagata   103380
atcttgttta caaagctaaa aataggtgaa aaattgattc ggatttataa cagttcgatt   103440
aatattcggt tcgggtctgt atcagttcgg gtaataaaca gttcgatctt aatcggtttt   103500
```

```
agtcgggttg cactcggttt cgtgcataaa tcaggtcgga tttagctcgg gtcgatcact 103560
gttgcgttcg ggtaacattt gttaatgttt atatgtcggt tataaaattc ggttgcagtt 103620
cgagttcaga tttcccattt tcggttgtca atcggttcgg gtacaacttc ggttcgggta 103680
ttaccggttc gataaaccta aaaaaggatc acattttcgg gtcggtttag tttcagtttc 103740
gggtcggatt ttcgggtcgg gtcgcttttg gacagctcta ctcactctcc tcttcatctt 103800
ccattttaat taaattaggg atctgacctg ggttgtcttc attctcacca tggttgccgg 103860
tggtgttttg ggttacagaa aaaccgatgg ctgctcttcc ttctttactt tgatctaacc 103920
tgggttgtct tcactctcct cttcatcttc catttttttt attttttatt ttctgaattt 103980
tttttcaaac tgggggtaca attgtacccc cttgtcactt aattgggtcc gcccatgtaa 104040
tagacaggta caattaattt attagtaaat tcaataatta gccaaattgt aggaatgtca 104100
agagtcttga caattgattc gtcataggag tatattttta cagacacaca aaaccaaaag 104160
ccaaattgta gtaatgtcaa gagtcttgac gattggttcg tcaatcgtct tatattatac 104220
actcatcaaa gcaaaagccc gtctctttac tcgaaaaaat aggaaagtaa ttgaagagaa 104280
atggatcggg gttcgagaac atgttcggtt tcaatagaga cgttctctgc accaagatta 104340
cactaattag cctaaatcca acatgagtac aaattatacc caaaaaaggt ttttcacaga 104400
cataaacata atggcaatgg ggttatggaa tgttgttgta gacataagct atcattcatc 104460
cttctagatc aacagaaata tcaaacatca aacttatcat tggcattgag ctccagccga 104520
ctttcagagt tacttgacgt ctcatggata ctatgggtgt caacatgaga acctcagca 104580 atatcacaag gcaggtcacc tgattcgtcg tctgcgactg catccatttt ccgctctcca 104640
gcaacatttt ccagtcctgt actatttcca gaatccattt caatgtcaat ttgctcttgt 104700
ggggcatatt ctagagacgc ttcaaatact cttgcaccat tttcaattta acttaaagga 104760
tgggattcca ccagaacagc tgaatggatg tagttcattg gctctgtgtc ctttgaactg 104820
gtatactcga caagattttt cttatcaaca ctatcagttg tatcatgcat ctcattaacc 104880
aaatcttttg atgttgttcc ctctacctca acctcctgac ttggagttgt gcaatgattt 104940
atacatgtac tagacattcg tgttgctatc ttggtttgtc tttggaagag aataaaggtg 105000
tgtaattatg ttcaacaaga attttttttac atacttttttc ttgcatttttt ttttgacttt 105060 tagtttttgt tttgatggat gttggcttca cttgagaatt tttgtgccaa ttttccatg 105120 ttttacttgc ttttaggcag tcaatatggt cggtatgtga aaggactcga ctcatttagt 105180
tttcttgctc atgtggtgtt atgttctgca caggaacaag atgccgcaag cttccaagta 105240
agccacctca taatcgtatg gtatgttgtg taatttgcaa atgtggccct tcttttgacc 105300
ataaaccacg tgcccctctt tattcattga ggggtcacat tctgcttctt ttgtcccatc 105360
atcatagcat acatcttccc cataaattaa agtagtaggg gtaataacat gtttagaatt 105420
agttggtttt aaaatttcaa tatcatcttc aataaattgt acctagggta aataaacaat 105480
aaaagacagg tacaattaat ttattagtaa attcaataat tagccaaatt gtaggaatgt 105540
caagagtctt gacaattgat tcgtcatagg agtatatttt tacagacaca caaaaccaaa 105600
agccaaattg tagtaatgtc aagagtcttg acgattggtt cgtcaatcgt cttatattac 105660
actcatcaaa gcaaaagccc gtctctttac ttgaagaaat aggaaagtaa ttgaagagaa 105720
atggatcggg gttcgagaac atgttgggtt tctgtctcaa aagagacgtt tgagtgagat 105780
aactcactct cctcttcatc ttccatttta attaaattag ggatctgacc tgggttgtct 105840
tcattctcac catggttgcc ggtggtgttt tgggttacag aaaaaccgat ggctgctctt 105900
```

```
ccttctttac tttgatctga cctgggttgt cttcactctc ctcttcatct tccattttt   105960
tttattttt  tttctgaatt ttttttcaa  actggggta  caactgtacc cccttgtcac   106020
ttaattgggt ccgcccatgt aatagacagg tacaattaat ttattagtaa attcaataat   106080
tagccaaatt gtaggaatgt caagagtctt gacaattgat tcgttatagg agtatatttt   106140
tacagacaca caaaaccaaa agccaaattg tagtaatgtc aagagtcttg acgattggtt   106200
cgtcaatcgt cttatattat acactcatca aagcaaaagc ccgtctcttt actcgaaaaa   106260
ataggaaagt aattgaagag aaatggatcg gggttcgaga acatgttggg tttctgtctc   106320
aaaagagacg ttctctgcac caagattaca ctaattagcc taaatccaac atgagtacaa   106380
attatacccca aaaaggttt  ttcacagaca taaacataat ggcaatgggg ttatggaatg   106440
ttgttgtaga cataagctat cattcatcct tctagatcaa cagaaatatc aaacatcaaa   106500
cttaccatca ttggcattga gctccagccg actttcagag ttacttgacg tctcatggat   106560
actatgggtg tcaacatgag aaacctcagc aatatcacaa ggcaggtcac ctgattcgtc   106620
gtctgcgact gcatccattt tccgctctcc agcaacattt tccagtcctg tactatttcc   106680
agaatccatt tcaatgtcaa tttgctcttg tggggcatat tctagagacg cttcaaatac   106740
tcttgcacca ttttcaattt cacttaaagg atgggattcc accagaacag ctgaatggat   106800
gtagttcatt ggctctgtgt cctttgaact ggtatactcg acaagatttt tcttatcaac   106860
actatcagtt gtatcatgca tctcattaac caaatctttt gatgttgttc cctctacctc   106920
aacctcctga cttggagttg tgcaatgatt tatacatgta ctagacattc gtgttgctat   106980
cttggtttgt cttttggaaga gaataaaggt gtgtaattat gttcaacaag aatttttta   107040
catacttttt tcttgcattt ttttttttga cttttagttt ttgttttgat ggatgttggc   107100
ttcacttgag aattttttgtg ccaattttttc catgttttac ttgcttttag gcagtcaata   107160
tggtcggtat gtgaaaggac tcgactcatt tagttttctt gctcatgtgg tgttatgttc   107220
tgcacaggaa caagatgccg caagcttcca agtaagccac ctcatattcg tatggtatgt   107280
tgtgtaattt gcaaatgtga tgtggccctt cttttgacca taagccacgt gccctctttt  107340
attcattgag gggtcacatt ctgcttcttt tgtcccatca tcatagcata catcttcccc   107400
ataaattaaa gtagtagggg taataacatg tttagaatta gttggtttta aaatttcaat   107460
atcatcttca ataaattgta cctagggtaa ataaacaata aaagacaggt acaattaatt   107520
tattagtaaa ttcaataatt agccaaattg taggaatgtc aagagtcttg acaattgatt   107580
cgtcatagga atatattttt acagacacac aaaaccaaag ccaaattgta gtaatgtcaa   107640
gagtcttgac gattggttcg tcaatcgtct tatattacac tcatcaaagc aaaagcccgt   107700
ctctttactt gaagaaatag gaagtaatt  gaaatgaat  ggatcgggt  tcgagaacat   107760
gttgggtttc tgtctcaaaa gagacgtttg agtgagataa ctcactctcc tcttcatctt   107820
ccatttaat  taaattaggg atctgacctg gttgtcttc  attctcacca tggttgccgg   107880
tggtgttttg ggttacagaa aaaccgatgg ttgctcttcc ttctttactt tgatctgaca   107940
tgggttgtct tcactctcct cttcatcttc cattttttt  ttattttttt ttctgaattt   108000
tttttcaaac tggggtaca  actgtacccc cttgtcactt aattgggtcc gcccatgtaa   108060
tagacaggta caattaattt attagtaaat tcaataatta gccaaattgt aggaatgtca   108120
agagtcttga caattgattc gtcataggag tatatttta  cagacacaca aaaccaaaag   108180
ccaaattgta gtaatgtcaa gagtcttgac gattggttcg tcaatcgtct tatattatac   108240
```

```
actcatcaaa gcaaaagccc gtctctttac tcgaaaaaat aggaaagtaa ttgaagagaa 108300
atggatcggg gttcgagaac atgttgggtt tctgtctcaa aagagacgtt ctctgcacca 108360
agattacact aattagccta aatccaacat gagtacaaat tatacccaaa aaggttttt  108420 cacagacata aacataatgg caatgggggt atggaatgtt gttgtagaca taagctatca 108480
ttcatccttc tagatcaaca gaaatatcaa acatcaaact taccatcatt ggcattgagc 108540
tccagccgac tttcagagtt acttgacgtc tcatggatac tatgggtgtc aacatgagaa 108600
acctcagcaa tatcacaagg caggtcacct gattcgtcgt ctgcgactgc atccattttc 108660
cgctctccag caacattttc cagtcctgta ctatttccag aatccatttc actgtcaatt 108720
tgctcttgtg gggcatattc tagagacgct tcaaatactc ttgcaccatt ttcaatttca 108780
cttaaaggat gggattccac cagaacagct gaatggatgt agttcattgg ctctgtgtcc 108840
tttgaactgg tatactcgac aagattttc  ttatcaacac tatcagttgt atcatgcatc 108900
tcattaacca aatcttttaa tgttgttccc tctacctcaa cctcctgact tggagttgtg 108960
caatgattta tacatgtact agacattcgt gttgctatct tggtttgtct ttggaagaga 109020
ataaaggtgt gtaattatgt tcaacaagaa ttttttttaca tactttttc  ttgcatttt  109080 tttttgactt ttagttttg  ttttgatgga tgttggcttc acttgagaat ttttgtgcca 109140 attttttccat gttttacttg cttttaggca gtcaatatgg tcggtatgtg aaaggactcg 109200
actcatttag ttttcttgct catgtggtgt tatgttctgc acaggaacaa gatgccgcaa 109260
gcttccaagt aagccacctc ataatcgtat ggtaagttgt gtaatttgca aatgtgatgt 109320
ggcccttctt ttgaccataa gccacgtgcc cctctttatt cattgagggg tcacattctg 109380
cttcttttgt cccatcatca tagcatacat cttccccata aattaaagta gtaggggtaa 109440
taacatgttt agaattagtt ggttttaaaa tttcaatatc atcttcaata aattgtacct 109500
agggtaaata aacaataaaa gacaggtaca attaatttat tagtaaatgc aataattagc 109560
caaattgtag gaatgtcaag agtcttgaca attgattcgt cataggagta tattttaca  109620 gacacacaaa accaaaagcc aaattgtagt aatgtcaaga gtcttgacga ttggttcgtc 109680
aatcgtctta tattacactc atcaaagcaa agcccgtct  ctttacttga agaaatagga 109740
aagtaattga agagaaatgg atcggggttc gagaacatgt tgggtttctg tctcaaaaga 109800
gacgtttgag tgagataact cactctcctc ttcatcttcc attttaatta aattaggggat 109860 ctgacctggg ttgtcttcat tctcaccatg gttgccggtg gtgttttggg ttacagaaaa 109920
accgatggtt gctcttcctt ctttactttg atctgacctg ggttgtcttc actctcctct 109980
tcatcttcca tttttttta ttttttttt ctgaattttt tttcaaactg ggggtacaac 110040 tgtacccct  tgtcacttaa ttgggtccgc ccatgtaata gacaggtaca attaatttat 110100
tagtaaattc aataattagc caaattgtag gaatgtcaag agtcttgaca attgattcgt 110160
cataggagta tattttaca gacacacaaa accaaaagcc aaattgtagt aatgtcaaga 110220
gtcttgacga ttggttcgtc aatcgtctta tattatacac tcatcaaagc aaaagcccgt 110280
ctctttactc gaaaaaatag gaaagtaatt gaagagaaat ggatcggggt tcgagaacat 110340
gttgggtttc tgtctcaaaa gagacgttct ctgcaccaag attacactaa ttagcctaaa 110400
tccaacatga gtacaaatta tacccaaaaa aggttttca cagacataaa cataatggca 110460 atgggggttat ggaatgttgt tgtagacata agctatcatt catccttcta gatcaacaga 110520
aatatcaaac atcaaactta ccatcattgg cattgagctc cagccgactt tcagagttac 110580
ttgacgtctc atagatacta tgggtgtcaa catgagaaac ctcagcaata tcacaaggca 110640
```

```
ggtcacctga ttcgtcgtct gcgactgcat ccattttccg ctctccggca acattttcca   110700
gtcctgtact atttccagaa tccatttcac tgtcaatttg ctcttgtggg gcatattcta   110760
gagacgcttc aaatactctt gcaccatttt caatttcact taaaggatgg gattccacca   110820
gaacagctga atggatgtag ttcattggct ctgtgtcctt tgaactggta tactcgacaa   110880
gattttctct atcaacacta tcagttgtat catgcatctc attaaccaaa tcttttgatg   110940
ttgttccctc tacctcaacc tcctgacttg gagttgtgca atgatttata catgtactag   111000
acattcgtgt tgctatcttg gtttgtcttt ggaagagaat aaaggtgtgt aattatgttc   111060
aacaagaatt tttttacata ctttttttctt gcatttttttt tttgactttt agttttttgtt 111120
ttgatggatg ttggcttcac ttgagaattt ttgtgccaat ttttccatgt tttacttgct   111180
tttaggcagt caatatggtc ggtatgtgaa aggactcgac tcatttagtt ttcttgctca   111240
tgtggtgtta tgttctgcac aggaacaaga tgccgcaagc ttccaagtaa gccacctcat   111300
aatcgtatgg tatgttgtgt aatttgcaaa tgtgatgtgg cccttctttt gaccataagc   111360
cacgtgcccc tctatattca ttgaggggtc acattctgct tcttttgtcc catcatcata   111420
gcatacatct tccccataaa ttaaagtagt aggggtaata acatgtttag aattagttgg   111480
ttttaaaatt tcaatatcat cttcaataaa ttgtacctag ggtaaataaa caataaaaga   111540
caggtacaat taatttatta gtaaattcaa taactagcca aattgtagga atgtcaagag   111600
tcttgacaat tgattcgtca taggagtata tttttacaga cacacaaaac caaaagccaa   111660
attgtagtaa tgtcaagagt cttgacgatt ggttcgtcaa tcgtcttata ttacactcat   111720
caaagcaaaa gcccgtctct ttacttgaag aaataggaaa gtaattgaag agaaatggat   111780
cggggttcga aacatgttg ggtttctgtc tcaaaagaga cgtttgagtg agataactca   111840
ctctcctctt catcttccat tttaattaaa ttagggatct gacctgggtt gtcttcattc   111900
tcaccatggt tgccggtggt gttttgggtt acagaaaaac cgatggctgc tcttccttct   111960
ttactttgat ctgacctggg ttgtcttcac tctcctcttc atcttccatt tttttatttt   112020
tttttttctga atttttttttt caaactgggg gtacaactgt accccttgt cacttaattg   112080
ggtccgccat gtaatagaca ggtacaatta atttattagt aaattcaata attagccaaa   112140
ttgtagtaat gtcaagagtc ttgacaattg attcgttata ggagtatatt tttacagaca   112200
cacaaaacca aaagccaaat tgtagtaatg tcaagagtct tgacgattgg ttcgtcaatc   112260
gtcttatatt atacactcat caaagcaaaa gcccgtctct ttactcgaaa aaataggaaa   112320
gtaattgaag agaaatggat cggggttcga aacatgttg ggtttctgtc tcaaaagaga   112380
cgttctctgc accaagatta cactaattag cctaaatcca acatgagtac aaattatacc   112440
caaaaaaggt ttttcacaga cataaacata atggcaatgg ggttatggaa tgttgttgta   112500
gacataagct atcattcatc cttctagatc aacagaaata tcaaacatca aacttaccat   112560
cattggcatt gagctccagc cgactttcag agttacttga cgtctcatgg atactatggg   112620
tgtcaacatg agaaacctca gcaatatcac aaggcaggtc acctgattcg tcgtctgcga   112680
ctgcatccat tttccgctct ccagcaacat tttccagtcc tgtactattt ccagaatcca   112740
tttcaatgtc aatttgctct tgtgggggcat attctagaga cgcttcaaat actcttgcac   112800
cattttcaat ttcacttaaa ggatgagatt ccaccagaac agctgaatgg atgtagttca   112860
ttggctctgt gtcctttgaa ctggtatact cgacaagatt tttcttatca acactatcag   112920
ttgtatcatg catctcatta accaaatctt tgatgttgt tccctctacc tcaacctcct   112980
```

```
gacttggagt tgtgcaatga tttatacatg tactagacat tcgtgttgct atcttggttt    113040
gtctttggaa gagaataaag gtgtgtaatt atgttcaaca agaatttttt tacatacttt    113100
ttcttgcatt ttttttgac ttttagtttt tgttttgatg gatgttggct tcacttgaga     113160 attttgtgc caattttcc atgttttact tgctttagg cagtcaatat ggtcggtatg       113220
tgaaaggact cgactcattt agttttcttg ctcatgtggt gttatgttct gcacaggaac    113280
aagatgccgc aagcttccaa gtaagccacc tcataatcgt atggtatgtt gtgtaatttg    113340
caaatgtgat gtggcccttc ttttgaccat aagccacgtg cccctctata ttcattgagg    113400
ggtcacattc tgcttctttt gtcccatcat catagcatac atcttcccca taaattaaag    113460
tagtaggggt aataacatgt ttagaattag ttggttttaa aatttcaatg tcatcttcaa    113520
taaattgtac ctagggtaaa taaacaataa aagacaggta caattaattt attagtaaat    113580
tcaataacta gccaaattgt aggaatgtca agagtcttga caattgattc gtcataggag    113640
tatattttta cagacacaca aaaccaaaag ccaaattgta gtaatgtcaa gagtcttgac    113700
gattggttcg tcaatcgtct tatattacac tcatcaaagc aaaagcccgt ctctttactt    113760
gaagaaatag gaaagtaatt gaagagaaat ggatcggggt tcgagaacat gttgggtttc    113820
tgtctcaaaa gagacgtttg agtgagataa ctcactctcc tcttcatctt ccatttaat    113880 taaattaggg atctgacctg ggttgtcttc attctcacca tggttgccgg tggtgttttg    113940
ggttacagaa aaaccgatgg ctgctcttcc ttctttactt tgatctgacc tgggttgtct    114000
tcactctcct cttcatcttc catttttttt atttttttt ctgaattttt tttcaaactg     114060
ggggtacaac tgtaccccct tgtcacttaa ttgggtccgc ccatgtaata gacaggtaca    114120
attaatttat tagtaaattc aataattagc caaattgtag taatgtcaag agtcttgaca    114180
attgattcgt tataggagta tattttaca gacacacaaa accaaaagcc aaattgtagt     114240
aatgtcaaga gtcttgacga ttggttcgtc aatcgtctta tattatacac tcatcaaagc    114300
aaaagcccgt ctctttactc gaaaaaatag gaaagtaatt gaagagaaat ggatcggggt    114360
tcgagaacat gttgggtttc tgtctcaaaa gagacgttct ctgcaccaag attacactaa    114420
ttagcctaaa tccaacatga gtacaaatta tacccaaaaa aggttttca cagacataaa     114480 cataatggca atggggttat ggaatgttgt tgtagacata agctatcatt catccttcta    114540
gatcaacaga aatatcaaac atcaaactta ccatcattgg cattgagctc cagccgacttt   114600 tcagagttac ttgacgtctc atggatacta tgggtgtcaa catgagaaac ctcagcaata    114660
tcacaaggca ggtcacctga ttcgtcgtct gcgactgcat ccattttccg ctctccagca    114720
acattttcca gtcctgtact atttccagaa tccatttcaa tgtcaatttg ctcttgtggg    114780
gcatattcta gagacgcttc aaatactctt gcaccatttt caatttcact taaaggatga    114840
gattccacca gaacagctga atggatgtag ttcattggct ctgtgtcctt tgaactggta    114900
tactcgacaa gattttcttt atcaacacta tcagttgtat catgcatctc attaaccaaa    114960
tcttttgatg ttgttccctc tacctcaacc tcctgacttg gagttgtgca atgatttata    115020
catgtactag acattcgtgt tgctatcttg gtttgtcttt ggaagagaat aaaggtgtgt    115080
aattatgttc aacaagaatt ttttacatac ttttttcttg cattttttttt tgactttag    115140 tttttgtttt gatggatgtt ggcttcactt gagaattttt gtgccaattt ttccatgttt    115200
tacttgcttt taggcagtca atatggtcgg tatgtgaaag gactcgactc atttagtttt    115260
cttgctcatg tggtgttatg ttctgcacag gaacaagatg ccgcaagctt ccaagtaagc    115320
cacctcataa tcgtatggta tgttgtgtaa tttgcaaatg tgatgtggcc cttcttttga    115380
```

```
ccataagcca cgtgcccctc tttattcatt gaggggtcac attctgcttc ttttgtccca   115440
tcatcatagc atacatcttc cccataaatt aaagtagtag gggtaataac atgtttagaa   115500
ttagttggtt ttaaaatttc aatgtcatct tcaataaatt gtacctaggg taaataaaca   115560
ataaaagaca ggtacaatta atttattagt aaattcaata attagccaaa ttgtaggaat   115620
gtcaagagtc ttgacaattg attcgtcata ggagtatatt tttacagaca cacaaaacca   115680
aaagccaaat tgtagtaatg tcaagagtct tgacgattgg ttcgtcaatc gtcatatatt   115740
acactcatca aagcaaaagc ccgtctcttt acttgaagaa ataggaaagt aattgaagag   115800
aaatggatcg gggttcgaga acatgttggg tttctgtctc aaaagagacg tttgagtgag   115860
ataactcact ctcctcttca tcttccattt taattaaatt agggatctga cctgggttgt   115920
cttcattctc accatggttg ccggtggtgt tttgggttac agaaaaaccg atggctgctc   115980
ttccttcttt actttgatct gacctgggtt gtcttcactc tcctcttcat cttccatttt   116040 tttattttt ttttctgaat ttttttttcaa actgggggta caactgtacc cccttgtcac   116100
ttaattgggt ccgcccatgt aatagacagg tacaattaat ttattagtaa attcaataat   116160
tagccaaatt gtaggaatgt caagagtctt gacaattgat tcgtcatagg agtatatttt   116220
tacagacaca caaaaccaaa agccaaattg tagtaatgtc aagagtcttg acgattggtt   116280
cgtcaatcgt cttatattat acactcatca aagcaaaagc ccgtcttttt actcgaaaaa   116340
ataggaaagt aattgaagag aaatggatcg gggttcgaga acatgttggg tttctgtctc   116400
aaaagagacg ttctctgcac caagattaca ctaattagcc taaatccaac atgagtacaa   116460
attataccca aaaaaggttt ttcacagaca taaacataat ggcaatgggg ttattgaatg   116520
ttgttgtaga cataagctat cattcatcct tctagatcaa cagaaatatc aaacatcaaa   116580
cttaccatca ttggcattga gctccagccg actttcagag ttacttgacg tctcatggat   116640
actatgggtg tcaacatgag aaacctcagc aatatcacaa ggcaggtcac ctgattcgtc   116700
gtctgcgact gcatccattt tccgctctcc agcaacattt tccagtcctg tactatttcc   116760
agaatccatt tcaatgtcaa tttgctcttg tggggcatat tctagagacg cttcaaatac   116820
tcttgcacca tttccaattt cacttaaagg atgggattcc accagaacag ctgaatggat   116880
gtagttcatt ggctctgtgt cctttgaact ggtatactcg acaagatttt tcttatcaac   116940
actatcagtt gtatcatgca tctcattaac caaatctttt gatgttgttc cctctacctc   117000
aacctcctga cttggagttg tgcaatgatt tatacatgta ctagacattc gtgttgctat   117060
cttggtttgt ctttggaaga gaataaaggt gtgtaattat gttcaacaag aattttttta   117120 catactttt tcttgcattt tttttgactt ttagttttg ttttgatgga tgttggcttc   117180
acttgagaat ttttgtgcca atttttccat gttttacttg cttttaggca gtcaatatgg   117240
tcggtatgtg aaaggactcg actcatttag ttttcttgct catgtggtgt tatgttctgc   117300
acaggaacaa gatgccgcaa gcttccaagt aagccacctc ataatcgtat ggtatgttgt   117360
gtaatttgca aatgtgattg tacaatctga ttagtggtat ttgatacata attgtttgtg   117420
caacaacagt caatatttgt ttctcaagca ctattttggc aataacaatt gagaatgaaa   117480
tttgatatgt tggatcattg aaattcaaga attgtaatat aatgaggttt tcaacgcaat   117540
ataaatcatt ttttaatgct agcaattgaa atggggattt agtttgatgg attttgtcac   117600
cagtcctgga tcccttaaga gcccttcaag acatacttaa gactgccgct tcaataccat   117660
aattttcact ccataaccac attacactct ttcaatacca gctattgcta ttgctaatat   117720
```

```
gcttctccta cctaccacta ccagtatctg taattccata tcatatccat gtacacgttg   117780
gacacagaat attgaatcat cctcatatta tttttacaaa aactagacat tgtatcagat   117840
gctgtacaac ttacaattac cacattaaac caatttgacc agaattactt catatattgg   117900
attggattga tgcaaaagct cctgaatcca attctataaa cattctcatt ctggattaca   117960
cgaaggtaac caagtgctta cattcacaag atttcacctc tcccatcaaa ttttttgaaat  118020 tcgtcctttc aatcatttat catacaaaca tgcaaaagga atacacgaaa ctaccacttc   118080
catatcaaat ttgtacagac ccagaggcta tattcaaacg ccgagggtgt aacgatgtca   118140
aaacatatgc aaaaaggata tcatgcaact caaaccagtc catcttttcc aataaacgtt   118200
aactggacac cgagcacctc taacacaaaa ttaactttaa cttttctatg tcctgtttgt   118260
gcccctagct caaccatcaa aaatgtcact cctatatttg tatgtatttt gattgttgag   118320
ctaggcgcac aaaccagctt agacaaggac acaaaaagtt tgaattaatt ttgtgtgtta   118380
gacttaaggt gctcagtgtc ctgtacctgt aaagagctcg tgctcttcat ttaccatatt   118440
acatacatga ttttaagtca agcgtatgtc ccagtagcta acagtggatt tattaaatat  118500
atatcaccaa ttgacaccag attttgtcat aaactccaaa caaataagtt gatctttcaa   118560
cagatgttaa agcttacagc tacatatagt caaacccata ttagcaatag aaataggtgt   118620
tgttaattgt tattcggtta gtaaagaaag ctaaagtagt gaaaaggtta ggtttagtta   118680
tgcagagttt gtgttgtgtt tggcttctga ttagaatagt ggtttgctct caattctttt   118740
catcagaatc atcattcatc actatatatt gagtccaggt aactaactaa atttcattaa   118800 ggattaaaact tcgtgaaagc cctaaattgc tacatgtacc atgttgcacc atcagatatt  118860
ttgctaccca ttgcttagcc taaatgaggt ccttccttcg tattgaattt tgcaccatca   118920
gatttctatt ttttgttagc tttgttgctt attttttagtg ttatttcatc ctaatttata   118980
aagttgaatg aatatcacgt tgaatagata tctcatttga tatgaacgct taaagttgaa   119040
caaggttgga actttgattg attatgcatt ttaatcttga ctttgaaaga ctcataaaaa   119100
tgatgaggca tgaatgtgat aattactgat ttaatatgca ttctggcctt agcagcaatt   119160
aaagaggtgg gaattgttga gcagtaatac aacacttata gatttgacct ttacaacaat   119220
tttatcaatg taaatttgaa agtgtatgtg tggagataat taagcattaa aaatatccgg   119280
catgttacag aaatcatagt gtttctctca accctcactt atagactact gcaactgccc   119340
tcatattata aaatttttcaa cttgcaatat attgcaatgg agaatgaata cggcccatat  119400
tagatttggg ttaaagtaaa gctatgaatc atagactaaa accacacaaa taagctgcat   119460
tgtctatctt tccatacgaa aacatcagtc atctcgatac atccaaattg cagcaatata   119520
tacaatctat actcaagtaa ctcaacaaca cagaatatca tcaaaagtta aagagcctag   119580
ccagtaaact ttttcaatcc aactaacaat ctatttagat ttttacatag tggacatttg   119640
gtataatttt gtatgaatta ctccatggaa aaacaacatt tgaaggtact gaaattagag   119700
aagcattgtt gaatatagtt ggtcaggcac taaagtgtcc attctgtggt caattgttac   119760
cgttctcgtc accaaccaat aaaacgttta gtcagaacct cataagttct tgggtcttcc   119820
ccaaacttgg tagcagcttc ttggtgtccg tagtccaccc tgaagatacg tggccactgc   119880
aaaccaagaa tacacacaga ttaatacatc aaacacgaaa atcacctatg tttctttagg   119940 gagaggggc aaaggtatgc ataccaaaaa gtaaatacat ctaaaacaat tctagagaaa   120000
gctgttaagc ttcacaagca tgcttcattc ttaaaagtct catttaaatt ctttagagtt   120060
tgaaaaattg aaggaaaagc tcacctgtgg ccatgtgggt tgccaggagc tcttgaattc   120120
```

```
ggtggctggg gaagaagttc caagtcatct aatatgctaa ggcttgattg cactgtcaat   120180
ttgaattttg acccttattg caagaaaatc acgttattat gcttgaacta agtagtgatc   120240
tttaatgcag acaattttgc acttggatac tcttacaaga tattttgttt tcttgtatta   120300
caatatcaga tgatttaggg gcttcttttc ttttgttagc aggttcttga aacgaggttt   120360
taatgaaaaa ggtcgagctc ataatgatgt tgagacagag caaattgtct ttgaggagat   120420
ccggaatgca gatgtattga aaatcagttc tattgtgcaa attagggggct caatttccct   120480 tctttggtct caagaaacgt caagattgaa tctaagacct gacattatat gtatgatcac   120540 tccattttt attttcctat cgtcttcttt tcttgctatt ccatgtaaca tattatttga   120600
atatagtgtc aaaggatgat tctcaatatg aagcaactcg gagacatttt caaaatcttg   120660
tggatagata tggtaatccg atattcatat tgaatccatt tcatttctga tattaagcaa   120720
atacatcaaa gaaaaaacca aactttttat gtgctaacaa tgatttcttc atcagagggt   120780 atttttccg ttaacgtatc attctatata tgtatcaatc cattctataa aagctatctt   120840 tacctttga tcaagtgagg aaagaagaca tggagatttc attgaggtca gaaacataag   120900
cattaacact actgatgcac ccagtattaa tagcagcagt aacagttggg ctaaaaatac   120960
tttcaacaac gtaaaggacc ttcccagtat cccgcccaag gcatccgagt gggaggtttt   121020 ctttttaaaga ataatgcaag tacatattat tatgcttaaa tttatcatac aaatgacttt   121080
ttaaaagcaa aaaattaaat aaattagtat ctacaacaaa ttttacaaag caaggatag    121140 ttctgagaaa tatatattaa tcagcatata tcatcattgc aacaaaattc atctggcgga   121200
agaatttagc cacttaaaga tcctaaggat aggtaaagta ttgtaaagaa gaagagaaga   121260
gccatactga gccaatatgc acagcagtgc aaattacaaa aacaactgct gcatcctcca   121320
tttgcgtgta tctccaaaac cagaattaga aaaaaaaaac aacaaacaga acgccacc    121380 agagatatta gcttttttgtt aaaaggacaa taaaatctac ttttgtagct tcaccaattc   121440
ttccctctta aatgtaaagt acttttctga ttttggggac tataaccaat gctgtgacat   121500 tagtttttcca aagtgctttt tctgattttg gggactataa ccaatgctgc cattttagat   121560
ttcccccatc ctgtcactca acattcatta tacatatatc ctgtcattca acattcatta   121620
ttcatatata tatatatata tatatatata tatatatata tatatatata tatatatata   121680
tacatgcctt agtccttctc actaacatca cagtacagca cacatcaagg ttagtcaagc   121740
tattctctct tcttttcatt ttatgacctg cttttgtgct gctaaataga ttactatgct   121800
aattgtgcta ctctttctaa tcagcttttg aatttgctaa atcaacaatg gatataaatg   121860
atagatcact gtgctaatta tgctgtttac attttctgat atgaatgtgc tgctgagttt   121920
gatcatatat atatatatat atatatcaaa gtttttcatta tttgaagata atatgatgga   121980
aattaatcag attggagggt ttatgttcta atcatttaa catgttattg ttgtgactta    122040
tttataatga aaacataca tcaatttatc acttgttgat ttacatgaaa agattttctc    122100
atatagttga gattcactgt gctaatcagc ttctatgact tatagtgcta tacatgttca   122160
gttatgccaa ttatgtcagc tttacctatt atacaattgt gaaccatatc atgtgtaatt   122220
ttattatgtt tttgttttgt attttgtgt tgattttaaa atcatttgt taggtatttt   122280 tttgatgttc ttataattta ctaatttcta ctggatttgc aataaccggc aaagacactg   122340
atattttgtt ctgattgagt gtaaattcat aataatgttt aagtgtaaat tcataataac   122400
gataaactcg tatcacatcc aatttgtgaa atatcccctta gaatagtcga gagacaggac  122460
```

```
ctgaaatacc caaagagatt ggatttagaa agggtaaaac tacattattt gacctgaaat   122520
gccttcatag aaagcagtta tttggcaatc attgaggtac atagtcacat tacacctgtg   122580
tcaaacacca gatatacaaa ggcaccacac caacaatttg tgcagcttaa ctttcaacct   122640
tttcacttac aaattacaat actctgaata atgttgcttt attaattgtg cttaaattta   122700
gttgtgggag atttactaaa aactgattct agcttatagc ttattagatt acatagacca   122760
tcatagaaat ctaatatcta gactgcaaat ataaacactt gattctaaaa cagaagaata   122820
tcttagatta agtttaattg gccaataagt ttaatttaat ttggtttaag aagagaactt   122880
agcactatct agcttactca ttacttattt tgatcaagtc atcgtgttga tggtgcattg   122940
aaagttttag cagatttata tctttccttt tgatgatcga gttttatcat gattctaatt   123000
ctttgaatat tttaagagga tgatattgta aatggatttt caaccatgca gatcatcacc   123060
atcatgaagg aaaaatactc aacattcaaa gaattatcag acaaagcaaa tatccacaag   123120
gtgaagataa aagtgataga aaagtccaga ccattccaat caccaggaaa aaaaaatatc   123180
aacgtctggt attccaagat gaaaatgtat gtcaatattc tatgcctata acctttttgag   123240 agataacgac aattcaaaca accattaaat aattcttttt atttcacttg ctgttagggt   123300
gatttgatga aggccaccct cttttgaagat gatattgatg catatgcaga tttaataaa   123360 cagaaccatg aatactttat ttctaatcca actattcgaa gcgtggaaga gcaataccgt   123420
tcaaaatctg gtgaatacca gatgaccttt aacagtcgca caactattca acccactggt   123480
tctgcaaccc agctatctga accaagctat tatactattt ctacaattcc tcgaatctct   123540
ggtttttatg atagatttgg tacgtaaatg aagttttgat tatttcttta gtatttagtc   123600
taatatttat attatacatc aaccttttgt taaacgttat gttttccaca ctactttaag   123660
tcaaaatttg ttttactttt agatatactc ggtattatcc tctttattgg atatactcgt   123720
actgtcaatg gagcatttga tcaaaagaat agcgtttctg aaataatgat tactgatcat   123780
aggtattttc ttaaactctt atcgtataca ctttttgaag cacatctatt taattagttt   123840
ttgttatatt gatcaatgat tttttttctta caattaatta tacaatgatg tagctcacat   123900 caaccttttaa caatttctgc ttggaatgat cttttccgact atttttaagga gaagcctatt   123960 gcatattcca ttttcgggtt tacttctctt cgagtaactt cacataaagg ttagacttaa   124020
atcaaatgag gcatttaaat aggattcgag gaagtatatg ttatcctcgc catgtgaaaa   124080
tcagttgtgt tttattattt gtgattaaca ctcacttttg caaaaattag gattcgggtt   124140
atcaaccaca atgtcctcat caattataac tgcaccaaca ggtgaaaagg cagaattgct   124200
aagaaaatgg taacgtatcc cgcatagaat ttttacgtaa gatcaactat tatacaaata   124260
actcatggtt ccatttatac agggcttctt cccatgcaga cttgcttcat gaacgcaaac   124320
aacaaatttt acaaagtcgc atttcatcaa caaagcgaca attgacaaca atagctttcg   124380
tcaagaaaaa aacagtatat cttacaattc acatgtttca tttcttatgt attgtgaata   124440
tcatatcagt aaatgttgtc ttccaatatt attagatacg tactatttgt ttacacccctt   124500 atcaaatgtc aagcaaccat taaaacaata gttgttctta aatatacaaa tattaaacta   124560
actttgatat tatataggca gcaaatacca tacaagatga aaggcattgg attaaagcat   124620
tcgtcaccaa ttgttgctat gatgatatac ggaaattcct aggctgcaat ggctgtaata   124680
aaaagaccga cacagaaaag aatgaagttt ttacttgcca atggtgtcac aaaaaagaca   124740
gcatatcaat gccaaggttt gctttataac tcttttgaaa tttaattaat gcaatacaaa   124800
ttgataaccc gtaaacaaaa attcaagaag attgtcaaga ctcaagatat actcatacac   124860
```

```
tcaagaagtg agattaacca gaaccgagat attataactg agcgaaaacc cgaatagaca   124920
ccgctaccta cattatataa atcttcacaa aagccaatgc acattgttat tcttcgagct   124980
ttaacaagga aagcacagtt atgttttttt tagtcagaca aatcattgaa taacacttga   125040
ttattgaaat ttgagtagct atgtaagcaa agccttctta acaaaaaaaa ggtaaaaaaa   125100
atagtaaatc atgcattcca ttcaaatcaa aggtcatctc tagggtttgg gcaatatgta   125160
acaggaaaca tggaaaagac aggaaaatgc caacatcaaa ctcatgaaac aaataaatac   125220
aagagaatta tattatactt aaaatattta aaattaatat tatcactatt tttttaaaa    125280 taaaattgca ttgtcttttt atgggtgtta tgggtagggg agaggatttt tccatacagc   125340
tgcttaaatt aaatttccat gatccaatac atctattctt gataagctat attcaattgt   125400
aatatatgtt ttacatttca gattagctct tagtttcgat gcccaagatg atacgggatc   125460
tatgagtctc acagccttta acgaaaccgt tgcacagctc tttggaagaa ctattagtga   125520
actatatgct cctgaaactt atgtacgtca ctacatctat acactctaaa tttacataac   125580
tctatacgtt tattcatctg tatctataca acaggacaag attaccactt atcaagaaat   125640
cgcagaatca attaaagcta agccaatata cattgaactt ggacctacaa cagctttagc   125700
aaaaaatggt gttctaaaat gggtgctaaa atcagtttcc cttaaaccat atagcttcac   125760
aagaacccaa aaacaaagga ttgctgctcc caacaagctc ttcaacatct gtcttaccaa   125820
cagacaaaaa acaagatcag ttatttactc ccccatctag aaaaagtgaa agctcactta   125880
agctatccac tccagctaca acaacactc ccctggactc ccaactacca agttccactt   125940
caataaattc agaatctatt cacaattcag aggcaactcc tcagactgaa gctgaactga   126000
aagtgcgtcg ggccttagat ttttctgtgg ttgaatcttc aatcaatcca gaagactcca   126060
tctactaagg ttcttcacta cctattgtaa tagataaatat cttttcttag gacttaaaca   126120
aatgcttggt gtttgaacat tgtcttttga agcatgtatt ttgggcaagt atgctatgtt   126180
ttgcttatta atatagcaac atatctacat atgttgtatg tgaacaactt gctattaaat   126240
tctagaatcc aagaagttgc ttattattaa atattctgaa ttgaatcagt tattacaaat   126300
taatctgctc atattgaatt gatgttccta tgtattactg tatttttgca tctgttgggc   126360
tgtttgtgca tctgctcata tagaatcaat tcacattcat gaagttagta ttgtttctgt   126420
ttgcagcaga actcaggtct atcatgacca ttccatcgtt tgtggttttt aatgaatgta   126480
tattggctgt atttattttg ttgaaacaat tgtagtatta tacttatgct aatgagtgtt   126540
attgagtatt tgttgagttg atgcatttgt ggtttttaat gaacgtatat taattatttg   126600
ttgaatgtag gaaacccaga aaagttattg tagtttattg gctgtatttg actaacaaat   126660
attacaaatt gaatgtatat tgggtgaccc aatgaaaact aacatttta ttgaatttt    126720 gttcactgtc ctgtttgagt tgatgcattt gtggtggata acaacactg tgttattgaa    126780 tgtatattgg gtgacccaat gaaaactaac atttcttaaa ttgattactt gcacctaggg   126840 cctagggtg ttcaatgggg attaaaaata ttttattaat tttttaaat gataatttaa     126900 ttgttataaa ttgaaaaatg gggattaaaa atatttttag tagtaaaaat gggccgaatt   126960
gggccagact gggcttttca aagcccggtc catttaaagc ccatattaat tctaaagggc   127020
ccttatccgg cccagcccat attactaggg ggccaaattg gccatatact aacaatactt   127080
tgtgaatgaa gcattacatc attgtaatat agttattgtg aatttgtat atgaaaatta    127140 cttccctgta ataaagtaac aacctgttgt atgattaatc taatgtttat atgaaatggc   127200
```

```
ggcgccttat tcacttgcta gatcactatt cttgtttgtt actgttctgt gttttacgtc   127260 ttagctctttt actaccttttt ttacctgtat cgtttgttag ttatctgtgt gatagtcact   127320
ctctttgctt gcagttaaat tatccctatt gcttggctaa cgtgggtgta agatgcaggt   127380
tttcggatat ttgcaggtcc tatccttgaa gactcctctt gagccgaagg actcttgtga   127440
ccgccctctc cttatgggta tgagacgccg tcgaccttcc ttccccggac cctaaccata   127500
gatttatcta tgtgcgggaa cactaggtat gatgatgatg atgatgatga tgatgatgat   127560
gattttggaa tttgccctaa tatttgctta agcttcatca attaaatttt ttttctataa   127620
tggaggatgg agatgaggat taaaacagtt gcatttaatt atttttttcta taatgtagaa   127680 gcttcatcaa tggcggttgg agatgagaga tgctgcaaaa aatccgaatg aaaacgtaga   127740
caatgaggat gaaaatctat atgaccgaca gttatatttg gaactatatt gtactatatt   127800
tggaattata atgtattaaa tttggaaata taagctattg aatttggaaa tataatgtat   127860
tatatttaga actatatttt accatatttg gaactataat atattgaatt tagaaaaata   127920
atctgttata tttttttcaac gttatactat tctataaacct caaatataag ttattataac   127980
cccaaatata gtatgttata accccaaata tattatatta taacgacaaa tatattatgt   128040
tataatcaca aatatattgt tataatccca aattcaatat attatagttc tagatatagt   128100
acattatagt tccaaatata atacaatata gttccaaata taattgttgg tcatatagat   128160
cttcatcttc attgtctccg ttttcattcg gttttttttga agcatcttca tctccaaccg   128220
ttattgatga agataaaata aagaaaaaat aaataagtta tgtgtgtcat tgacgaagct   128280
taaagaaggt tttctttttt acatacatta aaatgcacgc ttatggtcgt gcattttaat   128340
tagataaaca atattatatg atcgttgctt atggtcgttg tcatcatctc cattatagtc   128400
caaaacacag acattatagt cccaaaaaga taccaataga cccaaacaca gtcattataa   128460
ccccagaaaa caaaccaat ataattacac gtagggctga acaaagtttg gtctaaaccg   128520
taaaccaaat cggaccaaac cggaatttca atatttggta tggtctatgg tttaaatggt   128580
atggtctggt ttttttttcaa attaaattac ggtttacggt ctagtctcgg ttttttatttt   128640 tcagaccaga ccggaccgca aaccgttct atggtcgaaa atcataattt tatatttaaa   128700
aaatcaagtt gctacctaga tatttaagat atagttatttt ttatatagca atatatacat   128760
gaatgatgtt aatactatta attaattaca aattattata tttattaatt gtaggtgtga   128820
aatatttgca taaatacatg tgttaatttg gataaaacta taaaaatgaa aaaccgtaga   128880
ccagaccaga ccggaccgtt gtaaaacggt ttggtccggt ccggtctggt gatttaaacg   128940
gtccggtccg gtctagaaaa tttctagacc ggaatttctg gtttggtctg attttagtgt   129000
cagaccagac caaaccgaac cgtgttcacc cctaattaca cgcccaaaca cagacattat   129060
aatcccaaaa agatgattgt gtccgccatt gacgaagctt gggaaacaac cacttttgat   129120
gaagtttcgg gtacatccgc cattgataaa gcttgggcaa taaaaattaa aaattaaatt   129180
tttaaaaacg tttacaaaaa attaaaatca cccttgatga acaataaatt caattgacta   129240 ccatatctttt cgatatctgt ttcgaataag cttggtcgaa ttcactcaat aattcatcca   129300
tccttgtaga atgagaatta tgaaattttt gtttttttttt ttggagtgtt tggtcgaata   129360
aattggagat ttttcggttg aatttttttga attgaaatgg cagagaatga gtatgggtga   129420
agaaaacacc attttcagag aatgacaatg gttgaactta gagctgttca tgggcgggct   129480
tgggcgggta gcggaacggg tagcacctaa aaattctacc cgcgggctca aatattcaaa   129540
agtccgcccg catttgcggg catatatttt ttgtcgctac ctgcccattt ttaaagcggg   129600
```

```
cgggacccgc gggtaggcgg gtatttttat ataaaaattt aaaacataaa tcatattata  129660
aagttaagtt tttataagaa caacacaaaa ataatacatg atctaaaata ctctaagggc  129720
ctgttctctg atctgattga ataacgtctg aatttactaa agtctgatct gatctgatct  129780
gatctggtct gatctgatcg tcgtctgatc tgatctgatc tggtctgatc tggtctgatc  129840
tgatctgatc tgtctgttga tctgaacttc tgatctgcat agatttgatc tgatctgatc  129900
tggtctgatc tgatctgatt ccaataagaa taagtaataa gtcaaaaaaa taagttgaag  129960
agaacacctt ctaaatatat ataaagtctc aaaatactca aattacatga atattgaata  130020
tagacggtgg agtcggctac ttgttcgaac tttgatagtc gattgtttga gtgctttgag  130080
ggttaaaaat attaaagtca aaaaaaagta aactttaagg ctagtagaaa agtaataaac  130140
taaagttggg tataggtcat gtagtagact agtagtatag tttaatattt aatagaatta  130200
attatttaat aaataatata ttaaactaag cgggcgggcg ggtatacccg cggttatttt  130260
tttttggtgt cgttacccgc ccgtttatct tggcgggcgg gtattacccg tccaaacttt  130320
aaattttttg aaaaacgttg tctatacccg cccgttttc gggccgaatt aggcgggcct  130380
agcgggtagt ccgcccatga acagttctag ttgaattgaa gatgcttgtc tctaaaaatt  130440
ttgtaagctc tcaattgaag atgcgtgtct ctgaaaaatt gaagaagaag atgaaaatgg  130500
ggaaggataa ttctctgaaa attgaaggag taatgatgag taaatgggaa gttgaaatga  130560
gaaaactata caatattcaa tacatggcaa tcagttttt tcttttttt tatttatttt  130620 taattaaaaa aataagttaa gggaaatggg ctggcccaat tttgaggtat atcctataga  130680
ccgtctgttg tgagatcttg tttttattca aacccttatt cagatcaacc cttattcaac  130740
ccaacccttt taaaaccctt aaaatcaagg gttggagcag ggtccccaat gggcccccgg  130800
cccaatgcgc aggcctaatt agtaataatt aggaataagg ttaacttctt aatagggtaa  130860
ttataatgaa acccatatac ttaagcccaa aatacttaat tattatcgca ttataaaaaa  130920
tattacttaa cctcattatc aaatcttctt tatctccatt aaataaaaat aacttatttc  130980
taacgtaatg aaaataaatt atttaaaat ttcgaattct tacattctac cctagctact  131040
tgaaacaaat tttgtccttg aagttaaacc aaatataaaa tatccacatt atatgtatct  131100
caaaacaagc tcctcaacta atagtatttt cgagctagct attattccca aggtaccaca  131160
aaataaccac aacaataatt attctcattg tactaccta attgtaagta atcctaattt  131220
ctctctcgga ttcatacaat tggtcaccaa caactattat gactaacaaa agggtctata  131280
aaagagatcg tctcttgaac caaacaataa tataaattac taaaagtaat tgaatcaaag  131340
ttgttaaaat cgttattcta cttagaatcc tttagagaag tagaatcgaa tcggtcgaat  131400
cgaaacgtag aatcatacga ttcaacaaat aaacttaaat atattaaaaa tatctggttt  131460
cttatcatta ttatccaatt tcaaaagatt aaatttatga attaaagttt ctttgacttt  131520
atttttaaga atataacgaa aactttttaa taattagttt aaatctccat actgactaag  131580 atttttttt tttaaattca tgatggaaaa tttgaaattt atgtgtacat gtgaaagaga  131640
ttagtaaaag atggtacata agaaatatta aaataattc atacttaatt agtagtatcg  131700
aatcgtttaa tcgtagaatc gtgttatgat tctacctcta aaattttaat ttcaactaga  131760
atcgtaagat tctacaactt taagattata cttgcgattc aaatcgctcg cttgttttg  131820 gatagtagaa ccgtagatta aaattgcgat tttaacaaca atgattgaat tggtatacaa  131880
tatatcatat aagacttaaa ctcaattaaa tttatcctga tgtatcttcc cctaatactt  131940
```

```
gaattttgag attattaata cttttgactt caaacaacca tcattatctc atatatgcct    132000
tcccacataa ctattgtaac aatacttagt tttattgccc aattataaca ctcataattg    132060
tctttcgact cttttaattt aattagattt aacccctttg aatcatcgaa atatgtctat    132120
taaaagagat ttgttactca acatcttaat aagacaaaat gaacaaataa taaaaatgat    132180
gtcgacgtga tcattaagat tcaaggatga aagaattatt aagggcaata gtgcataaag    132240
aaatgagatt agcaatcgct acaatttcaa aaaggaccta ataaaataaa aataaaaata    132300
aaataaaaat aaaataaata tcatagaaat acccgttacc tgatgagtgg tatgaagaac    132360
tatgtgatgg gacaaaaaaa attaggatgc agcaagatat agactgctaa ttttattaaa    132420
ccgattaatc aaaatgaagg aaaaaaaatg tgatgataat ttttctgatt tgtgaaacga    132480
gagtaaattg aaaaaaataa ggttaacaag tgcacatatt tatattaagg gttatggtta    132540
acctcttaat agggtaatta taatgacata aacttaagcc caaatactta atttgtctcc    132600
cattaaaaaa tattactcaa cctcataatt aaatcttctt tatctcgata gccacgctta    132660
tttgtgtggt aaaacacaaa gaaaaacaaa ggggtatgaa ttcatacagc catgcttatc    132720
taatgaggga agtcttcaat acttatatgt gtggctaaaa ggtattatca gtcacgttta    132780
tatgaacctt agccacgctt ataagcgtgc ctgaaaattt agtaacacat gcagaggcca    132840
cgctaagttc agcgtgacta aatgtctcag cctcacatat aagcgtgcct aaatgcattt    132900
ttaagtgtgc ttaaatgcaa cattttttgt agtgctctaa taaataaaaa taatttatct    132960
ctaacgtaat aaaaaaattt attttttaaaa cttccaattg ttacaataaa tttggttgga    133020
tttggactta aaagttttaaa caaaattaat tttatttgat ttgaattgga ttgagactaa    133080
acttggtttg tatttggatt gaaatgccaa aaaaccaaat taaatttagt ttgttatttt    133140
acgagataac gaataaattc atgtaccttt attcaattaa gatgtgatgc ctaataatat    133200
tcaataaaac aattcaaata ctatttatga tcaaaattat tatctaatga aagattaaaa    133260
caaagtctta aaaagtagat tagcaaaatt aataaattat ttgaagatta aatttctaaa    133320
ataatttatg aatcgggtat taaaattttc acaaattctt gtgagagacg gtctctttga    133380
gagaccatct ctaattgagt tgatccatta ggaaaaatgt aaagtaaata taggcaataa    133440
gttttaatgg attgggcctg agaaacgtct ttcagaaaaa ctgtctctca gaaactcgct    133500
gattttcagt catcacaaaa acttggacga gatcgttcta ctctaagaca agatctgggc    133560
cggcccattg tttaggcgcg tgtactacac acgcgcgcgc tttaccctcc aaattttgtt    133620
tttttttttt gttttttttt tcattttttct ggaaaatctt caatttcgac cttaaatgta    133680
ccacttttga acttaaagat atcaatttta atgtaaagta atacttaaac atatcaatta    133740
aagtttaaat ttcaatttga acatatgagt gatcaattgt ggagttaaac tgatcaatat    133800
ctatctaagt atttgatgtt ttatgatcta actcaatttt gaacgtataa gcttcaatta    133860 tcgtttttcaa aataagtatt tcaaagtcta aaagatatt gtaaagttt tagttcattt    133920 tgaataagtt aatagttaaa ttatgacata taatttgacc atgatatttt ataatctaac    133980
ttaattttga acttttaata ttcaattatc gttttaaaaa taagtattca aattgtatag    134040
atatattgta taacatttg ttcaaattta attattgata gttttattta ttgaccattc    134100
attttgaaat tcatccatag aatgatagaa taacactatt ttttatataa cttcgttcta    134160
aaattttaaa gcataaccag aagtattagg tagcaattta tcactttaac atcaaaattg    134220
atcacttata ggttcaaatt gaaactttta ctttaattga tatgcttaag tactacttta    134280
aattgaaaat taatatcttt aaggttaaaa ttgataccct taagattagg aaaaattgtc    134340
```

```
gggaataatc cgaactattt gcaaactgct gtgaataatc ccacgtattg attatttatg    134400
aataatccca cctttcaagt gtatttgctc gtggcacccc caaatgaaat ttgacctatt    134460
ttagtaggtt atcttcttca atgtcttctt caatgcctct ttataaaccc agctactgat    134520
ttgtatccca caagccattg ttcttcttca atttattcca ctttgttctt caatcttcac    134580
ctttcttctt ccattgtgtt cttccttctt cactattaac cctacgcaag ccctcttcaa    134640
atgtattaca attttgaatc aaataataca attgatgctc ataattaaca ccaagactag    134700
tgaccaccaa atcattaaga tcaaaccatg aaatgcaatc aggatcaagt gaaaggcttc    134760
tatattcccc acccacataa ttcaaccccta ccccagtcct tttgaattta cccccatacc    134820
aaaacatcac ttgaaatttt tcaaaattat taacctaaaa aacaacacaa ttgaacataa    134880
ttaccaatgc atttctataa caacaaagaa aacattaaag aatcaaagat taaagtgagg    134940
aatggcaaag aaattaccat ggtttgattg agaacaagaa gacccaaaat tcgtctgcac    135000
agccccaaaa ttttcgcaca gagcagcaat accaccccca aaattcgaca ctgttgataa    135060
aaaataaacc ctaatttttt tgggaaatta cagttgatga atgtgagtgt tgattatggc    135120
gtgaagcttg atgattatga atgacaattg tgcttcaagt ttttgaaatt ttgaagtttt    135180
gaaggaagat ggtgtgaagg aatggtagaa caggaaatga agttaagggt atgcctttt    135240 gggttgaatg tttatttat ggaattaaag aatatgaaag atcatactct aacctgcaat    135300
agtaggtcaa atttcatttg ggggtgccac gagcaaatac acttgaaagg tgagattatt    135360
cataaataat caatacttgg gattattcac ataggtttgc gaatagttcg gattattccc    135420
aacaattttt ccttaagatt ataattaaaa aatccccaaa agatgaaaaa aagagaaagc    135480
atgtaaaaca cgcgaatcag accggtccac tcttgtttta atttgagaca attttgatgt    135540
tgagtcatcc cacaccaacc ccaaaaaatt caacaacaaa ctcttataat gattccctct    135600
actctactag agtctacacc aacccacttt ctctttgccc accaaaactt tggtttggta    135660
agaactaagc cctcttcttt cccttctctc tcttaaaagc ctaaaatcca cctaacttt    135720 tcagccaaca aacaacgcca aattcagagg aagaataatg gctcaagcta ctaccatcaa    135780
caatggtgtc catactggtc aattgcacca tactttaccc aaaacccagt tacccaaatc    135840
ttcaaaaact cttaatttg gatcaaactt gagaatttct ccaaagttca tgtctttaac    135900
caataaaaga gttggtggc aatcatcaat tgttcccaag attcaagctt ctgttgctgc    135960
tgcagctgag aaaccttcat ctgtcccaga aattgtgtta caacccatca aagagatctc    136020
tggtactgtt caattgcctg ggtcaaagtc tttatccaat cgaatccttc ttttagctgc    136080
tttgtctgag gtatttattt ctcaactgcg aaaacaatct ctatttgata ttggaattta    136140
tattacatac tccatcttgt tgtaattgca ttagtacata cttatgtttt gacctttgtt    136200 cgtttgttg ttgaattggt agtgttgaga atttgaatct aattatttgt ttttccatgt    136260 gaattaatc tgattaaatc cacttcttat ttatgttaag ttgcaatgat gtttgccaaa    136320
cggttatcat tgaaggataa gttcgcctac ttttgaccct cccaacttcg cgttggtaga    136380
gccattttat gttattgggg gaaagtagaa agatttattt gttttgccat tcgaaatagt    136440
agcgttcgtg attctgattt gggtgtcttt atagatatga tatatgggtt attcatgtaa    136500
tgtgtaggtt tatgcattat gttggatgca tgtctggtgt tattgctgta aatggatgaa    136560
tgttgttatt tggagacatt tttcattca ttttttccct tttaattgg aactggaaga    136620 gggaaagtta ttgggagtaa ttaaaaggtt gtgagttcga tacactgcat caaagacgaa    136680
```

```
gaacttgaca tagatgttga aggctaatcc ttatcactgc ttgaattcaa tatgtatctg   136740
aaaattttac ccctctatat gcatctgttt ttgctaataa agtgtttttg gactatcatg   136800
ttttgtgatg cttaagaggg tgatattact gagataaatg gaaatatcaa aataacatct   136860
attgtgaagt agtttttagag gcttttgatt ggtgcttcga ctttggattt acttgcatcc   136920
tagattgact cagtttgtgc aatctgaaaa tgatttcatc atggtatgaa tatggttcaa   136980
aaacaaggct gcatctcatc gaacacgttg taaagattta aaattaatca aattgatatt   137040
tctagcattg taaaggctta aaaaactgta tctcaggcta tattagggat tctcatgctc   137100
ttgaccgata tttaggtgtt acgataacca catcactcct acgatcgtta ccagatgttt   137160
gcactttgtt atgtgttaca agagataagt gttgcatgca gtggatccct tgtgattttg   137220
ttctaggtag acagtgttgt ttttgaattt caaagcagga attataacga gatttgatat   137280
tagggtttga attttttttaa aagttttttg cattcctccg atttgcaaca cggtttacct   137340
actgtttatt tgaattttttt gtgtgagaaa aggcttacag gcttgctctt gtatatgtgt   137400
atgtatttgc tttgtggtta aatatgctgc atgttgtaat gaaaactctg cccgggatg   137460
gtgggcttac acgccaaaga aaagattgt tttccacaac taaaaatatc ccattggcaa   137520
cagcgtgcaa ttatttaggg aatggtgtta gagcattaaa attggaaaat aaatgagctc   137580
tcattttgtt caaaccatga gaattttccc ctggtccaat attcagcgtt ttgtttcatt   137640
tgtaaaaatt acgatcatat ttctctttag tgaagcaact gattggaaaa ctttggtata   137700
tgccatgttt ctttccaagt taaagagttc ccaggcatca tcctcaatga tcttcctcta   137760
tattcctgta caatattgtt gataggaagt tcattcatgc caataacaat atgtctcttg   137820
cgaatttcta gaagaccaga aatttgttgt gacctgtgga gttcttccaa agtatcctc   137880
tgtgcgacgc atgaaaaaag cctttgggct agactactga gatgcagctg cctggtaatt   137940
catgcctctc tcccaagaga gtacgagaag tcatttatag ccgcttaaga gagccaagga   138000
tcaatttagg cgtgttctat ttccatatct taatgtatca ctgaagttta gcaagtaaac   138060
aaacatcaca atccctgatg cttgcatagt catggcaaat gttatactct ttgtttacat   138120
atgaaaaacc agatattact ccatattttt agaaaccagc aaccaaagga gcttaaatgg   138180
tccctgctcc taagtcatat ctcttggcaa tggggtgttt gtagatcttg agtgctgcca   138240
gtccacttac tgtaatgcaa tacatcaata ttgagctagt ttctcatggg aaaaaaccat   138300
agaaatggga caaatttgat gttaatgttc tgtaatccaa cttgaggatt agttttatca   138360
cataaaagct acattgaaag ttctattatt attttgagtt tgcatcttat gttgtttttc   138420
ctttgtgatt ttatccattt tcttaactag ttattcgttt cctgaagttt ttagtgtcat   138480
aactcctaat cacaatcatg ctacagggca caacagtggt cgacaacttg ctgtatagtg   138540
atgatattct ttatatgttg gacgctctca gaactcttgg tttaaaagtg gaggatgata   138600
gtacagccaa aagggcagtc gtagagggtt gtggtggtct gtttcctgtt ggtaaagatg   138660
gaaaggaaga gattcaactt ttccttggta atgcaggaac agcgatgcgc ccattgacag   138720
ctgcggttgc cgttgctgga ggaaattcaa ggtttgtcca attatattct ttatgtgagt   138780
gttgtttttt gtgttagttt caatcatgaa ggtactaatg cagaagccgt accctgaaa   138840
ttttcttatt ttgtatatat caattggtaa ttgatgtaag atattttttcc gagaggaata   138900
aaaaacaggg ggatagagaa tattaaagta ttgttctatc acattaactt tttatcaaag   138960
gtgtacattg tgtttgtgaa gtttatagag ctaaagggat ggaagggaag gggattgaag   139020
aagaggagaa aagaagaaga tcctcctttg aataccaagg tttgaacgga agggagaagg   139080
```

```
aggaaactct aaacaatatg gagatgaact gatgaagttt ttggatcaga accgcttgag   139140
aatcagagtt aagccatgtg aaagtctatg agcatgactt cacctggtta ataattttaa   139200
gctctcaact tctcatcctc ttttctttgt cgaaaatgtc atgtcttcat gtgatacgtg   139260
cttacataat cgtttctttt gtaaagcgat tgtctctcca gatttctccc cttacgaaaa   139320
taatccttga aggttgaaga aatcccttca tttccttttc ccctatttct ctacccttcc   139380
tactttggtg aaggattttg tatccctccc ttttcatggt ctatagtgtt agatattcaa   139440
acttaagctt ctcaagtttc atgtgggttc tgattattat tttatatatg cattaccaag   139500
gattcaaggt aatttgaacc aatcaagacc agaaccggat atgaattctt caacctagtc   139560
tgaacttgta catctaaaac atgctagtta caactgaaat atgatcaact tctatagcct   139620
ataagactct caccttcatt tgtaggttgc cacatagcac gtattgtcga tccatccatc   139680
ctcattattt gactcatcaa ataaaggaac cactcatgtg aaattcctgt cctacaaaat   139740
aatccatctc cctcatctca tttgtattca tgtagtttgc ttcctcaatc ctacaagtaa   139800
aaggacaact gcgattcaac tcttggacct atttgacagt aaatccacga atattaggac   139860
aatcacgttg gtaatgaacc atcgcttggc gcttgaaaca tttgatttcc tcaaaatcct   139920
ttgcttcccc caacatttca tcctttgctt tccacattaa agttggtgcc cgaacctcca   139980
tagccacaaa cttggttgta gacaacacac caacgtttct acctctaata gagataggat   140040
ttgtataagc cttactcttc ttagatcctt atgtttcata gacctttttc atcttgcacg   140100
tatcatcaaa agacaagttg gtatgtatct caggcttcac gcacaagtca acatccttat   140160 caccataccct caatatgaca agccctacct ctcaatcttc tacaaagcta tagatcttcc   140220
atctcaatgc aaggaacttc aacacacgta taaactttt ttgaatttaa ttgttcaaag   140280
gaaaaaacct ttctttcatg tgcatttta tgtcaacata gctattaatc aacgtctttc   140340
ctcttgtacg agctaattct caataccttt aagcccacat gaagccttct tcttgagctt   140400
gaatttaaaa aactggaaaa tttgcttttc gtacggagtt cttgttgttg taaaaacact   140460
ccgaacttct ctcctattca cgatgatctt ttgggtgtaa ggacatacta tcaaaatttt   140520
ctacgttatc ctgaagccat gatcatccac ctcgcaatat gctcaacttt cagttcacgc   140580
tgattcaata tctgcgtgaa tagattgatc aagcttgcca tttgctcaag aatagttgag   140640
ttttcctctt gtaatactcg attcctctct tctgtttttt tagtcatcct actatttgct   140700
agcgacaatc tcacaagaat ataagagggg attctcatct attataacgc actactctgt   140760
acctaaggaa ctagtgtggg tgtcttattt ttgtcctctc ctcgtaggat ataaagaga   140820 tgtgtatttg tgaatgattc aacataaaac aaaagtatgt aggctcttag attataccat   140880
ctcattaaca tatgatgaac tcttacatat gctccttcac atatatttgt tttttggg   140940 tcatttattc tagtagtcca ttgatattga atcccttagt tatggcatta ttgtccgtgc   141000
actgtctcag gagaatagat ggattgttat tgcttttct gtatctgatg gtaatacaaa   141060
gattgcaaca tttgctagac cttgctgttt ggatatagaa agaaaattat ttgccattca   141120
tttccaaggg gtcgaatgta gccttatcct tattcgtgat aacaaagaga ttgatttgta   141180
gtccttacat ttgaaaatcc tggacttcac tgaatttatg taactgttgc atgccatgaa   141240
atggaatact ttattgatta tgtgtttggg atatgtaagc tgaagaaggc aatttcccag   141300
ctcctattaa tgctatctac acttcatatt atcctttctg atatagttta cttttctttg   141360
catgtgtcga attagttatg tgcttgatgg agtaccaaga atgagggagc gccccattgg   141420
```

```
ggatctggta gcaggtctaa agcaacttgg ttcagatgta gattgttttc ttggcacaaa    141480
ttgccctcct gttcgggtca atgctaaagg aggccttcca gggggcaagg taatgtgact    141540
aaacttcttt atgttttgtt agatttcggg ttttactcca tctaattcaa tgaatgatga    141600
ttcatgcgtc aatttcttgg tagcaattcc tttccctacc taactatgac ttctctgatt    141660
gacctttcct atgaggtggg gaatagtgtt tttaatgtga ggaaaagaga aacccggggt    141720
atgagcttta gcatgataga gtatgtattt gatactaaaa ctgcaaatta gttggaatc     141780 aagaataaga agacttatac agtataaatc aacagaggtg tctgctgtgt atatgtgtaa    141840
tagacagtta tagttagcag gaattcagga gataaaatga agatggtgtt gatgaaactt    141900
aacagacaat tcagaaaaca aagtttgagt agtaagtaga cttttgagag gctgcttctc    141960
tctcaaatga gctataagtt ctaacaaaag tctcaataca taatttagat aataatcaga    142020
tgcctctctc acgctccatc cctttattat ctagatttct tgattttttt cataacttat    142080
gcaacttatt tcagcctctt ccttcattcc accttctact tgaaataaaa tgcaatctct    142140
accttgtttc tttatggttt gttcatttta ataaagattt agtatgaaag tcaatattgc    142200
ttttgcattg ttgtttgtct aagatcctaa tggcaagtcc acataagatg tttgttggta    142260
tatgctaggt tattaggatc gggattctac ttaggatcgt tgaggaggta ggattgaaat    142320
aggtagaatc ggttcgtact tcgtaggatt gtgccatgct acaaatatgc attgatgtgc    142380
tttggattat ttgttatcaa ttatatttgt tcttctgttc agttttaagg tgtaagtaaa    142440
aacttattcg atttcattta ttaagttttg aaaaaaatac tttaataatc acttttaaac    142500
tgcaaattga aaaaaattgc atttttagt gatgttttt tttttgaat atcagtgatg       142560 ttgatataat tattttatag aatatttata cataattgaa atcttgatta tgaaaaata    142620 ttttacgatt gaaactactt ttataggatc ggatcgtttg attgtaggat cttagaatcg    142680
tattatgatc ctaccaccta aattttgag ctagttctac cacattatga ctctacctaa     142740
gatccggatc gattgtttat ttttagatcg tagaatcgta gatcaaaatc gagactctaa    142800
tatctatggg tatatgtgtt aaattattag tcagtagaac aattctcttt tcttggtaa     142860 ataaaatcgt acgatacttt agtccggggg gcgcgctttg tgtcctgtac ggtaagtatc    142920
ctgtgacaaa actgtacttc aggtgtcttc ttcactcttg ggaaagtgta aatgtctttt    142980
gtcccgatta aggaagattt tatgagaaat ttttcccacat gcttggcacc aatttgtttt   143040
tatttagtag aagaagaaat tatgtataac atgcatactc aggatggtag tgaatatgaa    143100
atgaagaaag gaggtaaagt tgcatgctgg aaacttataa agagatgatt cattcaaaat    143160
tttgatattc ctaatagcat agttgtggtt ttcaatttca cagtcatgaa gtaagaacct    143220
ctctaatatt atccatttgt tttgtgaatt gatcaaatta gaactacaat ttcaatgttt    143280
gttgttaatg agaagttcta gcatagttgt ggttttcaat ttcacagtca tgaagtaaga    143340
acctctctaa tattatcgat ttgttttgta aactgtttgc aggtcaagct ctctggatcg    143400
gttagtagcc aatatttaac tgcacttctc atggctactc ctttgggtct tggagacgtg    143460
gagattgaga tagttgataa attgatttct gtaccgtatg ttgaaatgac aataagttg     143520 atggaacgct ttggagtatc cgtagaacat agtgatagtt gggacaggtt ctacattcga    143580
ggtggtcaga aatacaagta agtctctcat cttatattac atgtcctttt aacgtgtctc    143640
cattagtaga ctgaaaacac atgtaaatac atcagatctc ctggaaaggc atatgttgag    143700
ggtgatgctt caagtgctag ctacttccta gccggagccg ccgtcactgg tgggactgtc    143760
actgtcaagg gttgtggaac aagcagttta caggtataat gttaacccctt acccttcaca   143820
```

```
ttgttctgct aaattctaga ggaccctttc aattctgggt gggataagca cggcaatttg   143880
accgcaaaaa aattgcaaaa ttattctgct gatagaacat ctcgagatga gatcatattg   143940
agttttggcg tcaacataaa cctaatcaaa taatgaaaaa tacaaacatc atatggtttc   144000
ttttgtcttt atgactagac actctctatt attccttgat tgggatctta tttgaaattg   144060
ctgtgtagcc tacacctcat gttcagattt tgttcgtata ccagactttt cttgattggg   144120
atcttatttg tccctggat tttgcatagg gtgatgtaaa atttgccgaa gttcttgaga    144180
agatgggttg caaggtcacc tggacagaga atagtgtaac tgttactgga ccacccaggg   144240
attcatctgg aaagaaacat ctgcgtgcta tcgacgtcaa catgaacaaa atgccagatg   144300
ttgctatgac tcttgcagtt gttgccttgt atgcagatgg gcccaccgcc atcagagatg   144360
gtatgcttaa ctcttttcat tgaactgtgg cttatgtaga ctctttcaaa tattgataat   144420
gaaatttagt gtgtcataag aaaatcggaa tttggacttg tttttgtttt ggaatattca   144480
aacagctaga aagatgtttt ttttgctcta atggtggtta aactatcact gtccttgatg   144540
ggaaattatg attttgctg tccccaatgt gtttattggc atatcttgat acaattaagt    144600
gagggaccac tttgcaccat taagtttctc atagtcatca ccatttctaa ataattaaaa   144660
tttagtatt tgtagacttg ttatgaaatg acgttaattt ttaacaatac ttaatggtct    144720
taaaggggtg tttgggaaat gactgctgat taaaattgtt ttgactagat gattttatc    144780
aactgatttg acctattgaa tttgaacatg cttttaggaa tagcttgttc aaaaatagct   144840
tcttcagaac aataagttgt ttcaatcaac taatatacca aacactaacc aattatttac   144900
aattgtgcca aaataagcta aaattgtcaa atcaactatt atgcaacctc aggatgtgtt   144960
ccggggatat gaattgaaac ccatctttgg cagagtagag ataagacgaa aattgatcca   145020
atcttaggga tgaatgttga gatattattt ccataaatat actgtggtgg catttagggt   145080
ttttattta acaaggggtg tttagtttgg agaactttt attgaaaacc tgttttctcc     145140
atattcccat actgggttga caatgaaaat ttgaaaatta gggttgaaaa gaattattcc   145200
ttccattatt agcttacaaa cttatatagt tggatgaaaa ttaaatttca ttcacttttca  145260
ctccatctcc cttggtagca ttatcgtatt ccatcaaaca aaacaaaaga aaagtagtaa   145320
taattaacgt ttaattggaa aattgttttct catggaaaat gttctccgcc agaccaaata  145380
ctttcggaac gaggaagcat tttggaataa agaaccttgt gcttggatta atatatttgt   145440
ctatgagata gttttctcta gagtttactt gtatgtttat taactgaaca cgcctccttt   145500
gcaatcaaag aaaaaggaat tatttcacct ctaagcatac cgaaaacatc gacgcaaaat   145560
acatgtcaag atgtgtaatg attttgttat gtgaattaac agtggctagc tggagagtga   145620
aggaaaccga acgatgatt gccatttgca cagaactgag aaaggttagc agcctttac    145680
attctcgaaa gctgtaattg ttcttgagta atatatattc aaactataac tgatgttatt   145740
ttgcattcct atcaatacat tcagcttggg gcaacagttg aggaaggatc tgattactgt   145800
gtgatcactc cgcctgaaaa gctaaacccc accgccattg aaacttatga cgatcaccga   145860
atggccatgg cattctctct tgctgcctgt gcagatgttc ccgtcactat ccttgatccg   145920
ggatgcaccc gtaaaacctt cccggactac tttgatgttt tagaaaagtt cgccaagcat   145980
tgagtagcta tatacgagat ccttaaattg tacgccgaag ttttgatttt gagtctaata   146040
gtagataaaa ggctataaat aaactggctt tctgcttgag taattatgaa attctttgta   146100
ttatgtttgt gagattttaa gtagcttata aattacaatg tactaaagtc tagaaataag   146160
```

```
ttatgtatct tttaaatcaa tgagaaatgc atacttgaaa ggcttgacct tgtattcgtg    146220
acctaaagag tactaacttt ggagtttcca agtcatttgt ttatctcatt tttttttaatt   146280 tttgatttaa attgtttatt tcatgagta atcatgtact ccctccgttc cttttttgttt   146340 ttccaccttta ctaatacagg tagttccata agttttttcca ctttagaata ctttccattt  146400
ttggaaagtt ttcatcccag ttcccacatt tactccttaa aaccccactt tccttactttt  146460 acactactat ttaattattt tctctcttat acttccaata caagtattac attatactat   146520
tatttaatta tttttctctc atactttcaa tacaatcatt acttttcact actatgaagt   146580
aattaaaata atacccatta ccaccaaaga ttccattttt cttaatcttg gtgaaaaacc   146640
caaataggaa catcaaaaag gaacggaggg agtatctttc ttattctaac caaatgtaat   146700
actctttcca actctcttta aacgtccaca ctctctgggc acagagttta atagtgtggt   146760
ggttggagtc ttttaagtga ttataataat tgtaaaggtg gtagttaggg tattttaagt   146820
aatgtaggtg gggtattatg gtctttactt gttgaacata ggatatttag gtaaaaaatc   146880
tatgtcaaaa aaggaaagta agcaaataaa gcgaattgac ctgaaaagaa aagtggacat   146940
gtatagtgag ttggagggag tattttttatt ttcggcaaat taatcttaaa tgtcgtatttt  147000 tcttttatga taagtttttc gaatactttt actctcatgg gacaacttta ccattaatttt  147060 catcctcact taccccattt aacaatcaac tgacataata attaaaacat aaatctaatc   147120
ttaaaatttt ggtctaatgt ctcaactctc aataatgatt aatttatcg gacagatgcc    147180 ctcaataagt acttaaaatt aatccattgt ttttgcatgc tttacttaaa tgtataatga   147240
taaacaactt ttggtctaaa ttctttagga aataaacgct aaaaaagatt tacaaaaagt   147300
ccctattaaa ctaatttgtt acttatattt acaaaaagtt tgtatttgtt ccatgatatg   147360
tatactacaa aaagatgccc tcacaaacgc cattatagac tatagtgaca atgaactttt   147420 tttttaaaa cttttttttta aaaatatttg gctttttaag agctccctca aattatttgc    147480
aaaaataagc ttctacgcat aatgggctgg gggctgggtt ttgagctggt aatgggccgc   147540
tgttagtaca agcggacaat tcattatggg ctgatttacc aatcggccgc tgtttatatc    147600
agcgggccat tggtcttcat ggaatgggcc gcattcggcc gctgtttgta tcagcgggc    147660 attgggcttt caattaaaaa cattaatttt tcaaaaaatg tgaatgttta cctcctccac    147720
ttcagcttca tcttcttcgc tgctgcaatt catggtgatt gtgatttgcc gcaatcaatg   147780
ttgcagagta ataagcaccg accatgcaac ggaaacgaga atgagaaaat gtgatttaat   147840
tcgtgatgct tcaagttcta attgttgtca actttgcatc aattgcagat tattaacgac    147900
cgaaatgaca attgcagcaa tacgatcctt atattcaaca atggaagttc agatcaactg   147960
tagatgactt gcctgaaaat caattgaaga accaggttga agatgaattc gatcaacttc   148020
ggaacaattg gggttccgtt atttaacagt aaaacgtcct gggtctgaag cccaatggcc    148080
cgctgatata aacagcggcc gaatgcggcc cattccatga agaccaatgg cccgctgata   148140
taaacagcgg ccgattggaa aatagcccca aaatgaattg cccgcttgta ctaacagcgg   148200
cccattacca gctcaaaacc cagcccccag cccgttacgc gtagaagctt atttttgcaa   148260
ataatttgag ggagctctta aaaagccaaa tatttttaaa aaaagttaa aaaaaaaag    148320 ttcgacaatt acatttgcca ctaaagacca aattaagtgt cgctaaatca ctttatagta    148380
aaacttaaaa taaaaatcaa taattatcac attaaaagta tgaatcagtt tcattttttta   148440 ataccactaa atccaatatc gcaaaaggtt aagtttgttg tagtggcaac acattgccta    148500
atagaaataa taataaggca acgaactctt gtaaatagtt gaatgataaa aaaaacttgc    148560
```

```
tcccaccaat tactaattaa gtgccactat tcatcaccat tagacctggg aaacggtcgg   148620
atgggtgggt tacaggttgg gttaatttcg gtcgggtcat tttcggatca ggccattttc   148680
agatcggttt attttcgggt caggtcactc ccggttccgg gtcggtcggt cgctaaatca   148740
ctttatagta aaacttaaaa taaaaatcaa taattatcac attaaaagta tgaatcagtt   148800
tcattttttt aataccacta aatccaatat cgcaaaaggt taagtttgtt gtagtggcaa   148860
cacattgcct aatagaaata ataataaggc aacgaactct tgtaaatagt tgaatgataa   148920
aaaaacttgc tcccaccaat tactaattaa gtgccactat tcatcaccat tagacctggg   148980
aaacggtcgg atgggtgggt tacaggttgg gttaatttcg gtcgggtcat tttcggatca   149040
ggccatctct ttattctgtg tgcggcatat tgtccggtgt ccccttctcc gcactgaatt   149100
ttctctcctt ttcaaagtct ttagcattag gtaaatccta aaaccctaaa ttcatagtaa   149160
tttttaatgc ttagttttttt agtttcatgt ttattaagtt acaatcttta tgtatgttta   149220
tactttggat ttgtatgtac atcagatttc gtatatcttg aaggaccatc tatgttttta   149280
catgaatttt ttatggtttt gaaggaccat tttttgttta acaaaaatg aaaagagatg   149340 aatgattgat ccataattca agaggttggt ggatttgaat cacgccattt ttttttgatt   149400
ctaaaatgta taattgtgtt tagttgtgtc aatgttttg acatgagaaa ttactattta   149460
atggtagttg ctattttgt tcatgatgaa ttgatgacta caatgctaat atggaaatcc   149520
ttaattagct tgctcttggg gtttagttgt gtcaatgttt ttgacatgag aaaattggtt   149580
caggaggttg ttaatagtta tgtactctat cccatttta gtttaagata catttcgtcc   149640
tactttcttt aatttactta tttcaagatg ttaagttagg tgataaatgt tttagatgtt   149700
tgaatcatac agatttaatc ttccgtgaca taattgcagt ttcgaatatt ttagaggcct   149760
gattcatcaa gttgctaacg tctaagctta agataagttt agtagtttct atactgatag   149820
tcggtattac atagtaatga ttaatgttgt ttttgaattt actgtaacaa gaaaaagaga   149880
gttgtatcct gttaattgtc tctgaacttc cttttaatct aaaatgtaat tagactttgg   149940
ggtaacttgg cactttaaa ctgatttctt tttgtgccta ttaattgatt gttgaatacc   150000
cataagaaga aaattgtttt tgtgattgag ttgttttcat ggattaagta gtcatataat   150060
gagaattgga taaaaataat agactatata gttctatgga ttaagtagtc atatgatgat   150120
gatgatgact ttgtttgttg taaatgggtt ttgaaataat tcattgggtt aattttaat   150180 actttattgg ttttgaaaat ttgctacaat aaattaagga gcttttttgga tgagggggttg   150240 atatgttgtc attcttaatt ggaggaagat gaatgctaat gaggcaaatg aagctaatgg   150300
ttttgaattt gacaatattt ctaacacagg tatttttgtta atctaatggt tcaagtacct   150360
tataagttat atcaatatgt tttgtgtact ttatcattgt ttgcgattgt gacaatattg   150420
agatagatta ctaacatgtg tattatattt attgaaatta acagcgtttg aagagttaca   150480
aatgattgaa caacaacgac aagatgagtt actaagatcc caacaaacta tgcatccac   150540 tccaaggaat gtgaacccga accctagaca agttgtccaa cgtccaattc gtccaccaaa   150600
gcgtgcaaaa actagtagtg gaagaggtgg agtttcttta gctggaggtc gaaggcgaac   150660
tagaactgag tttcaagagg atattgtagg gcttggaaag cgtacctcac cagttggga   150720 tcatttttacc atagtgcctg agaaggatga taacgatgtt gttatttcat tacacgctgt   150780
ttgtcgccat tgtaagaata ctgactatag agctgaaggt cattatggaa cctccaattg   150840
tagaaatcac cttaagagtt gtgaaccttta ccaagaatgg cttgctaaaa atggtgatct   150900
```

```
cattggtgat tttaaccaga gaaaatattg ttctctgttt gcagaggcca ttatgtacca   150960
tggatatccc ttaagcatgg ttgagcacaa atttacaagg aagttgcatc gttacttaaa   151020
tccaaaggtg aagaacatat ctagatccac aattactcga tggtgcatga ggaaaaactc   151080
taagttgagg aagatgttat tcgaaacttt aaaggattta gatagcaagg tgtctttgac   151140
atgtgacatt tggacagctt gcacatctcg tggatacttg actttaacgg ctcattatat   151200
tgacaaagat tggtgtttga agtcgaaagt tctcaatttt tgtcatttcc ctccccctc    151260
cactggtcat gcgatttatg agcttgttta tgcaatgatc aaggattggg gtcttgaatc   151320
aaaggttatg tgcatgactg ttgacaatgc aaccaataat gattccatga tcccttgtt    151380
acaagaatgt ttaaatggtc attcgtcttt tccatgtgat ggtgcacatt ttcatattcg   151440
ttgtgcggcg catattttga atttgattgt taaagatgga ttaaaagcaa ttgatcccgc   151500
tgtcacactt gtgcgtgata atgtcaagta cattgattca tccgaggcaa ggatgaatag   151560
gtttagagat tttgtatctc agatagaaaa accttcttcg ctaaaattat ggttggatat   151620
tgtaacgaga tggaactcta cgtatctaat gttgaagcga gctcttcact atagagttgc   151680
gatgaatcgc tttggtagta tactgagcct gactacacct tcaagctcac tgatcgcgag   151740
tgggaatcag ttgaaaacat ggcttctatt cttgaacctt tctatgaaat gactaatctt   151800
ttctctgggt cagattatcc cactgcaaat ctatattttg aacaagtttg taaggcaaaa   151860
taccatctgc gacgtgcttg tgaaagtgag gatgcttgca ttagagagat gggaaattag   151920
atgtttgaga agttggagaa atattggggg gagtcctctt taattttgtc gattgctgcg   151980
gtgtttgacc ctaggcataa aattccatat ctaaaacatc attttagaaa ggtttatcaa   152040
tctgaggatg aggtttatca acaaattgag agagttcgca ctggacttgt caatcttttt   152100
aatgattaca agtctaaact tactttatcg actaaagctc atcaagcttc tgcatctgaa   152160
gatcgggcat cagttggtac atgctctcgt gattttgatg gctatgaggt atgtattact   152220
taatttatta ttattaatat ttatttcaat atgtttgtct ttccattata atatttatac   152280
cattaacaag tttcatatgt tttatcgttt ttttacagag ttttgaaagt tctcaagaag   152340
cacgtttttc ttcaaatatt atatcagaag tggaaaaata tcttgaatca cctttgcaca   152400
tgcatggtga ttccaaattt gatattttgt tgtattggaa agaccaacaa gctacttatc   152460
caattatgtc taaaatagct aaagacatat tggctatccc aataaccaca gttgcatccg   152520
aatcaacttt ttctatggga ggaagaatct tgaatagatg gagagcatcc cttttatcaa   152580
gacatgttga agccttgatt ttaactcgta attggttgtt tggatatgaa gaagaacctg   152640
atgaagtagg attaaatgtt ggcaatgact tagtccccga tgcagaatct catgctaagg   152700
gagatcaggg tccaagtgga tcctcatctt tagaatctgg tacgtatttt atttttaaaa   152760
ttaaggttag ttgattatca aatttttatta taactcgtgt tttgtgtact ttatgtactc   152820
agttatggat tgttcacttg attgttgcca tccaagtgat gttggttctt acggatctga   152880
atgtgagtca aattgaaaca cggaatctag acacaagtaa tttaacctta caagccacgt   152940
ggaaacttga tagccatttg ggttgggtga atgttatcca tgagtcttag tcttataggc   153000
aactttctaa tagccttatt tacttgggac taggcaatta gagatgtttc ctttgctatg   153060
attcatgttg gtagctttgc ctgagtcttt cataacgttt ccttgctgaa aatgcgacga   153120
ttgttgacct tgagaggcat tacaatgatc tcactggagt tggaacttga tattccggta   153180
gcaaagtttt aggcgtttat ttttttatct ttcttataag atttaattat tttcttttaa   153240
tacttttttt gtttgttttt gttcaagatt gaaatgttgt accacaagct aagcagcagt   153300
```

```
acgtgagaga ttttggtgct ggttgtcgac ttttatgttt cattttggag aaagtgtttt   153360
gtggtggaca tactcacgta catctggtgg atgacacttt tgtggtggat atatagctat   153420
ttatagttgt tgattgaatg ctaattttgt gggttaagac ttgatatttg tatatttaaa   153480
tttgatggat gtataaggga tgtaaatttt tggggttaaa acttaatatt tgtatatttg   153540
aattaggtgg atgtataagt gatggatgta aattttgggg gtttaatgct tgaacaattg   153600
gtggattact aacatgaaat atgtaattag caatagaaac caagaaaagt ctaggtggaa   153660
gtgttgaaga aactatcaag tttttgtatt gttccacttc aatatgtttc taaggttttt   153720
gtaatgtgct tattggttta tagtggatat caatatcaag ggaaatctta tttatttata   153780
gataatcttg tttacaaagc taaaaatagg tgaaaaattg attcggattt ataacagttc   153840
gattaatatt cggttcgggt ctgtatcagt tcgggtaata aacagttcga tcttaatcgg   153900
ttttagtcgg gttgcactcg gtttcgtgca taaatcaggt cggatttagc tcgggtcgat   153960
cactgttgcg ttcgggtaac atttgttaat gtttatatgt cggttataaa attcggttgc   154020
agttcgagtt cagatttccc attttcggtt gtcaatcggt tcgggtacaa cttcggttcg   154080
ggtattaccg gttcgataaa cctaaaaaag gatcacattt tcgggtcggt ttagtttcag   154140
tttcgggtcg gattttcggg tcggtcgct tttggacagc tctactcact ctcctcttca   154200
tcttccattt taattaaatt agggatctga cctgggttgt cttcattctc accatggttg   154260
ccggtggtgt tttgggttac agaaaaaccg atggctgctc ttccttcttt actttgatct   154320 aacctggggtt gtcttcactc tcctcttcat cttccatttt ttttattttt tattttctga   154380
attttttttt caaactgggg gtacaattgt accccttgtc acttaattgg gtccgcccat   154440
gtaatagaca ggtacaatta atttattagt aaattcaata attagccaaa ttgtaggaat   154500
gtcaagagtc ttgacaattg attcgtcata ggagtatatt tttacagaca cacaaaacca   154560
aaagccaaat tgtagtaatg tcaagagtct tgacgattgg ttcgtcaatc gtcttatatt   154620
atacactcat caaagcaaaa gcccgtctct ttactcgaaa aaataggaaa gtaattgaag   154680
agaaatggat cggggttcga gaacatgttc ggtttcaata gagacgttct ctgcaccaag   154740
attacactaa ttagcctaaa tccaacatga gtacaaatta tacccaaaaa aggttttca   154800 cagacataaa cataatggca atggggttat ggaatgttgt tgtagacata agctatcatt   154860
catccttcta gatcaacaga aatatcaaac atcaaactta tcattggcat tgagctccag   154920
ccgactttca gagttacttg acgtctcatg gatactatgg gtgtcaacat gagaaacctc   154980
agcaatatca caaggcaggt cacctgattc gtcgtctgcg actgcatcca ttttccgctc   155040
tccagcaaca ttttccagtc ctgtactatt tccagaatcc atttcaatgt caatttgctc   155100
ttgtggggca tattctagag acgcttcaaa tactcttgca ccattttcaa tttaacttaa   155160
aggatgggat tccaccagaa cagctgaatg gatgtagttc attggctctg tgtcctttga   155220
actggtatac tcgacaagat ttttcttatc aacactatca gttgtatcat gcatctcatt   155280
aaccaaatct tttgatgttg ttccctctac ctcaacctcc tgacttggag ttgtgcaatg   155340
atttatacat gtactagaca ttcgtgttgc tatcttggtt tgtctttgga agagaataaa   155400
ggtgtgtaat tatgttcaac aagaattttt ttacatactt ttttcttgca ttttttttg   155460 actttagtt tttgttttga tggatgttgg cttcacttga gaattttgt gccaattttt   155520 ccatgttta cttgcttta ggcagtcaat atggtcggta tgtgaaagga ctcgactcat   155580
ttagttttct tgctcatgtg gtgttatgtt ctgcacagga acaagatgcc gcaagcttcc   155640
```

```
aagtaagcca cctcataatc gtatggtatg ttgtgtaatt tgcaaatgtg gcccttcttt 155700
tgaccataaa ccacgtgccc ctctttattc attgaggggt cacattctgc ttcttttgtc 155760
ccatcatcat agcatacatc ttccccataa attaaagtag taggggtaat aacatgttta 155820
gaattagttg gttttaaaat ttcaatatca tcttcaataa attgtaccta gggtaaataa 155880
acaataaaag acaggtacaa ttaatttatt agtaaattca ataattagcc aaattgtagg 155940
aatgtcaaga gtcttgacaa ttgattcgtc ataggagtat attttacag acacacaaaa 156000 ccaaaagcca aattgtagta atgtcaagag tcttgacgat tggttcgtca atcgtcttat 156060
attacactca tcaaagcaaa agcccgtctc tttacttgaa gaaataggaa agtaattgaa 156120
gagaaatgga tcggggttcg agaacatgtt gggtttctgt ctcaaaagag acgtttgagt 156180
gagataactc actctcctct tcatcttcca ttttaattaa attagggatc tgacctgggt 156240
tgtcttcatt ctcaccatgg ttgccggtgg tgttttgggt tacagaaaaa ccgatggctg 156300
ctcttccttc tttactttga tctgacctgg gttgtcttca ctctcctctt catcttccat 156360
ttttttttat ttttttttct gaattttttt tcaaactggg ggtacaactg tacccccttg 156420
tcacttaatt gggtccgccc atgtaataga caggtacaat taatttatta gtaaattcaa 156480
taattagcca aattgtagga atgtcaagag tcttgacaat tgattcgtta taggagtata 156540
tttttacaga cacacaaaac caaaagccaa attgtagtaa tgtcaagagt cttgacgatt 156600
ggttcgtcaa tcgtcttata ttatacactc atcaaagcaa agcccgtct ctttactcga 156660 aaaaatagga agtaattga agagaaatgg atcggggttc gagaacatgt tgggtttctg 156720
tctcaaaaga gacgttctct gcaccaagat tacactaatt agcctaaatc caacatgagt 156780
acaaattata cccaaaaaag gttttcaca gacataaaca taatggcaat ggggttatgg 156840
aatgttgttg tagacataag ctatcattca tccttctaga tcaacagaaa tatcaaacat 156900
caaacttacc atcattggca ttgagctcca gccgactttc agagttactt gacgtctcat 156960
ggatactatg ggtgtcaaca tgagaaacct cagcaatatc acaaggcagg tcacctgatt 157020
cgtcgtctgc gactgcatcc attttccgct ctccagcaac attttccagt cctgtactat 157080
ttccagaatc catttcaatg tcaatttgct cttgtggggc atattctaga gacgcttcaa 157140
atactcttgc accattttca atttcactta aaggatggga ttccaccaga acagctgaat 157200
ggatgtagtt cattggctct gtgtcctttg aactggtata ctcgacaaga ttttttcttat 157260 caacactatc agttgtatca tgcatctcat taaccaaatc ttttgatgtt gttccctcta 157320
cctcaacctc ctgacttgga gttgtgcaat gatttataca tgtactagac attcgtgttg 157380
ctatcttggt ttgtctttgg aagagaataa aggtgtgtaa ttatgttcaa caagaatttt 157440
ttacatactt ttttcttgca tttttttttt tgacttttag ttttttgttt gatggatgtt 157500
ggcttcactt gagaattttt gtgccaattt ttccatgttt tacttgcttt taggcagtca 157560
atatggtcgg tatgtgaaag gactcgactc atttagtttt cttgctcatg tggtgttatg 157620
ttctgcacag gaacaagatg ccgcaagctt ccaagtaagc cacctcatat tcgtatggta 157680
tgttgtgtaa tttgcaaatg tgatgtggcc cttcttttga ccataagcca cgtgcccctc 157740
tttattcatt gaggggtcac attctgcttc ttttgtccca tcatcatagc atacatcttc 157800
cccataaatt aaagtagtag gggtaataac atgtttagaa ttagttggtt ttaaaatttc 157860
aatatcatct tcaataaatt gtacctaggg taaataaaca ataaaagaca ggtacaatta 157920
atttattagt aaattcaata attagccaaa ttgtaggaat gtcaagagtc ttgacaattg 157980
attcgtcata ggaatatatt tttacagaca cacaaaacca aagccaaatt gtagtaatgt 158040
```

```
caagagtctt gacgattggt tcgtcaatcg tcttatatta cactcatcaa agcaaaagcc  158100
cgtctcttta cttgaagaaa taggaaagta attgaaatga aatggatcgg ggttcgagaa  158160
catgttgggt ttctgtctca aaagagacgt ttgagtgaga taactcactc tcctcttcat  158220
cttccatttt aattaaatta gggatctgac ctgggttgtc ttcattctca ccatggttgc  158280
cggtggtgtt ttgggttaca gaaaaaccga tggttgctct tccttcttta ctttgatctg  158340
acatgggttg tcttcactct cctcttcatc ttccattttt ttttatttt ttttctgaat  158400 ttttttcaa actgggggta caactgtacc cccttgtcac ttaattgggt ccgcccatgt  158460
aatagacagg tacaattaat ttattagtaa attcaataat tagccaaatt gtaggaatgt  158520
caagagtctt gacaattgat tcgtcatagg agtatatttt tacagacaca caaaaccaaa  158580
agccaaattg tagtaatgtc aagagtcttg acgattggtt cgtcaatcgt cttatattat  158640
acactcatca aagcaaaagc ccgtctcttt actcgaaaaa ataggaaagt aattgaagag  158700
aaatggatcg gggttcgaga acatgttggg tttctgtctc aaaagagacg ttctctgcac  158760
caagattaca ctaattagcc taaatccaac atgagtacaa attatacccaa aaaaggttt  158820 ttcacagaca taaacataat ggcaatgggg ttatggaatg ttgttgtaga cataagctat  158880
cattcatcct tctagatcaa cagaaatatc aaacatcaaa cttaccatca ttggcattga  158940
gctccagccg actttcagag ttacttgacg tctcatggat actatgggtg tcaacatgag  159000
aaacctcagc aatatcacaa ggcaggtcac ctgattcgtc gtctgcgact gcatccattt  159060
tccgctctcc agcaacattt tccagtcctg tactatttcc agaatccatt tcactgtcaa  159120
tttgctcttg tggggcatat tctagagacg cttcaaatac tcttgcacca ttttcaattt  159180
cacttaaagg atgggattcc accagaacag ctgaatggat gtagttcatt ggctctgtgt  159240
cctttgaact ggtatactcg acaagatttt tcttatcaac actatcagtt gtatcatgca  159300
tctcattaac caaatctttt aatgttgttc cctctacctc aacctcctga cttggagttg  159360
tgcaatgatt tatacatgta ctagacattc gtgttgctat cttggtttgt cttggaaga  159420 gaataaaggt gtgtaattat gttcaacaag aattttttac atactttttt cttgcatttt  159480
tttttgactt ttagtttttg ttttgatgga tgttggcttc acttgagaat ttttgtgcca  159540
atttttccat gttttacttg cttttaggca gtcaatatgg tcggtatgtg aaaggactcg  159600
actcatttag ttttcttgct catgtggtgt tatgttctgc acaggaacaa gatgccgcaa  159660
gcttccaagt aagccacctc ataatcgtat ggtaagttgt gtaatttgca aatgtgatgt  159720
ggcccttctt ttgaccataa gccacgtgcc cctctttatt cattgagggg tcacattctg  159780
cttcttttgt cccatcatca tagcatacat cttccccata aattaaagta gtagggtaa  159840 taacatgttt agaattagtt ggttttaaaa tttcaatatc atcttcaata aattgtacct  159900
agggtaaata aacaataaaa gacaggtaca attaatttat tagtaaatgc aataattagc  159960
caaattgtag gaatgtcaag agtcttgaca attgattcgt cataggagta tatttttaca  160020
gacacacaaa accaaaagcc aaattgtagt aatgtcaaga gtcttgacga ttggttcgtc  160080
aatcgtctta tattcactc atcaaagcaa aagcccgtct ctttacttga agaaatagga  160140
aagtaattga agagaaatgg atcggggttc gagaacatgt tgggtttctg tctcaaaaga  160200
gacgtttgag tgagataact cactctcctc ttcatcttcc atttttaatta aattagggat  160260 ctgacctggg ttgtcttcat tctcaccatg gttgccggtg gtgttttggg ttacagaaaa  160320
accgatggtt gctcttcctt ctttactttg atctgacctg ggttgtcttc actctcctct  160380
```

```
tcatcttcca ttttttttta tttttttttt ctgaattttt tttcaaactg ggggtacaac   160440
tgtaccccct tgtcacttaa ttgggtccgc ccatgtaata gacaggtaca attaatttat   160500
tagtaaattc aataattagc caaattgtag gaatgtcaag agtcttgaca attgattcgt   160560
cataggagta tattttttaca gacacacaaa accaaaagcc aaattgtagt aatgtcaaga   160620
gtcttgacga ttggttcgtc aatcgtctta tattatacac tcatcaaagc aaaagcccgt   160680
ctctttactc gaaaaaatag gaaagtaatt gaagagaaat ggatcggggt tcgagaacat   160740
gttgggtttc tgtctcaaaa gagacgttct ctgcaccaag attacactaa ttagcctaaa   160800
tccaacatga gtacaaatta tacccaaaaa aggttttttca cagacataaa cataatggca   160860
atggggttat ggaatgttgt tgtagacata agctatcatt catccttcta gatcaacaga   160920
aatatcaaac atcaaactta ccatcattgg cattgagctc cagccgactt tcagagttac   160980
ttgacgtctc atagatacta tgggtgtcaa catgagaaac ctcagcaata tcacaaggca   161040
ggtcacctga ttcgtcgtct gcgactgcat ccatttttccg ctctccggca acattttcca   161100
gtcctgtact atttccagaa tccatttcac tgtcaatttg ctcttgtggg gcatattcta   161160
gagacgcttc aaatactctt gcaccatttt caatttcact taaaggatgg gattccacca   161220
gaacagctga atggatgtag ttcattggct ctgtgtcctt tgaactggta tactcgacaa   161280 gattttttctt atcaacacta tcagttgtat catgcatctc attaaccaaa tcttttgatg   161340
ttgttccctc tacctcaacc tcctgacttg gagttgtgca atgatttata catgtactag   161400
acattcgtgt tgctatcttg gtttgtcttt ggaagagaat aaaggtgtgt aattatgttc   161460
aacaagaatt ttttttacata cttttttctt gcatttttttt tttgactttt agttttttgtt   161520 ttgatggatg ttggcttcac ttgagaattt ttgtgccaat ttttccatgt tttacttgct   161580
tttaggcagt caatatggtc ggtatgtgaa aggactcgac tcatttagtt ttcttgctca   161640
tgtggtgtta tgttctgcac aggaacaaga tgccgcaagc ttccaagtaa gccacctcat   161700
aatcgtatgg tatgttgtgt aatttgcaaa tgtgatgtgg cccttctttt gaccataagc   161760
cacgtgcccc tctatattca ttgagggggtc acattctgct tcttttgtcc catcatcata   161820
gcatacatct tccccataaa ttaaagtagt aggggtaata acatgtttag aattagttgg   161880
ttttaaaatt tcaatatcat cttcaataaa ttgtacctag ggtaaataaa caataaaaga   161940
caggtacaat taatttatta gtaaattcaa taactagcca aattgtagga atgtcaagag   162000
tcttgacaat tgattcgtca taggagtata ttttttacaga cacacaaaac caaaagccaa   162060
attgtagtaa tgtcaagagt cttgacgatt ggttcgtcaa tcgtcttata ttacactcat   162120
caaagcaaaa gcccgtctct ttacttgaag aaataggaaa gtaattgaag agaaatggat   162180
cggggttcga gaacatgttg ggtttctgtc tcaaaagaga cgtttgagtg agataactca   162240
ctctcctctt catcttccat tttaattaaa ttagggatct gacctgggtt gtcttcattc   162300
tcaccatggt tgccggtggt gttttgggtt acagaaaaac cgatggctgc tcttccttct   162360
ttactttgat ctgacctggg ttgtcttcac tctcctcttc atcttccatt tttttatttt   162420
ttttttctga atttttttttc aaactggggg tacaactgta cccccttgtc acttaattgg   162480
gtccgccatg taatagacag gtacaattaa tttattagta aattcaataa ttagccaaat   162540
tgtagtaatg tcaagagtct tgacaattga ttcgttatag gagtatattt ttacagacac   162600
acaaaaccaa aagccaaatt gtagtaatgt caagagtctt gacgattggt tcgtcaatcg   162660
tcttatatta tacactcatc aaagcaaaag cccgtctctt tactcgaaaa aataggaaag   162720
taattgaaga gaaatggatc ggggttcgag aacatgttgg gtttctgtct caaaagagac   162780
```

```
gttctctgca ccaagattac actaattagc ctaaatccaa catgagtaca aattataccc  162840
aaaaaaggtt tttcacagac ataaacataa tggcaatggg gttatggaat gttgttgtag  162900
acataagcta tcattcatcc ttctagatca acagaaatat caaacatcaa acttaccatc  162960
attggcattg agctccagcc gactttcaga gttacttgac gtctcatgga tactatgggt  163020
gtcaacatga gaaacctcag caatatcaca aggcaggtca cctgattcgt cgtctgcgac  163080
tgcatccatt ttccgctctc cagcaacatt ttccagtcct gtactatttc cagaatccat  163140
ttcaatgtca atttgctctt gtggggcata ttctagagac gcttcaaata ctcttgcacc  163200
atttttcaatt tcacttaaag gatgagattc caccagaaca gctgaatgga tgtagttcat  163260
tggctctgtg tcctttgaac tggtatactc gacaagattt ttcttatcaa cactatcagt  163320
tgtatcatgc atctcattaa ccaaatcttt tgatgttgtt ccctctacct caacctcctg  163380
acttggagtt gtgcaatgat ttatacatgt actagacatt cgtgttgcta tcttggtttg  163440
tctttggaag agaataaagg tgtgtaatta tgttcaacaa gaatttttta catacttttt  163500
tcttgcattt ttttttgact tttagttttt gttttgatgg atgttggctt cacttgagaa  163560
ttttttgtgcc aattttttcca tgttttactt gcttttaggc agtcaaatatg gtcggtatgt  163620
gaaaggactc gactcattta gttttcttgc tcatgtggtg ttatgttctg cacaggaaca  163680
agatgccgca agcttccaag taagccacct cataatcgta tggtatgttg tgtaatttgc  163740
aaatgtgatg tggcccttct tttgaccata agccacgtgc ccctctatat tcattgaggg  163800
gtcacattct gcttcttttg tcccatcatc atagcataca tcttccccat aaattaaagt  163860
agtaggggta ataacatgtt tagaattagt tggttttaaa atttcaatgt catcttcaat  163920
aaattgtacc tagggtaaat aaacaataaa agacaggtac aattaattta ttagtaaatt  163980
caataactag ccaaattgta ggaatgtcaa gagtcttgac aattgattcg tcataggagt  164040
atatttttac agacacacaa aaccaaaagc caaattgtag taatgtcaag agtcttgacg  164100
attggttcgt caatcgtctt atattacact catcaaagca aaagcccgtc tctttacttg  164160
aagaaatagg aaagtaattg aagagaaatg gatcggggtt cgagaacatg ttgggtttct  164220
gtctcaaaag agacgtttga gtgagataac tcactctcct cttcatcttc cattttaatt  164280
aaattaggga tctgacctgg gttgtcttca ttctcaccat ggttgccggt ggtgttttgg  164340
gttacagaaa aaccgatggc tgctcttcct tctttacttt gatctgacct gggttgtctt  164400
cactctcctc ttcatcttcc atttttttta ttttttttc tgaatttttt ttcaaactgg  164460
gggtacaact gtacccccctt gtcacttaat tgggtccgcc catgtaatag acaggtacaa  164520
ttaattatt agtaaattca ataattagcc aaattgtagt aatgtcaaga gtcttgacaa  164580
ttgattcgtt ataggagtat attttacag acacacaaaa ccaaaagcca aattgtagta  164640
atgtcaagag tcttgacgat tggttcgtca atcgtcttat attatacact catcaaagca  164700
aaagcccgtc tctttactcg aaaaaatagg aaagtaattg aagagaaatg gatcggggtt  164760
cgagaacatg ttgggtttct gtctcaaaag agacgttctc tgcaccaaga ttacactaat  164820
tagcctaaat ccaacatgag tacaaattat acccaaaaaa ggttttttcac agacataaac  164880
ataatggcaa tggggttatg gaatgttgtt gtagacataa gctatcattc atccttctag  164940
atcaacagaa atatcaaaca tcaaacttac catcattggc attgagctcc agccgacttt  165000
cagagttact tgacgtctca tggatactat gggtgtcaac atgagaaacc tcagcaatat  165060
cacaaggcag gtcacctgat tcgtcgtctg cgactgcatc cattttccgc tctccagcaa  165120
```

```
cattttccag tcctgtacta tttccagaat ccatttcaat gtcaatttgc tcttgtgggg    165180
catattctag agacgcttca aatactcttg caccattttc aatttcactt aaaggatgag    165240
attccaccag aacagctgaa tggatgtagt tcattggctc tgtgtccttt gaactggtat    165300
actcgacaag atttttctta tcaacactat cagttgtatc atgcatctca ttaaccaaat    165360
cttttgatgt tgttccctct acctcaacct cctgacttgg agttgtgcaa tgatttatac    165420
atgtactaga cattcgtgtt gctatcttgg tttgtctttg aagagaata aaggtgtgta    165480 attatgttca acaagaattt ttttacatac ttttttcttg cattttttt tgacttttag    165540 tttttgtttt gatggatgtt ggcttcactt gagaattttt gtgccaattt ttccatgttt    165600
tacttgcttt taggcagtca atatggtcgg tatgtgaaag gactcgactc atttagtttt    165660
cttgctcatg tggtgttatg ttctgcacag gaacaagatg ccgcaagctt ccaagtaagc    165720
cacctcataa tcgtatggta tgttgtgtaa tttgcaaatg tgatgtggcc cttctttga    165780 ccataagcca cgtgccctc tttattcatt gaggggtcac attctgcttc ttttgtccca    165840
tcatcatagc atacatcttc cccataaatt aaagtagtag gggtaataac atgtttagaa    165900
ttagttggtt ttaaaatttc aatgtcatct tcaataaatt gtacctaggg taaataaaca    165960
ataaaagaca ggtacaatta atttattagt aaattcaata attagccaaa ttgtaggaat    166020
gtcaagagtc ttgacaattg attcgtcata ggagtatatt tttacagaca cacaaaacca    166080
aaagccaaat tgtagtaatg tcaagagtct tgacgattgg ttcgtcaatc gtcatatatt    166140
acactcatca aagcaaaagc ccgtctcttt acttgaagaa ataggaaagt aattgaagag    166200
aaatggatcg gggttcgaga acatgttggg tttctgtctc aaaagagacg tttgagtgag    166260
ataactcact ctcctcttca tcttccattt taattaaatt agggatctga cctgggttgt    166320
cttcattctc accatggttg ccggtggtgt tttgggttac agaaaaaccg atggctgctc    166380 ttccttctt actttgatct gacctgggtt gtcttcactc tcctcttcat cttccatttt    166440
tttttatttt tttttttctga atttttttt caaactgggg gtacaactgt acccccttgt    166500
cacttaattg ggtccgccca tgtaatagac aggtacaatt aatttattag taaattcaat    166560
aattagccaa attgtaggaa tgtcaagagt cttgacaatt gattcgtcat aggagtatat    166620
ttttacagac acacaaaacc aaaagccaaa ttgtagtaat gtcaagagtc ttgacgattg    166680
gttcgtcaat cgtcttatat tatacactca tcaaagcaaa agcccgtctc tttactcgaa    166740
aaaataggaa agtaattgaa gagaaatgga tcggggttcg agaacatgtt gggtttctgt    166800
ctcaaaagag acgttctctg caccaagatt acactaatta gcctaaatcc aacatgagta    166860
caaattatac ccaaaaaagg tttttcacag acataaacat aatggcaatg gggttatgga    166920
atgttgttgt agacataagc tatcattcat ccttctagat caacagaaat atcaaacatc    166980
aaacttacca tcattggcat tgagctccag ccgactttca gagttacttg acgtctcata    167040
gatactatgg gtgtcaacat gagaaacctc agcaatatca caaggcaggt cacctgattc    167100
gtcgtctgcg actgcatcca ttttccgctc tccggcaaca ttttccagtc ctgtactatt    167160
tccagaatcc atttcactgt caatttgctc ttgtggggca tattctagag acgcttcaaa    167220
tactcttgca ccatttccaa tttcacttaa aggatgggat tccaccagaa cagctgaatg    167280
gatgtagttc attggctctg tgtcctttga actggtatac tcgacaagat ttttcttatc    167340
aacactatca gttgtatcat gcatctcatt aaccaaatct tttgatgttg ttccctctac    167400
ctcaacctcc tgacttggag ttgtgcaatg atttatacat gtactagaca ttcgtgttgc    167460
tatcttggtt tgtctttgga agagaataaa ggtgtgtaat tatgttcaac aagaattttt    167520
```

```
ttacatactt ttttcttgca tttttttttt gacttttagt ttttgttttg atggatgttg  167580
gcttcacttg agaattttg tgccaatttt tccatgtttt acttgctttt aggcagtcaa  167640
tatggtcggt atgtgaaagg actcgactca tttagttttc ttgctcatgt ggtgttatgt  167700
tctgcacagg aacaagatgc cgcaagcttc caagtaagcc acctcataat cgtatggtat  167760
gttgtgtaat ttgcaaatgt gatgtggccc ttcttttgac cataagccac gtgcccctct  167820
atattcattg aggggtcaca ttctgcttct tttgtcccat catcatagca tacatcttcc  167880
ccataaatta aagtagtagg ggtaataaca tgtttagaat tagttggttt taaaatttca  167940
atatcatctt caataaattg tacctagggt aaataaacaa taaaagacag gtacaattaa  168000
tttattagta aattcaataa ctagccaaat tgtaggaatg tcaagagtct tgacaattga  168060
ttcgtcatag gagtatattt ttacagacac acaaaaccaa aagccaaatt gtagtaatgt  168120
caagagtctt gacgattggt tcgtcaatcg tcttatatta cactcatcaa agcaaaagcc  168180
cgtctcttta cttgaagaaa taggaaagta attgaagaga aatggatcgg ggttcgaaaa  168240
catgttgggt ttctgtctca aaagagacgt ttgagtgaga taactcactc tcctcttcat  168300
cttccatttt aattaaatta gggatctgac ctgggttgtc ttcattctca ccatggttgc  168360
cggtggtgtt ttgggttaca gaaaaaccga tggctgctct tccttcttta ctttgatctg  168420
acctgggttg tcttcactct cctcttcatc ttccattttt tttatttttt tttctgaatt  168480 ttttttcaa actgggggta caactgtacc cccttgtcac ttaattgggt ccgccatgta  168540
atagacaggt acaattaatt tattagtaaa ttcaataatt agccaaattg tagtaatgtc  168600
aagagtcttg acaattgatt cgttatagga gtatattttt acagacacac aaaaccaaaa  168660
gccaaattgt agtaatgtca agagtcttga cgattggttc gtcaatcgtc ttatattata  168720
cactcatcaa agcaaaagcc cgtctcttta ctcgaaaaaa taggaaagta attgaagaga  168780
aatggatcgg ggttcgagaa catgttgggt ttctgtctca aaagagacgt tctctgcacc  168840
aagattacac taattagcct aaatccaaca tgagtacaaa ttatacccaa aaaaggtttt  168900
tcacagacat aaacataatg gcaatggggt tatggaatgt tgttgtagac ataagctatc  168960
attcatcctt ctagatcaac agaaatatca aacatcaaac ttaccatcat ggcattgag   169020 ctccagccga ctttcagagt tacttgacgt ctcatggata ctatgggtgt caacatgaga  169080
aacctcagca atatcacaag gcaggtcacc tgattcgtcg tctgcgactg catccatttt  169140
ccgctctcca gcaacatttt ccagtcctgt actatttcca gaatccattt caatgtcaat  169200
ttgctcttgt ggggcatatt ctagagacgc ttcaaatact cttgcaccat tttcaatttc  169260
acttaaagga tgagattcca ccagaacagc tgaatggatg tagttcattg gctctgtgtc  169320
ctttgaactg gtatactcga caagattttt cttatcaaca ctatcagttg tatcatgcat  169380
ctcattaacc aaatcttttg atgttgttcc ctctacctca acctcctgac ttggagttgt  169440
gcaatgattt atacatgtac tagacattcg tgttgctatc ttggtttgtc tttgaagag   169500 aataaaggtg tgtaattatg ttcaacaaga attttttttac atactttttt cttgcatttt  169560
ttttttgact tttagttttt gttttgatgg atgttggctt cacttgagaa ttttgtgcc   169620 aattttcca tgttttactt gctttaggc agtcaatatg gtcggtatgt gaaggactc   169680 gactcattta gttttcttgc tcatgtggtg ttatgttctg cacaggaaca agatgccgca  169740
agcttccaag taagccacct cataatcgta tggtatgttg tgtaatttgc aaatgtgatg  169800
tggcccttct tttgaccata agccacgtgc ccctctatat tcattgaggg gtcacattct  169860
```

```
gcttcttttg tcccatcatc atagcataca tcttccccat aaattaaagt agtagggta    169920 ataacatgtt tagaattagt tggttttaaa atttcaatgt catcttcaat aaattgtacc   169980
tagggtaaat aaacaataaa agacaggtac aattaattta ttagtaaatt caataactag   170040
ccaaattgta ggaatgtcaa gagtcttgac aattgattcg tcataggagt atattttac   170100 agacacacaa aaccaaaagc caaattgtag taatgtcaag agtcttgacg attggttcgt   170160
caatcgtctt atattacact catcaaagca aaagcccgtc tctttacttg aagaaatagg   170220
aaagtaattg aagagaaatg gatcggggtt cgagaacatg ttgggtttct gtctcaaaag   170280
agacgtttga gtgagataac tcactctcct cttcatcttc cattttaatt aaattaggga   170340
tctgacctgg gttgtcttca ttctcaccat ggttgccggt ggtgttttgg gttacagaaa   170400
aaccgatggc tgctcttcct tctttacttt gatctgacct gggttgtctt cactctcctc   170460
ttcatcttcc attttttat tttttttc tgaatttttt tttcaaactg ggggtacaac    170520
tgtaccccct tgtcacttaa ttgggtccgc ccatgtaata gacaggtaca attaatttat   170580
tagtaaattc aataattagc caaattgtag taatgtcaag agtcttgaca attgattcgt   170640
tataggagta tattttaca gacacacaaa accaaaagcc aaattgtagt aatgtcaaga   170700
gtcttgacga ttggttcgtc aatcgtctta tattatacac tcatcaaagc aaaagcccgt   170760
ctctttactc gaaaaatag gaaagtaatt gaagagaaat ggatcggggt tcgagaacat   170820
gttgggtttc tgtctcaaaa gagacgttct ctgcaccaag attacactaa ttagcctaaa   170880
tccaacatga gtacaaatta tacccaaaaa aggttttca cagacataaa cataatggca    170940
atggggttat ggaatgttgt tgtagacata agctatcatt catccttcta gatcaacaga   171000
aatatcaaac atcaaactta ccatcattgg cattgagctc cagccgactt tcagagttac   171060
ttgacgtctc atggatacta tgggtgtcaa catgagaaac ctcagcaata tcacaaggca   171120
ggtcacctga ttcgtcgtct gcgactgcat ccattttccg ctctccagca acattttcca   171180
gtcctgtact atttccagaa tccatttcaa tgtcaatttg ctcttgtggg gcatattcta   171240
gagacgcttc aaatactctt gcaccatttt caatttcact taaaggatga gattccacca   171300
gaacagctga atggatgtag ttcattggct ctgtgtcctt tgaactggta tactcgacaa   171360
gattttctct atcaacacta tcagttgtat catgcatctc attaaccaaa tcttttgatg   171420
ttgttccctc tacctcaacc tcctgacttg gagttgtgca atgatttata catgtactag   171480
acattcgtgt tgctatcttg gtttgtcttt ggaagagaat aaaggtgtgt aattatgttc   171540
aacaagaatt tttttacata cttttttctt gcatttttt tttgacttt agttttgtt     171600 ttgatggatg ttggcttcac ttgagaattt ttgtgccaat ttttccatgt tttacttgct   171660
tttaggcagt caatatggtc ggtatgtgaa aggactcgac tcatttagtt ttcttgctca   171720
tgtggtgtta tgttctgcac aggaacaaga tgccgcaagc ttccaagtaa gccacctcat   171780
aatcgtatgg tatgttgtgt aatttgcaaa tgtgatgtgg cccttctttt gaccataagc   171840
cacgtgcccc tctttattca ttgaggggtc acattctgct tcttttgtcc catcatcata   171900
gcatacatct tccccataaa ttaaagtagt aggggtaata acatgtttag aattagttgg   171960
ttttaaaatt tcaatgtcat cttcaataaa ttgtacctag ggtaaataaa caataaaga    172020 caggtacaat taatttatta gtaaattcaa taattagcca aattgtagga atgtcaagag   172080
tcttgacaat tgattcgtca taggagtata ttttacaga cacacaaaac caaaagccaa    172140
attgtagtaa tgtcaagagt cttgacgatt ggttcgtcaa tcgtcatata ttacactcat   172200
caaagcaaaa gcccgtctct ttacttgaag aaataggaaa gtaattgaag agaaatggat   172260
```

```
cggggttcga gaacatgttg ggtttctgtc tcaaaagaga cgtttgagtg agataactca  172320
ctctcctctt catcttccat tttaattaaa ttagggatct gacctgggtt gtcttcattc  172380
tcaccatggt tgccggtggt gttttgggtt acagaaaaac cgatggctgc tcttccttct  172440
ttactttgat ctgacctggg ttgtcttcac tctcctcttc atcttccatt ttttttttat  172500
ttttttttct gaattttttt ttcaaactgg gggtacaact gtaccccctt gtcacttaat  172560
tgggtccgcc catgtaatag acaggtacaa ttaatttatt agtaaattca ataattagcc  172620
aaattgtagg aatgtcaaga gtcttgacaa ttgattcgtc ataggagtat attttacag  172680 acacacaaaa ccaaaagcca aattgtagta atgtcaagag tcttgacgat tggttcgtca  172740
atcgtcttat attatacact catcaaagca aaagcccgtc tttttactcg aaaaaatagg  172800
aaagtaattg aagagaaatg gatcggggtt cgagaacatg ttgggtttct gtctcaaaag  172860
agacgttctc tgcaccaaga ttacactaat tagcctaaat ccaacatgag tacaaattat  172920
acccaaaaaa ggttttttcac agacataaac ataatggcaa tggggttatt gaatgttgtt  172980
gtagacataa gctatcattc atccttctag atcaacagaa atatcaaaca tcaaacttac  173040
catcattggc attgagctcc agccgacttt cagagttact tgacgtctca tggatactat  173100
gggtgtcaac atgagaaacc tcagcaatat cacaaggcag gtcacctgat tcgtcgtctg  173160
cgactgcatc cattttccgc tctccagcaa cattttccag tcctgtacta tttccagaat  173220
ccatttcaat gtcaatttgc tcttgtgggg catattctag agacgcttca aatactcttg  173280
caccatttcc aatttcactt aaaggatggg attccaccag aacagctgaa tggatgtagt  173340
tcattggctc tgtgtccttt gaactggtat actcgacaag atttttctta tcaacactat  173400
cagttgtatc atgcatctca ttaaccaaat cttttgatgt tgttccctct acctcaacct  173460
cctgacttgg agttgtgcaa tgatttatac atgtactaga cattcgtgtt gctatcttgg  173520
tttgtctttg gaagagaata aaggtgtgta attatgttca acaagaattt ttttacatac  173580 tttttcttg cattttttt tgacttttag tttttgtttt gatggatgtt ggcttcactt  173640
gagaattttt gtgccaattt ttccatgttt tacttgcttt taggcagtca atatggtcgg  173700
tatgtgaaag gactcgactc atttagtttt cttgctcatg tggtgttatg ttctgcacag  173760
gaacaagatg ccgcaagctt ccaagtaagc cacctcataa tcgtatggta tgttgtgtaa  173820
tttgcaaatg tgattgtaca atctgattag tggtatttga tacataattg tttgtgcaac  173880
aacagtcaat atttgtttct caagcactat tttggcaata acaattgaga atgaaatttg  173940
atatgttgga tcattgaaat tcaagaattg taatataatg aggttttcaa cgcaatataa  174000
atcatttttt aatgctagca attgaaatgg ggatttagtt tgatggattt tgtcaccagt  174060
cctggatccc ttaagagccc ttcaagacat acttaagact gccgcttcaa taccataatt  174120
ttcactccat aaccacatta cactctttca ataccagcta ttgctattgc taatatgctt  174180
ctcctaccta ccactaccag tatctgtaat tccatatcat atccatgtac acgttggaca  174240
cagaatattg aatcatcctc atattatttt tacaaaaact agacattgta tcagatgctg  174300
tacaacttac aattaccaca ttaaaccaat ttgaccagaa ttacttcata tattggattg  174360
gattgatgca aaagctcctg aatccaattc tataaacatt tcattctgg attacacgaa  174420 ggtaaccaag tgcttacatt cacaagattt cacctctccc atcaaatttt tgaaattcgt  174480
cctttcaatc atttatcata caaacatgca aaaggaatac acgaaactac cacttccata  174540
tcaaatttgt acagacccag aggctatatt caaacgccga gggtgtaacg atgtcaaaac  174600
```

```
atatgcaaaa aggatatcat gcaactcaaa ccagtccatc ttttccaata aacgttaact  174660
ggacaccgag cacctctaac acaaaattaa cttaactttt tctatgtcct gtttgtgccc  174720
ctagctcaac catcaaaaat gtcactccta tatttgtatg tattttgatt gttgagctag  174780
gcgcacaaac cagcttagac aaggacacaa aaaagtttga attaattttg tgtgttagac  174840
ttaaggtgct cagtgtcctg tacctgtaaa gagctcgtgc tcttcattta ccatattaca  174900
tacatgattt taagtcaagc gtatgtccca gtagctaaca gtggatttat taaatatata  174960
tcaccaattg acaccagatt ttgtcataaa ctccaaacaa ataagttgat ctttcaacag  175020
atgttaaagc ttacagctac atatagtcaa acccatatta gcaatagaaa taggtgttgt  175080
taattgttat tcggttagta aagaaagcta aagtagtgaa aaggttaggt ttagttatgc  175140
agagtttgtg ttgtgtttgg cttctgatta gaatagtggt ttgctctcaa ttcttttcat  175200
cagaatcatc attcatcact atatattgag tccaggtaac taactaaatt tcattaagga  175260
ttaaacttcg tgaaagccct aaattgctac atgtaccatg ttgcaccatc agatattttg  175320
ctacccattg cttagcctaa atgaggtcct tccttcgtat tgaattttgc accatcagat  175380
ttctattttt tgttagcttt gttgcttatt tttagtgtta tttcatccta atttataaag  175440
ttgaatgaat atcacgttga atagatatct catttgatat gaacgcttaa agttgaacaa  175500
ggttggaact ttgattgatt atgcatttta atcttgactt tgaaagactc ataaaaatga  175560
tgaggcatga atgtgataat tactgattta atatgcattc tggccttagc agcaattaaa  175620
gaggtgggaa ttgttgagca gtaatacaac acttatagat ttgacccttta caacaatttt  175680 atcaatgtaa atttgaaagt gtatgtgtgg agataattaa gcattaaaaa tatccggcat  175740
gttacagaaa tcatagtgtt tctctcaacc ctcacttata gactactgca actgccctca  175800
tattataaaa ttttcaactt gcaatatatt gcaatggaga atgaatacgg cccatattag  175860
atttgggtta aagtaaagct atgaatcata gactaaaacc acacaaataa gctgcattgt  175920
ctatctttcc atacgaaaac atcagtcatc tcgatacatc caaattgcag caatatatac  175980
aatctatact caagtaactc aacaacacag aatatcatca aaagttaaag agcctagcca  176040
gtaaactttt tcaatccaac taacaatcta tttagatttt tacatagtgg acatttggta  176100
taattttgta tgaattactc catggaaaaa caacatttga aggtactgaa attagagaag  176160
cattgttgaa tatagttggt caggcactaa agtgtccatt ctgtggtcaa ttgttaccgt  176220
tctcgtcacc aaccaataaa acgtttagtc agaacctcat aagttcttgg gtcttcccca  176280
aacttggtag cagcttcttg gtgtccgtag tccaccctga agatacgtgg ccactgcaaa  176340
ccaagaatac acacagatta atacatcaaa cacgaaaatc acctatgttt ctttagggag  176400
agggggcaaa ggtatgcata ccaaaaagta aatacatcta aaacaattct agagaaagct  176460
gttaagcttc acaagcatgc ttcattctta aaagtctcat ttaaattctt tagagtttga  176520
aaaattgaag gaaaagctca cctgtggcca tgtgggttgc caggagctct tgaattcggt  176580
ggctggggaa gaagttccaa gtcatctaat atgctaaggc ttgattgcac tgtcaatttg  176640
aattttgacc cttattgcaa gaaaatcacg ttattatgct tgaactaagt agtgatcttt  176700
aatgcagaca atttttgcact tggatactct tacaagatat tttgttttct tgtattacaa  176760
tatcagatga tttaggggct tctttttcttt tgttagcagg ttcttgaaac gaggttttaa  176820
tgaaaaaggt cgagctcata atgatgttga gacagagcaa attgtctttg aggagatccg  176880
gaatgcagat gtattgaaaa tcagttctat tgtgcaaatt aggggctcaa tttcccttcc  176940
ttggtctcaa gaaacgtcaa gattgaatct aagacctgac attatatgta tgatcactcc  177000
```

```
attttttatt ttcctatcgt cttcttttct tgctattcca tgtaacatat tatttgaata   177060
tagtgtcaaa ggatgattct caatatgaag caactcggag acattttcaa atcttgtgg   177120 atagatatgg taatccgata ttcatattga atccatttca tttctgatat taagcaaata   177180
catcaaagaa aaaccaaac tttttatgtg ctaacaatga tttcttcatc agagggtatt   177240
ttttccgtta acgtatcatt ctatatatgt atcaatccat tctataaaag ctatctttac   177300
cttttgatca agtgaggaaa gaagacatgg agatttcatt gaggtcagaa acataagcat   177360
taacactact gatgcaccca gtattaatag cagcagtaac agttgggcta aaaatacttt   177420
caacaacgta aaggaccttc ccagtatccc gcccaaggca gggtccgagt gggaggtttt   177480 cttttaaag aataatgcaa gtacatatta ttatgcttaa atttatcata caaatgactt   177540
tttaaaagca aaaaattaaa taaattagta tctacaacaa attttacaaa gcaaggata   177600 gttctgagaa atatatatta atcagcatat atcatcattg caacaaaatt catctggcgg   177660
aagaatttag ccacttaaag atcctaagga taggtaaagt attgtaaaga agaagagaag   177720
agccatactg agccaatatg cacagcagtg caaattacaa aaacaactgc tgcatcctcc   177780
atttgcgtgt atctccaaaa ccagaattag aaaaaaaaaa caacaaacag aacacgccac   177840
cagagatatt agcttttgt taaaaggaca ataaaatcta cttttgtagc ttcaccaatt   177900
cttccctctt aaatgtaaag tacttttctg attttgggga ctataaccaa tgctgtgaca   177960
ttagttttcc aaagtgcttt ttctgatttt ggggactata accaatgctg ccatttaga   178020 tttcccccat cctgtcactc aacattcatt atacatatat cctgtcattc aacattcatt   178080
attcatatat atatatatat atatatatat atatatatat atatatatat atatatatat   178140
atatatacat gccttagtcc ttctcactaa catcacagta cagcacacat caaggttagt   178200
caagctattc tctcttcttt tcattttatg acctgctttt gtgctgctaa atagattact   178260
atgctaattg tgctactctt tctaatcagc ttttgaattt gctaaatcaa caatggatat   178320
aaatgataga tcactgtgct aattatgctg tttacatttt ctgatatgaa tgtgctgctg   178380
agtttgatca tatatatata tatatatata tcaaagtttt cattatttga agataatatg   178440
atggaaatta atcagattgg agggtttatg ttctaatcat tttaacatgt tattgttgtg   178500
acttatttat aatgaaaaac atacatcaat ttatcacttg ttgatttaca tgaaaagatt   178560
ttctcatata gttgagattc actgtgctaa tcagcttcta tgacttatag tgctatacat   178620
gttcagttat gccaattatg tcagctttac ctattataca attgtgaacc atatcatgtg   178680
taattttatt atgttttttgt tttgtatttt tgtgttgatt ttaaaatcat tttgttaggt   178740 attttttga tgttcttata atttactaat ttctactgga tttgcaataa ccggcaaaga   178800
cactgatatt ttgttctgat tgagtgtaaa ttcataataa tgtttaagtg taaattcata   178860
ataacgataa actcgtatca catccaattt gtgaaatatc ccttagaata gtcgagagac   178920
aggacctgaa atacccaaag agattggatt tagaaagggt aaaactacat tatttgacct   178980
gaaatgcctt catagaaagc agttatttgg caatcattga ggtacatagt cacattacac   179040
ctgtgtcaaa caccagatat acaaaggcac cacaccaaca atttgtgcag cttaactttc   179100 aacctttca cttacaaatt acaatactct gaataatgtt gctttattaa ttgtgcttaa   179160
atttagttgt gggagattta ctaaaaactg attctagctt atagcttatt agattacata   179220
gaccatcata gaaatctaat atctagactg caaatataaa cacttgattc taaaacagaa   179280
gaatatctta gattaagttt aattggccaa taagtttaat ttaatttggt ttaagaagag   179340
```

```
aacttagcac tatctagctt actcattact tattttgatc aagtcatcgt gttgatggtg   179400
cattgaaagt tttagcagat ttatatcttt ccttttgatg atcgagtttt atcatgattc   179460
taattctttg aatattttaa gaggatgata ttgtaaatgg attttcaacc atgcagatca   179520
tcaccatcat gaaggaaaaa tactcaacat tcaaagaatt atcagacaaa gcaaatatcc   179580
acaaggtgaa gataaaagtg atagaaaagt ccagaccatt ccaatcacca ggaaaaaaaa   179640
aatatcaacg tctggtattc caagatgaaa atgtatgtca atattctatg cctataacct   179700
tttgagagat aacgacaatt caaacaacca ttaaataatt cttttttattt cacttgctgt   179760 tagggtgatt tgatgaaggc caccctcttt gaagatgata ttgatgcata tgcagattta   179820
atacaacaga accatgaata ctttatttct aatccaacta ttcgaagcgt ggaagagcaa   179880
taccgttcaa aatctggtga ataccagatg accttttaaca gtcgcacaac tattcaaccc   179940
actggttctg caacccagct atctgaacca agctattata ctatttctac aattcctcga   180000
atctctggtt tttatgatag atttggtacg taaatgaagt tttgattatt tctttagtat   180060
ttagtctaat atttatatta tacatcaacc ttttgttaaa cgttatgttt tccacactac   180120
tttaagtcaa aatttgtttt actttttagat atactcggta ttatcctctt tattggagat   180180
actcgtactg tcaatggagc atttgatcaa aagaatagcg tttctgaaat aatgattact   180240
gatcataggt attttcttaa actcttatcg tatacacttt ttgaagcaca tctatttaat   180300 tagttttttgt tatattgatc aatgattttt ttcttacaat taattataca atgatgtagc   180360
tcacatcaac ctttaacaat ttctgcttgg aatgatcttt ccgactattt taaggagaag   180420
cctattgcat attccatttt cgggtttact tctcttcgag taacttcaca taaaggttag   180480
acttaaatca aatgaggcat ttaaatagga ttcgaggaag tatatgttat cctcgccatg   180540
tgaaaatcag ttgtgtttta ttatttgtga ttaacactca cttttgcaaa aattaggatt   180600
cgggttatca accacaatgt cctcatcaat tataactgca ccaacaggtg aaaaggcaga   180660
attgctaaga aaatggtaac gtatcccgca tagaattttt acgtaagatc aactattata   180720
caaataactc atggttccat ttatacaggg cttcttccca tgcagacttg cttcatgaac   180780
gcaaacaaca aattttacaa agtcgcattt catcaacaaa gcgacaattg acaacaatag   180840
ctttcgtcaa gaaaaaaaca gtatatctta caattcacat gtttcatttc ttatgtattg   180900
tgaatatcat atcagtaaat gttgtcttcc aatattatta gatacgtact atttgtttac   180960
acccttatca aatgtcaagc aaccattaaa acaatagttg ttcttaaata tacaaatatt   181020
aaactaactt tgatattata taggcagcaa ataccataca agatgaaagg cattggatta   181080
aagcattcgt caccaattgt tgctatgatg atatacggaa attcctaggc tgcaatggct   181140
gtaataaaaa gaccgacaca gaaagaatg aagttttac ttgccaatgg tgtcacaaaa   181200
aagacagcat atcaatgcca aggtttgctt tataactctt ttgaaattta attaatgcaa   181260
tacaaattga taacccgtaa acaaaaattc aagaagattg tcaagactca agatatactc   181320
atacactcaa gaagtgagat taaccagaac cgagatatta taactgagcg aaaacccgaa   181380
tagacaccgc tacctacatt atataaatct tcacaaaagc caatgcacat tgttattctt   181440
cgagctttaa caaggaaagc acagttatgt ttttttttagt cagacaaatc attgaataac   181500
acttgattat tgaaatttga gtagctatgt aagcaaagcc ttcttaacaa aaaaaaggta   181560
aaaaaaatag taaatcatgc attccattca aatcaaaggt catctctagg gtttgggcaa   181620
tatgtaacag gaaacatgga aaagacagga aaatgccaac atcaaactca tgaaacaaat   181680
aaatacaaga gaattatatt atacttaaaa tatttaaaat taatattatc actattttt    181740
```

```
ttaaaataaa attgcattgt cttttttatgg gtgttatggg taggggagag gattttttcca   181800
tacagctgct taaattaaat ttccatgatc caatacatct attcttgata agctatattc   181860
aattgtaata tatgttttac atttcagatt agctcttagt ttcgatgccc aagatgatac   181920
gggatctatg agtctcacag cctttaacga aaccgttgca cagctctttg gaagaactat   181980
tagtgaacta tatgctcctg aaacttatgt acgtcactac atctatacac tctaaattta   182040
cataactcta tacgtttatt catctgtatc tatacaacag gacaagatta ccacttatca   182100
agaaatcgca gaatcaatta aagctaagcc aatatacatt gaacttggac ctacaacagc   182160
tttagcaaaa aatggtgttc taaaatgggt gctaaaatca gtttccctta aaccatatag   182220
cttcacaaga acccaaaaac aaaggattgc tgctcccaac aagctcttca acatctgtct   182280
taccaacaga caaaaaacaa gatcagttat ttactccccc atctagaaaa agtgaaagct   182340
cacttaagct atccactcca gctacaaaca acactcccct ggactcccaa ctaccaagtt   182400
ccacttcaat aaaattcagaa tctattcaca attcagaggc aactcctcag actgaagctg   182460
aactgaaagt gcgtcgggcc ttagattttt ctgtggttga atcttcaatc aatccagaag   182520
actccatcta ctaaggttct tcactaccta ttgtaataga taatatcttt tcttaggact   182580
taaacaaatg cttggtgttt gaacattgtc ttttgaagca tgtattttgg gcaagtatgc   182640
tatgttttgc ttattaatat agcaacatat ctacatatgt tgtatgtgaa caacttgcta   182700
ttaaattcta gaatccaaga agttgcttat tattaaatat tctgaattga atcagttatt   182760
acaaattaat ctgctcatat tgaattgatg ttcctatgta ttactgtatt tttgcatctg   182820
ttgggctgtt tgtgcatctg ctcatataga atcaattcac attcatgaag ttagtattgt   182880
ttctgtttgc agcagaactc aggtctatca tgaccattcc atcgtttgtg gttttttaatg   182940
aatgtatatt ggctgtattt attttgttga aacaattgta gtattatact tatgctaatg   183000
agtgttattg agtatttgtt gagttgatgc atttgtggtt tttaatgaac gtatattaat   183060
tatttgttga atgtaggaaa cccagaaaag ttattgtagt ttattggctg tatttgacta   183120
acaaatatta caaattgaat gtatattggg tgacccaatg aaaactaaca ttttattga   183180
attttttgttc actgtcctgt ttgagttgat gcatttgtgg tggataaaca acactgtgtt   183240
attgaatgta tattgggtga cccaatgaaa actaacattt cttaaattga ttacttgcac   183300
ctagggccta ggggtgttca atggggatta aaaatatttt attaattttt tttaaatgat   183360
aatttaattg ttataaattg aaaaatgggg attaaaaata ttttttagtag taaaaatggg   183420
ccgaattggg ccagactggg cttttcaaag cccggtccat ttaaagccca tattaattct   183480
aaagggccct tatccggccc agcccatatt actaggggc caaattggcc atatactaac   183540
aatactttgt gaatgaagca ttacatcatt gtaatatagt tattgtgaat tttgtatatg   183600
aaaattactt ccctgtaata aagtaacaac ctgttgtatg attaatctaa ttctttcggt   183660
tctttgttgt tgcgatgaaa ctcctatgac tcaaccaaat tgcaatataa atcagagata   183720
acatgtgcaa gacaattcaa ctaataagat gtcataatac tcctaccata tgacgacatt   183780
gagatttttta tttttcatgt gtattattct taatagaaat gtataaaata acatttggaa   183840
aactcgatag tataacttgg aggaccgcgt gcgtagcacg cggccctaca actagttaag   183900
ggaaaatgtt cgtttttaaaa ttggattttg tgtgtatatt gatttttttac aaaattgtaa   183960
tgtataaatt tatttttaag tccgaaaata aaatgaatat caaacaattg agtttgttat   184020
gagaataacg atatggagta atgcgtcaac tttttcaatt ttatacgact caataataag   184080
```

```
gaatcaatca aacaacaaag gaaaagaata aatgactaac gtttgaaaag tttaaataag   184140
gaaaaaccca attttgttat tcggaaataa tattaggcaa aattgttaga aaatacctag   184200
aaaaacactc ttttttgtgaa aaactaccta gaacaatttt ttttgtcaaa aaatacctaa   184260
aaaatttggt ttgtttgtaa agtagtacct aatgacggaa gacatccaat tccgttagat   184320
ttaatgactt aaaaaaaata ataataataa taaaaagttg tttatcttta aaagccacgt   184380
ggacccaatt tgattctttc tttccaggaa cccaattacc caactaaaag aacccaacta   184440
agaatggaga agaaccctcc gaagaaccct aaaacaatag ggaagaagtt actggtttca   184500
agatgtaaga atggactaag aaacccatgt cacgtgattt ttaaaatttt tttattttcc   184560
ttctttaagt tattattttt atttatttt ttaagttatt aaatctaact ctgttagatg   184620
tcttccgtca ttaggtactt cttcacaaac aaactaaatt ttttaggtat tttttgacaa   184680
aaaaaaatgt tctaggtagt ttttcacaaa aaaggtgttt ttctaggtat tttccaacaa   184740
tttttccata atattaatat attactccct tccttaaaat tatttccatt tgttatgttg   184800
gatattatat ttgttgttta tataaaaatt ttctatttat atcacaactt ttgtttaaaa   184860
ataaccttat ttatcctcat ttaaatattt taatatcctt acatacattc cgctaattac   184920
tttattttaa cattttata ttccttagga tccaatatat atatatttcc cacttacact   184980
aaaaaaatat tttttattag ttgtgtttcc cataaccaaa caccacacta taacttggga   185040
tctcaaaccc gccggcataa aaaaaccccc gtagggaaaa aaagccattg gaagagggag   185100
accaagaaac aggccaccct aaacagcata gttgcagact aactacttta aatagttcca   185160
agtgaagaat gttctgattt ggatattttg agggttttaa tgtttctata agccaccgct   185220
aaggataagg ctcgcatcct ccaaaatcaa ctacattgt ctggccatag ataatgtttc   185280
aacaagcaat gtcttgtgaa ttgttgttat gaatagttgt aaattttca ttagatttca   185340 aactggcatt actagaattt gttgcttcaa cattactaga gtttgtaaca aaaacaatat   185400
agtttgtaat tgtaacaaca atacttcctc cgttccataa tacttgctac atattccatt   185460
ttgggaaatt tcttattact tgctacattt ccttatttgg taacaaacca atcatttaaa   185520
gttataccta ctcctacttt tatcctactc tatatctaat tattcctatt tttctttttc   185580 attttttcaac aaataatatt aaaaaatttc aaaaagcaac ttttcaccta ttgctaatca   185640
ttgcacagtt actccttaat atttgtgccc atgcaacggt agcaactaaa taagaacgga   185700
ggaagtatta aagttattgt tccgagtaaa ataagggcac tcatacgtga aaatgaacaa   185760
ttaaagtcac ccaaacagag ccaagcttca gccccatctt tattaagtat aaatttatat   185820
caaactagtg ccaaataata catattatat taaatgatct aaacctaatc ccaacttaaa   185880
tttctgggtc tttctcttaa atttctgggt catttacaaa aattaaaaaa acgtttgctc   185940
ttcactttgc gttctttcag tttctcttca tcagcttgct ttcttcctcc ctgtgcgact   186000
ggttctacct taagaaaaag cttttcttca cccactcact tcatattcat aattcctctc   186060
acttaagtaa atcaatcaac tacattctac caaacaccct tctcaaagtg aacaaaccct   186120
aattctcctt ggagaatcgc ttgacgcctg acggagaatc gcttcacctg agttgcttct   186180
ttccaccgga cgtttggcct gctggctgct gctccttggt tccctcgcag gtcgcagcct   186240
cgctgacgct gactgattcg cttcattcac caaaccctaa ttctccttgg agaatcgctt   186300
gacgccatca aagaaggaat tctcaagcga tacttgttac atacaaattt aagtacttgt   186360
gaattgctgt tacaaactgg tgaatttctg ttacaaaata atgttgttgt tacaacttca   186420
atattgttgt tataaacttg tgaattgctg ttataaactg gtgaattgct gctataactt   186480
```

```
tctgaattgc tgctataaat ttctgagata ttgttacaaa ctttggaatt gctgttaaac 186540
tggtgaactg ctgttataaa ttggtgaatt gttgtaaata tttgaattgc tattataaac 186600
tagtgaattg ttgttataaa ctttaatatt gttttcatat ctccttaacc acaacaccaa 186660
ttccaatgat tccaaagcca aatgtttctc aactcaatga agaatcccgt gtaaatttag 186720
ttttgaaaag aaatcacaat actatccccg aaacgccact gttttcgacc ccaaatgcag 186780
tcagtttctg acagcttctg ttcttgtttt tgtcgacttt ggctgcttct ttccaacaaa 186840
accaattgaa ttatgcaccc cactgattcg cttcattcac caaacagaac accctgctga 186900
gtgtgtactg ccgccggctt tcctactgcc cacagcccac cgccaccgga caggaggcca 186960
ccactgacaa ccatacgtcc agtccatacg gccaccaatt tcaggtatta ttattaatta 187020
aatgttatat tttataaatc cttaattccc aaaaattagt tttttttttt ttttcttatt 187080
tcaaaattca agatagtttc ttgattgaat tagatattat atgtcattat gtcaatgtta 187140
ttgtgctttg ttattattct tgccttcatc ttgagtattt gttttatgg gggatgaatg 187200 atgatgtatg tatgctaggt aaggaagata actttagggt ggccactgta tcaattcaga 187260
ataatgcctt tcatcttata caaattagtt atttagcgac taggtgtgat gttgattttg 187320
tgctggagta tgattgtttg taacattgtc ttgattttat ggtttaaggt tacattttac 187380
acatttgtag ttaaatttta tgatttcttt tgtatgcata taaagtgctt gatgaaatgt 187440
tacaatgaaa atttactact ttttttgta tttgaattga ccccttttaat aagtgttgta 187500 atactttatg atttctacaa tgaaatgcca cataaatttt tatgatttct tgtatacaag 187560
cggtcaaaac gactgctttt agggcttgat tcttgctctt cttcaaggta tacccattgt 187620
tgttcaagct tcattagttt gcttttaggg cttagttttt ttatactaat tttaattttg 187680
tttcattgta taggttatac acaacccacc attattgtct tcttcaagtt ctcaaaccca 187740
cgaaaaattc aagtatttt ttcattttcg attttgtaaa ttaggtttaa attgatcaaa 187800
attgatgaat gtgtatgtag ttgtatttat atttatacta tgtaaattag gtttaattag 187860
ggttgtttat ggttatatga atgagttggt tgatgttgat tattgataaa tttggttgta 187920
ataggggttt ttaagtttta aattaggttt aattaggggtt gtggattatt gataaattta 187980
tcatatgtta gtgcccctag ggagtgtgaa ccttagatcc gccactgttc acatcctcat 188040
ttaaggtatg aaccctaatt tttttcaatt tgcaaattga tttctttgtc atgattgttg 188100
tcatttgact tataatagat tgattgtttg taacattgtc ttgattttat ggtttaaggt 188160
tacattttac acatttgtag ttaaatttta tgatttcttt tgtataaata tgaagtgctt 188220
gatgaaatgt tacaatgaaa atttactact ttgttttgta tttgaattga ccccttttaat 188280 aagtgttgta atactttatg atttctacaa tgaaatgcca caagaaattt tatgatttct 188340
tgtatacaag tggtcaaaac gactgctttt agggcttgat tcttagttgt atttcatgat 188400
ttacatgtta tcaggagtaa gactagttca cgaataaagg acattaattc ttaggatgat 188460
gaagtgttta gtttgaccgg ataatttggg ttaatttgct atcaaattga tctataaaag 188520
tgaaaataaa ggatctttct tgacaaagag tccgaaataa gtggtgtata ggttgatcat 188580 tgaaaaagt atttttgtt aagaaattag acatttaatg acatcttcag aagatcaagt 188640
ataaagagtc cgaaataagt gatgtatagg ttgatcattg aaaaagtat tatttttgt 188700 taagaaatta gacatttaat gacatcttca gaagattaag tataaagtta acaaatgaat 188760
aaacgtgtag gaaagttaac gaatgaataa acgttctgaa gaactttatg agatgtcgga 188820
```

```
agtgggttgt acaacaggta actgatgtgc aacgctcttc atgagttcac tcggctcttc  188880
atgagttcat ttagacattt aatgacatct aaactagaac attattcacc tggcaccatt  188940
aagagtagtt cgtttgcaac gctcttcatg agttcactga tgtgccggaa gtgggttgtg  189000
caccaggtgc atattttca ggtgcactaa aatccggaaa aatggggact atgcagtagc  189060
actgcatagg caactttaac aaattcacta ttttcgcaaa ctttcatctc tatgttggtg  189120
cctctagaga gtgtgaacct tagatccgcc gctgtatgtt cttttgtgct tctgtttgtt  189180
ggaacattgg ctgttcactt tgcttcactc tccttcacca gcttgcttga cacttcttcg  189240
ttgttcacaa taaataaatt gatcatataa tgtgggctac tccctctttc cacttcaatt  189300
caactatttc ttgagtttca tctaacaagg aattatttat ctctttattt aaataaagga  189360
aaaattacaa aaaactacct attttaatgg gtaacttgca aaaaactacc tattttaatt  189420 tttttgcaa aaaactacct tatatgatat taacgtttgt taaacacaac ctcttgacgg  189480
tttcagttag ttgaccgtca aaagttagtt tgacttttca cgtgacttgc acgtgacctt  189540
cttttaaacc tttcccttta attgtttctt tgatttctta ggttttaaag cacgttttta  189600
gttcaaacct ttccccttc cccaagttcg tatgaaccct aatccgcctc tttttcttc  189660 aagcccaaat caattcatgg attcctctca ctccaaacaa tcgaagcttg acagatgtgg  189720
ttgcgatttc cttttgcaca gcgaatttcg tggactaaag aaaatccagg ttgacgtttc  189780
aaatttcaat gcttgccaat tttcgatcct gacactaatt ggaggggatg taagaagttt  189840
aagtggatcg atgaacttga aatggttgat ttcaagatat tgacatcaag gctttgttgc  189900
ttggaacatg agaagaaca agcaatttca gaatacaaaa ggcttaagaa gaaattaatg  189960
aaggagagaa agcttggaaa agagatatca tgttttattt tagggttttt atttggtttt  190020
ttcttgttgt tggttgtact aataaaggtt atgtaacctt tagatcatac tgtaagaata  190080
tttgttatgt aggaaaatat ggaaatgttg ttgtaacgct tttgcaaact tgaatgttga  190140
agctaattat agaacatcct tttttgatt acttgcttcc ataccataat tgttccataa  190200
caatacatac tacttatatc ttacattaga gtaggtggtt caaaatgaat aacaattcaa  190260
gattttcgat gatgtggacc tttccgtttt gaatccaatt tattgaagat caactccaag  190320
tctactaaag gggggggttga acaaaatttc aaactacttt acaaaaata tattgaggtc  190380 tgggaatctg tgactgctga tgaggagagc atgaattctt cacactgtag tcctagtcct  190440
agcaccattt cctctactcc ccttatttct catacccatt ctcctagtcc tagcaccatt  190500
ccatttccct ggaagagaaa gaggtgcacc ttggtctcga ccaggtatt ttgaacatag  190560 tcatgtgatt atttcggggt cttcttgagt gtgattctta cacattgaag atgaatcaat  190620
aaaatgaaat accttgaaaa taaaaaaaaa tcaaaaaaag ctatccgggt caaacgagta  190680
cctgagtcaa taaattatcg gcccatgacc cgacccggtt aaggcgggtc gggtacccga  190740
cccggaactt tgaattttt ttagttttcg acctgccatt tatgaggcgg tcggcgggt  190800 cggcgggtcg ggtcggcgg gtcggttgt tttgaacacc cctacttata tcttacaaag  190860
acaacaaaac ataaaagttc caacataacc tagcaaacat aacagacatt acaaatacac  190920 ttcttttgt tgctgagagc ttgaagaacc ttgggttgaa atcaccattg gcactgaacc  190980
ttttgctcct ctcttttgt aaccatatgc ccatgatttc tttctaacct ttttgtgctg  191040
gcagcattgt tggtaggggc aatagagctt gcagttgttg ttgtcaccaa tggtgttgag  191100 cttttcaaacg aaaagagaa ggtagattag aagaaaaaaa cgacaataat catatttcat  191160
gttaagagta aagcacaat acagaagttt ataacaatga gacagaagtt tataacaata  191220
```

```
aagcttaatt ttgttttggg atgaaattga ctctatttca gacatgtgaa tgactggcag   191280
cattgttggt aggggcaaca gagcttgcag ttgttgttgt caccaatggt gttgagcttt   191340
caaacgaaaa agagaaggta gattagaaga aaaaaacgac aataatcata tttcatgtta   191400
agagtaaaga cacaatacag aagtttataa caatgagaca gaagtttata acaataaagc   191460
ttaattttgt tttgggatga aattgactct atttcagaaa tgtgaatgaa atttgcaata   191520
tgttttgagt taaatgtgaa gatttaagaa tcatatttga cttaaatgtg aagatttaag   191580
aatcatattt gacttaaatg tgaagattta agaatcatat ttgactttg atggaaatgt   191640 ggttgtgttt gtgtgaattg ttgtggttgt ttgtaggggg gttcaaaact acccgacccg   191700
cccgacccga cccgccgacc cgctgacccg cctcataaat ggcgggtcga aaactaaaaa   191760
aaattcaaag ttccagggta gaaacatcct taacatgaaa cttattaatg agtgtaattc   191820
cactaatggt agacattggc ttaacttcaa gattatccat aaccatatat gttagatata   191880
agtactatgt tattcatttt gaaccaccta ctctaatgta agatataagt agtatgtatt   191940
gttatggaac aattatggta tggaagcaag taatcaaaaa aaggatgttc tataattagc   192000
ttcaacattc aagtttgcag aagtgttaca acaacatttc catatcttcc tacataacaa   192060
atattcttac agtataatct aaaggttaca taaccttat taatacaacc aacaacaaga   192120
aaaaaccaaa taataaccat atatgttaca acccctttta catacccacc atcatcccca   192180
ctgttcctaa tggcagatga aatccacaaa atctttgttt gcttacttgc tcaaaaaatt   192240
cacgcgccac gcgctgctgt ctggtcctac tgtaaaaatt cttaaaacat ataaactcgt   192300
gtttgtctac cttcgactgc ctaatatcta ctcggaattc gatctttaaa ataataatta   192360
aatttgaaaa atcaccaaaa ataataatcg ggtacccggt gtcccgaccc gttttatccg   192420
ggcacccgct aaccgggtac ccgcattaaa tgggacacgg gccgcaaaaa taggtaactg   192480
gctaactggg tacccggctt tccgggtacc cgtttagccg ggtacccggt tatgaacacc   192540
cctagttgtt tcacttgttt gtgtgtagtg tagtagttgt ttgttgttag ggacgatttg   192600
gaggcgctgc tacctcggct ctgttggtgc tgcagtagtg ctactgctgt tgtgggttgc   192660
atctgctgct gctactgttg ttagtggtcg ttttgggcag ttgttgtcgt tgtactattg   192720
ttgctacaaa cttgtgaatt gttgttggtt gagtgcttga cattcgtaaa tcgatttgtt   192780 taattttttgt tgatgatatt ttttccatcg tgttgctata attcgaagtg tttttgctta   192840
attgcggtgc ttaattggac ttttgattgt tgattctgat gatatttgtt catttattga   192900
tgatatttgt tcatttttaag acacaataca taagtttata actatgagac agaagtttat   192960
aacaataaag cagaagtttg tttcgggatg aaattgactc tatttcagaa atgttaatga   193020
aatttgcaat atgttttgag ttaaatgtga agaattaaga atcattttg acttaaatgt   193080 gatgatttaa aaatcatatt tgacttttga tggaaatgtg gttgttttgt gtgaattgtt   193140
gtggttgtgt gtgttaagtg tagtagttgt ttgttgttat taagaagtt accagatgat   193200 tgatgtatg aattattaat ttattgaatt tgtttcaatc aatttgatta agggtcacta   193260
aaaaactaaa gttggggtag ctacaactag atttggtgag gggttattca aaatcttaac   193320 tagggtaac tactgaacaa ctaattattg aatttcagat gtcaagctct tcaaattgtt   193380
atgaaaaccg agtaaaatgc tattgtggac atgacttatc tacgctaagg gcatggacag   193440
ttgaaaaccc cggaaggagg tttgtggcat gtcctgattt taattcaaga accaaaatca   193500
gaggatgctc cttctttagg tgggtggaca caccaatgac cgattggcaa aaagatgtca   193560
```

```
ttttaaagct aatggctgaa agagacagtc ttaaaaaga agttggtatt cttaaaagaa    193620
aatctgaatt gtcaaatcaa aagattagga agatttcaaa aagaagttgt ggatggagtc    193680
tcatctgtgt caaatgtgtt cttactttca tagtattttg gatcatttca aagcttgtat    193740
agggtcatca tgttagtctg atgttttttgt tggaaccatt gtatatatgg aatcaatgta    193800
attgaaatct agaagacaac tatgaattat tgtatatatg gaatctagtt tatttaacaa    193860
aatgaaagaa caagttggca ctctgtattt tgctttctgt aatggtctac cgtcttgctt    193920
tgtctatttt ctatactcta ttgctaccat ttgcttagta atcttgactt atatggttta    193980
taccataaga ctcggaagcc cactgaaatt tggttcttgt gatatacggt tgttcttca    194040 tattcctaac tttaagtatc tatgtgtggt ttgacattgt ttacttcaca aattcacatt    194100
gctgattttt ctgtgaaatt agatacttgt tacatacaaa attaagtact tgtgaattgc    194160
tgttacaaac ttgtgaattg atgttacaaa ataatgttgt tgttacaaac ttattattgt    194220
tgttataaac ttttgaattg ttgttataaa ctggtgaatt gctgctataa ctttctgaat    194280
tgctgtaagg aaatttctaa attgctgtta gggtaggctg ttataaattg cacacacaag    194340
cctagtgttc tatatgacat gaactcgaaa gcccactgaa atttggttct tgtgatatac    194400
ggtttgttct tcatattcct aacttaaaca atgtcacaaa cgcttgtttt tcagcaatga    194460
gacataacaa atcaaccgca aagacaatca gaacagtaag taaacttact tcagttcttc    194520
agtacattcg aatttgtgaa ttatttaatg atgcaattta tctttttatt ttacaggatg    194580
gaggacattc ctccaaaggg agttcgaagc ttaagactgt acatacacta tattcagagc    194640
ttgatgacga tttgaaggct cgtatcaaag caagaattga ttctaatggt cctggaagtt    194700
ctttgctacg actacttcat ttgaaaacag aaagctttga acttccggtt caattattag    194760
aattgttctt caataaatat caaaaggtca accactataa tctaacgcca aagagttcta    194820
tgtgtttctg catagatggc gagaggttaa accccacttt ggaggacgtt ttgtacttga    194880
ctggtttacc cattgtggga aagccagtca tcttcgacaa aacagttgat aatgaggctt    194940
tcatgagagt ttttgaagag caaggaacta atattataag tttgacaaca ttggatagaa    195000
ttgccaaaga tcacacgaga tcagatgata agaggataaa ggcaattctg ttgatttga    195060 tatgctgtat catagctcct tctacaagtg gacatgaatg tcgagccact ttggtccagt    195120
tcgttgaaca tttggaccaa gtgaactcat atgcttgggg tgcggcatta ttggcgtatc    195180
tttatagaga attgaagggc catgggaaaa agaagctaat caatggatttt acatggcttg    195240 tggtggtaag aacacttatt taacttattt tctcttatct tgtcattttc atcatctaac    195300
attttttttt acagggttc ttcttctacc gtattaaagg tctagcggag attttttggtg    195360 tggccatgaa tcaagagaac aataacactg ctccttgct acacacgatc aacttgaaag    195420
gcaaaggtta tgtatcaaat ctgaaggtca caacactctc cgagaagctg caacaggcaa    195480
aaaatctttt ggctaacgca acagaggtaa agcacttgt gcgtgatttc aattttcatt    195540
ttaattgtat tatatttctt tatctttgat tgatgaggtg actttttttt gatgttgtat    195600
gaaacagtgt attaattggc acccatatca gtcaattgtg ttgcctgatc atttgcgaag    195660
acatattcag ttttgctcca tcatcacacc aatgttttgt ttcaatcatg tggaaaatca    195720
tcttccacat gttgtagcaa aacaattcaa gattttcgat gatgtggacc tttccagttt    195780
tggatccaat ttattgaaga tcaactccaa gtctactaaa ggggggttg aacaaaattt    195840 caaactactt tacaaaaaat atattgaggt ctgggaatct gtgactgctg atgaggagag    195900
catgaattct tcacactgta gtcctagtcc tagcaccatt tcctctactc cccttatttc    195960
```

```
tcatacccat tctcctagtc ctagcaccat tccatttccc tctactcccc ttatttctca 196020
tacccattct cctagtccta gcaccattcc atttccctct actcccctta tttctcatac 196080
ccattctccc cccgatcatg atgtcttggt ttcttcacct aacgatgaag ttcaagtttc 196140
tcccccccact caggaagttc ggattttttaa aataagatct ccaagtaaaa gagaaacaaa 196200
ggggaaatcg ccaaaacgat tcacctttcc agaagatcaa ttgaaacata tgaacaaaag 196260
aaaagtatgt tcttttttctt atctttttttt tttttttttt tgcttgggag tcatagaatt 196320
gtcatgctaa catttttttt ttcatttcag aaacggtcct tgaagtaggc tatccatatg 196380
ctgtcaaggg tgaagaagaa gaatcattgt aagtaagagt gtatgaaact taaactataa 196440
tcaagttgta gtttgtttag gagtaactat ataatattat aaaaccaact ctttgttata 196500
cgggttgtgt ttgggtcaag gggtttctaa cctgtttata taacccgaac ccgaacctga 196560
cccaacctga tttgtttgac agatttcagt ttctcaatct tcttttccaa ttttttggtta 196620
gtgatccttgt ttttcttcac tcgtttttttt atttgggttt atttggtgat tgttgcccag 196680
aatccagtag tttatttggg tttatttggt gatagttgtc aagaattcaa catatttgag 196740
ttaatgtgtt ttatgtacat ttgcagagac tacaaacaaa taatagactg gtgattgttg 196800
atgctgcggt gcacatgatg aagctttcgg acaggaaaat gttaaggctt taggtaaaaa 196860
aatttcgaca atgtctgtac tataacaccg aagggaagta agggaaggta atggagggag 196920
gaacaaattt gtctattttt gaggagattt atttctgaca gtcattgaaa tgatctatct 196980
gttcattttt ctccccttca attccctttcc cttgtaatct aatatataaa tgaagtaatt 197040
ttctcccttc atttcctcta aagtttgggg tggatgatcc ttgaataata ggaattttgc 197100
gtttgaacgg tcattgcgaa atccttgtgt ttgaactcag ctctcgcgtt gattcatgtt 197160
tttcctgaac agcaggaggc tgaaccattc aaggttgtgg gtaagtttct tttgtttcat 197220
cctttttaat ttttttaattt agtattaggg ttaagggggct gtagcccttg ttggtttatt 197280
tgggcttctt gctggtaggt tactcacttt gtttcctact agcttctgag tttggttggg 197340
gctgttggtg tttgattagt ggtctgctgt tctgctactt gttggagtgc tgttctagca 197400
ttccagagct gctgttggtg cgtttctgat ttggcatgtt gttgccttttg tttgtggtgt 197460
tggagtggtg ctgcagtagt gctactgctg ttgttggttg tgtctactgc tgctactgtt 197520
gttagtggtc gttttcagtt gttgtcgttg tactatggtt gttacaaact tgtgaattgc 197580
tgttcgttga gtgcttgaca ttcgtaaatc gatttgttta attttggttg agtgcttgac 197640
attcgtaaat cgatgatatt ttttccatcg tgttgctata attcgaagtg tttttgcata 197700
attgcggtgc ttaattggac ttttgattgt tgattctgat gatatttgtt catttattga 197760
tgatatatgt tcatttaaga cacaatacag aactttataa caatgagaca taagtttata 197820
acaataaagc agaattttgt tttgggatga aattgactct atttgagaaa tgtgaatgaa 197880
atttgcaata tgttttgatt taaatgtgaa gatttaagaa tcatatttga cttaaatgtg 197940
aagatttaag aatcaaattt gacttatgat ggaaatgtgg ttgtttttggg tgaattgttg 198000
tggttgtttg tgtgaagtgt agtagttgtt tgttgttagg gacgatttgg aggcgctgct 198060
acctcggctc tgttggtgct gcagtagtgc tactgctgtt gtgggttgcg tctgctgctg 198120
ctactgttgt tagtgatcgt tttgggcagt tgttgtcgtt gtactattgt tgctacaaac 198180
ttgtgaattg ctgttggttg agtgcttgac aatcgtaaat cgatttgttt aattttttgtt 198240
gatgatattt tttccatcgt gttgctataa ttcgaagtgt ttttgcttaa ttgcggtgct 198300
```

```
taattggact tttgattgtt gattctgacg atatttgttc atttattgat gatatttgtt    198360
cattttaaga cacaatacat aagtttataa ctatgagaca gcagaagttt gtttcgggat    198420
gaaattgact ctatttcaga aatgtgaatg aaatttgcaa tatgttttga gttaaatgtg    198480
aagaattaag aatcattttt gacttaaatg tgatgattta aaaatcatat ttgacttttg    198540
atggaaatgt ggttgttttg tgtgaattgt tgtggttgtg tgtgttaagt gtagtagttg    198600
tttgttgtta ttaaagaagt taccagatga tttgatgtat gaattattaa tttattgaat    198660
ttgtttcaat caatttgatt aagggtcact aaaaaactaa agttggggta gctacaacta    198720
gatttggtga ggggttattc aaaatcttaa ctaggggtaa ctactgaaca actacttatt    198780
gaatttcaga tgtcaagctc ttcaaattgt tatgaaaacc gagtaaaatg ctattgtgga    198840
catgagttat ctacgctaag gagatggaca gttgaaaacc ccggaaggag gtttgtggca    198900
tgtcctgatt ttaattcaag aacattgagt ttataacaat agctgatgat ttattcagaa    198960
gattctaggc ctccgtatac agggaccgaa cttcgaactc catcttggcc ctagaccgag    199020
caagttataa acagtattgt tgttataaac ttgtgaattg atgttataaa ctggtgaatt    199080
gttgtaaatt tctgaattgc tgttataaac ttgtgaattg ctgttataaa ctggtgaatt    199140
gatgtaaatt tctgaattgc tgttataaac cattgaattg ctgttataaa ttcctctgct    199200
aaatgatata actgaagcac ataataataa ctatattcac tagtgttagg ttctgatatc    199260
cataacaata acaatattac atgattttgt aacaaatgta caatagttta taacaaatca    199320
gaattaaaac taccacaata gtaacaataa tgttcttaat tacaaaatgt tgaagttata    199380
cttctttgaa tttgaaatca cttcctttcg ttttggttt aatgtgaag ttataattct    199440
tccacagtaa tcaattctga gcttcttcaa gatttcagcc tgaacagtaa gaacattagt    199500
ttataacaat aatacatata tttataacat caatatcata attttataaca tataaacaat    199560
agtttataac aactcacatc atttatgtta atttggatgt cccaattttc accttgtccc    199620
tggtattctt ccatatgctt catggtagag ctgttcatgg gcgggctacc cgccaggccc    199680
ggcccgcccg gctcgaaaaa cgggctggtg cgggtattac ccgcccgcca agataaatgg    199740
gcgggtagcg acaataaaaa aatacccgcg ggtatacccg cccgcccgct tattttaata    199800
tattaatatt ttttttttatg aaaagtaata tattgatatt aagtatttta atatatatgt    199860
aatttgatta ttttgagact ttgaagtatt ttaatatata tgtaatttga ttattttgag    199920
acgttttatg ttttttgtagt attttggact atgtattgta ttttaattat tattaaaact    199980
taattttata ttttgtattg tattttggt atttatgaga aaatacccgc ggcgcccgcg    200040
gcacccgccc gctttaaaaa tgggcgggta gcgacaaaaa aatatgcccg caatcgcggg    200100
cgggcatttg aattttttgta gtaactaccc gccccgctac ccgcgcccgc ccgcccatga    200160
acgggctttg gtgtaaaggg tcgggtaata ttctaatggg tcattagcgg gtcgggttaa    200220
taatggggcg ggtcattaac gggctttggt gtaaagggtc gggccgggcc gggtcggata    200280
attataagta ttaattgcga aaataaaatt taccactttt tttatttttt taatgatat    200340
tattatatac ataactaggt cgacccacac tacatataat atatccgcca tttactaacc    200400
taaaatgcat atttgttttc taaatttact aatctctctt attactcagt ttatttttc    200460
gcaaataatt aattcagtta ataattgtaa tattattaat atactgataa ctacatttga    200520
atgaaaatct ttgaataaga taaagataat atggtgttga atcattaata aaaactagaa    200580
tttttatatt aatatatatt aaaaaaaccg tgcattgcac gggattctat actagtatag    200640
gataataaca gtaattatac agtaatgaaa tagattaaat taggaaatta attaaaagga    200700
```

```
cattcataaa ttagagttta taacggacat tcacaagttt ataacaacaa tacaatttat  200760
aacttgctcg gtctagggcc aatatggagt ttgaagttcg gtccctgtat aaggaggcct  200820
agaggcctat aatgtaataa taatatcatg accatatact aaagatatta atgtaaccca  200880
gaacaattgg tgaaattttc attgaagcat ttcaccaaac acttgatatt catacaaaac  200940
aaatcatata ttataactaa aatgaataaa ttgcacactt aatacagaaa ataagataat  201000
ataacaaaac aaccaaacta ttattagata aaaataagaa caatcatgaa caaaaagatc  201060
aatttgcaaa tttgaaaaaa ttagggttag attaatactt tgattgatga tgagcatgaa  201120
cttcaagtaa acaagagac aattgaaagg ttgttgatta atttagttga gttagtaatg  201180
ttgtgatgaa taaggagtga ttgggatttg ggaggagtaa aaacgttttt ttagaatgca  201240
attgcagcag agtgagtgag ggaggaaaga gggataggtt aaagaaggag gtaaatgagt  201300
ctatatataa ccgctacttg atgtagcggt ttatcatgtt taattttttt tttaatccta  201360
tgaaaaagaa aaacgctta tgaagtaacg gtttgttaga atttcataa ttgaccgctt  201420 tatgaggtag cggttttgtt aaaaaaaagg aaaaaaaaaa tttccctcac tgtcctacgt  201480
ggacagtatt ggaggtatta tttttcaact aacgtaaaat gggaaatatt ctttaataaa  201540
actatattaa gggaaaatgt tcgttttaaa attggatttt gtgtgtatat tgatttttta  201600
caaaattgta atgtataaat ttattttaa gtccgaaaat aaaatgaata tcgaacaatt  201660
gagtttgtta tgagaataac gatatggagt aatgcgtcaa ctttgtcaat tttatacgac  201720
tcaataataa ggaatcaatc aaacaacaaa ggaaaagaat aaatgactaa cgtttgaaaa  201780
gtttaaataa gaaaaaaccc aattttgtta ttcggaaata atattaggca aaattgttag  201840
aaaataccta gaaaaacact cttttttgtga aaaactacct agaacaattt tctttgtcaa  201900
aaaataccta aaaaatttgg tttgtttgta agtagtacc taatgatgga agacatccaa  201960
ttccgttaga tttaatgact taaaaaaaat aataataata ataaaagtt gtttatcttt  202020 aaaagccacg tgaacccaat ttgattcttt cttttccagga acccaattac ccaactaaaa  202080
gaacccaact aagaatggag gaaccctgcg aagaaccta aaacaatagg gaagaagtta  202140
ctggtttcaa gatgtaagaa tggactaaga aacccatgtc acgtgatttt taaaattttt  202200
ttattttcct tctttaagtt attatttta tttattttt taagttatta atctaactc  202260 tgttagatgt cttccgtcat taggtacttc ttcacaaaca aactaaattt tttaggtatt  202320
ttttgacaaa aaaaaatgtt ctaggtagtt tttcacaaaa aaggtgtttt tctaggtatt  202380
ttccaacaat ttttccataa tattaatata ttactccctt ccttaaaatt atttccattt  202440
gttatgttgg atattatatt tgttgtttat ataaaatttt ctatttata tcacaacttt  202500 tgtttaaaaa taaccttatt tatcctcatt taaatatttt aatatcctta catacattcc  202560
gctaattact ttatttaac attttatat tccttaggat ccaatatata tatatttccc  202620
acttacacta aaaaaatatt ttttattagt tgtgtttccc atagccaaac accacactgt  202680
aacttgggat ctcaaacccg ccggcataaa aaaaaccccc gtagggaaaa aaagccattg  202740
gaagagggag accaagaaac aggccaccct aaacagcata gttgcagact aactacttta  202800
aatagttcca agtgaagaat gttctgattt ggatattttg agggttttaa tgtttctata  202860
agccaccgct aaggataagg ctcgcatcct ccaaaatcaa ctacgtttgt ctggccatag  202920
ataatgtttc aacaagcaat gtcttgtgaa ttgttgttat gaatagttgt aaattttca  202980 ttagatttca aactggcatt actagaattt gttgcttcaa cattactaga gtttgtaaca  203040
```

-continued

```
aaaacaatat agtttgtaat tgtaacaaca atattaaagt tattgttccg agtaaaataa 203100
gggcactcat acgtgaaaat gaacaattaa agtcacccaa acagagccaa gcttcagccc 203160
catctttaag tataaattta tatcaaacta gtgccaaata atacatatta tattaaatga 203220
tttaaaccta atcccaactt aaatttctgg gtctttctct taaatttctg ggtcatttac 203280
aaaaattaaa aaaacgtttg ctcttcactt tgcgttcttt cagtttctct tcatcagctt 203340
gcttcttcc tccctgtgcg actggttcta ccttaagaaa aagcttttct tcacccactc 203400
acttcatatt cataattcct ctcacttaag taaatcaatc aactacattc taccaaacac 203460
ccttctcaaa ctgaacaaac cctaattctc cttggagaat cgcttgacgc ctgacggaga 203520
atcgcttcac ctgagttgct tctttccacc ggacgtttgg cctgctggct gctgctcctt 203580
ggttccctcg caggtcgcag cctcgctgac gctgactgat tcgcttcatt caccaaaccc 203640
taattctcct tggagaatcg cttgacgcca tcaaagaagg aattctcaag caaaatggga 203700
aaaaaatctg caaaaccatc aaagaaggaa atcgaaaagt tcaagtaagc attgttgtaa 203760
tttttataac tgtaaatatc cgattttcat agaattttt gtaaatatcc gacattctta 203820
cgatgcagga gaagaatcga gaatgacgca gaagaatcga cagcacctat cataccaaca 203880
cgaccaagaa tgtattataa ttcaaacctt tagtaactgc cattttttg gtttagaatt 203940
gctgattttt ctgtgaaatt agatacttgt tacatacaaa tttaagtact tgtgaattgc 204000
tgttacaaac tggtgaattt ctgttacaaa ataatgttgt tgttacaact tcaatattgt 204060
tgttataaac ttgtgaattg ctgttataaa ctggtgaatt gctgctataa ctttctgaat 204120
tgctgctata aatttctgag atattgttac aaactttgga attgctgtta aactggtgaa 204180
ctgctgttat aaattggtga attgttgtaa atatttgaat tgctattata aactagtgaa 204240
ttgttgttat aaactttaat attgttttca tatctcctta accacaacac caattccaat 204300
gattccaaag ccaaatgttt ctcaactcaa tgaagaatcc cgtgtaaatt tagttttgaa 204360
aagaaatcac aatactatcc ccgaaacgcc actgttttcg accccaaatg cagtcagttt 204420
ctgacagctt ctgttcttgt ttttgtcgac tttggctgct tctttccaac aaaaccaatt 204480
gaattatgca ccccactgat tcgcttcatt caccaaacag aacaccctgc tgagtgtgta 204540
ctgccgccgg ctttcctact gcccacagcc caccgccacc ggacaggagg ccaccactga 204600
caaccatacg tccagtccat acggccacca atttcaggta ttattattaa ttaaatgtta 204660
tattttataa atccttaatt cccaaaaatt agtttttttt tttttttttt cttatttcaa 204720
aattcaagat agtttcttga ttgaattaga tattatatgt cattatgtca atgttattgt 204780
gctttgttat tattcttgcc ttcatcttga gtatttgttt ttatggggga tgaatgatga 204840
tgtatgtatg ctgggtaagg aagatgactt tagggtggcc actgtatcaa ttcagaataa 204900
tgcctttcat cttatacaaa ttagttattt agcgactagg tgtgatgttg attttgtgct 204960
ggagtatgat tgtttgtaac attgtcttga ttttatggtt taaggttaca ttttacacat 205020
ttgtagttaa attttatgat ttcttttgta tgcatataaa gtgcttgatg aaatgttaca 205080
atgaaaattt actactttt tttgtatttg aattgacccc tttaataagt gttgtaatac 205140
tttatgattt ctacaatgaa atgccacaat aaatttatg atttcttgta tacaagcggt 205200
caaaacgact gcttttaggg cttgattctt gctcttcttc aaggtatacc cattgttgtt 205260
caagcttcat tagtttgctt ttagggctta gtttttttat actaatttta attttgtttc 205320
attgtatagg ttatacacaa cccaccatta ttgtcttctt caagttctca aacccacgaa 205380
aaattcaagg tattttttca ttttcgattt tgtaaattag gtttaaattg atcaaaattg 205440
```

```
atgaatgtgt atgtagttgt atttatattt atactatgta aattaggttt aattagggtt    205500
gtttatggtt atatgaatga gttggttgat gttgattatt gataaatttg gttgtaatag    205560
gggtttttaa gttttaaatt aggtttaatt agggttgtgg attattgata aatttatcat    205620
atgttagtgc ccctagggag tgtgaacctt agatccgcca ctgttcacat cctcatttaa    205680
ggtatgaacc ctaattttt tcaatttgca aattgatttc tttgtcatga ttgttgtcat    205740
ttgacttata atagattgat tgtttgtaac attgtcttga ttttatggtt taaggttaca    205800
ttttacacat ttgtagttaa attttatgat ttcttttgta taaatatgaa gtgcttgatg    205860
aaatgttaca atgaaaattt actactttgt tttgtatttg aattgacccc tttaataagt    205920
gttgtaatac tttatgattt ctacaatgaa atgccacaag aaattttatg atttcttgta    205980
tacaagtggt caaaacgact gcttttaggg cttgattctt agttgtattt catgatttac    206040
atgttatcag gagtaagact agttcacgaa taaaggacat taattcttag gatgatgaag    206100
tgtttagttt gaccggataa tttgggttaa tttgctatca aattgatcta taaaagtgaa    206160
aataaaggat cttcttgac aaagagtccg aaataagtgg tgtataggtt gatcattgaa    206220
aaaagtattt ttttgttaag aaattagaca tttaatgaca tcttcagaag atcaagtata    206280
aagagtccga aataagtgat gtataggttg atctttgaaa aaagtattat tttttgttaa    206340
gaaattagac atttaatgac atcttcagaa gattaagtat aaagttaaca aatgaataaa    206400
cgtgtaggaa agttaacgaa tgaataaacg ttctgaagaa ctttatgaga tgtcggaagt    206460
gggttgtaca acaggtaact gatgtgcaac gctcttcatg agttcactcg gctcttcatg    206520
agttcattta gacatttaat gacatctaaa ctagaacatt attcacctgg caccattaag    206580
agtagttcgt ttgcaacgct cttcatgagt tcactgatgt gccggaagtg ggttgtgcac    206640
caggtgcata ttttcaggt gcactaaaat ccggaaaaat ggggactatg cagtagcact    206700
gcataggcaa cttaacaaa ttcactattt tcgcaaactt tcatctctat gttggtgcct    206760
ctagagagtg tgaaccttag atccgccgct gtatgttctt ttgtgcttct gtttgttgga    206820
acattggctg ttcactttgc ttcactctcc ttcaccagct tgcttgacac ttcttcgttg    206880
ttcacaataa ataaattgat catataatgt gggctactcc ctctttccac ttcaattcaa    206940
ctatttcttg agtttcatct aacaaggaat tatttatctc tttatttaaa taaaggaaaa    207000
attacaaaaa actaccatt ttaatgggta acttgcaaaa aactaccat ttaattttt    207060
tttgcaaaaa actaccttat atgatattaa cgtttgttaa acacaacctc ttgacggttt    207120
cagttagttg accgtcaaaa gttagtttga cttttcacgt gacttgcacg tgaccttctt    207180
ttaaaccttt cccctttaatt gtttctttga tttcttaggt tttaaagcac gtttttagtt    207240
caaacctttc cccttcccc aagttcgtat gaaccctaat ccgcctcttt ttctttcaag    207300
cccaaatcaa ttcatggatt cctctcactc caaacaatcg aagcttgaca gatgtggttg    207360
cgatttcctt ttgcacagcg aatttcgtgg actaaagaaa atccaggttg acgtttcaaa    207420
tttcaatgct tgccaatttt cgatcctgac actaattgga ggggatgtaa aagtttaag    207480
tggatcgatg aacttgaaat ggttgatttc aagatattga catcaaggct tgttgcttg    207540
gaacatgaga aagaacaagc aatttcagaa tacaaaaggc ttaagaagaa attaatgaag    207600
gagagaaagc ttggaaaaga gatatcatgt tttattttag ggttttatt tggttttttc    207660
ttgttgttgg ttgtactaat aaaggttatg taacctttag atcatactgt aagaatattt    207720
gttatgtagg aaaatatgga aatgttgttg taacgctttt gcaaacttga atgttgaagc    207780
```

```
taattataga acatccttt  tttgattact tgcttccata ccataattgt tccataacaa    207840
tacatactac ttatatctta cattagagta ggtggttcaa aatgaataac aattcaagat    207900
tttcgatgat gtggaccttt ccgttttgaa tccaatttat tgaagatcaa ctccaagtct    207960
actaaagggg gggttgaaca aaatttcaaa ctactttaca aaaatatat  tgaggtctgg    208020
gaatctgtga ctgctgatga ggagagcatg aattcttcac actgtagtcc tagtcctagc    208080
accatttcct ctactcccct tatttctcat acccattctc ctagtcctag caccattcca    208140
tttccctgga agagaaagag gtgcaccttg gtctcgacca ggtattttg  aacatagtca    208200
tgtgattatt tcggggtctt cttgagtgtg attcttacac attgaagatg aatcaataaa    208260
atgaaatacc ttgaaaataa aaaaaaatca aaaaagcta  tccgggtcaa acgagtacct    208320
gagtcaataa attatcggcc catgacccga cccggttaag gcgggtcggg tacccgaccc    208380
ggaactttga atttttttta gttttcgacc tgccatttat gaggcgggtc ggcgggtcgg    208440
cgggtcgggt cgggcgggtc gggttgtttt gaacacccct acttatatct tacaaagaca    208500
acaaaacata aaagttccaa cataacctag caaacataac agacattaca aatacacttc    208560
ttttgttgc  tgagagcttg aagaaccttg ggttgaaatc accattggca ctgaaccttt    208620
tgctcctctc tttttgtaac catatgccca tgatttcttt ctaacctttt tgtgctggca    208680
gcattgttgg tagggcaac  agagcttgca gttgttgttg tcaccaatgg tgttgagctt    208740
tcaaacgaaa aagagaaggt agattagaag aaaaaaacga caataatcat atttcatgtt    208800
aagagtaaag acacaataca gaagtttata acaatgagac agaagtttat aacaataaag    208860
cttaattttg ttttgggatg aaattgactc tatttcagaa atgtgaatga ttggcagcat    208920
tgttggtagg ggcaacagag cttgcagttg ttgttgtcac caatggtgtt gagctttcaa    208980
acgaaaaaga gaaggtagat tagaagaaaa aacgacaat  aatcatattt catgttaaga    209040
gtaaagacac aatacagaag tttataacaa tgagacagaa gtttataaca ataaagctta    209100
attttgtttt gggatgaaat tgactctatt tcagaaatgt gaatgaaatt tgcaatatgt    209160
tttgagttaa atgtgaagat ttaagaatca tatttgactt aaatgtgaag atttaagaat    209220
catatttgac ttaaatgtga agatttaaga atcatatttg acttttgatg gaaatgtggt    209280
tgtgtttgtg tgaattgttg tggttgtttg taggggtgtt caaaactacc cgacccgccc    209340
gacccgaccc gccgacccgc tgacccgcct cataaatggc gggtcgaaaa ctaaaaaaaa    209400
ttcaaagttc cagggtagaa acatccttaa catgaaactt attaatgagt gtaattccac    209460
taatggtaga cattggctta acttcaagat tatccataac catatatgtt agatataagt    209520
actatgttat tcattttgaa ccacctactc taatgtaaga tataagtagt atgtattgtt    209580
atggaacaat tatggtatgg aagcaagtaa tcaaaaaaag gatgttctat aattagcttc    209640
aacattcaag tttgcagaag tgttacaaca acatttccat atcttcctac ataacaaata    209700
ttcttacagt ataatctaaa ggttacataa cctttattaa tacaaccaac aacaagaaaa    209760
aaccaaataa taaccatata tgttacaacc cctttacat  acccaccatc atccccactg    209820
ttcctaatgg cagatgaaat ccacaaaatc tttgtttgct tacttgctca aaaaattcac    209880
gcgccacgcg ctgctgtctg gtcctactgt aaaattctta aaacatataa actcgtgttt    209940
gtctaccttc gactgcctaa tatctactcg gaattcgatc tttaaaataa taattaaatt    210000
tgaaaaatca ccaaaaataa taatcgggta cccggtgtcc caacccgttt tatccgggca    210060
cccgctaacc gggtacccgc attaaatggg acacgggccg caaaaatagg taactggcta    210120
actgggtacc cggcttttccg ggtacccgtt tagccgggta cccggttatg aacaccccta    210180
```

```
gttgtttcac ttgtttgtgt gtagtgtagt agttgtttgt tgttagggac gatttggagg  210240
cgctgctacc tcggctctgt tggtgctgca gtagtgctac tgctgttgtg ggttgcgtct  210300
gctgctgcta ctgttgttag tggtcgtttt gggcagttgt tgtcgttgta ctattgttgc  210360
tacaaacttg tgaattgctg ttggttgagt gcttgacatt cgtaaatcga tttgtttaat  210420
ttttgttgat gatatttttt ccattgtgtt gctataattc gaagtgtttt tgcttaattg  210480
cggtgcttaa ttggactttt gattgttgat tctgatgata tttgttcatt tattgatgat  210540
atttgttcat tttaagacac aatacataag tttataacta tgagacagaa gtttataaca  210600
attaagcaga agtttgtttc gggatgagtg taattccact aatggtagac attggcttaa  210660
cttcaagatt gtccataacc atatatgtta caacccctta tacataccca ccatcatccc  210720
caacacgggc cgcaaaaata ggtaaccggc taaccgggta cccggctttc cgggtacccg  210780
tttagccggg tacccggtta tgaacacccc tagttgtttg tgtgtagtgt agtagttgtt  210840
tgttgttagg gacgatttgg aggcgctgct acctcggctc tgttggtgct gcagtagtgc  210900
tactgctgtt gtcgattgcg tatactgctg ctactgttgt tagtggtcgt tttgggcagt  210960
tgttgtcgtt gtactattgt tgttacaaac ttgtgaattg ctgttcgttg agtgcttgac  211020
attcgtaaat cgatttgttt aattttggtt gagtgcttga cattcgtaaa tcgatgatat  211080
ttttccgtc gtgttgctat aattcgaagt gttttgcat aattgcggtg cttaattgga  211140
cttttgattg ttgattctga tgatatttgt tcatttactg atgatatttg atattatgtc  211200
atatcatgag aaggttgtaa ttcctatgta attccatggg aggccagaca atctcgtgat  211260
ctttttaaca ttgccaaggg aaaacaagac tgaagtatga tattatgtca ttagggctga  211320
gcaaaactat ctgatgatcc aattatccga tgattcgatc tgacattcga ttcgatttt   211380
aggatatccg attcgaagtt acaattcgga tcaaatatcc gattcgaaaa ttcgaatatc  211440
ggatacaaat tcggatatca atatttgtag attcgaatat ccgacatttt ttcaattgtc  211500
agatatcgga tatcggatat cggatatccg aaattatttc ggatagtcgg atatcggatc  211560
tcggatatcc gcaaattata gatagtttcg gatatccgtt attcataaga aaaaaatata  211620
tttttataaa taaattattt tgactaaatt cggataccgg atatcagata tttcgaatat  211680
ccgactggaa attttgaatt ttttctcata ggcatcggat atcgaatatc tcgaatatcc  211740
gattcgaata ctgtcggata ccggatatcg gatatccgag tcggatcgaa tcgaatatcg  211800
gatatcagat ataccagttt tcggatatcg gatatccgac tgcctgtttc ggatcggata  211860
tccgatttt g cccaccctta tatgtcatat catgagaaag ttgtaattcc tatgaaaaaa  211920
atgagcgagg ataatcaaca actaaattgg ttcaagaata agcatgccaa agatcaaagg  211980
caaaataaag ccctagagga gtctttgtac attgtcactg caaagcttca taacactagt  212040
ggaaaaaagt cattggctgc aagacatagg ccgcggtttt aggatatacg caaccaatat  212100
ataaatttaa aaaaaaaaat agaataggct gcggttttaa taggtgaccg cagcaaaaaa  212160
aaaaaaaact atcctcatgg gctacggttt taatagtgtc cgcagccaaa gcccagccca  212220
aagtctaaga aaaaccctaa ttttctctgat aatataaagt actcggcgcc tattcatttc  212280
cctattctaa caaaaaccta tcgtccttct tcctaacaaa aaccctattc atttccgcct  212340
ccttcttttct attcatttcc ttctcacttc attcgcactt cctaagaaag tcattgataa  212400
tttcatcatc cctatctgaa ataatataaa gtcggcctat tcttccccta tctccttctt  212460
cctatctcct ccttctcact tcattctcac ttccttcttc gattaaatat tgaaatttcg  212520
```

-continued

```
ttttttttaga tttcaagtca ttcgatttca agcacaatga agattgaaat gtgagtgtat  212580
acacaatgaa gatttcaagc acaccagatt tgtatacttt ttgcacagtt ttcaaagtaa  212640
attttaagct taaatatgtc caaatacgca tcttaaaaaa ttataaaaaa tatacattaa  212700
gacgaatcta acgagatctc acatggatat attttgtctt ctatatatgt cttaaaaatc  212760
ttaattaaat ttctctttcc aaaacagaat attataaatg ggaagaacat taggaaacgg  212820
agggagtagt tactatacta ctacctccgt tccattttag ttgcaccatt gagttttga   212880 cttttgacac aatatttaag gattgtcaaa tcagtatggt aaaagtaggg atgatgtatg  212940
attgatggtg gtatgtgggg tagaaataaa aaaattatta taaatagata atggttgtga  213000
cttgtgggta tattaaataa ttaataggat gttaatgatt gatggtgata tgtggtagga  213060
ataaagtgag gataaaataa gtagattatt tttgccaaaa atagtaatgt tgcaagtaat  213120
atgaaacttt caaaatggt aagtgttgca agtaaaatgg aacaaggaa gtatattgat   213180 cttagagttt ccagtttgat cagtgctttc tataaatagt actcttgtag gaaacaataa  213240
ataaccatct caattctcag caaacattaa acatatatac cctaaacaaa ataagcaaaa  213300
atgagtttga aattaatggt agacaaaaag actaaggttt tgtttgcaga agcaagaagg  213360
aagttgttga tttcatcttc cacatactgt cgttaccgct tgctactgtt gttaaactca  213420
attgtagttg ttctttttta tgttttaagg tttaaattaa cacttatttg acttcaacta  213480
ttaagttttg taaaaatatc tttaataatc attattaaaa ttcgaatcga gtctcccaaa  213540 aaaaaaaaa aaaaaaaaa attcgaatcg agaaaaacgt gaattttagt caaattgata   213600
taattgttta gaaatattca tatatataca caagttaaat ctggattata agaaattttt  213660
atacgattga aactacccta gtaggatcgg atcgtaagat cgtaggatcg tagaatcgtg  213720
ttataatcct accacttaaa tcctggagct aagtaggacc gtacgattct accaatttaa  213780
gatcctacct acgatccgga tcggtcgcct aagtttggat cgtaagatcg tagaatcggt  213840
gatcatataa agtactcggc gcctattcat ttccctattc taacaaaaac ctatcgtcct  213900
tcttcctaac aaaaacccta ttcatttccg tctccttcaa tctattcatt tccttctcac  213960
ttcattcgca cttcctaaga aagtcattga taatttcatc atcccttatc gctgatttcc  214020
agatgatgac gatgtccagt ttcatgtcgc tgatttcatc gattatggcc gacggtatta  214080
gattttgtgc tcttttggat ttgggtatta gagtttgtgc ttttttggat ttgggtgata  214140
atggccgacg gtacttcgac gccattgtta cgccttggat tcttcttaat actcttgatt  214200
atcagcgtaa ttagggagta ttaaggtcca ttattctcta gaataatggc attaagttct  214260
atgatcatga aaagagcaca ttatcaccca aatccaaaag agcacaaact ctaataccta  214320
atttaacctc tgaacactcc gaaccctcca attgcaaaca caacggtcga aaacgtcgaa  214380
gaaacttgac aatttggtca taatcgatga aatcagcgac atgaaactgg acatcgtcat  214440
catctggaaa ttccacgaac ttaacgatca aagtatcggc tataagtaca atctgaacat  214500
tgtaccatgc accacttaga tcttaggatg tttacttgaa gatgagggc ttatatagct   214560 tgtatatgtg cgtatgaggt gtcaatggaa atcttaggat gtctaatttg gaataaaaag  214620
gatgatttgt tgaaggcata taagctgcca gaaactgttg tgatgaagtg gtagaaagat  214680
ggtgatgcat ctcttatttc tggagggata taagggcgtg taaggtacct atagaaagct  214740
tagagtgtta ggaaaaaatt ctaagtggta gcactcaatt atatagggta taacctagtt  214800
tcatgtcgct gatttcatcg attatgacca aattgtcaag tttcttcgac gttttcgacc  214860
gttgtgtttg caattggagg gttcggagtg ttcagaggtt aaattaggta ttagagtttg  214920
```

```
tgctcttttg gatttgggtg ataatgtgct cttttcatga tcatagaact taatgccatt   214980
attctagaga ataatggacc ttaatactcc ctaattacgc tgataatcaa gagtattaag   215040
aagaatccaa ggcgtaacaa tggcgtcgaa gtaccgtcgg ccattatcac ccaaatccaa   215100
aaaagcacaa actctaatac ccaaatccaa aagagcacaa actctaatac cgtcggccat   215160
aatcgatgaa atcaacgaca tgaaactgga catcgtcatc atctggaaat cagcgataag   215220
ggatgatgaa attatcaatg actttcttag gaagtgcgaa tgaagtgaga aggaaatgaa   215280
tagaaagaag gaggcggaaa tgaatagggt ttttgttagg aagaaggacg ataggttttt   215340
gttagaatag ggaaatgaat aggcgccgag tactttatat tatcagagaa atcagggttt   215400
ttcttagact ttgggctggg ctttggctgc ggacactatt aaaaccgtag cccatgagga   215460
tagttttttt ttttttttttt tttttttttt tttttttttt tttttgctg cggtcaccta    215520
ttaaaaccgc agcctattct attttttttt ttaaatttat atattggttg cgtatatcct   215580
aaaaccgcgg cctatgtctt gcagccaatg actttttttcc actagtgtta tgaagctttg   215640
cagtgacaat gtacaaagac tcctctaggg ctttattttg cctttgatct ttggcatgct   215700
tattcttgaa ccaatttagt tgttgattat cctcgctcat ttttttcata ggaattacaa   215760
ccttctcatg atatgacata atatcatact tcagtcttgt tttcccttgg caatgttaaa   215820
aagatcacga gattgtctgg cctcccatgg ttttaattat gaatactata ctacttgtga   215880
attgcccta cagctgcata atccttgaag tattctataa gctcttggtt tcccatgcca    215940
atccacttag gggctgtttg gttgggttat ttttggtaaa aggtaacgga ttcagataag   216000
gattctgtta cttggtgttt gttttgaaaa atagggtaac actttcccctt atttggaggt    216060
aatggaaact gttacatgtt accggtccca atcttagaga aacagttatc ctccttctcc    216120
ctcaaaccta ttctctcacc caatctttca ctcaccatga gaactttcca accaacaaac    216180
accaccatta gcagtggtca attgcatctc cgcctagcac cgttgttgat cgcatctcca    216240
ccagtcaatg tcgatcacat ctaacaccac caccagtcgt gggcttcatc tcaccaccgt    216300
cgtcgctggc cagtaaccac aacagagtcg ttggcaacgt caccttcacc aatcgccacc    216360
acacccttac cacctcactt tttccaacaa ttgcaccacc atgctagtta ctaccacttt    216420
gccgatttgc ttctcttaaa gcctttgaga aagttaatcc agtaatttcc tatctagaat    216480
gcaatggaga gaagtagata aagaaagaat ggaaaggtta ttgatggatt ttttttaagag    216540
acaaaagaga gaaaaaaagg actcaattca gtaaataaag cccctaattt atcatttcgt    216600
tttatacttt attaagtgtt tcccttacat ttaattatac caaacaacta ttaacaataa    216660
cacttaataa taccccttacc tcttttaacc tattccctttt ccattacagt ttcattttctt    216720
ataccaaaca ccccccttatt gttatcatct ttgtccagta tagtattcat aattaaaacc   216780
aatccactta tgataacatt gccaagggaa acaagactc tatttcagaa atgtgaatga    216840
aatttgcaat atgttttgat ttaaatgtga agatttaaga atcatatttg acttaaatgt   216900
gaagatttaa gaatcaaatt tgacttatga tggaaatgtg gttgttttgg gtgaattgtt    216960
gtggttgttt gtgtgaagtg tagtagttgt ttgttgttag ggacgatttg gaggcgctgc    217020
tacctcggct ctgttggtgc tgcagtagtg ctactgctgt tatgggttgc gtctgctgct   217080
gctactgttg ttagtggtcg tttgggcag ttgttgtcgt tgtactattg ttgctacaaa    217140
cttgtgaatt gctgttggtt gagtgcttga cattcgtaaa tcgatttgtt taattttgt    217200
tgatgatatt tttccatcgt gttcacttaa taatacccctt acctcttta acctattccc    217260
```

```
tttccattac agtttcattt cttataccaa acacccccct attgttatca tctttgtcca   217320
gtatagtatt cataattaaa accaatccac ttatgataac attgccaagg gaaaacaaga   217380
ctctatttca gaaatgtgaa tgaaatttgc aatatgtttt gatttaaatg tgaagattta   217440
agaatcatat ttgacttaaa tgtgaagatt taagaatcaa atttgactta tgatggaaat   217500
gtggttgttt tgggtgaatt gttgtggttg tttgtgtgaa gtgtagtagt tgtttgttgt   217560
tagggacgat ttggaggcgc tgctacctcg gctctgttgg tgctgcagta gtgctactgc   217620
tgttatgggt tgcgtctgct gctgctactg ttgttagtgg tcgttttggg cagttgttgt   217680
cgttgtacta ttgttgctac aaacttgtga attgctgttg gttgagtgct tgacattcgt   217740
aaatcgattt gtttaatttt tgttgatgat attttttccat cgtgttgcta tatttcgaag   217800 tgttttttgct taattgcggt gcttaattgg acttttgatt gatgattctg atgatatttg   217860
ttcatttatt gatgatattt gttcatttta agacacaata cataagttta taacaatgag   217920
acagaagttt ataacaataa agcagaagtt tgtttcggga tgaaattgac tctatttcag   217980
aaatgtgaat gaaatttgca atatatttga gttaaatgtg aggaattaag aatcattttt   218040
gacttaaatg tgaagattta agaatcatat ttgtctgaca aaagtaatta agaattcata   218100
aagtaattgg ctagctttca aaaagtaaag tacaactaca tttagagtct cttcgtcttc   218160
ttcagtttca tactttcatt ttctcagtct tcttcttctt cgtttcattt tctctgaaac   218220
tttttactgc ttcttccttt tcttccattc ttagatatct ctaaatctac attaaaaaac   218280
caaaaaaata taatggttaa cacatacatt gaaaattggc tggagacgat gatttggggt   218340
cgcccatggt agcgattggg tacgcgttcc acagtgttcc ggtacgccac cgttccgcgt   218400
ttgggtacga ccgttcccga tcggataacg ctccggcgtc ccgcgttccg ggtaactatg   218460
ggttaaaccc tactttggag gacgttttgt acttgactgg tttacccatt gtgggaaagc   218520
cagtcatctt cgacaaaaca gttgataatg atgctttcat gagagttttt gaagagcaag   218580
gaactaatat tataagtttg acaacattgg atagaattgc caaagatcac acgagatcag   218640
atgataagag gataaaggca attctgttga ttttgatatg ttgtatcata gctccttcta   218700
caagtggaca tgaatgtcga gccacttttgg tccagttcgt tgaacatttg gaccaagtga   218760
actcatatgc ttggggtgcg gcattattgg cgtatcttta tagcgaattg aaggaccatg   218820
ggataaagaa gcttatcaat ggatttacat ggcttgtggt ggtaaggaca cttatttaac   218880
ttattttctc ttatcttgtc attttatca tctaacattt ttttcacat ggtttcttct    218940 tctaccgtat taaaggtcta gcggagattt ttggtgtggc catgattcaa gagaacaata   219000
acactgctcc tttgctacac acgatcaact tgaaaggcaa aggttatgta tcaaatctga   219060
aggtcacaac actctccgag aagctgcaac aggcaaaaaa tcttttggct aacgcaacag   219120
aggtaaaagc actcgtgcgt gatttcaatt ttcatttaa ttgtattata tttctttatc   219180
tttgattgat gaggtgactt ttttttgatg ttgtatgaaa cagtgtatta attggcaccc   219240
atatcagtca attgtgttgc ctgatcattt gcgaagacat attcagtttt gctccatcat   219300
cacaccaatg ttttgtttca atcatgtgga aaatcatttt ccacatgttg tagcaaaaca   219360
attcaagatt ttcgatgatg tggacctttc cagttttgga tccaatttaa tgaagatcaa   219420
ctccaagtct actaaagggg gggttgaaca aaatttcaaa ctactttaca aaaatatat   219480 tgaggtctgg gaatctgtga ctgctgacga ggagagcatg aattcttcac actgtagtcc   219540
tagtcctagc accatttcct ctactcccct tatttctcat acccattctc ctagtcctag   219600
caccattcca tttccctcta ctccccttat ttctcatacc cattctcccc ccgatcatga   219660
```

```
agtcttggtt ttttccccta acgatgaagt tcaagtttct ccccccactc aggaagttca 219720
gatttttaaa ataagatctc caagtaaaag acaaacaaag gggaaatcgc caaaacgatt 219780
cacctttcca gaagatcaat tgaaacatgt gaacaaaaga agagtatgtt ctttttcttt 219840
tcttttattt tttgcttggg agtcatagaa ttgtcatgct aacattattt tttttcattt 219900
cagaaacggt ccttgaagta ggctatgcat atgctgtcaa gggtgaagaa gaagaatcat 219960
tgtaagtaag agtgtatgaa acttaaacta taatcaagtt gtagtttgtt taggagtaac 220020
tatataatat tataaaacca actgtttgtt aaacgggttg tgtttgggtc aagggtttc 220080
taacctgttt atataacccg aacccgaacc tgacccaacc tgatttgatt gacagatttc 220140
agtttctcaa tcttctttc caattttttgg tttgtgatct tgttttctt ccctcttgtt 220200
ttttttatt tgggtttatt tggtgatagt tgcccagaat ccagtagttt atttgggttt 220260
atttggtgat agttgtcaag aattcaacat atttgagtta atgtgtttta tgtacatttg 220320
cagagactac aaacaaataa tagactgatg attgttgacg ctgcggtgca catgatgtag 220380
cttctgata ggaaaatgtt aaggctttag gtaaaaaatt ttcgacaatg tctgtactaa 220440
aacaccgaag ggaagtaagg gaaggtaatg gagggaggaa caaatttgtc tattttcgaa 220500
gagatttatt tctgacagtc attgaaatga tctatatgtt catttttctc cccttcaatt 220560
cccttccctt gtaatctaat atataaatga agtaattttc tcccttcatt tcctctaagt 220620
ttggggtgga tgatccttga ataataggaa ttttgcgttt gaacggtcat tgcgaaatcc 220680
ttgtgtttga actcagctct cgcgttgatt catgtttttc ctgaactgca ggaggctgaa 220740
ccattcaagg ttatgggtaa gtttcttttg tttcatcctt tttaattttt taatttaata 220800
ttagggttaa ggggctgtag ccccttgttgg tttatttggg cttcttgctg gtaggttact 220860
cactttgttt cctactagct gctgagtttg gttgggggctg ttggtgtttg gttagtggtc 220920
tgctgttctg ctacttgttg gagtgctgtt ctagcattcc agagctgctg ttggtgcgtt 220980
tctgatttgg catgttgttg cctttgtttg tagtgttgga gtatgaacaa tgtgtgcacc 221040
catcaataac tcatggttca attcaagtgc aagaagagca tgactcatca attcatagtt 221100
caatccaaga gcgtgactca acatatgcct atgaggagga tgcatctaaa ttacatcaag 221160
aagaacactt tagggcagca aaacaacaca caaaatcaaa ggaaagcgca aaacagccca 221220
gcagacaacc ttgtgaatga cctaccttgc acactatgtg gagcctctac ttatgcacca 221280
atgaactaga taagggttga aacgtgatct ctacacatgg gccaagccat ccaagcccaa 221340
gagtcatgtt ggtggtgcaa aaagatgggt agaaacgtg cacaaggtgg cccggtcaac 221400
acgacattct gacagcacac tagcaacata ttgcgaccaa gcgaccttga gcgagttgaa 221460
aacaagggga ggaatcattt tcttgatcaa tccaaggggt taaagttata gtgcatgaca 221520
agctacaaat aaaagcatta aacaaaggaa aaggtggaaa tcacgagcca agaagtcacg 221580
cccaaacagc catgtcgcac agccaatgac gaagggctgc ggcttgtttt atttactgtt 221640
ttttctgaat ttatgggaag cacgtgcctt agggcgtgca ttttaaagta ggcaacggtc 221700
ctttcttgtt tttaggctta taaatagcta tggcttgtat tgtaatagac catttcttag 221760
atttgtattt tggagcacat aaaccgtgcc ttaataagtg aaaattagaa tttttgtttc 221820
tcttgttcat tgcattgtct ctttgatcat cccactcata aaggtgtgga acacctttta 221880
atctcttcat tgtggaacaa ttcaagagtg cattcttcat tggcattgag tgaaactcaa 221940
taaagaaggc gtagagtcca aacattggtg agggaaccaa taagtgttgg attgagggc 222000
```

```
tgatcaggaa atcaagaatt gatttcttgg gtactttggc gtgtgtattg tgggaagaat   222060
actcgaccat cctgcgtgca aatcgagggg ttgattgtgt gcaagatcga gactccgaag   222120
gaaccggtct tggtgcagag tgcgactttg cttctttgtt tgtggtgttg gagtgcgact   222180
ttgcttctgt tctgcttctt gttgtggttc tgttagagtg ctgttgaagg gcctgcttga   222240
tggctatctc tctgctggct tctttgctgc ttctgtttgg ctttgaccat tgctgatctg   222300
ggctggtgct tgctgttgat ggctgatttg tacaattggg atggttccat gatgcctgct   222360
gttatggttt gctgctagtt tgttctagtg cagctatttt gatgatggtt gtctttgttt   222420
ttgtctgttt ctttaccagc tttgttttgc tggttttttgt ttatacaact cacgtctttg   222480
tatagcttgg tttctttagc cggctttatt tgtcggctac tattttatt gtcggctact   222540 ataggcctct ctttcctcgt atgcacatga agagtgggac gaggaaacct ttcatagaag   222600
gtgggcctcg tttccacact gatgcaaata agaaaagttg agcttatttg tcaaaatgta   222660
ttattggttt ttctggtaaa tgaaaaaatt ttttatttgc caaaaaaatg tatagcttat   222720
ctggtgtata gcatatttta cagatactga tcttttagct gactctattt ttgtcggctg   222780
tttttaggcc tctcctgtct cgtatgcaca tgaagagtgg ggtgagaaaa cccttcataa   222840
aaggagggcc tcgtttccac actgatgcat ataagatggg attagattcc ttaccttgat   222900
gtatttgatt ttttctggtg attgaaaaaa aaaatttatt tgcaaaaaaa aaaatcaatg   222960
gtcaatgttg ttatttaact attttgcttt ctgtaaggcc aacttatatt atgctaacat   223020
gcatttacag tatatctcta agtctgtaac aatatatatc ataacctagt cccaactcaa   223080
tcccaaatta ccatgaccta gttccaactt atcataacct aattccaact taccaaaact   223140
taatcccgat ttacataatc taaataatct gaacccaaca attcacaagt tagtacaaca   223200
attcacaagt ttataacagc aataaagaaa tttacaacaa ttcaccagtt tataacagta   223260
attcacaagt ttataacaac aatacagttt ataacttgct cggtctaggg ccaagatggg   223320
gttcgaagtt cggtccctgt ataaggaggc ctagaatcct tcttaattac acgctctcgt   223380
attcttctaa ttacacactt ttaacatcaa ctaaactact aaaactgaaa attaaactac   223440
tataatcaac ttaatatata aatcagaagt tataccaaag gtggttccat aatttgcaag   223500
taagctcatg gaagtgcgta ctcatgatcc atagaatgct catgattgga cttggaatca   223560
cgaaccatag ctaagggaa gaaaacgggc aacagtcca attagtccta atatcaaata   223620
aagaaaggat acggccaaaa tctccggaat aaattcgaga agggcatata tcccaaaggc   223680
tataaatttt catgactagt gccatgttac tctagtttcg gggacgaaac ttcttttaag   223740
ggggtagtct gtaacacccc gagattttta atgacgtaat tatttaatat tttaaataac   223800
ttttggagat tttatgatcg tatagacctt aaaatagcta tgttggaatt aggttatgat   223860
aagttgggac taggttatga tatatattgt tacagatata atgtaaatgc atgttagcat   223920
gatataagtt gtatctcctc atccaagaca tcagcaaaag tgcgatgaag cttaactctt   223980
tgagaacctt tagttcttgc atgtgccaaa agtggctgga gccccttgta ccaatcaatg   224040
ggtccagggc caccttgaca agcagggcaa tgccactgcc tttcaggttc attgatttct   224100
tgcactgaca aagtttccaa actattgaaa aatttcttca gcattctgtg ttgcttcctt   224160
gtctcgtgag tttgaggtct atcatcagaa tcagaaccat cactcagcaa atactcatca   224220
tcatcggtga agtaatcctc ttcggaatcc actttctcct cattcacctg agaatcatgc   224280
tgaatgaggg gtttgactga tggtccagtc aaatgcctac catcaggcaa ggtcgcaacc   224340
ccagtttgtt ttctctggtc cttgcttgag gtagtttggg accttccaga ggcattattg   224400
```

```
ctatttaagc caagtctctg tgttgtatca gattgacccc atgctttggg aggggggttt   224460
tgctggaccc attgccccca ttgtcttcca ctattgtttc cagctttatt tttacttttc   224520
ctcgtgactg tctcccagtc gtcagaagat ccaaggctga tattcgaaac accctgacgt   224580
agcttatcaa cacctctacc tgaactcttc tcttcagctc ccgttgaggc aaataaagag   224640
gcaaaaatga agatagagaa ttgaagaagt tatgtgaaac atttgacaat atgttagatt   224700
gattaaattt taccttgcat aaagtaaaaa taacacattt ttgtgttcaa agtaaaaata   224760
aagtcttaat tataagttta agtatacgca tgttataaat tgagattttt tgatattta    224820
tatatattaa tgtttgaaat gttattcata tgtttatatt ataaattttc aagtattgcg   224880
attattaccc gaaatcggta ttaaattaaa gtcacaaaag aaaaatatat aaatctgaaa   224940
aatttatata aattttcaaa actagtatct tacttctaaa atcatttaaa aatagtaaat   225000
gagtgtattt tgaccccatc ttttaccata tcctccaaat gcatgttttt gaagatacct   225060
aatcactata ttgagatagc atatggtata attaaagaaa agaatataga tttgtacaga   225120
ggtcaggtaa aaagacagat ttgcagggtc tgaaagatac cttaatttac ctaggttata   225180
ccctatataa ttgagtgcta ccacttagaa ctttattatg gtataaaaat aggaggcatg   225240
tattaagaga atttgggata aaaatgataa tttgttgaag gcatataagc tgccagaaac   225300
ttttgtgatg aagtggtaga aagatgggga tgcatctctc atttctagag ggatataagg   225360
gcgtgtaagg tacctataga aagcttagag tgttaggaaa aagttctaag tggtgcatgg   225420
tacaatgtta agattgtact tatagccgat actttgatcg ttaaatttt tggaattcc    225480
agatgatgac gatgtccagt ttcatgtcgc tgatttcatc gattatgacc aaattttcaa   225540
gttccttcga cgttttcgac cgttgtgttt gcagttggag ggttcggagt gttcagaggt   225600
taaattaggt attagagttt gtgctctttt ggatttgggt gataatggcc gacggtactt   225660
cgacgccatt gttgaagggg tttgctttct ctctctctct ctctctctct ctctctctct   225720
ctctctctct cttgtgctgt ttctattttt tcatagttat tttaatgttg ggagctagga   225780
agcatcacat aatttaaatg aataatgtta cataaaaaag tgtttatttt tagaaatttg   225840
accaaagaat aaagtttgcc tatgctctat ggtgttgtca atggtggaag aaaatgggag   225900
aaaatgttt gttctttttt tctttatggt tgaaattgtg tgaatcaact atcaagtgat    225960
tggatttta ccatcacatt cttttacccc catggtccgt tcgatccttg atactaaatg    226020
gtcgggtggt aatgtgaatg atttacacta taaaatttca tgaatgtatt gtgatgttcc   226080
cataatgaaa ctttgatacc atctttcgga ataacaatgc aatgcaatca agtatgcaaa   226140
aaaatgagac gattggtatt gaataagcat gaccattaaa tttgtcaata gattttcat    226200
aattctcatc tctaactcca attataaaat tcatgttcaa cttaaaatcc aaattccttg   226260
atcattataa gtcccttttc ggcatgtctt actaaaatgc tcatatctct agcccgaact   226320
ccaaatccaa tgattcaagc gtctaattgc tcacaactca aagacacatg tttcttaaga   226380
acaaactata gtaataaaat gagaagaaga tggtcgaaaa tccacaaaac agaaagtgtt   226440
tgaaattttt tactcttagc tatccaaaat gttttagggc aaaacataaa ctttcatgct   226500
cgaattgatg caattcttgg gtttaaaatg tgagaaattt tatgtacaac accaccgtaa   226560
gttttctttta atttatacat gcatgaagag gaatatgggt aaacacttca aattgtattc   226620
aagtataaag ttgaccaaaa aagaacaaca agttctgaat gtttacttga agatgagggg   226680
cttatatagc ttgtatatgt gcgtatgagg tgtcaatgga aatcttagga tgtctagaat   226740
```

```
attatggtat aaaaatagga ggcatgtatt aagagaattt gggataaaaa ggataatttg    226800
ttgaaggcat ataagctgcc agaaactgtt gtgatgaatt ggtagaaaga tggggatgca    226860
tctctcattt ctggagggat ataaggacat gtaaggtacc tatagaaagg ttacagtgtt    226920
aggaaaaagt tctaagtggt agcactcaat tatatagggt ataacctagg taaattaggg    226980
tatctttcag accctgcaaa tctgtctctt tatctgacct ctgtacaaat ctataaagct    227040
ggaaacaata gtggaagaca atgagggcaa tgggtccagc aaaacccccc tcccaaagca    227100
tggggtcaat ctgatacagc acaaagactt ggcttaaata acaataatgc ctctggaagg    227160
tcccagacta cctcaagcaa ggaccagaga aaacaaactg tggttgcgac cttgtctgat    227220
tgtaagcatt ttcagttgat ttgcttttta ttttagccat tctcaattct cgaatttcgc    227280
cgttttttca gttgatttta ttaagaagca tcacttattc acttttttagt actccgacta    227340 taaatgtcat cctgtttact tgtagttttc atataagcca ttaatacaca aatggatcct    227400
ttatatccga aacagtggcg gacccaggaa tttcaaactg ggggtacaaa acacgaacgt    227460
catacagtgg cggacccagg aattccaaac gaggtcttgc catcgaatct cacctagccc    227520 tccoctccca tcaacctacc ccatattaaa aataaaaata aaaataaaaa taaaaatact    227580
tgcgctgggc agtcatgtga cacttgaagg aatgaaccct aatcaactca aagtctctag    227640
catcacaaac gatgggcgaa aattttttca aatattctga ccaactcatg caagtcaatt    227700
gtgaaaaatt caaagataat gttgtcatct aaagattttt taaataaaaa tagaaaaatc    227760
gaagaaaaat tttatgtgag agatcgggaa catataaaca attatttaaa ctcaagtttt    227820
ccgacaagga aattttttcct gctcctctaa ctttaatttc ttccccatta gcggttttaa    227880
tcaaaatttt agtcggtttc tcatacgtga cgaaatcatc gggatcatat gacatggtat    227940
ccgtcgctcc gcaatcgaaa atccaactaa aattactcat atggcgtgtg acattggaat    228000
taaagttaga gtggcccttc ttttgaccat aagccacgtg cccctcttta ttcattgagg    228060
ggtcacattc tgcttctttt gtcccatcat catagcatac atcttcccca taaattaaaa    228120
tagtaggggt aataacatgt ttagaattag ttggttttaa aatttcaata tcatcttcaa    228180
taaattgtac ctagggtaaa taaacaataa tagacaggta caattaattt attagtaaat    228240
tcaataatta gccaaattgt aggaatgtca agagtcttga caattgattc gtcataggag    228300 tatatttttta cagacacaca aaaccaaaag ccaaattgta gtaatgtcaa gagtcttgac    228360
gattggttcg tcaatcgtct tatattacac tcatcaaagc aaaagtccgt ctctttaatt    228420
gaagaaacag gaaagtaatt gaaaagaaat ggatcgggt tcgagaacat gttgggtttc    228480
tgtctcaaaa gagacgtttg agtgagataa ctcactctcc tcttcatctt ccattttaat    228540
taaattaggg atctgacctg ggttgtcttc attctcacca tggttgccgg tggtgttttg    228600
ggttacagaa aaaccgatgg ctgctgttcc ttctttactt tgatctgacc tgggttgtct    228660
tcactctcct cttcatcttc cttttttttt taaatatttt ttttctgaat tttttttttt    228720
caaacggggg gtacaactgt accctcttgt cacttaattg ggtccgccca tgatccgaaa    228780
aagtatataa aagattactt tttgaaggaa acaaatgaac aaatgaattt catcctcatt    228840
tttcttaaat agcatctcaa cattttttaaa agtgtgtttt gtaagtcatt tttagttacc    228900
gaattttttt ttaccggagt ttcattaccg aagtttcatt tacttgtagt tttcatataa    228960
gtcattaata tacaaatgga tcctttatat ccgaaaaagt atataaaaga ttactttttg    229020
aaagaaacaa atgaacaaat gaattcatc ctcattttc ttaaaaaaca tctcaacatt    229080
tttaaaagtg tgttttgtaa gtcattttttt tattaccgaa attttttagtt actgaagttt    229140
```

```
taataccgaa gtttcattac catccctaca tacaacccat catacgcata caaaatcttc  229200
tgcctagaat tcaatgcaag tcccctagc aactccaaca gctttttct cattcataat  229260 gctcgattcg caccttgag ttcttcatcc ataatgattt ggttcggttc gagaaaaaac  229320
aaaaaaaaaa aaaagaaaa aaaaatttca aaaaatattc ttacattttg cttgatttcg  229380
tttctagttt tgttctcctc tgttttaagt gcttctaaca atggaagttg aaaaccgtag  229440
agttactatt ctccgagatg actgagatta aacattatt tcgtgataaa tgcaaagaaa  229500
tctctaaaag tgagagggaa atcagaagag tcgatacaac agctttatca gaactaaaaa  229560
agaacgaaaa aaatggaatc aatccccatc catgttagca taatggtcgc aattagcatt  229620
atgttttttc agttgatttg cttttattt tagccattct aaattctcaa atttcgccgt  229680
tttttcagtt aattttatta cagaagcatc acttattcac tcctttagta ctccgactat  229740
aaatgtcatc ctgtttactt gtagttttca tataaggcat taatacacaa atggatcctt  229800
tatatccgaa aaagtatata aaagattact ttttgaagga aacaaatgaa caaatgaatt  229860
tcatcctcat ttttcttaaa aaacatctca acatttttaa aagtgtgttt tgtaagtcat  229920
ttttttatta ccgaagtttt tagttaccga agttttagt taccgaagtt atattaccga  229980
agttgaccaa aaaagaacaa caagttctga atgtttactt gaagatgagg ggcttatata  230040
gcttgtatat gtgcgtatga ggtgtcaatg aaaatcttag gatgtctaga atattatggt  230100
ataaaaatag gaggcatgta ttaagagaat ttgggataaa aggataattt gttgaaggca  230160
tataagctgc cagaaactgt tgtgatgaag tggtagaaag atggggatgc atctctcatt  230220
tctggaggga tataagggca tgtaaggtac ttatagaaag cttacagtgt taggaaaaag  230280
ttctaagtgg tagcactcaa ttatataggg tataacctag gtaaattagg gtatctttca  230340
gaccctgcaa atctgtctct ttatctgacc tctgtacaaa tctatactct tttctttaat  230400
tataccacat gctatctcaa tctaatgatt tagtatcttc aacaacatgc atgtggagga  230460
tatggtaaaa gatggggtca aaatacactc atttacaatt tttaaatgat tttggaagca  230520
agatactagt tttgaaaatt tatataaaat tttcagattt atatatttt cttttgtgac  230580 tttaatttaa caccgatttc aggtaataat cgcaatactt gaaaatttat aatataaaca  230640
tatgaataac atttcaaaca ttaatatata taaaatatca aaaaatctca atatataata  230700
tgcgtatact taaacttata attaagactt tatttttact ttgaacacaa aaatgtgtta  230760
ttcttacttt atgcaaggta aaatttaatc aatctaacat attgtcaaat gtttcacata  230820
acttcttcag ttctctatct tcattttgc ctctttattt gcctcaacgg gagctgaaga  230880
gatgagttca agtagaggtg ttaataagtt acgtcagggt gtttcgaata tcagccttag  230940
atcttctgac gactgggaga caatcacgag taaatgtaaa aataaagctg gaaacaatag  231000
tggaagacaa tgagggcaat gggtccagca aaaccccccct cccaaagcat ggggtcaatc  231060
tgatacagca caaagatttg gcttaaataa caataatgcc tctggaagat cccagactac  231120
cttaagcaag gaccagagaa aacaaactgg ggttgcgacc ttgtctgatt gtaagcatt  231180 tcagttgatt tgtttttat tttagccatt ctcaattctc gaatttcgcc gttttttcag  231240
ttgattttat tacaaaagca tcacttattc acttttagt actccgatta taaatgtcat  231300 cctgttact tgtagtttc ataagcca ttaatacaca aatggatcct ttatatccga  231360
aaaagtatat aaaagattac tttttgaagg aaacaaatga acaaatgtat tttattttca  231420
tttttcttaa atagcatctc aacatttta aaagtgtgtt ttgtaagtca ttttaatta  231480
```

```
tcgaatttttt ttgttaccga agtttcatta ccgaagtttc atttacttgt agttttcata  231540
taagtcatta atatacaaat ggatccttta tatccgaaaa agtatataaa agattacttt  231600
ttgaaagaaa caaatgaata ggggtgaaac ttatttggat taaaaccgca aatcgaacca  231660
gaccaaaccg aataagaaat atggtttggc gatttttttaa ttttggtttg gactaggttt  231720
gaaaattcat aaaccgaaat aattaggttt ggattaggtt tgtaattttt aaaaaccgaa  231780
aaccgaatta ttagaccgaa caccgaaatt tttaagaaaa tactatagcc cactaacact  231840
agtaactagc ccaggcccaa atattctaa ctctaaagaa aagtcaaaaa ctaaaaaacc  231900
taagcccaac gccccaccca gccgtcctaa tcccctcctt ttttttcattc tcttattcct  231960
acttccattc tctcactaaa tttgagtaac ctaagcccag tcatcccctc ccttttttcat  232020
tctctattac tgttcttcaa ttttccctttt gtgttccaac cggccactcc agccgtcgac  232080
tttacgcctg ccgacgtcca agtccaact gtccaaataa gccttcttcc cctttcattc  232140
ttcgtttgat ttgtgttcat ttaggatttg acggttcgtc ttttgtgttg aatctttgtt  232200
ttttctgttt aatctttttt ttgtgtttaa tctttgtcta gggttcgttt aaggtttta  232260
gggtttgttt agtgtttgtt taatatctgt gctttatatg tttatgtgtt cgtttagggt  232320
tcgattaatg agtctatgat tttaagtgtt tctgtgtttta atgaatcttt attatcaatt  232380
tatgtaattg tagttaaatt gctattcggc aaaaaaaaat ttcggcctaa acaattcggt  232440
tttgcggttt ggattcggtc tgcaaattaa aaatacggtt cggtgcggta attaatttgg  232500
tttggtgatg gtctgaaatt atggagaccg aatttaatat ggtctgatt ggttttggta  232560
aaagaccaaa ccgtagaccg aactttcacc cctacaaatg aacaaatgaa tttcatcctc  232620
attttttctta aataacatct caacattttt aaaagtgtgt tttgtaagtc attttttagtt  232680
accgaatttt tttgttaccg aagttttatt accgaagttt taatacaatt aatttattag  232740
taaattcaat aattagccaa attgtaggaa tgtcaagagc atcttgttcg tttagtacac  232800
cataccttg aactaacatc taaagatgaa attaggggtt ttaaagaatc aatgaaacga  232860
gagatcgact tgtgtaaatg gaattttaga aagagttaaa atatatttcg aatgtaatt  232920
aaagtggcgg gttcattttc aaacagacaa ataatgtgca atgagtgggg acaatcaaaa  232980
atagtatcta tatctaatac taaaacagag accacctaag gacacgtgtc atgttctgat  233040
gagtttattt cccgcctaaa aactagagca ctgaatacgc tattacctca tatagccttt  233100
aatatctaga ttatctacaa taataattcc tgcaattaag gaattaatta ctacaaatga  233160
cttcttatgt ctcattaaac taattatcac attttttaaaa gatcattgca cttgtggggc  233220
cctaattata tataaaaaaa tttaatgtca cgaaaggaaa atgtatatga attaatatag  233280
gtatagaaga ttttttgtacc cctttttaccc gagggagtat acaacccaca attgtttgat  233340
cacgaagatc acaaaggcct aatttcctga gctaaatctc tctttgacac aaagaactac  233400
tcagtaagtt tgctgtttaa ttacttattc atcttcaatt cctcttttt aacttagtaa  233460
tctaaaattc attttgttta attgaatatc tagctatttg gaaagttagg gtttcgttta  233520
tgtgttgatt ttaaattgta gtaatgtcaa gagtcttgac gattggttcg tcaatcgtct  233580
tatattacac tcatcaaagc aaaagcccgt ctcttactt gaagaaatag gaaagtaatt  233640
gaagagaaat ggatcggggt tcgagaacat gttgggtttc tgtctcaaaa gagacgtttg  233700
agtgagataa ctcactctcc tcttcatctt ccattttaat taaattatgg atctgacctg  233760
ggttgtcttc attctcacca tggttgccgg tggtgttttg ggttacagaa aaaccgatgg  233820
ctgctcttcc atctttactt tgatctgacc tgggttgtct tcactctcct cttcatcttc  233880
```

```
cttttttttaa attttttttt tctgaatttt tttttttcaaa ccgggggtac aactgtaccc 233940
ccttgtcact taattgggtc cgcccatgat ccgaaaaagt atataaaaga ttactttttg 234000
aaggaaacaa atgaacaaat gaatttcatc ctcattttc ttaaatagca tctcaacatt 234060
tttaaaagta tgttttgtaa gtcattttta gttaccgaat tttttttttac cgaagtttca 234120 tttatatccg aaaaagtata taaaagatta cttttgaaa gaaacaaatg aacaaatgaa 234180
tttcatcctc atttttctta aaaacatctc caacattttt aaaagtgtgt tttgtaagtc 234240
atttttttat taccgaagtt tttagttacc gaagttttat taccgaagtc tcattaccat 234300
ccctacatac aacccatcat acgcatacaa aatcttctgc ctagaattct atgcaagtcc 234360
ccctagcaac tctaacaact tgtagttttc atataaggca ttaatacaca aatggatcct 234420
ttatatccga aaagtatat aaagattac tttttgaagg aaacaaatga acaaatgaat 234480
ttcatcctca ttttttcttaa aaaacatctc aacattttta aaagtgtgtt ttgtaagtca 234540
tttttttatt accgaagttt ttagttaccg aagttatatt accgaagttt cattacttga 234600
gttgcatgtt tataggtacc aataaaagtt tctagatacc actaaaagat tcatgtttat 234660
atgtaaatat aaatagtcaa atttgtaggg atcggaatag gtcactacga cactaactaa 234720
atcacccact caagacaatc cttcaaatat ccaaaccaat caacccaaat atcacacaac 234780
aagaatatga aatatggata gcaatatttt agtaacaaag catcaataat aataagttga 234840
ataagatgca aacaacacac acaaattata cgtagaaaac cctttcgatg tgaaggataa 234900
aaaccacggg acctcttgag gagtccaccc ttaatcttct cttattgatg ataaaaattg 234960
aaggtaaaat gtgttgggtt tttgggtcca ttcctatgtg gagaaaccca ttttatatta 235020
aggataaata tcctcttatt ttctaaccca tgtgggggtc aagcatttag cttctatgag 235080
aagcttaggg ttttatatt tggtcttcta tcataagaca aaatatcatc ttttgaatga 235140
gtgaaaaaaa gaaaaacata aaaattgaga aagcatcccg tagagaactt gcacagctcc 235200
acgaaatagc catttcccgg agtttcaact gttggatcgt cctataattt taccagcttg 235260
ttggggacac atagggcttc atttggacgg ttggatcatc gttttgaact tcggttcgtt 235320
ggttatactt cctggacaga agctgttgtt tggtgatttc tttcttcttt gtttctcaat 235380
tgttgattat tatggttgtt tgttcttggg tagtttgaag accctttgga gaactttgga 235440
ttggtttgtg taacctcctt ttcatcataa taagagaagt ttgggtggac tcctaaagtc 235500
ccgtggtttt tactcttcac accgaagagg ttttccacgt aaaaatcttg tgtctttgct 235560
cttgattatt acttgctttt gtcttgttta cttgttgatc tcattgtggt ttattggtga 235620
tatttgagtg tgttgatttt ggtgttttgg tgaattaatt ttgtacgggt tatttccgct 235680
atttgtgtgt tatcaatttg tgtaattggt agcttttgga ggtgttctta cctcatcaac 235740
tggtatcaga gccggattaa ttgttaattc tctaaatgga tggtaatctc aacactagta 235800
ggatgattag tttaaatggg actaataatc atttgtggaa accgaagatg aaagacttgt 235860
tgtatgttaa aagttggcat ctacctgttt ttaccactca aaaccggat ggcaaaagtg 235920 aagaacaatg ggaatttgag catgagcaag tttgtgggtt tattcgtcaa tgggttgatg 235980
ataatgtttt gaatcacatt aatgaagaag ttaatgctag aaccttgtgg aaaaaacttg 236040
agtcacttta tgctagcaag tcgggaaata ataagttgtt cttgatcaag caattgatga 236100
atttaaagta taatgagaac aaggcacttt ccgatcactt gagtgatttt catggcatta 236160
ctcaacaatt gtcggccatg gagatcaagt ttgatgatga agttcaggga cttttgttac 236220
```

```
ttagtactct tcctgattct tgggatactt ttagaatgac actttgtaat ggagctcctt   236280
ctgggaaggt tactttagac tttgttaaag ttggcatctt gaatgaagaa atgcgaaaga   236340
agtctcatgg tgtgtcatct tcacaacccg agaaagctta tgttgcagaa aatagggaa    236400 gaaataatag tagagcttca aatgatagag gttctagcta gtaggagcaa gtcccttgga   236460
aaatccaaga acatgaaatg caactattgt gataaaatgg gtcacattca aaattttgc    236520 tacaagtgga aaagagataa caagggaggc aaaggcaaac atgtgaatta tcatgataag   236580
aaagatgatg ataaggatga tcgagcagca accgcgacta ccaatgatct tgtcattgtt   236640
tatgatggag atgttgttaa tttagctagt tgtaaaacta gttgggtagt tgatagtgga   236700
gcctcacgac atgtgacatc aaagaaagag ttctttacca cttatacacc tggagatttt   236760
ggggtattga agatgggtaa tgatggcttg actcaggttg ttggtgttgg agatatttgc   236820
ttggtgactg atagtggtgc taagcttcta ctcaaggatg ttaggcatgt tcctgacatt   236880
aggttgaatt tgatctccac tagtaagctc gatgaagaag gatattgtag tacctttat    236940 ggtgggcaat ggaagctcac taagagaagt ttagtgtttg ctcgtgggat gaagcactct   237000
agtctatatt ggatgcaagc ctctatttct acagatagta tcaatgtagc agctagtgat   237060
ccagcacagt tatggcatag gagacttggt catatgagtg agaaaggcct tggatgcttg   237120
atgaaaaaga atgtgttacc tggtttaaag aatgcaaagt tggagagatg tccacactgc   237180
ttagcaggga agcagaacag agtttcattc aagaaactcc ctcctccaag aaattctgat   237240
tcagtgaaaa tgttttacgc cctaacaaac ggagccttag taataaactt aagttagggg   237300
tcctaagaag aaaaacaata tctatttgtc ctaattttga tgcaagaacc aatacatgag   237360
tatattctca aaagatccca ttataagcta catcttagaa aaaacaatat ctatttgtcc   237420
tgattttaat gaagaaccaa tacaagagtt tattatcaaa agagcccatt atatataaga   237480
tacatcctca aatttcactt caatttggtt gagacattcc agttaggagt cagttaatta   237540
ctttagaggt aatatggttt agtttactta gattttgtta gttttatctt tgttggtat    237600 tttatttgaa gcttcaagga tattttaatg gagcattggt gttagatatt tatgggtatt   237660
tattatttgg tcttcaatca tcctcacatt ttgtgggtaa cttctaatca tcctctattt   237720
tagtatttta tcatctatttt cttgatttaa gttgttttat ttatttctct ttttttcttg   237780
attatttctt gtcatgttca tcttcatgtt atttgtgcta gaatggttta tttgttgttg   237840
atgattttgt tagttgtgat gtgtattagt gagtagttag ttgggtttgg gcttagctca   237900
acccttgtgg atggcttgat aatggtggaa tattggttga tagtggtttg aatggagact   237960
tagtagaagg gtagcctcac ccattgtttg agggttgcca tggttgcttt tgggaggcca   238020
acgagggttg gatcccggag taacctaaac ccttgctcaa tgaatggagc cgagtgcaag   238080
ggatcgacga gagttgaacc ttgcaatcac cccttcaact aggagttttc cccttcgcct   238140
acgagtaggg atggcaacgg gtcggatctg ggccgggtct aggtggaccc ggatccagat   238200
ccgttttcaa gcactgggtc cagatccgga tccggacccg cgggtctatt tttacaggac   238260
ccagatccgg gtccgtggat attgcggatc cagtaccggg tccgggtcca aaacgggtcc   238320
cacttttttt tgccattttt ggtgtatttt cgaatcgttt tgagattgcg atgatgctat   238380
tcatagacta atgattataa atacataatt tcacaatcta gtacttaaaa aatatttata   238440
caactacaaa ttgtcttcaa aatatccaac gaacaaaaat aaacatagcc gatcaatatt   238500
caaaaacggg tatttaatat tcaaaaaaaa aaaaaaaact ttatagctta ggttttatca   238560
ggcttctctc ccatttggtt agatctttta acatagagtt tgtccattca tgttttctga   238620
```

```
ctttaccaaa aaggcattta ccagcacttg aagcatttat ttctacactg tacaccccac 238680
aaggtagctc ttcccagtaa gctgcgttgc ttgctccacc tttcaacttc aggatctaga 238740
aacagataat attcagcaca aaaaaatgtt ttacaattta cataagtaaa gtagggatgt 238800
aaactaaagg gtaagaacag gaccaagaag gagaaattaa ctttattagt agaaactgat 238860
tatatttttt taaataaacg ggtctgcggg taaacgggtc caggtctggg tattttctc 238920 agatccggat ccgacccgt gaattttaaa tggacccgga tccgatccgg acccgacggg 238980
tctatttttt taagacccag atccgtgaaa acgggtacgg atccacggat ccgggtcggg 239040
tccaataccc attgccatcc ctacctacga gagtagggaa ggattgacgg atagtggact 239100
tttgttgcct gattatcttg tctttactca tgagagtgag aaggaagaga ttttcggagg 239160
tgatcccaag cccgatccag gatcggatca ctctttgtat tgtgttccac ttctctctaa 239220
tcaaactaaa agaaatcaaa acatctatca aaggatagtc gtcacaagtg agctaacacc 239280
catcccattg tttctttgtt tgttattttc atagttatag ttgtagtcta gctcgtcatc 239340
tatccctact tacatgatcc cccaataacct aaagaggccc taagtctcac actcgtctcc 239400
ctgtggatcg accacttact tgccactaca cttctgtaga gttaagctag ggtgtttata 239460
aattttgttt gattagaggc tttagcgacg accaaaaagc cctctatcag ttcatcatag 239520
acatagcttg ccctcataat atccaattca gaacattctt gacttggaac cattgaaagt 239580
agttcgtctg caactttctt catgagtcca agcgaccct catcatctct ttcggaagta 239640
ccctcatccc tatcacaact ctttcttttg gaactcctag ttgtccaagt aactgatgta 239700
ccagaagtgg gtattacatc aggtatatat tccgcagtcg aatttggaaa atcgggatt 239760 ttgcaggtac actgcatatg caaccgccgg ccataaataa atgagggtcg tgtaaactta 239820
tatatcaatt tgaaggttgt aatgatcaac ttaccgtacc ttttccgca cagttgcacc 239880 attgtaaaaa ttttcccatt ccaatcaaat cagtttgaga gctagtagga atagttaagc 239940
gttggtactt aatttccttg ttgtaattat aactaaaaat tcgccataat ttcttgtctg 240000
tccatttaaa cttttgatta ataactagag ggaagacata tttcttcatc acatatatat 240060
agtgtacttt ttcgtcttca atcatctgtc aataaaaata caagtgaaag ctcaaagaaa 240120
ttctctcaac attactaaat cttaaaaaaa aaaatttcg ctaaacattt taccttacta 240180
gcagaggatg atgtgacact ctcagtgtcg gatacgctta attcttcttt tcctgcaaga 240240
taagtttaat ttcacacaaa acaaccacat ttccataaga agtcaaccaa cactataaat 240300
acgatatcta aacctactgc acacaatagt acgacaacaa ctgcacaaaa cgaccaccaa 240360
caatagtagc aagtcaacca acactataaa tacgatacct aaacctactg cacacaatag 240420
tacaacgaca aaaactgcac aaaatgatca ccaacaacag tagcagcagt agacgcaacc 240480
aagagaacaa gttgtaacag taactcagaa atttataaca gcaattcaca agtttgtaac 240540
aacaatagta caacgacaac aactgcccaa aacgaccact aacagtagca gcaccaacag 240600
agccgaggta gcagcaccaa ctatcatcac agcgcctcca aatcgtccct aacaacaaac 240660
aactactaca cttcacacaa acaaccattg atgttgatga agaaacatta tatttgtcta 240720
gacaaactta gttgatattt gaggatgcga ggcttagact tagcggtggc ttgtagaaac 240780
attaaaaccg ggatcagttg attttctttt actagttcat catagacata gcttgccctc 240840
ataatatcca cttcagaaca ttcttgactt ggaaccattg aaagtagttc gtctgcaact 240900
ttcttcatga gtccaagttt cctgtcatca tctctttcgg aagtaccatc atccctatca 240960
```

```
caagtctttc tttttggaact cctagttctc caagtaactg atgtaccaga agtgggtatt   241020
acatcaggta tatattccgt aatcgtattt ggaaaaatcg ggatttggca ggtacactgc   241080
atatgcaacc gccggccata aataaatgag ggtcgtgtaa acttatatat caatttgaag   241140
gttgtaatga tcaacttacc gtactttttt ccgcacagtt gcaccattgc aaaaattttc   241200
ccattccaac caaaacagct gcagagcgat caggaatagt taactgtcgt ttcttaattt   241260
ccctgttgta attattacta aaacatcgcc ataagatggg gtctgaccac ttatattgtt   241320
gcttaataac tagagggaag acatatttct tcatcacata tatatagata gattttcga    241380 cttcaatcat ctgtcaataa aaatacaagt gaaagctcaa agaaattctc tcaacattac   241440
taaatcttta aaaaaaaaat tcgctaaaca ttttaccgta ctagcagagg aggatgcgca   241500
ctctcagtgt cggatacgct taattcttct tttcctgcaa gataagttta atttcacaca   241560
aaacaaccac atttccataa gaagtcaacc aacactataa atacgatatc taaacctact   241620
gcacacaata gtacgacaac aactgcacaa acgaccacc aacaatagta gcaagtcaac    241680
caacactata aatacgatac ctaaacctac tgcacacaat agtacaacga caaaaactgc   241740
acaaaatgat caccaacaac agtagcagca gtagacgcaa ccaagagaac aagttgtaac   241800
agtaactcag aaatttataa cagcaattca caagtttata acaacaatag tacaacgaca   241860
acaactgccc aaaacaacca ctaacaacag tagcagcacc aacagagccg aggtagcagc   241920
accaaatatc atcacagcgc ctccaaatcg tccctaacaa caaacaacta ctacacttca   241980
cacaaacaac caaaactgtt ttggtccatt tacttggtca agaagcctgg tcatacaatc   242040
aaaagtccaa ttaagcaccg caattaagca aaaacacaac acgatggaaa aaatatcatc   242100
aacaaaaatt aaacaaatcg atttacgaat gtcaagcaca caaccaacag caattcacaa   242160
atttgtagca acaatagtac aacgacaaca actgcccaaa acgaccacta acaacagtag   242220
cagcagcaga cgcaacccac aacagcagta gcactactgc agaaccaaca gagccgaggt   242280
agaagcgcct ccaaatcgtc cctaacaaca acaactact acacttcaca caaacaacca    242340
caacaattca cccaaaacaa ccacatttcc atcataagtc aaatttgatt cttaaatctt   242400
cacatttaag tcaaatatga ttcttaaatc ttcacattta aatcaaaaca tattgcaaat   242460
ttcattcaca tttctgaaat agagtcaatt tcatcccaaa acaaaattct tctttattgt   242520
tataaacttc tgtctcattg ttataaacta gtttataata gcaattcaaa tatttacaac   242580
aattcaccaa tttataacag cagttcacca gtttaacagc aattccgaag tttgtaacaa   242640
tatctcagaa atttatagca gcaattcaga aagtttatagc agcaattcac cagtttataa   242700
cagcaattca caagttataa caacaatatt gaagtttgta acaacaacat tattttgtaa   242760
cagaaattca ccagtttgta acagcaattc acaagtactt aaatttgtat gtaacaagta   242820
tctaatttca cagaaaaatc agcaattcta aaccaaaaaa atggcagtta ctaaaggttt   242880
gaattattat tttttttttt ttgaataata cctgattcat taataaagag tcatacgaca   242940
tctacatcag agataaaaat tagcaagtac atagcaatta aaaccaaata taattcaaaa   243000
ataacaaaac tacgatcgtt gtgtatgaga tctgacaatt ctgaatatcc tcttccacat   243060
cgctgtttga tacagccttc tacgagggg tctttcgatc tgttgtaatc ttgagataga    243120
attaaatttg atgtagttga tgatacttgc aatttttggtg tctgctgcat catcgcatta   243180
atctctacta ataaatcaac taatgaccaa aattcataac tccaaactct cacaaggaga   243240
gactttaaaa cccaatatat gggtagaatc aacccaatga atgggtagaa caactctctt   243300
ttaaggagag gacaaaaatt tattctaatc atattaaaaa aacttaaaaa gaagaaatta   243360
```

```
ggggcttacc atcaatcttt aaagattgat gatagcccca aactcactat agatattagg 243420 gcttttttg gagagagaaa taataataat aataataata acaataataa ataataataa 243480
taaaaacaat aataatataa ataataatat aaataataat aataataatt caaaccttaa 243540
acattaattt gtagatctcc atttaatta acaaatatcc attttaaaaa taaataatta 243600
attttgtaat ttctcaattg attcaatggc ggctagggtt tcttatcaat tgattcaatc 243660
taggtagatt tctcaatata tattttgtaa tttcatccta acaattcaat atatgtatat 243720
ttaatttaac aaatatccat tttaaaaata aataattaat tttggacaga cttttaagct 243780
aggatatgat gaaatagtcg ttcctaataa gtaaacataa cctaaaagca tctctggaaa 243840
attaaaatct gaaagaggc aaaaacaagt aaacaaacca aagcacagaa taaaaaagaa 243900
aatcgaaaca gcaaatgtag aaattgttga aatataaata aatgaaataa aagagaaata 243960
taaaaatacc tagaaaagat aatcttgaaa aatggagaga aagagaaatg gagatctaca 244020
aattaatgtt taaggtttga attattatta ttattattat ttatattatt atttatatta 244080
ttattgtttt tattattatt atttattatt gttattatta ttattattat tattattatt 244140
attattatta ttattattat tattattatt attattatta ttattattat tattattatt 244200
attattattt atattattat tattattata attattatta ttactattag tatcgaattc 244260
agaatttaat taataaatac taatattatt taattaatta attaaaaaat aattattaaa 244320
tagtcattta tattattatt atctaattaa ttaattaatt aaaaaatatt gttaattaat 244380
aaataaatta acatgataat attattacat tatttatatt attaaaaata ttattattat 244440
tattattatt attattatta ttattattat tattattatt attattatta ttattattat 244500
tattattatt attattatta ttgttaatat tattattaat attaatattg ttagtataat 244560
atattattat tattattatt attattatta ttattattat tattattatt attttttattt 244620 aaatttatta ttattattac ttattactta ttattattaa ttaattaatt attattttaa 244680
agatcgaatt ctgagtagac attaggcagt cgaaggtaga caaacgtgag tttatatgtt 244740
ttaagaattt ttacagtagg accagacagc agcgcgtggc gcgtgaattt tttgagcaag 244800
taagcaaaca aagattttgt ggatttcatc ttccacataa tgtctctgcc attaggaaca 244860
gtggggatga tggtgggtat gtaaaagggg ttgtactaat aaaggttatg taacctttaa 244920
ttttgactat actgtaagaa tatttgttat gtaggaagat atgaaaatgt tgttgtaaca 244980
cttctgcaaa cttgaatgtt gaagctaatt atagaacatc ctttttttga ttacttgctt 245040
ccatatcata attgttccat aacaatacat actacttata tcttacatta gagtaggtgg 245100
ttcaaaatga ataacatagt acttatatct aacatatata gttatggata atcttgaagt 245160
taagccaatg tctaccatta gtggaattac actcgttaat aagtttcatg ttaaggatgt 245220
ttctaccctg gaagagaaac aggtgcacct tggtctcgac caggtatttt tgaacatagt 245280
cattttgtta tttcggggtc ttcttgggtg tgtttcttac acattgaaaa tgaatcaaga 245340
aaatgaaata ccatgaaaat aaaaaaaaaa ttcaaaaaaa gctacccagg tcaaacgggt 245400
acccgggtca ataaattatc ggaccatgac ccgatccgga actttgaagt ttttatagtt 245460
ttcaacccgc catttatgag gcgggtcagc gggtcgggtc gggcgggtcg ggttgttttg 245520
aacaccccta caaacaacca caacaattca cacaaagcaa ccacatttcc atcaaaagtc 245580
aaatatgatt cttaaattt cacatttaag tcaaatatga ttcttaaatc ttcacattta 245640
actcaaaaca tattgcaaat tttattcaca tttctgaaat agagtctatt tcatcccaaa 245700
```

```
acaaaattaa gctttattgt tataaacttc tgtctcattg ttataaactt ctgtattgtg   245760
tctttactct taacatgaaa tatgattatt gtcgtttttt tcttctaatc taccttctct   245820
ttttcgtttg aaagctcaac accattggtg acaacaacaa ctacaagctc tgttgcccct   245880
accaacaata ctgccagcac aaaaaggtta gaaagaaatc atgggcacat ggctacaaaa   245940
agagaggagc aaaaggttca atgccaatgg tgatttcaac ccaaggttct tcaagctctc   246000
aacaacaaaa agaagtgtat ttgtaatgtc tgttatgatt gctaggttat gttggaactt   246060
ttatgttttg ttgtctttgt aagatataag tagggtgtt caaaacaacc cgacccgccc    246120
gacccgaccc gccaacccgc cttataaatg gcaggtcgaa aactaaaaaa aattcaaagt   246180
tccgggtcgg gtatccgacc tgccttaatc gggtcgggtc atgggccgat aaattattga   246240
ctcgggtatc cgtttgaccc ggatagcttt ttttgattta tttttatttt caaggtattt   246300
cattttattg attcatcttc aatatgtaag aatcacactc aagaagaccc cgaaataatc   246360
acatgactat gttcaaaaat acctggtcga gaccaaggtg cacctctttc tcttccaggg   246420
cagaaacatc cttaacatga aacttattaa tgagtgtaat tccactaatg gtagacattg   246480
gcttaacttc aagattatcc ataaccatat aagttagata taagtactat gttattcatt   246540
ttgaaccacc tactctaatg taagatataa gtagtatgta ttattatgga acaattatgg   246600
tatgaaagca agtaatccaa aaaggatgt tctataatta gcttcaacat tcaagtttgc     246660
aaaagcgtta caacaacatt tccatatctt cctacataac aaatattctt acagtataat   246720
ctaaaggtta cataaccttt attagtacaa ccaacaacaa gaaaaaacca aataaaaacc   246780
ctaaaataaa atatgatatc tcttttccaa gctttctctc cttcatcaat tcttcttaa    246840 gcctttgta ttctgaaatt gcttgttctt tctgatgttc caagcaacaa agccttgatg     246900
tcaatatctt gaaatcaacc ttaagttcat cgatccactt aaacttcttg catcccctcc   246960
aattagtgtt aggatcgaaa aattggcatg cattgaaacg tctacctgga ttttctttag   247020
tccacgaaat tcgctgtgca aaaaggaaat tcgcaaccac atctgtcaag cttcgattgt   247080
ttggagtgag aggaatccat gaattgattt gggcttgaaa gaaaagagg cggattaggg     247140 ttcatacgaa atagggaa ggtgaaaggt ttaggtttga actaaaaacg tgctttaaaa       247200
cctaagaaat caaagaaaca attaaaggga aaggtttaaa agaaggtcac gtgcaagtca   247260
cgtgaaaagt caaactaact tttgacggtc aactaactga aaccgtcaag aggttgtgtt   247320
taacaaacgt taatatcata taaggtagtt ttttgcaaaa aaattagaat aggtagtttt   247380
ttgcaagtta cccattagaa taggtagttt tttgtaattt acccataaag agataaatga   247440
ttccttgtta gatgaactaa ataaatagtt gaattgaagt ggaagagggg agtagtccac   247500
attatatgat caatttattt attgtgaaca accaagaagt gtcaagcaag ctggtgaagg   247560
agagtgaagc aaagtgaaca gccaatgttc caacaaacag aagcacaaaa gaacatacag   247620
tggcggatct agggttcaca ctccctagag gcaccaacat agagatgaaa aatatgcacc   247680
tggtgcacaa cccacttccg gcacatcagt tacttgggaa aaccgttatg aggtggaact   247740
aaataccatt gtaaagccga gtgaactcat gaagagcgtt gcaaacgaac tactcttaat   247800
ggtgccaggt gaataatgtt ctagtttaga tgtcattaaa tgtctaaacg aacccatgaa   247860
gagccgagtg aactcatgaa gagcgttgca catcagttac ctgttgtaca acccacttcc   247920
gacatctcat aaagttcttc agaacgttta ttcattcgtt aactttccta cacgtttatt   247980
gcatagaact ttatacttga tcttctgaag atgtcattaa atgtctaatt tcttaacaaa   248040
aaataatact ttttttcaatg atcaaccctat acatcactta tttcggactc tttgtcaaga   248100
```

```
aagatccttt attttcactt ttatagatca atttgatagc aaattaaccc aaattatccg 248160
gtcaaactaa acacttcatc atcctaaaaa cttatgtcct ttattcgtga actagtctta 248220
ctcctgacaa catgtaaatc atgaaataca actaagaatc aagccctaaa agcagtcgtt 248280
ttgaccactt gtatacaaga aatcataaaa tttcttgtgg catttcaatg tagaaatcat 248340
aaagtttgcg aaaattttag caaagtttgc gaaaatcatg aaatacaact aaacaattca 248400
tcttaaatcc tagtagaacg ttatagtcca catcataaat tatgataaat ttatcaataa 248460
tccacaaccc taattaaacc taatttaaaa cttaaaaacc cctattacaa ccaaatttat 248520
caataatcaa catcaaccaa ctcattcata taaccataaa caaccctaat taaacctaat 248580
ttacatagta taaatataaa tacaactaca tacacattca tcaattttga tcaatttaaa 248640
cctaatttac aaaatcgaaa atgaaaaaat accttgaatt tttcgtgggt ttgagaactt 248700
gaagaagaca ataatggtgg gttgtgtata acctatacaa tgaaacaaaa ttaaaattag 248760
tataaaaaaa ctaagcccta aaagcaaact aatgaagctt gaacaacaat gggtatacct 248820
tgaagaagag caagaatcaa gccctaaaag cagtcatttt gaccacttgt atacaagaaa 248880
aatttattgt ggcatttcat tgtagaaatc ataaagtatt acaacactta ttaagggggg 248940
caattcaaat acaaaaaaaa gtagtaattt tcattgtaac atttcatcaa gcactttata 249000
tgcatacaaa agaaatcata aaatttaact acaaatgtgt aaaatgtaac cttaaaccat 249060
aaaatcaaga caatgttaca aacaatcaat ctattataaa tgacaacaat catgaacaaa 249120
gaaatcaatt tgcaaattga aaaaaattag ggttcatacc ttaaatgagg atgcgaacag 249180
tggcggatct agggttcaca ctccctaggg gcaccaacat atagatgaaa gtttgcgaaa 249240
attttagcat agttttgttt gcaaaatgaa caaccaaata ttttcattc ctccaataat 249300 caaacataaa aaagacttgt tcagcataat caatagcata aggttttata tacatatcaa 249360
gtacagaagc atttagttga tcgtcatcac caaacccatg tttctctgct agacaatgca 249420
attgaagtga caatctagga caaccaagac cagaacaagc catcatcaca cataaaaaag 249480
agggcaatcc aggagaaatg aaacaatctc tcaatagtaa agtaaacact tttatagtat 249540
ctaaaggtct aacattgtta aaatagcctg tccggtggcg gtgggctgtg ggcagtagga 249600
aacacaaatc gattacaaat gtaggaaaca caaatcgatt acaataacat aagagaacaa 249660
caaaccaaca tagcagtagc aagataagaa taccgacatt cggaattcct atttaaaacc 249720
ttttatttaa atccaaattt cataatctaa attttggaat atattcttgt gcttaaattc 249780
tcatttctgc gattattatg aattcaaaat tcctagctgt tgccgaatat ccaatatcaa 249840
tttataggaa agaggtgaga atcaatacct cagttgcctt gccgccctgc caactgccga 249900
tagcctattg cagtggtgca ccacatgagg ggaatgggc aattgggagt gaagattagg 249960
aatttagggt ttacaataac aatactctga ggagtgagga ggaagtataa ggtagacttg 250020
gtccaaatta acttgtaact tcaatcctaa ttcctaattt ttttctttt gcttcctgaa 250080 ccctaacatt tctttcttca ctatcattgt ccgtaattag atgtatgttt atagagtacg 250140
atcgagttta gggtttgttc agtttgagaa gggtgtttgg tagaatgtag ttgattgatt 250200
tacttaagtg agaggaatta tgaatatgaa gtgagtgggt gaagaaaagc ttttcttaa 250260 ggtagaacca gtcgcacagg gaggaagaaa gcaagctgat gaagagaaac tgaaagaacg 250320
caaagtgaag agcaaacgtt ttttaatttt ttgtaaatga cccagaaatt taagagaaag 250380
acccagaaat ttaagttggg attaggttta gatcatttaa tataatatgt attatttggc 250440
```

```
actagtttga tataaattta tacttaataa agatggggct gaagcttggc tctgtttggg 250500
tgactttaat tgttcatttt cacgtatgag tgcccttatt ttactcggaa caataacttt 250560
aatattgttg ttacaattac aaactatatt tttttgttac aaactctagt aatgttgaag 250620
caacaaactc tagtaatgct agtttgaaat ctaatgaaaa atttacaact attcataaca 250680
acaattcaca agacattgct tgtagaaaca ttatctatgg ccagacaaac gtagttgatt 250740
ttggaggatg cgagccttat ccttagcggt ggcttgtaca aacattaaaa ccctcaaaat 250800
atccaaatca gaacattctt cacttggaac tatttaaagt agttagtctg caactttctt 250860
catgagtcca ctcgactctt cagttttatt ctcttctaca tcatttcttt cgaactccta 250920
atttgcaagt aaaactgtat tgcgtgtaat tcagaaggat tctaggcctc cttatacagg 250980
gaccgaactt cgaactccat cttggcccta gaccgagcaa gttataaact tgtattgttg 251040
ttataaactt atgaatttct gttataaact ggtgaattgt tgtaaatttc tgaattgctg 251100
ttataaactt attttttgaa attctaattt attttgaatt tttatatact caattctttg 251160
ggcagtaagt ctcatgggag acggtctatt ctatagacgg aattcatgag cccagcccaa 251220
aatataacat agtatatttg gggttataat aaattatttg ggttataata acttatattt 251280
ggggttatag aatagtatat tcgacattat aataccttac atttaggatt ataacataat 251340
ataattgata ttataataaa aaaaatcaat taagggaaat gggctggccc aattttgtgg 251400
tctatcctat atactcaatt taggattatt atcattatta ttattattat tattattatt 251460
attattatta ttattattat tattattatt attattatta ttattattat tattattatt 251520
attattatta ttattattat tattattatt attattatta ttatgattat tattattatg 251580
attattatta ttatgattat tattattatt attattatta ttattattat tattattatt 251640
attattatta ttattattat tattattatt attattatta ttattattat tattattatt 251700
attattatta ttattattat tattattatt attattatta ttattattat ttttattatt 251760
attattatta ttattattat tattattatt attattatta ttattattat tattatgatt 251820
agggatggtc atggggcggg tctggagcgg gtctagctag acccggaccc ggactctttt 251880 attttttga gatccagacc cggatccgga ccctaagggt ccaaaatttt cagacccaga 251940
cccggaccct cctaatctga tgggtctagg gtccttaatg ggtccttagt gggtataaaa 252000
taagtctcct tgatttgtca aatttgaaac atttgtaagt cattgtattt ttcgtatatt 252060
tgtacgagag ttattatcat attttacaaa tatttaatac taatttaaca tctaaactcg 252120
cataacgtca ccaatatacg cttaaatttt attataaaca ctagttcgag tccatgaaat 252180
aagggtaatt gggttaacac ttagcaagta acatatatat tatttatata tattatgatt 252240
atcttggagt tgggggactc cttttggccg tgctctcctt cacgggtatg agttgccgcc 252300
gtccttccct ccccagaccc tgctcatagt tttctatgag cgggatatac tgggtaggat 252360
gatgatgatg atgattatga ttatatgaaa ataaaataag tgttgagggc ataattcata 252420
catagaagag aaacaaaaat ggacaattta ataattataa gggtccaagg ggcgggtcca 252480
gggtccatat tttggacccg gaccggaccc cgtcaaatat tttttagatc cagatccgac 252540
ccagatccga tggatctcaa aaaattagac ccagacccta aaaaagggg cgggtccggg 252600 gcgggtccaa cagggtcctg gacccgtgac catacctaat tatgattatt attattatta 252660
ttattattat tattattatt attattatta ttattattat tattattatt attattatta 252720
ttattattat tattattatt attataggtt ctgattctga tgagggacct ctaactcacg 252780
agacaaggaa gcaacacaga atgatgaaga aatttttcaa tagtttggaa actttgtcag 252840
```

```
tgcaagaaat caatgaacgt gaaaggcagt ggcattgccc tgcttgtcaa ggtgtccctg   252900
gagccattga ttggtacaag gggctccagc tattttggc acatgcaaga actaaaggtt   252960
ctcaaagagt taagcttcat cgcacatttg ctaatgtctt ggatgaggag ctccaactta   253020
tatcatgcta acatgcattt acagtatatc tgtaacaata tatatcataa cctagtccca   253080
acttatcata acctaattcc aacatagcta ttttagggtc ttaaataaca atgtaatgca   253140
atcaagtatg ccaaaaaaat gagatccaat ggaaggcttt taggttcact aacattctta   253200
tatgcttggt atttgctgaa gaagtatggc aatgtgaaca gtgtgattga atgggagaaa   253260
aatttcaagg taacatgcga caagaggctt gtttctgaac ttgaatctag taaattgcaa   253320
aatggagaat atggcttctc ttttgctgtt ccagctggtg ttgacgatct tgacgtttat   253380
attcggcaaa aaataggcag caatcgattg tctagaactg gtgttgtcaa tggtggaaga   253440
aaatgggaga aaatgttttg ttcttttttc tttatggttg aaattgtgtg aattaactat   253500
caagtgattg gatttaccca tcatattctt taccccatg gcccgttcga tccttgatac   253560
taaatggtcg ggtggtaatg tgaatgattt acactataaa atttcatgaa atgtactgtg   253620
atgttcccat tatgaaactt tgataccatc tttcggaata gcaatgcaat gcaatcaagt   253680
atgccaaaaa atgagacgat tggtatagaa taagcatgac cattaaattt gtcaacagat   253740
ccaggatgaa gaaatgggga aatttgctgc tgagagagac gagttgatac ggattcatga   253800
gtacaaaaag atggagatga agaagaagca ttgggaggag gagttggagc tagaaaaga   253860 atttgatacc gagctgacat gaactactag ttgttatact atacaagctt attactgctg   253920
ttactattat tattattatt attgccgcca ttaatgagca tactgctaga tgatgatgat   253980
tattgttttg gaggagttaa gatagcttta cctggaatag ctttcagatc ataatccgaa   254040
tacgggtcgg ttaatacttg agaattttga gtagggtttc gaatcggatc tacaattgac   254100
ccaattgacg gagaagtatc aaaactagct gctggattga acccagaaat cacagattct   254160
aacgtttaca gggagtatcc catctgagat tgggaatttg catcaatggc gcaagtaaag   254220
gaattaagag ggagcttcaa gaaggaagaa gaccctattt aagaaataaa acaagggcaa   254280
ttatgtaaat tcaccactta tcggaaaatc taacgttttt aggctaataa cgctacggca   254340
gatgattttg cataagttga gtgctatttg gtagaattgc aaacaagaat agctagtttg   254400
tgaatttcgt tatacctggt gcttaccagg tagaatatcc ctataatata aatgtcacat   254460
agtaaaaagg ttaagaaatg tgtaccatgg gccaccaagg ctgcaagaga tataataaga   254520
attaagaact ccaatataag agaatataat ctccaacaat aatcttcaag gttgtaagaa   254580
aataatccaa gctcccaaaa taataatact ataatcttac aaatattgat tatttgggct   254640
tagaaaatga taattctgat ctctaactcc aattataaaa ttcatattta acttaaaatc   254700
caaattcttt gaccattata agtccctttt cggcatgtct tactaaaatg atcataacct   254760
ctagctccga actccaaatc caatgattca agtgtctaat tgctcataac tcaaagaccc   254820
atatttctta agaacaaaat atagtaataa aatgagaaaa agatggtcga aaatccacaa   254880
acagaaagtg tttgaaaatt tcttactctt agctatccaa aatgcttgag ggcaaaacat   254940
aacctttcat gctcgaattt atgcaattat tgagtctaaa atgtgaaaaa ttttatgtac   255000
aacaccaccg taaggtttct ttatgcatgc atgaagagga atatgggtaa tgtattcatg   255060
tataaagctg accaaaaaag aacaacaagt tgtgaatgtt tgcttgaaga tgagggcctt   255120
atatagcttg tatatgtgcg tataaggtgt caatgaaaat cttaggatgt ctacaatatt   255180
```

```
atggtataaa aataggaggc atgtattaag acaatttggg ataaaaagaa tgatttgttg   255240
aaggcatata agctgccaga aatgttgtga tgaagtggta gaaagatggg gatgcatctc   255300
tcatttctgg agggatataa gggcgtgtaa ggtacctata gaaagcttag agtgttagga   255360
aaaagttcta agtggtagca ctcaattata tagggtataa cctaggtaaa ttagggtatc   255420
tttcagaccc tgcaaatctg tctctttacc tgacctctgt acaaatctat attcttttct   255480
ttaattatac cacatgctat ctcaatataa ttattctgga aggtcccaaa ctacctcaag   255540
catggaccag agaaaacaaa ctggggttgc gaccttgcct gatggtaggc atttgactgg   255600
accatcagtc aaaccCctca ttcagcatga ttctcaggtg agtgaggaga agtggattc    255660 cgaagaggat gctttcaccg atgatgatga gtatttgctg agtgatggtt ctgattctga   255720
tgagggacct ctaactcacg agacaaggaa gcaacacata atgctaaaga aattttttcaa  255780 tagtttggaa actttgtcag tgcaagaaat caatgaacgt gaaaggcagt ggcattgccc   255840
tgcttgttaa ggtggccctg gagccattga ttggtacaag gggctccagc tattttttggc 255900 acatgcaaga actaaaggtt ctcaaagagt taagcttcat cgcacatttg ctaatgtctt   255960
ggatgaggag ctccaactta tatcatgcta acatgcattt acagtatatt tgtaacaata   256020
tatatcataa cctagtccca acttatcata acctaattcc aacatagcta tttttaggtc   256080
ttaaataaca atgtaatgca atcaagtatg ccaaaaaaat gagatccaat ggaaggcttt   256140
taggttcact aacattctta tatgcttggt atttgctgaa gaagtatggc aatgtgaaca   256200
gtgtgattga atgggagaaa aatttcaagg taacatgcga caagaggctt gtttctgaac   256260
ttgaatctag taaattgcaa aatggagaat atggcttctc tttttgctgtt ccagctggtg   256320 ttgacgatct tgacgtttat attcggcaaa aaataggcag caatcgattg tctagaactg   256380
gtgttgtcaa tggtggaaga aaatgggaga aaatgttttg ttcttttttc tttatggttg   256440
aaattgtgtg aatcaactat caagtgattg gattttacca tcatattctt taccccatg    256500 gcccgttcga tccttgatac taaatggtcg ggtggtaatg tgaatgattt acactataaa   256560
atttcatgaa atgtactgtg atgttcccat tatgaaactt tgataccatc tttcggaata   256620
gcaatgcaat gcaatcaagt atgccaaaaa atgagacgat tggtattgaa taagcatgac   256680
cattaaattt gtcaacagat ccaggatgaa gaaatgggga aatttgctgc tgagagagac   256740
gagttgatac ggattcatga gtacaaaaag atggagatga agaagaagca ttgggaggag   256800
gagttggagc tagaaaaaga atttggacat aacaaaagat ttgtcacctt ctagattgag   256860
attgagattc ggattcagat ttagattgcg attgagattg agattcagat tgttgataaa   256920
gacacataat ctgtgaaaac caatcagggg gagacaatga acataagttc tgaaggaagc   256980
ttgaaaaatc cttcaacagt tggctataac cattattgaa ttagattatt attttgtgac   257040 taattttgt ccttagtttg atatcagcat aactatctat acttaatact aaaacaaaca    257100
ccacctactg ccacgtatcg tgcttttcaga gaatttttc ctgcctaaaa tcttattcta   257160
tgtacatcta catttgaaaa cttaaagatt accaaaattg ttgcccaatt agctcggttt   257220
tgaccaaatg ttgttaaata aatataatta aacttgacag gcaatggcga ccaatgaggc   257280
tactaaactt gttccgaag aaagatagag aaatttttt gagaaaaaga taaaagtaat     257340
tttctatgac aagtgcaatg atccgttggg ccgggggtgtt acaaatggta tcagagcaac   257400
cctgcgaccg tggctgattg tgtgttcagc gcacctagcg agggaaaaga tcctgaagtg   257460
acggtccaac gaggacgttg tattcttaag tgggggtgaa tgtgatacCc cagatttagc   257520
ttgaaaagag attgatagac tactcatatt aacaaggtgc atcttctttt ctagggagcc   257580
```

```
catttgctaa gaactccaca gttaagcgtg cttggtgggg agcaatctta ggatgggtga 257640
cctcctggga agttttccgg gtgcgcacga gtggggccaa agtgcgctgg aaagacttgt 257700
gttggtctgt ggggctagtc tacagtctcc atgagtagtc accggtggtc cgttgggccg 257760
gggtgttaca ccttaaccat cagcttaagc gtttggttgg cagtttgctc acttaaaaaa 257820
caacgttcat atagagtaat ttaatacctg atttgtagaa gtcatatatg gtctacagag 257880
gctacccttt cttggagtct ttggatcagg tgctgacagg gccggccctg agttttcggg 257940
ggcccggggc gaaatatatt ttttggggcc ctaattatat ataaaaaaat ttaatgtcac 258000
gaaaggaaaa tgtatatgaa ttaatatagg tatagaagat ttttgtacct cttttttaccg 258060 agggagtata caatacaaac cacaattgtt tgatcacgaa gatcacaaag gcctaatttc 258120
ccgagctaaa tctctctttg acacaaagaa ctactcagta agtttgttgt ttaattactt 258180
cttcatcttc aattcctctt ttttaactta gaaatctaaa attcattttg tttaattgaa 258240
tatctagcta tttggaaagt tagggtttcg tttatgtgtt gatttttaaac ttgacaggca 258300 atggcgacca atgaggctac taaacttgtt tccgaagaaa gatagagaaa ttttttttgag 258360 aaaaagataa aagtaatttt ctatgacaag tgcaatgatc ctgaacacac aatcagccac 258420
ggtcgcaggg ttgctctgat accatttgta acaccccggc ccaacgagga cgttgtattc 258480
ttaagtgggg gtgaatgtga taccccagat ttagcttgaa aagagattga tagactactc 258540
atattaacaa ggtgcatctt cttttctagg gagcccattt gctaagaact ccacagttaa 258600
gcgtgcttgg tggggagcaa tcttaggatg ggtgacctcc tgggaagttt tccgggtgcg 258660
cacgagtggg gccaaagtgc gctggaaaga cttgtgttgg tctgtggggc tagtctacag 258720
tctccatgag tagtcaccgg tggtccgttg ggccggggtg ttacaccctta accatcagct 258780 taagcgtttg gttggcagtt tgctcactta aaaaacaacg ttcatataga gtaatttaat 258840
acctgatttg tagaagtcat atatggtcta cagaggctac ccctttcttgg agtctttgga 258900 tcaggtgctg acagggccgg ccctgagttt tcggggcc ggggcgaaat atatttttg 258960 gggccctaat tatatataaa aaaatttaat gtcacgaaag gaaatgtat atgaattaat 259020 ataggtatag aagatttttg tacctctttt taccgaggga gtatacaata caaaccacaa 259080
ttgtttgatc acgaagatca caaaggccta atttcccgag ctaaatctct cttttgacaca 259140 aagaactact cagtaagttt gttgtttaat tacttcttca tcttcaattc ctctttttta 259200
acttagaaat ctaaaattca ttttgtttaa ttgaatatct agctatttgg aaagttaggg 259260
tttcgtttat gtgttgattt taaacttgac aggcaatggc gaccaatgag gctactaaac 259320
ttgtttccga agaagatag agaaattttt ttgagaaaaa gataaagta attttctatg 259380 acaagtgcaa tgatcctgaa cacacaatca gccacggtcg cagggttgct ctgataccat 259440
ttgtaacacc ccggcccaac gaggacgttg tattcttaag tgggggtgaa tgtgataccc 259500
cagatttagc ttgaaaagag attgatagac tactcatatc aaaaggtgc atcttctttt 259560 ctagggagcc catttgctaa gaactccaca gttaagcgtg cttggtgggg agcaatctta 259620
ggatgggtga cttcctggga agttttccgg gtgcgcacga gtggggccaa agtgcgctgg 259680
aaagacttgt gttggtctgt ggggctagtc tacagtctcc atgagtagtc accggtggtc 259740
cgttgggccg gggtgttaca ccttaaccat cagcttaagc gtttggttgg cagtttgctc 259800
acttaaaaaa caacgttcat atagagtaat ttaatacctg atttgtagaa gtcatatatg 259860
gtctacagag gctacccttt cttggagtct ttggatcagg tgctgacagg gccggccctg 259920
```

```
agttttcggg ggcccggggc gaaatatatt ttgtggggcc ctaattatat ataaaaaatt 259980
taatgtcacg aaaggaaaat gtatatgaat taatataggt atagaagatt tttgtacccc 260040
tttttaccga gggagtatac aacccacaat tgttcagtgc tctagttttt atgcgggaaa 260100
taaactcatc agaacatgac acgtgtcctt aggtggtctc tgttttagta ttagatatag 260160
attctatttt tgattgtccc cactcattgc acattatttg tctgtttaaa aatgaacccg 260220
ccactttaaa ttacattcga aatatatttt aactctttct aaaattccat ttacacaagt 260280
cgatctctcg tttcattgat tctttaaaac cctaaatttc atcttagat gttagttcaa 260340
aggtatggtg tactaaacga acaagatgct caaacttcat aaatggcaaa accaacaaac 260400
taaattcttt ttcataactc tcctatggag gatcatctag taccattcaa catattacac 260460
gatacgaacc caaaataacc ataaatattt actaccggta gtgacatttc gtacacatta 260520
ttcacaatca attcaagtat ttcgaaacgg agtaatagat tgcaaaccaa ttgacacatc 260580
cctaaaacaa atttcccaaa atagcaactt caagtaaatc ctgctcctaa tggtttttca 260640
atacccactt catcagtaaa aggaagcatc ttagacaaat tagccatacc ttcatcatat 260700
tccttctcta aatcatctag tttggctaat cttataccat tttcatgtga atcaaccagt 260760
aaaacttgtc tagatccaga cccagatcca gattcagcta tatccatgtt tgaataacta 260820
gagggtttta atcttttagc ctctcgtgat gaacatgaac tactagttgt tatactatac 260880
aagcttatta ctactgttac tattattatt attattgccg ccattaatga gcatactgct 260940
agatgatgat gatgattgtt ttggaggagt taagatagct ttacctggaa tagctttcag 261000
atcataatcc gaatacgggt cggttaatac ttgagaattt tgagtagggt ttcgaatcgg 261060
atctacaatt gacccaattg acggagaagt atcaaaacta gctgctggat tgaacccaga 261120
aatcacagat tctaacgttt acaggagta tcccatctga gattgggaat ttgcatcaat 261180
ggcgcaagta aaggaattaa gagggagctt caagaaggaa gaagacccta tttaagaaat 261240
aaaacaaggg caattatgta aattcaccac ttatcggaaa atctaacgtt tttaggctaa 261300
taacgctacg gcagatgatt ttgcataagt tgagtgctat ttggtagaat tgcaaacaag 261360
aatagctagt ttgtgaattt cgttatacct ggtgcttacc aggtagaata tccctataat 261420
ataaatgtca catagtaaaa aggttaagaa atgtgtacca tgggccacca aggctgcaag 261480
agatataata agaattaaga actccaatat aagagaatat acactacaac aaaattagct 261540
ttttgcgaca ttggatttag tggcatttaa aaaatgccac taattcatat ttttagtata 261600
ataaatatta gtttttattt taaattccac catgaaagtg ctttagcgac acttaatata 261660
atttttagtg acatatgtaa ttgtcattat agtctatagt ggcatttgtg ggaaatgtca 261720
ctagatccta tgtcgctaaa agctttagtg tgcttttttt atatgctgct aaagggtcta 261780
ataaatgtca ctaaatccta tgtatacact ataagaaatt tgaaatagcg acatttaaat 261840
taaatgtcgc taaatatatg ccactaaaag caaattatgt tgtagtgata atctccaaga 261900
ataatcttca aggttgtaag aaaataatcc aagctcccaa aataataata ctataatctt 261960
acaaatattg attatttggg cttagaaaat gataattctg atctctaact ccaattataa 262020
aattcatatt caacttaaaa tccaaattct ttgaccatta taagtccctt ttcggcatgt 262080
cttactaaaa tgatcataac ctctagctcc gaactccaaa tccaatgatt caagtgtcta 262140
attgctcata actcaaagac ccatatttct taagaacaaa atatagtaat aaaatgagaa 262200
aaagatggtc gaaaatccac aaacagaaag tgtttgaaaa tttcttactc ttagctatcc 262260
aaaatgcttg agggcaaaac ataacctttc atgctcgaat ttatgcaatt attgggtcta 262320
```

```
aaatgtgaaa aatttatgt acaacaccac cgtaaggttt tattcatgta taaagctgac  262380
caaaaaagaa caacaagttg tgaatgtttg cttgaagatg aggggcttat atagcttgta  262440
tatgtgcgta taaggtgtca atgaaaatct taggatgtct acaatattat ggtataaaaa  262500
taggaggcat gtattaagac aatttgggat aaaaagaatg atttgttgaa ggcatataag  262560
ctgccagaaa tgttgtgatg aagtggtaga aagatgagga tgcatctctc atttctggag  262620
ggatataagg gcgtgtaagg tacctataga aagcttagag tgttaggaaa aagttctaag  262680
tggtagcact caattatata gggtataacc taggtaaatt agggtatctt tcagaccctg  262740
caaatctgtc tctttacctg acctctgtac aaatctatat tcttttcttt aattatacca  262800
catgctatct caatataatt attctggaag gtcccaaact acctcaagca tggaccagag  262860
aaaacaaact ggggttgcga ccttgcctga tggtaggcat ttgactggac catcagtcaa  262920
accccctcatt cagcatgatt ctcaggtgag taaggagaaa gtagattccg aagaggatgc  262980
tttcaccgat gatgatgagt atttgctgag tgatggttct gattctgatg agggacctct  263040
aactcacgag acaaggaagc aacacataat gctaaagaaa ttttttcaata gtttggaaac  263100
tttgtcagtg caagaaatca atgaacgtga aaggcagtgg cattgccctg cttgtcaagg  263160
tggccctgga gccattgatt ggtacaaggg gctccagcta ttttttggcac atgcaagaac  263220
taaaggttct caaagagtta agcttcatcg cacatttgct aatgtcttgg atgaggagct  263280
ccaacttata tcatgctaac atgcatttac agtatatctg taacaatata tatcataacc  263340
tagtcccaac ttatcataac ctaattccaa catagctatt ttagggtctt aaataacaat  263400
gtaatgcaat caagtatgcc aaaaaaatga gatccaatgg aaggcttta ggttcactaa  263460
cattcttata tgcttggtat ttgctgaaga agtatggcaa tgtgaacagt gtgattgaat  263520
gggagaaaaa tttcaaggta acatgcgaca agaggcttgt ttctgaactt gaatctagta  263580
aattgcaaaa tggagaatat ggcttctctt ttgctgttcc agctggtgtt gacgatcttg  263640
acgtttatat tcggcaaaaa ataggcagca atcgattgtc tagaactggt gttgtcaatg  263700
gtggaagaaa atgggagaaa atgttttgtt cttttttctt tatggttgaa attgtgtgaa  263760
tcaactatca agtgattgga ttttaccatc atattcttta cccccatggc ccgttcgatc  263820
cttgatacta aatggtcgag tggtaatgtg aatgatttac actataaaat ttcatgaaat  263880
gtactgtgat gttcccatta tgaaactttg ataccatctt tcggaatagc aatgcaatgc  263940
aatcaagtat gccaaaaaat gagacgattg gtattgaata agcatgacca ttaaatttgt  264000
caacagatcc aggatgaaga aatggggaaa tttgctgctg agagagacga gttgatacgg  264060
attcatgagt acaaaaagat ggagatgaag aagaagcatt gggaggagga gttggagcta  264120
gaaaaagaat ttggacataa caaaagattt gtcaccttct agattgagat tgagattcgg  264180
attcagattt agattgcgat tgagattgag attcagattg ttgataaaga cacataatct  264240
gtgaaaacca atcaggggga gacaatgaac ataagttctg aaggaagctt gaaaaatcct  264300
tcaacagttg gctataacca ttattgaatt agattattat tttgtgacta atttttgtcc  264360
ttagtttgat atcagcataa ctatctatac ttaatactaa aacaaacacc acctactgcc  264420
acgtatcgtg ctttcagaga atttttcct gcctaaaatc ttattctatg tacatctaca  264480
tttgaaaact taaagattac caaaattgtt gcccaattag ctcggttttg accaaatgtt  264540
gttaaataaa tataattaaa cttgacaggc aatggcgacc aatgaggcta ctaaacttgt  264600
ttccgaagaa agatagagaa attttttttga gaaaaagata aaagtaattt tctatgacaa  264660
```

```
gtgcaatgat ccgttgggcc ggggtgttac aaatggtatc agagcaaccc tgcgaccgtg 264720
gctgattgtg tgttcagcgc acctagcggg ggaaaagatc ctgaagtgac ggtccaacga 264780
ggacgttgta ttcttaagtg ggggtgaatg tgatacccca gatttagctt gaaaagagat 264840
tgatagacta ctcatattaa caaggtgcat cttcttttct agggagccca tttgctaaga 264900
actccacagt taagcgtgct tggtggggag caatcttagg atgggtgacc tcctgggaag 264960
ttttccgggt gcgcacgagt ggggccaaag tgcgctggaa agacttgtgt tggtctgtag 265020
ggctagtcta cagtctccat gagtagtcac cggtggtccg ttgggccggg gtgttacacc 265080
ttaaccatca gcttaagcgt ttggttggca gtttgctcac ttaaaaaaca acgttcatat 265140
agagtaattt aatacctgat ttgtagaagt catatatggt ctacagaggc taccctttct 265200
tggagtcttt ggatcaggtg ctgacagggc cggccctgag ttttcggggg cccggggcga 265260
aatatatttt ttgggggccct aattatatat aaaaaaattt aatgtcacga aaggaaaatg 265320
tatatgaatt aatataggta tagaagattt ttgtacctct tttaccgagg gagtatacaa 265380
tacaaaccac aattgtttga tcacgaagat cacaaaggcc gcacggccaa aaggagtccc 265440
ccgtgctctc cttcacgggt atgagttgcc gccgtccttc cctccccaga ccctgctcat 265500
agttctctat gagcgggata tactgggtag gatgatgatg atgatgatag aagatttttg 265560
tacctctttt accgagggag tatacaaatac aaaccacaat tgtttgatca cgaagatcac 265620
aaaggcctaa tttcccgagc taaatctctc tttgacacaa agaactactc agtaagtttg 265680
ttgtttaatt acttcttcat cttcaattcc tcttttttaa cttagaaatc taaaattcat 265740
tttgtttaat tgaatatcta gctatttgga aagttagggt ttcgtttatg tgttgatttt 265800
aaacttgaca ggcaatggcg accaatgagg ctactaaact tgtttccgaa gaaagataga 265860 aaatttttt gagaaaaaga taaaagtaat tttctatgac aagtgcaatg atccgttggg 265920
ccggggtgtt acaaatggta tcagagcaac cctgcgaccg tggctgattg tgtgttcagc 265980
gcacctagcg agggaaaaga tcctgaagtg acggtccaac gaggacgttg tattcttaag 266040
tgggggtgaa tgtgataccc cagatttagc ttgaaaagag attgatagac tactcatatt 266100
aacaaggtgc atcttctttt ctagggagcc catttgctaa gaactccaca gttaagcgtg 266160
cttggtgggg agcaatctta ggatgggtga cctcctggga agttttccgg gtgcgcacga 266220
gtggggccaa agtgcgctgg aaagacttgt gttggtctgt ggggctagtc tacagtctcc 266280
atgagtagtc accggtggtc cgttgggccg ggtgttaca ccttaaccat cagcttaagc 266340
gtttggttgg cagtttgctc acttaaaaaa caacgttcat atagagtaat ttaatacctg 266400
aaacgttatt gaatgactca aatatgtaga agtcatatag agtaattta caccttaacc 266460 atcagcttaa gcgtttggtt ggcagtttgc tcacttaaaa aacaacgttc atatagagta 266520
atttaatacc tgatttgtag aagtcatata tggtctacag aggctaccct tcttggagt 266580 ctttggatca ggtgctgaca gggccggccc tgagttttcg ggggcccggg gcgaaatata 266640
ttttttgggg ccctaattat atatcaaaaa aatttaatgt catgaaagga aaatgtatat 266700
gaattaatat aggtatagaa gatttttgta cccctttta ccgagggagt atacaataca 266760
aaccacaatt gtttgatcac gaagatcaca aaggcctaat ttcccgagct aaatctctct 266820
ttgacacaaa gaactactca gtaagtttgt tgtttaatta cttcttcatc ttcaattcct 266880
cttttttaac ttagaaatct aaaattcatt tttgtttaat tgaatatcta gctatttgga 266940
aagttagggt ttcgtttatg tgttgatttt aaacttgaca ggcaatggcg accaatgagg 267000
ctactaaact tgtttccgaa gaaagataga aaatttttt tgagaaaaag ataaaagtaa 267060
```

```
tttctatga caagtgcaat gatccgttgg gccggggtgt tacaaatggt atcagagcaa 267120
ccctacgacc gtggctgatt gtgtgttcag cgcacctagc gagggaaaag atcctgaagt 267180
gacggtccaa cgaggacgtt gtattcttaa gtggggtgaa tgtgataccc cagatttagc 267240
ttgaaaagag attgatagac tactcatatc aacaaggtgc atcttctttt ctagggagcc 267300
catttgctaa gaactccaca gttaagcgtg cttggtgggg agcaatctta ggatgggtga 267360
cctcctggga agttttccgg gtgcgcacga gtggggccaa agtgcgctgg aaagacttgt 267420
gttggtctgt ggggctagtc tacagtctcc atgagtagtc accggtggtc cgttgggccg 267480
gggtgttaca ccttaaccat cagcttaagc gtttggttgg cagtttgctc acttaaaaaa 267540
caacgttcat atagagtaat ttaatacctg atttgtagaa gtcatatatg gtctacagag 267600
gctacccttt cttggagtct ttggatcagg tgctgacagg gccggccctg agttttcggg 267660
ggcccggggc gaaatatatt ttgtggggcc ctaattatat ataaaaaatt taatgtcacg 267720
aaaggaaaat gtatatgaat taatataggt atagaagatt tttgtacccc tttttaccga 267780
gggagtatac aacccacaat tgttcagtgc tctagttttt aggcgggaaa taaactcatc 267840
agaacatgac acgtgtcatt aggtggtctc tgttttagta ttagatatag attctatttt 267900
tgattgtccc cactcattgc acattatttg tctgtttgaa aatgaacccg ccactttaaa 267960
ttacattcga aatatatttt aactctttct aaaattccat ttacacaagt cgatctctcg 268020
tttcattgat tctttaaaac cctaaatttc atctttagat gttagttcaa aggtatggtg 268080
tactaaacga acaagatgct caaacttcat aaatggcaaa accaacaaac taaattcttt 268140
ttcataactc tcctatggag gatcatctag taccattcaa catattacac gatacgaacc 268200
caaaataacc ataaatattt actaccggta gtgacatttc gtacacatta ttcacaatca 268260
attcaagtat ttcgaaacgg agtaatagat tgcaaaccaa ttgacacatc cctaaaacaa 268320
atttcccaaa atagcaactt caagtaaatc ctgctcctaa tggttttttca atacccactt 268380
catcagtaaa aggaagcatc ttagacaaat tagccatacc ttcatcatat tccttctcta 268440
aatcatctag tttggctaat cttataccat tttcatgtga atcaaccagt aaaacttgtc 268500
tagatccaga cccagatcca gattcagcta tatccatgtt tgaataacta gagggtttta 268560
atcttttagc ctctcgtgat gaacatgaac tactagttgt tatactatac aagcttatta 268620
ctactgttac tattattatt attattgccg ccattaatga gcatactgct agatgatgat 268680
gatgattgtt ttggaggagt taagatagct ttacctggaa tagctttcag atcataatcc 268740
gaatacgggt cggttaatac ttgagaattt tgagtagggt ttcgaatcgg atctacaatt 268800
gacccaattg acggagaagt atcaaaacta gctgctggat tgaacccaga aatcacagat 268860
tctaacgttt acagggagta tcccatctga gattgggaat ttgcatcaat ggcgcaagta 268920
aaggaattaa gagggagctt caagaaggaa gaagacccta tttaagaaat aaaacaaggg 268980
caattatgta aattcaccac ttatcggaaa atctaacgtt tttaggctaa taacgctacg 269040
gcagatgatt ttgcataagt tgagtgctat ttggtagaat tgcaaacaag aatagctagt 269100
ttgtgaattt cgttatacct ggtgcttacc aggtagaata tccctataat ataaatgtca 269160
catagtaaaa aggttaagaa atgtgtacca tgggccacca aggctgcaag agatataata 269220
agaattaaga actccaatat aagagaatat acactacaac aaaattagct ttttgcgaca 269280
ttggatttag tggcatttaa aaaatgccac taattcatat ttttagtata ataaatatta 269340
gttttttattt taaattccac catgaaagtg ctttagcgac acttaatata attttagtg 269400
```

```
acatatgtaa ttgtcattat agtctatagt ggcatttgtg ggaaatgtca ctagatccta 269460
tgtcgctaaa agctttagtg tgcttttttt atatgctgct aaagggtcta ataaatgtca 269520
ctaaatccta tgtatacact ataagaaatt tgaaatagcg acatttaaat taaatgtcgc 269580
taaatatatg ccactaaaag caaattatgt tgtagtgata atctccaaga ataatcttca 269640
aggttgtaag aaaataatcc aagctcccaa aataataata ctataatctt acaaatattg 269700
attatttggg cttagaaaat gataattctg atctctaact ccaattataa aattcatatt 269760
caacttaaaa tccaaattct ttgaccatta taagtcccct ttcggcatgt cttactaaaa 269820
tgatcataac ctctagctcc gaactccaaa tccaatgatt caagtgtcta attgctcata 269880
actcaaagac ccatatttct taagaacaaa atatagtaat aaaatgagaa aaagatggtc 269940
gaaaatccac aaacagaaag tgtttgaaaa tttcttactc ttagctatcc aaaatgcttg 270000
agggcaaaac ataacctttc atgctcgaat ttatgcaatt attgggtcta aatgtgaaa 270060 aattttatgt acaacaccac cgtaaggttt tattcatgta taaagctgac caaaaagaa 270120 caacaagttg tgaatgtttg cttgaagatg aggggcttat atagcttgta tatgtgcgta 270180
taaggtgtca atgaaaatct taggatgtct acaatattat ggtataaaaa taggaggcat 270240
gtattaagac aatttgggat aaaaagaatg atttgttgaa ggcatataag ctgccagaaa 270300
tgttgtgatg aagtggtaga aagatgagga tgcatctctc atttctggag ggatataagg 270360
gcgtgtaagg tacctataga aagcttagag tgttaggaaa aagttctaag tggtagcact 270420
caattatata gggtataacc taggtaaatt agggtatctt tcagaccctg caaatctgtc 270480
tctttacctg acctctgtac aaatctatat tcttttcttt aattataccca catgctatct 270540 caatataatt attctggaag gtcccaaact acctcaagca tggaccagag aaaacaaact 270600 gggggttgcga ccttgcctga tggtaggcat ttgactggac catcagtcaa accctcatt 270660 cagcatgatt ctcaggtgag taaggagaaa gtagattccg aagaggatgc tttcaccgat 270720
gatgatgagt atttgctgag tgatggttct gattctgatg agggacctct aactcacgag 270780
acaaggaagc aacacataat gctaaagaaa ttttttcaata gtttggaaac tttgtcagtg 270840
caagaaatca atgaacgtga aaggcagtgg cattgccctg cttgtcaagg tggccctgga 270900
gccattgatt ggtacaaggg gctccagcta ttttttggcac atgcaagaac taaaggttct 270960
caaagagtta agcttcatcg cacatttgct aatgtcttgg atgaggagct ccaacttata 271020
tcatgctaac atgcatttac agtatatctg taacaatata tatcataacc tagtcccaac 271080
ttatcataac ctaattccaa catagctatt ttagggtctt aaataacaat gtaatgcaat 271140
caagtatgcc aaaaaaatga gatccaatgg aaggctttta ggttcactaa cattcttata 271200
tgcttggtat ttgctgaaga agtatggcaa tgtgaacagt gtgattgaat gggagaaaaa 271260
tttcaaggta acatgcgaca agaggcttgt ttctgaactt gaatctagta aattgcaaaa 271320
tggagaatat ggcttctctt ttgctgttcc agctggtgtt gacgatcttg acgtttatat 271380
tcggcaaaaa ataggcagca atcgattgtc tagaactggt gttgtcaatg gtggaagaaa 271440
atgggagaaa atgttttgtt ctttttttctt tatggttgaa attgtgtgaa tcaactatca 271500
agtgattgga ttttaccatc atattcttta ccccccatggc ccgttcgatc cttgatacta 271560
aatggtcgag tggtaatgtg aatgatttac actataaaat ttcatgaaat gtactgtgat 271620
gttcccatta tgaaactttg ataccatctt tcggaatagc aatgcaatgc aatcaagtat 271680
gccaaaaaat gagacgattg gtattgaata agcatgacca ttaaatttgt caacagatcc 271740
aggatgaaga aatggggaaa tttgctgctg agagagacga gttgatacgg attcatgagt 271800
```

```
acaaaaagat ggagatgaag aagaagcatt gggaggagga gttggagcta gaaaaagaat   271860
ttggacataa caaaagattt gtcaccttct agattgagat tgagattcgg attcagattt   271920
agattgcgat tgagattgag attcagattg ttgataaaga cacataatct gtgaaaacca   271980
atcaggggga gacaatgaac ataagttctg aaggaagctt gaaaaatcct tcaacagttg   272040
gctataacca ttattgaatt agattattat tttgtgacta attttgtcc ttagtttgat   272100 atcagcataa ctatctatac ttaatactaa aacaaacacc acctactgcc acgtatcgtg   272160 cttcagaga atttttcct gcctaaaatc ttattctatg tacatctaca tttgaaaact   272220
taaagattac caaaattgtt gcccaattag ctcggttttg accaaatgtt gttaaataaa   272280
tataattaaa cttgacaggc aatggcgacc aatgaggcta ctaaacttgt ttccgaagaa   272340
agatagagaa attttttga gaaaaagata aaagtaattt tctatgacaa gtgcaatgat   272400
ccgttgggcc ggggtgttac aaatggtatc agagcaaccc tgcgaccgtg gctgattgtg   272460
tgttcagcgc acctagcggg ggaaaagatc ctgaagtgac ggtccaacga ggacgttgta   272520
ttcttaagtg ggggtgaatg tgataccccca gatttagctt gaaaagagat tgatagacta   272580
ctcatattaa caaggtgcat cttcttttct agggagccca tttgctaaga actccacagt   272640
taagcgtgct tggtggggag caatcttagg atgggtgacc tcctgggaag ttttccgggt   272700
gcgcacgagt ggggccaaag tgcgctggaa agacttgtgt tggtctgtag gctagtcta   272760 cagtctccat gagtagtcac cggtggtccg ttgggccggg gtgttacacc ttaaccatca   272820
gcttaagcgt ttggttggca gttttgctcac ttaaaaaaca acgttcatat agagtaattt   272880
aatacctgat ttgtagaagt catatatggt ctacagaggc taccctttct ggagtctttt   272940
ggatcaggtg ctgacagggc cggccctgag ttttcggggg cccggggcga aatatattt   273000 ttggggcct aattatatat aaaaaatt aatgtcacga aaggaaaatg tatatgaatt   273060
aatataggta tagaagattt ttgtacctct tttaccgagg gagtatacaa tacaaaccac   273120
aattgtttga tcacgaagat cacaaaggcc gcacggccaa aaggagtccc ccgtgctctc   273180
cttcacgggt atgagttgcc gccgtccttc cctccccaga ccctgctcat agttctctat   273240
gagcgggata tactgggtag gatgatgatg atgatgatag aagattttg tacctctttt   273300 accgagggag tatacaatac aaaccacaat tgtttgatca cgaagatcac aaaggcctaa   273360
tttcccgagc taaatctctc tttgacacaa agaactactc agtaagtttg ttgtttaatt   273420
acttcttcat cttcaattcc tctttttaa cttagaaatc taaaattcat tttgtttaat   273480
tgaatatcta gctatttgga aagttagggt ttcgtttatg tgttgatttt aaacttgaca   273540
ggcaatggcg accaatgagg ctactaaact tgtttccgaa gaaagataga aaattttt    273600 tgagaaaaag ataaaagtaa ttttctatga caagtgcaat gatccgttgg gccggggtgt   273660
tacaaatggt atcagagcaa ccctgcgacc gtggctgatt gtgtgttcag cgcacctagc   273720
gagggaaaag atcctgaagt gacggtccaa cgaggacgtt gtattcttaa gtggggtga   273780 atgtgatacc ccagatttag cttgaaaaga gattgataga ctactcatat taacaaggtg   273840
catcttcttt tctagggagc ccatttgcta agaactccac agttaagcgt gcttggtggg   273900
gagcaatctt aggatgggtg acctcctggg aagttttccg ggtgcgcacg agtggggcca   273960
aagtgcgctg gaaagacttg tgttggtctg tggggctagt ctacagtctc catgagtagt   274020
caccggtggt ccgttgggcc ggggtgttac accttaacca tcagcttaag cgtttggttg   274080
gcagtttgct cacttaaaaa acaacgttca tatagagtaa tttaatacct gaaacgttat   274140
```

```
tgaatgactc aaatatgtag aagtcatata gagtaatttt acaccttaac catcagctta    274200
agcgtttggt tggcagtttg ctcacttaaa aaacaacgtt catatagagt aatttaatac    274260
ctgatttgta gaagtcatat atggtctaca gaggctaccc tttcttggag tctttggatc    274320
aggtgctgac agggccggcc ctgagttttc ggggcccgg ggcgaaatat attttttggg     274380
gccctaatta tatatcaaaa aaatttaatg tcatgaaagg aaaatgtata tgaattaata    274440
taggtataga agattttgt accccttttt accgagggag tatacaatac aaaccacaat     274500
tgtttgatca cgaagatcac aaaggcctaa tttcccgagc taaatctctc tttgacacaa    274560
agaactactc agtaagtttg ttgtttaatt acttcttcat cttcaattcc tctttttaa     274620 cttagaaatc taaaattcat ttttgtttaa ttgaatatct agctatttgg aaagttaggg    274680
tttcgtttat gtgttgattt taaacttgac aggcaatggc gaccaatgag gctactaaac    274740
ttgtttccga agaaagatag aaaaatttt ttgagaaaaa gataaaagta attttctatg     274800
acaagtgcaa tgatccgttg ggccggggtg ttacaaatgg tatcagagca accctacgac    274860
cgtggctgat tgtgtgttca gcgcacctag cgagggaaaa gatcctgaag tgacggtcca    274920
acgaggacgt tgtattctta agtggggtga atgtgatacc ccagatttag cttgaaaaga    274980
gattgataga ctactcatat caacaaggtg catcttcttt tctagggagc ccatttgcta    275040
agaactccac agttaagcgt gcttggtggg gagcaatctt aggatgggtg acctcctggg    275100 aagtttccg ggtgcgcacg agtggggcca aagtgcgctg gaaagacttg tgttggtctg     275160
tggggctagt ctacagtctc catgagtagt caccggtggt ccgttgggcc ggggtgttac    275220
accttaacca tcagcttaag cgtttggttg gcagtttgct cacttaaaaa acaacgttca    275280
tatagagtaa tttaatacct gatttgtaga agtcatatat ggtctacaga ggctacccctt   275340 tcttggagtc tttggatcag gtgctgacag ggccggccct gagttttcgg ggccccgggg    275400
cgaaatatat tttgtggggc cctaattata tataaaaat ttaatgtcac gaaaggaaaa     275460
tgtatatgaa ttaatatagg tatagaagat ttttgtaccc cttttaccg agggagtata    275520 caacccacaa ttgttcagtg ctctagtttt taggcgggaa ataaactcat cagaacatga    275580
cacgtgtcat taggtggtct ctgttttagt attagatata gattctattt ttgattgtcc    275640
ccactcattg cacattattt gtctgtttga aaatgaaccc gccactttaa attacattcg    275700
aaatatattt taactctttc taaaattcca tttacacaag tcgatctctc gtttcattga    275760
ttctttaaaa ccctaaattt catctttaga tgttagttca aaggtatggt gtactaaacg    275820
aacaagatgc tcaaacttca taaatggcaa aaccaacaaa ctaaattctt tttcataact    275880
ctcctatgga ggatcatcta gtaccattca acatattaca cgatacgaac ccaaaataac    275940
cataaatatt tactaccggt agtgacattt cgtacacatt attcacaatc aattcaagta    276000
tttcgaaacg gagtaataga ttgcaaacca attgacacat ccctaaaaca aatttcccaa    276060
aatagcaact tcaagtaaat cctgctccta atggttttc aatacccact tcatcagtaa     276120
aaggaagcat cttagacaaa ttagccatac cttcatcata ttccttctct aaatcatcta    276180
gtttggctaa tcttatacca ttttcatgtg aatcaaccag taaaacttgt ctagatccag    276240
acccagatcc agattcagct atatccatgt ttgataact agagggtttt aatcttttag     276300
cctctcgtga tgaacatgaa ctactagttg ttatactata caagcttatt actgctgtta    276360
ctattattat tattattatt gccgccatta atgagcatac tgctagatga tgatgattat    276420
tgttttggag gagttaagat agctttacct ggaatagctt tcagatcata atccgaatac    276480
gggtcggtta atacttgaga attttgagta gggtttcgaa tcggatctac aattgaccca    276540
```

```
attgacggag aagtatcaaa actagctgct ggattgaacc cagaaatcac agattctaac   276600
gtttacaggg agtatcccat ctgagattgg gaagttgcat caatggcgca agtaaaggaa   276660
ttaagaggga gcttcaagaa ggaagaagac cctatttaag aaataaaaca agggcaatta   276720
tgtaaattca ccacttatcg gaaaatctaa cgttttuagg ctaataacgc tacggcagat   276780
gattttgcat aagttgagtg ctatttggta gaattgcaaa caagaatagc tagtttgtga   276840
atttcgttat acctggtgct taccaggtag aatatcccta taatataaat gtcacatagt   276900
aaaaaggtta agaaatgtgt accatgggcc accaaggctg caagagatat aataagaatt   276960
aagaactcca atataagaga atataatctc caagaatctc aatgttaaaa gttatgaaac   277020
aaatccatgg ctaatattca tttggcaatt tcaatgttaa gatctctttt tattctttac   277080
ataaagtaac tttagatgcc tagctttcac tttgtcatca ttgtgattga tttatttgt    277140
cttttgctta ttttatttaa tattatatat ttagtttcaa tttagtagat cttaaattat   277200
aagctcttat ttgttctttt tttataattt tcccgctcaa tgcacgatta taagcctata   277260
gtcgccttca actgtgtaga ccgtaaattt tgaaaaaaat aagactttcc ttgaattcat   277320
tctagttccc tgtaatataa aaaattcata ttatatggac agttgaaaac cccggaagga   277380
ggtttgtggc atgtcctgat tttaattcaa gaacattgag tttataacaa tagctgatga   277440
tttattcaga agattctagg cctccgtata cagggaccga acttcgaact ccatcttggc   277500
cctagaccga gcaagttata aacagtatta ttgttataaa cttgtgaatt gctgttataa   277560
actggtgaat tgttgtaaat ttctgaattg ctgttataaa cttgtgaatt gctgttataa   277620
actggtgaat tgatgtaaat ttctgaattg ctgttataaa ccattgaatt gctgttataa   277680
attcctctgc taaatgatat aactgaagca cataataata actatattca ctagtgttag   277740
gttctgatat ccataacaat aacaatatta catgattttg taacaaatgt acaatagttt   277800
ataacaaatc agaattaaaa ctaccacaat agtaacaata atgttcttaa ttacaaaatg   277860
ttgaagttat acttctttga atttgaaatc acttcctttc gttttggtt taatgttgaa    277920
gttataattc ttccacagta atcaattctg agcttcttca agatttcagc ctgaacagta   277980
agaacattag tttataacaa taatacatat atttataaca tcaatatcat aatttataac   278040
atcaatatca taatttataa catataaaca atagtttata acaactcaca tcatttatgt   278100
taatttggat gtcccaattt tcaccttgtc cctggtattc ttccatatgc ttcatggtaa   278160
ataatccaca atcgatgaaa ttgtcatttt ttctccattt catttcgttt atgacaatat   278220
cgaacttagc aacaaggtca ccattttttc ctagactttt ttcatcaagg aattttgaaa   278280
atgcgtctat ctttatacaa aaagaggtt aatgcattag tatatcagtt tagaattata    278340
aacttgtgaa ttgctgttat aaactggtga attgttgtaa atttctgaat tgctgttatg   278400
aacttgtgaa ttgctgttat aaattcctct gctaaatgat actccctcca atttagttca   278460
gttgtattgc aaaccaattg acacatccct aaaacaaatt tcccaaaata gcaacttcaa   278520
gtaaatcctg ctcctaatgg ttttttcaata cccacttcat cagtaaaagg aagcatctta   278580
gacaaattag ccataccttc atcatattcc ttctctaaat catctagttt ggctaatctt   278640
ataccatttt catgtgaatc aaccagtaaa acttgtctag atccagaccc agatccagat   278700
tcagctatat ccatgtttga ataactagag ggttttaatc ttttagcctc tcgtgatgaa   278760
catgaactac tagttgttat actagagtag atcgttcaaa tcaccagcca gactggacca   278820
aacagtttta gaacggtcca atattttta tttttatatt ttaatccaaa ttaatacatg    278880
```

```
tattatgcat atatatcaca cctacaatta ataaatatag taatttgtaa ttagttgatt  278940
acatcaacat cattcaagta tatattgcta tctaaacata actatatctt aaaatatcta  279000
gatagcaaca taatttttata tatacaaaat tataattttt gaccacagta cgatttgcag  279060
tccgatttgg tctgaaaaaa aaaacagaga ccagaccgta aaccgtaatt caatttgaaa  279120
aaaaaaatca atcaagacca tttaccgtag atctgaccaa atactaacat ttcgatttgg  279180
tcagatttga tttacagttt agaccaaatt ttattcaacc ctatatgata cggaggaagt  279240
atatccgatt tccgaatact ttattggata aatggagatt aataatccca actttgcgtg  279300
atccgctcaa aacaatccca actttcgatt attttctaat atacctaact ttgccacttt  279360
gttgctcagg acatacccctt taatatggta accggttata acagaaaata tgcgaaagtt  279420
gggattgttt tgagcggatc acgcaaagtt gggattatta atctccatta tccttcttat  279480
ttccatgaca aaaaggtga tttacctgtt ataaccggtt accatattaa agggtatgtc  279540
ctgagcaaca aagtggcaaa gttaggtata tttaaaaata atcgaaagtt gggattgttt  279600
tgagcggatc acgcaaagtt gggattatta atctccattt atcctacttt attttaccta  279660
tgttttgatt tttgactctt taattttgat atcaaaagcg agacaaaata atacaagtat  279720
tatatctcaa aaaaaaaaaa aataaatacaa gtattaattc gaaaaggtac gttaagtggt  279780
ggaaaaaaaa aaatacaagt attatatctc aagagtaatg aatacgagta atgaatactg  279840
atcttcaaaa aaaagagta atgaatactg gggtctgggg aatacgcgaa atcactttct  279900
gggtttcaac tttgaacttc gaacattgaa aggggagact ttgattttt atcgcttcaa  279960 tctttcatag ccatggctgg gtaagctttg cgaaatcact ttctgggttt caactttgaa  280020
cttcgaacat tgaaagggga gactctgaat tttgatcgct tcaatctttc atagccatgg  280080
ctgggtaagc tttgcgaaat cactttctgg gtttcaactt tgaacttcga acattgaaag  280140
gggagactct gaattttgat cgcttcaatc tttcatagcc atggctgggt aagctttcta  280200
cattctatct atgactaaac cactgctaaa actggctttt tatattgcat tttatttaat  280260
gtttagaaaa atttactttt aaaaatctga ccttgggtt gttctcttct ataaatcaac  280320
cttttgatta tttctaaaa atcccaccctt tgcaccccat cttcacttaa agtcacacaac  280380 ccattgtcta tctgaagaac cggttaaaat gaatttata aaaaggaaa atttacttt  280440 taaaattcga cctttaggtt gttctcttct aaaaatcaga cctttagtgg tgcaaaggtg  280500
ggatttttag aaaataatca aaaggtaaat ttttttttc acatttattt ttagtttagt  280560
attggtagta taatccattc caattatctt gaactttcat cttcttttgc ttaatttttt  280620
tgtcttttga tgcgaattta actgattttt ttgttgtttt atttttattta ttcaaataaa  280680 attattgcct tttcgcgctt tacttcagtg ccgtaccgat ttttgtcgaa gtatctactt  280740
ttactaaata ttaattgata tttaaaattc aatcagtcta gttattgggt taattttgca  280800
attgatttta tcacaaaaac atttgggtaa ttgggttata tcataatttc ttttaaattt  280860
ataattttga tgaagaggga tgatgtcatt aatttggcag gtagtttcca gtttgtacaa  280920
gtctgtaaat ttatttaggt tgtagtatga cttattttcc tgcaaaaatc aaccaagatt  280980
gatgatttca taacttttgt attttggtt ttgctgtgtt gaagaggttt agaagaagtc  281040
attgtcattc aaaaaaattt cattacccaa atgccattaa gagactccca aataggtggg  281100
gtttgaggag gccgaatgtt tgcagcctta ccgttcttaa tgataacaaa gagtttgttt  281160
ctgattggtc tagtcagatt ttagtattgg tgtaaaacac ctcataagaa atgttcatcc  281220
aatcccaact ctcactttg ctattcaatt gctttggttt tgggtggtta ggaaagtttt  281280
```

```
gattttttt  attacttgac  agggtgttcc  ttgtggggaa  atttaattgg  ttgatgaggg   281340 gcttttgct  cttttgtga  tgtaaatcat  ggctaataat  gtgttctttt  agtctgcttt   281400
gttgccattg  agtttaatga  ttgacatatt  taagttgtgg  ccggaaaaga  tagatggtgc   281460
taaaatattc  cctaaatctg  tttttagttg  gattataacc  tcatagttat  catagtttga   281520
taaagttgtt  tcagtcatat  gacattactc  gattgatttc  ttagtggctg  ttttttatgg   281580
ttgtatgctg  tatattgtgt  aaaatctcct  caatcctcaa  agtgattgaa  attaaagtat   281640
tgtagggata  ttgataccc   attagtgaaa  aatgttggtt  ggttaaaagg  ttggaatttg   281700
cataggttat  ttcatgctat  aaaaatgcat  caattgtgta  ttatatatga  tagtgaatgc   281760
cgttagtgtt  tcggggtata  gtattaaaga  agaatagtgg  gactaacata  ataatagctg   281820
ctgagtagag  gaagcatcgt  cttcagggc   tatgacgtgc  ctggtgacca  ttgcttttga   281880
atttatttat  tgaaatagtt  tcgcttcatc  gtcataattt  gatcaaactg  tgtaaatcac   281940
catttattct  ttacaaattt  agcctggaat  tttgtacatt  acatagtatg  caaagtgcaa   282000
acataaatgg  cgactgaagt  ttgagtgaac  tatcttatct  tctgtgtgaa  tacaatacta   282060
tcgatacact  taattgtttt  aatagtctaa  tatagtgaaa  taacagtcta  tgatgaatgt   282120
cttggcatgg  tttggggact  attgagaccc  attacagaac  aatagttttt  agcagaatgg   282180
taaactgaca  tttttattat  agaatgactc  taatgtaact  tatctgtttt  tttgtttcca   282240
ttgaaagaat  tttatttttt  tttcatttat  tgtgcttgcc  atactttaag  gtgttgtttg   282300
ctaatagtgg  ccaatgtcca  tttaataaca  ccaatacagg  attactttgc  caagtaactg   282360
aagaaccttt  attagttata  ttacaataca  ttggatgcct  taacattttt  tgttctcatt   282420
caatgattca  actcttgata  gccatagagt  agtgctggat  gacctagatg  taattgtatg   282480
tttgagtttg  atctggattg  cttttgtctt  taaaaatttt  gatttgtttt  tatcttttat   282540
attttagttg  aatatgagtg  atgaaatatt  gatcatggat  attgaatgct  ttaactgtta   282600
tgggtgatac  tatattggag  atgatggcca  ttctatattt  gtaatgctct  tcttaccttt   282660
atgaagtggt  ctctaagggt  gattccgatt  tcatgagttt  taattgtttg  aacattgcag   282720
accttcatgg  ttagtggatg  gtaacagaat  tgctacaaaa  ataaagtgtg  catccggaac   282780
atgtgataca  ggcaaaatca  agtggaaaag  caacccaact  agattgtgcc  ccagctgcca   282840
gcatactatt  gacaacaatg  atgtattttt  ttcttctgtc  tcatgtgttt  tttaattcgt   282900
ttccacgttc  tagctgctag  atatctcttt  tttgtggttt  ggaattttc   tttgaatgtc   282960 aaacatcaat  atgtcgtggc  tttaccttgg  ttttgaaaag  cttgcctaaa  cctagcgctt   283020
agggcaggct  ctgagttggg  agtcttgata  gcgctaggtg  agatgatttc  ttaagatgag   283080 cttttagag   tgcctaaagg  caagagactc  tgagcgcttt  agagagtttt  ttgctcttag   283140
cctagaagat  tatttgatgc  gaatattatc  acatgtgctt  tctatttct   ttgtttctct   283200 tcacttattc  ttctttttta  ttccccttcc  tatttttggat ttttttgtttt tttttttgtt   283260 tttaatattt  tcaaattatg  ttttactaga  tttttaaagt  gcctcgcacc  caaaagccaa   283320
tgtgtttact  atttcttccg  ctgttagagg  cttgactcta  gggacccttta gcgccttaaa   283380 gcacctcaca  ccttttaaac  taaggggctt  aaatctactt  agtcatggct  tatcttctgc   283440
ttgaaattct  ttggtttcat  tgctctcttg  gtgttgcaat  atctactagt  ctctagacat   283500
gtattaagat  gctacatatt  tataatggta  agaaatcagg  aatcgatttt  ttgttttcaa   283560
agtcttgatc  tattcgtttt  caaatcgcga  gtttcatgct  cataaataaa  ggagatggaa   283620
```

```
acgagaatga ggaattcaac ctagtttgac tagagaaaga ttaggtacga gatacattat 283680
gattggaaaa taaagtttaa taataaaaga aatgaagttg atttatgtgc ttggaaaagt 283740
tgttttaaga aggttttttt acttttactct tctttatctt ttgattccct cacttttctc 283800
tcatttaata ttaaaatgaa ggtcactttc atctcaatta agacaaaaaa taagtgaata 283860
gaaaaatatg tagatgagat aacgagagta aatgagtttg tgggtgaact agaagaaaga 283920
atgcgagatc acaaccataa ataaaactac acaaaaatta aagggattaa aagtatagcc 283980
aaattaaaga gacaaagggg gaatttcaaa tgcattttat tgatcgaaac acaatgtgac 284040
ttgctgatac gcacacattt tctttgtttc ctacttgcaa ggcttcacca gaggtatttc 284100
atttataatt atgaatttca attatgaaat catgaataaa ggatttgaga ataacaaggt 284160
ttgggcagtc attctcaaat tttcaacttt aacaagttat aaacagtatt gttgttataa 284220
acttgtgaat tgctgttata aactggtgaa ttgttgtaaa tttctgaatt gctgttataa 284280
acttgtgaat tgctgttata aactggtgaa ttgatgtaaa tttctgaatt gctgttataa 284340
accattgaat tgctgttata aattcctctg ctaaatgata taactgaagc acataataat 284400
aactatattc actagtgtta ggttctgata tccataacaa taacaatatt acatgatttt 284460
gtaacaaatg tacaatagtt tataacaaat cagaattaaa actaccacaa tagtaacaat 284520
aatgttctta attacaaaat gttgaagtta tacttctttg aatttgaaat cacttccttt 284580 cgttttggt ttaatgttga agttataatt cttccacagt aatcaattct gagcttcttc 284640
aagatttcag cctgaacagt aagaacatta gtttataaca ataatacata tatttataac 284700
atcaatatca taatttataa catataaaca atagttata acaactcaca tcatttatgt 284760
taatttggat gtcccaattt tcaccttgtc cctggtattc ttccatatgc ttcatggtag 284820
agctgttcat gggcgggcta cccgccaggc ccggacccct agcgccttaa agcacctcac 284880 acctttaaa ctaaggggct taaatctact tagtcatggc ttatcttctg cttgaaattc 284940
tttggtttca ttgctctctt ggtgttgcaa tatctactag tctctagaca tgtattaaga 285000
tgctacatat ttataatggt aagaaatcag gaatcgattt tttgttttca aagtcttgat 285060
ctattcgttt tcaaatcgcg agtttcatgc tcataaataa aggagatgga aacgagaatg 285120
aggaattcaa cctagtttga ctagagaaag attaggtacg agatacatta tgattggaaa 285180
ataaagttta ataataaaag aaatgaagtt gatttatgtg cttggaaaag ttgttttaag 285240 aaggttttt tactttactc ttctttatct tttgattccc tcacttttct ctcatttaat 285300
attaaaatga aggtcacttt catctcaatt aagacaaaaa ataagtgaat agaaaaatat 285360
gtagatgaga taacgagagt aaatgagttt gtgggtgaac tagaagaaag aatgcgagat 285420
cacaaccata aataaaacta cacaaaaatt aaagggatta aaagtatagc caaattaaag 285480
agacaaaggg ggaatttcaa atgcattta ttgatcgaaa cacaatgtga cttgctgata 285540
cgcacacatt tctttgttt cctacttgca aggcttcacc agaggtattt catttataat 285600
tatgaatttc aattatgaaa tcatgaataa aggatttgag aataacaagg tttgggcagt 285660
cattctcaaa ttttcaactt taactacttt aaaaacaatt tgaaatttga tccaaatcca 285720
gatttaaatt ttttgatttg ccagacaata atttttaattc aatttcaaat tttcaaatga 285780
aatatttgtt ctcaaacatg gcattaaatt aattcttcaa cacaaacttc cttttgtta 285840 aaatgaaacc caaaaactca acaaatgatc ctattaaaaa ttgtccttaa caaaaaactc 285900
actctaagaa ttaaaaaatt atgaaagtca gtagtttcac gttgtgtttc ttgcttcaaa 285960
tctgatttca ttccatgtaa cattggttat ccactaagaa ttaaaaactc ttgtaataaa 286020
```

```
ctatgccttt ccttatgtcc ttagtttaga aaagtgtgcc tagcattaga tgcgcggtgc  286080
gagtaagcca ataaggtttg aggcgtaggt agatatgatg atgaacgtta tgttagggct  286140
aggcgagaca attcctcttg gagacgcctc agatcacctt gtagcatctg tggagagcgc  286200
ctcacaacct tctataagca cttgaaaagc cattgtgatg cgagcacctg ccatgtaaat  286260
ctgtattggc ataaggttcg aggtgtaggt agatatgatg atggacgtta agagacaatt  286320
ctaaaggctg caaatcagaa agcaatgcta tttattgatc tcaacaaatt tgaagctctg  286380
aaattgtttg aatacttgaa ctatttatgt ctgtaaatct gtattggcgt tcattatttg  286440
ttattctttt gcttttagat tgtagtgatg taatgaatgg ctcattaaat tgcctgtgca  286500
tgcattcatc catgactttt cctgactttc catcttgctt ccgttgtccc taagagtttg  286560
caacaacaca tacagcccaa tgagaaagag cgaagatgtg tggaaaagaa taagaaagtg  286620
gtgaggacat tatctaaaag cgatggacca taatagatgg gacaaagatg tgtggaaaat  286680
aatgttttc gcatttcaat gagttcatac tttaaattag catcttaact aaaattttct  286740
agttggtgtc attgaagacc atgctagtaa gaaaaacttt gtaaaaaaat agcaacaaaa  286800
acaccactac gttctatttg aagaatttgt catagtgctt tttaagtgag cggatgacta  286860
cagtgcaatc ttatggtcga tggggtggct tattaatatt tcattatctt aatgccatta  286920
agtggttccc aactgaatgt ggtttggaag ggccggatgt acgctacctt accttgtta   286980
gtgataccaa agaggttatt tccgataaac ccttgctaaa catcatctat aatttcacat  287040
tagtataaag tgcgcatgat ttaatgagcc ttgttaatct ttggtctcat tgaaataggg  287100
gacatagtaa gtatctaaaa tataaatttt aaaattgcat acttagaaca tatttttctt  287160
cctcttttctc aggttgttca ggagtggcct ggattaccaa gaggtgtaaa atttgatcca  287220
actgaccagg agataatcca acatttactt gcaaaatctg gcattggaaa tgagacaccg  287280
catcccttca ttaatgagtt tatccctact gttgaggaag aggatgggat tgttacact   287340
catcctcaga atttaccagg tcggttgcaa tttattgttc atgctagctt cttaattata  287400
ttgagaatcg tgtcttgtct cagttagagt aagtaccact tttcctaggt aagatccttg  287460
attcgattct catttagcca tccccttttc tcaactataa taaaaatag ggaaatttca   287520
tgtggtgacc ctgagttctt ggcttttcca cgtagtagac aataaattca cgtggtgatc  287580
ctaagcttcc aactttttcca tgtggtaaac aaaatgtaaa tttttggtta aattaagtac  287640
tcatttcgac tggattacaa aatatgtggc aaattagggt gatcgcgacg tcgattttt   287700
gaataagaag tcattatgtt cgggaaaaat agcgtaaagt taacaaaaat tctactcttt  287760
ctagtttcta ccatgaaagt tgaaacacca cgtggattaa aaaaatgctt gccttccacg  287820
tagaaaagcc gataattcag ggttaccacg tggaatttcc ctaaaaaata actatagcaa  287880
tgtattcacc cttttgaatt tgactttgat taataaggtg tcaagcaaga tggaactgca  287940
tctcatttct ttcatagagc tatcaaagcg tataacactg gtacacgcaa gcgtcgaaaa  288000
atccatgggg ttgatttggg tgatgttcgt tggcacaaga ccggacggac taagccaatt  288060
tctcttaatg gtgtacaaaa aggatgcaag aaaattatgg ttctttatgt cagttctgct  288120
aaaggtggta agccggagaa aacaaattgg gttatgcatc aatatcaatt gggtacagag  288180
gaagatgaga agatggaga atatgttatt tcaaagtgt tatatcagca acaaccaggg    288240
aaacaaattg acaagactac cgggtatgtt tttgatgcaa tagatgacat tagtgtaaaa  288300
ctagatcctg tgactcctga gccttctcga catatgactc ctgagcctcc tcgaaaggaa  288360
```

```
atccagcttg accttgcaga aatgacctca tacagttgca ttgactttt cacccaggta    288420 ctgtgttgga acttcctttc tagcgtgcga tgcatctttt gacggtgatt tacatgtgac    288480
aataattctt gtgcaatatg gatgctttc tgacagcatt ttatcagtaa acatttctt    288540 tagaattaaa cagtatcctg agaaaattta ttttatcatt taagaagtat atatgacaaa    288600
tagaaaaggg cttattttt caaacaaaca ttaacgacca gaatcgaccc tctatagaaa    288660
gggcctattt cttcagttt gtctagtgcc cacaaaatgt caagaacggc accgcgcaaa    288720
acttatgcag tacaaaattt aatgtgattc tgttgcacta tcgtgtaggt attttcact    288780 attttacccg gatagaagaa agtgtgtttg cttggtaata cggtgcttat tagtgttaca    288840
cttacatagc tctcttgaaa gttttctgtt ttcatatcat gattgttggt cagtttattg    288900
ggttttttgt catcacatac aactctgaat ttacaggatc aacacataga tttcgaaaag    288960
catcatgaca tgtttcctga cgaagtgcaa caacctaaaa cacaacaaac tgagattacc    289020
aaatcaagtt atactgatgc tgctgcttca acacttgtag atgatcaagc tctagaacac    289080
gatgacaacc aggtttgtgg ggaaaatttg tggtttagtg agtcacaatt tacgataaat    289140
tctcaacaat tagcggaagg cctctcttta tgtgatgatt tgcttcgaag tcagtctcaa    289200
gacagaggcg aaactgccaa caatgtgcca aacaagaaat ctgttctttc ggagtatgct    289260
aagttgggtc cggaacatct aaagaaggat ttggaagagt gccagaattt ggtccttgat    289320
cctgcaaaca tagatttagg tacaccacct gatttcagac taagtcagct ggtaagcccg    289380
atgacatttt cccactcttt ttttgtttt gatcttatat atgatgatgt atcgttgcac    289440
ccgacattat ctctcatttg tctatctagg aatttggatc acaagaaagc tttggcaact    289500
gtggtttagg caagatctgc tactaaccgt ggtaccatta caattttccc gtttcgactc    289560
cataaagtca agggcatcac aacactgtag gtaacgtttt gatgcagatt tccaccaata    289620
tttttgttgt aaaacttcgg tgtagatcaa atgtatagtg ttctctccgt catttctt    289680 gctttctca gttattctta gtttttagta atcaatgtga ttagtcatca tctgtcatac    289740 agtcggttc cttaccttgt aacagatcaa tggtaccttc atgtatgcat gcgatctaaa    289800
ttttgttaat gtgaaacttg gcaaggggcg tctataatgc tgacactgac ttaccgtgta    289860
cttttgctcg taaaggaatc ttattatcta tgtgtattgc agcggatgaa atctaaatgc    289920
atcatgcttg ttcggttgtt tgtaaagcat cccgtctttt cgttcttgag cttttcgcttt    289980 actataacat gatgtacact catatgtgaa gactaaaggt tggagtttgt aagactggtg    290040
ggtcatattg agaacagggg tcattatcct gttatggttt ttgagaaaca ttcatgaact    290100 taaaggttg ttgacacaag ttgtttccga agaaagatag agaaattatt cacaatcaat    290160
tcaagtattt cgaaacggag taatagattg caaaccaatt gacacatcct taaaacaaat    290220
ttcccaaaat agcaacttca agtaaatcct gctcctaatg gttttcaat acccacttca    290280 tcagtaaaag gaagcatctt agacaaatta gccatacctt catcatattc cttctctaaa    290340
tcatctagtt tggctacttc cttaaggagt ctcgacttct taacggaggc ttgaatcttc    290400
aacagtccga ggttgtgcaa agactccacc ggtggcttgc tttggtgcaa ttccaaggcc    290460
ttctcgacat acggagtaag ccaacttaca tcaaagcaaa tgactctcag atcagttaat    290520
gtagacttca aattatgaga ttgattgtcg ctcatgtcta aggccgagtt ttcctcaagg    290580
gtcaggacta cattcgctac caactctaat gctcttgatt tcaagtcacc attagataaa    290640
atgcaatttt ctatgatgtt tccgtgtttt gaccagatct tctgcaatgt cgggatcaaa    290700
ttagacttta tatcgagtcc ctcaaacttt gtcgttggtg ttttgctcgt gttactctgc    290760
```

```
aagtgaaagc aaaaggataa gctaacatta atcgatacta gagtagagct ccgacaaaag  290820
ttcaacccct gcaatttgtt agtctactag agtatataac atatcctaga gcctcaacca  290880
ttagctcaag cttttggttg agttggttcc ttgccatgtt attagagcca gtgtgacaag  290940
aggtcatagg ttcaaatctc aacccctaa ttgaagtcgt atatttagcg ctaggtatga   291000
gaagggcatg tgctacatcc acacttctag cgtaaagggc tctcgtgtga ggaggcgtgt  291060
tagggtatat aacatatttt ggggccttat gtgatacccc agatttagct tgaaaagaga  291120
ttgatagact actcatatca acaaggtgca tcttcttttc tagggagccc atttactaag  291180
aactccacag ttaagcgtgc ttggtgggga gcaatcttag gatgggtgac ctcttgggaa  291240
gttttccggg tgcgcacgag tggggccaaa gtgcgctgga aagacttgtg ttggtctgtg  291300
gggctagtct acagtctcca tgagtagtca ccggtggtcc gttgggccag ggtgttacaa  291360
atggtatcag agcaaccctg cgaccgtggc tgattgtgtg ttcagcgcac ctagcggggg  291420
aaaagatccc gaagtgacgg tccaacgagg acgttgtatt cttaagtggg ggtgaatgtg  291480 atacccaga tttagcttga aaagagattg atagactact catatcaaca aggtgcatct    291540
tcttttctag ggagcccatt tgctaagaac tccacagtta agcgtgcttg gtggggagca   291600
atcttaggat gggtgacctc ctgggaagtt ttccgggtgc gcacgagtgg ggccaaagtg   291660
cgctggaaag acttgtgttg gtctgtgggg ctagtctaca gtctccatga gtagtcaccg   291720
gtggtccgtt gggccggggt gttacacctt aaccatcagc ttaagcgttt ggttggcagt   291780
ttgctcactt aaaaaacaac gttcatatag agtaatttaa tacctgattt gtagaagtca   291840
tatatggtct acagaggcta ccctttcttg gagtctttgg atcaggtgct gacagggccg   291900
gccctgagtt ttcgggggcc cggggcgaaa tatattttt ggggccctaa ttatatataa    291960
aaaaatttaa tgtcacgaaa ggaaaatgta tatgaattaa tataggtata gaagattttt   292020 gtacccctttt ttaccgaggg agtatacaat acaaaccaca attgtttgat cacgaagatc  292080
acaaaggcct aatttcccga gctaaatctc tctttgacac aaagaactac tcagtaagtt   292140
tgctgtttaa ttacttattc atcttcaatt cctcttttt aacttagaaa tctaaaattc     292200
attttgttta attgaatatc tagctatttg gaaagttagg gtttcgttta tgtgttgatt   292260
ttaaacttga caggcaatgg cgaccaatga ggctactaaa cttgtttccg aagaaagata   292320
gagttgctct gataccattt gtaacacccc ggcccaacgg atcattgcac ttgtcataga   292380
aaattacttt tatctttttc tcaaaaaaat ttttctatct ttcttcggaa acaagtttag   292440
tagcctcatt ggtcgccatt gcctgtcaag tttaaaatca acacataaac gaaaccctaa    292500
ctttccaaat agctagatat tcaattaaac aaaatgaatt ttagatttct aagttaaaaa    292560
agaggaattg aagatgaaga agtaattaaa caacaaactt actgagtagt tctttgtgtc    292620
aaagagagat ttagctcggg aaattaggcc tttgtgatct tcgtgatcaa acaattgtgg    292680
tttgtattgt atactccctc ggtaaaaaga ggtacaaaaa tcttctatac ctatattaat    292740
tcatatacat tttcctttcg tgacattaaa tttttttata tataattagg gccccaaaaa    292800
atatatttcg ccccgggccc ccgaaaactc agggccggcc ctgtcagcac ctgatccaaa    292860
gactccaaga aagggtagcc tctgtagacc atatatgact tctacaaatc aggtattaaa    292920
ttactctata tgaacgttgt tttttaagtg agcaaactgc caaccaaacg cttaagctga    292980
tggttaaggt gtaacacccc ggcccaacgg accaccggtg actactcatg gagactgtag    293040
actagcccta cagaccaaca caagtctttc cagcgcactt tggccccact cgtgcgcacc    293100
```

```
cggaaaactt cccaggaggt cacccatcct aagattgctc cccaccaagc acgcttaact 293160
gtggagttct tagcaaatgg gctccctaga aaagaagatg caccttgtta atatgagtag 293220
tctatcaatc tcttttcaag ctaaatctgg ggtatcacat tcaccccac ttaagaatac 293280 aacgtcctcg ttggaccgtc acttcaggat cttttcccc gctaggtgcg ctgaacacac 293340
aatcagccac ggtcgcaggg ttgctctgat accatttgta acaccccggc ccaacggatc 293400
attgcacttg tcatagaaaa ttacttttat cttttctca aaaaaatttc tctatctttc 293460
ttcggaaaca agtttagtag cctcattggt cgccattgcc tgtcaagttt aattatattt 293520
atttaacaac atttggtcaa aatcgagcta attgggcaac aattttggta atctttaagt 293580
tttcaaatgt agatgtacat agaataagat tttaggcagg aaaaaattct ctgaaagcac 293640
gatacgtggc agtaggtggt gtttgtttta gtattaagta tagatagtta tgctgaaatc 293700
aaactaagga caaaaattag tcacaaaata ataatctaat tcaataatgg ttatagccaa 293760
ctgttgaagg attttcaag cttccttcag aacttatgtt cattgtctcc ccctgattgg 293820
ttttcacaga ttatgtgtct ttatcaacaa tctgaatctc aatctcaatc gcaatctaaa 293880
tctgaatccg aatctcaatc tcaatctaga aggtgacaaa tcttttgtta tgtccaaatt 293940 cttttctag ctccaactcc tcctcccaat gcttcttctt catctccatc tttttgtact 294000
catgaatccg tatcaactcg tctctctcag cagcaaattt ccccatttct tcatcctgga 294060
tctgttgaca aatttaatgg tcatgcttat tcaataccaa tcgtctcatt ttttggcata 294120
cttgattgca ttgcattgct attccgaaag atggtatcaa agtttcataa tgggaacatc 294180
acagtacatt tcatgaaatt ttatagtgta aatcattcac attccacccc gaccatttag 294240
tatcaaggat cgaacgggcc atggggtaa agaatatgat ggtaaaatcc aatcacttga 294300
tagttgattc acacaatttc aaccataaag aaaaagaac aaaacatttt ctcccatttt 294360
cttccaccat tgacaacacc agttctagac aatcgattgc tgcctatttt ttgctgaata 294420
taaacgtcaa gatcgtcaac accagctgga acagcaaaag agaagccata ttctcccttt 294480
tgcaatttac tggattcaag ttcagaaaca agcctcttgt cgcatgttac cttgaaattt 294540
ttctcccatt caatcacact gttcacattg ccatacttct tcagcaaata ccaagcatat 294600
aagaatgttg gtgaacctaa aagccttcca ttggatctca ttttttttggc atacttgatt 294660 gcattacatt gttatttaag accctaaaat agctatgttg gaattaggtt atgataagtt 294720
gggactaggt tatgatatat attgttacag atatactgta aatgcatgtt agcatgatat 294780
aagttggagc tcctcatcca agacattagc aaatgtgcga tgaagcttaa ctctttgaga 294840 accttttagtt cttgcatgtg ccaaaaatag ctggagcccc ttgtaccaat caatggctcc 294900
agggccacct tgacaagcag ggcaatgcca ctgccttca cgttcattga tttcttgcac 294960
tgacaaagtt tccaaactat tgaaaaattt ctttagcatt atgtgttgct tccttgtctc 295020
gtgagttaga ggtccctcat cagaatcaga accatcactc agcaaatact catcatcatc 295080
ggtgaaagca tcctcttcgg aatccactt ctccttactc acctgagaat catgctgaat 295140 gagggggtttg actgatggtc cagtcaaatg cctaccatca ggcaaggtcg caaccccagt 295200
ttgttttctc tggtccatgc ttgaggtagt ttgggacctt ccagaataat tatattgaga 295260
tagcatgtgg tataattaaa gaaaagaata tagatttgta cagaggtcag gtaaagagac 295320
agatttgcag ggtctgaaag ataccctaat ttacctaggt tatacctat ataattgagt 295380 gctaccactt agaactttt cctaacactc taagctttct ataggtacct tacacgcct 295440 tatatccctc cagaaatgag agatgcatcc tcatctttct accacttcat cacaacattt 295500
```

```
ctggcagctt atatgccttc aacaaatcat tcttttatc ccaaattgtc ttaatacatg  295560
cctcctattt ttataccata atattgtaga catcctaaga ttttcattga caccttatac  295620
gcacatatac aagctatata agcccctcat cttcaagcaa acattcacaa cttgttgttc  295680
ttttttggtc agctttatac atgaatacat tacccatatt cctcttcatg catgcataaa  295740
gaaaccttac ggtggtgttg tatataaaat ttttcacatt ttagacccaa taattgcata  295800
aattcgagca tgaaaggtta tgttttgccc tcaagcattt tggatagcta agagtaagaa  295860
attttcaaac actttctgtt tgtggatttt cgaccatctt tttctcattt tattactata  295920
ttttgttctt aagaaatatg ggtctttgag ttatgagcaa ttagcacttt gaatcattgg  295980
atttggagtt cggagctaga ggttatgatc attttagtaa gacatgccga aaagggactt  296040
ataatggtca aagaatttgg atttaagtt gaatatgaat tttataattg gagttagaga  296100
tcagaattat cattttctaa gcccaaataa tcaatatttg taagattata gtattattat  296160
tttgggagct tggattattt tcttacaacc ttgaagatta ttcttggaga ttatattctc  296220
ttatattgga gttcttaatt cttattatat ctcttgcagc cttggtggcc catggtacac  296280
atttcttaac ctttttacta tgtgacattt atattatagg gatattctac ctggtaagca  296340
ccaggtataa cgaaattcac aaactagcta ttcttgtttg caattctacc aaatagcact  296400
caacttatgc aaaatcatct gccgtagcgt tattagccta aaaacgttag attttccgat  296460
aagtggtgaa tttacataat tgcccttgtt ttatttctta aatagggtct tcttccttct  296520
tgaagctccc tcttaattcc tttacttgcg ccattgatgc aacttcccaa tctcagatgg  296580
gatactccct gtaaacgtta gaatctgtga tttctgggtt caatccagca gctagttttg  296640
atacttctcc gtcaattggg tcaattgtag atccgattcg aaaccctact caaaattctc  296700
aagtattaac cgacccgtat tcggattatg atctgaaagc tattccaggt aaagctatct  296760
taactcctcc aaaacaatca tcatcatcat ctagcagtat gctcattaat ggcggcaata  296820
ataataataa taatagtaac agcagtaata agcttgtata gtataacaac tagtagttca  296880
tgttcatcac gagaggctaa aagattaaaa ccctctagtt attcaaacat ggatatagct  296940
gaatctggat ctgggtctgg atctagacaa gttttactgg ttgattcaca tgaaaatggt  297000
ataagattag ccaaactaga tgatttagag aaggaatatg atgaaggtat ggctaatttg  297060
tctaagatgc ttccttttac tgatgaagtg ggtattgaaa aaccattagg agcaggattt  297120
acttgaagtt gctatttggg aaacttgttt tagggatgtg tcaattggtt tgcaatacat  297180
ttgaacgatc tactctagtt tggaaaatgt tcaaaccgga attactgatt tggtttgatt  297240
ttagtgtcaa atcagaccaa accggaccat gttcacccct tagcttcataa tacttgctac  297300 tgatattgac attttcctac acaacacgtc acactcatta gcaagtatta tgaaacggag  297360
aaagtataag tatagaaata agaaagtata gagtaaaatt cgtggtttgt ttagataaac  297420
gaaaaataaa aataaggtaa attaaataga acgttttttt acttctttta ttgttttta  297480 gtaaactttc ccataaagaa tatttacggg aattaataaa aatatattta aagagaaaaa  297540
tcagtcggtc tcctctgaga gacgtctatg agacacagcc cattaaagct taaacaaaaa  297600
cataatctat tcccgtatca atggcggctg cgtggttgca gagacggtag cttatggtgg  297660
ttttaggtga tatttgggcct ctggtgttcg ggtatgacgg tggttgtagc tggtgatggt  297720
aggttctgtt ttggtgtggt ggtggatgct ttaggtgttg ggtcctggac aattaggtgt  297780
tttggatgct gaattctgga gtttgagtgt ttgggtgatg ggtcttgacg ctttgggtgg  297840
```

```
tgggtgttgg gttaatctac tggtgtggtt atacaattgg tgttagattt tctggtttaa    297900
tttacaggtt ggagatggtg gttttcgccg gtttcgaggt gtttggaggt ggttggtctt    297960
ttgatacgtt ggggatggtg gtctataggg ctgggtggcg taatggctgc cggtgatggt    298020
ggtcttttga tacgttggcg gtggagatgc tgtgcattgc agcctgcagg cgttttcttg    298080
ttggtggaat ttgaacagct attttgttgt ttttttcgag tcgtaggcct gcagtgtagc    298140
tgcctaaaat ttgggtaggc gaggggtttg gagaaagctg tccttatttt gggatatcca    298200
aggtgtttgt cattgtcggt gaacatgggg cttttcgaaa ttatggtgtt ttcaaatggt    298260
gttttgctgt tagaggtgat attggtgctt cttattgatg gttgcaggct cctgtttcgt    298320
ggtggtcgtg gtgtatttgt ttttcgtggt tttcgtgtct tggtgttttt agcttttctt    298380
ggtgtttgta ttagctcttt gtggtgctca aacctgttgg ttttggtgtt ttttgaaaaa    298440
cgatgtgcat agcccacccc tatgctgttt agggtggcct gtttcttggt ctccctcttc    298500
caatggcttt tttttcccta cgggggtttt tttatgccgg cgggtttgag atcccaagtt    298560
acagtgtggt gtttggtttt tcctccattt tattaataat attccaaatt ttcaaaaaaa    298620
aaaaaaaaaa aaaaaaaaa ggttgatcta attagaaatg gactcccata aagaccgtcc    298680
tcacaaaaaa ttgtgccaaa atattaata taaagtaatt ggaaaaaatt atgggaaaca    298740
caactaataa aaaatatttt tttagtgtaa gtgggaaata tatatatatt ggatcctaag    298800
gaatataaaa atgttaaaat aaagtaatta gcggaatgta tgtaaggata ttaaaatatt    298860
taaatgagga taaataaggt tattttttaaa caaaagttgt gatataaata gaaaattttt    298920
atataaacaa caaatataat atccaacata acaaatggaa ataattttaa ggaagggagt    298980
aatatattaa tattatttcc gaataacaaa attgggtttt tccttatttta aacttttcaa    299040 acgttagtca tttattcttt tcctttgttg tttgattgat tccttattat tgagtcgtat    299100
aaaattgaca aagttgacgc attactccat atcgttattc tcataacaaa ctcaattgtt    299160
tgatattcat tttattttcg gacttaaaaa taaatttata cattacaatt ttgtaaaaaa    299220
tcaatataca cacaaaatcc aatttttaaaa cgaacatttt cccttaatat agttttatta    299280
aagaatattt cccatttttac gttagttgaa aaataatacc tccaatactg tccacgtagg    299340
acagtgaggg aaaattttttt ttttcctttt ttttaacaaa accgctacct cataaagcgg    299400
tcaattatga aaattctaac aaaccgttac ttcataaagc gttttttcttt ttcataggat    299460 taaaaaaaat taaacatgat aaaccgctac atcaagtagc ggttatatat agactcattt    299520
acctccttct ttaacctatc cctctttcct ccctcactca ctctgctgca attgcattcc    299580
aaaaaaacgt ttttactcct cccaaatccc aatcactcct tattcatcac aacattacta    299640
actcaactaa attaatcaac aaccttttcaa ttgtctcttt gtttacttga agttcatgct    299700
catcatcaat caaagtatta atctaaccct aatttttttca aatttgcaaa ttgatctttt    299760
tgttcatgat tgttcttatt tttatcttat aatagtttgg ttgttttgtt atattatctt    299820
aatttctgta ttaagtgtgc aatttattca ttttagttat aatatatgat ttgttttgta    299880
tgaatatcaa gtgtttggtg aaatgcttca atgaaaattt caccaattgt tctgggttac    299940
attaatatct ttagtatatg gtcatgatat tattattaca ttatatgttt ctgattgtat    300000
ttgttcttat aaaactcattt gcagattgtg tttgcaaatt accaagaccg agctgtgcaa    300060
taggtatttt aatcctttgg taggcgtgga gaaccttgcg aacttatcct agtattagtt    300120
tgaagtacta tttggaaaga gcactaaatc catcttgtg tagagcattt ggtgattggg    300180
tctcaaattt ttgcgtgaag agtatttgat cacattccca ggtgctttca aggttttcaa    300240
```

```
gctgggtttc tttgcaattt gtggctgatg cagtattctt tttggctttg aaacagaaga 300300
gacagttgca attagccttt accaggtttt tttttttgtt ttgcatgcac taggaaaccg 300360
ctaccttaag tagcgtttta gtttagagag caaaccgcta cttcatgtag cggtttagta 300420
tgaatttttt tcaaaaataa ttcgctgctg acatggacgg tatttaggga attattttcc 300480
cttttggcgc atggtgggaa atattttcac tctaagcatt attatgggaa aaggttctct 300540
aaaactctta ttttgaaatc gactttaaaa ttcaaatgga caccgtctta tcctcaaagg 300600
tatccaaagt ttgctacatc ctttagagta gtggtgttta atgggtcgga taagagcctt 300660
taaagtttaa acataacatg ggcttaaaat gagctggacc ctgacaaaac ccttcttaaa 300720
acgggccgaa taagggctca aaatggaggc tcagcccatt gaacacccct atattagatg 300780
ttatagatta acaaattctt acttgagacc gtcttatgcg caaattgtgg aacatacaga 300840
atgacgaggt tgcaactgct tggctcaatg ataaagccgt gagaaaagca cttcacgctg 300900
atgatgtaag aacatagcgt gttttcgtgt aatcgtcaat caaaatacgc aaatagatta 300960
tgtaacgacg agtttcaatg ttgttcggtt atgcaccagg aaagtgtggc tggtccatgg 301020
gagctttgta caggcagaat tgcgtacaat cacgatgctg gaagtatgat caaataccat 301080
aagaacctca ctactcgagg ctatcgagcc ctcatataca ggtatgtcag ctttattcaa 301140
actgttgaat taggctgaac ttatcgtgaa atcagcata ttaacgagga aacacaaggt 301200
gccacacact tcataaagtg tgcacaacaa aaacagtaga gtttgacagt gtgattttgc 301260
tgataaatgc gcgatttgtg tgtatgtacg acagtggaga ccatgatatg tgtgtcccat 301320
acaccggaag tgaagcgtgg acaaaatcgt tgggtacaaa gtagtggatg agtggcggcc 301380
atggatgtgc aacgatcaag ttgctgggtg agtctcttag ccaagaaact agacaatttt 301440
ttttggtcgg gttattatca ggtcattgac gctagattga ttaagcatat atgcttgaaa 301500
tgtgttaata tcagttattg ttgcactaaa attgtaggtt tacacaagga tatgagaata 301560
atttaacttt ccttactata aaggttagtc catgaagttc tttaatcttt ttagctagta 301620
tatatatata tatatatata tatatatata tatatatata tatatatata tatatatata 301680
tatacattac tttatataat gtttgaaaat tctaacatga ttaatattgc tggtgcaggg 301740
atcaggacac acggtaccag aatacaagcc gagggaagca ctatacttt atagtcggtt 301800 tttagcgggt caaagcatat gatagattta atgttaattt cattctatta ccccaatgtc 301860
attaaataga acttgcttag acgaattcag aggggtctac agggccgtct ttgacatttt 301920
gggggcccta ggcaaattag tataatacgg cccttattaa acaataatac aattataaca 301980
atggtgagat actcctattt atctataatc tagctagtac aattattatt attatagtat 302040
ataaatcaaa tactatatag taccattatt atctaattac tccctctgtt ttcatatgtt 302100
cttctcactt tccccatttg gaaattttta aaagttcttc ccatttagaa tctttctatt 302160
ttagtaacca atagaattca aggaaattat tacacttaca ctctaatcta taaaaattaa 302220
tttacatgtt aattcccaat acatttactt tacatacacc caatgaaatt taatgatatt 302280
attacactta cactataatc aatagaacct ttattttta tattatttta ctcaactctc 302340
atagtatcta ttttgtaatt atagttttta ttggtttctt ccccgattcc aaatgggaag 302400
aacaaatgaa aacggaggga gtatatcata tcaaatttcc atttgaaaac aaaacaaaat 302460
cataaaacta aaattaagag aatcttaaaa aaaaaaaaaa aaaaaaaaaa cactaaaatt 302520
aagagaagct ctaaaatttt atttgcccca aacaatcttc ggtagtatat aatttaaaag 302580
```

```
aataactact acatataact taaaagatga cttttttttc tttatttagt ctagttatga  302640
aatttatgac ttttttatta gacctaaatc tctaaacatt taagttgggc ctttggccta  302700
cccttgggtc gggcctggtt cctttgagac tttttttat ttattttttt tcgttttata   302760 attttttataa tcaaattcat tgttgcaaaa atctaaattg gggtacggaa aggaaataca  302820
tcaatagatt tacatcaatg gaaatacaaa ctacatcatt tatgaaaatc taaaaacgaa  302880
ttcaaactct aaaagaatc tatctccttg agtttagatc tgaaaataaa caaaattaca   302940
ataaacaaat cttacaataa taaaatctat caaaaaaaca aatctagatc tgaaaatatt  303000
attgggagac atacaggaaa aggttgacaa tgatgatctt gaagcatagc aagtctatga  303060
gcaaccaagg aaagcttcaa ctcttttttg aaattgctga tttttccttt ttctactgaa  303120
aaacaaaaca aaacaaaaca gagaaaatgt gagtaaaatc aaaagaccca gaaatttaag  303180
agtaagaccc agaaatttaa gagaaagacc cagaaattta agagaagaaa aaccattgat  303240
gttgatgaag aaacattata tttggctaga caaacttagt tgaattttga ggatgcgagg  303300
cttatcctta gtcgtggctt gtagaaacat taaaatcggc aacgtttgat ttttctttac  303360
tagttcatca tagacatagc ttgcccttat aatatccaat tcagaacatt cttgacttgg  303420
agccattgaa agtagttcgc ctgcaacttt cttcatgagt ctaaacgacc cctcatcatc  303480
tctttcggaa gtaccctcat ccctatcacc tgcaactttc ttcatgagtc taaacgaccc  303540
ctcatcatct ctttcggaag taccctcatc cctatcacaa ttctttcttt tgaaactcct  303600
agttgtccaa gtaactgatg taccagtcga atttggaaaa atcgggattt tgcaggtaca  303660
ctgcatatgc aaccgccggc cataaataaa tgagggtcgt gtaaacttat atatcaattt  303720
gaaggttgta atgatcaact taccgtactt ttttccgcac agttgcacca ttgtaaaaat  303780
tttcccattc caatcaaatc agtttgagag cgagtaggaa tagttaagcg ttggtactta  303840
atttccttgt tgtaattatt agtaaaaatt tgccataatt tcttgtctgt ccatttaaac  303900
ttttgattaa taactagagg gaagacatat ttcttcatca catatatata gtgtactttt  303960
tcgtcttcaa tcatctgtca ataaaaatac aagtgaaagc tcaaagaaat tctctcaaca  304020
atactaaatc tttaaaaaaa aaaatcgcta aacattttac cttactagca aaggaggatg  304080
tgacactctc agtgtcggat acgcttaatt cttcttttcc tgcaagataa gtttaatttc  304140
acacaaaaca accacatttc cataagaagt caaccaacac tataaatacg atatctaaac  304200
ctactgcaca caatagtacg acaacaactg cacaaaacga ccaccaacaa tagtagcaag  304260
tcaaccaaca ctataaatac gatacctaaa cctactgcac acaatagtac aacgacaaaa  304320
actgcacaaa atgatcacca acaacagtag cagcagtaga cgcaaccaag agaacaagtt  304380
gtaacagtaa ctcagaaatt tataacagca attcacaagt ttataacaac aatagtacaa  304440
cgacaacaac tgcccaaaac aaccactaac aacagtagca gcaccaacag agccgaggta  304500
gcagcaccaa atatcatcac agcgcctcca aatcgtccct aacaacaaac aactactaca  304560
cttcacacaa acaaccaaaa ctgttttggt ccatttactt ggtcatgaag cctggtcata  304620
taaagaagta ttgtttgcat cttattccac ttattattga tgctttattg ttataaactg  304680
gtttggtctg tgacagtaat atttggagga ttgtcttgag tgggtgattt agtgagtgtc  304740
gtaatgacct caaaccaaa gtcacaaagc tcaaaaccaa agtttaattc ttcttttcct   304800
gcaagacaag tttaatttca cacaaaacaa ccacatttcc ataagaagtc aaccaacact  304860
ataaatacga tacctaaacc tactgcacac aatagtacga caacaactgc acaaaacgac  304920
caccaacaat agtagcaagt caaccaacac tataaatatg aatccttaac ctactgcaca  304980
```

```
caatagtaca acgacaaaaa ctgcacaaaa cgatcaccaa caaggcaaca atagtagcag 305040
cagtagacgc aaccaagaga acaagtagta acagtaactc agaaatttat aacagaaatt 305100
cacaagtttg taacaacaat agtacaacga caacaactgc ccaaaacgac cattaacaac 305160
agtagcagca ccaacagagc cgaggtagcg gcaccaacta tcatcacaac gcctccaaat 305220
cgtctacact tcatacaaac aaccaaaact gttttggtcc atttacttgg tcaagaagcc 305280
tggtcatatc aagaagtatt gtttgcatct cattccactt attattgatg ctttattgtt 305340
aaaaactgtt ttgatccatt tcttattctt gttgtgtgac aaaattattt ggaggattgt 305400
cttgagtggg tgatttagtg agtgtcgtag tgacctcttc cgatccctac ataaactttt 305460
gtattgtgtc ttgaaatgaa caaatatgat aaatgaacaa atatgataaa tgaacaaata 305520
tcatcagaat caacaatcaa aagaccaatt aagaatttct ttgcaactgc tcacattcga 305580
atttcataaa cacttcgaat tacagcaaca cgatggaaaa aatatcatcg atggaaaatt 305640
aaacaaatcg atttacgaat gtcaagcact caccaaaatt aaacttaccc agaaaaatta 305700
aacaaacaaa gaaattaaca aacacacctt tgaagatagt taacggcttt gaggaagttt 305760
gactactcaa tctgtttcgc gtcctgacaa aaactaacac atttgagagg gagtgaatgc 305820
acaaaaaaaa ttaacaaaaa aatttcaaaa ttgaagaact gtaaagaaaa aaattacgta 305880
ctcttttaag tctggacttt ggttttgagc tttgcagata gttaacgact ttgaggaagt 305940
ttgactactc aatttgtttc gcatcctgac aaaaattaac acatttgaga gggagtgaat 306000
gcacaaaaaa aattaacaaa aaatttcaa aattgaagaa ctgtaaagaa aaaaattacg 306060
tactctttta agtctggact ttggttttga gctttgtgac tttggttttg agctttgtga 306120
gacatttgag agggactttg gttttgagca gtcacgtgat tcggtggttt taccaacgaa 306180
gaaatctgaa tataaaagga taaaaacctt acttgataaa tcaaactaga atattgaaga 306240
agatagacaa attgaagatg gtatttccgc cattaaagct tatttcaagc ttctgcaact 306300
cactgtagta tgaagtactt cattaagtat tattttttt tttttgaatt gaagtattat 306360
tttattatat actactcata attgtattgt actagttcac agattattaa atgtaaaatg 306420
agtagaaaca gtagtttaaa tattttttgg agatagtagt tctaatactt ttgtataaac 306480
ttatattaga attttggttt acatatgtaa taagtaatac tccctattct atttatttta 306540
ttgtcacatt attattatac atattaaatt gtaaacatct aaaattttat ttagttaaaa 306600 atttaatat tttaagtttta ataaaattta caaagaaaca ttaaatttaa aacaatgtcg 306660
caattactta tatataatga gataactaaa ttcatttata taaaatgtaa gaataatgc 306720 tattatttat gtagaatgcg atcactatat caattaaaat gaaatgtata acaatgtcac 306780
aaagtatttt tatataatgc aatttcgttt atataaattg tataaaatgt cacaagtatt 306840
aatatagaat gcgaacattt tattttattc attaatataa aacgtagaac taggatgcaa 306900
gcgctatatt aatataaagc gtagaactat gtcgctagta tttaattagg atgcgagcgc 306960
tataatgtac aacaatgtca ccagtgttcc ctctactccc cttatttctc atacccaaat 307020
acgaaatgta gaacaatgtc gctagtactt acatagaatg tgatcactaa ccaatatgaa 307080
atgcagaaca atgtcgctag tacttacata gaatgtgatc actaactcat acgaaatgtt 307140
gtacgatgtc gccagtactt gtatagaatg tgatcgctaa ctaatatgaa atataattat 307200
attatataat aatctaatta gtctaaacat attacaaaca aacgtaccac tacattatat 307260
aataatctaa ttagtctaac tcatacgaaa tgttgtacga tgtcgctagt acttgtatag 307320
```

```
aatgtgatcg ctaactaata tgaaatataa ttatattata taataatcta attagtctaa 307380
ttagtctaaa cattttacaa acaaacgtac cactacataa taataatact accaaataaa 307440
ataaaatgtt tttaatggaa tagagaagac tggtaatggt aagtaattgc tgagtatctg 307500
cttcaagcta tcatagagat tggtccttct aatgtgctac aagttgtaac agacaatgca 307560
aagaattgtg ttgctgctgg aaaagagatt gaaaaggtac acaatcatat tttctggtct 307620
ccatgtgtct gtcataccat caatttaatt tttaaagact ttgctaagga gttatgctgg 307680
atgaatgata cttataaaac tggaaaacag attgtgaagt ttttactgc tcattatgct 307740 cttgcgttgt ttaagacaca ttcaaataaa attctgttaa aggtagccaa aactagattt 307800
gggtcgcact atatattgtt gaagagattg ttacaatgta gagaagcact agaaaatact 307860
gttgtcttaa gagcatggag agaatggtta gaaaaacaag atgctgctac taaaacatta 307920
gggaggttga tagcagagaa cattcagaat aatagatttt gaatgaagtt caagaggtga 307980
tcaaatgcac taagccactt tataagttgt taaaattttg tgatggcgaa ggaccccgaa 308040
tgggagagat atatgaaaga aaggataata tattaggaga ggtaaaagat ataatggatg 308100
atagcaagta cagctcaaac tttactaaga tggagaatat tatagtcact aggtgggata 308160
aaatgacgat acctttgcat tgcttaggat ttgctcttac acctcgtttt tatgatcgtg 308220
catatcttaa tgcatcagca cctggaggct atgttaggag ggctcctaat gaagatagg 308280 aggttgtttt gggatgtatg gaagctttca agaaaatatc agaagatagt gatgaagaaa 308340
agaaattaag tgatcaattt attgagtttc aattaaagaa aggtatatat tccatgcctc 308400
aagctcaaat ggatgctgtg acattagaag caatagattt gtggtccatg tatggatcac 308460
aaactcctga tttggctgag gtggctaaga aggttttatc tcaacctatc agtagttcat 308520
cggcaaagag ggcatggagc acttttggga atgtccatac tctcaaaagg aatagattgg 308580
actgtacaag agcggacaaa ctggtcaata ttcatagcaa tcttcgctta gcatctcgtt 308640
ttactgaaag ctataagagt gggcctcata gaaagtggga cattaatccg gagcactctg 308700
gtttggagga ctcacccttta gaattagagg atatgagatg gttaggtctt gatgatgatg 308760
atgatgatgt ttcactaatc aatgaaatct gggtaagttt aattttggga tgaaattgac 308820
tagtttataa caataagaca gacgttttata acaataaaac agaagtttat aacaataaac 308880
agaagtttat agcaataaaa caaaatcaat gaaatatggg taagtttaat tttgggatga 308940
aattgactct actgctgtat tggttgactt ctgatggaaa tgtggttgtt ttgtgtggat 309000
gccaagttat tgttttcttg ctggattgtt atttacggtt atatgttgag ataatttaa 309060 aagatttagt aatgtttaaa tgggaaaagt tttacaatgt gttacgcctt acaagctggt 309120
cacctattac agaaaacgca aggggaagaa atctcaaggg taaacaagta aatgctgagg 309180
tggttaattg tcagaacaca agaaggaggc catatgggta ttcgtgggta gcatattcta 309240
gaagggaata attctattat gctgagctgt atgtaagaat agtactctat aaatatgtac 309300
tattgtaata ccttgagatc atgcaaagaa agaagttaag aagtaccatt tggagtgtac 309360
tgatactcga aaatcagtgt agtagcatag cagtcctttt ctctttttctc tttttacttt 309420 tgctgtactt ttcttgctag aaattcatac caaatctggt atcagagtag aatggtgaat 309480
aacacccaaa gaatcgacct acttgagggg gagattcgag ccacaccaca ccttattaac 309540
tctgaaatca gcagactacg ttcggagtta gacctaaaca cccaaaacat taattcccaa 309600
atcagtaacc taaccctaaa ttcccaaaat cttcaagccc aaattaatac catgacccaa 309660
gaaagccaaa tcagtaacca tgccttcgct actgaaatgg cgaacctaag ccgcaccatt 309720
```

```
cgaaaactag atgaaaaact caccaacccc gacttcatca atcctctaca ccaaaatcca   309780
ccaaacacag taaacccaaa caactcaatc ccaaactcgc ctataaccgt tagcccaaac   309840
tcgattacac ccgaaaattt tgaaactcag gagaacgaag atggagggag aggaaattgg   309900
aggaacagga aatcagactt acctacgttt tggggagaag acccggatgg gtggatcctc   309960
caagcggaac ggtatttcac attttatagt ttgagtgaga aagagaagat ggaatcatgt   310020
gtggtgagcc ttgaaggggc ggctttgcat tggtttcatt gggaacatca acggagaccg   310080
ataacgcggt gggaggagct taaggggctc attttgcggc ggtttagatc ggtggaggaa   310140
gggacgttgc acgaacagtg gatgtcagta gaacaaacac gatctgtcgc cgaatataat   310200
ttggagtttg tggagaaagc taatgctctt gggatgatac ccgaaaattt tgccatggga   310260
gcttacttga agggattgga tgagagagta aggaaggagt tgagacccct tgaaccagta   310320
agtgtggatc atgccatgtc cttggcagta ttgatagata aaaacaaaa ccccaaatta   310380 tctcttaccc aaaatacccc cggattgccc ggagattttg aggaggagct ggaggaagtc   310440
gaagaggagg tggcggagga ggaattacaa acagtagctg aaatctctct acaatctgtg   310500
gtgggaattt caagtccaaa aacgatgaaa atgcgaggca ctgtgaacga gcaatcggtt   310560
attgtcatga ttgactcagg agctaccaat aattttgtgt cgactcatat ggtaagacgc   310620
ctcaacttgc ctttaatag caattaaaag ttcggggtga tgctgggaaa cggtgaacaa   310680
attaaaaagg ctggaatttg tcaaaaatta tccgtggaga tacagggcat tgtgatagtg   310740
gatgattttt tgttgttgga gttaggcaac actgatatga tacttggttt acaatggttg   310800
gaaagacttg gtgaaatcac agtgaattgg agggagcaaa ttatgagatt tttgtgggag   310860
gaaaccatgg tggaacttag gggtgatcct tctttgggac actcccaggt ttcgttgaag   310920
gcgataatgc gaaccgtcag gaaggagaaa cagggactct tgattggaat tgaatgaagt   310980
taggcaaata ataatgttat ttcatcaaat aacatctcgt tattagatag aagtaaaacta   311040 gaacgaagga aatataaaac gtagataaaa gaatttaaat ttataatgtt ggaaaagaaa   311100
aataaagtaa gcacccctac ataatataaa atcaaacaaa gacatttttt gatgcaaatc   311160
actaacaaga gtgtctaaat gaagagaagt ttttatact aattattgca aagtaatgaa   311220
tctgcattat attgagagag acaaaacaaa aaatatataa tttgaaaaat aaggttacac   311280
aacttaaaat ccacttatcc ttgcaatcaa tcaaatattt aatcaaaata gtacgacttt   311340
aaatgaccac ataaaaatcc atatgactgc ttcataattt catatatctt cacatagcaa   311400
agagaaaata ttaaacattc acaaatatag gttaaatcaa taaatataaa attagtttaa   311460
taaacgaaaa ataatatatt atatgaagtt atgataagtt gaacaggata tattgttcct   311520
aggattggat gtgaccccat catatttgtc tggaaagtag catcaagtat gcagcttggc   311580
gaaagcaagc tataaatcaa gccattaaga tggtctgttg gatggagagg atgaagtcaa   311640
catatctgaa tcatatctac cgatgttttg agatatcacc cttaccccca cctcgaccac   311700
aggaccacgc tatacacttg aaggaaggag ctagcccgat tagcgtgcgc ccttatagat   311760
atccgcagat acagaaggat gagattgaga ggatggtcag ggaaatgcta caagcgcaga   311820
taattcgtcc ttcgaccagc ccattttcaa gccctatcat cttagtgaag aagaaagatg   311880
ggtcgtggcg tttttgcgtc gactatcggg cccttaataa agtaacggtg cctgacaaat   311940
atccgatccc aatgatcgat gagttgctag acgagttata tggggcgaat atttttcacaa   312000 agctcgattt aaaatccgga tatcatcaga taaggatgaa ggagaaggat gtggagaaaa   312060
```

```
cggcctttag gactcatgaa gggcattatg agttcttggt aatgccgttc gggttgacca    312120
acgcgccggc aacgtttcaa gccctgatga acgaaatttt ccggccgcat ttacgtaagt    312180
tcgttcttgt tttctttgat gatattttgg tttacaaact gaagaggagc ataaatttca    312240
tttgtctgtg gtatttgaat tattgagggc caattaatta catgtgaatc gtggcaagtg    312300
tagtatagga gttaaggagg tggtgtatct agggcatgtc atttctggtg caggtgtgtc    312360
aatggaccct tctaaggtgg atgctgtgct ttcatggcca acacccacca atcttaagga    312420 gttgcgggt ttcctaggcc tttccggtta ttataggaaa tttatttggc gatacgctgc      312480
tgtggctaaa ccacttacta atcaattgaa gaaagactca tttggatgga atgagtatgc    312540
gaccaaggcc tttgaagatc tcaaggtagc cattactcag gctcctattt tggcactccc    312600
agatttcact aaattgttca tcgtggagac cgacgcctcg ggtattggct tgggggcagt    312660
gttaaaacag gagcagcatc ccattgcatt ttttagtaag aatttgggga taagagctca    312720
gctgaaacca atttatgaga aagagctcat ggcgatagtt tttgcggtgc tcaaatggcg    312780
gcactatctt ttgggcgta aatttgtggt gaaaaccgat caaagtagtc tcaaatttct       312840
atgggagcag agggaaattg gtacggaata tcagaagtgg gtcactagac ttatggggtt    312900
tgattttgac atcatttaca atccaggggc atcaaacaag gtagctaacg ctttgtctcg    312960
aaggagccat ggagtagttg gccttggggc tttgtggagt acgcatagag tcgattgggc    313020
taagttggat gaggagattt cgaaggaccc cttcctcata tcacttaggg aacaggtagc    313080
taaaggggag gaaatgctca aagggttcca ataatgaac gggcagctgt ggtataaaga     313140
taggatggtc attcccaaaa attcagcttt cattccagcc ttgttgaagg agtatcatga    313200
ttcacccata gggggcata ccggggaaca caaaacctat gctcgtattg caacgcattg      313260
gttttgagag ggtatgagga gacaaattat taattatgtg aagcagtgtc cgatatgtca    313320
aaggcaaaag cactcacgcc ttaatccagc tgggttactc caaccattgc ccataccgga    313380
catggtttgg gagcatattt cgatggactt tattgagggg ctgcctaaat cgcaaggaaa    313440
ggatactata tttgtggttg ttgatcggct aacgaagtat gctcacttca ttgggcttaa    313500
gcatcctttt acagctcaca cagtcgcact tgagttcata aaggagatag tgcgacttca    313560
tgggttccct agctcgataa tatccgatcg tgataaagtc ttcttgagtc tattttggaa    313620
agagcttttt cgcctacagg gcacagaatt gagatacagt tcagcttacc atccacaaac    313680
ggatggccaa tcggaggcgg tcaacaaaac tcttgagacg taccttcgtt gtttcatcaa    313740
cgggcgtcca aagaagtggc tagagtggtt accatgggcg gaatacagtt acaacacctc    313800
cattcactca tctactaagg tctcaccatt ttttgcttta tatgggagag accctcctca    313860
cttgggtaga gctgctcatg aaaacaccaa ggtggggagt ttggatgatt tgcttcgaga    313920
aagggattct atattagatg aactgaaatt tcagttgcta cgggctcaac aattgatgaa    313980
attaaatgct gataaacata ggagagatgt ggttcttatc ccgggagata tggtctacct    314040
caagctacaa ccttaccgtc agaaatcctt gtctcgcaca cataatgaga agctagcttc    314100
aaggttttat gggccgtata aggtgctgga agaattgga gccactgcct acaaattgga     314160
gctaccaaat catagccgta tacatccggt ttttcacatt tctcaattga agaaggcaat    314220
tgggaacaag gcagccttgg agattccacc tcaactcaat gaggcaaatg agcttgagct    314280
ccatccagac aagttactgc aatgaggta taatgcagct ggtaaattgg aagtcttgat     314340
tcactgggag tctgaaactg ccctagaggc tacttgggag gatgccacac tacttgatgc    314400
acgctttcct actttcaacc ttgaggacaa ggtcaagctg caatccgggg gtattgttac    314460
```

```
gccttacaag ctggtcacct attacagaaa atgcaagggg aagaaatctc aagggtaaac  314520
aagtaaatgc tgaggtggtt aattgtcaga acacaagaag gaggccatat gggtattcgt  314580
gggtagcata ttctagaagg gaataattct attatgctga gctgtatgta agaatagtac  314640
tctataaata tgtactattg taataccttg agatcatgca agaaagaag ttaagaagta   314700 ccatttggag tgtactgata atcgaaaatc agtgtagtag catagcagtc cttttctctt  314760
ttctcttttt acttttgctg tactgttctt gctagaaatt cataccacaa tggtgcaact  314820
gtgcggataa aactagggta agttgatcat tacaaccttc taattgatat ataagtttac  314880
acgaccctca aatatttatg tgtggctgtt gcatatgcag tgctactgca tagtccccat  314940
ttttccgtat tttggtgaac ctgaaaatat gtacctggtg tacaactcac ttccggcaca  315000
tcagttactt gggaaaaccg ttatgaggtg aactaaaata ccattgaaga gccgaatgaa  315060
ctcatgaaga gcgttgcaga cgaactactt ttaatggtgc catgtgaaga attttctagt  315120
ttagatattt cgagggcaag ccatatctat aatgatctaa taatgaataa gcagttcatg  315180
ccagttttga tgtttctaca agcctccaag aaggataagc ctcgaatcct cgtaaatcaa  315240
ctacgtatat ctgccaatga taatggggtc gaggatatag atgtggtctc gaatacacca  315300
gattagatta ttgttataaa ctttacgatt attgttataa gaatttataa caacattata  315360
ttatttgagg aagtcctaaa taggatggtt gttagatttg atttatgttg ttttatgtgt  315420
atgaacgtag gtgcaacagc atcatcacgg tgcaacagca tttgtaaaaa ctaaatcgtt  315480
attcaaccct acttcaagcc ttcttggtag ttggtaccaa aacctatact ttgcgcattt  315540
attagatact ttgtacaatg ataggatcat cacaaaattg ctgattttc tgtgaaatta    315600 gacacttgtt acatacaaat ttaagtactt gtgaattgtt gttacaaact gctagaagga  315660
tcattatatg aacacaaacc atcaattcaa gaagcgatcc ataaaatttg attacaaaca  315720
acgttagaaa agaaatacaa cctgaaataa caataacaat taacaataat accaaatttc  315780
aaagtccaaa cacattcact tcttcacaaa tcacattaac attaacatat atatagaatt  315840
ataacatatg aaataacaaa aaatgtaaca aacaataaca ttaataattc aagaaactaa  315900
cttgagtttg aaataacaat aaaaaaaacc ctaaattttg agaattggag atttgaaaat  315960
ataacattta attaataata ataccctgaaa atctgaaatt ggtttgattg tttgaaggtg  316020
ggttagtaat tggtatggtg gtggactagc cggtgggaag taggcaagcc ggcagccgca  316080
ggacagaaac ccaacgtgat agcgactcgc gagggagcag gcgacagaag actaaaaagc  316140
agcaggacag aaacccagac gcaatagttt ggagttgata ttcaagaaac caacggccg    316200 tttggtttgt gagagaaatc accggcgaga atggcaaaag gtcctaaaaa ctcaatctcc  316260
cttaatattg taatttgaga aaatattccc tgttaaagta tagtgtgaaa ggttgaaata  316320
tagtgtgaaa ggtaattaat gtatttacct taatgtgaat gcatttatgg ataaaatttg  316380
cctataaata tggatcttca ccattgtaaa aactacacca atgagtaaaa acatcacttt  316440
ctctaacttt actcattata cttcctcttt atctctctaa attttaacat gttatcagca  316500
ccagctctac cgttaataat caagaaggta atattttaa aacctaatta agtattcttt   316560
ttatcggtac ccacaaatgg accaacaatc aaatggtatc aacatcgtca tcctcatcca  316620
aggtgtttcc aacacatttt tgtatttat aattgagcat aattccatac ccttcaccac    316680
aaacccagca aggactgatt taaatcagct ccgacataat aatcccaata atactaatga  316740
tccaccagta ccaccaaccc gtaattcaca tatacgacca actaataatc cactagttcc  316800
```

```
accgactaat attccaccag tacaaccaac aaataattca tcaacacaac caactaacaa   316860
cgctccaaca acatcaactg aaaataaacc ctcatcaagt aataaaagaa ctaaagatga   316920
tgagggagaa ccaaatacta aacgtagcaa gacaaataac ccgtaaaata atttattgga   316980
catacgtcat ctttacagat gacaaggaca ttttttttt ctgcttttgt tattattta    317040 tttcatacag cctatatggc cggttaacta ttttgtttta ccgcctgatt ggacggttag   317100
tattatttat ttcttttgtt atcttttgtt attatcctat aaaccgccta tatggctggt   317160
taattgcttt tcttttaccg cctgaatgga cggttagaat tattttttctt tcttgtacat  317220 ttatatgcat ttttatttca tttgcattta tatctgtgca tttttttatta ttcacatatt  317280 actttacgta tttttaagag tatacataaa caatacggta tattgtacaa tttgggataa   317340
ccctctataa aaccggatta ccccattttt ttaccacata ctccttatcc tctcaacttt   317400
actctttaca tcaaaaccct tcctcctcca tcctccttcc accgacaatg tactcccata   317460
acaaaaataa ttcatcttct tcctctaccc ataattttag atttgaagaa aattttgcca   317520
aactcaaatt atatatctcc ataattatgg ggttggtggc ccttcttgta gcatttggaa   317580
ttataataat tatgaagaag taatttattt tgaagaagaa acaaaatgca catgatttat   317640
tttgtcatat tttttgttta ttagtgcatt ttgtataata aattgtacta acatattgtc   317700
tatatgctat ttgttttacc ttatttagca tttattgttt ttaagtttct ctccttttca   317760
tttttcttat tattactaat attatctctc ttgttcttgg tttattccta actatattat   317820
ctacaacaaa ttcataataa taaaccaagg gggagattat catggaatta aactatcata   317880
attttcttta tggtttatta ttatgaaaat agaagaatta ttgcattgtc atatatactt   317940
acaaaacaat tatatattat gtagcaagta tggcagagat tactaaaaga ttattcaaca   318000
tattagactt aactggacaa aaattcttag aatggaaaga agatgccatt atgaatttag   318060
aagctcaggg acttgaacac accgtaatgg aagtaaaaga aaaagatcca acagatggta   318120
ttcaagctac taaaataaag gtagctacaa atcaagaaaa ggccaaagcc ttagtcctct   318180
tgaggcatca tattcatgat agccttaaat ctgaatattt gtttataaaa gatcccaaaa   318240
cattgtggga ctccattgtt gaaagatttg atcaccacaa aagggtgctt cttccacaag   318300
ctagtcatga gtggaagaat ttaagatttt ctgatttttaa gactctcagt gagtataatt   318360
caacattata ccgaattgca tctatgttga aatactgtga gcacccggtg actgatgcag   318420
aaatgattga actcacatta tctacttttc atccatcaaa tattattctg caacaacaat   318480
atagggaaag aaattttaaa agatattcag atctgagtgt agtactctcc ttggccgaac   318540
aacataatga tcttgtctgg aaaaatcaca atatgagacc tattggatct caagctatcc   318600
gtgagacaca ctctataaaa acacatgtgc ctgaagcaca tgctgttgaa aataaaggcc   318660
atagaaatta taataaccgt ggcagaggac gcagaaattt ccgaggaaaa ggaagaggac   318720
gaggccaagg tcgtggaaat tttcatgggc atggtagaaa gttccacgaa tctggtagag   318780
gccagtttcc ccaaaattat caaaatggtt attacaaaaa taattttcga aggggaaaac   318840
aagttggata ccataatagc catcaagaaa gaaagaaag tatttgtcac agatgtggca   318900
tgacagggca ttggtcacgt acctgtcgta ctgccaagca tttagtggat ctatatttag   318960
cttcccaaaa gaaaagggaa aaggtgtag aagcaaattt taatgaagca agcacctcaa   319020
tggctaatgt tgatccatat aataaagcaa gcacatcaat gcccaattta gatctttctg   319080
acttctattt agatgacaat gaaaatgaaa gagaatatga tgaagctatt taaatttct    319140 tttgataatg ttgtgatgtt actgatttgt atttccttt tatatatatg cagtttcttg   319200
```

-continued

```
ttatgtattg tcatattata taatattaat gaaattttat tttaactaat catctactta 319260
tttaatatga agatatggat caatttgaaa ataagttgaa atatcaatgc ctcctagata 319320
gtgggacaac tcacaccatc ctaaagcaca aaaatatttt ttctgaattg aagatggtga 319380
aagcagatgt cactacaatc tctggaacta ccaaactaat agaaggatat ggaaaagctt 319440
taataatact tccaaatgga acaaaactag aaattgatga tgctttatat tcgagtaaat 319500
ctcgacgaaa tctcataagt ttcaaagatg tacgccaaaa tggctatcat ttagaaacaa 319560
tgaccgaaaa tcatattgaa tatttatgca tcacatctga gaaatgcggc aagaaatgca 319620
ttcatgaaaa attgccagca tactcatcag gattatatcg tattgatata aaaccagttg 319680
aaataaacat ggtgtctaac cagaagttag ataatagaga aatgataaat ttatggcatg 319740
accgattggg tcatcctggt gtgggaatga tgcgaaaaat tattgaaaat tcaattgggc 319800
atccaatgaa gaaaataaga attccccaac caaatgaatt attatgttct gcatgctcac 319860
aaggcaaatt gataattaga ccatcgttaa ataaaattgc tactgaaact cctaaatttc 319920
tagaaagaat tcatggagat atatgtgggc caattaatcc cgcttctggg ccatttagat 319980
attttatggt attaattgat gcatcaacac gatggtcaca tgtaagtctc ctatcaacta 320040
gaaatgtggc atttgcaaaa ttacttgctc aaatcattcg attgagaaat caatttccag 320100
atcatacaat taaacgaata aggcttgaca atgccggaga atttacatct caaacttttta 320160 atgattattg tacgtcaatt ggaattgacg tagaacatcc agtagctcat gttcatactc 320220
aaaatggtct ggccgaatca ttgattaaaa gactccaatt aatagcaaga ccattattaa 320280
tgaggtcgaa attgccatca tctgcgtggg gccacgcaat aatacatgca tcatcattaa 320340
taagattgag accaagtgct tatcataaat attcaccaca acaattggtg aatggtcaag 320400
aaccaaatat atcacacctg aaaatatttg gatgtgcagt atatgtccct attgcaccac 320460
cccagcgtac aaaaatgggt ccacaaagaa ggatgggaat ttatgttgga tttgaatgcc 320520
catcaattat caaatatttta gaaccaatga ctggtgattt gtttaatgct agatttgcag 320580
attgtcattt tgatgagaca atattcccat ccttaggggg agagaaagtg gacccaaata 320640
aaagagaagt agatctcaca tggaatgcaa tgcatttgaa aatatatgat ccaaaaacaa 320700
atgcttctga acaagaagtt agaaaaattg tccataacca atatattgca aacagattac 320760
ctgatgcatt tgtagaaaca aagcaagtga caaaatcata tattcctgcg gctaatgttc 320820
cggcacgaat tgaaattcca actgataaca aggccactga aaatgaatct attacacgcc 320880
ggaagcgtgg aaggccactt ggttcaaagg atttgaaaca aagaaaatcc aaaaggttga 320940
atgaaatggc aaatgttatc aaaattacat cttcaatgaa ttccaaagaa gcaagttttg 321000
gagatgatga aaatcacaga gaaggagaaa acaatataaa agataacaat gaaatttcga 321060
ttaattacat ttcaaaaatg caacttaatc gaaagaatgt tattatcaat gatgcatttg 321120
cgtattcaat ggcaaatgaa ataacacttg atgagaatga cgtagagcca agaacgctac 321180
aagagtgtcg gcgtaggaat gattggccaa aatggaaaga tgcaattcaa gcagaattaa 321240
agtcactcga gaaacgagaa gtttttggac aaattaccca aaccccaaag ggtataaaac 321300
cagtcggtta taaatgggtg ttcgtgagaa aaaagaatga gaaaaatgaa gttgtcagat 321360
ataaggcacg acttgtagca caaggttttt cccaaagacc aggaattgat tatgaggaaa 321420
catattctct agtagtagat gcaactacac tgagattttt gataagccta acggtctcaa 321480
acagattaca aatgcggctt atggatgttg tgaccgcata tttatatgga tcacttgata 321540
```

```
cagaaattta tatgaaagtc cctgaaggac ttcaattacc agaaaaccac aaaccacgag 321600
aaatgttttc cataaagcta aaaaggtcac tttatggcct aaaacaatct ggaagaatgt 321660
ggtacaaccg tcttagtgaa tatctcctga aagaaggatt taaaaatgat caaattagtc 321720
cttgtgtatt cattaaacgg actcaatcag gattttctat aattgcagtt tatgttgatg 321780
atttaaacat cattggaacc cccaaagagc ttgaagaaac tgcaaaatac ctgatgaaag 321840
aatttgaaat gaaagatctt gggaaaacga aattttgcct tggattacaa atagagcact 321900
taagggggtgg aatctttgtg caccaatcca actatacaga aaagattcta aaagatttc 321960
atatggacaa agctcatcca ttgagctccc caatgatagt gagatcatta aaacaaaag 322020
atgatccatt tcgaccttgt gaagaaggcg aggaaattct tggccctgaa gtgccatact 322080
taagcgcaat tggagctttg atgtatctag ctaataatac aagacctgat attgctttcg 322140
ctgttaattt attagctaga tatagcaatt caccaacaaa gagacattgg gacgggataa 322200
aacatttgtt gcgatatctt cgaggaacta aagatcttgg attatttat cgatcaaagc 322260
aagatgctac acttgttgga tatccagatg ctggatactt atcagatcct cataaggcta 322320
aatcacaaaa tggatatgta ttcacttatg gaggtaccgc catatcttgg agatccacaa 322380
aacagacact gacagctaca tcatcaaacc atgcaaaatt gatcgctctt tatgaaacaa 322440
gtagagaatg tgtttggtta aggtcagtaa ttggtcatat tcaagaagaa tgtgggataa 322500
actcgataat aaattctcca actgtaattt ttgaagacaa taccggttgt attgaacaag 322560
ttagtgaagg cttcataaaa ggggatagaa ccaagcacat agcaccaaaa cttttcttcg 322620
cacatgacct ccagaagtat aaaatagtaa aagtcaaaca aattcaatca agcgaaaatc 322680
ttgcagattt gttcactaag tcccttccat caaagaagtt cgaacaactt gtacgagaaa 322740
ttggaatgtg tcatctacga gatatttgtt gaactcaggg ggagaatcat actcactgca 322800
ctctttttcc cttcgttcag gttttatcc cattgggttt ttcctgacaa ggttttaat 322860
gaggcggtgt taatagaaa tattgtaata atatttaca cttttgataa ttagaatgca 322920
ttcaagggg agtgttaaag tatagtgtga aaggttaaa tatagtgtga aaggtaatta 322980
atgtatttac cttaatgtga atgcatttat ggataaaatt tgcctataaa tatggatctt 323040
caccattgta aaaactacac caatgagtaa aaacatcact ttctctaact ttactcatta 323100
tacttcctct ttatctctct aaattttaac attcccccact ttatgttgat aggaaactta 323160
ttcccataat accgtccatg taggatggct ttttttaaaaa atagatttgt tagattaaac 323220
cgctaattga attggcgatt tgataccaat actaaaatcg ccacctaaga taaaagttta 323280
ggctaatttg ttcttttttaa aaaatatgtt ttattacaaa accgctacct gagattaggg 323340
gtgtaaattc ggtgtttggt ttggttttga tgcaaaacca aatcaaaccg aataaaattc 323400
ggtgttaata ttttccaatc caaatccaaa ttacatttt caaaaaccaa atcgaaccga 323460
accaaatttc atttttatcaa tccaaattga accgaaaaac caatttaacc gaaatttaac 323520
cgaaatttct aaatgaactg aacaatctta aaatcatttt ttctggctaa tgtagtacca 323580
tacagaattt aaataagaag cactacacaa acatttttctt gtacttacaa attaaaatga 323640
aaatgaaaat ttatataaac actaagaata actaatttta gtgattcaaa atctaaatca 323700
aatgcaatag aatacacaat tgccaaaatt agtagccaat agtttgaatg tcatattcaa 323760
gatattaaag ttcccaagaa gcatttcaa cttgattctg gcttgataga tgcagattat 323820
ctctcttatt ttcaattctt cttccttgaaa tttaacctaa acaaaagtaa aaccaaaaat 323880
catgaccaaa acataaaaat ccaaattaaa ctagaaaata aaactcaaaa taaatgaaac 323940
```

```
ataataaaat ggtcaaaatt agaaaatgaa aatgaaaaga aattaaaaac tatatctagt 324000
aaatcataaa taaaaacgaa atcaataata aaaacagtaa aattcggaga tggtgagatg 324060
agaaacaatc attgagagag agactatgat gaacaaaatc ataaacaaaa aaatgaaacg 324120
taaccctcta aacataaaag taaaaacgaa atcatagaca aaaaatgaaa ttacaataaa 324180
aaaacaaaga aatcaaacct ttagtctagt aaagtgaaga acaatcggtt agttgctttg 324240
ttgataaagt gtagtagaga gccttagaga gtgaaacttt gggagagaaa gagagagaat 324300
gcgccgcagt agggattgaa agagtgagtt gtgtttttt tagggttttt aattttatac 324360
tccttgggtt gggctttaaa tttacactcg ggagtcggga ctaacataaa tacccttata 324420
atttcggttt tcggttttt cggtgtagaa acccttgca ccgactccaa accatacacc 324480
gaaatgaaaa taaaatacaa tccaaatcaa accaaatttc aaaaaggttt ggtgttcggt 324540
ttttcaccaa attaattaca cccctacctg agatgacggt ttgcttaagc aggttaaaaa 324600
aaataaaaca aaaatacgtg aattttttaa tacggtctaa tcaaggaata agataaataa 324660
attaagtgtg aatatatata tatatatata tatacatata tatatatata tatatatata 324720
tatatatata tatatatata tatatatata tatatatata tatatatata tatatatata 324780
taggggaggg atccaatgag aagggtattg aaaatgagaa gggtaagaag gattctacac 324840
ccttgatttc acttacttaa aaaaatctat ggtcacgatt gagccaaaaa cacataattg 324900
taaaagtaac tatgttacac agaaaggtaa ctatgatata aattttaaaa tgttcttttt 324960
ttataacata gtatcctttt taggatacat agtaaccaaa caattcaaac aaaaatcctt 325020
ctcatccttc tcattttaaa atccttctca tttgatccta tatatatata tatatatata 325080
tatatatata tatatatata tatataat atatatatat atatatatat atatatatat 325140
atatatatat atatatatat atattatagc aatatgtatt tagttaatca caacatgcta 325200
atagttaata agaactatat tgaactataa tacaaagaga ataagtttgg aacaatgttt 325260
accatgggaa atgtgctgaa gaaaaatctc tctttctttt cctttgaatg agggttttt 325320 tttttctgtt tgcttcattg agaatgtgtg tgcaagtatc aatcatttcg tttacaatat 325380
gagtgccctc cttcaatgat gaaaattcga atctggtgat attgttcaag ccatcataaa 325440
ataacaattc ccttcatatt catcaacgta aagtaacatt agtatgttgt acacaaatat 325500
aaggctagaa ttgaagttta attgtaaagt ttggaacact tacgtttcgt ctttaagcaa 325560
caaagcataa tcaacaactc tctttaattc aacttctgat aatggttttt cattctgaac 325620
tataaatgga gatctttggt tcagtggaag gctttggact attcttctcg ttctcttaca 325680
ttgacctact gttttgatc tcttacgttt aactttcggt tgttcactag gagcatcatg 325740
agcagcggta ggttcgacgg atacaacagg agaaggggaa tcatgagcag ctggactaga 325800 attttttcagt ggggaatcat gagattgtcc tgcaagataa aaatccagcg gtggtaaata 325860
acttggcttt cacacaaaac aaccacattt ccatcagagt ttgtaacagc tcagaaattt 325920
ataacagcaa ttcagaaatt tataacagca attcaccagc agatacaaca ggtgaagaat 325980
gtcgctagta ctagctaata caaaatgttg aacaatgtcg ctagtactta catagcatgt 326040
gatcactaac taatacgaaa tgtagaacaa tgtcgctagt acttacatag aatgtaatca 326100
ctaaccaatt tgaaatgcag aaaaatgtcc tgctgtttaa cttcagttg ttcaacaatt 326160 tgtattagtt agtgatcaca ttctcttaca ttgacctact gttttgatc tcttacgttt 326220 aactttcgat tgttctctag gagcatcatg agcagcggta ggttcgacgg atacaacagg 326280
```

```
agaaggggaa tcatgagcag ctagactaga attttcagt gggaaatcat gagattgtcc   326340
aacaagataa aaatccagcg gtggtaaata acttggcttt cacacaaaac aaccacattt   326400
ccattagagt ttgtaacagc tcagaaattt ataacagcaa tttagaaatt tataacagca   326460
attcaccagc agatacaaca ggagaagatt gtccaggttc aggagcatca tgagcagcag   326520
taggttcgac ggatacaaca ggagaagggg aatcatgagc agctagacta gaattttca    326580
gtgggaaatc atgagattgt cctgcaagat aaaaatccag cggtggtaaa taacttggct   326640
ttcacacaaa acaacacatt tccattagag tttgtaacag ctcagaaatt tataacagca   326700
atttagaaat ttataacagc aattcatcgg cagatacaac aggagaagat tgtccaggtt   326760
cttgtgtttg tgcccaaact tcataaattt cagtgatgtt tgaagcacat tcttcaaaga   326820
acacctccat ggcaggggca gacccttcag cctcttgggc agctgcccaa actttataaa   326880
tctcagtgca atttgaagca aattttttcat agaactcctt catcttaggg gcaggctttt   326940
cagcctcttg ggcagaccga gcctcttggg caggcttcaa tcggcgcatg acaacaccat   327000
ttccataccc cttttctgc tcaatattta tccttgattt aaccatatcc tggttccata    327060
ctgatataag agggaattgt cttggggatg taaaatttcc tcttttcatt ctatcaaaat   327120
agttaatctg gtataaaagc ataaaaaata agtttatta aacttttgta catcataaag    327180
aaactttgta acagttattt attcttacca tgagaaaggg cagtggacct gtgaagaatg   327240
ttgatccatc cttccactct gtaactgagt ctaacagttg ttggtgagta aaagaagacc   327300
agtcataaga gtttatttt gaaatatctt tacaacaatg taaaaattta agtaaacta    327360
actgattgtt tgttgaccta atacaacaat ttacagcagc tacgacaaaa tttaataaaa   327420
actccgcaga aacttcagcc tctcttgttt gttcttctat tcttttcact agactggcat   327480
ttgaaggact tccatacgtt aatccgaatt gggctctcca tttctgaata cacacagtat   327540
aacacaacac aaaacttaaa gtgtataaca acaaattaca gtttataaca ataaaataaa   327600
agtttacgaa tgtcaagcac acaaccaaaa ttaaacaaat cgatttacga atgtcaagca   327660
atcaaccaac agcaattcac aagtttgtaa caacaatagt acaacgacaa caactaccca   327720
aaacgaccac tgacaacatt tctgaaatag agtcaatttc atcccaaaac aaacttctgc   327780
tttattgtta taaacttctg tattgtgtct taaaatgaac aaatatcatc aataaatgaa   327840
caaatatcat caaaatcaac aatcaaaagt ccaatttaac accgcaatta agcaaaaaca   327900
cttcgaatta tagcagcacg ctggaaaaaa tataatcgat ttacgaatgt caagcactga   327960
accaaaatta acaaatcgat ttacgaatgt caagcattca accaacagca attcacaagt   328020
ttgtaacaac aatagtacaa cgacaacaac tgcccaaaac gaccactaac agtagcagca   328080
gcagacgcaa ccaataacag cagtagcact actgcagcac caacagagcc gaggtagcag   328140
cgcctccaaa tcgtccctaa caacaaacaa ctactacact tcacacaaac aaccacaaca   328200
attcacacaa aacaaccaca tttccatcaa aagtcaaata tgattcttaa atcttcacat   328260
ttaagtcaaa tatgattctt aaatcttcac atttaactta aaacatattg caaatttcat   328320
tcacatttct gaaatagagt caatttcatc ccaaaacaaa cttctgcttt attgttacaa   328380
acttctgtgc tttattgtta caaacttctg tcacattgtt tatatgcgat gaataaatat   328440
gtgaaagcca agttacttac caccgctgga tttttatctt gcaggaaaag aaaaattaaa   328500
cttatccacg gaccaccact gagagtgtct catccagtgc tattactgta atatgttgag   328560
agaattttt ttttaagatt tataatgttt ttatgttgag gataagttct ttgaactttg    328620
tgataagctt gttttcatgg attttattg acagatgatt gaagcagaga agaaaaagtc   328680
```

```
ttgaaatggt gcaactgtgt agaaccctct caagtaagtt gatcattaca accttcaaat 328740
tgatatataa gtttacacga ccctcaatta tttatggttg gcagttgcat atgcagttta 328800
tctggaaaat cccgtgtttt cggagtgtgt gggctcctgt agaatatgta tctcttgtac 328860
aacccacttt cgatacatcg gttacttgga aaactcgtgg tttcaaaaga aagaattatg 328920
atgtggatga gggtagttcc aaaagaatga gctatgatgt ggaacaaaat agaattcaag 328980
tgccgagtgg acttgaacaa tatttactct ttctatactt tggcatgtca aacttacaag 329040
caatgtatag aaagattgag ataatattga cactttatcg atctcaaacc attttctcaa 329100
aagagcccat tgtaagtttt gtattgtaag tttttgcttt cagctactaa actattaatg 329160
tcacgaacag aagctacatc ctcaagttta cctctaaagt aattaactga ctggaatgtc 329220
tcaaccaaat tgaagtaaaa tttgagaatg tagcttataa tgggctcttt tgataataaa 329280
ctcttgtatt ggttcttcat taaaatcagg acaaatagat attgtttttt ctaagatgta 329340
gcttataaga tcttttgaga atatactcat gtattggttc ttgaatcaaa atcaggacaa 329400
ataaatattg ttttcttct taggaccta acttaagttt attacaaagg ctccgtttgg 329460
tagggcgtaa aacattttcg ctgaaaagtg ttttcccatt ttatattgtt tggtttaaag 329520
taaaatatta aaatgtaaaa cttggggtgg aaaataggaa aaatcatttt ccaccttatt 329580
gaaacatttt tcccccaatt tagaaggaaa acattttca tcgcaagtgg agggaaaaca 329640
ttttcgatca caagtggagg gaaaacaatt gaaaatctgt gtatatgtta tgaatcagag 329700
ttttgatcga atctaatcac aaattcaaga aagtaataa cttattacaa acttacttat 329760
tcttaaaact gtaactcaac tattttgagg atcgcattat caatggcgga gaaacgtagt 329820 tgattttta ggattcgaac cttattctca aaaagctaaa ggataaggtt cgaatactca 329880
aaaatcaact acgtttgtct gtcattgata atgggatcct aaaaaatagt tgagttacgg 329940
ttttaacaat aagtaagttt gtaacaagtt attacttttc ttgaatttgt gattagattc 330000
gatcaaaact ctgattcata acattataca cagatttca attgttttca ctccacttgt 330060 gatgaaaat gttttctctc cacttgtgat ggaaaatgtt ttctttctac attggggaa 330120 aatgttttca ataaggtgaa aaatgatttt ccccattttc caccccaagt tttacatttt 330180 aatatttta actaaaccaa acaatataaa atgggaaaac actttcagt gaaaatgttt 330240 tacgccctac caaacggagc cttagtaata aacttaagtt aggggtccta agaaggaaaa 330300
acaatatcta ttcatcctga ttttgatgca agaaccaata caagagtata tattctcaaa 330360
agatcccatt ataaggtaca tcttagaaaa acaatttgt cttgattttg atgcaaaaac 330420
caatacaaga gtatattctc aaaagagccc attataagct acatcctcaa atttcacttg 330480
aatttggttg agacattcca gttaggagtc agttaattac tttagaggta aatttgagga 330540
tgtagcttca gttcgtgaaa ttaatagttt agtagctaaa agcaaaaaac ttacaataca 330600
aacttacaat gggctcgttt gagaaaatgg tgtgggatcg ataaagtgtc aatattatat 330660
caaactttct ataaattgtt gtatcgtatt tatagtgttg gttgacttt gatggaaatg 330720 tggttgtttt gtgtgaaagc caagttactt accaccgctg gatttatct tgcaggaaaa 330780 gaaaaattaa acttattcac cactgagagt gtctcatcca gtgctattat tgtaatatgt 330840
tgagagaatt ttttttttt ttaagattta taatgtttct acgttgagga taagttcttt 330900
gaactttgtg ataagcttgt tttccttggat ttttattgac agattattga agcagagaag 330960
aaaaagtctt gaaatggtgc aactgtgtag aaccctctca gttcatctgg aaaatcccgt 331020
```

```
gttttcggag tgtgtgggct cctgtagaat atgtatctct tgtacaaccc actttcgata 331080
catcggttac ttggaaaact cgtggtttca aagaaaaaa ttatgatgtg gatgagggta 331140
gttccaaaag aatgagctat gatgtggaac aaaatagaat tcaagtgccg agtggacttg 331200
aacaatattt actctttcta tactttggca tgtcaaactt acaagcaatg tatagaaaga 331260
ttgagataat attgacactt tatcgatctc aaaccatttt ctcaaaagag cccattgtaa 331320
gttttgtatt gtaagttttt gctttcagct actaaactat taatgtcacg aacagaagct 331380
acatcctcaa gtttacctct aaagtaatta actgactgga atgtctcaac caaattgaag 331440
taaaatttga gaatgtagct tataatgggc tcttttgata ataaactctt gtattggttc 331500
ttcattaaaa tcaggacaaa tagatattgt tttttctaag atgtagctta taagatcttt 331560
tgagaatata ctcatgtatt ggttcttgaa tcaaaatcag gacaaataga tattgttttt 331620
tttcttagga ccctaactta agtttattac aaaggctccg tttggtaggg cgtaaaacat 331680
tttcgctgaa aagtgttttc ccatttata ttgtttggtt taaagtaaaa tattaaaatg 331740
taaaacttgg ggtggaaaat agggaaaatc attttccacc ttattgaaaa cattttcccc 331800
caatttagaa ggaaaacatt tttcatcgca agtggaggga aaacattttc gatcacaagt 331860
ggagggaaaa caattgaaaa tctgtgtata tgttatgaat cagagttttg atcgaatcta 331920
atcacaaatt caagaaaagt aataacttat tacaaactta cttattctta aaactgtaac 331980
tcaactattt tgaggatcgc attatcaatg gcggagaaac gtagttgatt tttaaggatt 332040
cgaaccttat tctcaaaaag ctaaaggata aggttcgaat actcaaaaat caactacgtt 332100
tgtctgtcat tgataatggg atcctaaaaa atagttgagt tacggtttta acaataagta 332160
agtttggaac aagttattac ttttcttgaa tttgtgatta gattcgatca aaactctgat 332220
tcataacatt atacacagat tttcaattgt ttccctcca cttgtgatgg aaaatgtttt 332280
ctctccactt gtgatggaaa atgttttcct tctacattgg gggaaaatgt tttcaataag 332340
gtgaaaaatg atttttcccca tttttccaccc caaattttac attttaatat tttacactaa 332400
accaaacaat ataaaatggg aaaacacttt tcagtgaaaa tgttttacgc cctaccaaac 332460
ggagccttag taataaactt aagttagggg tcctaagaag gaaaaacaat atctattcat 332520
cctgattttg atgcaagaac caatacaaga gtatatattc tcaaaagatc ccattataag 332580
gtacatctta gaaaaacaa tttgtcttga ttttgatgca aaaaccaata caagagtata 332640
ttctcaaaag agcccattat aagctacatc ctcaaatttc acttgaattt ggttgagaca 332700
ttccagttag gagtcagtta attactttag aggtaaattt gaggatatag cttcagttcg 332760
tgaaattaat agtttagtag ctaaaagcaa aaaacttaca atacaaactt acaatgggct 332820
cgtttgagaa aatggtgtgg gatcgataaa gtgtcaatat tatatcaatc tttctataaa 332880
ttgttgtatc gtatttatag tgttggttga cctctgatgg aaatgtggtt gttttgtgtg 332940
aaagccaagt tacttaccac cgctggattt tatcttgcag gaaaagaaaa tttaaactta 333000
tccaccactg agagtgcctc atcccatgct attactgtaa tatgttgaga gaattttcct 333060
tctctgcttc aatcatctgt caataaaaat ccaagagaac aagcttatca aaagctcaa 333120
agaacttatt ctcaacataa aaacattata aatcttaaaa aaaaaattc tctcaaccta 333180
taacagtaat agcattggat gagacactct cagtggtgga taagtttaat ttttcttttc 333240
ctgcaagata aaaatccagc ggtggtaaat aacttggatt tcacacaaaa caaccacatt 333300
tctatcagaa gtcaaccaac actataaata cgatacagta acacaatatc gcaacaacaa 333360
tagtacaacg actacaactg cacaaaacga ccaccaacaa ctgtagcagc agcagacgaa 333420
```

```
accaagagaa caagtttata acatcaattc aagtttgtaa caacaagtta ttaaagttta 333480
acaatatcaa tgtttgtaac agtaactcag aaatttataa cagcaattca gatatttata 333540
acagcaattt acaagtgtgt aacaacaata gtacaacgac aacaactgcc caaaacgacc 333600
attaacaaca gtagcagcag cagacgcaac ccacaacagc agtagcacta ctgcagcacc 333660
aacagagctg aggtagcagc gcctccaaat cgtccctaac aacaaacaac tactacactt 333720
catacaaaca accacaacta ttcacacaaa acaaccacat ttccatcaaa agtcaaatat 333780
gattcttaaa tcttcacatt taagtcaaat atgattctta aatcttcaca tttaactcaa 333840
aacatattgc aaatttcatt cacatttctg aaatagagtc aatttcatcc caaacaaac 333900 ttctgcatta ttgttataaa cttctgtctc attgttataa acttctgtat tgtgtcttaa 333960
aatgaacaaa tatcatcaat aaatgaacaa atatcatcag aatcaacaat caaagtcca 334020 attaaacacc gcaattaagc aaaaacactt cgaattatag catcacgctg gaaaaaatat 334080
aatcgatata cgaatgtcaa gcactaaacc aaaattaaac aaatcgattt acgaatgtca 334140
agcactcaac caaaacttaa agtgtataac aacgaattat agtttataac aataaaataa 334200
aagttataac attagtagta ttcagtcctc aatacctgaa agaaaggttg attttctgca 334260
tctgcagctt tggagacatc aatcttagct cctctggcgg gaactccata gaccagatgt 334320
acatccttag gcttaatctt tatccgctcc ttggaaggaa atactaataa tcttctagca 334380
acgtcaaagc tctttaccaa ttcagcacag aaaaatcccc tggatgtcca gccaatatcc 334440
aggtctaaga accctccgaa accaatattt cttatggctt ccttgtgatt ctcagacata 334500
ccctttttaa gcatattgat gaatgctttt ggaggtattc tttgtactaa gagatttctg 334560
tctgttgctt caacactcct gataagagat tatgtatgca agataattta attgagccaa 334620
gacattatga acaataaaat gcataacaga catttacacc tccaatataa caatattaca 334680
gtttataact gcaccatgtt tgatatggtg caggtcttaa ggtgaaccaa gtatccttgg 334740
cacacttggt tcatacgcag actcaatgaa tgtaaaggat tatcaagaag tgaacaagac 334800
cgtgaaaaac aaccagaaaa tcactaataa caacccacag aaccagcagc acaattatgg 334860
cgaacagcag accttggaag caacttctag aaaaaatacg tgcgtctttg aagactccaa 334920
cagtagtttt ggaatcttta cacatgggcg ttgctgttat ggtccaagaa cacttctaac 334980
catcattgga gccaccagaa acaagactca aggtcccctg gtcaatcgaa gaagctgtca 335040
gaacaaacca gtgcacacgt gaaaactcgc gaccagctga ccttgtgcaa catgtggaga 335100
acaggtctgg acatcaatga ccaagaaaac acaaggaatg gcatcttggt acatggaact 335160
tgaagtcaag gaccaaggga attctatgag tccttagaga atcatctgga cccatgtcaa 335220
ggtcccctgt tcagctgctg ctccgtcagt gttcatttgc tgtattttcg tgttttttt 335280 aattttgggg atcatattgt gatgtctttt caaaactgtt tttacaccgg attcttgaag 335340
aagtggttga ataccttgt gttgagggta ttaaagagct tgaataggtt gttgagacaa 335400
cttacatgga ggatatgggt tctacaaaag agtgcgtaga ataattgat tctcatccaa 335460 gattggcggt tcttttacaa attgagcaag ctagtaagta tgggttttc aaggtggatt 335520 ttgtgcttga aaaatcacct ttattggagt atgttcatgt gagtagattt gttgaattta 335580
atcctacaaa gattcgaggt agagtttttg ctaagaaggg taaaatgcaa caagttagtt 335640
ggagttgtgg caacacaagc aagctaatca acttggtatt ggagtatgtt catgtgagta 335700
gatttgttga atttaatcct acaaagattc gaggtagagt ttttgctaag aagggtaaaa 335760
```

-continued

```
tgcaacaagt tagttggagt tgtggcaaca caagcaagct aatcaacttg gttagtttgt 335820
ttaatatatg ggtttggttc atcaagcaag tgagggcatt catccttaca tgcttgatga 335880
ttttgggaaa cgtggtttct aagttaagtc aaaagaatgg tagtgtagtt gtggaacaga 335940
ttcgtaataa aacaagtagc aaggtcagca tgtggttcgt tattttggta gctgatgtag 336000
aaaatcagta aatgcaagag caaatcaatg ttctgttcag atgtgcagta ttgggtcaaa 336060
atctgaattt tgtgtgtcgt tgagaaggtt tttgatcatg cttgaaactg gttggttcgt 336120
taaaggtgca gcactgaagg aaaattatta gtgcagtaag tacagcagca agttgtttgt 336180
tcagcacata aaacatgtgc agcacagaag gttcaggaac atttatatgt gcagcaagat 336240
gcttggttta gctatgatca ataggaagat cacttgtgca gtttgggttg tgtattcaga 336300
acagcaagac atcgtgaaaa ttaaactagt acagcagcag cgtaggtatt ggttcaatat 336360
atgcaattca gtttgggtgg ttatgcgtta tgtcagccag cagcattata tgcacaagta 336420
tgtcacgtgc ctcctaaccg ttaattttag atgggctgag ttgtttaaag ccttaactaa 336480
ttttagagtg tctcttagcc atgatgcatt gtaaactcag ttttgatgat taataaagtt 336540
tctttggaga atgcttggca tttccttttc tatcttcttt tctttgtgag agaagcaacg 336600
ggagaacata gcaagattca accaagatca aggtgagtga agctttgatt gaagttgaag 336660
ggcaagggtt gaaaaggtga gtgaagcctt gaaacgtcca aaatcagaga aatctgatca 336720
tatctttttc aatttcagta gtttttagag ggtccaattt aattccgcaa caacccaat 336780 ttggtctcac ctttgggtcc aaatatggtg caaatggtat caaagcctta aaatccttgt 336840
ggggtgcata attcaattgg ttttgttgga agaagcagc caaagtcgac aaaaacaaga 336900
acagaagctg tcagaaactg actgcatttg gggtcgaaaa cagtggcgtt tcgggaatag 336960
tattgtgaat tcttttcaaa actaaattta cacgggattc ttcattgagt tgagaaacat 337020
ttggctttgg aatcattgga attggtgttg tggttaagga gatatgaaaa caatattaaa 337080
gtttataaca acaattcact agtttataat agcaattcaa atatttacaa cagttccacca 337140 atttataaca gcagttcacc agtttaacag caattccaaa gtttgtaaca atatctcaga 337200
aatttatagc agcaattcag aaagttatag cagcaattca ccagtttata acagcaattc 337260
acaagtttat aacaacaata ttgaagtttg taacaacaac attattttgt aacagaaatt 337320
caccagtttg taacagcaat tcacaagtac ttaaatttgt atgtaacaag tatctaattt 337380
cacagaaaaa tcagcaattc taaaccaaaa aaatggcagt tactaaaggt ttgaattata 337440
atacattctt ggtcgtgttg gtatgatagg tgctgtcgat ttttctgcgt cattctcgat 337500
tcttctcctg catcgtaaga atgtcggata ttcacaaaaa attctatgaa aatcggatat 337560
ttacagttat aaaaattaca acaatgctta cttgaacttt tcgatttcct tctttgatgg 337620
ttttgcagat ttttttccca tttcgcttga gaattccttc tttgatggcg tcaagcgatt 337680
ctccaaggag aattagggtt tggtgaatga agcgaaacag tcagcgtcag cgaggctgcg 337740
acctgcgagg gaaccaagga gcagcagcca gcaggccaaa cgtccggtgg aaagaagcaa 337800
ctcaggtgaa gcgattctcc gtcaggcgtc aagcgattct ccaaggagaa ttagggtttg 337860
ttcactttga gaagggtgtt tggtagaatg tagttgattg atttacttaa gtgagaggaa 337920
ttatgaatat gaagtgagtg ggtgaagaaa agcttttttct taaggtagaa ccagtcgcac 337980
agggaggaag aaagcaagct gatgaagaga aactgaaaga acgcaaagtg aagagcaaac 338040 gttttttttaa ttttttgtaaa tgacccagaa atttaagaga aagacccaga aattaaaaaa 338100
aaaaaaaaaa aaaatcattg atgttgatga agattgttca gtaattctga gagaaaatag 338160
```

```
agttgtttta ttttatgggt gttgttctac attcttactt cttagtaggg aaaggaaaga 338220
gaccgtttgg gtttgaatta agttttggta agttaggatt aggtttacat catttgatat 338280
ttttttccca tttcgcttaa aattccttct ttgatggttg taaaatttcg atttacagtt 338340
taaaacggaa gttttaaaat caaatggaac tatgacttgt ttgtcaaata tattttcaga 338400
gaattctctt aattccactt tgtgatattc gaaattgcga atcgaagaat tgttaggtt 338460
tttgaattag acaattctct taggtgtcaa atataaaatc aaatgcttac tttttttttg 338520
aattattcaa atgcttactt tagttccacc tcataacggt tttcccaagt aactgatgtg 338580
ccgaaagtgg gttgtgcacc aggtgcatat ttttcatctc tatgttggtg cctctaggga 338640
gtgtgaaccc tagatctgcc actgtatgtt cttttgtgct tctgtttgtt ggaacattgg 338700
ctgttcactt tgcttcactc tccttcacca gcttgcttga cacttcttgg ttgttcacaa 338760
taaataaatt gatcatataa tgtggactac tccctctttc cacttcaatt caactattta 338820
tttagttcat ctaacaatga atcatttatc tctttattta aataaaggaa aaattacaaa 338880
aaactaccta ttctaatggg taacttgcaa aaaactacct attctaattt ttttgcaaaa 338940
aactacctta tatgatatta acgtttgtta aacacaacct cttgacggtt tcagttagtt 339000
gaccgtcaaa agttagtttg acttttcacg tgacttgcac gtgaccttct tttaaaccttt 339060
tccctttaat tgtttctttg atttcttagg ttttaaagca cgtttttagt tcaaacccttt 339120
cccctttccc caatttcgtt caaaccttc acatttcccc aatttcgtat gaaccctaat 339180
ccgcctcttt ttctttcaag cccaaatcaa ttcatggatt cctctcactc caaacaatcg 339240
aagcttgaca gatgtggttg cgaatttcct ttttgcacag cgaatttcgt ggactaaaga 339300
aaatccaggt agacgtttca atgcatgcca atttttcgat cctaacacta attggagggg 339360
atgcaagaag ttttagtgga tcgatgaact tgaaatggtt gatttcaaga tattgacatc 339420
aaggctttgt tgcttggaac atcagaaaga acaagcaatt tcagaataca aaaggcttat 339480
ttcagaatac aaaaggctta agaagaaatt gatgaaggag agaaagcttg gaaagagat 339540
atcattatat acataactag gtcgacccaa cgggtcaagg gtcgggtaat attttaatgg 339600
gtcattagcg ggtcgggtta ataatggggc gggtcattaa cgggctttgg tgtaaagggt 339660
cgggccgggc cgggtcggat aattataagt attaattgcg aaaataaaat ttaccacttt 339720
tttttatttt tttaaatgat attattatat acataactag gtcgacccac actacatata 339780
atatatccgc catttactaa cctaaaatgc atatttgttt tctaaattta ctaatctctc 339840
ttattactca gtttattttt tcgcaaataa ttaattcagt taataattgt aatattatta 339900
atatactgat aactacattt gaatgaaaat ctttgaataa gataaagata atatggtgtt 339960
gaatcattaa taaaaactag aattttttata ttaatatata ttaaaaaaac cgtgcattgc 340020
acgggattct atactagtat aggataataa cagtaattat acagtaatga aatagattaa 340080
attaggaaat taattaaaag gaaaacaaac ttattgttac ggtattgata ttccccaaac 340140
ttctcaaatt aaatactcca gtttctaaat tccttctgta tttccaaagt aattttatca 340200
attccccaaa tttaagtgtc caaagtaatt gaccaacatt aatggcatta tccgtcccct 340260
tcccgtccgt caatcttctc aattttccca taagttgatg tttaagcatg gcattgtaat 340320
gataggtttt tcatcaattt aatttgattt attttatctc atgcaacaat caatttgtcc 340380
tctctagatc aagttcattt agatttaaaa atttgacaat atatttattt tccccaaacc 340440
aagttcatca tttcacgctc atctcatagt tggttggtcg gcggtcgtcg gcggctttgc 340500
```

```
ggtaagttgg tcactgtatt acagttttac ttcatcttga attgtattat tagtttttac 340560
tagatttcga atgattttt  attggatatt gaagactgaa tttcaattgt gatttttgat 340620
gaattttga atgatttaa tttggtatag ctttgattga agctttttat tgaatttcag 340680
taatagtttt tactagattt ggattttaa tgaatgattt tcatcttgaa tttcagcatt 340740
aggcttgtag aagatcctta agtatgtttt atcattatca ttttttttt tctaaattta 340800
tcttttttta gtaatagtca agcttaatat tattttctca caattttttt tactttaaat 340860
tcttcagaaa ataataatgc taattagtaa ttatgatagt aattatgatt tcataaaag 340920
gatgtatgta gagatatgta agaattattt tttaaattag tttgtctttc tatgctgtat 340980
ccctgtattg atgattcctc tactattagt aaatttgcac ttgaaatata tttctcataa 341040
taaaagggcc ccaatctacc attttgccta gggccccaag aaagtcaggg acgggcatgt 341100
caagacgcaa tctatttctc ttgatttgct cctcactttg ctcttcaaaa gcatgtgaa 341160
tatgtccttt ttgatttaga aggtcttaa tagtttgaac tgcattatta tgaggggagc 341220
aaggaccttc tccaatatgg gcaagaaagg cacactttt cccatcattg accttttcc  341280
aatttttata cccctttcta gtaaatgtat ctgtgcgagg atttggtttc tctgagcata 341340
aataacactt aagacaaaaa gcagcatctt gagctggtga atactctaac caatctttga 341400
aactatcaaa ccaagaagat tgaaatctac gtctagtttt gctgtcaagc ttgtcaaaag 341460
gataactttg tagaataggt tgataaggct tcatcttcaa ataagctctt cgtacttcat 341520
cgcgtttctc cggaggataa aaccacatag gtggacgcaa tccgggatct ctttctaaat 341580
taatggtatc gacatttgat aggtcaattt taggaacttt agaaggacct tcatcgtggt 341640
ggtcattgtg tgaaactctc gatggatttc cttcgttacc aatcgtagca ttcgtatttg 341700
agaccaccgt tcttttaaag aaagatgtaa tattttttg tgtattcata ataaaacctt 341760
aggcaattaa aatccttaga tagtagaaaa attcaatata ttaggcaaca attgtaaaat 341820
tccaattaca taccgctttt attgtgtaga tgaaatttag agagtgttta aatatataaa 341880
tgagattaaa agaaaatgat gaattattat tcaaaaataa aaatgataca aaataagtga 341940
gacgaaataa aagtaattat gagacgaaat aaaaataagt agtggcgtgt acaaatttat 342000
caaatgctaa aggacactac tcttacctac aaggcctaaa agctcaattt tcaagcatac 342060
tactctacca ttcccatttc ccaatttatt aaaactccaa aatcctcctt cctctagaat 342120
accaaaatcc aaaaactcca tggattattg gatttctaat tatactccat ggttatattc 342180
atccatttta attttttctt taatttaatt tcattcttca acaaaattga aaaatttct  342240
cctgatcaca ttctctcatg gtcttgataa tttgaagtta gtaaaagaaa ttaagaaggc 342300
aaatgcaaca agtacaaaaa tactcacttc ttattgaact ctatttcaag tatatccatt 342360
cgattaggaa ttagggtttt atttaatcga tgataataaa agttgtttct aaaaaaaaat 342420
tagggattag ggttttattt aatcgatgat aataaaagtt gtttctaaaa aaattaggga 342480
ttagggtttt ttaataattg attttgttat tgtatggtat attagtgatt caaactaatt 342540
attaataaaa caagaaaaat tttgaacata taccttccc  cttcggcttc aattgtggat 342600
gaacttaatt ttgattatgt tgattcctct ccacccaaat tgctttcttg ttttgttgtt 342660
tcgattgtta aaaaatatga attattttca gttttataga atttaatttc agttatagga 342720
aagttattat atttctataa ttgtgtcttt ttattaatgg gctgaaattt ttaggttttt 342780
agaatatttt cagttatttt ttcctataat tatgaaatta ttgtttaatg ggtcaaaatt 342840
ataaaaaaat tatataataa cattaactat taaaaaaatt tcaaaattct cggggggggc 342900
```

```
aaagcccta cccgaacgta ggaatagacg aaccatttag atggacacat tgatgaatga   342960
tagaacatgt agggagcaat tacgtttaga gtttagacaa acattgtttt gagaaattgt   343020
gcagtatttt acaatccaag ggtggtttag tgactacaag atatgttaca gttaaagaaa   343080
tagtagctat gtttcttcgt gttcttgcac atgatttaaa aaatagaaca atacaagcga   343140
catgtcaata atgaaatcaa agtatggaag aaacatcatt cagttatcac agatattcgc   343200
acttacacca agttcaagtg agatgatgat aagaagatgt tgttatccc aattgaagac    343260 tacgtggaat ggagtgccta ttgtaaggtg caatctcata ggttgacttt atctaaatat   343320
ttgctagtaa tgttattaat tagttttaat tccttattat catctattaa aattctacac   343380 cttaatatttt ttagtatttg cttgtctgtg tcttttgtat tattatctaa taaacaaata   343440
gaggtataaa taacttgtat ttttatcttt ataatattta tctaataatt tttgtaaaca   343500
ggccaatcat gtagcttctg cttatagaaa taagaacttt gatcattggg atgagatatg   343560
tatactattt gccatggata gagctacggg tcaagaagct gagcaacatg aagaatcgat   343620
tgcaaccatg gagaaagaaa atgaaacatg cagtgcatct gaggcaaact cggcaccatc   343680
tgacaagagg gtagattaca tcttccacct tatgacttta ccccctcgcca ctatccctaa   343740 aatcatctcg tatagccaag ccatggaatc atgcaattta gtagccttgt accaatccat   343800
atctcatttt gcctctaatt cttttcaaac atatcgcaac aaagattttt tattaacccc   343860
caaaacagct agcctgttta ataaatgtga tacatgtgat acatgtgatc atgatacatt   343920
cttttattcc tgcgattacg cgtgtctgtc tcacgattgg actccagata tgtaaagagt   343980
gatacagcat atttagtgac agataagatg gaagttaagc cctccacgat ttctttgtt    344040 gtgtcgcttc tcaaaaattt ggatttgaat tacttggaag agcaacacgt tcaagttagt   344100
cacgaacagg taattatttg taactctttt ttattctcag ctctttttt ttttaggtgg     344160 tcaaaggaac cacaatataa atgaagatac taaaaaacta tttaaaatac gtaattaaaa   344220
cttacattaa gaagaattca acgagatctc acttagatat atattttatc ttctaaatat   344280
gtctcaaaaa gttaatcaaa tttatttctt cttaagaatg aaatatttga aatgtgatta   344340
aagaatatag ggagtaatat ttatatgaaa tttcatgcct ctgtatcttt ctcagcggat   344400
gacccccaaa gttcataccct ctaaaaaata aacgaaagtt cgaatgttta taagcaaatg   344460
ttgcaaagtt catatgttta ttaattggca cccatatcaa caaaattca aactactta     344520 caaaaaatat attgatgtct gagaataatt tgtgactgct gacgaggaga gcatgaattc   344580
tccacactgt agtcctagtc ctagcaccat ttcctcaact cccctattt ctcatacccca   344640 ttctcctagt cctagcacca ttccctctac tccccttatt tctcatacccc attctccccc   344700 cgatcatgaa gttctggttt ctcctagtcc tagcaccatt ccctctactc cctaatatc    344760 tcatacccat tctccccctg tcatgaagtc ttggttctt cccctaatga tgaagttcaa    344820
gtttctcccc cccactcatg aagttcaggt ttttaaaaca agatctccaa gtaaaaaaga   344880
atatcaacgg gtcaatcact ataatctaac gccaaagagt tatatgtgtt tctgtataga   344940
tggcgagagg ttaaaccca ctttggagga cgtttttgtac ttgactggtt tacccatttt   345000
gggaaagcca gtcatcttcg acaaaacagt tgataatgat gctttttga gagttttcga    345060 agagcaagga acttattctt taaggttgac aacattgaag aaaattgcca aagatcacac   345120
gagatcagat gataagagga taaaggcaat tctgttgatt ttgatatgtt gtatcatatc   345180
tccttctaca agtggacatg aatgccgagc cactttggtc cagttcgttg aacatttgga   345240
```

```
ccaagtgaac tcatatgctt ggggtgcggc attattggca tatctttata ccgaattgaa    345300
gatgcatgga aaaagaagct aaacaatagc aattcacaag tttataacaa cataattgaa    345360
gtttgtaaca acaatattat tttgtaatag cagttcacca gtttgtaaag caaattcaca    345420
agtacttatt gttgtgtaaa tatactagta tttatcacca actattcaaa acctgatttc    345480
tcggggtaaa agtatcagtg gaaaatcgcg cgttttttgta tggtactaca agaacaactt   345540
caatccagat caaattagtg ccaaaataat acattaaatg atccaggctc ctacagaagg    345600
aacgaagttg gcattaaaac atgtcaattt acaaaaattt aatcccaact tataataata    345660
taaatcctac caacaaaaat ctaaatccac ctattcccaa cttataataa tgttgttgtt    345720
cagctacaag ttcaggcttc aactacataa aacaatgtaa agtttaatca ccaagtcgaa    345780
catcatcaga aatattaggc tcagaagaat cagtattagg agtattcggg accagttctt    345840
catcatcctt gtcaaacata tttagttgat ttttgaggat ttgaggctta tcctgcttgg    345900
aggctcgcaa aaacatcaaa actggcgtaa tctgatcctt cattattaac tcattataga    345960
cattgcttgc tttcaaaata tctaaaccag aacatgtctt atctggcatc attaaaagta    346020
gttcatttgc aacgctcttc gacaattcac acggatcttc gatggtatct agtttcacgt    346080
catcacacat ttcccaagaa attggtgtgt ttgaaatggg atgtttacca ggtacatatt    346140
tttctggctc accaaaagac ggaaaattgg gggttatgca atagcactgc atctgcaaca    346200
gccacacata aatatttgag ggtcgtgtaa acttatatat caatttgaag gttgtaatga    346260
tcaacttacc ttcacgttaa cttcacagtt gcaccatcgt atttcttttc ccattgcaat    346320
caagtcattt acagagcgtg aattaagtaa tgcgcctttt gattcgattt cggcattgta    346380
cttgttagaa aataattgcc acaattcttt gtccgtccag gaatacttct cggacaaaat    346440
aagagggaag acatatttgt acatcacata taaataatgt tgcttctctt cttcatacat    346500
ctgtcaataa aaatccaaga gaaaagcttt atcatataaa caatgttcct tctcttctct    346560
tctaaaaact tctgttttat tgttataaac ttctattgtt ataaacttct gttttattgt    346620
tataaacgtc tgtcttattg ttataaactt ctgtattgtg tcttaaaata aacaaatatg    346680
ataaatgaac aaatatcatc agaatcaaca agcaaaagta caattaagaa aaagcttatc    346740
atataaacaa tgttccttct cttctcttct aaaaacttct gttttattgt tataaacttc    346800
tattgttata aacttctgtt ttattgttat aaacgtctgt cttattgtta taaacttctg    346860
tattgtgtct taaaataaac aaatatgata aatgaacaaa tatcatcaga atcaacaagc    346920
aaaagtacaa ttaagaattt atttgcaact gctcacattc gaatttcata aacacttcga    346980
atttctttgc aacacgatgg aaaaaatatc atcgatggaa aattaaacaa atcgatttac    347040
gaatgtcaag cactcaacca tataatacca atttctagct atataatgta agcactagtt    347100
gccgacttat aataattata taatgccaat ttatagctag catatagtgc caatttaaaa    347160
atatataatg caaatttaaa atatataatg ccaatttcaa accatataat accaacttct    347220
agctatataa tgccagttta aaatccaaga agtgtcaagc aagctggtga aggagagtga    347280
agcaaagtga acagccaatg ggctgcggtt ttaatagtgt ccgcagccaa agcccagccc    347340
aaagtctaag aaaaacccta atttctctga taatataaag tattcggcgc ctattcattt    347400
ccttattcta acaaaaacct atctccttcc taacaaaatg tcataaagtt tttcataaag    347460
tttgcaaaga tagtgaattt gttgaagttt gcaacataga gatgaaagtt tgcaaagata    347520
gtgaatttgt tattactaat gtactattat cttagcataa ttctcatctt aatggaatat    347580
ggatggctta tcttttttttt atttgtttat tttaatatta gcataattac gaatcatcca    347640
```

```
cctaaaaatc aaatcaaaca acatctcgaa tcgtgtgaca ttggttttga gctttgtgac 347700
tttagttttg agctttgtta ctgttgtttg ttttctgata gtaatgcatg tctcgtcaaa 347760
aaataaaatt ttttgacccg ccttgggtac ccgacccgcc ttaaccggat tgggtcatgg 347820
gccaattttt aattgatccg ggtacccgtt aatgacccgc ttaatagtta atatatatac 347880 tttttttta gggtttcaga tgcaagcctt cattcactag cagtactaga ggtgttcaaa 347940
actgggtacc tggcttctcg accgtcggca taattcttta ctagtgccaa ataatacat 348000 atttgagtca ttcaataacg ttttacggga agctagaggg aagcctatta tttctcttat 348060
ggaatggatt aggagatatg tgacgcaaag aagtgcggca aaagggaag gattgagtaa 348120 ctttgagggt gttttaatgc catccgttag gaaattaatt gaaaaaatg caagggacat 348180 atacggtttg agggtaatcc cagtggatgt atttgagttt gaggtggatg atggtgaaga 348240
gtcgtacgtt gtcaacctaa cgaacaagac ttgccattgt ggaagttgga cactaattgg 348300
gataccttgc aaacatgcaa tggcttgtat tgttcttagg aaattagacg ccaacgaatt 348360
tgttcacgag gcctatcata tagaaaggta tgcgaagacc tatggtccta agtttcatgg 348420
tatgccaggg cataaaatgt ggcccacaac cactttcgcc aaaccacttc cgcctccatt 348480
ccgcaaaatg cctggaagac ctgacaagag gaaagaaag aaggaggctg acgaaggaaa 348540
gggagggaat aaagctgcta ctgttgttag agaatacaag ccacgaaaat gtagcaactg 348600
tggtgatctt ggtcactaca aaagaaatg taagaatcca cccaaaccgc caacgacgaa 348660
ggagaaatca aagggtggta ggcctaaaaa ggggtcttct tcaactcagc aattaacaac 348720
aaatgatatg ccatgcacca gcagtcaacc acaaacacaa tccgcttcat gtgtaatcga 348780
tcaaattagt caaatcaagt agtttggatt gtaatggatt ttttgcaag aactcatgta 348840 ttttcaagta atgtacttag tgtagtagtt tggtttgtaa ttttcaacta atgtatttgg 348900
caagaacaag tatattttgg tgctattgta ttttgcaaga acttgtgtag tagtttggat 348960
tgtaattttc aactaatgta tttggaaaga acttgtgtat tttctactaa tatatatgat 349020
gttggtatga tgttctgatt tgagtttgtg tgcaagcata tgtgtaggtg tgctgtgtgc 349080
aagtatttgt gtatttggtc tgctgttctg atgttggtag agatgtgctg tgtgctgtgt 349140
gcaagtagag ctgtgcaagc aaacatcagt gtgcaagtag agctgtgttg tgtgtatttt 349200
gcaagtagag ctgttctgat ttgcataatg ttctgatcag tgtgcaagca acatcagtg 349260 ttatgataag tgtgcaagca acaacaaac ccaagatcag tgcaagcata atgtgtatat 349320
gttttgcata ccaaacagaa aacaccaatt gttcatgtgc tgtataatct gatgtgctgt 349380
atagaatgtg tatgttgtgt atgtataggg aatgtgtgca aatgatgttc tgtatgggga 349440
tgtgctgtgt gctgtgtgct gtgtgctgtg tgctgtgtgt tgtgtgcagc gtgcagtgtg 349500
caatttgtgt actgatatgc tgttaatata ccaactgtat gctgtgttag tgtgcaaagt 349560
gaatgttcat ttaccaattt tgattttgtt gttcatatca gcaagcaagc aaatgatgtt 349620
gttcatatca gcaagcaagc ctataccata attctgattt tgttcatcaa atgatgttta 349680
ttagtgtatg ctgattttgt gtaatcagtt tgtgcaatgt aatgtatgct gcttgtgtat 349740
aatcagtaat gtataagcat tacaaaagca tatactcaat cagtctgtaa tgattttgat 349800
gcaagatatc agcaacattt gctctttgc aaactttaat attatacaag gtagttttt 349860 gaaaaaaatt ttatatcagg tagttttttg aaaaagagg ttgattacaa acaacgttag 349920
aaagaaaata caacctgaaa taacaataac aattaacaat aataccaaat ttcaaagtcc 349980
```

```
aaacacattc aaatttcaaa gtccaaacac attcacttct tcacaaatca cattaacatt  350040
aacatatata tagaattata acatatgaaa taacaaaaaa tgtaacaaac agtaacatta  350100
ataattcaag aaactaactt gagtttgaaa taacaataaa aaaaaccta attttttgaga  350160 attgggatt tgaaaatata acatttaatt aataataata cctgaaaatc tgaaattggt  350220
ttgattgttt gacggtgggt tagtaattgg tatggtggtg gactagccgg tgggaagtag  350280
gcaagccggc agccgcagga cagaaaccca acgtgatagc gactcgcgag ggagcaggcg  350340
acaggagact gaaaagcagc aggatagaaa cccagacgca atagtttgga gttgatattc  350400
aagaaaccaa acgcccgttt ggtttgtaag agaaatcacc ggcaaagata ggagagtggc  350460
aaacggtcct caaaacattt aaattcgaat tttaaaccat aattgtctat tgttgttgtt  350520
aaattttaca ttttttgaaat tctaatttat tttgaatttt tcttactca attctttggg  350580 attaaatgtc ttgaaaattt atgactttt tattggacct aaatctctaa acatttaagt  350640
tgggcctttg gcctacccctt gggtcgggtc tggttgtaca tcgcttcttg cgaggcccaa  350700
ctaaaaaact caccttgtg tgctcacaca ttttaataaa ataataattt taattcgaac  350760
ctctttattt ttgaaatcgt aactattat tatttcata taaatatgtt aatatttaaa  350820
ttcgtatatg aaaggaattt attaaaacta attcaaataa tttaatatac aatcataaaa  350880
tctccaaaag ttatttaaaa tattaaataa ttacgtcatt aaaaatctcg gggtattaca  350940
gactaccacc ttaaaagaag tttcgtcccc gaaactagag taacaaggca ctagtcatga  351000
aaatttatag ccttgagata tatgcccttc tcggatttat tccggagatt ttggccgtat  351060
ccttgcttta tttgatatta aaactaattg gactgttggc ccgttttctt cccccttagct  351120 atggttcgtg agtccaagtc caatcatgag tatgctatgg atcatgagta cgcacttcca  351180
tgaggttact tgcaaattat ggagccacct tttgtataac ttctgatcat tatatgttaa  351240
gttgattata gtattttaat tttcagtttt agtagtttag ttgatgttaa aagtgtgtgt  351300
aattagaaga ataattaggt ttagatcatt tgatataata cgtattattt ggcactagtt  351360
tgatataaat ttatacttaa tgatggggct gaagcttggc tctgtttggg tgactttgaa  351420
tgttattttc acgtatgagt gcccttattt tacgcggaac aataacttta atattgttgt  351480
tacaattaca aactatattg ttttttgttac aaactctagt aatgttgaag caacaaactc  351540
tagtaatgcc agtttgaaat ctaatgaaaa atttacaact attcataaca attcacaaga  351600
cattgcttgt agaaacatta tctatggcca gataaacgta gttgattttg gaggatgcga  351660
gccttatctt tagcggtggc ttgtagaaac attaaaactc tcaaaatatc ctcatttatt  351720 accactttt ttatattcac ttattttctc tttgctacta attcatcaga acggagtagt  351780
agttgctatg taggagtttt ataagatcac cagtctaaag tttaatagaa gtattttcgc  351840
tgtattaaat ttgatatttt ttaactataa gttatgggta ttatgctttt ctattaatta  351900
tgctttttta aatgctacgg tattaataat ttcaatttat actgtttttt actcctcaat  351960
ttgattcaat tgtctcgtta attagctcga gcacgaatat taagagtgag atgaagttta  352020 caaaaaggt ggtagttgga atattttaat tgattaaatt aattatattg gtcattacat  352080
gtgttattgt gtaaaaatag ggtatttagg taaaaaatca ttgaccaata taaaaaaaaa  352140
aagacaaatg acactctctt ttgatctact ttttcttaat taatacaaca aaattatttg  352200
tattatgtac gattttctcc tgtttaatct acttgtctta tttacctctt tcacatattt  352260
acaaagataa tattttaact cttaatatct ttcattgtac atatttaaaa ataataaaca  352320
aaaaatgaat tattttaat aatgtaataa taaataaata aagaaagaat agatattata  352380
```

```
aatgtacaaa tgaagtgtgt cggatcaaac aaaaactatt cccttcgatt cagtactaat   352440
gtgcaatttg cttttttgcac actattcatc actctgaatt tgtattttat ttttttttgg   352500
aaatctgaat ttgtatttta ttactacctt ctattcaaac taaatgtctt atttagtttt   352560
ttgggactat tcacacatca ctcttaattt ttaaatattc ttaatctata agttaaaaca   352620
tagacatgtg gaatcttgtt tgattcgtct caatacaaag attattaata tcaaattttt   352680 atattttta attacgaata atttgagatg ttaagggata aaatgttgtc tcggcaagtg   352740
tgaaaaacta aatgggacat ataggctgaa ttcaatgcac cgaaaaccta aagtccaatt   352800
atatagtatg aaatgaacaa ggattttaca gttttttaaa ataatataat gggtgcatta   352860
aaacaaatat aatcaaatcc gcgaaattaa agcagcaaac aaattaaatg attcgtcttc   352920
ctagaatgga gtattgtgaa acgtataaag gtgggtggac aggtggtata ggaggttttg   352980
agcatattca acatgttcaa tcttacacag ggcttcgaaa aattaggagc cttaatatga   353040
agatacttag tactctctct gttttttttt tatcttccac taatctttgg tggtagtgga   353100
tattatttta aggaaaattt acttttaaac atacaaactt taacccattt tcttttaaac   353160
atacaaactt tcgtttatta tttaaacata cgaactttgg ggggtatatt cccaaaaaga   353220
tatagccggt ttttttgaagc tttttttaacc ttttttaacc ggttaccctc tcaaatgttg   353280
aagacaagct gttgttcttc ttcttcaagc ttccttcttca atggcttcaa tggcttcttc   353340
tgggttgaat taaggtttgt tttattaaca taccagaata tgatcagact gttcttctcc   353400
ttcaagcttc ttcttcaatg gcttcaaatc tctaaaaatt aatacaaatt ccagattttt   353460
taaaatttca gatttgtttt caatttgggt tgattttagt gggatggttg ctggatctta   353520
taaaaaacaa atttgagcaa ttacccattt taaatctcta aaaatttgtt gatttgttct   353580
tcatttgggt tgaattaggg ttgaagataa agaatggaat ggcttgttct tcaatttgtt   353640
gatttgttct tcatttgggt tgaattaggg ttcaatttgt ttttgggttt gaattaatca   353700
aaggattttc agcaatttag caatttagtt tttgagttttt cattgttttt gggttttcat   353760
tttttagtga gaattgaaaa aagaaaaaaa ttggtgagaa ataaatgtaa aaaagaaaaa   353820
agaaacccca ttttttgatat atatgaaagg ttgatagact tacaggaaaa ggctgatagt   353880
catgatcttg aagcatagca agtctttgag caaccaagga aagcttcaat tctttctttg   353940
acattgctga ttttttccttt ttctgctgaa aaaacaaaac agacaaaaag tgagtaaaaa   354000
tagaaggaac cagtttgatt gaagaaattt agagtaaaac acagaaatga atagatgaaa   354060
aaccatgggg gaaattgatt ttgatgaaga atgatcaag ttagccatgt ttttgggtt   354120 tccttcacga gagaatagac tatggccttg ttttatggga aattgatttt gatgaagaat   354180
gatctaagtt agccagaaat gatctaaaaa gaacccagaa aatttttcccc acaaaaactc   354240 tgattctgaa tcaataaata ctgaatctaa gttagccaga aatgggaaat tgattttgat   354300
gaagaaacgt ttgtaactga aaatagaacc agattttttt ttttttttt tttttttttt   354360 ttttggttg ataatggtga agatgaagat ggtgaagatg gtgaagatga agatggtgaa   354420
gatggtgaag atgaaatggt gaagatgaag atggtgaaga taagaagatg aagatggtga   354480
agaagtaacc ggttcatccg gttataagtc atccatatct ttttgggaat atccccccca   354540
aagttcgtat gtttaaataa taaacgaaag tttgtatgtt taaagaaaaa tgggtcaaag   354600
tttgtatgtt taaagtaaaa ttttcccttat tttaattata tagtagtgag aaataataat   354660
tgtatggtat tatgagagaa aaataataaa atagtagtat gaagtaatga ttgtattgaa   354720
```

```
cgtatgagag agaaaataat tgaatagtag tgtgaagtta gaaaagtgggg gttttaaggg 354780 cctcttctct tcgtctgatc tgattggata aagtctgaat ttactaaggt ctgatctgat 354840
ctgatctgat ctggtctgat ctggtctgat tcagtctgat ctgatctgaa tctttctgat 354900
ctagtctggt ctgatctggt ctgatctgat ctggtctagt ctgatctgat ctgatctgat 354960
ttgatttcat aaagttatta ttattatttt tattattatt attattatta ttattattat 355020
tattattatt attattatta ctattattat tattattatt attattatta ttattattat 355080
taattactag tatagaaacc cgtgcaatgc acggattttt cttaatagaa gttaacataa 355140
aaatattaat tataattaat gatttaatta tatattatct taatcatatt tatgagtctc 355200
ccttcaaata taaataacat ttataataat ataataataa atacgtaaca aagcattaga 355260
tatgaatatt tatgtgaatc atacatactt aatttctgaa aaactataaa gatatcaaaa 355320
gtaatattgt ataacatcta aaggttttga aagacctctt tgtatacaac attatcagtg 355380
ctagaagtta tctcatcatt cttatcacat atgagaattt ttagaccttt tctgctagta 355440
actctagaac atgcgacata taattgtcca tgactaaaaa caggcttagg aaggaacaaa 355500
ctaacgtgcg ataacgattg tccttggctc ttattgatcg tcatggcgaa acacaatgac 355560
accggaaatt gccttctttg aagagcaatt gggattttag agctatcaga aggtgtgaga 355620
gtgatccttg gaatgaaaat cttatcacca atgttagatc cggatataac agttgctttt 355680
ataactcgtt cacctaaatg atcaactaat aaccgtgtac cattgcataa gccagctgaa 355740
tgattcatgt tccttagcat cattattgga gcaccaactt ttaacaatag cttatggtta 355800
ggaactccag atgcacgtat ttctagatgt gtactttacc catgtatcaa tgctaaatac 355860
aaaattatgg tgggtgtcaa ataaataaaa aatagctaat attttaatcg tactttttt 355920 ttagtttgtc ttttttattt tgcacttttt tgtttttaat cacctatttt tatcacttac 355980
ttttttttat cctattttaa aatcaatttc tatcaatagt agaacattta ttagtttttt 356040
aatttcaaaa aaaagataga acaaatattt ttaactttga atagtccctt atgaagtaaa 356100
aaaaaaaata caatctacct atgtctagaa gtctcctagc tcttaatttg cctaaagttt 356160
acctattaaa ccatcaatag ctctataaaa aaatactcca actcaaccta tatctagctt 356220
tataaagtag ccagcctaaa aagtttgtct aacattacac cttttgtcac tactttatat 356280
aaagcttctg acattataaa gcttttgata gttttttaggc aaattgatca ttcatgctat 356340
ttcatacatt atatttaggc aaattgatgg ttcatttttt caagggaaaa gtgttaaaaa 356400
atacttcctc tgttctttta tattgtcggt actctaaaag ttaaaacata gccatatgag 356460
atcttgtttg aatcgtctcg atttaaagtt tatttatttt gagtttttat attttttga 356520 tatgtatact tagatatatt aaaaattgaa ttcatacatt ggggagtgtg aaaaagcaaa 356580
tggtgcaact aatatggaac ggaggaagta tctaataaat ttcttttctt aaaaaagtac 356640
ttaataaaaa aatatttttca acaaaatacc taacaaaaat ttttcttttc caagagtac 356700 caactaacgg ctgaggttaa gtgtttcgtt atctttttttt gtccatcttt aaaaagtacc 356760
taaaaaaaat tgttttcaat aaagtaccta atcaaaattt tcttttcaaa aagttaggt 356820 acttttttaat ggatgatgtt tttaaagtta ctagttgtgg ggccgcgtgc tacgcacgcg 356880
gtcctccaag ttacactatt aaatttaata atgttttttt aaatactttt tattagcaaa 356940
aatccgaatg aaaatattag aatgttaatg tgttacaaag gtgtgaaaga tgcaagtgtt 357000
gaagatggtt aactataagt gttacatgtc ctcgaattaa actcaagact tgtccaagaa 357060
atgtgatact tgattcggtc gaaacaaaaa tcagttctcc ttaacatggt ttttcacaga 357120
```

```
aagttgattg tataataaga aaaattacca tcacattaaa gcagcgttta gtaacattta 357180
tatatatata tatatatata tatatatata tatatatttg catgaacaaa tgttaaatca 357240 ttatataacct gtctttttat ataagaattc tgaaaattaa tgacagtaat attttattat 357300
tttgatatca ttatatcaat atgattcccc tgcaaacaag aaaaatctta gctaccaata 357360
aaacaaatat tgtcaaagtg attttaagt ctaccaataa aacaaatatt gtcaaagtga 357420
tttttaagtc ttactatctc taaatatgca ttattaaaaa tatataataa aaagtatat 357480 taaaaacgaa tctaacgaga tctcacatgg atatatttta tcatcgatat atatcttaaa 357540
aatcttaatc aattttctct ctccaaaata gaatattcta aacggaaaaa acatttggaa 357600
acggaggtag tagaacagac ccagaaagaa tgaagaaaag gagcacataa atcattttac 357660
aaaatagatt tatatcattg cattaaaatg ttgataccaa aatttcaagt aactatgttt 357720
atgtttaaaa aatcaataat atgggataaa ataaatgtca acaataaata gagtatttaa 357780
ctgttccaaa atccaaaatg cccatcaaaa tttagaaagt attttgatct aaaagcaaat 357840
aagatttaga aactgcttga gtagtctcaa tttattcctg aaagcaatag agaacaaatt 357900
ccaagaaaca gtctgatcac ataaaattgc cctaattaat cgaataagat caagatctaa 357960
caggggttgc accagtcttg gctgtatcct cctgatgaga gataacaaaa tcgataagtt 358020
agtaaccctc caaacgtact aaagagacat gagcttacaa catacacatc taaaaaatga 358080 ttcttttgaaa acataaaaag gtccacaaca tttcaaaatt taaaagaaca aaacaaattc 358140
acaatagatg caattactaa agacgtataa catcgaccga tactattaca agaagcttca 358200
acttctcatt tattacatat agtcgtgcag tagacttaag ttggctaacc taaacaattt 358260
gaatcgaaag tagctctcag aatcggatcg tgaaattaga tcatcatatc ggtcaattct 358320
acaatttggt agattgtagt tattgatatt tggatttagt ttcaagatag tttataaatg 358380
aaaaaaactt ggattcatct attatcaata tgttattcat aaaatattct acatgaacat 358440
atcaagtgca tgaagcttaa aggatagaaa tacaaaaaca taaatcttga aattagattc 358500
aacataaaaa tacccaaaaa aaaaaaaaaa aaaaaacaat tatcaatgca ataacactat 358560
ggaataccat aatctatatt cttcaaacag cctaactaac ttaaaaaaaa aaccactcaa 358620
cgggataaaa ggtggggtaa tcgaaaataa cattgcagat taattcatag gaaataatgt 358680
gatacttttg actaaatcct cgagccaaat aaagaactct aaacagaaaa agtcgcacgc 358740
aagagctaac ctaattgtct aaacttgtag agaaataggc tcgcaaataa gaagtatgaa 358800
tctctgtaaa aagatatact gatttaaaaa caaaaactca aagaaacata catcatgaaa 358860
tcagattcaa aacaagaatc actcacaaaa ttcatatcaa aataacaaaa ttaaaattca 358920
aaatagacaa caaaatactc aaatgtgaat tggttcaaca ggaaatcaca aaatcaaata 358980
aaaaattaag ttacaatact aaatcatgga taaatcaaat tcctaacgaa atcaaaaaca 359040
caattacaaa tgaaataaaa aaaatcaatt ctaaaaacta atcaaagaa gaataaatta 359100 gaaagttctt acagtcacaa aggaaatggc attgaagaat gattgaaaat gggtaagcaa 359160
aaagccatga aaatggtgaa gatttgaatg gcgaagatga acaatggaga taaacccata 359220
aaataatagg gaaatggcga catgtttaga catcgcatga gatattgcgt gaatctaagc 359280
aactgaatgt aatgaaagaa aatcatatta ttgaatgaac cctgttgcag attaagatct 359340
tacatcgggg ctttgattca tttctatgaa tacttcttcc atttggtcat agatttcagt 359400
gctggtatta ttgttcttca tgtattcttt gcgcacttta ccatcttctt ccccataagc 359460
```

```
tgttattaga tgttgatata agaatcttac aaatctaata atcgctaaca gaatgatttt    359520
taccaataaa agtaatacaa ttacctgctt cttaagggta gcaaggctct aactatacac    359580
attcgagact gtagaaggac gtcattcgat ggaggaagtc taattagtcc gcatagcaat    359640
tctacaattg cacaagattt tttcagtcag caacatcgat gactatactt tatattcatt    359700
gaaatacaat gttaaagaac atatttatag gcgttgttgg atttgttcta gattttgtgg    359760
tactattaag gtatcaccat actcattagt atagattaat tgcccttcct attcatagca    359820
ttcaaagaac ttttttgaaag ctgtaaaaat atcagctatt aaagtaatca atattgtagt    359880
ttagattgtc cttatttagc atcaacactc ataaaggata tactccatat ttcattacat    359940
ttcttaagtg gatttgatct tttaaagtac cgaagaaagt tttctattgt gggatcagac    360000
taccatccta ggttagatca tcgaaccaca tgtcattgat atggaaggcc cggtgatact    360060
aatgcagcaa aagaaaaacg tcaaaattaa cctagctcaa tcaataaaat gaaaaaaaaa    360120
actcaaaaag taaaatagtt tacctgaaat aagagtgcgc acaaagaat tctctacttg     360180 aaagacgcat aagtctaaca aaccagatag tgtaaataac tcctataatt tattaggaat    360240
gattaatata ccataatatg agaggaacaa ttctaatcag ttaaataaat aagctacaaa    360300
ataaagaaga aaaaaaacct gcaaaagat agtgtcataa ggccaattgg gcttctccct     360360
acgaacactg aagaagttgc acaaatacac acaagctgac ataccatac tccaacaatt     360420 aaaatattag atgcaagaca tcaaaatatc cacaaaaatc acaagaaaag ctaatgatac    360480
actggaaatt catacatgtg ttggaattga aataagaaa tcaacaaact caattcatct     360540
tagataatgg ctatgatacc ccaagtcttc cacttagctc acttgtccag cattagttat    360600
aattattggg taaaataaga atcaatagtg cttaacccaa aatataaata taataaaaac    360660
tataattaat aataaatcat atcacatatt tatatttgat ctttatttct agaaatataa    360720
aaatgaatta aacaattatt acacttataa tttaatatca ataatcaata atagataata    360780
aaaaaaaaaa gcgaaattat gattaaaaaa atataaaggt acataaaaaa agaagaaaag    360840
acctgtcaat tcactttac caactagttg gagggggtgcg tgctacgcac gcgctccccc    360900
aagaaatcct attagtttta aatattaagt taaataaatt attttatctt taacatttca    360960
actaatggaa aatgaaattg agactattat ccaatatgcc tgtagggtgt aatagatcaa    361020
tattgcgatc acatgtacat gcttctaagt tgtattgggc aataactgtc atttggttgt    361080
ttcccatgct gtgaacccctt tgttgagcct gtagatgttg tacaagcctc attagattag    361140
aaaacctcac tctataatta atgtaaagag taataccttg tacttcatat cttttcatta    361200
gaaatgactt actctttacc tataatgctt cgttaatcta tctgagactt gagagcccgc    361260
gctcgaatga ctctagcatc cttagagatg tttgtctta tacttgaatg gaagatttat     361320
acttgaacat cacttgatgt aatgtttata agttagagat ctattttcgt gtttgattag    361380
cttgtgattt ggtttggagt gcaacaaaat gcaattgttt ttgcaattgg tagagaaaat    361440
aataatgagc tttctactga ttgtgtttcc ctatgccaaa caagtaacag gattagggat    361500
agatatgcat aatttatgaa ctacttttga caatggaaat ttacaataca gtaatagtta    361560
gaggggtctt ggaggtgtgc gaggtgatcg gccacacagg gtgtgatacc ccagatttag    361620
cttgaaaaga gattgataga ctactcatat caacaaggtg catcttcttt tctagggagc    361680
ccatttgcta agaactccac agttaagcgt gcttggtgga gagcaatctt aggatgggtg    361740
acctcctggg aagttttcct gggtgcgcac gagtgaggcc aaagtgcgct ggaaagactt    361800
gtgttggttt gtggggctag tctacagtct ccatgagtag tcaccggcgg tccgagggggc   361860
```

```
cggggtgtta caaatggtat cagagcgacc ctgcgaccgt ggctgattgt gtgttcagcg  361920
cacctagcgg gggaaaagat cctgaagtga cggtccaacg aggacgttgt attcttaagt  361980
gggggtgagt gtgataccCC agatttagct tgaaaagaga ttgatagact actcatatca  362040
acaaggtgca tcttcttttc tagggagccc atttgctaag aactccacag ttaagcgtgc  362100
ttggtggaga gcaatcttag gatgggtgac ctcctgggaa gttttcctgg gtgcgcacga  362160
gtgaggccaa agtgcgctgg aaagacttgt gttggtttgt ggggctagtc tacagtctcc  362220
atgagtagtc accggcggtc cgaggggccg gggtgttaca cagggcctct tctttctcca  362280
gtatataaaa aagttactaa aaagaaata tgttaaatta ttaataaaat aaaaatattt  362340
actataaata agacgcaaaa taaaaatttt acacagggcc cccaaaattt tcaagacggc  362400
tctggtaatg gtagtaatag tcaccattca tgaccgtggg tttgccttgt tgtttaattg  362460
aaattagctt atcgtataca tagtcgacgc acaatgattg atcacacttg gattgtgagc  362520
cctttgcagt gtaacgcatt acgctaacta tatgcttaac acgaagcttt tttggatact  362580
attgaggaaa tccaagaaag gtcaaaaaga tatgaggact cctgaacttt gaaagaacat  362640
tccacagccg ccatactatg caaagctggt gaaagaataa aaaaaggtac ctctattcaa  362700
gcaagaacct atgagctttg ataagatatt taatcgtaaa atcaaaaaaa ccagatcttc  362760
aatgcaaaac ccatgaacca aaacccaat aaaaaatcca aaatctgat ttcaaagtgg  362820
aagaaaacca tacctaaaag ctcacatctt caaccatttg cacaactctt catttcgaat  362880
tgaattgatt gatcctaaac gaaaatataa aaaattacat taaactcttc aatttggact  362940
gattttagat atattttaca tttctttgcc gaattttgtt ttcgctgcca gttaatttgg  363000
cagtcaagaa atcaaatgaa atcaaagtt agaatatata tatatatata tatatatata  363060
tatgtagaga gagaatggcg ggtggtatgg tgagctgcta gctgccttgc gccgcctttc  363120
cgaacactag atttcaccgg aacacccatg agaggagggc gtggttcacg tggtagaggt  363180
agaggtagag gtgaggacct tagagatctt agcaccataa caagaagtgg ctctgaaaag  363240
gcaaattcta gggttacaaa tgaaactgaa attggcgaag aatcaggagg tattgagcac  363300
aaggagcgtg aagaagctag cattccaagt tcaggcatag tttcgaacag tgggcagaat  363360
gaaattaatg ctgagagtat tgaaatgcag acaattaagg accagctggt agcactatct  363420
aaaatggtgt cggcaatttc agaaaaaaga ggtagtttgg aatccgaaaa tcagccgagt  363480
aaagaggact ttcctcccctt agtcaagcag ccagaggaag gaacacaatc aaaatcatca  363540
tctcctctcc aattgatgaa ttagagagac aaggtaacta gtcctactcc acctattggt  363600
atgcaattga aatatgtacc ccctgtagtt gagaatggtt gtcaagttgt tcatattgat  363660
gctcatgatg ctagtgactt agtaaaattg tgggaacgag ctgttgttgt ctatattgtt  363720
gggagtcaag tttccataga aattcttaaa ggcttcattc gtaaacattg cacaatgtt  363780
agcatgcccg ctatccaccg tcatgaagaa ggatattta ttttgagatt taattcggac  363840
aatgaatgtg aggaaataat aaaaggagga ccctattttc ttaatcgtgc acctatggtt  363900
gtgaaaaagt ggaataggag ctttgatttt agagaagaaa ttatgagagt aatcccggtg  363960
tgggtaagac ttcctaacct cccgctccat tgttggggag tggatacttt gagtagaata  364020
gtaagtgcta tagggggttcc aattcttgca gacgaatgca cggcgaaaca actaaaagtg  364080
tcttatgcta gagtttttagt tgaagttgat gtaacacaag agtttattaa ggagataaaa  364140
gttcgagaaa attcgggaag agaatttgtt caattagcga ttccggaatg gaaaccgttc  364200
```

```
tattgtagca aatgtgataa gttggggcat aattgtcatg ggaatgcaaa tgaaatacaa  364260
ggcattccta aaaagaatct tagggaggag aatggtacta tggagaacaa gaaggtttgg  364320
ataccttcaa ccattgtgag tatgttacaa ggagtccata cagtgagcca gcttagacat  364380
aaattaaaag agggctgttt gggagagaat gaagatcagt ctgttgaggg agttactacg  364440
atacaagatc agaacattgg ttccatgatg caaggtcaga acacgagtaa aactgatgtg  364500
caggctgctg tttcctcgtg tgtagatcag tctgctgagg gagctgctgt tgtgacgtgc  364560
tcaggtcaga caattgaggg tgctactgat cctagtacag gagctgttct cacccaacaa  364620
tttgatacga ttgggcagtg ttcagatcag aaaagcgctg acgaagaggg ctggacacct  364680
gtttcgtatg gtaaatcatc caaaaaggtc cagattacag tatcacacag gggtactcaa  364740
aatgctagaa cagaaactga tccaaggctt atagtgaaag agaaacttga tgttgctgca  364800
gctcaaaata atccaaggga cgggaaccct ataattccct cccgaaaatg attatttctt  364860
cttggaacgt gcggggcatg aatagcccca ttaaaatcag ggaaataaaa tctttccttg  364920
agagacgtaa cataagtatt attgggttgg tggaaactaa aatcaaagct cctaacgcaa  364980
agaaaatcca aaagaagttc ggtagcaatt ggagttggtg caataattat tctcatcatg  365040
atagaggcag aatttgggtc gggtggagac atgacagatg caagcttgat caatgtgata  365100
ctcatccgca gttcttggct accagagtta cccccattaa ctctgatacg agtatgcaca  365160 ttgtcttttgt ctatgggctc catacagtta cagaccgaag agatttgtgg gagggtttga  365220
tgaagcttaa ctacaactca gcgtgcctgt acttgggta tttcaacgca atctataaag  365280
atgagcacag gatgaatggt acgcaagtga ataccatga gaccggtgac atgcagaatt  365340
ggctagatca gaaagagctt catcctctcc cagaaagagg tcaccagttc tcttggacaa  365400
acaaagagga gggggagaac cgcattctca caaaaattga tcatgcaatt gggaatattc  365460
agtggctttc cagatacaac caagttggtg tcttgtacga taatcatcaa tcctcagacc  365520
atacgctgtt gattgtaaac ctcctagagc atgggcagaa gcaaaacact ccgttccggt  365580
tcttcaatta cctgtgtgat cataaggatt ttctcaaggt ggtcgatgaa gcttggcaaa  365640
tagaggttag aggtgatggg cttcagaaat tatggcacaa aatgaagaat gtcaagagag  365700
ggctaaagca gttacataac aaagattttg caggggtcaa ggataaaatc atgcattggg  365760
aacaacaact tcagaaaacc caaactgacc ttcaatccaa cccaacaagt gaagagctcc  365820
atcatcgtga aaagaaatt tcctcaattg ttcacaagtg gaggaaaatt gaagataaag  365880
ctcttcacca gaaagctagg attacttgga tgagaaatgg agatgataat acagcgtact  365940
tccatgctgc tataaaagag agaatttctt ctaacagcat ccacgagctc caggatagag  366000
atggtaactg gatttccaaa tctcaggaga tccataatga aataacccag ttttataaag  366060
gcctccaagg cacagccacc cccaaccttg agggcatcga tagcagggtt atgagagaag  366120
gtcttcaagt tgatagtagg agtaggcttg atctcattcg ggatgttgag gaggaggaaa  366180
tcaagaatgc tctttttggg atgaacgaca ataaagctcc gggcattgat ggtttcaacg  366240
cttgcttctt caagaggaca tgggctatca tcaaggggga tttcatcaac gccatcaaag  366300
gcttcttcag aagtaactac ctctttgctc cctacaactg cactgcggtt accctaattc  366360
ctaaaacatc caatgctaac cgagttggag acttcagacc tatagcttgt tgcacggtga  366420
tctacaaggt tatatcgagg gtcctcgcgg ggagacttca gatggttatg ggatcgatta  366480
ttgatcaagc tcagtcaggg ttcatcccag gtagacagat ggcagataat attttacttg  366540
cagcagagct tatcaaggga tacaacagga aaatataag ccctagatgc atgatcaaaa  366600
```

```
tggatcttcg caaagcttac gactccatta gctgggagtt cctttctct gttatttctg  366660 aaatggggtt tcccccaagg ttcgttgaat ggatcaaagt gtaaccgccc tagattatga  366720
aggcaaagac taattggaat ttagtattaa tcaagcggaa gcttgctttt gccaacacta  366780
taaaggggat tacttaaagg ataaaccaat gtccaagtat aatacttgaa caacaaccaa  366840
agcaatataa cggaagtctt aactgtctaa aataaaggaa aattacaacc atatcgaaat  366900
aagtccaaag ttcaaattac atccttaaaa tagtccaaac ctaaacaacc aaactaatag  366960
tctctcaaat acaataaaga ggtctaaaca aaaggggagt catactccaa ctcgggttca  367020
tcttccgctc gcatatccat tcttcgtcga ggtgccatag gggtttactc taaaaacaaa  367080
accattgaaa aacatacaaa gcatagtatc agcaaaaagg ctgagtataa acacactagt  367140
gtccgtcaaa caagttatca aaacctttt gatttgagta aattcattt gaaagatgct  367200 ttttcatttg ataaatcata ttatcattca aacccagttc aatggtttta tagtaatttc  367260
aaattcacaa ttttcattat aaatcttacg atctcaatgg atccaatcaa tttcaaactc  367320
atatcataag ttttcatggg tactctgtga gtcatcctgt gactcgtttg gtagtcggtc  367380
taccgtccgc gacatgtccg gcaagtgtaa cacaatggta ttgtgaacaa tacgcgctca  367440
gcattggtga gccgtttaat catgcacaca acatttgttg tggcatatgt acccgccatt  367500
taggctaaaa cattttgta tataatatat ataccttgta atttcaatag catttgaaaa  367560
gtcaaaaaaa tattaactt tttccttatga taaacatctt ttatttgcaa catagcaaaa  367620
catactttct ttacaatata gcaaaaatca aatcatataa tatttcccac atgggtaaaa  367680
catgcttagc ataattatat aatcaaacat aacctttgta ttatattggg gcatcactaa  367740
catgtatgga aatgcattgc aacaaaaagt gattaaaatg caagacgatt tttcaaggaa  367800
accattaaaa tgtttagttt caatcaaaga gttttgaaat taattcaaaa taactatgat  367860
atagttcata agtccttaaa atcattatga caaaagattt cataaaacac tattccctta  367920
aatacgaaat aattttgccg ataataaaat cgataattga tttacaaaaa tacatattaa  367980
ttctccaaca agacccaagt taatcaagtt attataatac cttaattaaa atgagtttaa  368040
tgttgtccca tcagattatg attggttatg gcacttataa tcatttacg attgttcg  368100 acaattacgg tatttaccgt tatttaaata atgttttaaa ttcataaata ttaagaaaca  368160
tctaagtaaa acttatttta cactatgagg cagtaggtta ctaacaaaat tataagttt  368220 tgatataggt ctatttttac tcaaatttaa ttaacaatat tacacttta aataattaaa  368280 caatatttat taatttgata aattagtaaa taatcaataa ttagcttaat aaaattttac  368340
taaagttcta gaagccatat aatacttta ttagctcatt ttaactaata aatatcatt  368400 ataatatttt atatctttta tatagacatt ttatcgataa atcaatagaa tcggtttaaa  368460
ttatttaagt ccaaataaat taatttaaaa acttttatga tgttccagaa actatttaa  368520 ggaatataaa attttaaata accattaaaa accgtgtggg gcattttaaa taattaatat  368580
tgttatttta ccgataaacc gaataaaatt tatttaagtc catatatggt cacgaaaatc  368640
catataaact tgtcgacatg tatttactgt ttatataagt gtctcataaa tttttcatgc  368700
tcaaaggacg tcatttagta tttattttgt attttaccgt tttctaactt accgattatt  368760
aatatccgag taaaaattat taaggtcctt aaacgtcaac aaaatcttct caaattta  368820 ccaaatttat ttactgtcca tataagtatg tgacaaaaat ttcaagtcca tatgtcttca  368880
tttagtaatt attttatatt ttactattta acaatttacc gataaacatt ttaacgatta  368940
```

-continued

```
ctcaaaaatc atgaaaaatt acaaattaat tatattctgg ccaaatcttg ttggagacat 369000
tataatatga ttttattaat tatttttgat gatgaagagt ttatgtagta ccatatttca 369060
taataagagt atttaacacc ttaaaaccca ttaaaatatc gatttaacga ataaatttca 369120
acaaaattat tcaagagatt attttaacat atagctactg gaaattactc ttaaaatgca 369180
tttcaaatat tttctaagtt cataaaatca tttccatcac aattactttc acaaagtagt 369240
gtaaatcatg cctttaaaca tataacaatt cttaaaatca acatgcatga tgcccacaat 369300
aataatacat gtaataaatc attgcatatt caaaattatc attttgatat cattttcaa 369360
gatttaagaa cttctctttg ggaattttat ttttttttt tttaaaaaaa acaagttcat 369420
acaaactttt cccaacttgt tcttaaaccc tttaaaaatc accccatgtg acatacctcg 369480
actccaagcc tatataagta tttcgtaagc tcctacgtaa gctccgatgc gttcttagaa 369540
atggttccaa cttcgggtcc ttgcccttca agtctcaact ccaactcttc aactaaacac 369600
attggattta tccaaaaatc aataataatt ttggatttct aacatgcact taattttct 369660
tagttggagt tgttaaacta atacttgtga tgattttaac atatttggag tatacttatt 369720
atgttgagca acatatatac ttaatcaagt ctcataattt tacttaaatt tttaaagtaa 369780
gaaaatatat aagtttgtga aaagaaagtt ttttttttat agagatttta taagtgatga 369840
ttttcttag ttttagagac aaaatatcca tattaaaatg attttagttt atagaaagat 369900
tcaagtaaaa gtgttctaca tgaacaagtt ttacaaaaac tagtggaata aggaaatgaa 369960
tgtaacttac tctatacttg gtggatttct tcaagtttgg tgtctatgga agctcttga 370020
aatgaagatt atttttatgg aatatttgag tttataaaca taaattttca gaagtataag 370080
atgagttttt gaagaagatt tgatgagaaa agaaggtgtc ttagtagttg aaagtttgga 370140
ggatgctagt ggttgttcat ggatgaactt gggagcaatg tgttgggtgt ttatggctga 370200
attcttattc agaaaaatag agtgtctttg cttcaaatat tagcctcttg catgcttgta 370260
atgatgcata atctaggtta gaacaaaagg gtactttggt tagagtgttt tgcttgagta 370320
tgtaagtgta taaggggta taagagggt ttgggacagc tattggggct gttgtttggg 370380
gctgttttgg atgtggtttt tgtctcattt tgatctatta tagtgtagga aaggtttatc 370440
taagatagtt taagtttgg gtaaaaattg ttgtacatgt aacaagttat gtaacttgta 370500
ttatatgttt aaaatcactt gtatatgtgt atgaaatatt taatttactc ccatcatctt 370560
taaataatac gatcgggtaa taattaaatt ttctcgaact attatcggta gttgctcaac 370620
tttaagttt acctccaaag tttacgtttc ttgttacgat tcataaccac gttatgattt 370680
aacaagtttc taatcatcgt agaaattttt caaatctcta ccatcactaa ttaaatttta 370740
attagcgaat gacaaatatt aaaaaaaaaa ttaggcgcta aaaatgacga ataaaacctc 370800
attaataatg cgactgtttc agtcttccct tcttacaaga gtttcgtcct cgaaactaat 370860
tcaaactaat ggctatcaat acatcactca aataaataag ggtatctaat taacatgtcg 370920
tcctcttttt cccaagtagc actatcgtca tcttgtccac tccataacac tttcacaagt 370980
ggaatcgtgc ggctacggag ttttctaacc tctcgaccta ggatccttac aggcttctcc 371040
tcatactgca agctctcaac aagttgaatc ggctcatgct ggagaacgtg tgatggatca 371100
aatacatacc ggcgcaattg tgatacatgg aacacattgt gaaccttagc taactgtggt 371160
ggtagtgcta actcataagc tacttcccca actctgcgca aaatctcata gggtccaatg 371220
taccgaggat caagctttcc ttgcattccg aacctcttga ctcccttcgt cggcgagact 371280
ttaaggaaca ccttctcacc gacttggaac tcaagtttcc tcctcctacg atctgcgtag 371340
```

```
gatttttgtc gatcttgggc agtcttcatc cgatctctaa tgattctgac ttgttctgcg 371400
gtctctctta tcatctctgg tccaacaacc acgccgggcc tcccggtgtc ccagcaaagc 371460
ggtgtcctac acctttgacc atacaaggcc tcatatggag ccataccaat actactctgg 371520
tagctattgt tgtaagagaa ttctaccaag ggtaagatgt cctcccacga acactggaaa 371580
tcaagggcac atgcccgaag catatcctct agagtctgga tggtcctctc tgtctgccca 371640
tctgtagctg ggtgaaaagc ggtgctgtaa ttaagggttg tgccgaatgc cctttgtagt 371700
tcattccaaa atcgagccac aaattttgta tcccgatctg aaactattgt cttcggtaca 371760
ccatgtagtc taagtacttc tttcacataa gcatcggcta attgttttgc cttccaagtt 371820
actttagcag gaacaaatct ggccgtctta gtgagtcgat caacaattac ccaaattgaa 371880
tcatttcctc ttctcgaacg gggcaatcca acaataaagt ccatactcac tgattcccac 371940
ttccactcag gcacaggaag tggttgcaat tcccccggag tgcgttgatg gtcaatcttg 372000
acttgctgac atactagaca tcgagctatg aaatcctcga catctttctt catgttcatc 372060
caccaaaagt attgtttcag atctgctagc atcttatccc gtcctgggtg gacagaatac 372120
atagtcgaat gtgcctcttt gagtattttc tcgatcaatt caggatctcg gggcacgcat 372180
aaccttccct ctagatgaat gctcccatct ttagcaatgc tgaagtcttt aactgcaccc 372240
ttttcaatac caatcttcaa ctcggacaag aagtcatcat actgttgtag ctcacgtatc 372300
tcctcatgta gacttggcgt tgtactcata gcatttagaa cactgtcata tgatcccttc 372360
ttaaccacaa tcaattctag ctccttcatc tccttataga tctcgtaggg tactgaaatt 372420
agtccattaa tgaccatcct cggttttcgg cttaaggcgt ctgctacacg gtttgctttt 372480
ccgggatgat actccaaagt gaggtcataa tctttcatca attctagcca ccttctctgc 372540
ctcatgttaa gctccttctg tgtgaacaga taagtcaaac tcttgtgatc ggtgtagatc 372600
ttgcaagtag tgccgtagag ataatgcctc caaatttta aggcaaatat aactcctgct 372660
aattccaaat cgtgcaccgg gtagttcttt tcatttggcc tcaattgtct cgaagcgtag 372720
gcaatcacct tcccctcttg catgagtaca caacccaagc cttctaaaga tgcatcactg 372780
tataccgtga actcttccc atcctcaggc aatactagca ctggagccgt tgtcaacctc 372840
ttcttcaatt ctaggaaggc atcttcgcac ttttgtgacc acacaaactt ggtatttttt 372900
cggaccaaac tggtgatcgg tagtgcgatc ttagaaaacc catcaacata tcttcggtaa 372960
taacctgcca aacccataaa gcttctaacc tcagttacac tagtcggtgt tggccaatca 373020
ataatagtct ttatcttctc ggggtccacc gttatgccat cttttgagat tacatgacct 373080
aaaaagacaa ctcgatccaa ccaaaattca cacttgctca acttcccata aaagcttctt 373140
tccctcaatc gtgtcaatac caatcttaag tgctcctcat gatctttctc gttcttagag 373200
tacaccaaga tatcatcaat gaaaaccact acaaacttat caagatagtc gtggaatgtt 373260
cgattcatca agtccatgaa tgctgcaggg gcattggtta acccaaatgg catcactcta 373320
aactcatagt gcccatacct ggtgcgaaaa gcagttttag gtatgtcttc ttccgctatc 373380
ctcaactgat ggtaaccaga tctcaggtca attttagaga aaactccggc tcccttcaac 373440
tgatcaaata gatcatcgat tctaggaagt gggtacttgt tcttgattgt gatttttattc 373500 agctcccgat agtcaataca tagcctcaaa gacccatctt tcttcttcac aaacaacact 373560
ggagcccccc atggtgacac acttggtctg ataaacccttt tgtcttgtaa ctcctcaagt 373620 tgggtttttta gtttagtcaa ctcaagtggt gccattctat acggtgcctt tgatatcggg 373680
```

```
cttgaccctg gaactaagtc aatatgaaaa tcgatctccc tctttggagg taacccaggt 373740
agatcatcag ggaatacgtc agaaaattct cgcactatca agatctggct taagtcaacc 373800
tccttgtatg ttgattcact catgtggtag acataggctt ccccacctct ctttggaaat 373860
gtggtaagcc tctcaatcat ctctggctca atattaggca tggtcccatc actaaaagct 373920
actcggtccc ctggattgtt cccaatcctt acatttctct catagcactc aatcactgcc 373980
ctgtgtttac ctagccagtc cattcccaga ataacatcaa accctcctaa gtcaaataca 374040
atcaggtcca catggaactc cttacccttg atcactaatg ggcaagcaat caactttgta 374100
ttacatgata ccgttgatcc atcgggtaaa tcaactctat gcattatagg gcatacatta 374160
acagaacagt tcaaggatct cacgaatgac ttagaaacat aagacttgtc ggccccggaa 374220
tcaaataaga ctcgggcaga cttaccaagc aataacagta atccggaaat gactttacct 374280
tctgttttag gaacaaaggt gttaggctcc cccgctgcag taatggcaaa gaattttctt 374340
cctcccgggc gctggttccc ttggcctcca gaagatgagg ctctattacc gcctttatat 374400
tcaaggcgga gctgagagtt gttacgctga ttcctctgat ttcctgagta atgtgctcca 374460
ccattcccag ggtttccccg attcttaccc caacaatctc gagctaaatg acctggtttt 374520
ccacaattca gacacacagc tttaccctca cagttgattc cctttgagtg ccatttcttg 374580
catttgttgc acaattgact ttttaacgga ttggagtttt gtgagttttt gttgctactg 374640
aagcggtttt ggttttggaa gtttctgggg ttttggttct gattcccctt gaagtttccc 374700
tcagctctag gcttcttgct cagacctccc tgatctccac ccgatctctt tttcctcata 374760
tcttcctctc tcttgcagac catttctttc tccacagcat gttcatacat agcttgaaaa 374820
gactcatatt ggcccatcaa cttttggtag ctgaagttga accattgta gaaacgatcc 374880 atctttttct tctcatcaag cacataatct ggagcaaatc gagccaactc caagaatttg 374940
ttagcatatt cagtaacgct aagagaatgc tgcctcaagt aaagaaattc tgattctttt 375000
tatctctgta gagctgctgg gtagaacctc tcccttagtt tcttcaagaa atcatcccat 375060
gtccaacttg tgggttgtgc tgctccacca gcagatgtgg aggtagacga gacacccttt 375120
agggctctcc accaaagctc tgcaggtcct actaaatega atgctgcaag tttaaccttc 375180
atattttctg ggcaattcac cacctcaaga attttctcag tttcattgat ccaatcttca 375240
aggacaactg gatctgtagc accattgtag gtcttaggcc tgtgtgtagc aagccttttg 375300
tagaacttag tctcgtcatc cacactagca tgttggttgg ctataagctg aactaattga 375360
gcattggtct cttgtatgac tctaagttgc tctgttaaca tattcagctg ggcttgggga 375420
tccattcctt ccccgatttc ctcctggttc ctgccatgag gtaataacta attaataact 375480
atgcctttaa gacaaatagg tatgcacatg cataacactc tttcttaatt acttttgact 375540
tagtaactta ctaacttgtc aatttccatc tcattcgata ttccaacact tttaatgacg 375600 actttacccct caacttaata taccgtcatg cttaggcaac ttagccacat aattagatca 375660
tcacttgctt actaagaacc tttaagactt ctagtttact aatggttctt agttaattat 375720
ttgatttaag ttagacttac aacttaaatc atttctttac caataatctt tagtttaagt 375780
ttatttccta attactttca ttggttactc ctaacttaaa cttctctaaa ctagactagt 375840
tgtctaattt tccaaatatt ttagacatgc ttccaaagcc ttggctctga taccaactgt 375900
aaccgcccta gattatgaag gcaaagacta attggaattt agtattaatc aagcggaagc 375960
ttgcttttgc caacactata aagggggatta cttaaaggat aaaccaatgt ccaagtataa 376020
tacttgaaca acaaccaaag caatataacg gaagtcttaa ctgtctaaaa taaaggaaaa 376080
```

```
ttacaaccat atcgaaataa gtccaaagtt caaattacat ccttaaaata gtccaaacct 376140
aaacaaccaa actaatagtc tctcaaatac aataaagagg tctaaacaaa aggggagtca 376200
tactccaact cgggttcatc ttccgctcgc atatccattc ttcgtcgagg tgccataggg 376260
gtttactcta aaaacaaaac cattgaaaaa catacaaagc atagtatcag caaaaaggct 376320
gagtataaac acactagtgt ccgtcaaaca agttatcaaa accttttttga tttgagtaaa 376380 ttcattttga aagatgcttt ttcatttgat aaatcatatt atcattcaaa cccagttcaa 376440
tggttttata gtaatttcaa attcacaatt ttcattataa atcttacgat ctcaatggat 376500
ccaatcaatt tcaaactcat atcataagtt ttcatgggta ctctgtgagt catcctgtga 376560
ctcgtttggt agtcggtcta ccgtccgcga catgtccggc aagtgtaaca caatggtatt 376620
gtgaacaata cgcgctcagc attggtgagc cgtttaatca tgcacacaac atttgttgtg 376680
gcatatgtac ccgccattta ggctaaaaca ttttttgtata taatatatat accttgtaat 376740
ttcaatagca tttgaaaagt caaaaaaata ttaactttttt ccttatgata aacatctttt 376800
atttgcaaca tagcaaaaca tactttcttt acaatatagc aaaaatcaaa tcatataata 376860
tttcccacat gggtaaaaca tgcttagcat aattatataa tcaaacataa cctttgtatt 376920
atattggggc atcactaaca tgtatggaaa tgcattgcaa caaaaagtga ttaaaatgca 376980
agacgatttt tcaaggaaac cattaaaatg tttagtttca atcaaagagt tttgaaaatta 377040 attcaaaata actatgatat agttcataag tccttaaaat cattatgaca aaagatttca 377100
taaaacacta tttccttaaa tacgaaataa ttttgccgat aataaaatcg ataattgatt 377160
tacaaaaata catattaatt ctccaacaag acccaagtta atcaagttat tataataccct 377220 taattaaaat gagtttaatg ttgtcccatc agattatgat tggttatggc acttataatc 377280
attttacgat ttgtttcgac aattacggta tttaccgtta tttaaataat gtttttaaatt 377340 cataaatatt aagaaacatc taagtaaaac ttattttaca ctatgaggca gtaggttact 377400
aacaaaatta taagtttttg atataggtct attttttactc aaatttaatt aacaatatta 377460
cacttttaaa taattaaaca atatttatta atttgataaa ttagtaaata atcaataatt 377520
agcttaataa aattttacta aagttctaga agccatataa tacttttatt agctcatttt 377580
aactaataaa tatcatttat aatattttat atcttttata tagacatttt atcgataaat 377640
caatagaatc ggtttaaatt atttaagtcc aaataaatta atttaaaaac ttttatgatg 377700
ttccagaaac tattttaagg aatataaaat tttaaataac cattaaaaac cgtgtggggc 377760 atttaaata attaatattg ttattttacc gataaaccga ataaaattta tttaagtcca 377820
tatatggtca cgaaaatcca tataaacttg tcgacatgta tttactgttt atataagtgt 377880
ctcataaatt tttcatgctc aaaggacgtc atttagtatt tattttgtat tttaccgttt 377940
tctaacttac cgattattaa tatccgagta aaaattatta aggtccttaa acgtcaacaa 378000
aatcttctca aaatttttacc aaatttattt actgtccata taagtatgtg acaaaaattt 378060
caagtccata tgtcttcatt tagtaattat tttatatttt actatttaac aatttaccga 378120
taaacatttt aacgattact caaaaatcat gaaaaattac aaattaatta tattctggcc 378180
aaatcttgtt ggagacatta taatatgatt ttattaatta ttttttgatga tgaagagttt 378240 atgtagtacc atatttcata ataagagtat ttaacacctt aaaacccatt aaaatatcga 378300
tttaacgaat aaatttcaac aaaattattc aagagattat tttaacatat agctactgga 378360
aattactctt aaaatgcatt tcaaatattt tctaagttca taaaatcatt tccatcacaa 378420
```

```
ttactttcac aaagtagtgt aaatcatgcc tttaaacata taacaattct taaaatcaac 378480
atgcatgatg cccacaataa taatacatgt aataaatcat tgcatattca aaattatcat 378540
tttgatatca tttttcaaga tttaagaact tctctttggg aattttattt tttttttttt 378600
ttaaaaaaaa caagttcata caaaactttc ccaacttgtt cttaaaccct ttaaaaatca 378660
ccccatgtga catacctcga ctccaagcct atataagtat ttcgtaagct cctacgtaag 378720
ctccgatgcg ttcttagaaa tggttccaac ttcgggtcct tgcccttcaa gtctcaactc 378780
caactcttca actaaacaca ttggatttat ccaaaaatca ataataattt tggatttcta 378840
acatgcactt aattttcctt agttggagtt gttaaactaa tacttgtgat gattttaaca 378900
tatttggagt atacttatta tgttgagcaa catatatact taatcaagtc tcataatttt 378960
acttaaattt ttaaagtaag aaaatatata agtttgtgaa aagaaagttt ttttttttata 379020 gagattttat aagtgatgat ttttcttagt tttagagaca aaatatccat attaaaatga 379080
ttttagttta tagaaagatt caagtaaaag tgttctacat gaacaagttt tacaaaaact 379140
agtggaataa ggaaatgaat gtaacttact ctatacttgg tggatttctt caagtttggt 379200
gtctatggaa agctcttgaa atgaagatta ttttatgga atatttgagt ttataaacat 379260
aaattttcag aagtataaga tgagtttttg aagaagattt gatgagaaaa gaaggtgtct 379320
tagtagttga aagtttggag gatgctagtg gttgttcatg gatgaacttg ggagcaatgt 379380
gttgggtgtt tatggctgaa ttcttattca gaaaaataga gtgtctttgc ttcaaatatt 379440
agcctcttgc atgcttgtaa tgatgcataa tctaggttag aacaaagggg tactttggtt 379500
agagtgtttt gcttgagtat gtaagtgtat aaggggtat aaagagggtt tgggacagct 379560
attggggctg ttgtttgggg ctgttttgga tgtggttttt gtctcatttt gatctattat 379620
agtgtaggaa aggtttatct aagatagttt aaagtttggg taaaaattgt tgtacatgta 379680
acaagttatg taacttgtat tatatgttta aaatcacttg tatatgtgta tgaaatattt 379740
aatttactcc catcatcttt aaataatacg atcgggtaat aattaaattt tctcgaacta 379800
ttatcggtag ttgctcaact ttaagttttta cctccaaagt ttacgtttct tgttacgatt 379860
cataaccacg ttatgattta acaagtttct aatcatcgta gaaatttttc aaatctctac 379920
catcactaat taaattttaa ttagcgaatg acaaatatta aaaaaaaaat taggcgctaa 379980
aaatgacgaa taaaacctca ttaataatgc gactgtttca caaagcttgt gtgactactg 380040
tatccttctc catttttggtt aatggtaccc cccttaagcc tttcgatgct aagaaaggcc 380100
tgcgtcaggg cgaccccatc tctccttacc tgtttgccat tgccatggat tatttgtcaa 380160
gactcatgca gaaacagaat aacttcagtt ttcatcccag atgtaaagct acccggatca 380220
ctcatctcct ctttgcagat gatctcctta tgttctgcag agcggatatt tcttcggttc 380280
aaagcatgat gcgctccttc cagatctttt cgagagcctc aggtcttgaa gctaacaact 380340
ccaagagcaa cgtctatatc tcaggggttg atgatcagtg caaaatgact attcttagct 380400
atcttcagat ggaagagggt tctttcccgt ttcggtacct gggagttcct ttacattcca 380460
agaagcttaa ctcccgagac tgcagaccgc tggtagataa aattgtgggt agaattggct 380520
actggtcctc aaagctcctc tcctatgcag gtagaattca gctggttcga agtgtgatta 380580
gaggcatcca aaacttctgg gcccaaattt tttgtatccc aaaaaaggtt ctaaaaatgg 380640
tcgaaaacat ctgcagatcc ttcatttgga cgggcaaaga gggcttatcc aggaaagctg 380700
ctatctcctg gctccaaatg ggcctccctt attccaaagg tggtcttaac ctgagagata 380760
tgtaccagtg gaacagggtg gctatcctta agcatctatg gaatattgca gtcaagaaag 380820
```

```
acaatttgtg ggtcaaatgg gtgcacagct actatgtgaa agatcgaaat ctgaatgaag   380880
ttcgtccttc tattcatgca tcttggagct tcaaaaagat catcaaacaa tgggagctgg   380940
ttgaaaggct aggtggttgg aattcgattg tcagcggggg tgtgttctgc attgggaaag   381000
tctatgatcg tctgattgct aatcatccga aagtcgattg gggtcctatc atgatcaaaa   381060
atgttgccag tcctagtgct agattcataa cttggctcgc catccaaaac agactagcta   381120
ctcgggatcg attagctaaa tggttagagt tgacagatga caggtgtgtc ctatgcaaca   381180
acgccagtga gtcagcccat catctctttt ttgattgccg aaatgcgaaa gaaatcagag   381240
ccaaaatctt taatttcctt tcctggaacc tcaatgaagc taatttccat gatgagatcc   381300
agtgtatgtc taaactcaac aaaaagaaga ctgatcgagc caagctgatt gtaggtctct   381360
ggactgagat gatttataac atctggatgc agcgtaacag gaaaattttt gataaccatt   381420
ccttcaatca gaaggaggtt atagattgta tagttttttag gattgcagga agagtaaaca   381480
gtagaatgaa tgatatgctt gtatctaggt agatagtcgc ttttttgggc tagtgctctc   381540 cttttttgtaa agagcactgg tgtttttggg cgtttcaggg ggagttaatt tccccctgt   381600 cttgttttt tttctcttct tggtatataa tacaaatcat ttggcaaaaa aaaaaaaaa   381660 aaaaaaaaa tatatatata tatatatata tatatatata tatatatata taaggaagga   381720
gataaggaaa atttaacgcg tatgtgtatg ttcgatatta ttgtcataac ccaaacttcg   381780
ctttgagatt ggagggaatt ccgaataggg aaattaaacg tgtatgctaa aatttgatga   381840
gtagaccata atgcatatgt tcctgcagca ttagaaattt tttttgtctt ggtgaaggat   381900
ctttaatatt gatgatgcca agatgtagaa tggtagtaat agtagtgcac tgattccggt   381960
gatgacccat gatcttttgca agtattcttt acattccttc actctaccaa gtaacaatca   382020
tgtcaattca tgtaattcaa tgcctagaag tgaaactatg tatttctatt aagaataatg   382080
catgtttact gaaataatgt gtatcaatta atgcaagata ttcctatggt gtaaaaagtc   382140
acatttcttt ttcaccagaa gccttattat accattctag gtccttgatt gaaagagtag   382200
aaggaaattg aagtcctaag gaagtggaga gtttggttga caaaaataca cactatacca   382260
tccagtagaa aagaatctaa tgcgtaatcc agttgaaaca tctacaatcc atctaaataa   382320
caattaaaga aatccaacaa aatcatatca gtcagtttgc aagcagtact ttaaagctcc   382380
aacagttgaa aggtgaccaa aacatcaagg ttcaaaccat gacagtctta ttcatctgat   382440
tctagcctcg atgctctaat ccaactctac tcttagacaa taaaagaaga aaaggcgaat   382500
atatatatat atctaaattc caccaaaaaa gtagagtaga gtatattaat gctcatggtc   382560
tagctctaca gtttgctact gtatttgaag ataataggat tacctcaacg ctcgagttgt   382620
ttaacagcgg agtaccttag gtttatgaat gtactgtttg gtttatggta ttcaaagcat   382680
tgagaaaagc aatgcatagt tatatatcac aaaatttggt aaaaaagaat aatcatgact   382740
ttatgcttat tattgtttta gaggtaatta ggagacctcg actctagatg agccatgact   382800
gctacgaact tataccttct ttatacaaac catagctgaa ctgacactgt aaaatttatg   382860
attccttaca aattcacggg cctcgatagt tcaagaatta gtattttata tgttaagaag   382920
acaaataatt gtatatttgt atatgttaaa aaacacaagt gttcaaaaca aaattccagt   382980
gaatacatgt aacttattct tacatcaact caatttaata gaatctgaag cattcatacc   383040
tagtaaccca tcaacctaaa cagaagttgc ttgcacctgg ggaagatctc gtcaatccac   383100 caaactaaa tcaaaacaaa acaaaaaaaa ggtcacaaaa aaccacacct aaaatgaatg   383160
```

```
caaaggattg ttgttcaact gcctatgaaa atcaacaatc catcccaata caccaaaacc  383220
ctcgaaatca atttctt tcttattccc aattaatcag aaaagctaaa aatggttaaa  383280
aaataataat aataaaaaaa aaacttgcaa caaactacaa atcaactta aacttgaaga  383340
ttaacaagaa aatagagcta aaccataacc tgaagatcaa ccaagcgtag taggaagaac  383400
actaaatcat gtttatatta agtaaatata attttcatga aaaattatac attgcataca  383460
caccaaaaac atccttcatg aaaaattcca cattgatata agtaaattaa atacctaatt  383520
ttgacatgaa caccaagatc atactaccag tgatgaataa ttgttgcaat gcaagtgttt  383580
caatttccat tttcagaaac aaaattgtaa ttcatactac caattatgag aaataaaaaa  383640
gggattagag aaataaatta aaagatctca tgaacttgaa gagcaatcct tgaagctcct  383700
taaattattg atcatcatca aactcacaaa taggagaatt aatagcagga cattgaatag  383760
aacacaattg aagaaaaagc aaattattat gttcatcatg aaaataacta atcatgtgac  383820
tgctcttcat ctgtcagttg ccttccaaac tccacaataa cccaaaatta aactaatatt  383880
caccaagagt ttcctcaaaa acccacattt gtaataatca aaattataag aggggaaagc  383940
agttaagtga aaatggcaaa aagatacaag cttcaaagaa gagaattcat tcttgaaaac  384000
aaacttattt ttttaatcat aataatcaat caaaatacca gctacaaata atcttcttcg  384060
cactatcatg gagcaatgtt ctaaatatca gcaagccatg caaacactaa acataactaa  384120
taaattggat ttttacatct gattcactta caatatctat ctccttgatg atttattcta  384180
gcatcaatga gtgagcatgc ttctttaaca tctatacatg aaaattgtac ctaatctcaa  384240
atccctcaag catacaaccc ctgccatttt gcgtccatca taatacaggg caaatccaca  384300
acctcctatt caaaataaaa attctaacaa gatttaagct ctatttcaaa tttcatgacc  384360
cttaaaccaa caaaaatgta aaattttaag ttttgtcaca ttggagcaac cattacagat  384420
gactgaaatt agaaagttca tagcaactaa gaaggtttgt gaagctaacc taattttcca  384480
agttgctctg atatcttaat taggtcagat cctccaacaa caccaactgc aacaacctgt  384540
aaaaataaat ggatttaaga atatacccat taaagtatca aaaaaaacaa cagaaaactt  384600
gaaacgaaaa aagcttggaa agatacagtg agtttggagg aaaaaataaa aaagaaaatt  384660
agaaaaaaaa aaacggaaaa cgcatatcaa attagggcga aaatcaaaaa ctaaaaaatg  384720
aaaatcaatt tttgcaggtg ttgaatagca aagtaggaaa aatcaaaagt acatttacaa  384780
agtaggacaa ttaggattga agaacaaaag gaaaaaaaga acaaaaataa accaaaatga  384840
acaaatgcag tatgatgatg aacaaaagaa atcagtaatc atagcttcaa atgcctaatt  384900
taagatatca aaaatacctg atttaccgtg gtagggttag cgacgttgat ctgcaaatgc  384960
cacaataaaa acaaatttaa aattccatga aaaactttta tcacatcaca aagattacaa  385020
ttaattaaac cataagaaaa tttctggaat tgatgaattg aattatcgaa ccttcgtgat  385080
tgaagaaagc tagaacggcg gaagtgaaat gagggagagg ggaaagagaa attgtggtcc  385140
tagggttttt gataaatgaa gaaattaaga agagtcaatg gaactgagca tagcaaggga  385200
aagcaaaaag gaaggaacag tgatttact gttcattttg aaattgtgaa cagttatacc  385260
ctcttagaca ttttttatag tttaaagata acaaaattga gtactgcaaa tctacaattc  385320
tctattcaaa ggaagactca aaaaataaag caaagcaact gacatacgtc aacacttaac  385380
agtgatatat cagtcttcaa atttcgtttg tcttcttctc cggcaagcta ccacacatct  385440
caccggcacg acggaactta caggcgcacc agcagttcaa caggcggtac tgcatcagat  385500
tttgtttgta cgttttcatc ggtttttttcc ggcgaaaaat tcatcttctt catatcatgt  385560
```

```
ttctcttttt tagtttaggg gttttttaaga tgcaattttg tattttaaag acatatttat    385620
cttctttttt cttttatata ttaatttgtg tacaaaaact tctgatttat gatttttttt    385680
ttcataacct gggccctggc ccatggaggc ccgggtttgg attcgcccag acagactaca    385740
accaataata taaatggaac taaattaata tttgagtgat gaatttaacc tgaatcccca    385800
aggagacatg attaagctag cagagacaca tacatcattt agaaattcat agccttgtcc    385860
acagctttag ctgcttctct tttagttttg ttctttgacc tcgtgacgca aagattcaaa    385920
atactgcaaa ttaatcacaa ataatttcat ttagaaaatt ggttgtatat aacaataatg    385980
tcaaagtctt aatcccaaca ataggtgg atgtgtataa aaaatcataa aactggatga     386040
tttttatctg taaaaacctt accagttttt gattctcaag ctgtatggag agaatttcat    386100
tatattcatt cacaatctag caaagacaac ccaattgcaa acaaaatcaa catcttcaac    386160
gactaatgaa catcaagcgg aacctaagca aagttctgaa gctaaaagca cggagaaaaa    386220
ggtgaaaaag aaaacataca gcttcaactt tactactgaa tattggtagc ctcactaata    386280
tcagcttcaa ctcaaaataa actaaagctt gacgctttta gacgccacaa aatgaaagaa    386340
aaagaaaaat aataacaaca aacgcaacat ctttcattat tgcttcaaca gcaaaaattg    386400
ttgttgttac tgaattttc aacgatgaag atgatattgt agggaggaag agagagacag    386460
aagaaagtgt tttgaggagt gtgaaaatga gacagagaaa atcacattta ggacgaagtg    386520
aggcaaagca acgaaaagg cggaaaaaaa agtaaatgaa cagtgatttt actgttcatt     386580
ggcaaaatgt gaatagtgtt cttgccttag aaacttttta tagttagagg atatattata    386640
ttgtgatggt atattatatt gtgattatga acttgtttat ggatgatgtt tttagagttt    386700
tatattatat tgtgattgtt ttggataatt atattgtgtt cttggtactt gtttaaaaaa    386760
aaatttttat taggtaaatt tttgaaaaga aatatttat taggtacttt ttaaaagatg      386820
aataaaaaaa tatattagat acttttgac aattatcttt ttttaataag ctaactatta     386880
aatgtaataa gaaatctctt atttgcctaa atattgtatt atataataaa aaagaatga     386940
gagtaagaaa tgttgtctta gcttattat taggagattg tgcattgatg gttatttact    387000
cttcaacaa cccatatcat atagaagtac ttcactcaac aatcaacatc atttctctc      387060
tcaaaaaaaa ccctcctaat ttttcctcta atcttcactc tttcaatcat ctaaacaaat    387120
tatacaatcc aactctacat tttttcaaga ctcaacatta tcaacaaatc ataaactccg    387180
tttcaaataa cttatttatc cgatacatca atttacaaaa aaataacaaa tatactttcc    387240
accattgatg attgttcaag aaattcagg tttgctttct tattttgaga catagttttt    387300
tttagatgca taaaaaaatg taaagttcta tgaatagtat gtattttttt atcttaatta   387360
atttttctt gatattaaag atgagttgta tatatagttg tataattact ttttctggg    387420
tatttaaaac gatttatatg tgtagttgta taatatcgat atatatttc ttgttctgta    387480
gatcttataa cacaaataaa ggatcaaaga aaatgaagat caatggaata taagctgatt   387540
tttatttcgt ataaaatatt gtatttatct aataataaaa cacattttta acgttttta    387600
ggtatgaatt ttagttatta tgtataatta tgtttgtcat ttttttttgca tgttttaata  387660
tttattgtgg taatgtcatt tcttctagaa ttttaactt taaaaatatt tcttactctt    387720
tttctttctt tagtatataa taaaatatag aattttaac ttaaaaaata tttcttactc     387780
tttttttag tatataatga aaaatttct ttatctaaaa ataagacatt ttttttattt     387840
tttaccttt ttttatagt agatctgtta tttctgataa gtacaaataa agttcttgaa    387900
```

```
taattgttaa attagtatgt tgaatttgtc gttaaaacga ttcatttcaa atatggtatg    387960
aataattaaa tggttaatac ccgtttggaa tctcaatgtt aaaagttatg aaacaaatcc    388020
atggctaata ttcatttggc aatttcaatg ttaagatctc ttttattct ttacataaag     388080
```

```
taattgttaa attagtatgt tgaatttgtc gttaaaacga ttcatttcaa atatggtatg    387960
aataattaaa tggttaatac ccgtttggaa tctcaatgtt aaaagttatg aaacaaatcc    388020
atggctaata ttcatttggc aatttcaatg ttaagatctc tttttattct ttacataaag    388080
taactttaga tgcctagctt tcactttgtc atcattgtga ttgatttatt ttgtcttttg    388140
cttattttat ttaatattat atatttagtt tcaatttagt agatcttaaa ttataagctc    388200
ttatttgttc ttttttata attttcccgc tcaatgcacg attataagcc tatagtcgcc     388260
ttcaactgtg tagaccgtaa attttgaaaa aaataagact ttccttgaat tcattctagt    388320
tccctgtaat ataaaaaatt catattatat tctattttga attaagtaac aacgcttttg    388380
atgtaacaca tcaaacataa aacaaaagaa aaagatataa atcagtacgg taaccttctc    388440
atcagctaaa atcatatgaa gtgttttga tacctccta ttttaaatt cccatatatg       388500
tataacttta gccttaacct tccaatttcc cctatcactt tttatttctt gtatataatt    388560
taaacccatt gtaaattgat ttatttagaa agctactcta gcaagcaagt ataattgctg    388620
tcgacatttg taagagaatg ctgggttttt atagaattt tggcatccaa cacttgcaag     388680
aataattgct gtcaacatta gtctagaata attgctgtca tatttttatt tcctttcttg    388740
ttaaaaaaat aagttctaat ttcggtaaga ataatgacat cagtcaccaa atcagggatt    388800
ttaggaattt ttctagacta atttgaaat ttaaatatgt caacaattct ttgtcaataa     388860
atcagtcatt aactttatt attgtcattg atatcagtct ttaaatcagt caataattcc     388920
ttgagtatat aaattgggct aattttggca tttaaaaaac tcaattattc actgccaata    388980
tattagtcaa taattctag actaaatttg aaatttaaat atgtcaacaa ttctttgtca     389040
ataaatcagt cattaacttt tattattgcc attgatatca gtctttaaat tagtcaataa    389100
ttccttgagt atataaattg ggcttatttt ggcatttaaa aaactgaatt attcattgcc    389160
aatatattag tcaataattt tgtattattt ccatggattt atttcagtaa ttaagtcagt    389220
ctttcattaa attaattcct gcaaccaaat ttcgggaagt caccaaatca gggatttag    389280
gaatttttat agactaattt tgaaatttaa ataagtcaac aattctttgt caattaatca    389340
ctcattgata ttgttaatca atacatcagt catccaatac agttgtggca cttgacaatg    389400
atccaataaa attgttccac ctggcaaagc tcttgaaaaa aatgacatct ggcttttacc    389460
aactcttta gtttatgtta tgattattca taacaattca caagacattg cttgtagaaa     389520
cattatctat ggccagataa acgtagttga ttttggagga tgcgagcctt atctttagcg    389580
gtggcttgta gaaacattaa accctcaaa atattcaaat cagaacatcc ttcacttgga    389640
atttttaaag tagttagtct gcaactttct tcatgagtcc actcgactct tcagttttat    389700
tctcttccac atcatttctt tcgaactcct aatttgcaag taaaactgta ttgcgtgtaa    389760
ttcagtgcgt gtaattcaga atgattctag gcctccttat acagggaccg aacttcgaac    389820
tccatctttg ccctagaccg agcaagttat aaattgtatt gttgttataa aattgtgaat    389880
tgctgttata aactggtgaa ttgttgtaaa ttctgaatta ctgttataaa cttgttttt     389940
gaaattctaa tttatttga attttatat actcaattct ttggaatgta atgtcttaga     390000
aatttatgac tttttattg gacctaaatc tctaaacatt taagttgggc ctttggccta    390060
cccttgggtc aggcctggtt gtacatcgct tcttgcgagg cccaactaaa aaactcacct    390120
ttgtgtgctc acacatttta ataaaataat aatttaatt cgaacctctt tatttttgaa    390180
atcgtaacta tttattattt taatataaat atgttaatat tttaattcgt atatgaaagg    390240
agtttattaa aactaattca aataatttaa tatacgatca taaaatctcc aaaagttatt    390300
```

```
taaaatatta aataattacg tcattaaaaa tctcggggtg ttacagacta ccccctaaa  390360 agaagtttcg tccccgaaac tagagtaaca aggcactagt catgaaaatt tatagccttg  390420
ggatatatgc ccttctcgga tttattccgg agattttggt tgtatccttg ctttatttga  390480
tattaggact aattggactg ttggcccgtt ttcttcccct tatctatgct tgtgagtcc   390540 aagtacaatc atgagtatgc tatggatcat gagtacgcac ttccatgaga ttacttgcaa  390600
attatggagc cacctttggt aaacttctga ttattatata ttaagttgat tataatagtt  390660
taattttcag ttttagtagt ttagttgatg ttaaaagtgt gtgtaattag aagaatacga  390720
gagcgtgtaa ttaagaagga ttctaggcct ccttatacag ggaccgaact tcgaactcca  390780
tcttggccct agaccgagca agttataaac tgtattcttg ttataaactt gtgaattact  390840
attataaact ggtgaattgt tgtaaatttc tgaattgctg ttataaactt gtgaattgtt  390900
gtactgactt gtgaattgct gggttcaaat tattttgatt atgtaaatcg ggattaagtt  390960
ttggtaagtt ggaattaggt tatgataagt tgggactagg tcatggtaat ttgggattga  391020
gttgggacta ggttatgata tatattgtta tagacttaca gatatactgt aaatgcatgt  391080
tagcatgata taagttggca ttagatcatg ccaatttaca ataatctaat cccaacttat  391140
actaatataa atccaactta caaaaacgca acaaaaatct aaatccacct attcccaact  391200
cacgttaagc tttaacaaaa aaaaaaaagt aatatcagtc aatcagatta tcaagaaaca  391260
agcatcccca gcatactcca caactagcaa aatggaggca aacagacatt aatagtaagc  391320
ataagtgtaa aaaatggtct cattgacatc aagccccaat agtctattat tctccattca  391380
gaacattttg gtataaatca gatgagaaca gcagaacacc tccaatagct taggttatag  391440
tgtctacagt atccaattca taaggtcatt ctaaacagtt tatgcacctc aagtaaaaaa  391500
tattctggag aagatggtgc aatcgaacgt tgattacttc tacactaatt aaatgataaa  391560
catcggccga agcagctcct acaggaagat aattggtttc atctgccaaa atacaatgat  391620
gagataatag aattagacta tattttaaaa taaactgatg aactctatct tactatcata  391680
tgttgtatcc caccaggtaa cagttaattc agattttaat gaagcataga tatgcttaga  391740
ttatgacaaa aataagatag gattacggaa agtggtatta aagatgaga cgccaataga   391800 caaaagatca gaaatgtcaa tggggttttc ttaccaaagc aaaaccacgt ctgaagcatc  391860
cgtaactcca ttgaagtatg catcaataag ccgctctata ttgtccgcag gtggaggagc  391920
ccttaagcgt aggttgtctt ctttcaattc agccacttcc tttcttaggt tgtcttctag  391980
atctttcaag ttggccactt cctttcttag gttgtcttct agatctttca agctggccac  392040 ttccttttc aagtccgcca cttgactttt caattcacca tttcatttt gaagctcaac    392100 aaaatcattt ggctttgact tctcaaattc taaaacacgt tctccctaaa tattgcacat  392160
ttatataagg ttgtcaacaa agaaggatag gtaaaaacaa aatgcagagc ttctgcttta  392220
gagcatggga agcacatcat taaatagaaa acacatattt gttattaaat agaaaaccat  392280
tggctttgat ttcttgaatg tgtttctatc ttcaacgtaa tatacaattc aacctcatac  392340
ataagaagat aaaccattag tgaagataag ctttagggta tataaccttg acacggtgag  392400
agttctcttc tctctggtcc tcttgcaaaa catacgagga acaatccatt aaaagtagtt  392460
catttgcaac gctcttcatc agttcactcg ggtcttcagt ggtatcttgt ttcacgtcat  392520
cacacatttc ccaagaaact gatgtgtttg aagtgggtgg tttaccaggt acatattttt  392580
ctggctcacc aaaagacgga aatttgggga ttatgcagta gcactgcata tgcaacagcc  392640
```

```
acacataaat atttgagggt cgtgtaaact tatatatcaa tttgaaggtt gtaatgatca  392700
acttacattc ttgttaagtt cacagttgca ccatcgtaat tcttttccca ttgcaatcaa  392760
gtcatttaca aagcgtggat caagtaatgc gccttttgat tcgatttcgg cattgtactt  392820
gttagaaaaa aattgccaca gttctctgtc cgtccaggaa tacgtctcag acataataag  392880
agggaagaca tatttgtcca tcacatataa ataatgttgc ttctctttgt catacatctg  392940
tcaataaaaa tccaagagaa aaagcttatc atataaacaa tgttccttct cttctcttct  393000
aaaaacttct gttttattgt tataaacttc tattgttata aacttctgtt ttattgttat  393060
aaacgtctgt cttattgtta taaacttctg tattgtgtct taaaataaac aaaaatgata  393120
aatgaacaaa tatcatcaga atcaacaagc aaaagtccaa ttaagaattt atttgcaact  393180
gctcacattc gaatttcata aacacttcga atttctttgc aacacgatgg aaaaaatatc  393240
atcaatggaa aattaaacaa atcgatttac gaatgtcaag cactcaacca tataatacca  393300
atttctagct atataatgta agcactagtt gccgacttat aataatctaa tgccaatttg  393360
caaatatata atgccaattt atagctagca tataatgcca atttaaaaat atataatgca  393420
gtattcaaaa aaaatatat atatataatg caaatttaaa atatataatg ccaatttcaa  393480
accatataat accaacttct agctatataa tgccagttta aaatccaaga agtgtcaagc  393540
aagctggtga aggagagtga agcaaagtga acagccaatg ggctgcggtt ttaatagtgt  393600
ccgcagccaa agcccagccc aaagtctaag aaaaaccta atttctctga taatataaag  393660
tattcggcgc ctattcattt ccttattcta acaaaaacct atcctcctcc ttcctaacaa  393720
aatgtcataa agttttttcat aaagtttgca agatagtga attttttgaa gtttgcaaca  393780
tagagatgaa agtttgcaaa gatagtgaat tgttattac taatgtacta ttatcttagc  393840
ataattctca tcttaatgga atatggatgg tttatctttt tttatttgtt tattttaata  393900
ttagcataat tacgaatcat ccacctaaaa gtcaaatcaa acaacatctc gaatcgtgtg  393960
acattggttt tgagctttgt gactttagtt ttgagctttg ttactatcgt ttgttttctg  394020
atagtaatgc atgtgtaacg aatggggaag ggcaaccggt taggccttt ttattagacc  394080 taaatctcta aacatttaag ttgggccttt ggcctaccct tgggtcgggc ctggttcctt  394140
tgagactttt tttatttat ttttttttcgt tttataattt ttataatcaa attcattgtt  394200
gcaaaaatct aaattggggt acggaaagga taaattcatt gttgaaaact aacggtcaat  394260
gacgaaaatt cataacaagg tagtcttttg caaacttaa tattatacaa ggtagttttt  394320
tgaaaaaaat tttatattag gtagttttt gaaaaaaag gttgattaca aacaacgtta  394380 gaaagaaat acaacctgaa ataacaataa caattaacaa caataccaaa ttacaaagtg  394440
caaacacatt caaatttcaa agtccaaaca cattcacttc ttcacaaatc acattaacat  394500
taacatatat atagaattat aacatatgaa ataacaaaaa atgtaacaaa cagtaacatt  394560
aataattcaa gaaactaact tgagtttgaa ataacaataa aaaaaccct aattttgag  394620 aattggggat ttgaaaatat aacatttaat taataataat acctgaaaat ctgaaattgg  394680
tttgattgtt tgacggtggg ttagtaattg gtatggtggt ggactagccg gtgggaagta  394740
ggcaagccgg cagccgcagg acagaaaccc aacgtgatag cgactcgcga gggagcaggc  394800
gacaggagac tgaaaagcag caggatagaa acccagacgc aatagtttgg agttgatatt  394860
caagaaacca aacgcccgtt tggtttgtaa gagaaatcac cggcaaagat aggagagtgg  394920
caaacggtcc tcaaaacatt taaattcgaa ttttaaacca taattgtcta ttgttgtgt  394980 taaattttac attttgaaa ttctaattta ttttgaattt tttcttactc aattctttgg  395040
```

```
gattaaatgt cttgaaaatt tatgactttt ttattggacc taaatctcta aacatttaag   395100
ttgggccttt ggcctaccct tgggtcgggt ctggttgtac atcgcttctt gcgaggccca   395160
actaaaaaac tcacctttgt gtgctaacac attttaataa aataataatt ttaattcgaa   395220
cctctttatt tttgaaatcg taactattta ttatttaat ataaatatat taatatttta   395280
attcgtatat gaaaggagtt tattaaaact atcaaataat ttaatatacg atcataaaat   395340
ctccaaaagt tatttaaaat attaaataat tacgtcatta aaaatctcgg ggtgttacag   395400
actacgccct taaaagaagt ttcgtccccg aaactagagt aacaaggcac tagtcatgaa   395460
aatttatagc cttgggatat atgcccttct cggatttatc ccggagattt tggtcgtatc   395520
cttgctttat ttaatattag gtctaattgg attgttggcc cgttttcttc cccttatcta   395580
ttctttgtga gtccaagtac aatcatgagt atgctatgga tcatgagtac gcacttccat   395640
aaggttactt gcaaattatg gagccaccett tggtataatt tctgattatt atatattaag   395700
ttgattatag tagtttaatt ttcagtttta gtagttagt tgatgttaaa agtgtgtgta   395760
attagaagaa tacgagagcg tgtaattaag aaggattcta ggcctcctta tacagggacc   395820
gaacttcgaa ctccatcttg gccctagacc gagcaagtta taaactgtat tgttgttata   395880
aacttgtgac ttactgttat aaactggtga attgttgtaa atttctgaat tgctgttata   395940
aacttgtgaa ttgttgtact aacttgtgaa ttgctgggtt caaattattt agattatgta   396000
aatcgggatt aagttttggt aagttggaat taggttatga taagttggga ctaggtcatg   396060
gtaatttggg attgagttgg gactaggtta tgatatatat tgttaatttg ttatagactt   396120
acagatatac tgtaaatgca tgttagcatg atataagttg gcattagatc atgccaattt   396180
acaataatct aatcccaact tatactaata taaatccaac ttacaaaaat gcaacaaaaa   396240
tctaaatcca cctattccca actcacgtta agctttaaca aaaaaagta ataccagtca   396300 atcagattat caagaaacaa gcatcccag catactccac aactaacaaa atggaggcaa   396360
acagacatta atagtaagca taagtgtaaa aaatggtctc attgacatca agccccaata   396420
gtcctaatta atttatttct tcatcatttt atgagatgtt aatgactgct agagagcatt   396480
aagcttcata caaaaaaatc gatataatca gagattttca gataatatta ttgatagcat   396540
attgacatca caaattgtct attattctcc attcagaaca ttttggtata aatcagatga   396600
gattcagatt cagattaaaa ttgcgattga gattgagatt cagattgctg ataaagacac   396660
ataatctgtg aaaaccaata aggggagac aatgaacata agctctgaag gaagcttgaa   396720
aaatccttca acagttggct ataaccatta ttgaattaga ttattatttt gtgactaatt   396780
tttgtcctta gtttgctatc agcataacta ttactaaaac aaacaccacc tactgccacg   396840
tgtcgtgttt tcagagaatt ttttcctgcc taaaatctta ttctatgtac atctacatttt   396900 gaaaacttaa agattaccaa aattgttgcc caattagctc ggttttgacc aaatgttgtt   396960
actattaatt ttatttatct tgataacagc aattcacaag tttataacaa caattcagaa   397020
atttacaaca attcaccagt ttataacagc aattcacaag tttataacaa caatacaatt   397080
tataacttgc tcgatctagg gcaaagatgg agttcgaagt tcggtccctg tataaggagg   397140
cctagaatca ttctgaatta cacgcaatac agttttactt gcaaattagg agttcgaaag   397200
aaatgatgtg gaagagaata aaactgaaga gtcgagtgga ctcatgaaga aagttgcaga   397260
```

```
ctaactactt taaatagttc caagtgaaga atgttttgat ttggatattt tgagggtttt  397320
aatgtttcta caagccaccg ctaaggataa ggctcgcatc ctccaaaatc aactacgttt  397380
gtctggccat agataatgtt tgtacaagca atgtcttgag aattgttgtt atgaatagtt  397440
gtaaattttt cattagattt caaactgaca ttactagagt ttgttgcttc aacattacta  397500
gagtttgtaa caaaaacaat atagtttgta attgtaacga caatattaaa gttattgttc  397560
cgagtaaaat aagggcactc atacgtgaaa atgaacaatt aaagtcaccc aaacagagcc  397620
aagcttcagc ccaatcatta agtataaatt tatatcaaac tagtgccaaa taatacgtat  397680
tatattaaat gatctaaacc taatcccaac ttaaatttct gggtctttct cttaaatttc  397740
tgggtcattt acaaaaatta aaaaaacgct gctcttcact ttgcgttctt cagtttctct  397800
tcatcagctt gctttcttcc tccctgtgcg actggttcta ccttaagaaa gaatgaggct  397860
gggagagttc tgggagtttc tggggaccgt ttgccgctct cctccgatga ctgtcgtcgg  397920
cactcatcgt agcctatgat ttctccgatt aaccaaacgg ccctcaaaca caaccccccaa  397980
aacacttcat attcataatt cctctcactt aagtaaatca atcaactaca ttctaccaaa  398040
cacccatctc aaactgaaca aaccctaatt ctccttggag aatcgcttga cgcctgacgg  398100
agaatcgctt cacctgagtt gcttctttcc accggacgtt tggcctgctg gctgctgctc  398160
cttggttccc tcgcaggtcg cagcctcgct gacgctgact gattcgcttc attcaccaaa  398220
cagaacaccc tgctgagtgt gtactgccgc cggctttcct actgcccaca gcccaccgcc  398280
accggacagg cagccaccac tgacaaccat acgtccagtc catatggcca ccaatttcag  398340
gtattattat taattaaatg ttatatttta taaatcccca attcccaaaa attaggtttt  398400
tttttcttat ttcaaaattc aagatagttt cttgattgaa ttagatatta tatgtctgtc  398460
attatgtcaa tgttattgtg ctttgttatt attcttgcct tcatcttgag tatttgtttt  398520
tatgggggat gaatgatgat gtatgctatg tatgctaggt aaggaagatg actttagggt  398580
ggccactgta taaattcaga ataatgcctt tcatcttatg ctatgtttgg gaatgatgat  398640
ttgatttgaa aatatagatt tgactcaaaa ttagtgtttg gcaaacacta gaattttaaa  398700
tgtggatttg agtcaaatcc atgattgtta tcaaaatggt ttaaagatga ggatttgaga  398760
atgacctccc taaccttgtc attctcaaat tctacattca tgattccata attgaaatca  398820
ttaatttgaa atgaaatgct agttcccaaa cacaacctta tacaaattag ttatttagcg  398880
actaggtgtg atgttgattt tgtgctggag tatgaactga atttatcccc taaatagaaa  398940
gaatcataga tgttgatttt gtgctggagt atgaactgaa tttaccctac gtttatttga  399000
tgaagcttgt ggggtctttt ccaatattga atttcctaat gttttagct ggaatactat  399060
gattaaaggg ttttttgaat gtgggaaaat taacaatgca gttaagatat tcgatataat  399120
gcctgaaaga gatgttgttt catggatatt cgatataatg cctgaaagag atgttattaa  399180
agggtttttt gaatgtggga aaatcaacaa tacacactaa tgactcaacc ctaacacttg  399240
agaacaacct ctcaagcttg tgtttccatt caacaatgga agacacccac aaactaatac  399300
aagaagaaga ctctcttggt tactctaaac cctagcctct cttagtgtat tagactctct  399360
tacatgccct aagactcccc taatactcct tttatagtgt aatgactcaa ccctaacact  399420
tgagaacaac ctctc                                                   399435
```